United States Patent
Cianchetta et al.

(10) Patent No.: US 11,957,680 B2
(45) Date of Patent: *Apr. 16, 2024

(54) PYRUVATE KINASE ACTIVATORS FOR USE IN TREATING BLOOD DISORDERS

(71) Applicant: Agios Pharmaceuticals, Inc., Cambridge, MA (US)

(72) Inventors: Giovanni Cianchetta, Boxford, MA (US); Tao Liu, Wellesley, MA (US); Anil Kumar Padyana, Lexington, MA (US); Zhihua Sui, Audubon, PA (US); Zhenwei Cai, Shanghai (CN); Dawei Cui, Shanghai (CN); Jingjing Ji, Shanghai (CN)

(73) Assignee: Agios Pharmaceuticals, Inc., Cambridge, MA (US)

(*) Notice: Subject to any disclaimer, the term of this patent is extended or adjusted under 35 U.S.C. 154(b) by 4 days.

This patent is subject to a terminal disclaimer.

(21) Appl. No.: 17/744,806

(22) Filed: May 16, 2022

(65) Prior Publication Data

US 2022/0395503 A1    Dec. 15, 2022

Related U.S. Application Data

(63) Continuation of application No. 16/639,075, filed as application No. PCT/US2018/000127 on Aug. 15, 2018, now Pat. No. 11,364,240.

(60) Provisional application No. 62/673,533, filed on May 18, 2018, provisional application No. 62/673,526, filed on May 18, 2018.

(30) Foreign Application Priority Data

Aug. 15, 2017  (WO) ................ PCT/CN2017/097496

(51) Int. Cl.

| | | |
|---|---|---|
| A61K 31/5025 | (2006.01) | |
| A61K 31/506 | (2006.01) | |
| A61K 31/519 | (2006.01) | |
| C07D 241/36 | (2006.01) | |
| C07D 513/14 | (2006.01) | |
| A61K 45/06 | (2006.01) | |

(52) U.S. Cl.
CPC ........ *A61K 31/5025* (2013.01); *A61K 31/506* (2013.01); *A61K 31/519* (2013.01); *C07D 241/36* (2013.01); *C07D 513/14* (2013.01); *A61K 45/06* (2013.01)

(58) Field of Classification Search
CPC .................... C07D 513/14; A61K 31/5025
See application file for complete search history.

(56) References Cited

U.S. PATENT DOCUMENTS

| | | |
|---|---|---|
| 4,405,635 A | 9/1983 | Schnettler et al. |
| 4,883,914 A | 11/1989 | Alvarado et al. |
| 11,040,036 B2 | 6/2021 | Cianchetta et al. |
| 11,364,240 B2 | 6/2022 | Cianchetta et al. |
| 2010/0331307 A1 | 12/2010 | Salituro et al. |
| 2012/0142717 A1 | 6/2012 | Jin et al. |
| 2014/0155374 A1 | 6/2014 | Su |
| 2020/0206225 A1 | 7/2020 | Cianchetta et al. |
| 2020/0207785 A1 | 7/2020 | Cianchetta et al. |
| 2022/0127267 A1 | 4/2022 | Liu et al. |

FOREIGN PATENT DOCUMENTS

| | | |
|---|---|---|
| AR | 112690 A1 | 11/2019 |
| EA | 201590881 A1 | 8/2015 |
| WO | 2001/009121 A2 | 2/2001 |
| WO | 2001/017956 A1 | 3/2001 |
| WO | 2010/042867 A2 | 4/2010 |
| WO | 2011/002817 A1 | 1/2011 |
| WO | 2011/137089 A1 | 11/2011 |
| WO | 2012/092442 A1 | 7/2012 |
| WO | 2012/151448 A1 | 11/2012 |
| WO | 2012/151450 A1 | 11/2012 |
| WO | 2012/151451 A1 | 11/2012 |
| WO | 2012/151452 A1 | 11/2012 |
| WO | 2014/074848 A1 | 5/2014 |
| WO | 2014/139144 A1 | 9/2014 |
| WO | 2014/139325 A1 | 9/2014 |
| WO | 2019/008025 A1 | 1/2019 |
| WO | 2019/034690 A1 | 2/2019 |
| WO | 2019/035865 A1 | 2/2019 |
| WO | 2019/035911 A1 | 2/2019 |

OTHER PUBLICATIONS

Adem et al., Pyruvate kinase activators as a therapy target: a patent review 2011-2017. Expert Opin Ther Pat. Jan. 2018;28(1):61-68.
Belikov, Pharmaceutical Chemistry. MEDpress-inform. Pages 27-29, (2007).
Dyson et al., Chemistry of Synthetic Drugs. pp. 12-19, (1964).
Gupta et al., Human pyruvate kinase M2: a multifunctional protein. Protein Sci. Nov. 2010;19(11):2031-44.

(Continued)

*Primary Examiner* — Alicia L Otton
(74) *Attorney, Agent, or Firm* — McCarter & English, LLP; Michael J. DeGrazia

(57) ABSTRACT

Described herein are compounds that activate pyruvate kinase R, pharmaceutical compositions and methods of use thereof. These compounds are represented by Formula (I): wherein $R^1$, $R^2$, $L^1$, and $L^2$ are as defined herein.

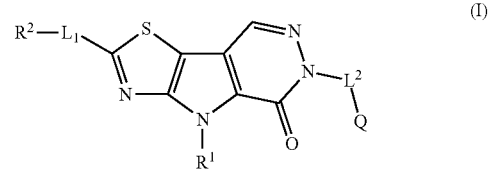

14 Claims, 10 Drawing Sheets

(56) References Cited

OTHER PUBLICATIONS

Gura, Systems for identifying new drugs are often faulty. Science. Nov. 7, 1997;278(5340):1041-2.

Jiang et al., Evaluation of thieno[3,2-b]pyrrole[3,2-d]pyridazinones as activators of the tumor cell specific M2 isoform of pyruvate kinase. Bioorg Med Chem Lett. Jun. 1, 2010;20(11):3387-93.

Johnson et al., Relationships between drug activity in NCI preclinical in vitro and in vivo models and early clinical trials. Br J Cancer. May 18, 2001;84(10):1424-31.

Linghu et al., Development of a Practical Synthesis of ERK Inhibitor GDC-0994. Org Process Res Dev. 2017;21:387-98.

Marelli et al., Tumor Targeting via Integrin Ligands. Front Oncol. Aug. 30, 2013;3:222.

Merck Manual, Acute Leukemia. Retrieved online at: https://www.merckmanuals.com/professional/hematology-and-oncology/leukemias/overview-of-leukemia. 6 pages, (2013).

Palsson-McDermott et al., Pyruvate kinase M2 regulates Hif-1a activity and IL-1beta induction and is a critical determinant of the warburg effect in LPS-activated macrophages. Cell Metab. Jan. 6, 2015;21(1):65-80.

Pearce et al., Failure modes in anticancer drug discovery and development. Cancer Drug Design and Discovery. Elsevier Inc., Stephen Neidle (Ed.). Chapter 18, pp. 424-435, (2008).

Simone, Introduction. Cecil Textbook of Medicine, 20th Edition, vol. 1. W.B. Saunders Company, Philadelphia. J. Claude Bennett, (Ed.). Part XIV, Oncology, pp. 1004-1010, (1997).

Sofan et al., Antimicrobial Activity of Newly Synthesized Thiadiazoles, 5-benzyl-2H-tetrazole and Their Nucleosides. Der Pharma Chemica. 2012;4(3):1064-73.

Su et al., The role of pyruvate kinase M2 in anticancer therapeutic treatments. Oncol Lett. Dec. 2019;18(6):5663-5672.

Tamada et al., Pyruvate kinase M2: multiple faces for conferring benefits on cancer cells. Clin Cancer Res. Oct. 15, 2012;18(20):5554-61.

Wang et al., Mathematical modeling in cancer drug discovery. Drug Discov Today. Feb. 2014;19(2):145-50.

International Search Report for Application No. PCT/US2018/000127, dated Nov. 30, 2018, 11 pages.

Russian Office Action for Application No. 2020110573 dated Dec. 24, 2021, 14 pages.

Copending U.S. Appl. No. 17/586,777, filed Jan. 27, 2022.

| Cpds in Examples | Synthesis of the intermediates |
|---|---|
| E2-14 |  |
| E2-19 |  |
| E2-21 |  |
| E4-7 |  |
| E4-15 |  |
| E4-16 |  |
| E7-6 |  |

FIGURE 3 - Continued
| Cpds in Examples | Synthesis of the intermediates |
|---|---|
| E7-7 | 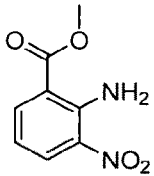 |
| E7-10 | 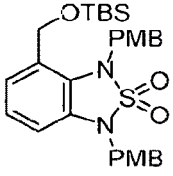 |
| E7-12 | 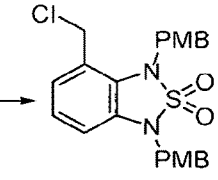 |
| E7-14 | 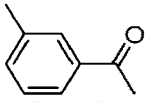 |
| E7-15 | 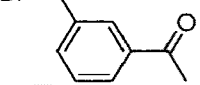 |
| E7-17 | 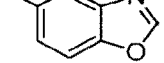 |
| E7-18 | 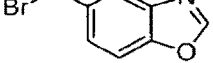 |
| E7-20 |  |

FIGURE 3 - Continued

| Cpds in Examples | Synthesis of the intermediates |
|---|---|
| E7-22 | 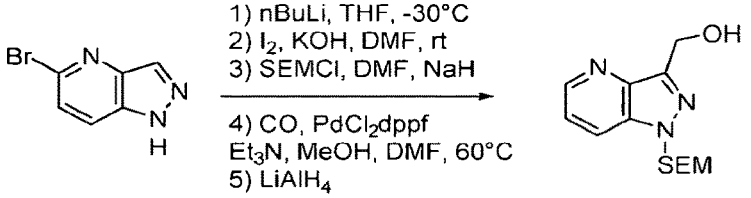 1) nBuLi, THF, -30°C; 2) I$_2$, KOH, DMF, rt; 3) SEMCl, DMF, NaH; 4) CO, PdCl$_2$dppf, Et$_3$N, MeOH, DMF, 60°C; 5) LiAlH$_4$ |
| E7-23 | 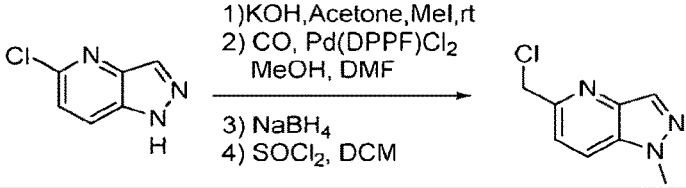 1) KOH, Acetone, MeI, rt; 2) CO, Pd(DPPF)Cl$_2$, MeOH, DMF; 3) NaBH$_4$; 4) SOCl$_2$, DCM |
| E8-13, E8-14 | 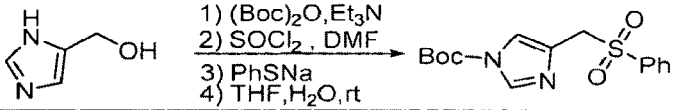 1) (Boc)$_2$O, Et$_3$N; 2) SOCl$_2$, DMF; 3) PhSNa; 4) THF, H$_2$O, rt |
| E8-15 | 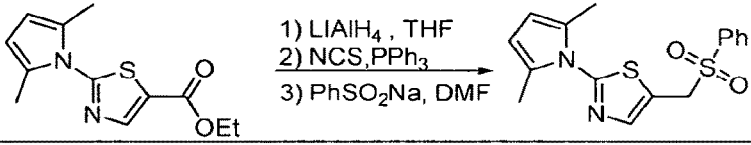 1) LiAlH$_4$, THF; 2) NCS, PPh$_3$; 3) PhSO$_2$Na, DMF |
| E8-17 | 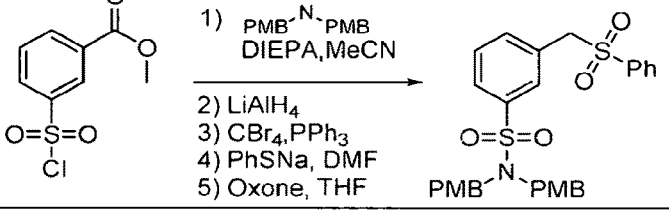 1) PMB-NH-PMB, DIEPA, MeCN; 2) LiAlH$_4$; 3) CBr$_4$, PPh$_3$; 4) PhSNa, DMF; 5) Oxone, THF |
| E8-18 | 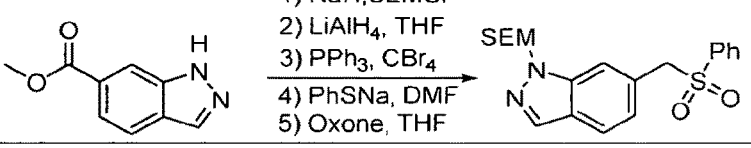 1) NaH, SEMCl; 2) LiAlH$_4$, THF; 3) PPh$_3$, CBr$_4$; 4) PhSNa, DMF; 5) Oxone, THF |
| E8-20 | 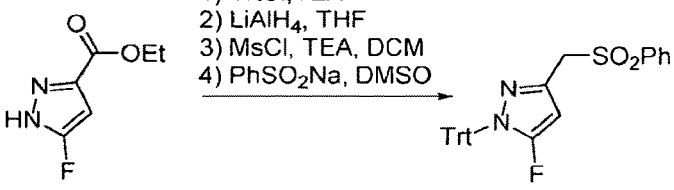 1) TrtCl, TEA; 2) LiAlH$_4$, THF; 3) MsCl, TEA, DCM; 4) PhSO$_2$Na, DMSO |

FIGURE 3 - Continued
| Cpds in Examples | Synthesis of the intermediates |
|---|---|
| E8-21 | 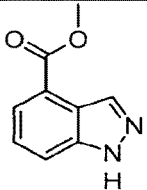 |
| E8-22 | 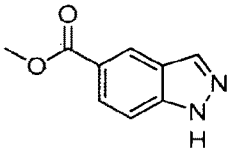 |
| E8-24 | 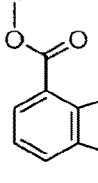 |
| E8-26 | 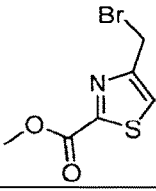 |
| E8-27 | 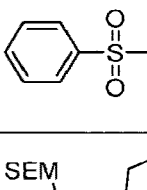 |
| E8-31 | 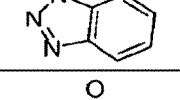 |
| E8-34 | 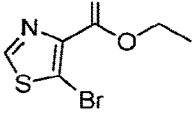 |

FIGURE 3 - Continued
| Cpds in Examples | Synthesis of the intermediates |
|---|---|
| E8-35 | 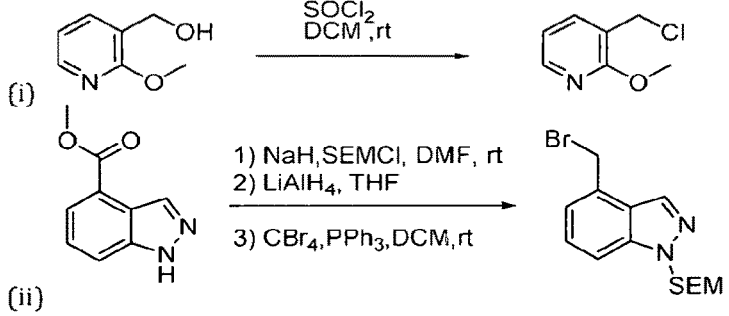 |
| E8-38 | 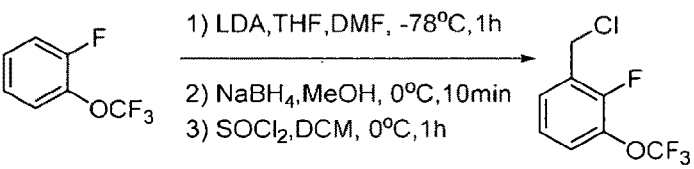 |
| E9-9 | 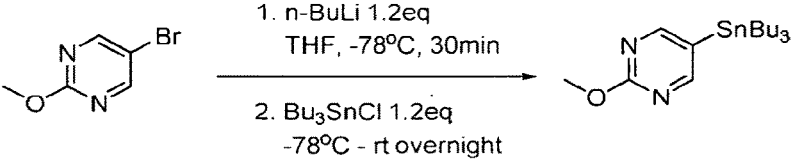 |
| E9-14<br>E9-28 | 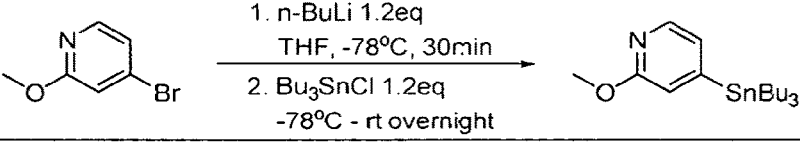 |

PYRUVATE KINASE ACTIVATORS FOR USE IN TREATING BLOOD DISORDERS

CROSS REFERENCE TO RELATED APPLICATIONS

This application is a continuation of U.S. application Ser. No. 16/639,075, filed Feb. 13, 2020, which is a 35 U.S.C. § 371 national stage filing of International Application No. PCT/US2018/000127, filed on Aug. 15, 2018 which in turn claims the benefit of priority of U.S. Provisional Patent Application Nos. 62/673,526 and 62/673,533, both filed May 18, 2018. This application also claims the benefit of priority of International Patent Application No. PCT/CN2017/097496, filed Aug. 15, 2017. The entire contents of each of the aforementioned priority applications are hereby incorporated by reference.

BACKGROUND

Pyruvate kinase deficiency (PKD) is a disease of red blood cells caused by a deficiency of pyruvate kinase R (PKR) enzyme as a result of autosomal recessive mutations of the PKLR gene (Wijk et al. *Human Mutation*, 2008, 30 (3) 446-453). PKR activators can be beneficial to treat disorders and conditions such as but not limited to PKD, thalassemia (e.g., beta-thalessemia), hereditary elliptocytosis, abetalipoproteinemia or Bassen-Kornzweig syndrome, sickle cell disease, paroxysmal nocturnal hemoglobinuria, anemia (e.g., congenital anemias (e.g., enzymopathies), hemolytic anemia (e.g. hereditary and/or congenital hemolytic anemia, acquired hemolytic anemia, chronic hemolytic anemia caused by phosphoglycerate kinase deficiency, anemia of chronic diseases, non-spherocytic hemolytic anemia or hereditary spherocytosis).

SUMMARY

Described herein are compounds of Formulas (I), (II), (I), (III-a), (III-b), (III-c), (III-c-1), (III-d), (III-d-1), (III-e), (III-e-1), (III-f), (III-f-1), (III-g), (III-g-1), (III-g-2), (III-h), (III-h-1), (IV), (IV-a), (IV-a-1), (V-a) (V-a-1), (V-b) (V-b-1), (VI), (VI-a), (VI-b), (VI-b-1), (VI-b-2), (VI-b-3), (VI-b-4), (VI-b-5), (VI-b-6), (VI-b-7), (VI-b-8), (VI-b-9) (VI-b-10), (VI-c), (VI-c-1), (VII), (VII-a), (VIII), (VIII-a), (D), (IX-a), (X), (X-a), (XI), (XII), (XII-a), (XII-b), (XII-c), (XIII), (XIII-a), (XIII-b), (XIII-c), (XIV), (XIV-a), (XIV-b), (XIV-c), (XV), (XV-a), (XV-b), and (XV-c) (collectively referred to herein as "Formulas (I)-(XV-c)"), that activate pyruvate kinase R (PKR), wild type and/or mutant enzymes (such as those described herein), and pharmaceutically acceptable salts thereof.

In one embodiment, the invention provides a compound of Formula (I) or a pharmaceutically acceptable salt thereof:

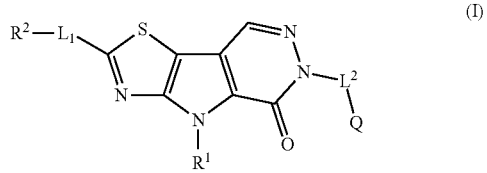

(I)

wherein Q, $R^1$, $R^2$, $L^1$, $L^2$ and Q are as defined herein.

In one embodiment, the compound or pharmaceutically acceptable salt thereof is selected from the compounds of Table 1, Table 3, and FIGS. 1A-1C and 2A-2C.

Also provided are pharmaceutical compositions comprising a compound of Formulas (I)-(XV-c), or a pharmaceutically acceptable salt thereof and a pharmaceutically acceptable carrier.

The present disclosure further provides a method of treating anemia in a subject comprising administering to the subject a therapeutically effective amount of (1) a compound described herein or a pharmaceutically acceptable salt thereof; (2) a pharmaceutically acceptable composition comprising a compound described herein or a pharmaceutically acceptable salt thereof, and a pharmaceutically acceptable carrier. In certain embodiments, the anemia is a dyserythropoietic anemia such as congenital dyserythropoietic anemia type I, II, III, or IV.

The present disclosure further provides a method for treating sickle cell disease comprising administering to a subject a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present disclosure further provides a method for treating hemolytic anemia (e.g., chronic hemolytic anemia caused by phosphoglycerate kinase deficiency, Blood Cells Mol Dis, 2011; 46(3):206) comprising administering to a subject a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In certain embodiments, the hemolytic anemia is hereditary and/or congenital hemolytic anemia, acquired hemolytic anemia, chronic hemolytic anemia caused by phosphoglycerate kinase deficiency, anemia of chronic diseases, non-spherocytic hemolytic anemia, or hereditary spherocytosis.

In certain embodiments, the hemolytic anemia is congenital anemia. In certain embodiments, the hemolytic anemia is hereditary (e.g. non-spherocytic hemolytic anemia or hereditary spherocytosis).

The present disclosure further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), sickle cell disease, or anemia of chronic diseases comprising administering to a subject a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In one embodiment, the acquired hemolytic anemia comprises congenital anemias. In certain embodiments, the provided method is to treat thalassemia. In certain embodiments, the thalassemia is beta-thalassemia.

The present disclosure further provides a method for treating pyruvate kinase deficiency (PKD) in a subject, the method comprising administering to the subject a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In certain embodiments, the PKD is a deficiency of PKR. In certain embodiments, the deficiency of PKR is associated with a pyruvate kinase R mutation.

Compounds and pharmaceutical compositions described herein are activators of PKR having lower activities compared to the wild type, thus are useful for methods of the present disclosure. In certain embodiments, the PKR is a wild type. In certain embodiments, the PKR is a mutant. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, R479H, R479K, R486W, R532W, K410E, R510Q, and R490W. Without being bound by theory, in certain embodiments, the compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in the Examples. In certain embodiments, the compounds described herein are also activators of wild type PKR.

In an embodiment, the disclosure provides a method for activating mutant PKR in red blood cells comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q.

DETAILED DESCRIPTION OF THE INVENTION

Figure 1A:
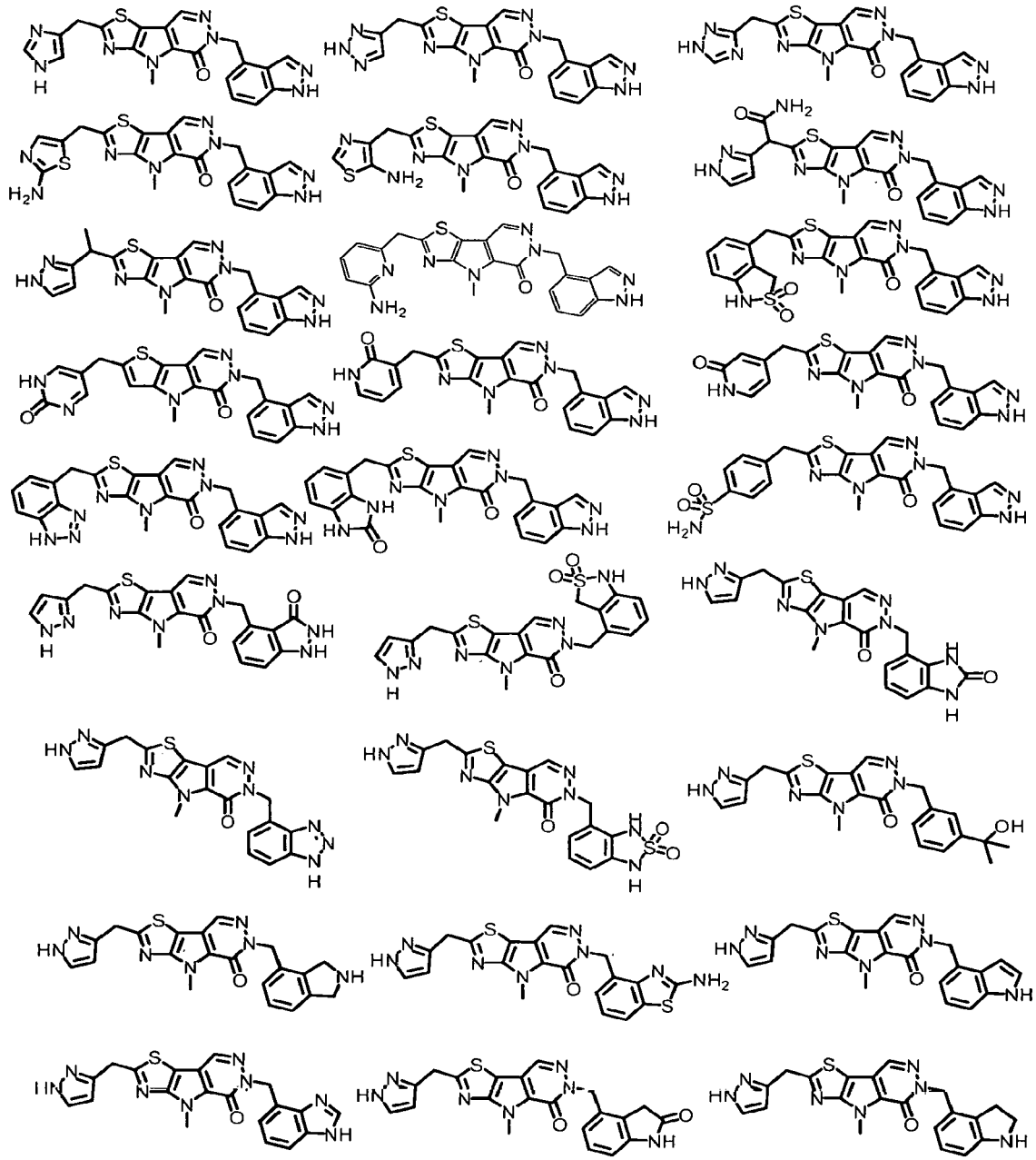
FIGS. 1A-1C are listings of the structures of other exemplary compounds of the invention.

The details of construction and the arrangement of components set forth in the following description or illustrated in the drawings are not meant to be limiting. Embodiments can be practiced or carried out in various ways. The phraseology and terminology used herein is for purpose of description and shouldn't be regarded as limiting.

Definitions

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, IN 1972).

The compounds provided herein may also comprise one or more isotopic substitutions. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. If a tautomer of a compound is aromatic, this compound is aromatic. Similarly, if a tautomer of a substituent is a heteroaryl, this substituent is heteroaryl.

The term "alkyl" refers to a radical of a straight-chain or branched saturated hydrocarbon group having from 1 to 10 carbon atoms ("$C_{1-10}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is unsubstituted —$C_{1-10}$ alkyl. In certain embodiments, the alkyl group is substituted —$C_{1-10}$ alkyl.

The term "haloalkyl" refers to a substituted alkyl group, wherein one or more of the hydrogen atoms are independently replaced by a halogen, e.g., fluoro, bromo, chloro, or iodo and includes alkyl moieties in which all hydrogens have been replaced by halo (e.g., perfluoroalkyl). In some embodiments, the haloalkyl moiety has 1 to 8 carbon atoms ("$C_{1-8}$ haloalkyl").

The term "alkoxy" or "alkoxyl" refers to an —O-alkyl radical. E.g., with between 1 and 6 carbon atoms.

The term "aryloxy" refers to an —O-aryl radical. In some embodiments the aryloxy group is phenoxy.

"Hydroxyalkyl" or "hydroxylalkyl" can include alkyl structures that are substituted with one or more hydroxyl groups.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). The one or more carbon-carbon double bonds can be internal (such as in 2-butenyl) or terminal (such as in 1-butenyl). Examples of —C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Unless otherwise specified, each instance of an alkenyl group is independently unsubstituted (an "unsubstituted alkenyl") or substituted (a "substituted alkenyl") with one or more substituents. In certain embodiments; the alkenyl group is an unsubstituted —C$_{2-10}$ alkenyl. In certain embodiments, the alkenyl group is a substituted —C$_{2-10}$ alkenyl. In an alkenyl group, a C=C double bond may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). Examples of alkynyl groups include ethynyl (C$_2$), 1-propynyl (C$_3$), 2-propynyl (C$_3$), 1-butynyl (C$_4$), 2-butynyl (C$_4$), pentynyl (C$_5$), hexynyl (C$_6$) heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted —C$_{2-10}$ alkynyl. In certain embodiments, the alkynyl group is a substituted C$_{2-10}$ alkynyl.

The term "carbocyclyl" or "carbocyclic" refers to a radical of a non-aromatic monocyclic, bicyclic, or tricyclic or polycyclic hydrocarbon ring system having from 3 to 14 ring carbon atoms ("C$_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("C$_{3-10}$ carbocyclyl").

The term "cycloalkyl" as employed herein includes saturated cyclic, bicyclic, tricyclic, or polycyclic hydrocarbon groups having 3 to 14 carbons containing the indicated number of rings and carbon atoms (for example a C$_3$-C$_{14}$ monocyclic, C$_4$-C$_{14}$ bicyclic, C$_5$-C$_{14}$ tricyclic, or C$_6$-C$_{14}$ polycyclic cycloalkyl). In some embodiments "cycloalkyl" is a monocyclic cycloalkyl. Examples of monocyclic cycloalkyl groups include cyclopentyl (C$_5$), cyclohexyl (C$_5$). cyclopropyl (C$_3$) cyclobutyl (C$_4$), cycloheptyl (C$_7$) and cyclooctyl (C$_8$). In some embodiments "cycloalkyl" is a bicyclic cycloalkyl. Examples of bicyclic cycloalkyls include bicyclo[1.1.0]butane (C$_4$), bicyclo[1.1.1]pentane (C$_5$), spiro[2.2] pentane (C$_5$), bicyclo[2.1.0]pentane (C$_5$), bicyclo[2.1.1]hexane (C$_6$), bicyclo[3.3.3]undecane (C$_{11}$), decahydronaphthalene (C$_{10}$), bicyclo[4.3.2]undecane (C$_{11}$), spiro[5.5]undecane (C$_{11}$) and bicyclo[4.3.3]dodecane (C$_{12}$). In some embodiments "cycloalkyl" is a tricyclic cycloalkyl. Examples of tricyclic cycloalkyls include adamantine (C$_{12}$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl").

Exemplary heterocyclyl groups include aziridinyl, oxiranyl, thiiranyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dine, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Arylalkyl" or "aralkyl" is a subset of "alkyl" and refers to an alkyl group substituted by an aryl group, wherein the point of attachment is on the alkyl moiety. Examples of "arylalkyl" or "aralkyl" include benzyl, 2-phenylethyl, 3-phenylpropyl, 9-fluorenyl, benzhydryl, and trityl groups The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In some embodiments the heteroaryl can be a 5-8 membered monocyclic heteroaryl containing 1-4 heteroatoms. In some embodiments the heteroaryl can be an 8-12 membered bicyclic heteroaryl having 1-6 heteroatoms. In some embodiments the heteroaryl can be an 11-14 membered tricyclic heteroaryl ring system having 1-9 heteroatoms. In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a monocyclic 5-10 membered aromatic ring system having ring carbon atoms and 1-4 ring heteroatoms provided in the aromatic ring system, wherein each heteroatom is independently selected from nitrogen, oxygen, and sulfur ("5-10 membered monocyclic heteroaryl"). In some embodiments, a heteroaryl group is a bicyclic 8-12 membered aromatic ring system having ring carbon atoms and 1-6 ring heteroatoms provided in the aromatic ring system, wherein each heteroatom is independently selected from nitrogen, oxygen, and sulfur ("8-12 membered bicyclic heteroaryl"). Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl. As used herein, if a tautomer of a radical is heteroaryl, this radical is heteroaryl. The term "tautomers" or "tautomeric" refers to two or more interconvertible compounds/substituents resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

Exemplary monocyclic heteroaryl groups include pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinylphenanthridinyl, dibenzofuranyl, carbazolyl, acridinyl, phenothiazinyl, phenoxazinyl and phenazinyl.

A "5- or 6-membered monocyclic heteroaryl" or "5-membered or 6-membered heteroaryl" refers to a 5- or 6-membered monocyclic and unfused 4n+2 aromatic ring system having ring carbon atoms and 1-4 ring heteroatoms. Exemplary monocyclic 5- or 6-membered heteroaryl groups include pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, and tetrazinyl.

"Heteroaralkyl" or "heteroarylalkyl" refers to an alkyl group substituted by a heteroaryl group, wherein the point of attachment is on the alkyl moiety.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "optionally substituted" refers to being substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent (e.g. $C_{1-6}$ alkyl, halogen, nitro, cyano, hydroxyl, $C_{1-6}$ haloalkyl, $C_{1-6}$ haloalkoxy, $C_{1-6}$ acyl, $C_{3-6}$ cycloalkyl, $C_{6-10}$ aryl, monocyclic or bicyclic heteroaryl, and monocyclic or bicyclic heterocyclyl), at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valences of the heteroatoms and results in the formation of a stable moiety. The invention is not intended to be limited in any manner by the exemplary substituents described herein.

The term "halo" or "halogen" refers to fluorine, chlorine, bromine, or iodine.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched $C_{1-10}$ alkyl; cyclic or acyclic, substituted or unsubstituted, branched or unbranched $C_{2-10}$ alkenyl; substituted or unsubstituted $C_{2-10}$ alkynyl; substituted or unsubstituted $C_{6-12}$ aryl, substituted or unsubstituted heteroaryl, when valency permits. Exemplary acyl groups include aldehydes (—CHO), carboxylic acids (—CO$_2$H), ketones, acyl halides, esters, amides, imines, carbonates, carbamates, and ureas.

In certain embodiments, the substituent present on a nitrogen atom, on an oxygen atom or on a sulfur atom is a nitrogen protecting group, an oxygen protecting group or a sulfur protecting group, respectively. Nitrogen, oxygen and sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups include, but are not limited to, formamide, acetamide, chloroacetamide, trichloroacetamide, trifluoroacetamide, phenylacetamide, methyl carbamate, ethyl carbamate, 9-fluorenylmethyl carbamate (Fmoc), t-butyl carbamate (BOC or Boc), 1-adamantyl carbamate (Adoc), vinyl carbamate (Voc), allyl carbamate (Alloc), 2-(trimethylsilyl)ethoxy]methyl (SEM), p-toluenesulfonamide (Ts), benzenesulfonamide, 2,3,6-trimethyl-4-methoxybenzenesulfonamide (Mtr), 2,4,6-trimethoxybenzenesulfonamide (Mtb), phenothiazinyl-(10)-acyl derivative, N'-p-toluenesulfonylaminoacyl derivative, Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), tetrahydropyranyl (THP), methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf).

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomologus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. In certain embodiments, the subject is a patient. The term "patient" refers to a human subject in need of treatment of a disease. In certain embodiments, the term "patient" is a human adult over 18 years old in need of treatment of a disease. In certain embodiments, the term "patient" is a human child no more than 18 years old in need of treatment of a disease. In certain embodiments, the patient is not under regular transfusion (e.g. having had no more than 4 transfusion episodes in the 12-month period). In certain embodiments, the patient is under regular transfusion (e.g. having had at least 4 transfusion episodes in the 12-month period). In certain embodiments, the subject has undergone splenectomy. In certain embodiments, the subject has undergone splenectomy and is under regular transfusion. In certain embodiments, the subject has undergone splenectomy and is not under regular transfusion.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed (i.e., therapeutic treatment). In other embodiments, treatment may be administered in the absence of signs or symptoms of the disease. For example, treatment may be administered to a susceptible subject prior to the onset of symptoms (i.e., prophylactic treatment) (e.g., in light of a history of symptoms and/or in light of exposure to a pathogen). Treatment may also be continued after symptoms have resolved, for example, to delay or prevent recurrence. In certain embodiments, treatment includes delaying onset of at least one symptom of the disorder for a period of time.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, the effective amount is to generate a subject's hemoglobin response of ≥1.5 g/dL increase in Hb concentration from baseline. The subject's baseline Hb concentration is the average of all available Hb concentrations before the treatment with the compound. In certain embodiments, the effective amount is to generate a subject's hemoglobin response of ≥1.0 g/dL increase in Hb concentration from baseline. In certain embodiments, the effective amount is to generate a subject's hemoglobin response of ≥2.0 g/dL increase in Hb concentration from baseline. In certain embodiments, an effective amount is the amount of a compound described herein in a single dose. In certain embodiments, an effective amount is the combined amounts of a compound described herein in multiple doses. In certain embodiments, the effective amount is therapeutically effective amount.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for eliciting measurable activation of wild-type or mutant PKR. In certain embodiments, a therapeutically effective amount is an amount sufficient for regulating 2,3-diphosphoglycerate and/or ATP levels in blood in need thereof or for treating pyruvate kinase deficiency (PKD), hemolytic anemia (e.g., chronic hemolytic anemia, hereditary non-spherocytic anemia), sickle cell disease, thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g., liver diseases). In certain embodiments, a therapeutically effective amount is an amount sufficient for eliciting measurable activation of wild-type or mutant PKR and for regulating 2,3-diphosphoglycerate levels in blood in need thereof or for treating pyruvate kinase deficiency (PKD), hemolytic anemia (e.g., chronic hemolytic anemia, hereditary non-spherocytic anemia), sickle cell disease, thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g., liver diseases). In one aspect, the therapeutically effective amount is the amount required to generate a subject's hemoglobin response of ≥1.0 g/dL (such as ≥1.5 g/dL or ≥2.0 g/dL) increase in Hb concentration from baseline. The subject's baseline Hb concentration is the average of all available Hb concentrations within at least two weeks (e.g. 3 weeks, 4 weeks, 5 weeks, or 6 weeks) before treatment with a compound described herein. In certain aspects, the therapeutically effective amount is the amount required to reduce the patient's transfusion burden. In one aspect, the therapeutically effective amount is between 0.01-100 mg/kg body weight/day of the provided compound, such as e.g., 0.1-100 mg/kg body weight/day. In certain embodiments, the therapeutically effective amount is to reduce the patient's transfusion burden.

As used herein, reduction in transfusion burden means at least 20% reduction in the number of RBC units transfused within at least 5 weeks of treatment. In certain embodiments, the reduction in transfusion burden is ≥33% reduction in the number of RBC units transfused within at least 5 weeks of treatment. In certain embodiments, reduction of transfusion burden is observed in at least 10 weeks (e.g., at least 20 weeks or at least 24 weeks) of treatment.

As used herein, sickle cell disease (SCD), Hemoglobin SS disease, and sickle cell anemia are used interchangeably. Sickle cell disease (SCD) describes a group of inherited red blood cell disorders. In certain embodiments, subjects with SCD have abnormal hemoglobin, called hemoglobin S or sickle hemoglobin, in their red blood cells. In certain embodiments, people having SCD have at least one abnormal genes causing the body to make hemoglobin S. In certain embodiments, people having SCD have two hemoglobin S genes, Hemoglobin SS.

Thalassemia is an inherited blood disorder in which the body makes an abnormal form of hemoglobin. In certain embodiments, the abnormal form of hemoglobin results in deficiency of either alpha or beta globin. In certain embodiments, the disorder results in large numbers of red blood cells being destroyed, which leads to anemia. In certain embodiments, the thalassemia is alpha thalassemia. In certain embodiments, the thalassemia is beta thalassemia.

The term "activator" as used herein means an agent that (measurably) increases the activity of wild type pyruvate kinase R (wt PKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The term "packed red blood cells" or PRBCs as used herein refer to red blood cells made from a unit of whole blood by centrifugation and removal of most of the plasma. In certain embodiments, a PRBC unit has a hematocrit of at least about 95%. In certain embodiments, a PRBC unit has a hematocrit of at least about 90%, 80%, 70%, 60%, 50%, 40%, 30%, 20%, or 10%.

The term "ex vivo" referring to a method as used herein means that the method takes place outside an organism. For example, a cell (e.g., red blood cells), a tissue or blood (containing at least red blood cells, plasma and hemoglobin) may be extracted from the organism to be contacted with one or more compounds provided herein or a pharmaceutically acceptable salt thereof or a pharmaceutical composition thereof, optionally under artificially controlled conditions (e.g., temperature).

The term "in vitro" referring to a method as used herein means that the method takes place outside an organism and is contained within an artificial environment. For example, a cell (e.g., red blood cells), a tissue or blood (containing at least red blood cells, plasma and hemoglobin) may be extracted from the organism to be contacted with one or more compounds provided herein or a pharmaceutically acceptable salt thereof or a pharmaceutical composition thereof, in a contained, artificial environment (e.g., a culture system), such as in a test tube, in a culture, in flask, in a microtiter plate, on a Petri dish, and the like.

Compounds

Described herein are compounds and compositions that activate wild type PKR and/or mutant PKRs such as those described herein. In one embodiment, provided is a compound of Formulas (I)-(XV-c), or a pharmaceutically acceptable salt thereof, or a pharmaceutical composition comprising a compound of Formulas (I)-(XIV-c), or a pharmaceutically acceptable salt thereof.

In a first embodiment of the invention, provided is a compound of Formula (I) or a pharmaceutically acceptable salt thereof, wherein:

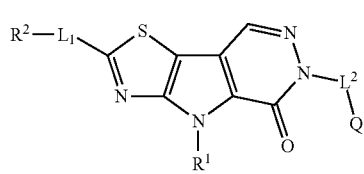

(I)

Q is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^1$ is hydrogen, optionally substituted alkyl, optionally substituted haloalkyl, optionally substituted alkenyl, optionally substituted alkynyl, optionally substituted cycloalkyl, optionally substituted heterocyclyl, optionally substituted aryl, $-OR^{o1}$, $-C(=O)R^{c1}$, or a nitrogen protecting group;

$L^1$ is a bond, optionally substituted alkylene, $-O-$, $-S-$, $-S-CH_2-$, $-S(=O)CH_2-$, $-S(=O)_2CH_2-$, $-NR^3-$, $-NR^3C(=O)-$, $-C(=O)NR^3-$, $-C(=O)-$, $-OC(=O)-$, $-C(=O)O-$, $-NR^3C(=O)O-$, $-OC(=O)NR^3-$, $-NR^3C(=O)NR^3-$, $-OC(R^4)_2-$, $-C(R^4)_2O-$, $-NR^3C(R^4)_2-$, $-C(R^4)_2NR^3-$, $-S(=O)_2-$, $-S(=O)-$, $-S(=O)_2O-$, $-OS(=O)_2-$, $-S(=O)O-$, $-OS(=O)-$, $-S(=O)_2NR^3-$, $-NR^3S(=O)_2-$, $-S(=O)NR^3-$, $-NR^3S(=O)-$, $-NR^3S(=O)_2O-$, $-OS(=O)_2NR^3-$, $-NR^3S(=O)O-$, $-OS(=O)NR^3-$, or $-S(=O)(=NR^3)-$, wherein the point of the attachment to $R^2$ is on the left-hand side;

$L^2$ is a bond, optionally substituted alkylene, $-C(=O)-$, $-S(=O)_2-$, or $-S(=O)-$, wherein the point of the attachment to Q is on the right-hand side;

$R^2$ is hydrogen, halogen, optionally substituted alkyl, optionally substituted alkoxy, optionally substituted alkenyl, optionally substituted alkynyl, optionally substituted cycloalkyl, optionally substituted heterocyclyl, optionally substituted aryl, or optionally substituted heteroaryl, or a nitrogen protecting group when $L^1$ is $-NR^3-$, $-NR^3C(=O)-$, $-NR^3C(=O)O-$, $-NR^3C(R^4)_2-$, $-NR^3S(=O)_2-$, $-NR^3S(=O)-$, $-NR^3C(=O)NR^3-$, $-NR^3S(=O)_2O-$, or $-NR^3S(=O)O-$, an oxygen protecting group when $L^1$ is $-O-$, $-OC(=O)-$, $-OC(=O)NR^3-$, $-OC(R^4)_2-$, $-OS(=O)_2-$, $-NR^3S(=O)_2O-$, $NR^3S(=O)O-$, or $-OS(=O)-$, or a sulfur protecting group when $L^1$ is $-S-$;

each instance of $R^3$ is independently hydrogen, $-OR^{o2}$, optionally substituted alkyl, optionally substituted alkenyl, optionally substituted alkynyl, optionally substituted cycloalkyl, optionally substituted heterocyclyl, optionally substituted aryl, optionally substituted heteroaryl, or a nitrogen protecting group;

each instance of $R^{o1}$ and $R^{o2}$ is independently hydrogen, optionally substituted alkyl, or an oxygen protecting group;

each instance of $R^{c1}$ is independently optionally substituted alkyl or $-N(R^{cn})_2$, wherein each instance of $R^{cn}$ is independently hydrogen, $-C_{1-6}$ alkyl, or a nitrogen protecting group; and each instance of $R^4$ is independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

provided that Q and $R^2$ are not both optionally substituted 5- or 6-membered monocyclic heteroaryl.

In a second embodiment of the invention, provided is a compound or pharmaceutically acceptable salt thereof of Formula (I) as described above wherein:

Q is hydrogen, optionally substituted —$C_1$-$C_6$ alkyl, optionally substituted —$C_3$-$C_{12}$ cycloalkyl, optionally substituted 3- to 14-membered heterocyclyl, optionally substituted 6- to 14-membered aryl, or optionally substituted 5- to 14-membered heteroaryl;

$R^1$ is hydrogen, optionally substituted —$C_1$-$C_6$ alkyl, optionally substituted —$C_1$-$C_6$ haloalkyl, optionally substituted —$C_2$-$C_6$ alkenyl, optionally substituted —$C_2$-$C_6$ alkynyl, optionally substituted $C_3$-$C_{12}$ cycloalkyl, optionally substituted 3- to 14-membered heterocyclyl, optionally substituted 6- to 12-membered aryl, —$OR^{o1}$, —$C(=O)R^{c1}$, or a nitrogen protecting group;

$L^1$ is a bond, optionally substituted $C_{1-6}$ alkylene, —O—, —S—, —S—$CH_2$—, —$S(=O)CH_2$—, —$S(=O)_2CH_2$—, —$NR^3$—, —$NR^3C(=O)$—, —$C(=O)NR^3$—, —$C(=O)$—, —$OC(=O)$—, —$C(=O)O$—, —$NR^3C(=O)O$—, —$OC(=O)NR^3$—, —$NR^3C(=O)NR^3$—, —$OC(R^4)_2$—, —$C(R^4)_2O$—, —$NR^3C(R^4)_2$—, —$C(R^4)_2NR^3$—, —$S(=O)_2$—, —$S(=O)$—, —$S(=O)_2O$—, —$OS(=O)_2$—, —$S(=O)O$—, —$OS(=O)$—, —$S(=O)_2NR^3$—, —$NR^3S(=O)_2$—, —$S(=O)NR^3$—, —$NR^3S(=O)$—, —$NR^3S(=O)_2O$—, —$OS(=O)_2NR^3$—, —$NR^3S(=O)O$—, —$OS(=O)NR^3$—, or —$S(=O)(=NR^3)$— wherein the point of the attachment to $R^2$ is on the left-hand side;

$L^2$ is a bond, optionally substituted $C_1$-$C_6$ alkylene, —$C(=O)$—, —$S(=O)_2$—, or —$S(=O)$—, wherein the point of the attachment to Q is on the right-hand side;

$R^2$ is hydrogen, halogen, optionally substituted $C_1$-$C_6$ alkyl, optionally substituted $C_1$-$C_6$ alkoxy, optionally substituted $C_3$-$C_{12}$ cycloalkyl, optionally substituted 3- to 14-membered heterocyclyl, optionally substituted $C_6$-$C_{12}$ aryl, or optionally substituted 3- to 14-membered heteroaryl, or a nitrogen protecting group when $L^1$ is —$NR^3$—, —$NR^3C(=O)$—, —$NR^3C(=O)O$—, —$NR^3C(R^4)_2$—, —$NR^3S(=O)_2$—, —$NR^3S(=O)$—, —$NR^3C(=O)NR^3$—, —$NR^3S(=O)_2O$—, or —$NR^3S(=O)O$—, an oxygen protecting group when $L^1$ is —O—, —$OC(=O)$—, —$OC(=O)NR^3$—, —$OC(R^4)_2$—, —$OS(=O)$—, —$OS(=O)_2$—, —$NR^3S(=O)_2O$—, —$NR^3S(=O)O$—, or —$OS(=O)$—, or a sulfur protecting group when $L^1$ is —S—;

each instance of R3 is independently hydrogen, —$OR^{o2}$, optionally substituted —$C_1$-$C_6$ alkyl, optionally substituted —$C_2$-$C_6$ alkenyl, optionally substituted —$C_2$-$C_6$ alkynyl, optionally substituted $C_3$-$C_{12}$ cycloalkyl, optionally substituted $C_3$-$C_{12}$ heterocyclyl, optionally substituted $C_6$-$C_{12}$ aryl, optionally substituted $C_5$-$C_{12}$ heteroaryl, or a nitrogen protecting group;

each instance of $R^{o1}$ and $R^{o2}$ is independently hydrogen, optionally substituted —$C_1$-$C_6$ alkyl, or an oxygen protecting group;

each instance of $R^{c1}$ is independently optionally substituted —$C_1$-$C_6$ alkyl or —$N(R^{cn})_2$, wherein each instance of $R^{cn}$ is independently hydrogen, —$C_1$-$C_6$ alkyl, or a nitrogen protecting group;

each instance of $R^4$ is independently hydrogen, optionally substituted —$C_1$-$C_6$ alkyl, optionally substituted —$C_2$-$C_6$ alkenyl, optionally substituted —$C_2$-$C_6$ alkynyl, optionally substituted $C_3$-$C_{12}$ cycloalkyl, optionally substituted 3- to 14-membered heterocyclyl, optionally substituted $C_6$-$C_{12}$ aryl, or optionally substituted 5- to 14-membered heteroaryl;

provided that Q and $R^2$ are not both optionally substituted 5- or 6-membered monocyclic heteroaryl.

In a third embodiment of the invention, provided is a compound of Formula (I) or pharmaceutically acceptable salt thereof, wherein:

Q is $C_6$-$C_{12}$ aryl, 5- to 6-membered monocyclic heteroaryl, or 8- to 12-membered bicyclic heteroaryl, each of which is substituted with 0-3 occurrences of $R^c$;

$R^1$ is selected from hydrogen, —$C_1$-$C_6$ alkyl, —$C_1$-$C_6$ haloalkyl, $C_3$-$C_7$ monocyclic cycloalkyl and 3- to 14-membered heterocyclyl, —$OR^{o1}$, —$C(=O)R^{c1}$, or a nitrogen protecting group; wherein each alkyl, cycloalkyl or heterocyclyl is substituted with 0-3 occurrences of $R^d$;

$R^2$ is selected from hydrogen, halogen, —$C_1$-$C_6$ alkyl, —$C_1$-$C_6$ alkoxy, $C_3$-$C_7$ monocyclic cycloalkyl, $C_6$-$C_{12}$ bicyclic cycloalkyl, 3- to 14-membered heterocyclyl, $C_6$-$C_{12}$ aryl, 5- to 6-membered monocyclic heteroaryl, 8- to 12-membered bicyclic heteroaryl, wherein each alkyl, cycloalkyl, heterocyclyl, aryl and heteroaryl is substituted with 0-3 occurrences of $R^e$, or a nitrogen protecting group when $L^1$ is —$NR^3$—, —$NR^3C(=O)$—, —$NR^3C(=O)O$—, —$NR^3C(R^4)_2$—, —$NR^3S(=O)_2$—, —$NR^3S(=O)$—, —$NR^3C(=O)NR^3$—, —$NR^3S(=O)_2O$—, or —$NR^3S(=O)O$—, an oxygen protecting group when $L^1$ is —O—, —$OC(=O)$—, —$OC(=O)NR^3$—, —$OC(R^4)_2$—, —$OS(=O)$—, —$OS(=O)_2$—, —$NR^3S(=O)_2O$—, —$NR^3S(=O)O$—, or —$OS(=O)$—, or a sulfur protecting group when $L^1$ is —S—;

$R^3$ is selected from hydrogen, —$OR^{o2}$, —$C_1$-$C_6$ alkyl, $C_3$-$C_7$ monocyclic cycloalkyl, $C_6$-$C_{12}$ bicyclic cycloalkyl, 3- to 14-membered heterocyclyl, $C_6$-$C_{12}$ aryl, 5- to 6-membered monocyclic heteroaryl, and 8- to 12-membered bicyclic heteroaryl, wherein each alkyl, cycloalkyl, heterocycloalkyl, aryl and heteroaryl is substituted with 0-3 occurrences of $R^f$;

$R^4$ is selected from hydrogen, —$C_1$-$C_6$ alkyl, $C_3$-$C_7$ monocyclic cycloalkyl, and 3- to 14-membered heterocyclyl, wherein each alkyl, cycloalkyl or heterocyclyl is substituted with 0-1 occurrences of $R^g$;

$L^1$ is a bond, an alkylene substituted with 0-3 occurrences of $R^h$, —O—, —S—, —S—$CH_2$—, —$S(=O)CH_2$—, —$S(=O)_2CH_2$—, —$NR^3$—, —$NR^3C(=O)$—, —$C(=O)NR^3$—, —$C(=O)$—, —$OC(=O)$—, —$C(=O)O$—, —$NR^3C(=O)O$—, —$OC(=O)NR^3$—, —$NR^3C(=O)NR^3$—, —$OC(R^4)_2$—, —$C(R^4)_2O$—, —$NR^3C(R^4)_2$—, —$C(R^4)_2NR^3$—, —$S(=O)_2$—, —$S(=O)$—, —$S(=O)_2O$—, —$OS(=O)_2$—, —$S(=O)O$—, —$OS(=O)$—, —$S(=O)_2NR^3$—, —$NR^3S(=O)_2$—, —$S(=O)NR^3$—, —$NR^3S(=O)$—, —$NR^3S(=O)_2O$—, —$OS(=O)_2NR^3$—, —$NR^3S(=O)O$—, —$OS(=O)NR^3$—, or —$S(=O)(=NR^3)$—, wherein the point of the attachment to $R^2$ is on the left-hand side;

$L^2$ is a bond, an alkylene substituted with 0-3 occurrences of $R^h$, —$C(=O)$—, —$S(=O)_2$—, or —$S(=O)$—, wherein the point of the attachment to Q is on the right-hand side;

each $R^c$ is independently selected from halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —$N(C_1$-$C_6$ alkyl)$_2$, —$C(=O)OC_1$-$C_6$ alkyl, —$C(=O)OH$, —$C(=O)C_1$-$C_6$ alkyl, —$C(=O)NH_2$, —$C(=O)NH(C_1$-$C_6$ alkyl), —$C(=O)N(C_1$-$C_6$ alkyl)$_2$, —$NHC(=O)NH_2$, —$NHC(=O)NH(C_1$-$C_6$ alkyl), —$NHC(=O)N(C_1$-$C_6$ alkyl)$_2$, —$NHC(=O)(C_1$-$C_6$ alkyl), —$N(C_1$-$C_6$ alkyl)$C(=O)(C_1$-$C_6$ alkyl), —$S(=O)_2NH_2$, —$S(=O)_2NH(C_1$-$C_6$ alkyl), —S(=O)₂N(C₁-C₆ alkyl)₂, —NHS(=O)₂(C₁-C₆ alkyl), —NH₂, —CN, and —NO₂; or two instances of R^c attached to the same or adjacent carbon atoms, are taken together with the carbon atoms to which they are attached form a cycloalkyl or a heterocyclyl;

each R^d is independently selected from halo, —C₁-C₆ alkyl, —OH, —OC₁-C₆ alkyl, —NH₂ and —CN;

each R^e is independently selected from halo, —C₁-C₆ alkyl, —C₁-C₆ haloalkyl, —C₁-C₆ hydroxyalkyl, —OH, —OC₁-C₆ alkyl, —C₁-C₆ aminoalkyl, —NH(C₁-C₆ alkyl), —N(C₁-C₆ alkyl)₂, —C(=O)OC₁-C₆ alkyl, —C(=O)OH, —C(=O)C₁-C₆ alkyl, —C(=O)NH₂, —C(=O)NH(C₁-C₆ alkyl), —C(=O)N(C₁-C₆ alkyl)₂, —NHC(=O)NH₂, —NHC(=O)NH(C₁-C₆ alkyl), —NH(C=O)N(C₁-C₆ alkyl)₂, —NHC(=O)(C₁-C₆ alkyl), —N(C₁-C₆ alkyl)C(=O)(C₁-C₆ alkyl), —S(=O)₂NH₂, —S(=O)₂NH(C₁-C₆ alkyl), —S(=O)₂N(C₁-C₆ alkyl)₂, —NHS(=O)₂(C₁-C₆ alkyl), —NH₂, —CN, and —NO₂; or two instances of R^e attached to the same or adjacent carbon atoms, are taken together with the carbon atoms to which they are attached form a cycloalkyl or a heterocyclyl;

each R^f is independently selected from halo, —C₁-C₆ alkyl, —C₁-C₆ haloalkyl, —C₁-C₆ alkoxy, —OH, NH₂, —CN and NO₂;

each R^g is independently selected from halo, —C₁-C₆ alkyl, —C₁-C₆ haloalkyl, —C₁-C₆ alkoxy, —OH, NH₂, —CN and NO₂; and each R^h is independently selected from halo, —C₁-C₆ alkyl, —C₁-C₆ haloalkyl, —C₁-C₆ hydroxyalkyl, —OH, —OC₁-C₆ alkyl, —C₁-C₆ aminoalkyl, —NH(C₁-C₆ alkyl), —N(C₁-C₆ alkyl)₂, —C(=O)OC₁-C₆ alkyl, —C(=O)OH, —C(=O)C₁-C₆ alkyl, —C(=O)NH₂, —C(=O)NH(C₁-C₆ alkyl), —C(=O)N(C₁-C₆ alkyl)₂, —NHC(=O)NH₂, —NHC(=O)NH(C₁-C₆ alkyl), —NH(C=O)N(C₁-C₆ alkyl)₂, —NHC(=O)(C₁-C₆ alkyl), —N(C₁-C₆ alkyl)C(=O)(C₁-C₆ alkyl), —S(=O)₂NH₂, —S(=O)₂NH(C₁-C₆ alkyl), —S(=O)₂N(C₁-C₆ alkyl)₂, —NHS(=O)₂(C₁-C₆ alkyl), —NH₂, —CN, and —NO₂, S(=O)₂aryl, S(=O)₂heteroaryl and =NOH or two instances of R^h attached to the same or adjacent carbon atoms, are taken together with the carbon atoms to which they are attached form a cycloalkyl or a heterocyclyl;

provided that Q and R² are not both optionally substituted 5- or 6-membered monocyclic heteroaryl; and the reminder of the variables are as described in the first or second embodiment.

In a fourth embodiment of the invention, provided is a compound of Formula (II) or a pharmaceutically acceptable salt thereof:

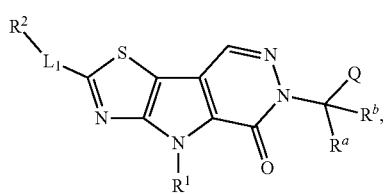

(II)

R^a and R^b are each independently hydrogen, halogen, —CN, —NO₂, —N₃, optionally substituted alkyl, —OR^{o3}, —N(R^{n1})₂, —C(=O)N(R^{n1})₂, or —C(=O)R^{c2}, or R^a and R^b can be taken together with the carbon atom to form optionally substituted cycloalkyl or optionally substituted heterocyclyl;

each instance of R^{n1} is independently hydrogen, optionally substituted alkyl, or a nitrogen protecting group;

each instance of R^{o3} is independently hydrogen, optionally substituted alkyl, or an oxygen protecting group;

each instance of R^{c2} is independently optionally substituted alkyl; and the remainder of the variables are as described in the first, second or third embodiments.

In a fifth embodiment of the invention, the compound of the invention is of Formula (I) or (II) or a pharmaceutically acceptable salt thereof, Q is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl; and the remainder of the variables are as described in the first, second, third or fourth embodiments. Alternatively, Q is optionally substituted heterocyclyl. In certain embodiments, Q is optionally substituted 3- to 14-membered heterocyclyl. In certain embodiments, Q is optionally substituted 5-membered or 6-membered monocyclic heterocyclyl. In certain embodiments, Q is optionally substituted 8- to 12-membered bicyclic heterocyclyl. In certain embodiments, Q is optionally substituted heteroaryl. In certain embodiments, Q is optionally substituted 3- to 14-membered heteroaryl. In certain embodiments, Q is optionally substituted 5-membered or 6-membered monocyclic heteroaryl. In certain embodiments, Q is optionally substituted 8- to 12-membered bicyclic heteroaryl. In certain embodiments, Q is one of the following formulae:

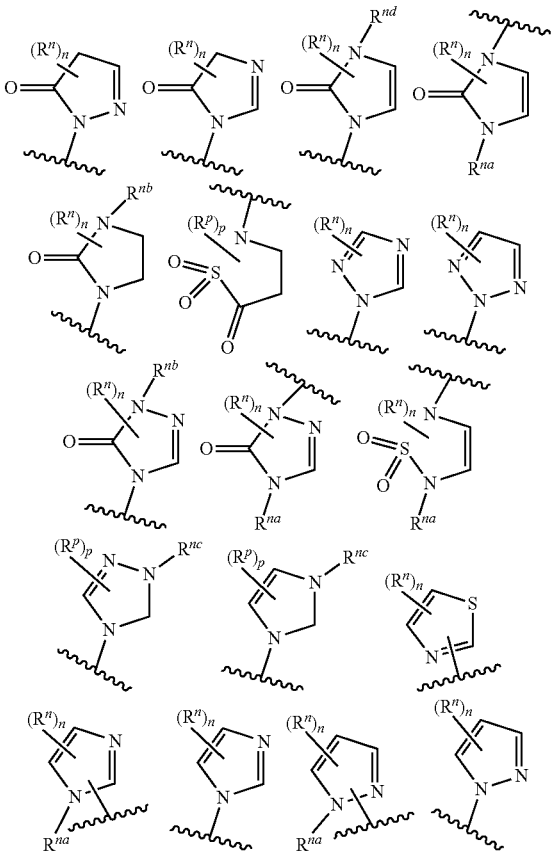

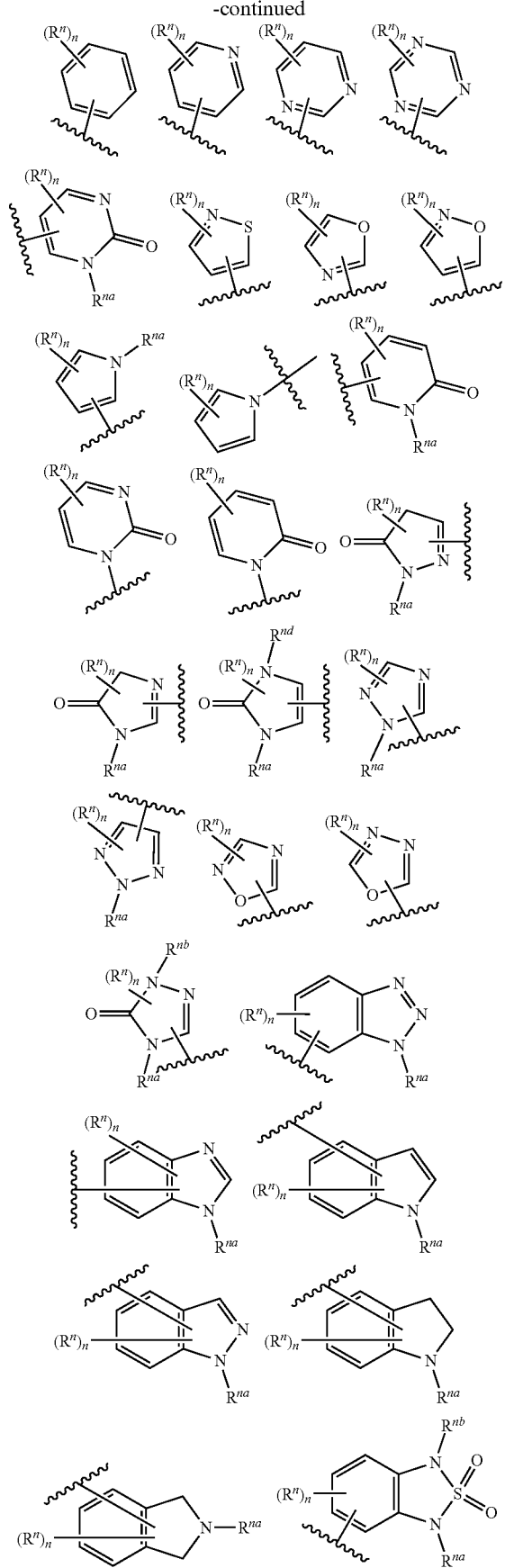
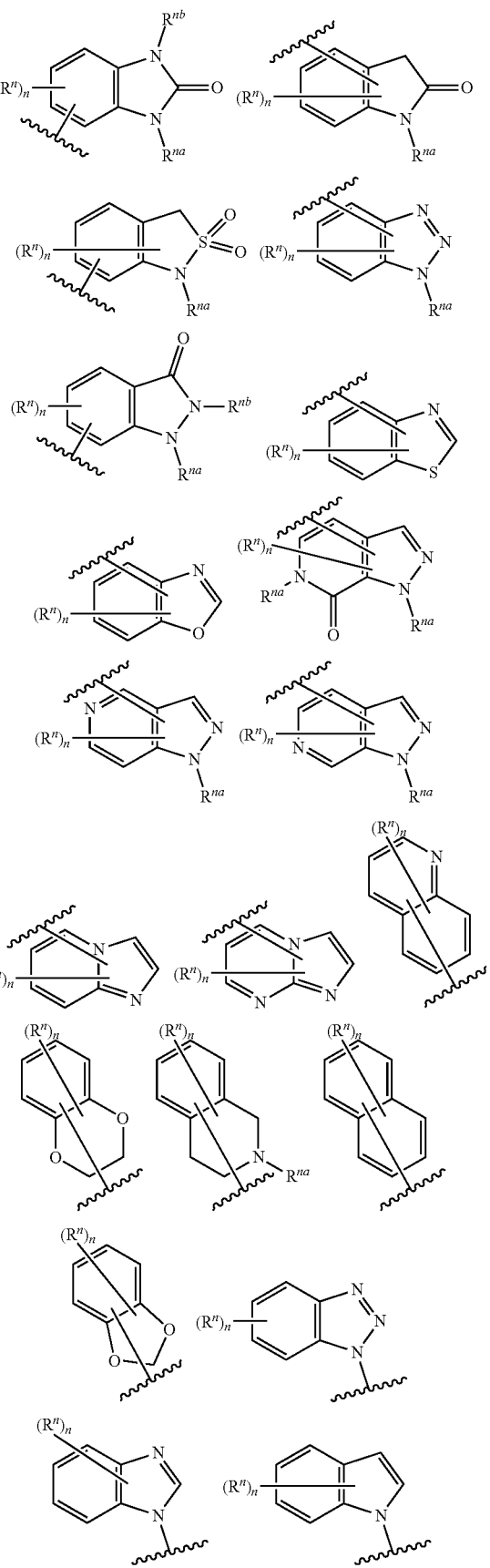

-continued

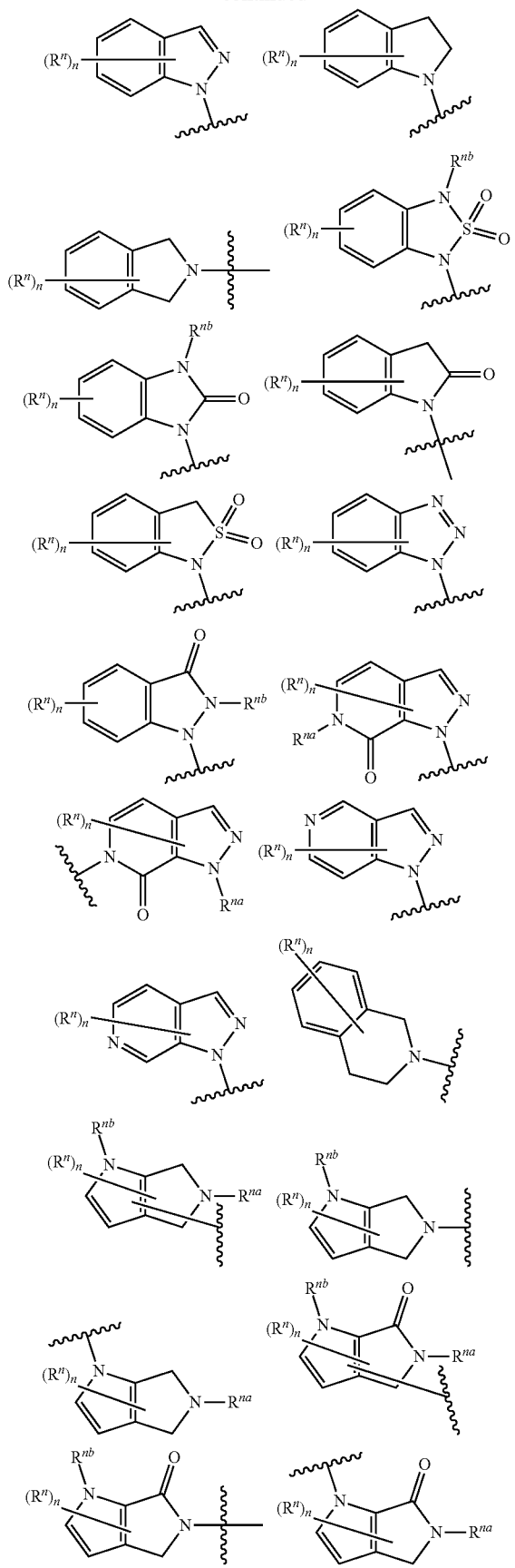

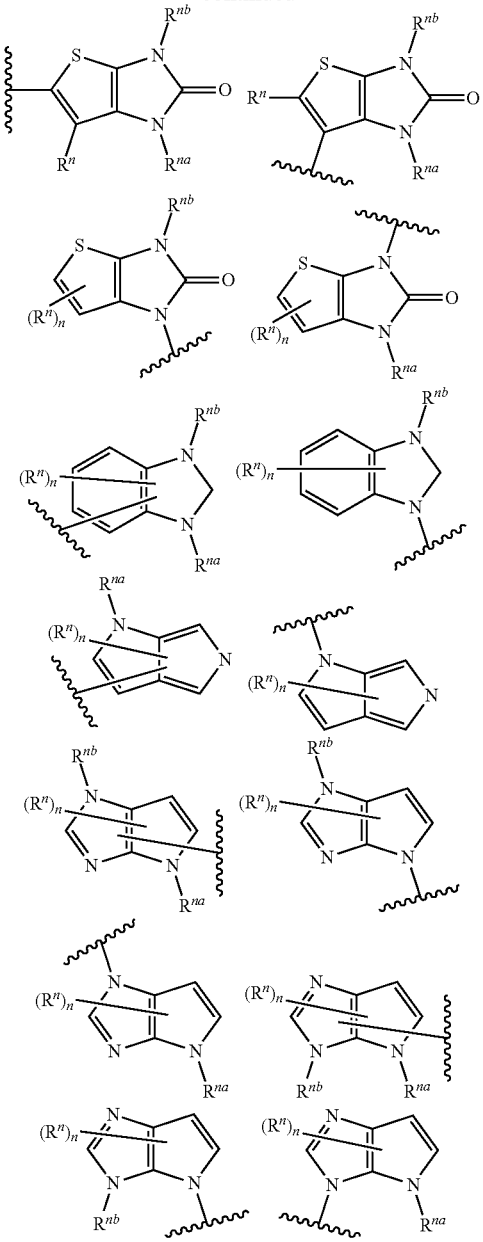

wherein each instance of $R^n$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, —OS(=O)$_2$N(R$^{n2}$)$_2$, or two instances of $R^n$ attached to the same or adjacent carbon atoms, taken together with the atoms to which they are attached form an optionally substituted cycloalkyl or a heterocycloalkyl;

each instance of $R^{na}$ and $R^{nb}$ is independently hydrogen, optionally substituted —$C_1$-$C_6$ alkyl, or a nitrogen protecting group;

each instance of $R^{n2}$ is independently hydrogen, optionally substituted —$C_1$-$C_6$ alkyl, or a nitrogen protecting group;

each instance of $R^{o4}$ is independently hydrogen, optionally substituted —$C_1$-$C_6$ alkyl, or an oxygen protecting group;

each instance of $R^{c3}$ is independently optionally substituted —$C_1$-$C_6$ alkyl;

each instance of $R^{s1}$ is independently optionally substituted —$C_1$-$C_6$ alkyl, or a sulfur protecting group; and n is 0, 1, 2, or 3, as valency permits.

In another embodiment, Q is one of the following formulae:

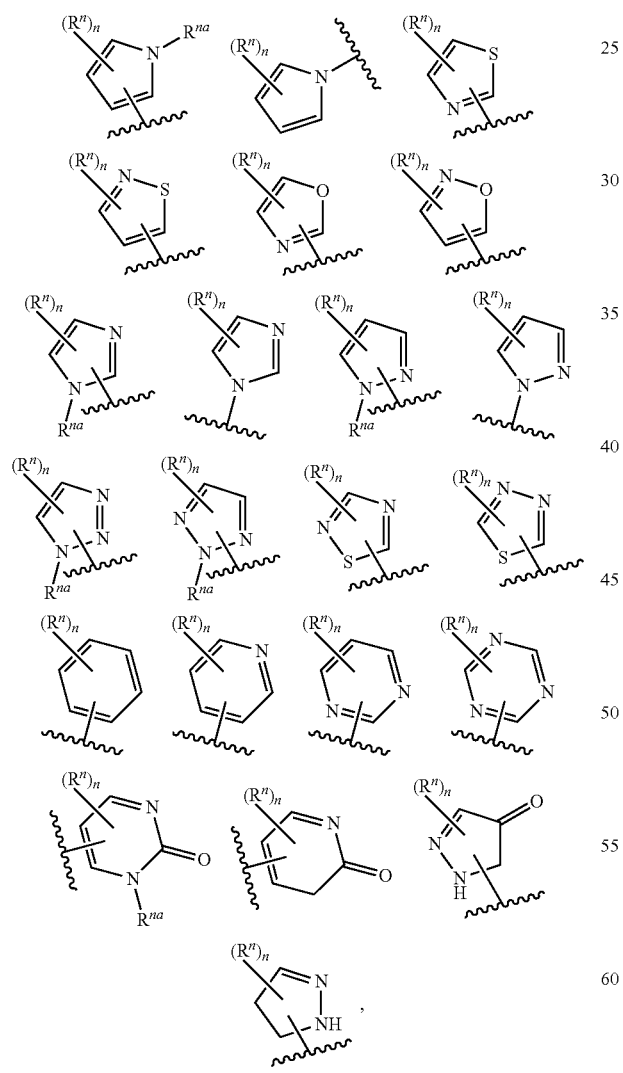

wherein each instance of $R^n$, $R^{na}$ and n are as defined for the Q values immediately above.

In another embodiment, Q is of one of the following formulae:

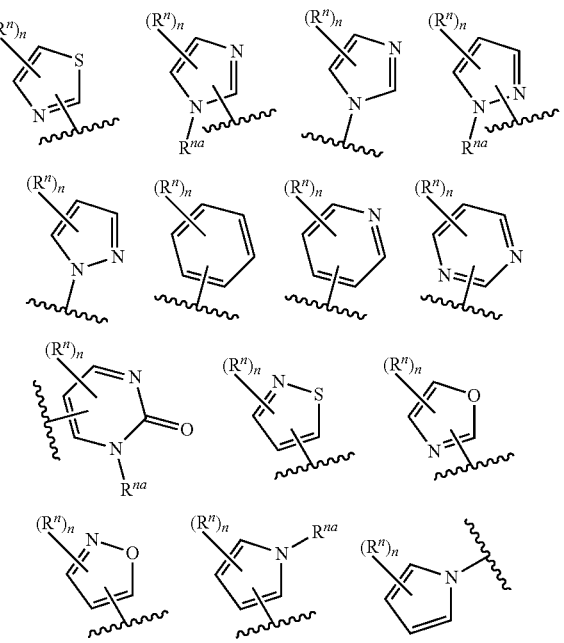

wherein each instance of $R^n$ $R^{na}$ and n are as defined for the Q values immediately above.

In another embodiment, Q is of one of the formulae:

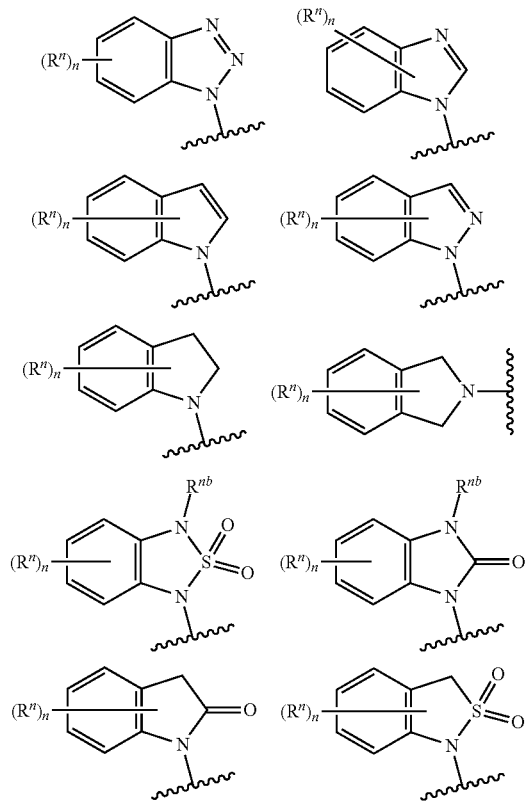

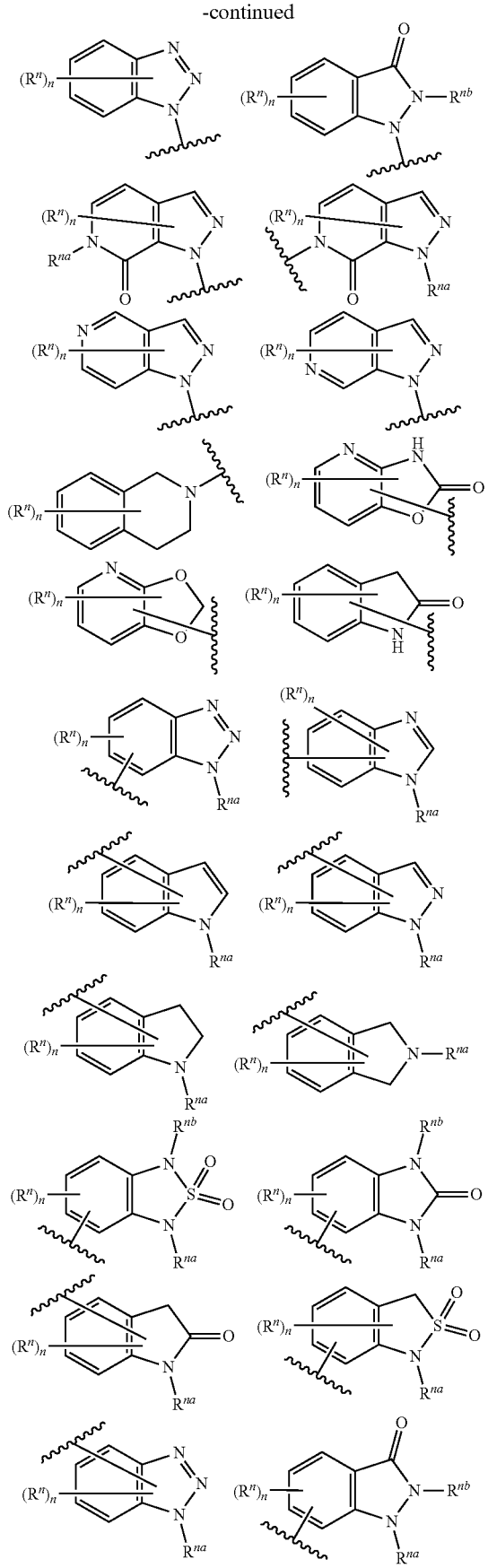
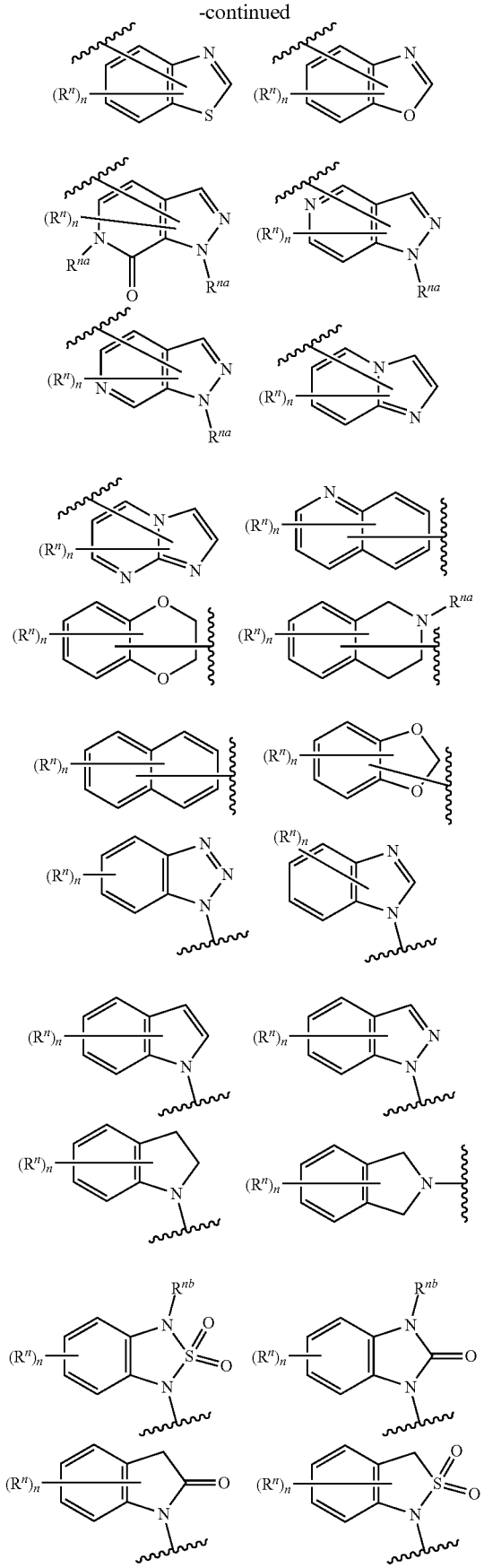

-continued

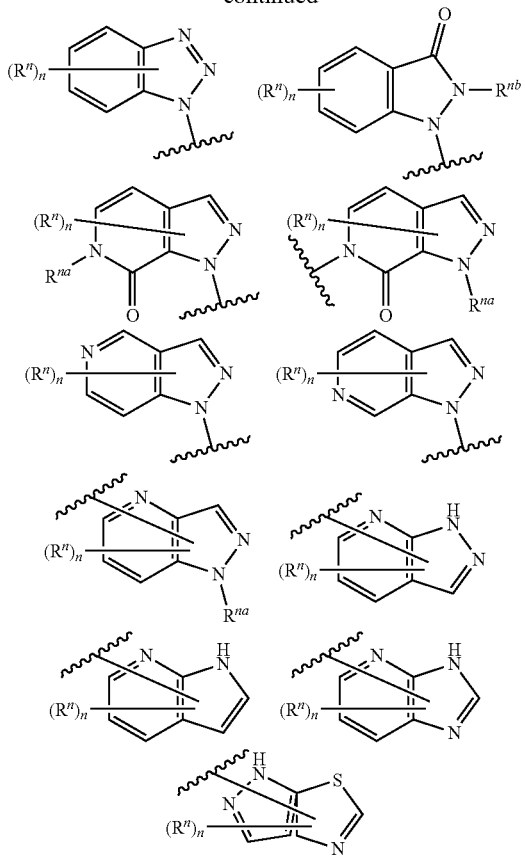

wherein each instance of $R^n$ and $R^{na}$ and n are as defined for the Q values immediately above.

In a sixth embodiment of the invention, provided is a compound of Formula (I) or (II) or a pharmaceutically acceptable salt thereof, wherein $L^2$ is a bond, optionally substituted alkylene, —C(=O)—, —S(=O)$_2$—, or —S(=O)—, wherein the point of the attachment to Q is on the right-hand side, and the remainder of the variables are as described in any one of the first through the fifth embodiments. Alternatively, $L^2$ is a bond, optionally substituted $C_1$-$C_6$ alkylene, —C(=O)—, —S(=O)$_2$—, or —S(=O)—, wherein the point of the attachment to Q is on the right-hand side. In some embodiments, $L^2$ is a bond, an alkylene substituted with 0-3 occurrences of $R^h$, —C(=O)—, —S(=O)$_2$—, or —S(=O)—, wherein the point of the attachment to Q is on the right-hand side. In certain embodiments, $L^2$ is —S(=O)$_2$—. In another embodiment, $L^2$ is optionally substituted $C_{1-4}$ alkylene. In one embodiment, $L^2$ is $C_{1-4}$ alkylene. In a further embodiment, $L^2$ is —CH$_2$— or —CH$_2$CH$_2$—. In another embodiment, $L^2$ is substituted $C_{1-4}$ alkylene. In one embodiment, $L^2$ is $C_{1-4}$ haloalkylene. In one embodiment, $L^2$ is —CHF—. The reminder of the variables are as described in the first through the fifth embodiments.

In a seventh embodiment of the invention, provided is a compound of Formula (I) or (II) or a pharmaceutically acceptable salt thereof, wherein $R^1$ is hydrogen, optionally substituted alkyl, optionally substituted haloalkyl, optionally substituted alkenyl, optionally substituted alkynyl, optionally substituted cycloalkyl, optionally substituted heterocyclyl, optionally substituted aryl, —OR$^{o1}$, —C(=O)R$^{c1}$, or a nitrogen protecting group; and the remainder of the variables are as described in any one of the first through the sixth embodiments. Alternatively, $R^1$ is hydrogen. In a further embodiment, $R^1$ is optionally substituted —C$_{1-4}$ alkyl. In a further embodiment $R^1$ is —C$_{1-4}$ alkyl. In another embodiment, $R^1$ is methyl, ethyl, n-propyl, or iso-propyl. In one embodiment the compound is a compound or pharmaceutically acceptable salt thereof as described in any of the preceding embodiments, $R^1$ is optionally substituted —C$_{2-6}$ alkynyl. In one embodiment, $R^1$ is —C$_{2-6}$ alkynyl. In one embodiment, $R^1$ is substituted —C$_{2-6}$ alkynyl (e.g. ethynyl). In another embodiment, $R^1$ is straight chain —C$_{2-6}$ alkynyl substituted with one instance of hydroxyl. In one embodiment the compound is a compound or pharmaceutically acceptable salt thereof as described in any of the preceding embodiments, wherein $R^1$ is —OR$^{o1}$. In one embodiment, $R^1$ is —OH. In one embodiment, $R^1$ is —C(=O)R$^{c1}$. In one embodiment, $R^1$ is —C(=O)R$^{c1}$, wherein $R^{c1}$ is —C$_{1-6}$ alkyl (e.g. methyl or ethyl).

In an eighth embodiment of the invention, provided is a compound of Formula (I) or (II) or a pharmaceutically acceptable salt thereof, wherein, $R^2$ is hydrogen, halogen, optionally substituted alkyl, optionally substituted alkoxy, optionally substituted alkenyl, optionally substituted alkynyl, optionally substituted cycloalkyl, optionally substituted heterocyclyl, optionally substituted aryl, or optionally substituted heteroaryl, or a nitrogen protecting group when $L^1$ is —NR$^3$—, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when $L^1$ is —O—, —OC(=O)—, —OC(=O)NR$^3$—, —OC(R$^4$)$_2$—, —OS(=O)$_2$—, —NR$^3$C(=O)NR$^3$—, —NR$^3$S(=O)$_2$O—, or —NR$^3$S(=O)O—, or —OS(=O)—, or a sulfur protecting group when $L^1$ is —S—; and the remainder of the variables are as described in any one of the first through the seventh embodiments. Alternatively, $R^2$ is hydrogen. In certain embodiments, $R^2$ is selected from hydrogen, —C$_1$-C$_6$ alkyl, —C$_2$-C$_6$ alkenyl, phenyl, 5-membered heteroaryl, wherein each alkyl, alkenyl, phenyl, and heteroaryl is substituted with 0-3 occurrences of $R^e$. In certain embodiments $R^2$ is selected from hydrogen, halogen, or optionally substituted —C$_1$-C$_6$ alkyl. In certain embodiments, $R^2$ is halogen (e.g. F, Cl, Br, or I). In certain embodiments, $R^2$ is optionally substituted —C$_{1-6}$ alkyl. In certain embodiments, $R^2$ is —C$_{1-6}$ alkyl (e.g. methyl, ethyl, propyl, or iso-propyl). In certain embodiments, $R^2$ is substituted —C$_{1-6}$ alkyl (e.g. with one or two occurrences of halogen, amino, or hydroxyl). In certain embodiments, $R^2$ is optionally substituted heterocyclyl. In certain embodiments, $R^2$ is optionally substituted 3- to 14-membered heterocyclyl. In certain embodiments, $R^2$ is optionally substituted 5-membered or 6-membered monocyclic heterocyclyl. In certain embodiments, $R^2$ is optionally substituted 8- to 12-membered bicyclic heterocyclyl. In certain embodiments $R^2$ is optionally substituted aryl or heteroaryl. In certain embodiments, $R^2$ is optionally substituted heteroaryl. In certain embodiments, $R^2$ is optionally substituted 3- to 14-membered heteroaryl. In certain embodiments, $R^2$ is optionally substituted 5-membered or 6-membered monocyclic heteroaryl. In certain embodiments, $R^2$ is optionally substituted 8- to 12-membered bicyclic heteroaryl. In certain embodiments, $R^2$ is one of the following formulae:

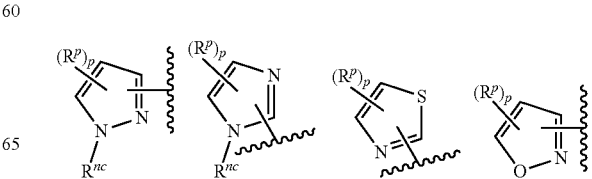

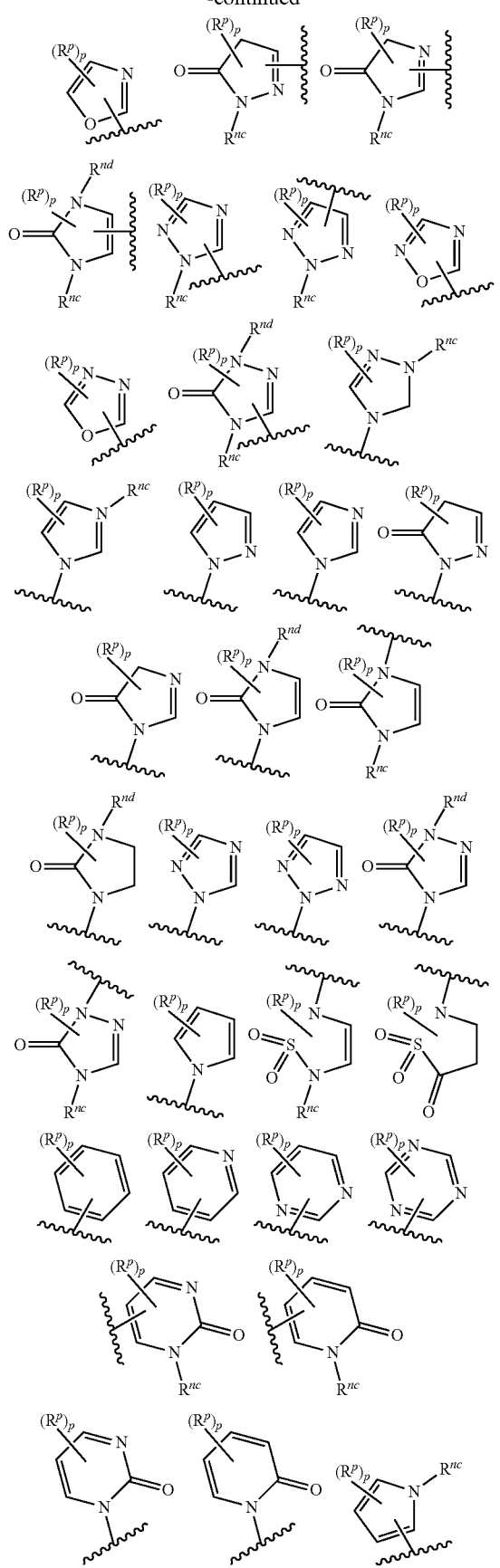
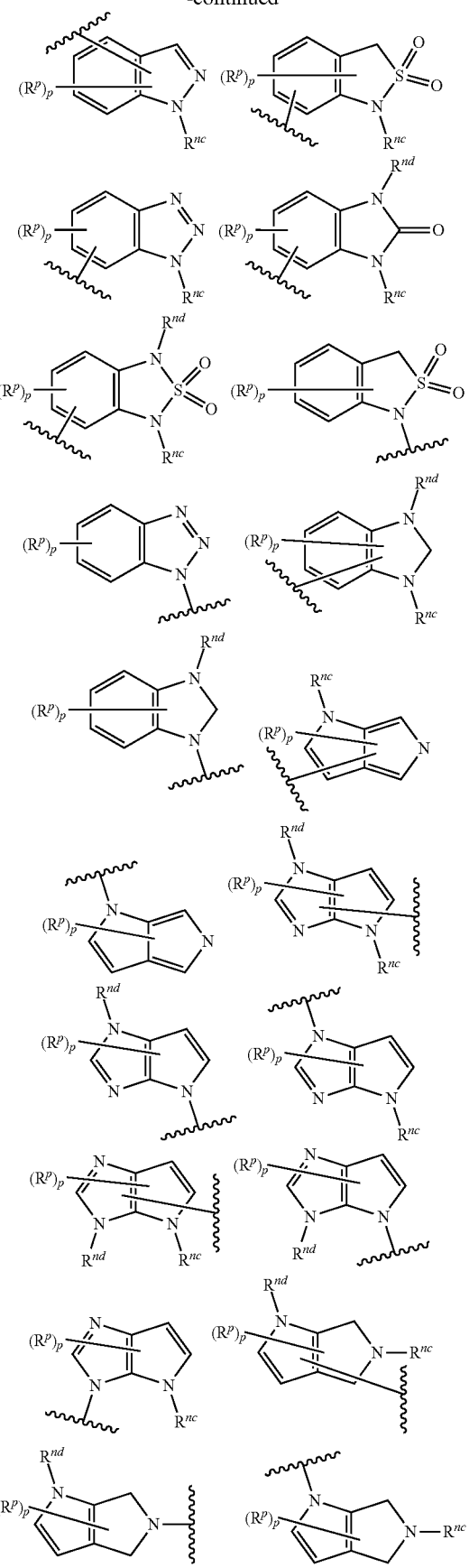

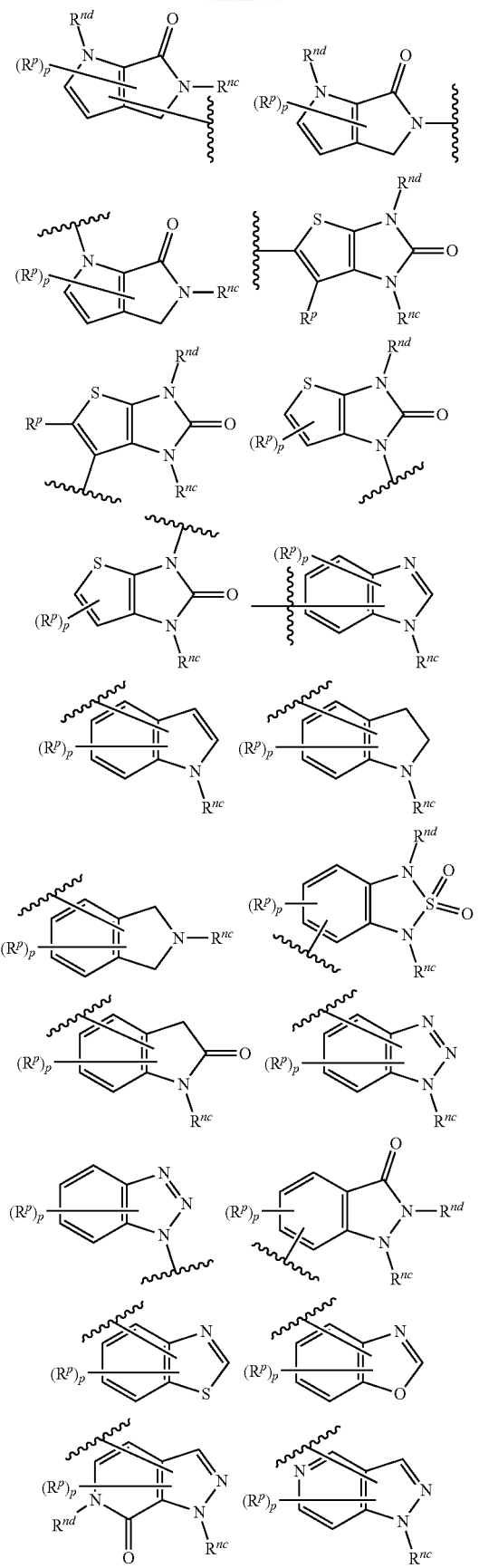
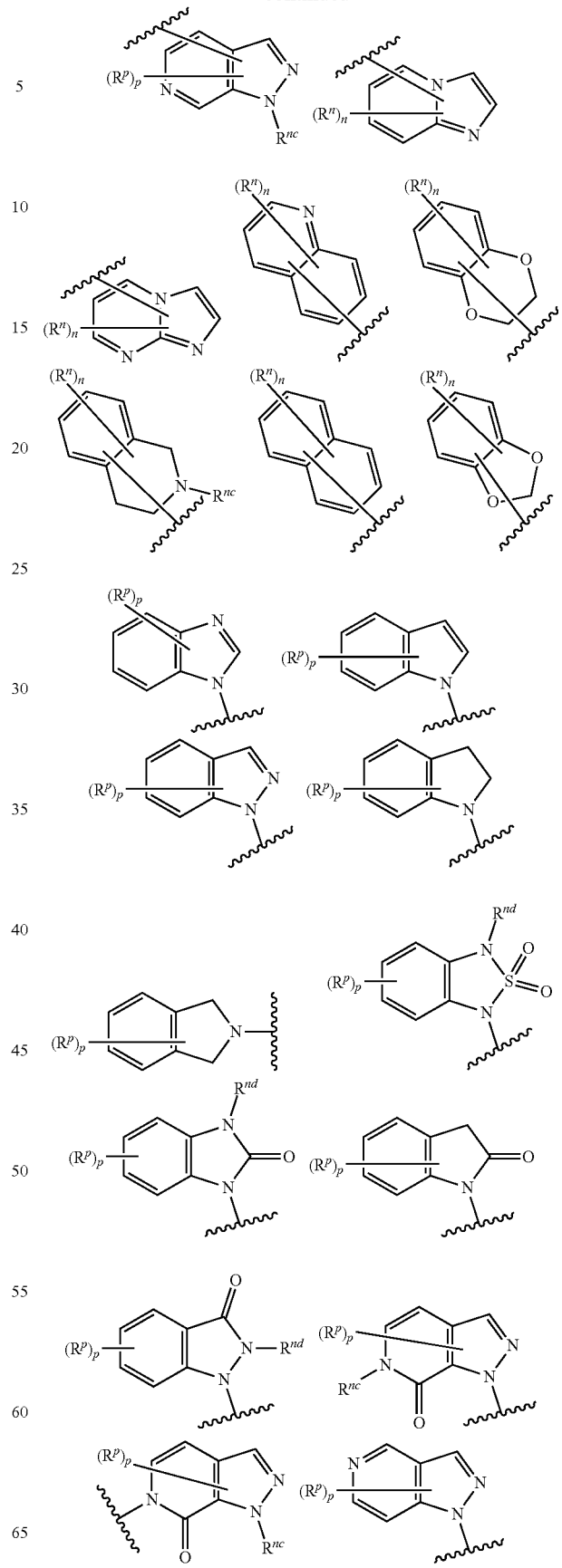

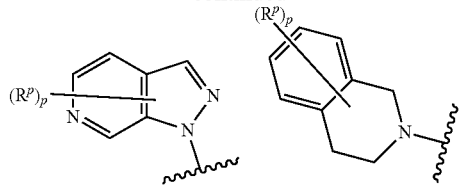

wherein each instance of $R^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of $R^p$ attached to the same or adjacent carbon atoms, taken together with the atoms to which they are attached form an optionally substituted cycloalkyl or a heterocycloalkyl;

each instance of R$^{n3}$, R$^{nc}$, and R$^{nd}$ is independently hydrogen, optionally substituted —C$_1$-C$_6$ alkyl, or a nitrogen protecting group;

each instance of R$^{o6}$ is independently hydrogen, optionally substituted —C$_1$-C$_6$ alkyl, or an oxygen protecting group;

each instance of R$^{c4}$ is independently optionally substituted —C$_1$-C$_6$ alkyl;

each instance of R$^{s2}$ is independently optionally substituted —C$_1$-C$_6$ alkyl, or a sulfur protecting group;

p is 0, 1, 2, or 3, as valency permits.

In certain embodiments, $R^2$ is selected from hydrogen, —C$_1$-C$_6$ alkyl, —C$_2$-C$_6$ alkenyl, phenyl, and 5-membered heteroaryl, wherein each alkyl, alkenyl, phenyl, and heteroaryl is substituted with 0-3 occurrences of $R^e$, wherein $R^e$ is as defined herein.

In certain embodiments, R2 is one of the following formulae:

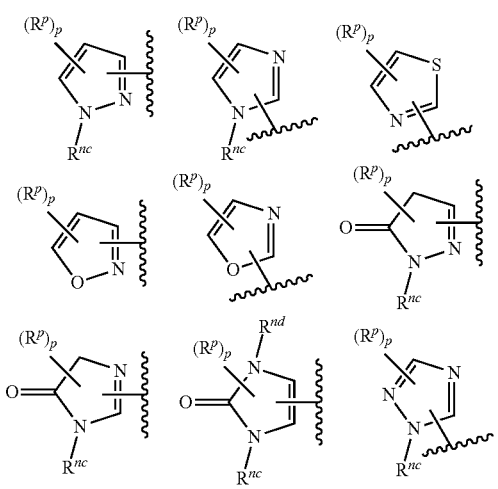

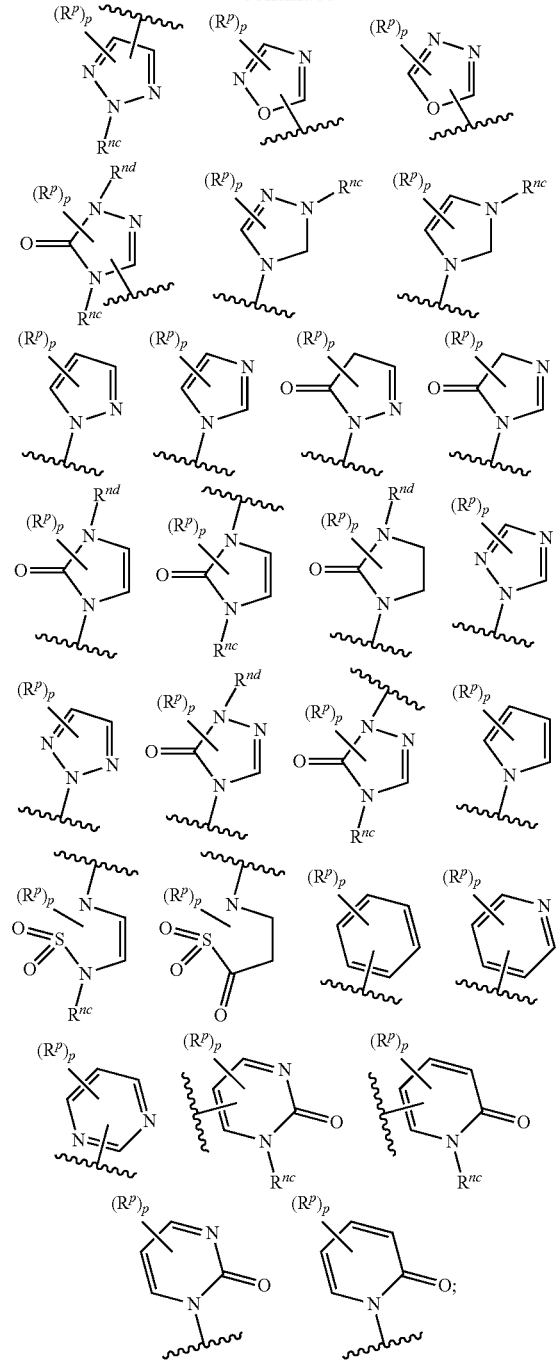

wherein R$^p$, R$^{nd}$, R$^{nc}$ and p are as defined immediately above for the values for $R^2$.

In certain embodiments, $R^2$ is one of the following formulae:

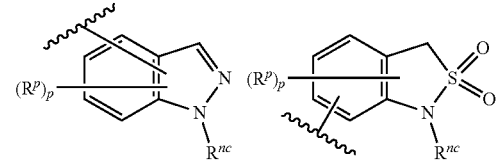

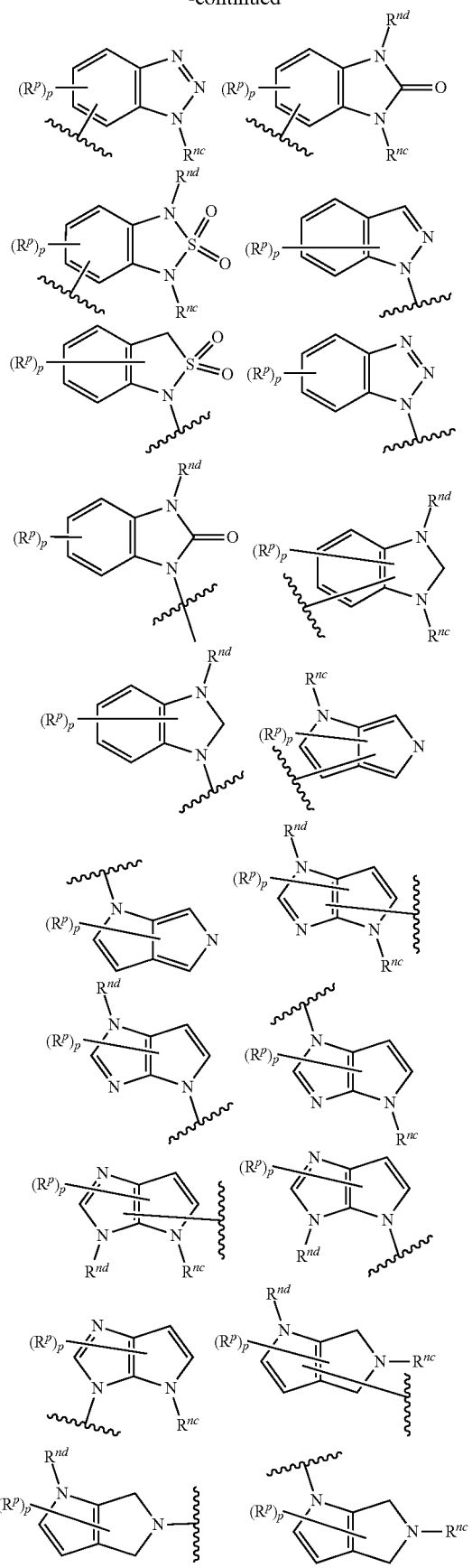
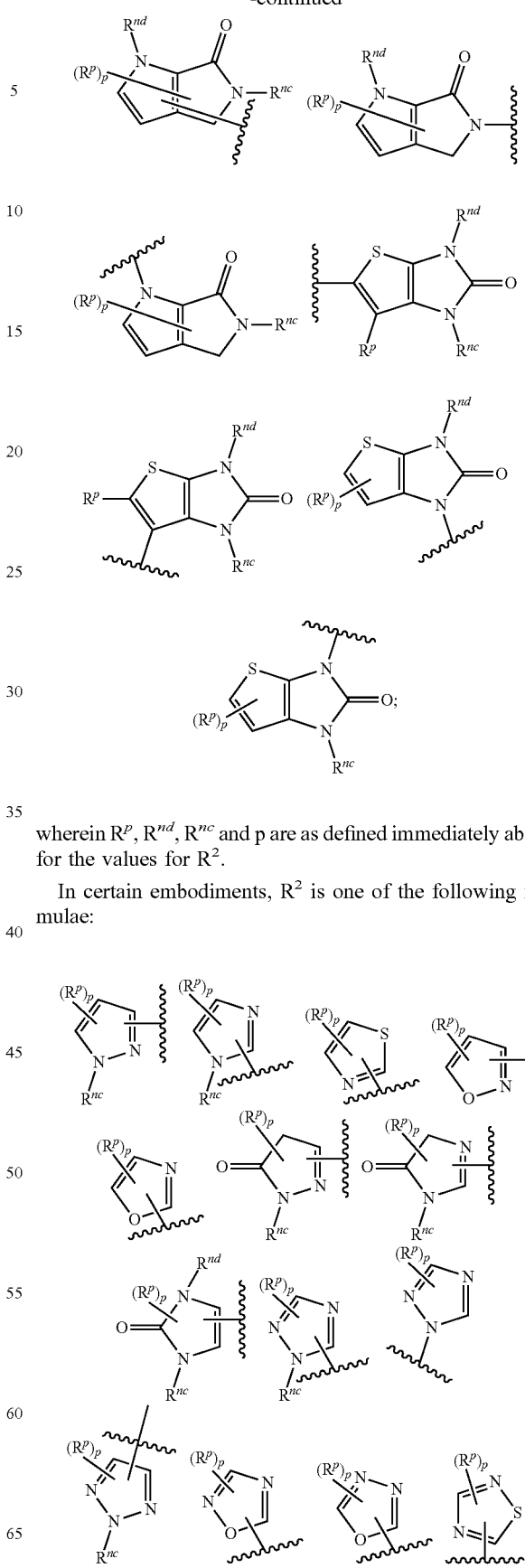
wherein $R^p$, $R^{nd}$, $R^{nc}$ and p are as defined immediately above for the values for $R^2$.
In certain embodiments, $R^2$ is one of the following formulae:

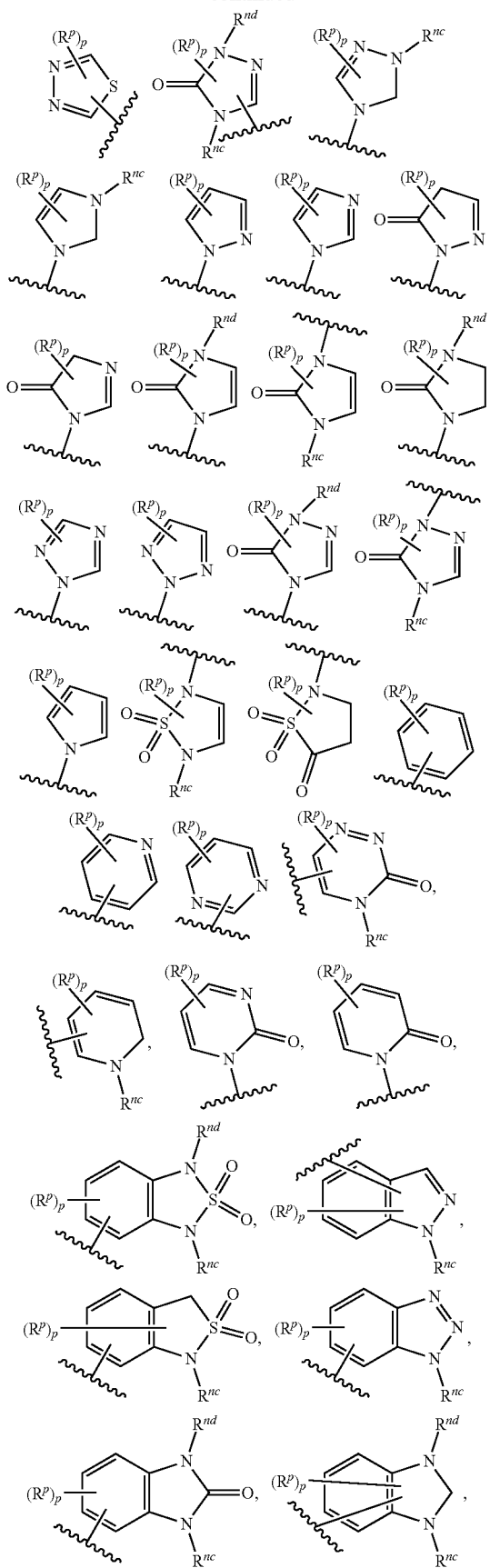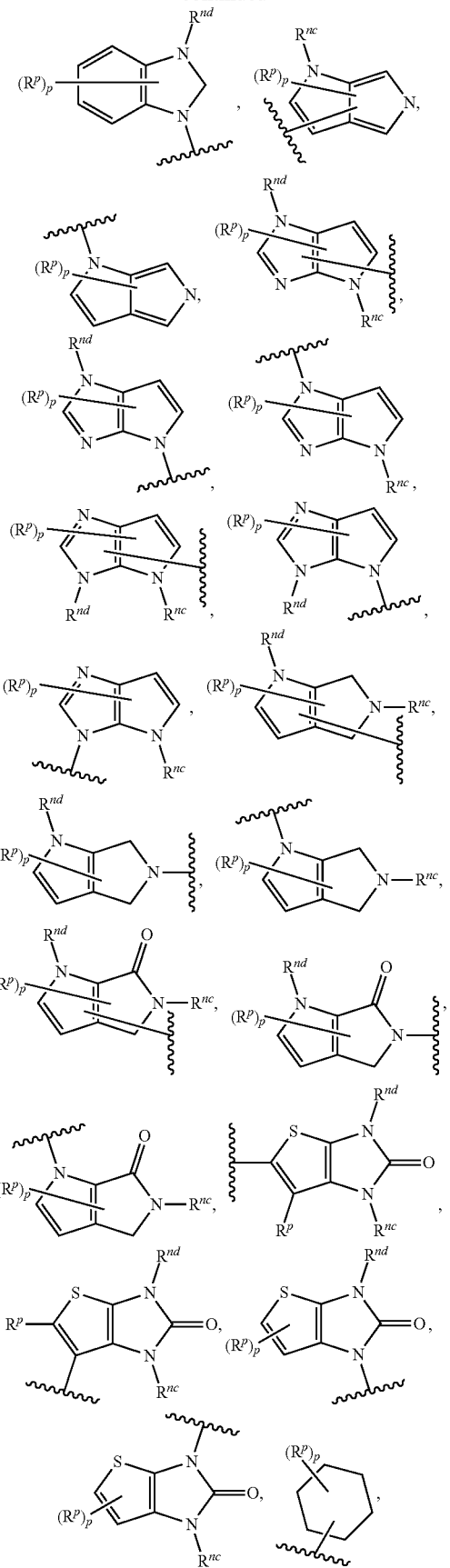

-continued

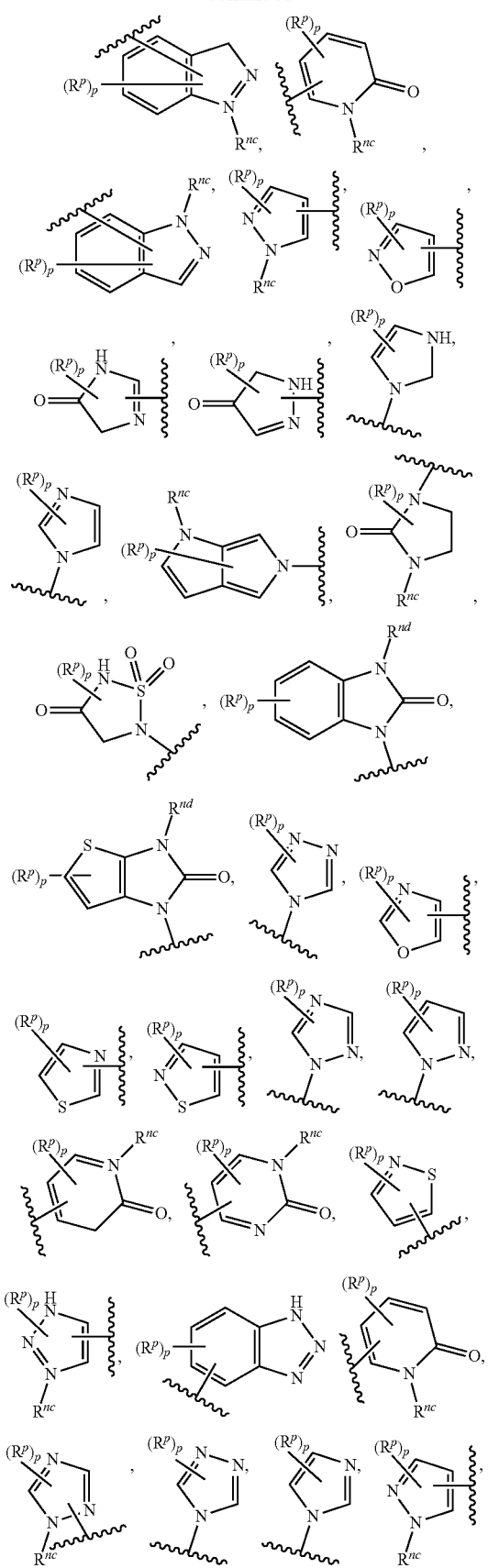

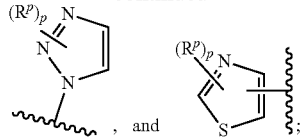

wherein $R^P$, $R^{nd}$, $R^{nc}$ and p are as defined immediately above for the values for $R^2$.

In a further embodiment according to the first to the sixth embodiments, $R^2$ and Q are the same. In a further embodiment according to the first to the sixth embodiments, $R^2$ and Q are different.

In another embodiment of the invention, provided is a compound or pharmaceutically acceptable salt thereof, wherein the compound is of Formula (III):

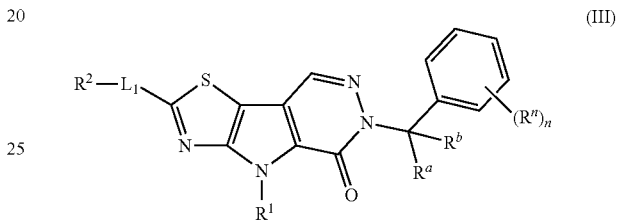

(III)

wherein each instance of $R^n$ is independently selected from hydrogen, halogen, —CN, —$NO_2$, —$N_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —$OR^{o4}$, —$SR^{s1}$, —$N(R^{n2})_2$, —$C(=O)N(R^{n2})_2$, —$N(R^{n2})C(=O)R^{c3}$, —$C(=O)R^{o3}$, —$C(=O)OR^{o4}$, —$OC(=O)R^{c3}$, —$S(=O)R^{s1}$, —$S(=O)_2R^{s1}$, —$S(=O)OR^{o4}$, —$OS(=O)R^{c3}$, —$S(=O)_2OR^{o4}$, —$OS(=O)_2R^{c3}$, —$S(=O)N(R^{n2})_2$, —$S(=O)_2N(R^{n2})_2$, —$N(R^{n2})S(=O)R^{s1}$, —$N(R^{n2})S(=O)_2R^{s1}$, —$N(R^{n2})C(=O)OR^{o4}$, —$OC(=O)N(R^{n2})_2$, —$N(R^{n2})C(=O)N(R^{n2})_2$, —$N(R^{n2})S(=O)N(R^{n2})_2$, —$N(R^{n2})S(=O)_2N(R^{n2})_2$, —$N(R^{n2})S(=O)OR^{o4}$, —$N(R^{n2})S(=O)_2OR^{o4}$, —$OS(=O)N(R^{n2})_2$, —$OS(=O)_2N(R^{n2})_2$, or two instances of $R^n$ attached to the same or adjacent carbon atoms, taken together with the atoms to which they are attached form an optionally substituted cycloalkyl or a heterocycloalkyl;

each instance of $R^{na}$ and $R^{nd}$ is independently hydrogen, optionally substituted —$C_1$-$C_6$ alkyl, or a nitrogen protecting group;

each instance of $R^{n2}$ is independently hydrogen, optionally substituted —$C_1$-$C_6$ alkyl, or a nitrogen protecting group;

each instance of $R^{o4}$ is independently hydrogen, optionally substituted —$C_1$-$C_6$ alkyl, or an oxygen protecting group;

each instance of $R^{c3}$ is independently optionally substituted —$C_1$-$C_6$ alkyl; each instance of $R^{s1}$ is independently optionally substituted —$C_1$-$C_6$ alkyl, or a sulfur protecting group; and n is 0, 1, 2, or 3, as valency permits;

$R^a$ and $R^b$ are as described for Formula (II); and the remainder of the variables are as defined for the first through the eighth embodiment.

In one embodiment the compound or pharmaceutically acceptable salt thereof is a compound of Formula (III) as described above wherein each instance of $R^n$ is independently selected from —$C_1$-$C_4$ alkyl, —$C_1$-$C_4$ haloalkyl, —$C_1$-$C_4$ hydroxyalkyl, —$C_1$-$C_4$ aminoalkyl, —OH, —$OC_1$-$C_4$ alkyl, —$NH_2$, —CN and —$NO_2$. In one embodiment the compound or pharmaceutically acceptable salt thereof is a compound of Formula (III) as described above wherein $L^1$ is a bond, —S(=O)—, —S(=O)$_2$—, or $C_{1-6}$ alkylene. In one embodiment the compound or pharmaceutically acceptable salt thereof is a compound of Formula (III) as described above wherein $R^2$ is hydrogen, halogen, or optionally substituted —$C_1$-$C_6$ alkyl.

In another embodiment of the invention, provided is a compound is a compound of Formula (III-a) or Formula (III-b) or pharmaceutically acceptable salt thereof:

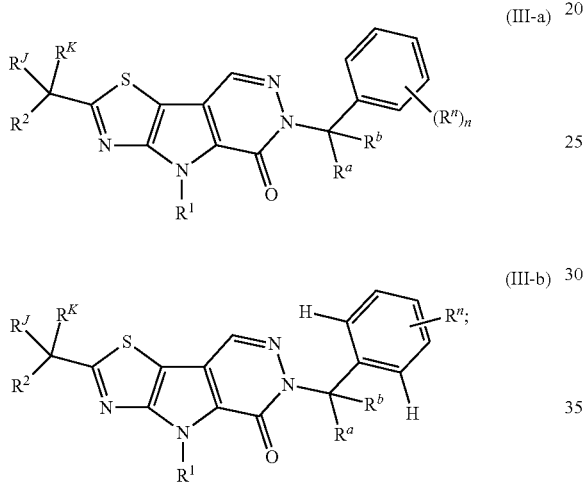

wherein $R^a$ and $R^b$ are described for Formula (II), each instance of $R^j$ and $R^k$ is independently selected from H, halogen, —CN, —$OR^{o7}$, —$N(R^{n5})_2$, —$N(R^{n5})C(=O)R^{c5}$, —$C(=O)N(R^{n5})_2$, —$C(=O)R^{c5}$, —$C(=O)OR^{o7}$, —$SR^{js}$, —$S(=O)_2R^{js}$, or —$S(=O)R^{js}$, optionally substituted —$C_1$-$C_6$ alkyl; or $R^j$ and $R^k$ can be taken together with the carbon atom to form C=O, an optionally substituted $C_1$-$C_6$ monocyclic cycloalkyl ring or an optionally substituted $C_3$-$C_6$ monocyclic heterocyclyl ring;

$R^{n5}$ is hydrogen, optionally substituted —$C_1$-$C_6$ alkyl, —$OR^{o8}$, or a nitrogen protecting group;

each instance of $R^{o7}$ and $R^{o8}$ is independently hydrogen, optionally substituted —$C_1$-$C_6$ alkyl, or an oxygen protecting group;

each instance of $R^{o5}$ is independently optionally substituted —$C_1$-$C_6$ alkyl; and each instance of $R^{js}$ is independently optionally substituted —$C_1$-$C_6$ alkyl, optionally substituted $C_{6-12}$ aryl, optionally substituted heteroaryl, or a sulfur protecting group; and the remainder of the variables are as described for Formula (III).

In another embodiment of the invention, provided is a compound of Formula (III-c), Formula (II-c-1), Formula (III-d) or Formula (III-d-1) or a pharmaceutically acceptable salt thereof:

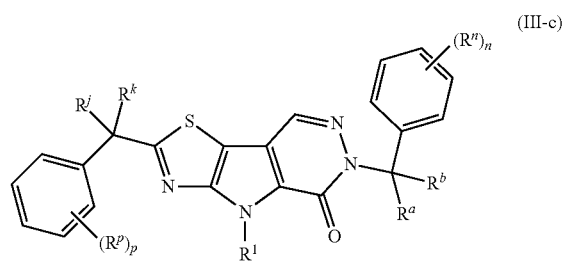

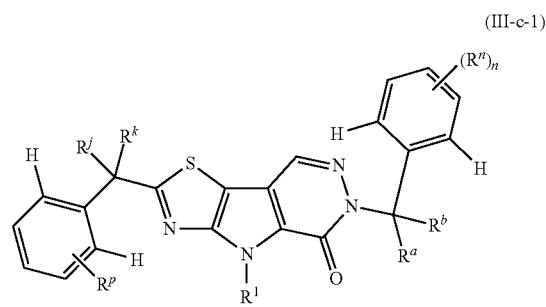

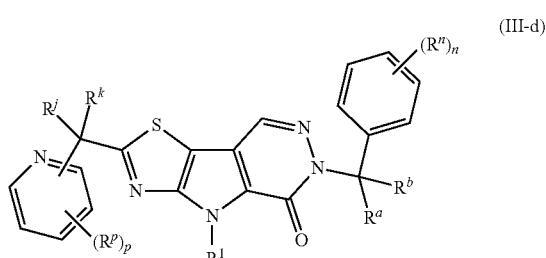

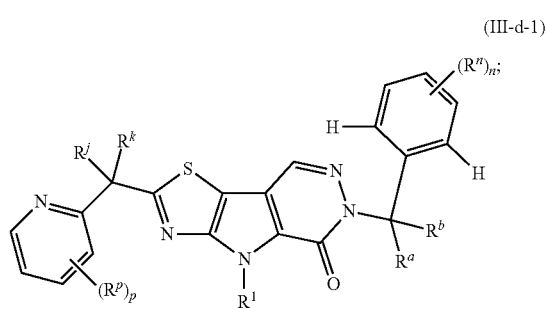

wherein each instance of $R^p$ and p are as described in the eighth embodiment; and the remainder of the variables are as described for Formulas (III), (III-a) or (IIIb).

In another embodiment of the invention, provided is a compound of Formula (III-e) or Formula (III-e-1) or a pharmaceutically acceptable salt thereof:

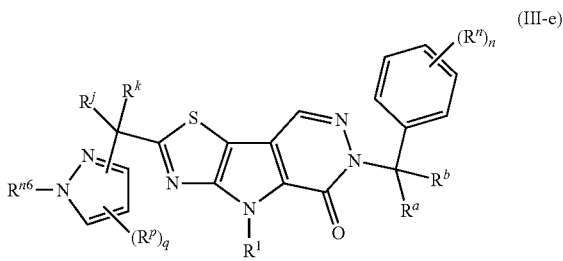

-continued

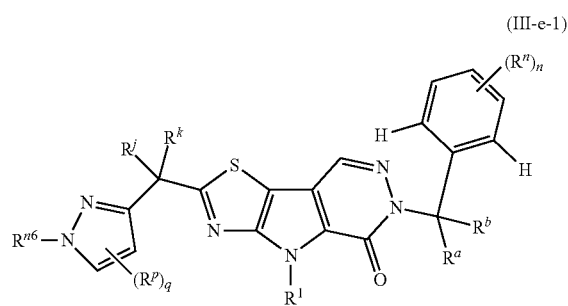

(III-e-1)

wherein $R^{nd}$ is hydrogen, optionally substituted —$C_1$-$C_6$ alkyl, or a nitrogen protecting group and; q is 0, 1 or 2; and the remainder of the variables are as described for Formulas (III-c) (II-c-1), (III-d-1).

In certain embodiments, $R^{n6}$ is hydrogen. In certain embodiments, $R^{n6}$ is optionally substituted —$C_1$-$C_6$ alkyl. In certain embodiments, $R^{n6}$ is —$C_1$-$C_6$ alkyl (e.g. methyl ethyl, propyl or isopropyl). In certain embodiments, q is 0. In certain embodiments, q is 1.

In another embodiment of the invention, provided is a compound of or pharmaceutically acceptable salt thereof of Formula (III-f) or Formula (III-f-1):

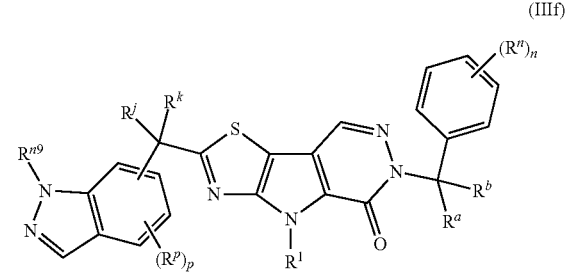

(IIIf)

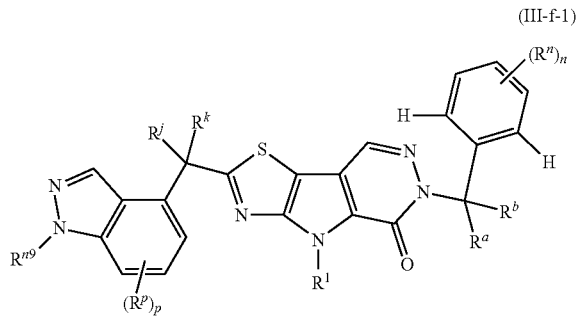

(III-f-1)

wherein $R^{n9}$ is hydrogen, optionally substituted —$C_1$-$C_6$ alkyl, or a nitrogen protecting group; wherein the remainder of the variables are as described for Formulas (III-c), (III-c-1), (III-d) or (III-d-1).

In certain embodiments, $R^{n9}$ is hydrogen. In certain embodiments, $R^{n9}$ is optionally substituted —$C_1$-$C_6$ alkyl (e.g. with 1-3 instances of halo or hydroxy). In certain embodiments, $R^{n9}$ is —$C_1$-$C_6$ alkyl (e.g. methyl, ethyl, propyl or isopropyl).

In another embodiment of the invention, provided is a compound of or pharmaceutically acceptable salt thereof of Formula (III-g), Formula (III-g-1), Formula (III-g-2), Formula (III-h), or Formula (III-h-1):

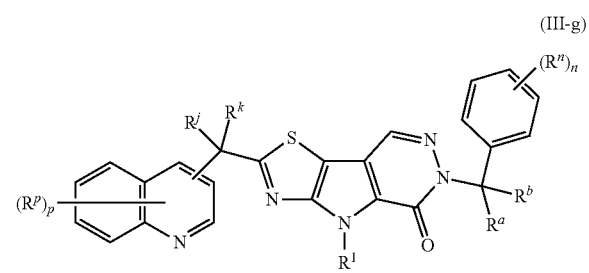

(III-g)

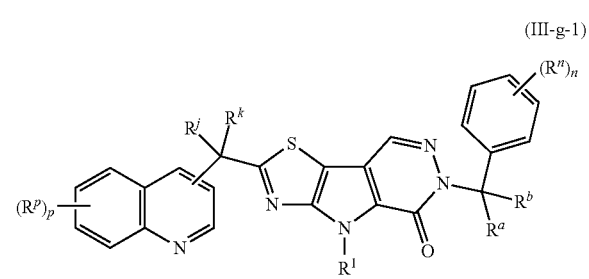

(III-g-1)

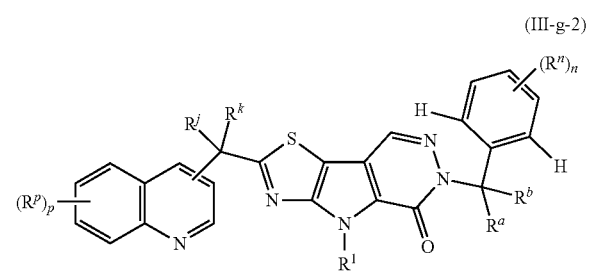

(III-g-2)

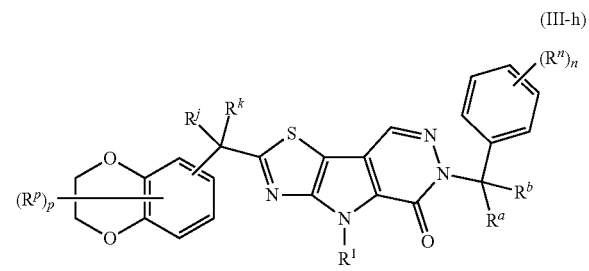

(III-h)

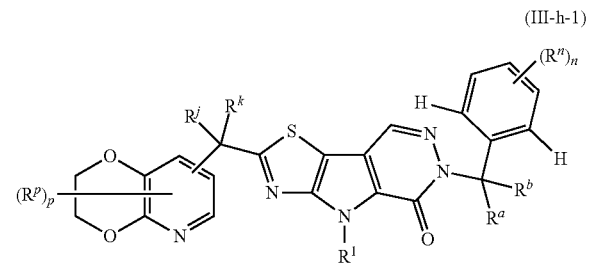

(III-h-1)

wherein the variables are as defined for Formulas (III-c), (III-c-1), (III-d) or (III-d-1).

In another embodiment of the invention, provided is a compound of the compound is of Formula (IV) or pharmaceutically acceptable salt thereof:

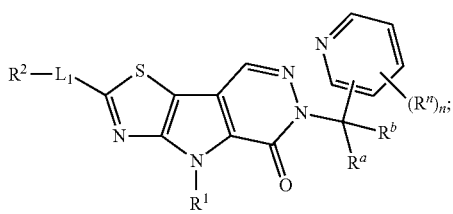

(IV)

wherein $R^a$ and $R^b$ are as described for the Formula (II); $R^n$ and n are as described in the fifth embodiment; and the remainder of the variables are as described for the first embodiment. Alternatively, the remainder of the variables are as defined in any one of the second through the eighth embodiments.

In another embodiment of the invention, provided is a compound of Formula (IV-a) or a pharmaceutically acceptable salt thereof:

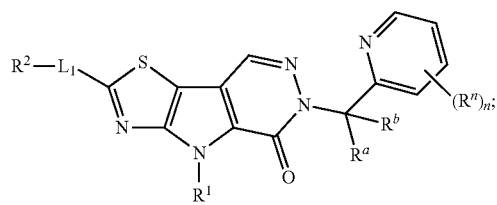

(IV-a)

wherein the variables are as described for Formula (IV).

In certain embodiments of Formulae (IV) or (IV-a), $L^1$ is a bond, —S(=O)$_2$—, or optionally substituted $C_{1-6}$ alkylene. In one embodiment of Formulae (IV) or (IV-a), $R^2$ is hydrogen, halogen, or optionally substituted —$C_1$-$C_6$ alkyl.

In another embodiment of the invention, provided is a compound of Formula (IV-a-1) or a pharmaceutically acceptable salt thereof:

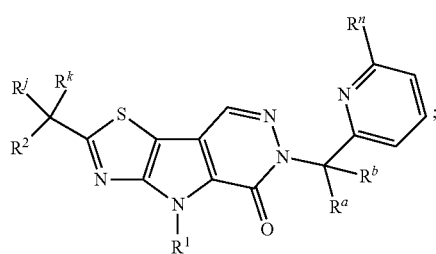

(IV-a-1)

wherein $R^j$ and $R^k$ are as described for Formulas (III-a) and (III-b); and the remainder of the variables are as described for formulas (IV) and (IV-a).

In another embodiment of the invention, provided is a compound of Formula (V-a) or pharmaceutically acceptable salt thereof:

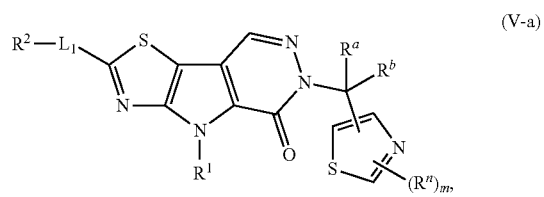

(V-a)

wherein m is 0, 1, or 2; $R^n$ is as described in the fifth embodiment; $R^a$ and $R^b$ are as described for Formula (II); and the remainder of the variables are as described for the first, second, third or fourth embodiments.

In another embodiment of the invention, provided is a compound of Formula (V-a-1) or a pharmaceutically acceptable salt thereof:

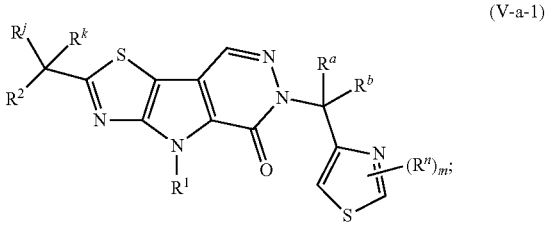

(V-a-1)

wherein $R^j$ and $R^k$ are as described for Formulas (III-a) and (III-b); and the remainder of the variables are as described for Formula (V-a).

In another embodiment of the invention, provided is a compound of Formula (V-b) or pharmaceutically acceptable salt thereof:

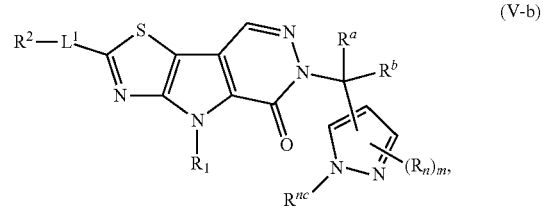

(V-b)

wherein m is 0, 1, or 2; $R^{nc}$ is independently hydrogen, optionally substituted —$C_1$-$C_6$ alkyl, or a nitrogen protecting group; and the remainder of the variables are as described for Formula (V-a).

In certain embodiments, m is 0. In certain embodiments, m is 1.

In another embodiment of the invention, provided is a compound of Formula (V-b-1) or a pharmaceutically acceptable salt thereof:

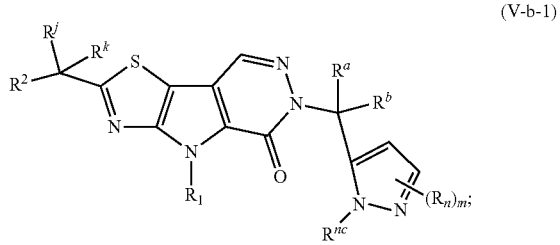

(V-b-1)

wherein $R^j$ and $R^k$ are as described for Formulas (III-a) and (III-b); and the remainder of the variables are as described for Formula (V-b).

In one another embodiment of the invention, provided is a compound of Formula (VI), (VI-a) or (VI-b) or pharmaceutically acceptable salt thereof:

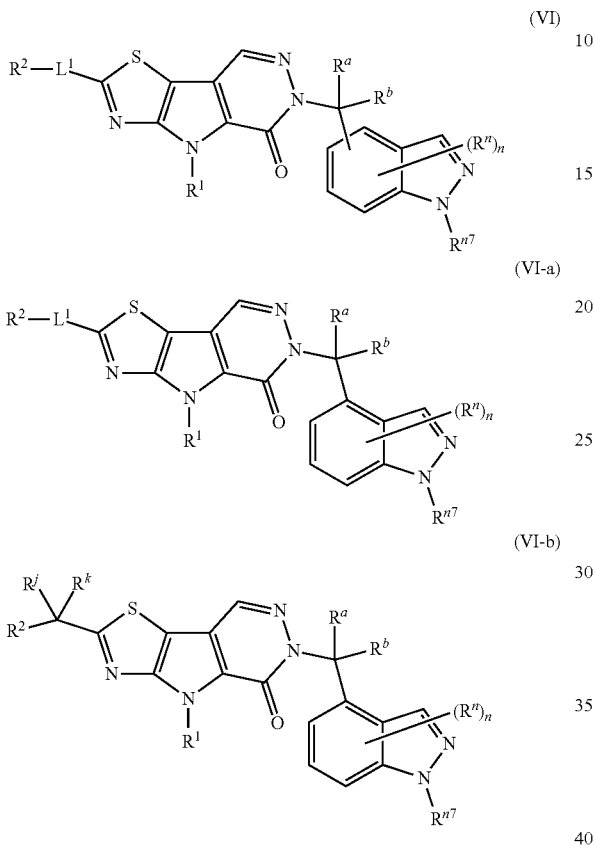

wherein $R^a$ and $R^b$ are as described for Formula (II); $R^j$ and $R^k$ are as described for Formulas (III-a) and (III-b); $R^n$ and n are as described in the fifth embodiment; $R^{n7}$ is hydrogen, optionally substituted —$C_1$-$C_6$ alkyl, or a nitrogen protecting group; and all the other substituents are as described for the first embodiment. In certain embodiments, $R^{n7}$ is hydrogen. In certain embodiments, $R^{n7}$ is optionally substituted —$C_1$-$C_6$ alkyl (e.g. with 1-3 occurrences of halo and/or hydroxy). In certain embodiments, $R^{n7}$ is —$C_1$-$C_6$ alkyl (e.g. methyl, ethyl, propyl or isopropyl). In a further embodiment of Formula (VI) or (VI-a), $L^1$ is a bond, optionally substituted $C_1$-$C_6$ alkylene, —O—, —S—, —S(=O)—, —S(=O)$_2$—, or —C(=O)—. In certain embodiments of Formula (VI), (VI-a), or (VI-c), R2 is hydrogen, halogen, or optionally substituted —$C_1$-$C_6$ alkyl.

In certain embodiments of Formula (VI), (VI-a) or (VI-b), $R^2$ is one of the following formulae:

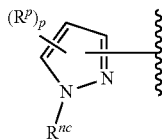

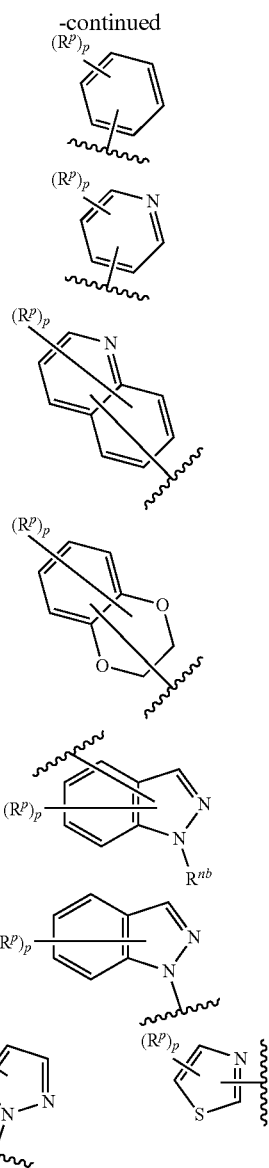

wherein each instance of $R^p$ and p are as defined in the eighth embodiment.

In another embodiment of the invention, provided is a compound Formula (VI-b) is of Formula (VI-b-1), Formula (VI-b-2), Formula (VI-b-3), Formula (VI-b-4), Formula (VI-b-5), Formula (VI-b-6), Formula (VI-b-7), Formula (VI-b-8), Formula (VI-b-9) or Formula (VI-b-10), or pharmaceutically acceptable salt thereof:

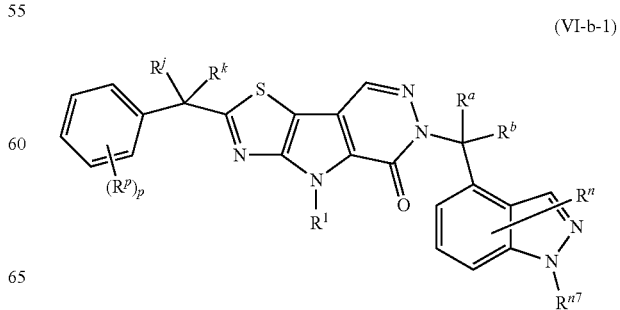

(VI-b-2)
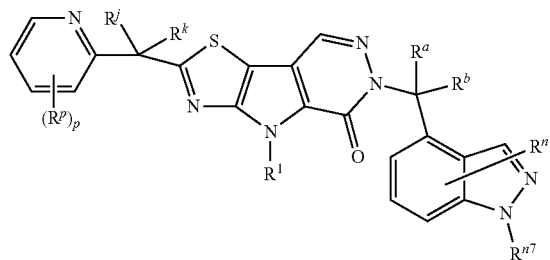

(VI-b-3)
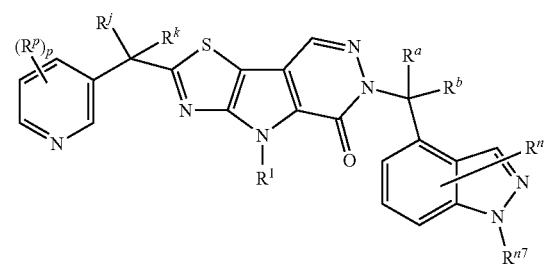

(VI-b-4)
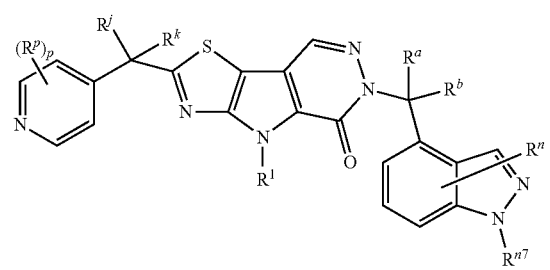

(VI-b-5)
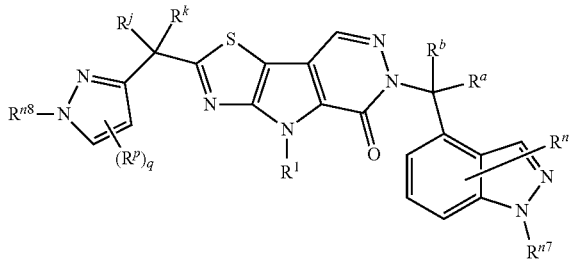

(VI-b-6)
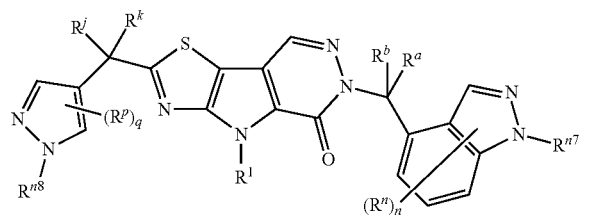

(VI-b-7)
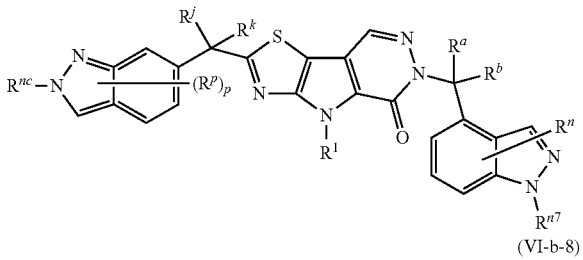

(VI-b-8)
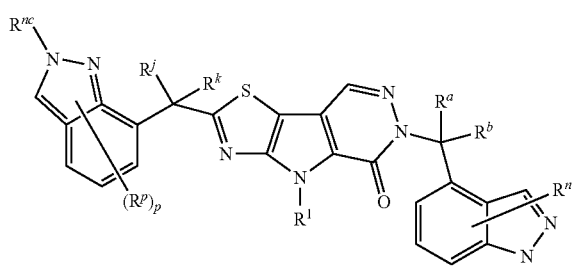

(VI-b-9)
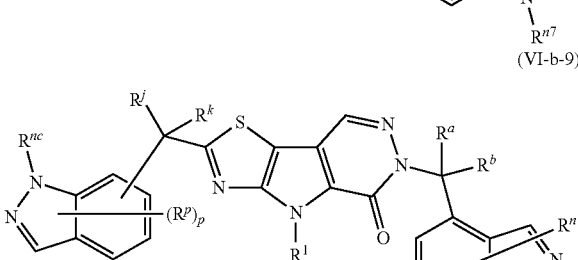

(VI-b-10)
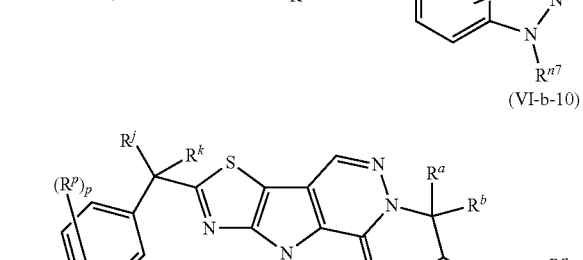

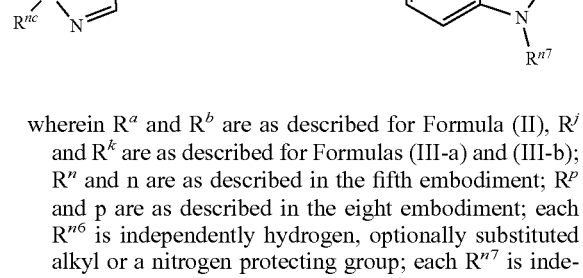

wherein $R^a$ and $R^b$ are as described for Formula (II), $R^j$ and $R^k$ are as described for Formulas (III-a) and (III-b); $R^n$ and n are as described in the fifth embodiment; $R^p$ and p are as described in the eight embodiment; each $R^{n6}$ is independently hydrogen, optionally substituted alkyl or a nitrogen protecting group; each $R^{n7}$ is independently hydrogen, optionally substituted —$C_1$-$C_6$ alkyl, or a nitrogen protecting group; and each instance of $R^{nc}$ is independently hydrogen, optionally substituted —$C_1$-$C_6$ alkyl, or a nitrogen protecting group. In certain embodiments, $R^{n7}$ is hydrogen. In certain embodiments, $R^{n7}$ is —$C_1$-$C_6$ alkyl (e.g. methyl or ethyl). In certain embodiments, $R^{n7}$ is a nitrogen protecting group. In certain embodiments, $R^{nc}$ is hydrogen. In certain embodiments, $R^{nc}$ is —$C_1$-$C_6$ alkyl. In certain embodiments, $R^{nc}$ is a nitrogen protecting group.

In another embodiment of the invention, provided is a compound of Formula (VI-c) or Formula (VI-c-1) or pharmaceutically acceptable salt thereof:

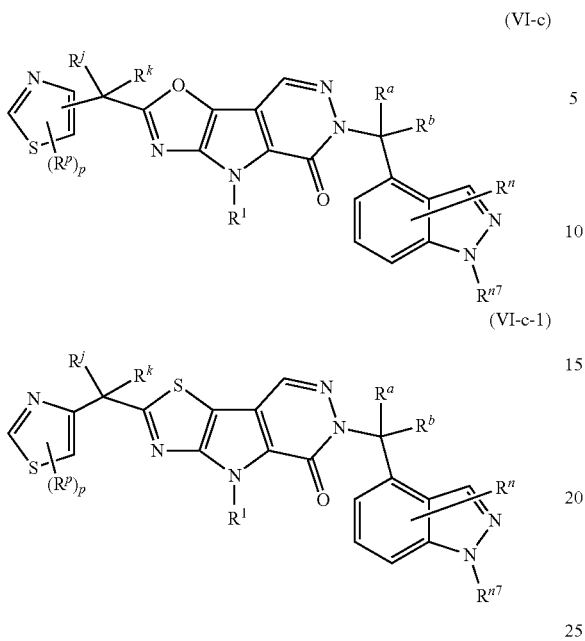

(VI-c)

(VI-c-1)

wherein the variables are defined for Formulas (VI), (VI-a) and (VI-b).

In another embodiment of the invention, provided is a compound of Formula (IX) or pharmaceutically acceptable salt thereof:

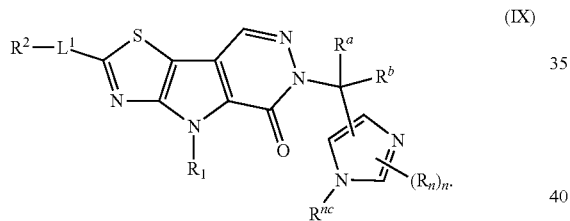

(IX)

wherein $R^{nc}$ is independently hydrogen, optionally substituted —$C_1$-$C_6$ alkyl, or a nitrogen protecting group; $R^n$ and n are as described for the fifth embodiment; and the remainder of the variables are defined as for Formula (II).

In another embodiment of the invention, provided is a compound of Formula (IX-a) or pharmaceutically acceptable salt thereof:

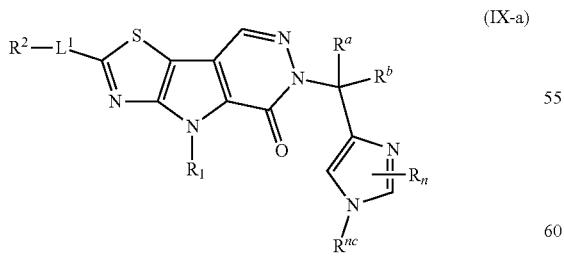

(IX-a)

wherein the variables are as defined for Formula (IX).

In another embodiment of the invention, provided is a compound of Formula (IX) or (IX-a) or a pharmaceutically acceptable salt thereof, wherein $R^2$ is one of the following formulae:

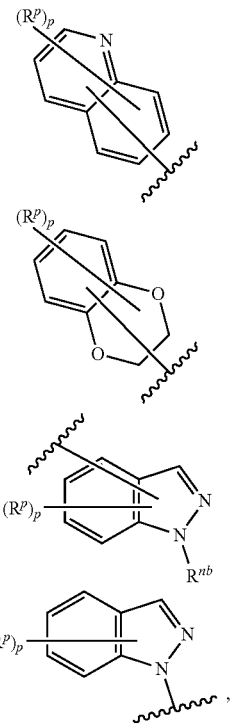

wherein each instance of $R^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of $R^p$ attached to the same or adjacent carbon atoms, taken together with the atoms to which they are attached form an optionally substituted cycloalkyl or a heterocycloalkyl;

each instance of $R^{n3}$, $R^{nc}$, and $R^{nb}$ is independently hydrogen, optionally substituted —$C_1$-$C_6$ alkyl, or a nitrogen protecting group;

each instance of $R^{o6}$ is independently hydrogen, optionally substituted —$C_1$-$C_6$ alkyl, or an oxygen protecting group;

each instance of $R^{c4}$ is independently optionally substituted —$C_1$-$C_6$ alkyl;

each instance of $R^{s2}$ is independently optionally substituted —$C_1$-$C_6$ alkyl, or a sulfur protecting group; and p is 0, 1, 2, or 3, as valency permits.

In another embodiment of the invention, provided is a compound of Formula (IX) or (IX-a) or a pharmaceutically acceptable salt thereof, wherein R2 is one of the following formulae:

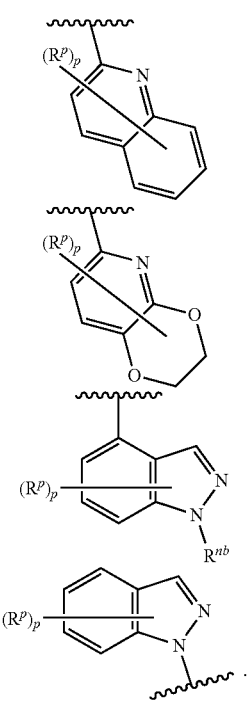

In another embodiment of the invention, provided is a compound of Formula (IX) or (IX-a) or a pharmaceutically acceptable salt thereof, wherein p is 1.

In another embodiment of the invention, provided is a compound of Formula (X) or (X-a) or pharmaceutically acceptable salt thereof:

(X)
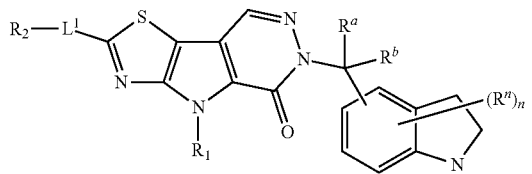

(X-a)
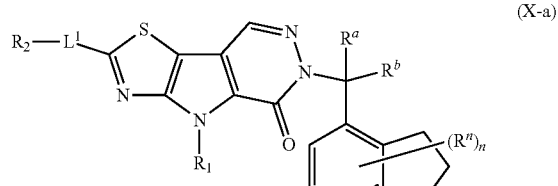

wherein each instance of $R^{n8}$ is independently hydrogen, optionally substituted —$C_1$-$C_6$ alkyl, or a nitrogen protecting group; $R^n$ and n are as described for the fifth embodiment; and the remainder of the variables are defined as for Formula (II). In certain embodiments, $R^{n8}$ is hydrogen. In certain embodiments, $R^{n8}$ is optionally substituted —$C_1$-$C_6$ alkyl. In certain embodiments, $R^{n8}$ is —$C_1$-$C_6$ alkyl (e.g. methyl, ethyl, propyl or isopropyl). In certain embodiments, $R^{n8}$ is substituted —$C_1$-$C_6$ alkyl (e.g. haloalkyl or hydroxylalkyl). In certain embodiments, $R^{n8}$ is a nitrogen protecting group.

In another embodiment of the invention, provided is a compound of Formula (VII), Formula (VII-a), Formula (VIII), or Formula (VIII-a) or pharmaceutically acceptable salt thereof:

(VII)
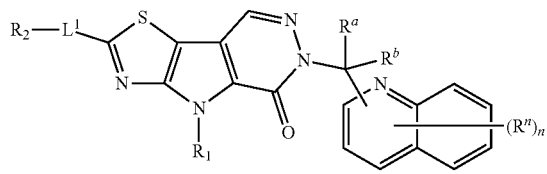

(VII-a)
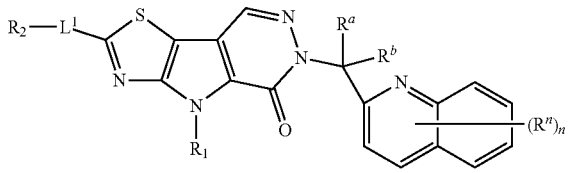

(VIII)
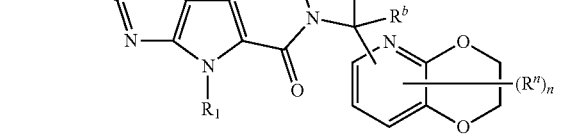

(VIII-a)
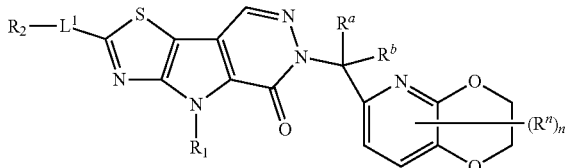

wherein $R''$ and n are as defined for the fifth embodiment and the remainder of the variables are defined for the first, second, third or fourth embodiments.

In another embodiment of the invention, provided is a compound of Formula (VII), Formula (VII-a), Formula (VIII), Formula (VIII-a), Formula (X), or Formula (X-a) or a pharmaceutically acceptable salt thereof, wherein $R^2$ is one of the following formulae:

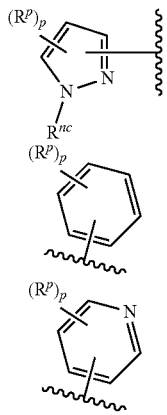

-continued

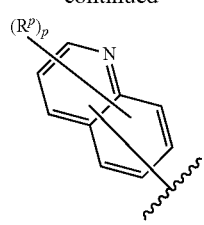

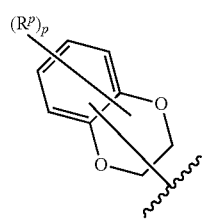

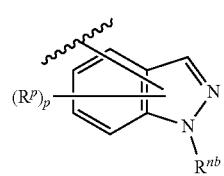

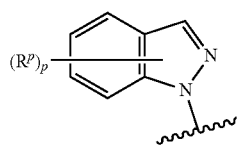

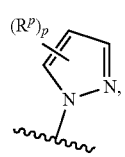

wherein $R^p$ and p are defined for the a compound of the Formula (IX) or (IX-a) or a pharmaceutically acceptable salt thereof.

In another embodiment of the invention, provided is a compound of Formula (VII), Formula (VII-a), Formula (VIII), Formula (VIII-a), Formula (X), or Formula (X-a) or a pharmaceutically acceptable salt thereof, wherein $R^2$ is one of the following formulae:

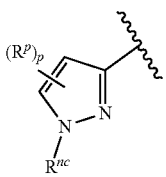

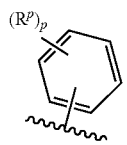

-continued

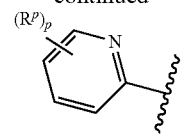

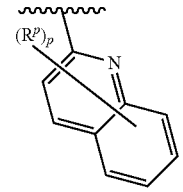

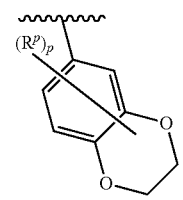

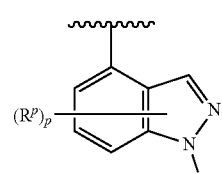

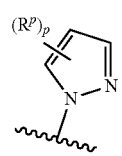

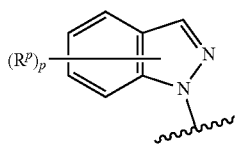

In another embodiment of the invention, provided is a compound of Formula (VII), Formula (VII-a), Formula (VIII), Formula (VIII-a), Formula (X), or Formula (X-a) or a pharmaceutically acceptable salt thereof, wherein p is 1.

In another embodiment of the invention, provided is a compound of Formula (XI) or a pharmaceutically acceptable salt thereof:

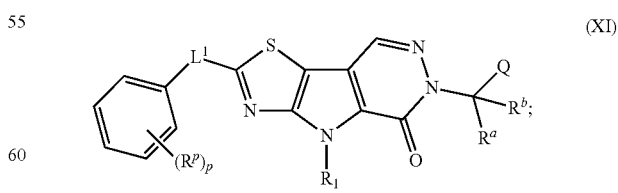

(XI)

wherein $R^p$ and p are as described in the eight embodiment, $R^a$ and $R^b$ are as described for Formula (II), and $R^1$ and Q are as described in the first, second, third or fourth embodiment.

In another embodiment of the invention, provided is a compound or a pharmaceutically acceptable salt thereof of Formula (XII):

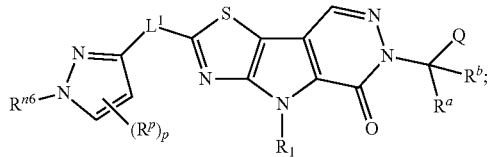
(XII)

wherein $R^{n6}$ is independently hydrogen, optionally substituted —$C_1$-$C_6$ alkyl, or a nitrogen protecting group; $R^p$ is described in the eight embodiment; q is 0, 1, 2 or 3; $R^a$ and $R^b$ are as described for Formula (II); and $R^1$ and $L^1$ are as described in the first, second, third or fourth embodiment.

In another embodiment of the invention, provided is a compound of Formula (XII-a), (XII-b) or (XII-c) or a pharmaceutically acceptable salt thereof:

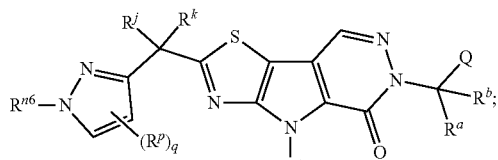
(XII-a)

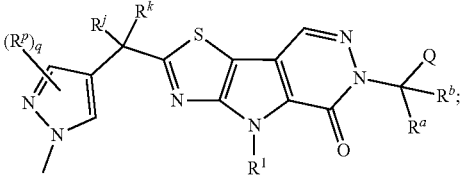
(XII-b)

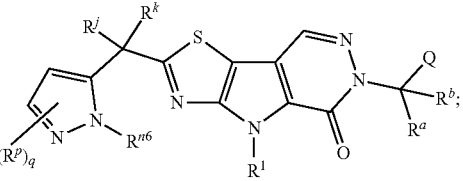
(XII-c)

wherein $R^j$ and $R^k$ are as described for formulas (III-a) and (III-b); q is 0, 1, 2 or 3; and the remainder of the variables are as defined in Formula (XII).

In another embodiment of the invention, provided is a compound or a pharmaceutically acceptable salt thereof of Formula (XIII):

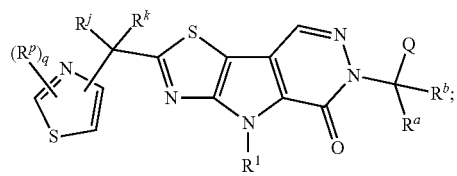
(XIII)

wherein $R^k$ are as described in the eight embodiment; q is 0, 1, 2 or 3; $R^a$ and $R^b$ are as described for Formula (II);

R and R are as described for Formulas (III-a) and (II-b); and $R^1$ and Q are as described for the first, second, third or fourth embodiments.

In another embodiment of the invention, provided is a compound or a pharmaceutically acceptable salt thereof Formula (XIII-a), (III-b) or (III-c):

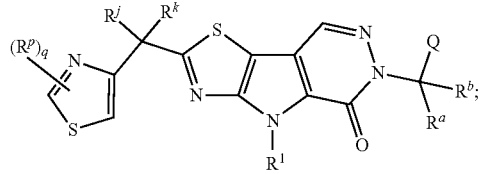
(XIII-a)

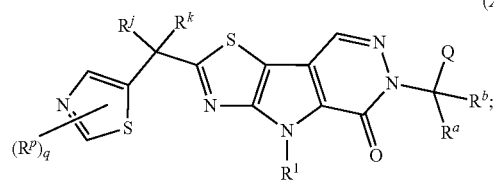
(XIII-b)

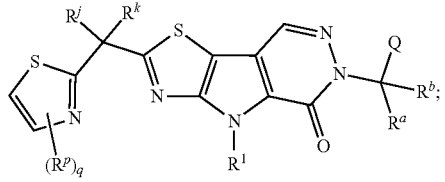
(XIII-c)

wherein the variables are as defined in Formula (XIII).

In another embodiment of the invention, provided is a compound of Formula (XIV) or a pharmaceutically acceptable salt thereof:

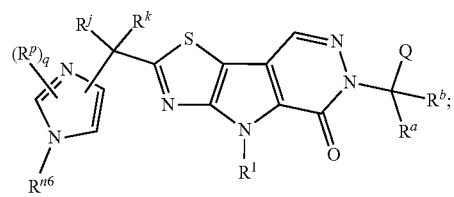
(XIV)

wherein each instance of $R^{n6}$ is independently hydrogen, optionally substituted —$C_1$-$C_6$ alkyl, or a nitrogen protecting group; and the remainder of the variables are as defined in Formula (XIII).

In another embodiment of the invention, provided is a compound or a pharmaceutically acceptable salt thereof of Formula (XIV-a), Formula (XIV-b) or (XIV-c):

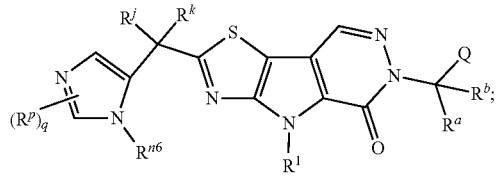
(XIV-a)

-continued (XIV-b)
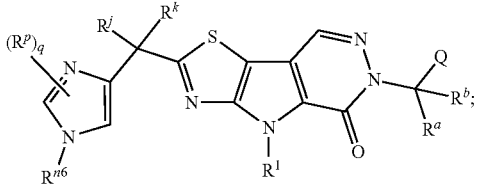

(XIV-c)
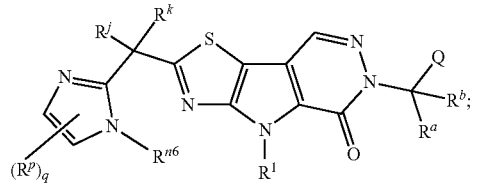

wherein the variables are as defined in Formula (XIV).

In another embodiment of the invention, provided is a compound of Formula (XV) or a pharmaceutically acceptable salt thereof:

(XV)
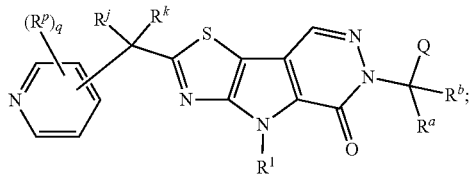

wherein the variables are as defined in Formula (XIV).

Another embodiment of the invention is a compound of Formula (XV-a), (XV-b) or (XV-c) or a pharmaceutically acceptable salt thereof:

(XV-a)
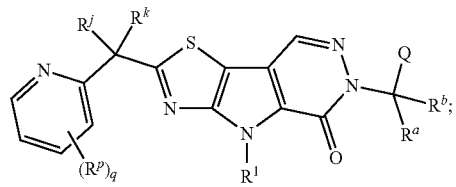

(XV-b)
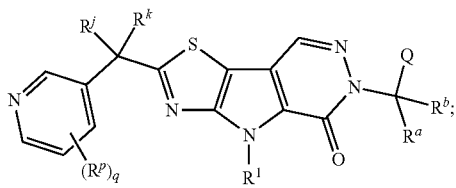

(XV-c)
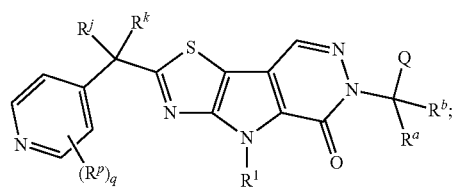

wherein the variables are as defined in Formula (XV).

In another embodiment of invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein Q is optionally substituted phenyl, optionally substituted bicyclic heteroaryl, or optionally substituted 5- to 6-membered monocyclic heterocyclyl.

In another embodiment of the invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein Q is

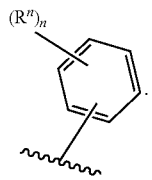

In another embodiment of the invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein $R^n$ is hydrogen, halogen, optionally substituted $C_{1-4}$ alkyl, —CN, —NO$_2$, —N$_3$, —OR$^{o4}$, —N(R$^{n2}$)$_2$, —C(=O)N(R$^{n2}$)$_2$, —C(=O)R$^{c3}$, or —C(=O)OR$^{o4}$.

In another embodiment of the invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein q is 0, 1 or 2.

In another embodiment of the invention, provided is a compound or a pharmaceutically acceptable salt thereof as described in any of the preceding embodiments, wherein $R^p$ is hydrogen, halogen, optionally substituted $C_{1-4}$ alkyl, —CN, —NO$_2$, —N$_3$, —OR$^{o4}$, —N(R$^{n2}$)$_2$, —C(=O)N(R$^{n2}$)$_2$, —C(=O)R$^{o3}$, or —C(=O)OR$^{o4}$.

In another embodiment of the invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein $R^{na}$ is hydrogen or $C_{1-4}$ alkyl.

In another embodiment of the invention, provided is a compound or a pharmaceutically acceptable salt thereof of any one of Formulas (XII), (XII-a), (XII-b), (XII-c), (XIII), (XIII-a), (XIII-b), (XIII-c), (XIV), (XIV-a), (XIV-b), (XIV-c), (XV), (XV-a), (XV), (XV-a), (XV-b), and (XV-c), wherein $R^{n6}$ is hydrogen or $C_{1-4}$ alkyl.

Figure 1B:
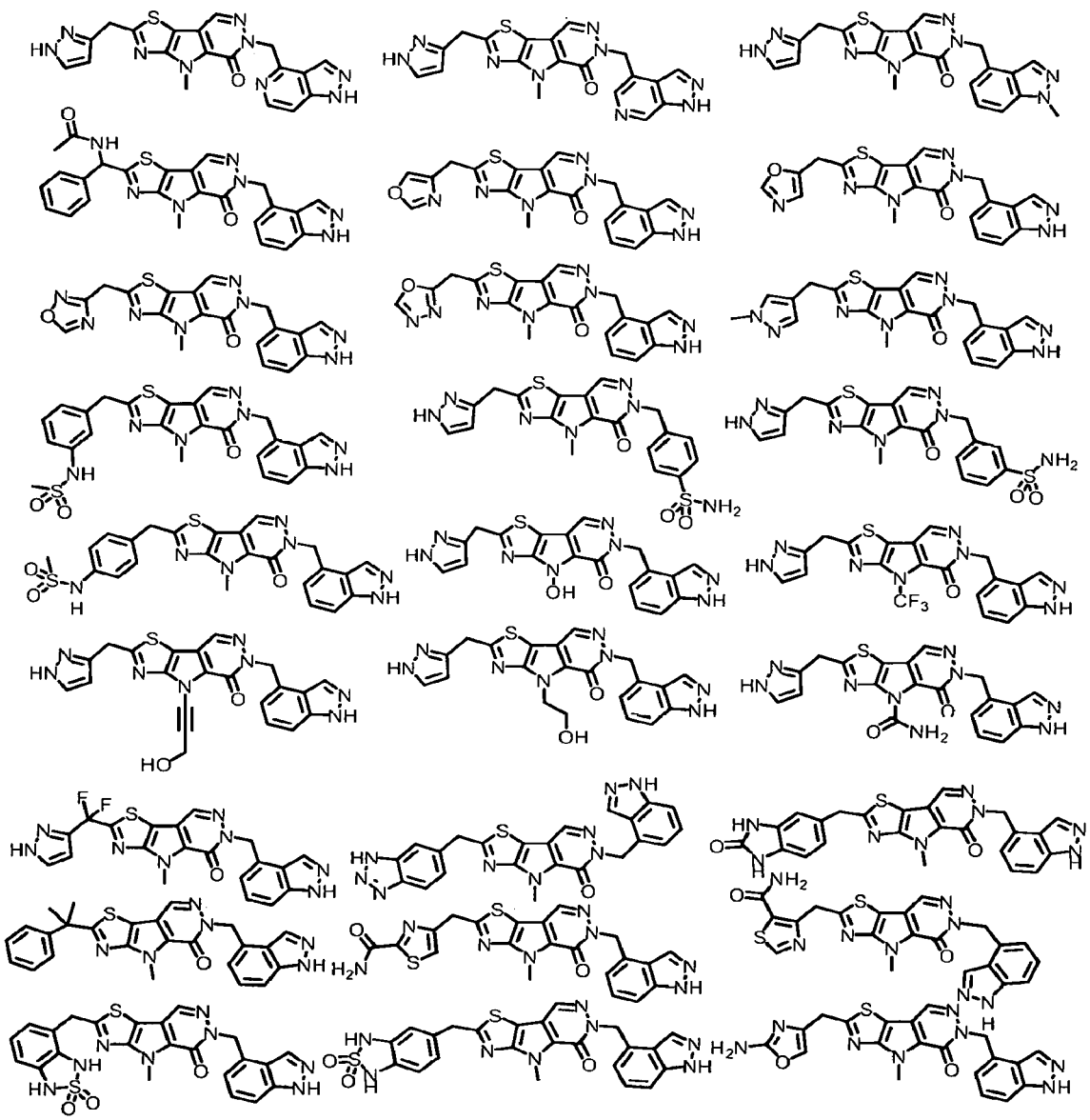
Figure 1C:
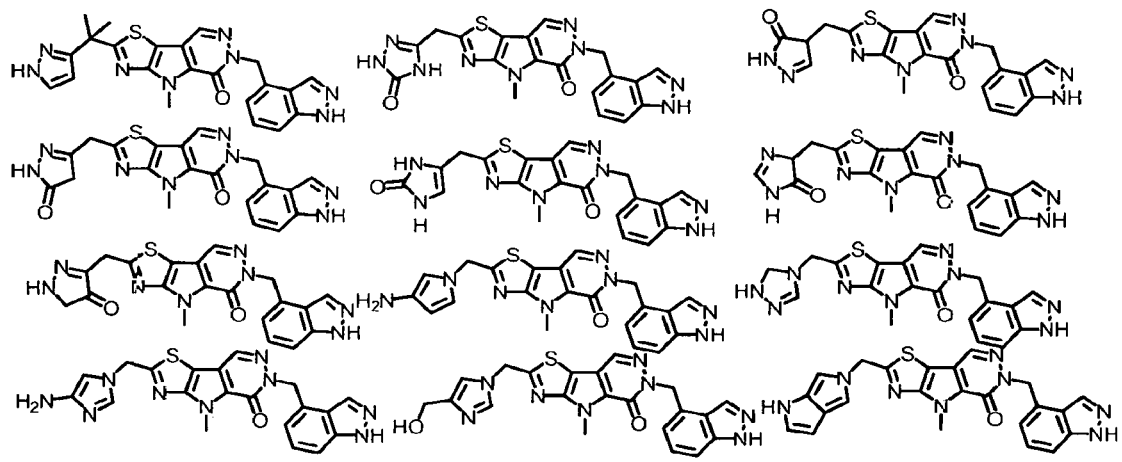
Figure 2A:
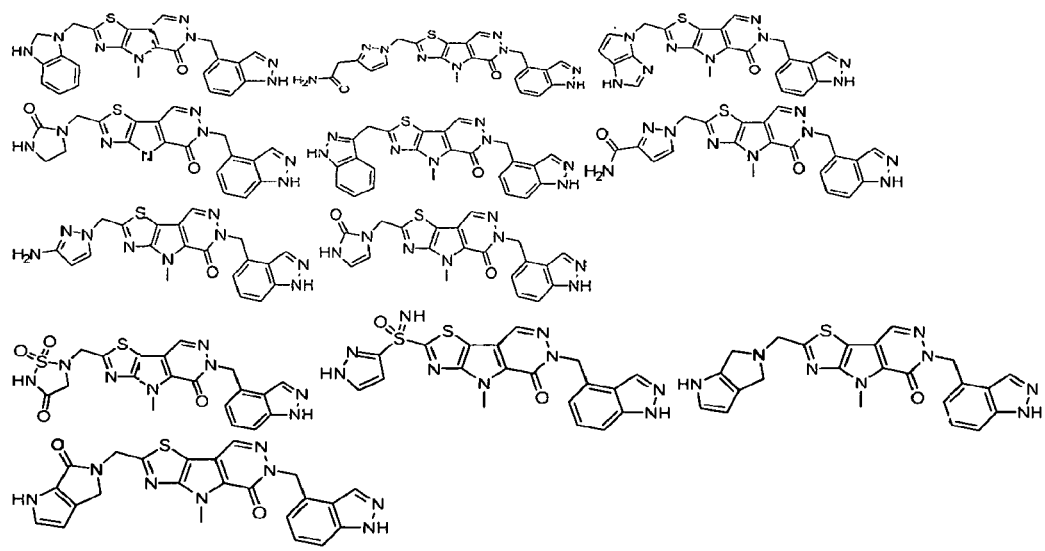
FIGS. 2A-2C are listings of the structures of other exemplary compounds of the invention.
Figure 2B:
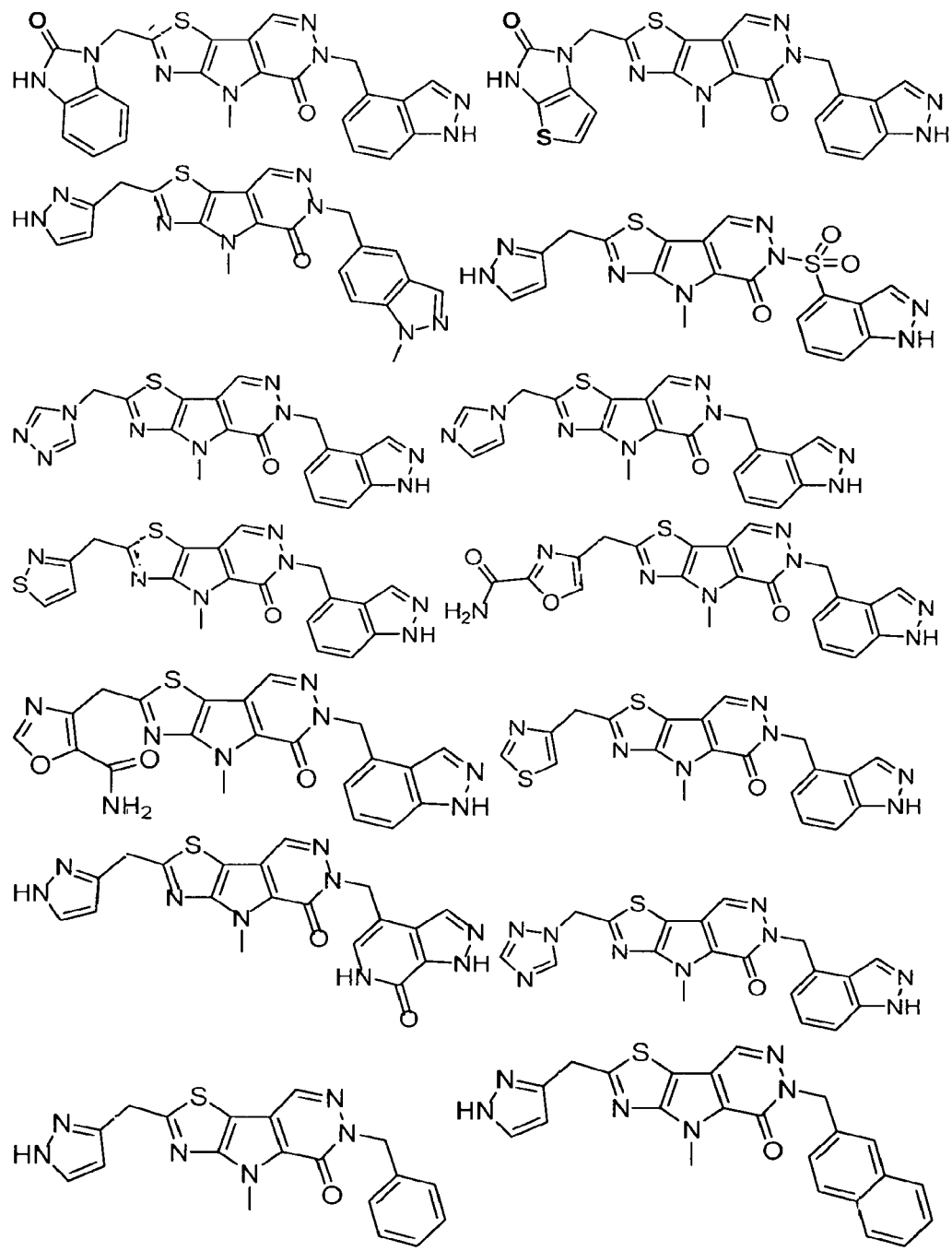
Figure 2C:
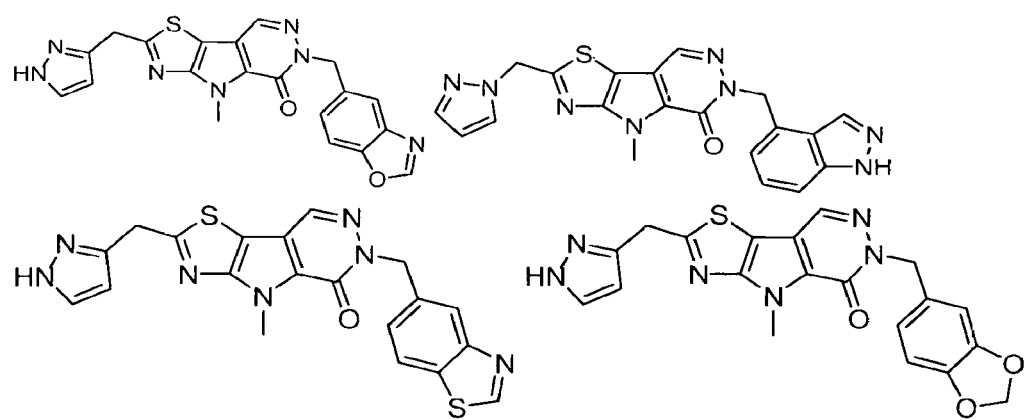
Figure 3:
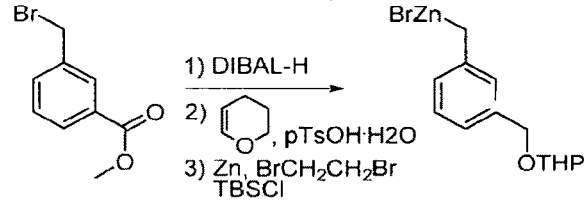
FIG. 3 shows synthesis of exemplary intermediates used in Examples 1-10.
Figure 3:
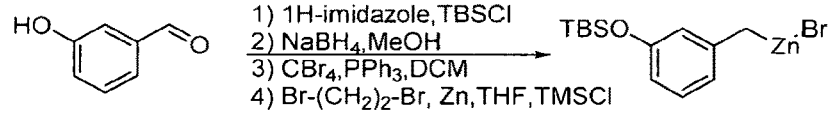
Figure 3:
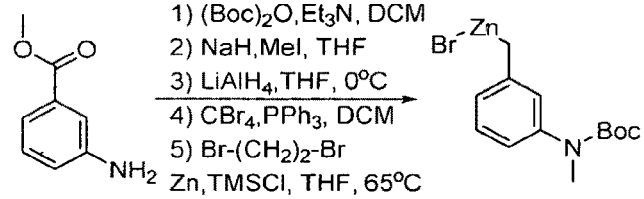
Figure 3:
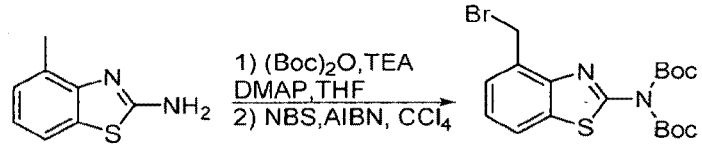
Figure 3:
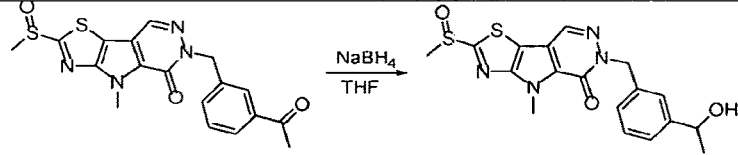
Figure 3:
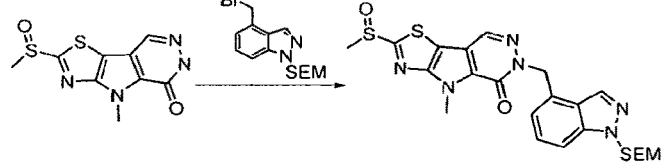
Figure 3:
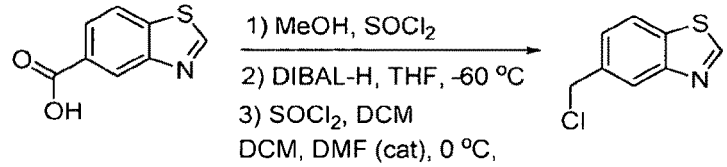

In one embodiment, the compound of pharmaceutically acceptable salt thereof is selected from the compounds of Table 1, Table 3, and FIGS. 1A-1C and 2A-2C.

In another embodiment for the compound of Formulas (I)-(XV-c), n is 0, 1, 2, or 3 as valency permits. In certain embodiments, n is 0. In certain embodiments, n is 1. In certain embodiments, n is 2. In certain embodiments, n is 3.

In another embodiment for the compound of Formulas (I)-(XV-c), p is 0, 1, 2, or 3 as valency permits. In certain embodiments, p is 0. In certain embodiments, p is 1. In certain embodiments, p is 2. In certain embodiments, p is 3.

In another embodiment for the compound of Formulas (I)-(XV-c), n and p are 0. In certain embodiments, n and p are 1. In certain embodiments, n is 0 and p are 1. In certain embodiments, n is 1 and p is 0. In certain embodiments, n is 0 and p is 2. In certain embodiments, n is 2 and p is 0.

In another embodiment for the compound of Formulas (I)-(XV-c), each $R^c$ is independently selected from halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of $R^c$ attached to the same or adjacent carbon atoms, are taken together with the carbon atoms to which they are attached form a cycloalkyl or a heterocyclyl. In certain embodiments, each $R^c$ is independently selected from halo, —$C_1$-$C_4$ alkyl, —$C_1$-$C_4$ haloalkyl, —$C_1$-$C_4$ hydroxyalkyl, —OH, —$OC_1$-$C_4$ alkyl, —NH$_2$, —CN, and —NO$_2$; or two instances of $R^c$ attached to the same or adjacent carbon atoms, are taken together with the carbon atoms to which they are attached form a cycloalkyl or a heterocyclyl.

In another embodiment for the compound of Formulas (I)-(XV-c), each $R^d$ is independently selected from halo, —$C_1$-$C_6$ alkyl, —OH, —$OC_1$-$C_6$ alkyl, —NH$_2$ and —CN; In certain embodiments each $R^d$ is independently selected from halo, —$C_1$-$C_4$ alkyl, OH, —$OC_1$-$C_4$ alkyl, —NH$_2$ and —CN.

In another embodiment for the compound of Formulas (I)-(XV-c), each $R^e$ is independently selected from halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of $R^e$ attached to the same or adjacent carbon atoms, are taken together with the carbon atoms to which they are attached form a cycloalkyl or a heterocyclyl. In certain embodiments each $R^e$ is independently selected from halo, —$C_1$-$C_4$ alkyl, —$C_1$-$C_4$ haloalkyl, —$C_1$-$C_4$ alkoxy, —OH, —NH$_2$, —CN and —NO$_2$; or two instances of $R^e$ attached to the same or adjacent carbon atoms are taken together with the carbon atoms to which they are attached to form a cycloalkyl or a heterocyclyl.

In another embodiment for the compound of Formulas (I)-(XV-c), each $R^f$ is independently selected from halo, —$C_1$-$C_6$ alkyl, —$C_1$-$C_6$ haloalkyl, —$C_1$-$C_6$ alkoxy, —OH, NH$_2$, —CN and NO$_2$. In certain embodiments each $R^f$ is independently selected from halo, —$C_1$-$C_4$ alkyl, —$C_1$-$C_4$ haloalkyl, —$C_1$-$C_4$ alkoxy, —OH, NH$_2$, —CN and NO$_2$.

In another embodiment for the compound of Formulas (I)-(XV-c), each $R^g$ is independently selected from halo, —$C_1$-$C_6$ alkyl, —$C_1$-$C_6$ haloalkyl, —$C_1$-$C_6$ alkoxy, —OH, —NH$_2$, —CN and —NO$_2$. In certain embodiments each $R^g$ is independently selected from halo, —$C_1$-$C_4$ alkyl, —$C_1$-$C_4$ haloalkyl, —$C_1$-$C_4$ alkoxy, —OH, NH$_2$, —CN and NO$_2$.

In another embodiment for the compound of Formulas (I)-(XV-c), each $R^h$ is independently selected from halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$, S(=O)$_2$aryl, S(=O)$_2$heteroaryl and =NOH or two instances of $R^h$ attached to the same or adjacent carbon atoms, are taken together with the carbon atoms to which they are attached form a cycloalkyl or a heterocyclyl. In certain embodiments each $R^h$ is independently selected from halo, —OH, —NH$_2$, —$C_1$-$C_4$ alkyl, —$C_1$-$C_4$ haloalkyl, —$C_1$-$C_4$ hydroxyalkyl, —$OC_1$-$C_4$ alkyl, —C(=O)$C_1$-$C_4$ alkyl, —C(=O)OH, —C(=O)NH$_2$, —NHC(=O)$C_1$-$C_4$ alkyl, —S(=O)$_2$aryl, S(=O)$_2$heteroaryl and =NOH.

In another embodiment for the compound of Formulas (I)-(XV-c), each instance of $R^n$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —$OR^{o4}$, —$SR^{s1}$, —N($R^{n2}$)$_2$, —C(=O)N($R^{n2}$)$_2$, —N($R^{n2}$)C(=O)$R^{c3}$, —C(=O)$R^{c3}$, —C(=O)O$R^{o4}$, —OC(=O)$R^{c3}$, —S(=O)$R^{s1}$, —S(=O)$_2$$R^{s1}$, —S(=O)O$R^{o4}$, —OS(=O)$R^{c3}$, —S(=O)$_2$O$R^{o4}$, —OS(=O)$_2$$R^{c3}$, —S(=O)N($R^{n2}$)$_2$, —S(=O)$_2$N($R^{n2}$)$_2$, —N($R^{n2}$)S(=O)$R^{s1}$, —N($R^{n2}$)S(=O)$_2$$R^{s1}$, —N($R^{n2}$)C(=O)O$R^{o4}$, —OC(=O)N($R^{n2}$)$_2$, —N($R^{n2}$)C(=O)N($R^{n2}$)$_2$, —N($R^{n2}$)S(=O)N($R^{n2}$)$_2$, —N($R^{n2}$)S(=O)O$R^{o4}$, —N($R^{n2}$)S(=O)$_2$N($R^{n2}$)$_2$, —N($R^{n2}$)S(=O)O$R^{o4}$, —N($R^{n2}$)S(=O)$_2$O$R^{o4}$, —OS(=O)N($R^{n2}$)$_2$, —OS(=O)$_2$N($R^{n2}$)$_2$, or two instances of $R^n$ attached to the same or adjacent carbon atoms, taken together with the atoms to which they are attached form an optionally substituted cycloalkyl or a heterocycloalkyl.

In another embodiment for the compound of Formulas (I)-(XV-c), $R^n$ is independently selected from hydrogen, halo, —CN, —NO$_2$, —N$_3$, —$C_1$-$C_6$ alkyl, —$C_1$-$C_6$ haloalkyl, —$C_1$-$C_6$ hydroxyalkyl, —$C_2$-$C_6$ alkenyl, —$C_2$-$C_6$ alkynyl, —$C_1$-$C_6$ aminoalkyl, $C_{3-8}$ monocyclic cycloalkyl, aryl (e.g., phenyl), $C_{5-8}$ monocyclic heterocyclyl, $C_{5-6}$ monocyclic heteroaryl, —$OR^{o4}$, —$SR^{s1}$, —N($R^{n2}$)$_2$, —C(=O)N($R^{n2}$)$_2$, —N($R^{n2}$)C(=O)$R^{c3}$, —C(=O)$R^{c3}$, —C(=O)O$R^{o4}$, —OC(=O)$R^{c3}$, —S(=O)$R^{s1}$, —S(=O)$_2$$R^{s1}$, —S(=O)O$R^{o4}$, —OS(=O)$R^{c3}$, —S(=O)$_2$O$R^{o4}$, —OS(=O)$_2$$R^{c3}$, —S(=O)N($R^{n2}$)$_2$, —S(=O)$_2$N($R^{n2}$)$_2$, —N($R^{n2}$)S(=O)$R^{s1}$, —N($R^{n2}$)S(=O)$_2$R1, —N($R^{n2}$)C(=O)O$R^{o4}$, —OC(=O)N($R^{n2}$)$_2$, —N($R^{n2}$)C(=O)N($R^{n2}$)$_2$, —N($R^{n2}$)S(=O)N($R^{n2}$)$_2$, —N($R^{n2}$)S(=O)$_2$N($R^{n2}$)$_2$, —N($R^{n2}$)S(=O)O$R^{o4}$, —N($R^{n2}$)S(=O)$_2$O$R^{o4}$, —OS(=O)N($R^{n2}$)$_2$, —OS(=O)$_2$N($R^{n2}$)$_2$, or two instances of $R^n$ attached to the same or adjacent carbon atoms, taken together with the atoms to which they are attached form an optionally substituted cycloalkyl or a heterocycloalkyl. In certain embodiments each alkyl, alkenyl, alkynyl, cycloalkyl, aryl, heterocyclyl and heteroaryl group of $R^n$ is substituted with 0-3 occurrences of halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-

$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$.

In another embodiment for the compound of Formulas (I)-(XV-c), $R''$ is independently selected from halo, —$C_1$-$C_6$ alkyl, —$C_1$-$C_6$ haloalkyl, —$C_1$-$C_6$ hydroxyalkyl, —OH, —O$C_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of $R''$ attached to the same or adjacent carbon atoms, are taken together with the carbon atoms to which they are attached form a cycloalkyl or a heterocyclyl. In certain embodiments, $R''$ is independently selected from —$C_1$-$C_4$ alkyl, —$C_1$-$C_4$ haloalkyl, —$C_1$-$C_4$ hydroxyalkyl, —$C_1$-$C_4$ aminoalkyl, —OH, —O$C_1$-$C_4$ alkyl, —NH$_2$, —CN and —NO$_2$. In certain embodiments, $R''$ is hydrogen, halogen, —CN, —NO$_2$, —N$_3$, —OR$^{o4}$, —N(R$^{n2}$)$_2$, optionally substituted $C_1$-$C_6$ alkyl, —C(=O)N(R$^{n2}$)$_2$, —C(=O)R$^{c3}$, or —C(=O)OR$^{o4}$. In certain embodiments, $R''$ is hydrogen. In certain embodiments, $R''$ is halogen (e.g. F, Cl, Br, or I). In certain embodiments, $R''$ is —CN. In certain embodiments, $R''$ is —OR$^{o4}$ (e.g. —OH or —OCH$_3$). In certain embodiments, $R''$ is —N(R$^{n2}$)$_2$. In certain embodiments, $R''$ is —NHR$^{n2}$. In certain embodiments, $R''$ is NH$_2$. In certain embodiments, $R''$ is —$C_{1-6}$ alkyl (e.g. methyl, ethyl, n-propyl, or iso-propyl). In certain embodiments, $R''$ is substituted —$C_{1-6}$ alkyl. In certain embodiments, $R''$ is optionally substituted —$C_{1-6}$ haloalkyl. In certain embodiments, $R''$ is —$C_{1-6}$ alkyl substituted with 1-3 occurrences of hydroxyl or —$C_{1-6}$ alkoxy. In certain embodiments, $R''$ is —$C_{1-6}$ alkyl substituted with 1-3 occurrences of optionally substituted aryl (e.g. phenyl). In certain embodiments, $R''$ is —$C_{1-6}$ alkyl substituted with 1-3 occurrences of optionally substituted heteroaryl.

In another embodiment for the compound of Formulas (I)-(XV-c), each instance of $R^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$—N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$— or two instances of $R^p$ attached to the same or adjacent carbon atoms, taken together with the atoms to which they are attached form an optionally substituted cycloalkyl or a heterocycloalkyl.

In certain embodiments $R^p$ is independently selected from hydrogen, halo, —CN, —NO$_2$, —N$_3$, —$C_1$-$C_6$ alkyl, —$C_1$-$C_6$ haloalkyl, —$C_1$-$C_6$ hydroxyalkyl, —$C_2$-$C_6$ alkenyl, —$C_2$-$C_6$ alkynyl, —$C_1$-$C_6$ aminoalkyl, $C_{3-8}$ monocyclic cycloalkyl, aryl (e.g., phenyl), $C_{5-8}$ monocyclic heterocyclyl, $C_{5-6}$ monocyclic heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^4$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$—N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of $R^p$ attached to the same or adjacent carbon atoms, taken together with the atoms to which they are attached form an optionally substituted cycloalkyl or a heterocycloalkyl. In certain embodiments each alkyl, alkenyl, alkynyl, cycloalkyl, aryl, heterocyclyl and heteroaryl group of $R^p$ is substituted with 0-3 occurrences of halo, —$C_1$-$C_6$ alkyl, —$C_1$-$C_6$ haloalkyl, —$C_1$-$C_6$ hydroxyalkyl, —OH, —O$C_1C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$ In another embodiment for the compound of Formulas (I)-(XV-c), $R^p$ is independently selected from halo, —$C_1$-$C_6$ alkyl, —$C_1$-$C_6$ haloalkyl, —$C_1$-$C_6$ hydroxyalkyl, —OH, —O$C_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of $R^p$ attached to the same or adjacent carbon atoms, are taken together with the carbon atoms to which they are attached form a cycloalkyl or a heterocyclyl. In certain embodiments $R^p$ is independently selected from —$C_1$-$C_4$ alkyl, —$C_1$-$C_4$ haloalkyl, —$C_1$-$C_4$ hydroxyalkyl, —$C_1$-$C_4$ aminoalkyl, —OH, —O$C_1$-$C_4$ alkyl, —NH$_2$, —CN and —NO$_2$. In certain embodiments, $R^p$ is hydrogen, halogen, —CN, —NO$_2$, —N$_3$, —OR$^{o6}$, —N(R$^{n3}$)$_2$, optionally substituted $C_1$-$C_6$ alkyl, —C(=O)N(R$^{n3}$)$_2$, —C(=O)R$^{c4}$, or —C(=O)OR$^{o6}$. In certain embodiments, $R^p$ is hydrogen. In certain embodiments, $R^p$ is halogen (e.g. F, Cl, Br, or I). In certain embodiments, $R^p$ is —CN. In certain embodiments, $R^p$ is —OR$^{o6}$ (e.g. —OH or —OCH$_3$). In certain embodiments, $R^p$ is —N(R$^{n3}$)$_2$. In certain embodiments, $R^p$ is —NHR$^{n3}$. In certain embodiments, $R^p$ is —NH$_2$. In certain embodiments, $R^p$ is —$C_{1-6}$ alkyl (e.g. methyl, ethyl, n-propyl, or iso-propyl). In certain embodiments, $R^p$ is substituted —$C_{1-6}$ alkyl. In certain embodiments, $R^p$ is optionally substituted —$C_{1-6}$ haloalkyl. In certain embodiments, $R^p$ is —$C_{1-6}$ alkyl substituted with 1-3 occurrences of hydroxyl or —$C_{1-6}$ alkoxy. In certain embodiments, $R^p$ is —$C_{1-6}$ alkyl substituted with 1-3 occurrences of optionally substituted aryl (e.g. phenyl). In certain embodiments, $R^p$ is —$C_{1-6}$ alkyl substituted with 1-3 occurrences of optionally substituted heteroaryl.

In another embodiment for the compound of Formulas (I)-(XV-c), each instance of $R^{na}$, $R^{nb}$, $R^{nc}$, $R^{nd}$, $R^{n1}$, $R^{n2}$, $R^{n3}$, $R^{n6}$, $R^{n7}$, $R^{n8}$ and $R^{n9}$ is independently hydrogen, optionally substituted —$C_1$-$C_6$ alkyl, or a nitrogen protecting group. In certain embodiments, at least one instance of $R^{na}$, $R^{nb}$, $R^{nc}$, $R^{nd}$, $R^{n1}$, $R^{n2}$, $R^{n3}$, $R^{n6}$, $R^{n7}$ $R^{n8}$ and $R^{n9}$ is hydrogen. In certain embodiments, at least one instance of $R^{na}$, $R^{nb}$, $R^{nc}$, $R^{nd}$, $R^{n1}$, $R^{n2}$, $R^{n3}$, $R^{n6}$, $R^{n7}$ $R^{n8}$ and $R^{n9}$ is optionally substituted —$C_1$-$C_6$ alkyl (e.g. with 1-3 occurrences of halo and/or hydroxy). In certain embodiments, at least one instance $R^{na}$, $R^{nb}$, $R^{nc}$, $R^{nd}$, $R^{n1}$, $R^{n2}$, $R^{n3}$, $R^{n6}$, $R^{n7}$ $R^{n8}$ and $R^{n9}$ is —$C_1$-$C_6$ alkyl (e.g. methyl, ethyl, propyl or isopropyl). In certain embodiments, at least one instance of $R^{na}$, $R^{nb}$, $R^{nc}$, $R^{nd}$, $R^{n1}$, $R^{n2}$, $R^{n3}$, $R^{n6}$, $R^{n7}$ $R^{n8}$ and $R^{n9}$ is methyl.

In another embodiment for the compound of Formulas (I)-(XV-c), $R^{n5}$ and $R^{jn}$ are independently hydrogen, optionally substituted —$C_1$-$C_6$ alkyl, —$OR^{o8}$, or a nitrogen protecting group. In certain embodiments at least one instance of $R^{n5}$ and $R^{jn}$ is hydrogen. In certain embodiments at least one instance of $R^{n5}$ and $R^{jn}$ is optionally substituted —$C_1$-$C_6$ alkyl (e.g. with 1-3 instances of halo and/or hydroxy). In certain embodiments at least one instance of $R^{n5}$ and $R^{jn}$ is —$C_1$-$C_6$ alkyl (e.g. methyl, ethyl, propyl, isopropyl).

In another embodiment for the compound of Formulas (I)-(XV-c), each instance of $R^a$ and $R^b$ is independently hydrogen, halogen, —CN, —$NO_2$, —$N_3$, optionally substituted alkyl, —$OR^{o3}$, —$N(R^{n1})_2$, —$C(=O)N(R^{n1})_2$, or —$C(=O)R^{c2}$, or $R^a$ and $R^b$ can be taken together with the carbon atom to form optionally substituted cycloalkyl or optionally substituted heterocyclyl. In certain embodiments, $R^a$ is hydrogen. In certain embodiments, $R^a$ is halogen (e.g. F, Cl, Br, or I). In certain embodiments, $R^a$ is optionally substituted alkyl. In certain embodiments, $R^a$ is —$C_{1-6}$ alkyl (e.g. methyl or ethyl). In certain embodiments, $R^a$ is —$OR^{o3}$ (e.g. —OH). In certain embodiments, $R^b$ is hydrogen. In certain embodiments, $R^b$ is halogen (e.g. F, Cl, Br, or I). In certain embodiments, $R^b$ is optionally substituted alkyl. In certain embodiments, $R^b$ is —$C_{1-6}$ alkyl (e.g. methyl or ethyl). In certain embodiments, $R^b$ is —$OR^{o3}$ (e.g. —OH). In certain embodiments, $R^a$ and $R^b$ are both hydrogen. In certain embodiments, $R^a$ is hydrogen and $R^b$ is halogen. In certain embodiments, $R^a$ is hydrogen and $R^b$ is —$OR^{o3}$. In certain embodiments, $R^a$ is halogen (e.g. F) and $R^b$ is halogen (e.g. F). In certain embodiments, $R^a$ is halogen and $R^b$ is —$OR^{o3}$.

In another embodiment for the compound of Formulas (I)-(XV-c), $L^1$ is a bond, optionally substituted alkylene, —O—, —S—, —S—$CH_2$—, —S(=O)$CH_2$—, —S(=O)$_2CH_2$—, —$NR^3$—, —$NR^3C$(=O)—, —C(=O)$NR^3$—, —C(=O)—, —OC(=O)—, —C(=O)O—, —$NR^3$C(=O)O—, —OC(=O)$NR^3$—, —$NR^3$C(=O)$NR^3$—, —OC($R^4$)$_2$—, —C($R^4$)$_2$O—, —$NR^3$C($R^4$)$_2$—, —C($R^4$)$_2NR^3$—, —S(=O)$_2$—, —S(=O)—, —S(=O)$_2$O—, —OS(=O)$_2$—, —S(=O)O—, —OS(=O)—, —S(=O)$_2NR^3$—, —$NR^3$S(=O)$_2$—, —S(=O)$NR^3$—, —$NR^3$S(=O)—, —$NR^3$S(=O)$_2$O—, —OS(=O)$_2NR^3$—, —$NR^3$S(=O)O—, —OS(=O)$NR^3$—, or —S(=O)(=$NR^3$)—, wherein the point of the attachment to $R^2$ is on the left-hand side. In certain embodiments, $L^1$ is a bond, optionally substituted $C_{1-6}$ alkylene, —C(=O)—, —S(=O)—, —S(=O)$_2$—, —$NR^3$C(=O)—, or —C(=O)$NR^3$—. In one embodiment, $L^1$ is optionally substituted $C_{1-6}$ alkylene. In a further embodiment $L^1$ is $C_{1-6}$ alkylene. In a further embodiment, $L^1$ is —$CH_2$—, —(CH$_2$)$_2$—, or —(CH$_2$)$_3$—. In certain embodiments, $L^1$ is $C_{1-6}$ alkylene substituted with $R^j$ and $R^k$, wherein each instance of $R^j$ and $R^k$ is independently selected from H, halogen, —CN, —$OR^{o7}$, —$N(R^{n5})_2$, —$N(R^{n5})$C(=O) $R^{c5}$, —C(=O)N($R^{n5}$)$_2$, —C(=O)$R^{c5}$, —C(=O)$OR^{o7}$, —$SR^{js}$, —S(=O)$_2R^{js}$, or —S(=O)$R^{js}$, optionally substituted —$C_1$-$C_6$ alkyl; or $R^j$ and $R^k$ can be taken together with the carbon atom to form C=O, C=$NR^{jn}$, an optionally substituted $C_3$-$C_6$ monocyclic cycloalkyl ring or an optionally substituted $C_3$-$C_6$ monocyclic heterocyclyl ring; each of $R^{n5}$ and $R^{jn}$ is independently hydrogen, optionally substituted —$C_1$-$C_6$ alkyl, —$OR^{o8}$, or a nitrogen protecting group; each instance of $R^{o7}$ is independently hydrogen, optionally substituted —$C_1$-$C_6$ alkyl, or an oxygen protecting group; each instance of $R^{c5}$ is independently optionally substituted —$C_1$-$C_6$ alkyl; and each instance of $R^{js}$ is independently optionally substituted —$C_1$-$C_6$ alkyl, optionally substituted $C_{6-12}$ aryl, optionally substituted heteroaryl, or a sulfur protecting group.

In another embodiment for the compound of Formulas (I)-(XV-c), $R^j$ and $R^k$ are hydrogen. In certain embodiments, $R^j$ is hydrogen and $R^k$ is halogen (e.g. F, Cl, Br, or I). In certain embodiments, $R^j$ is halogen (e.g. F, Cl, Br, or I) and $R^k$ is halogen (e.g. F, Cl, Br, or I). In a further embodiment, $R^j$ and $R^k$ are both halogen. In one embodiment, $R^j$ and $R^k$ are both F. In certain embodiments, $R^j$ is hydrogen and $R^k$ is optionally substituted —$C_1$-$C_6$ alkyl. In certain embodiments, $R^j$ is hydrogen and $R^k$ is —$C_1$-$C_6$ alkyl (e.g. methyl, ethyl, n-propyl, or iso-propyl). In certain embodiments, $R^j$ is hydrogen and $R^k$ is —$OR^{o7}$, —$N(R^{n5})_2$, —$C(=O)OR^{o7}$, —C(=O)N($R^{n5}$)$_2$, —CN, or —S(=O)$_2R^{js}$. In certain embodiments, $R^j$ is hydrogen; $R^k$ is —C(=O)$R^{c5}$, and $R^{c5}$ is —$C_{1-6}$ alkyl. In certain embodiments, $R^j$ is hydrogen; and $R^k$ is —C(=O)N($R^{n5}$)$_2$. In certain embodiments, $R^j$ is hydrogen; and $R^k$ is —C(=O)$OR^{o6}$. In certain embodiments, $R^j$ is hydrogen; and $R^k$ is —$OR^{o6}$. In certain embodiments, $R^j$ is hydrogen; and $R^k$ is —$N(R^{n5})_2$ or —$NHR^{n5}$. In certain embodiments, $R^j$ is hydrogen; and $R^k$ is —$SR^{s1}$, —$SO_2R^{s1}$, or —$SOR^{s1}$, and $R^{s1}$ is hydrogen, optionally substituted —$C_{1-6}$ alkyl, optionally substituted aryl, optionally substituted heteroaryl, or a sulfur protecting group. In certain embodiments $R^j$ is hydrogen and $R^k$ is —$N(R^{n5})_2$ or —$N(R^{n5})$C(=O)$R^{c5}$ wherein $R^{n5}$ is H. In certain embodiments, $R^j$ is —$OR^{o7}$, and $R^k$ is optionally substituted —$C_1$-$C_6$ alkyl, —$OR^{o7}$, —$N(R^{n5})_2$, —C(=O)$OR^{o7}$, —C(=O)N($R^{n5}$)$_2$, —CN, or —S(=O)$_2R^{js}$. In certain embodiments, $R^j$ is —$OR^{o7}$ and $R^k$ is —$C_1$-$C_6$ alkyl (e.g. methyl, ethyl, n-propyl, or iso-propyl). In certain embodiments, $R^j$ and $R^k$ can be taken together with the carbon atom to form C=O. In certain embodiments, $R^j$ and $R^k$ can be taken together with the carbon atom to form an optionally substituted $C_3$-$C_6$ monocyclic cycloalkyl ring.

In another embodiment for the compound of Formulas (I)-(XV-c), $L^1$ is a bond,

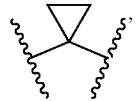 [SMILES: *C1(*)CC1]

—OC(=O)—, —C(=O)O—, —CH(OH)—, —CH(CH$_3$)—, —CH(NH$_2$)—, —CH(NHCOCH$_3$)—, —CH(OH)(CH$_3$)—, —CH(CO$_2$CH$_3$)—, —CH(CN)—, —C(OH)(CONH$_2$)—, —CH(CONH$_2$)—, —CF$_2$—, —C(CH$_3$)$_2$—, —NH—, —CH(SO$_2$Ph)-, —C(=O)NH—, —NHC(=O)—, —SO$_2$—, —S(=O)—, —S(=O)(=NH)—, —SO$_2$NH—, —NHSO$_2$—, —C(=O)—, —C(=N)OH—, —S—, or —O—.

In another embodiment for the compound of Formulas (I)-(XV-c), each instance of $R^3$ is independently hydrogen, —$OR^{o2}$, optionally substituted alkyl, optionally substituted alkenyl, optionally substituted alkynyl, optionally substituted cycloalkyl, optionally substituted heterocyclyl, optionally substituted aryl, optionally substituted heteroaryl, or a nitrogen protecting group. In certain embodiments, $R^3$ is hydrogen. In certain embodiments, $R^3$ is —$OR^{o2}$, wherein $R^{o2}$ is hydrogen, optionally substituted —$C_{1-6}$ alkyl, or an oxygen protecting group. In certain embodiments, $R^3$ is —OH. In certain embodiments, $R^3$ is —$OR^{o2}$, wherein $R^{o2}$ is —$C_{1-6}$ alkyl (e.g. methyl, ethyl, n-propyl, or iso-propyl). In certain embodiments, $R^3$ is —$C_{1-6}$ alkyl (e.g. methyl, ethyl, n-propyl, or iso-propyl). In certain embodiments, $R^3$ is substituted —$C_{1-6}$ alkyl (e.g. haloalkyl). In certain embodiments, $R^3$ is a nitrogen-protecting group.

In another embodiment for the compound of Formulas (I)-(XV-c), each instance of $R^4$ is independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl. In certain embodiments, $R^4$ is hydrogen. In certain embodiments, $R^4$ is —$C_{1-6}$ alkyl (e.g. methyl, ethyl, n-propyl, or iso-propyl). In certain embodiments, $R^4$ is substituted —$C_{1-6}$ alkyl (e.g. haloalkyl). In certain embodiments, $R^4$ is optionally substituted cycloalkyl. In certain embodiments, $R^4$ is optionally substituted heterocyclyl. In certain embodiments, $R^4$ is optionally substituted aryl. In certain embodiments, $R^4$ is optionally substituted heteroaryl.

In another embodiment for the compound of Formulas (I)-(XV-c), each instance of $R^{o1}$, $R^{o2}$, $R^{o3}$, $R^{o4}$, $R^{o5}$, $R^{o6}$, $R^{o7}$, and $R^{o8}$ is independently hydrogen, optionally substituted alkyl, or an oxygen protecting group.

In another embodiment for the compound of Formulas (I)-(XV-c), each instance of $R^{o1}$, $R^{o2}$, $R^{o3}$, $R^{o4}$, $R^{o5}$, $R^{o6}$, $R^{o7}$, and $R^{o8}$ is independently hydrogen, optionally substituted $C_1$-$C_6$-alkyl, or an oxygen protecting group. In certain embodiments, at least one instance of $R^{o1}$, $R^{o2}$, $R^{o3}$, $R^{o4}$, $R^{o5}$, $R^{o6}$, $R^{o7}$, and $R^{o8}$ is independently hydrogen. In certain embodiments, at least one instance of $R^{o1}$, $R^{o2}$, $R^{o3}$, $R^{o4}$, $R^{o5}$, $R^{o6}$, $R^{o7}$, and $R^{o8}$ is independently optionally substituted —$C_{1-6}$ alkyl (e.g. with 1-3 instances of halo and/or hydroxyl). In certain embodiments at least one instance of $R^{o1}$, $R^{o2}$, $R^{o3}$, $R^{o4}$, $R^{o5}$, $R^{o6}$, $R^{o7}$, and $R^{o8}$ is —$C_{1-6}$ alkyl (e.g. methyl, ethyl, propyl or isopropyl).

In another embodiment for the compound of Formulas (I)-(XV-c), each instance of $R^{c1}$ is independently optionally substituted alkyl or —$N(R^{cn})_2$, wherein each instance of $R^{nc}$ is independently hydrogen, —$C_{1-6}$ alkyl, or a nitrogen protecting group. In certain embodiments, $R^{c1}$ is optionally substituted —$C_{1-6}$ alkyl. In certain embodiments, $R^{c1}$ is —$C_{1-6}$ alkyl (e.g. methyl, ethyl, n-propyl, or iso-propyl). In certain embodiments, $R^{o1}$ is substituted —$C_{1-6}$ alkyl (e.g. haloalkyl or hydroxylalkyl). In certain embodiments, $R^{c1}$ is —$N(R^{cn})_2$. In certain embodiments, $R^{c1}$ is —$NHR^{cn}$.

In another embodiment for the compound of Formulas (I)-(XV-c), $R^{c2}$, $R^{c3}$, $R^{c4}$ and $R^{c5}$ are each independently optionally substituted —$C_1$-$C_6$ alkyl (e.g. substituted with 1-3 instances of halo, —OH or —$NH_2$). In certain embodiments at least one instance of $R^{c2}$, $R^{c3}$, $R^{c4}$ and $R^{c5}$ is independently —$C_1$-$C_6$ alkyl (e.g, methyl, ethyl, propyl or isopropyl).

In another embodiment for the compound of Formulas (I)-(XV-c), each instance of $R^{s1}$ and $R^{s2}$ is independently optionally substituted —$C_1$-$C_6$ alkyl, or a sulfur protecting group. In certain embodiments, at least one instance of $R^{s1}$ and $R^{s2}$ is hydrogen. In certain embodiments, at least one instance of $R^{s1}$ and $R^{s2}$ is —$C_1$-$C_6$ alkyl (e.g. methyl or ethyl). In certain embodiments, at least one instance of $R^{s1}$ and $R^{s2}$ is substituted —$C_1$-$C_6$ alkyl (e.g. with 1-3 occurrences of halogen and/or hydroxyl). In certain embodiments, at least one instance of $R^{s1}$ and $R^{s2}$ is a sulfur protecting group.

In another embodiment for the compound of Formulas (I)-(XV-c), each instance of $R^{js}$ is independently optionally substituted —$C_1$-$C_6$ alkyl, optionally substituted $C_{6-12}$ aryl, optionally substituted heteroaryl, or a sulfur protecting group. In certain embodiments, $R^{js}$ is $C_{6-12}$ aryl (e.g. phenyl). In some embodiments $R^{js}$ is optionally substituted $C_{6-12}$ aryl (e.g. with 0-3 occurrences of methyl, ethyl, isopropyl, methoxy, halo, trifluoromethoxy, —CN, —$NH_2$). In certain embodiments, each instance of $R^{js}$ is independently optionally substituted —$C_1$-$C_6$ alkyl (e.g. with 1-3 occurrences of halo and/or hydroxy). In certain embodiments, each instance of $R^{js}$ is independently —$C_1$-$C_6$ alkyl (e.g. methyl, ethyl, propyl or isopropyl). In certain embodiments, each instance of $R^{js}$ is independently a sulfur protecting group.

In another embodiment of the invention, provided is a compound of formulae (VII), (VII-a), (VIII), (VIII-a), (IX), (IX-a), (X), or (X-a) or a pharmaceutically acceptable salt thereof, wherein R2 is one of the following formulae:

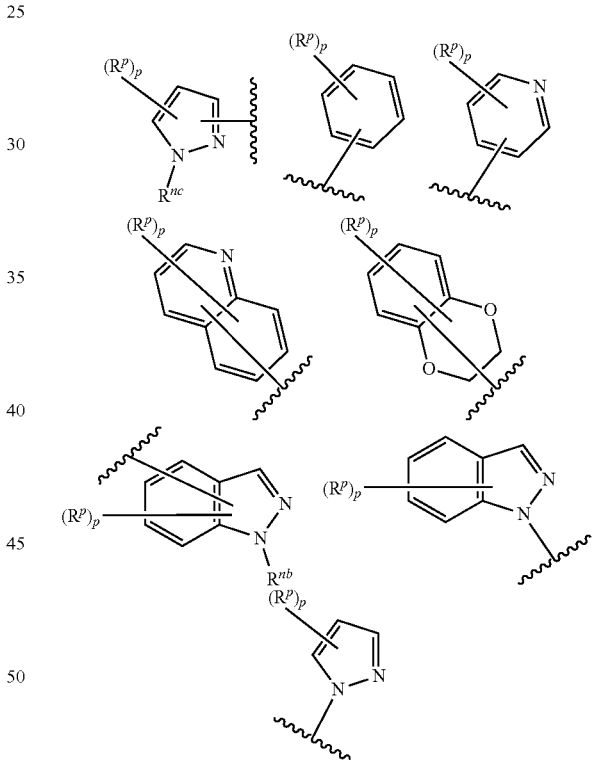

wherein $R^p$ and p are as defined in the eighth embodiment, $R^{nc}$ and $R^{nb}$ are each independently hydrogen, optionally substituted —$C_1$-$C_6$ alkyl, or a nitrogen protecting group. In another embodiment, p is 1.

In another embodiment of the invention, the compound or a pharmaceutically acceptable salt thereof as described in any of the preceding embodiments, wherein $R^2$ is optionally substituted phenyl, optionally substituted 5- to 6-membered monocyclic heteroaryl, or optionally substituted 5- to 6-membered monocyclic heterocyclyl, provided that Q and $R^2$ are not both optionally substituted 5- or 6-membered monocyclic heteroaryl.

In another embodiment of the invention, the compound or pharmaceutically acceptable salt thereof is as described in any of the preceding embodiments, wherein $R^2$ is one of the following formulae:

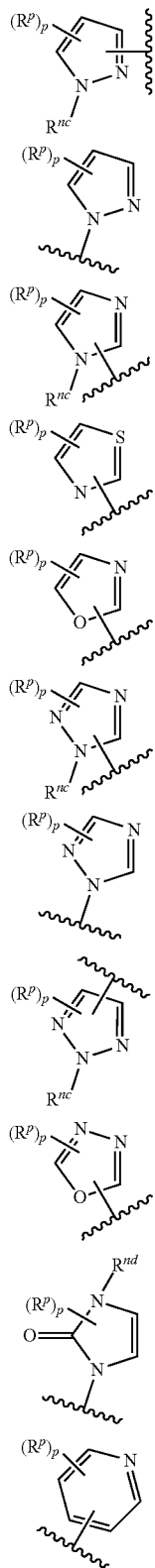

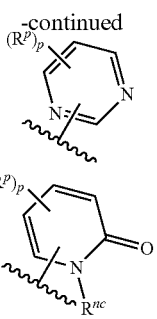

wherein $R^p$ and p are as defined in the eighth embodiment, $R^{nc}$ is independently hydrogen, optionally substituted —$C_1$-$C_6$ alkyl, or a nitrogen protecting group. In another embodiment, p is 1.

Throughout all of the embodiments of the compounds of Formulas (I)-(XV-c) or pharmaceutically acceptable salts thereof, $R^2$ and Q are not both optionally substituted 5- or 6-membered monocyclic heteroaryl.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, R479H, R479K, R486W, R532W, K410E, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 11-17. Compounds described herein are also useful as activators of wild type PKR.

In an embodiment, to increase the lifetime of the red blood cells, a compound, composition or pharmaceutical composition described herein is added directly to whole blood or packed red blood cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the level of 2,3-DPG and/or ATP from the blood. A decrease in the level of 2, 3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed red blood cells extracorporeally or be provided to the patient directly (e.g., by i.p., i.v., i.m., oral, inhalation (aerosolized delivery), transdermal, sublingual and other delivery routes). In another embodiment, a compound, composition or pharmaceutical composition described herein can increase the level of ATP and help to protect the cells from reactive oxygen species (Mol Cell. 2012 Oct. 26; 48(2): 158-167).

In Tables 2 and 4, a compound described herein may have an AC50 of wild type PKR, PKR K410E or PKR 510Q. "A" refers to an AC50 less than 0.300 μM; "B" refers to an AC50 from 0.301 μM to 0.800 μM, and "C" refers to an AC50 greater than 0.800 μM. The AC50 of wild type PKR for certain compounds was additionally determined in a cell-based ATP assay. "AA" refers to an AC50 less than or equal to 1 μM and "BB" refers to an AC50 more than 1 μM.

TABLE 1

Activation of wild type and mutant PKR by exemplary compounds

| Cpd Nr | Compound |
|---|---|
| 1 | *structure* |
| 2 | *structure* |
| 3 | *structure* |
| 4 | *structure* |
| 5 | *structure* |
| 6 | *structure* |

TABLE 1-continued

Activation of wild type and mutant PKR by exemplary compounds

| Cpd Nr | Compound |
|---|---|
| 7 | 2-methyl-thiazolo-pyrrolo-pyridazinone with N-(3-hydroxybenzyl) substituent |
| 8 | 2-methyl-thiazolo-pyrrolo-pyridazinone with N-(2-methoxybenzyl) substituent |
| 9 | 2-methyl-thiazolo-pyrrolo-pyridazinone with N-(4-fluorobenzyl) substituent |
| 10 | 2-methyl-thiazolo-pyrrolo-pyridazinone with N-(3-ethoxycarbonylbenzyl) substituent |
| 11 | 2-methyl-thiazolo-pyrrolo-pyridazinone with N-(3-carboxybenzyl) substituent |
| 12 | 2-(fluoro(phenyl)methyl)-thiazolo-pyrrolo-pyridazinone with N-(3-methoxybenzyl) substituent |

TABLE 1-continued

Activation of wild type and mutant PKR by exemplary compounds

| Cpd Nr | Compound |
|---|---|
| 13 | |
| 14 | |
| 15 | |
| 16 | |
| 17 | |
| 18 | |
| 19 | |

TABLE 1-continued

Activation of wild type and mutant PKR by exemplary compounds

| Cpd Nr | Compound |
|---|---|
| 20 | |
| 21 | |
| 22 | |
| 23 | |
| 24 | |
| 25 | |
| 26 | |

TABLE 1-continued
Activation of wild type and mutant PKR by exemplary compounds
| Cpd Nr | Compound |
|---|---|
| 27 | 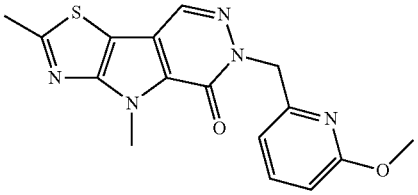 |
| 28 | 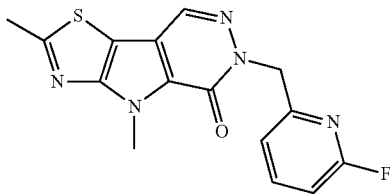 [SMILES: Cc1nc2c(s1)c1cnn(Cc3cccc(F)n3)c(=O)c1n2C] |
| 29 | 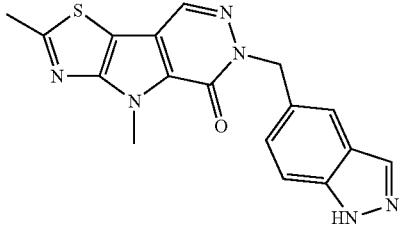 [SMILES: Cc1nc2c(s1)c1cnn(Cc3ccc4[nH]ncc4c3)c(=O)c1n2C] |
| 30 | 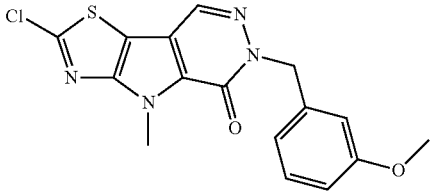 [SMILES: COc1cccc(Cn2ncc3c4sc(Cl)nc4n(C)c3c2=O)c1] |
| 31 | 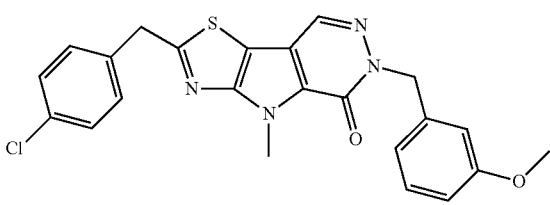 [SMILES: COc1cccc(Cn2ncc3c4sc(Cc5ccc(Cl)cc5)nc4n(C)c3c2=O)c1] |
| 32 | 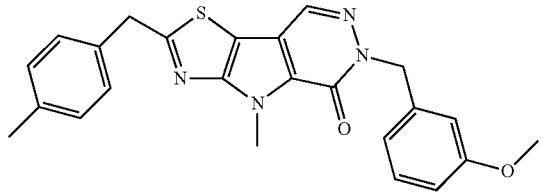 |
| 33 | 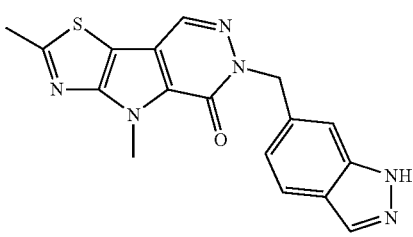 |

TABLE 1-continued
Activation of wild type and mutant PKR by exemplary compounds
| Cpd Nr | Compound |
|---|---|
| 34 | 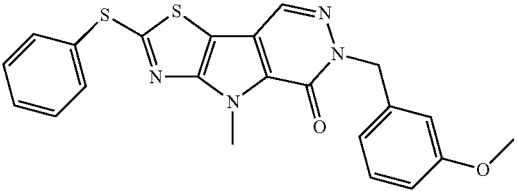 |
| 35 | 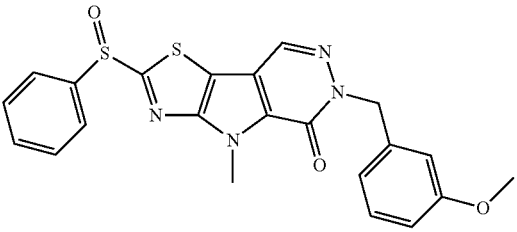 [SMILES: COc1cccc(Cn2ncc3c4sc(S(=O)c5ccccc5)nc4n(C)c3c2=O)c1] |
| 36 | 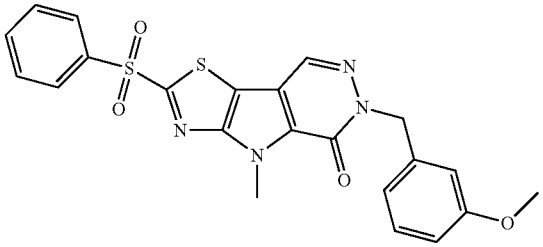 [SMILES: COc1cccc(Cn2ncc3c4sc(S(=O)(=O)c5ccccc5)nc4n(C)c3c2=O)c1] |
| 37 | 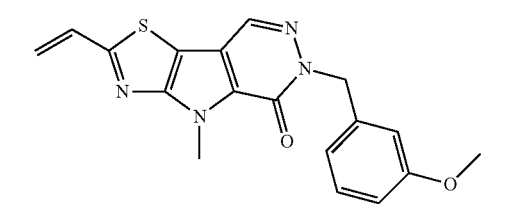 [SMILES: C=Cc1nc2c(s1)c1cnn(Cc3cccc(OC)c3)c(=O)c1n2C] |
| 38 | 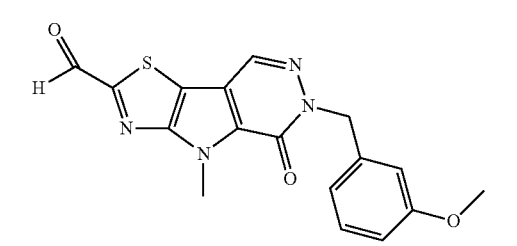 [SMILES: COc1cccc(Cn2ncc3c4sc(C=O)nc4n(C)c3c2=O)c1] |
| 39 | 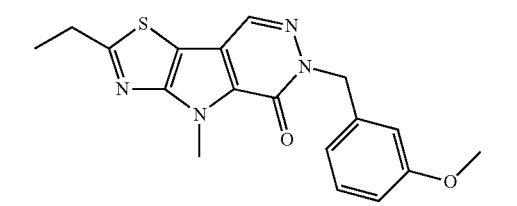 [SMILES: CCc1nc2c(s1)c1cnn(Cc3cccc(OC)c3)c(=O)c1n2C] |
| 40 | 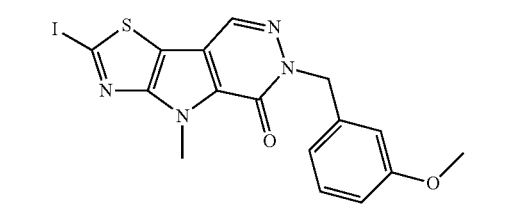 [SMILES: COc1cccc(Cn2ncc3c4sc(I)nc4n(C)c3c2=O)c1] |

TABLE 1-continued

Activation of wild type and mutant PKR by exemplary compounds

| Cpd Nr | Compound |
|---|---|
| 41 | (structure) |
| 42 | (structure) |
| 43 | (structure) |
| 44 | (structure) |
| 45 | (structure) |
| 46 | (structure) |
| 47 | (structure) |

TABLE 1-continued

Activation of wild type and mutant PKR by exemplary compounds

| Cpd Nr | Compound |
|---|---|
| 48 | |
| 49 | |
| 50 | |
| 51 | |
| 52 | |
| 53 | |

TABLE 1-continued

Activation of wild type and mutant PKR by exemplary compounds

| Cpd Nr | Compound |
|---|---|
| 54 | *(structure)* |
| 55 | *(structure)* |
| 56 | *(structure)* |
| 57 | *(structure)* |
| 58 | *(structure)* |
| 59 | *(structure)* |
| 60 | *(structure)* |

TABLE 1-continued
Activation of wild type and mutant PKR by exemplary compounds
| Cpd Nr | Compound |
|---|---|
| 61 | 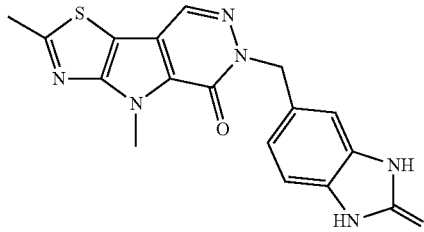 |
| 62 | 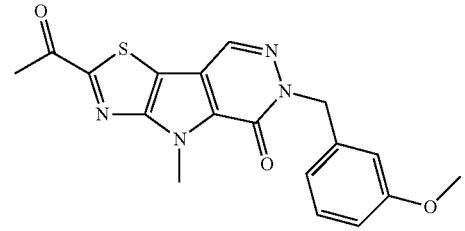 [SMILES: COc1cccc(Cn2ncc3c4sc(C(C)=O)nc4n(C)c3c2=O)c1] |
| 63 | 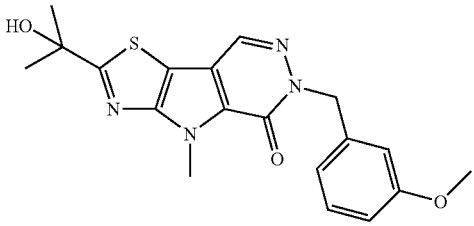 [SMILES: COc1cccc(Cn2ncc3c4sc(C(C)(C)O)nc4n(C)c3c2=O)c1] |
| 64 | 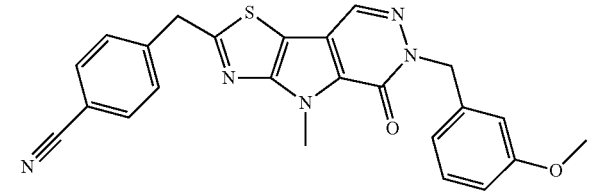 [SMILES: COc1cccc(Cn2ncc3c4sc(Cc5ccc(C#N)cc5)nc4n(C)c3c2=O)c1] |
| 65 | 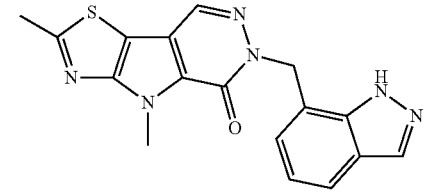 [SMILES: Cc1nc2c(s1)c1cnn(Cc3cccc4cn[nH]c34)c(=O)c1n2C] |
| 66 | 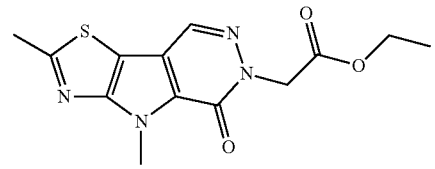 [SMILES: CCOC(=O)Cn1ncc2c3sc(C)nc3n(C)c2c1=O] |
| 67 | 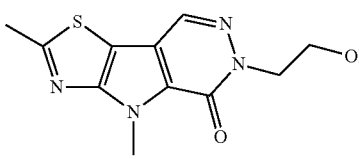 |

TABLE 1-continued

Activation of wild type and mutant PKR by exemplary compounds

| Cpd Nr | Compound |
|---|---|
| 68 | |
| 69 | |
| 70 | |
| 71 | |
| 72 | |
| 73 | |
| 74 | |

TABLE 1-continued

Activation of wild type and mutant PKR by exemplary compounds

| Cpd Nr | Compound |
|---|---|
| 75 | |
| 76 | |
| 77 | |
| 78 | |
| 79 | |
| 80 | |

TABLE 1-continued

Activation of wild type and mutant PKR by exemplary compounds

| Cpd Nr | Compound |
|---|---|
| 81 | |
| 82 | |
| 83 | |
| 84 | |
| 85 | |
| 86 | |

TABLE 1-continued

Activation of wild type and mutant PKR by exemplary compounds

| Cpd Nr | Compound |
|---|---|
| 87 | |
| 88 | |
| 89 | |
| 90 | |
| 91 | |
| 92 | |

TABLE 1-continued
Activation of wild type and mutant PKR by exemplary compounds
| Cpd Nr | Compound |
|---|---|
| 93 | 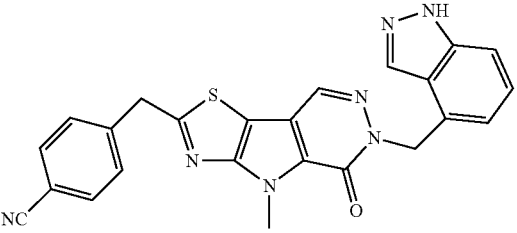 [SMILES: Cn1c2nc(Cc3ccc(C#N)cc3)sc2c2cnn(Cc3cccc4[nH]ncc34)c(=O)c21] |
| 94 | 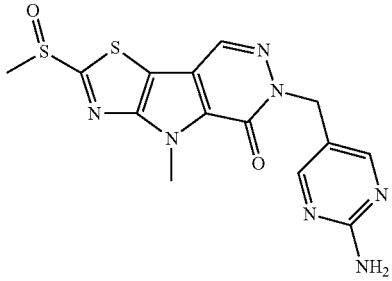 [SMILES: Cn1c2nc(S(C)=O)sc2c2cnn(Cc3cnc(N)nc3)c(=O)c21] |
| 95 | 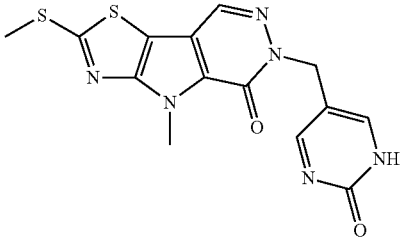 [SMILES: CSc1nc2c(s1)c1cnn(Cc3cnc(=O)[nH]c3)c(=O)c1n2C] |
| 96 | 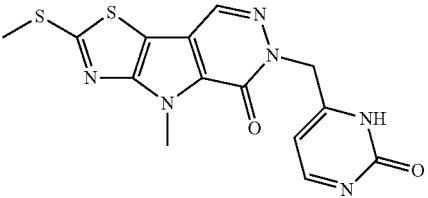 [SMILES: CSc1nc2c(s1)c1cnn(Cc3ccnc(=O)[nH]3)c(=O)c1n2C] |
| 97 | 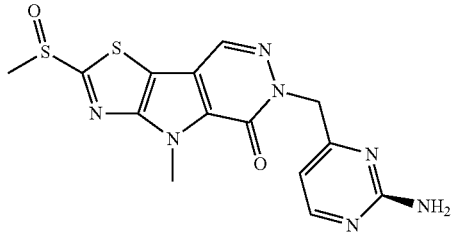 |
| 98 | 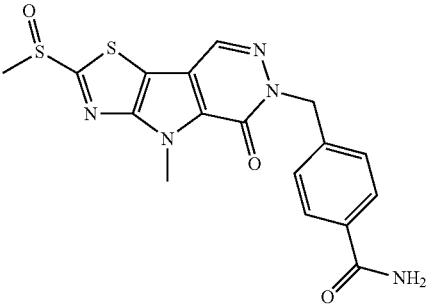 [SMILES: Cn1c2nc(S(C)=O)sc2c2cnn(Cc3ccc(C(N)=O)cc3)c(=O)c21] |

TABLE 1-continued

Activation of wild type and mutant PKR by exemplary compounds

| Cpd Nr | Compound |
|---|---|
| 99 | |
| 100 | |
| 101 | |
| 102 | |
| 103 | |
| 104 | |

TABLE 1-continued
Activation of wild type and mutant PKR by exemplary compounds
| Cpd Nr | Compound |
|---|---|
| 105 | 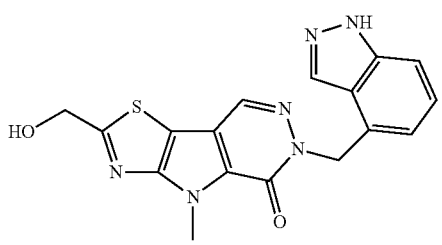 [SMILES: Cn1c2nc(CO)sc2c2cnn(Cc3cccc4[nH]ncc34)c(=O)c21] |
| 106 | 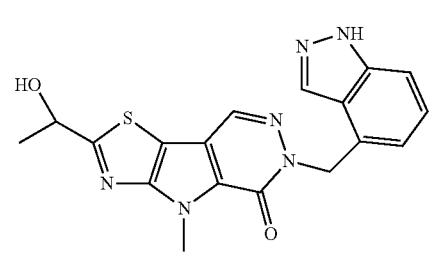 [SMILES: CC(O)c1nc2c(s1)c1cnn(Cc3cccc4[nH]ncc34)c(=O)c1n2C] |
| 107 | 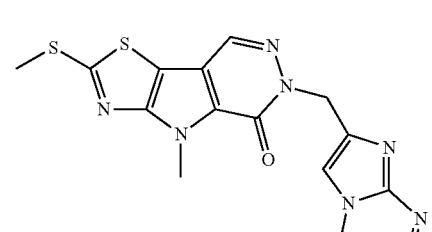 |
| 108 | 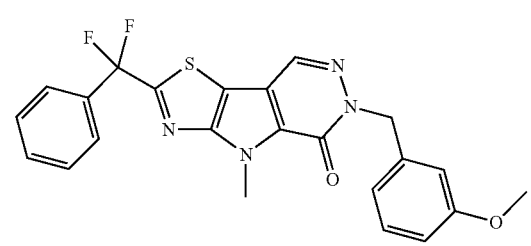 [SMILES: COc1cccc(Cn2ncc3c4sc(C(F)(F)c5ccccc5)nc4n(C)c3c2=O)c1] |
| 109 | 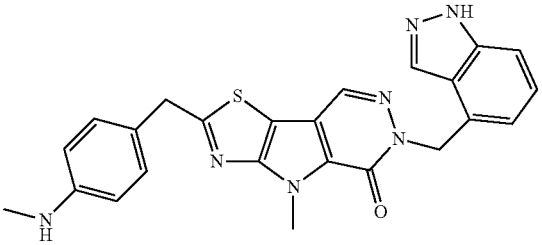 [SMILES: CNc1ccc(Cc2nc3c(s2)c2cnn(Cc4cccc5[nH]ncc45)c(=O)c2n3C)cc1] |
| 110 | 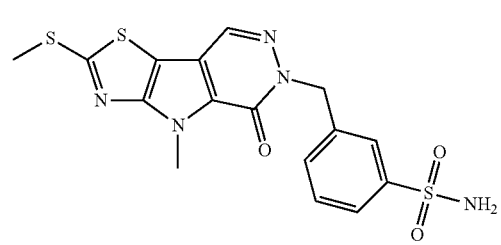 [SMILES: CSc1nc2c(s1)c1cnn(Cc3cccc(S(N)(=O)=O)c3)c(=O)c1n2C] |

TABLE 1-continued
Activation of wild type and mutant PKR by exemplary compounds
| Cpd Nr | Compound |
|---|---|
| 111 | 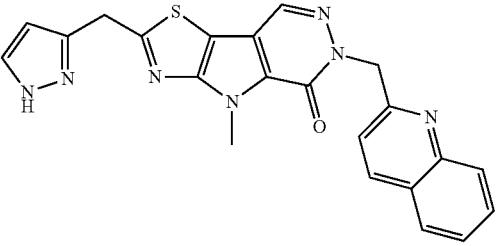 [SMILES: Cn1c2nc(Cc3cc[nH]n3)sc2c2cnn(Cc3ccc4ccccc4n3)c(=O)c21] |
| 112 | 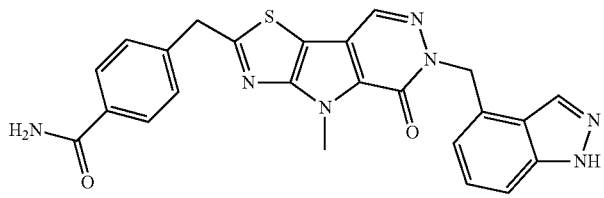 [SMILES: Cn1c2nc(Cc3ccc(C(N)=O)cc3)sc2c2cnn(Cc3cccc4[nH]ncc34)c(=O)c21] |
| 113 | 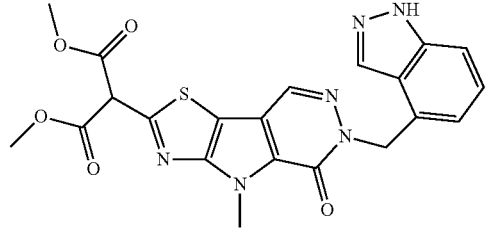 [SMILES: COC(=O)C(C(=O)OC)c1nc2c(s1)c1cnn(Cc3cccc4[nH]ncc34)c(=O)c1n2C] |
| 114 | 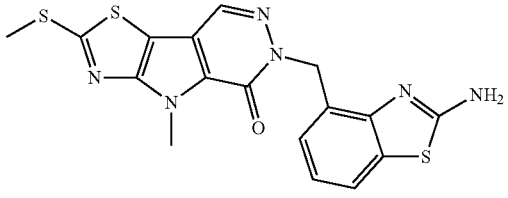 [SMILES: CSc1nc2c(s1)c1cnn(Cc3cccc4sc(N)nc34)c(=O)c1n2C] |
| 116 | 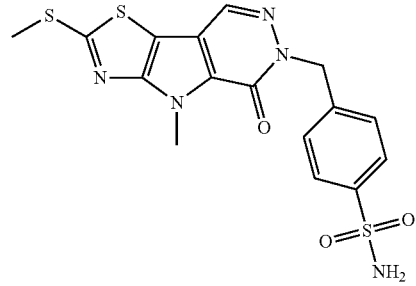 [SMILES: CSc1nc2c(s1)c1cnn(Cc3ccc(S(N)(=O)=O)cc3)c(=O)c1n2C] |
| 117 | 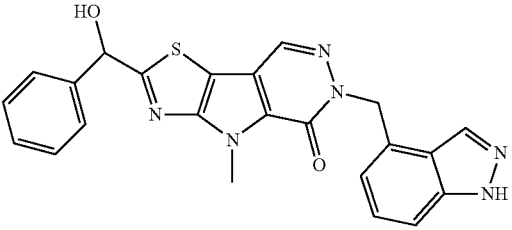 [SMILES: Cn1c2nc(C(O)c3ccccc3)sc2c2cnn(Cc3cccc4[nH]ncc34)c(=O)c21] |

TABLE 1-continued

Activation of wild type and mutant PKR by exemplary compounds

| Cpd Nr | Compound |
|---|---|
| 118 | |
| 119 | |
| 120 | |
| 121 | |
| 122 | |
| 123 | |

TABLE 1-continued
Activation of wild type and mutant PKR by exemplary compounds
| Cpd Nr | Compound |
|---|---|
| 124 | 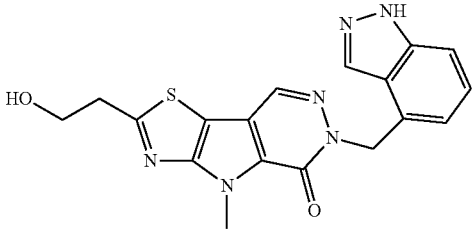 [SMILES: Cn1c2nc(CCO)sc2c2cnn(Cc3cccc4[nH]ncc34)c(=O)c21] |
| 125 | 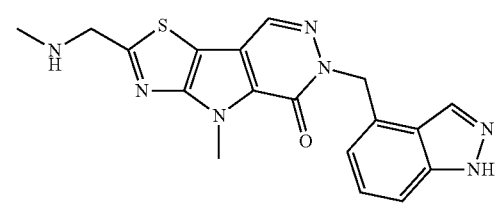 [SMILES: CNCc1nc2c(s1)c1cnn(Cc3cccc4[nH]ncc34)c(=O)c1n2C] |
| 126 | 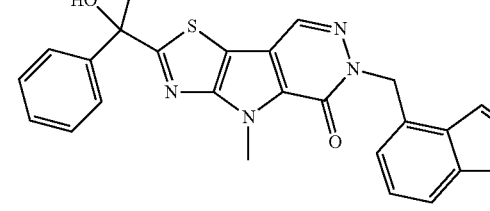 |
| 127 | 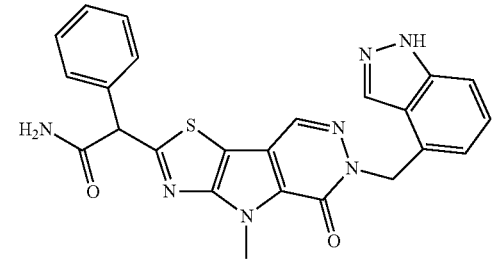 [SMILES: Cn1c2nc(C(C(N)=O)c3ccccc3)sc2c2cnn(Cc3cccc4[nH]ncc34)c(=O)c21] |
| 128 | 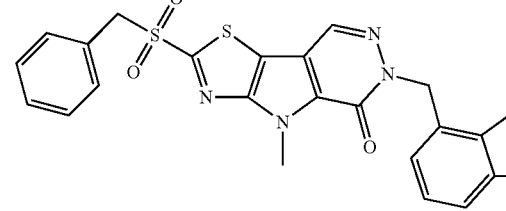 |
| 129 | 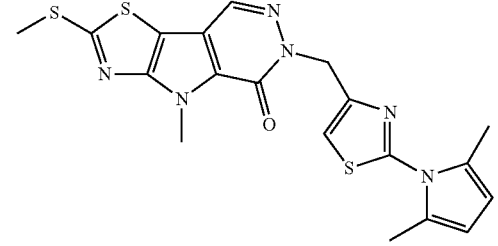 [SMILES: CSc1nc2c(s1)c1cnn(Cc3csc(-n4c(C)ccc4C)n3)c(=O)c1n2C] |

TABLE 1-continued

Activation of wild type and mutant PKR by exemplary compounds

| Cpd Nr | Compound |
|---|---|
| 130 | |
| 131 | |
| 132 | |
| 133 | |
| 134 | |
| 135 | |

TABLE 1-continued
Activation of wild type and mutant PKR by exemplary compounds
| Cpd Nr | Compound |
|---|---|
| 136 | 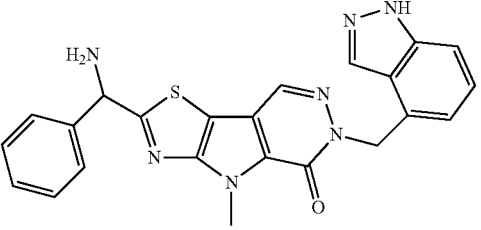 [SMILES: Cn1c2nc(C(N)c3ccccc3)sc2c2cnn(Cc3cccc4[nH]ncc34)c(=O)c21] |
| 137 | 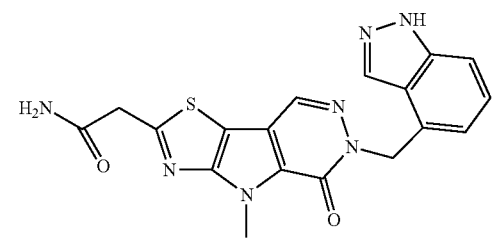 [SMILES: Cn1c2nc(CC(N)=O)sc2c2cnn(Cc3cccc4[nH]ncc34)c(=O)c21] |
| 138 | 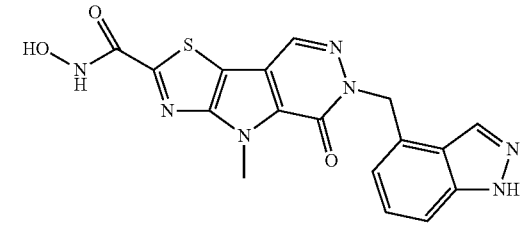 [SMILES: Cn1c2nc(C(=O)NO)sc2c2cnn(Cc3cccc4[nH]ncc34)c(=O)c21] |
| 139 | 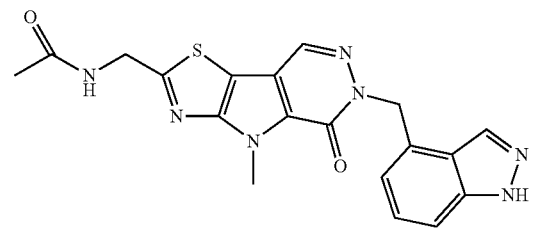 [SMILES: CC(=O)NCc1nc2c(s1)c1cnn(Cc3cccc4[nH]ncc34)c(=O)c1n2C] |
| 140 | 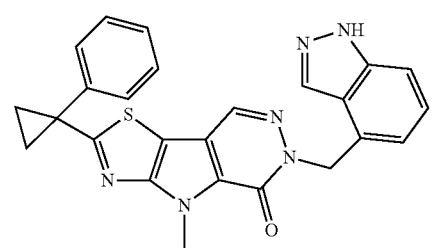 [SMILES: Cn1c2nc(C3(c4ccccc4)CC3)sc2c2cnn(Cc3cccc4[nH]ncc34)c(=O)c21] |
| 141 | 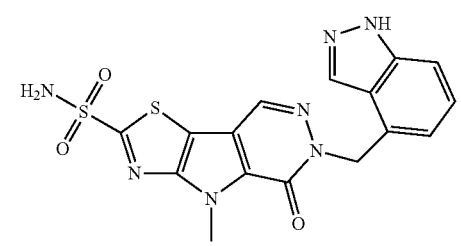 [SMILES: Cn1c2nc(S(N)(=O)=O)sc2c2cnn(Cc3cccc4[nH]ncc34)c(=O)c21] |

TABLE 1-continued

Activation of wild type and mutant PKR by exemplary compounds

| Cpd Nr | Compound |
|---|---|
| 142 | *(structure)* |
| 143 | *(structure)* |
| 144 | *(structure)* |
| 145 | *(structure)* |
| 146 | *(structure)* |
| 147 | *(structure)* |

TABLE 1-continued

Activation of wild type and mutant PKR by exemplary compounds

| Cpd Nr | Compound |
|---|---|
| 148 | |
| 149 | |
| 150 | |
| 151 | |
| 152 | |
| 153 | |

TABLE 1-continued

*Activation of wild type and mutant PKR by exemplary compounds*

| Cpd Nr | Compound |
|---|---|
| 154 | |
| 155 | |
| 156 | |
| 157 | |
| 158 | |
| 159 | |

TABLE 1-continued
Activation of wild type and mutant PKR by exemplary compounds
| Cpd Nr | Compound |
|---|---|
| 160 | 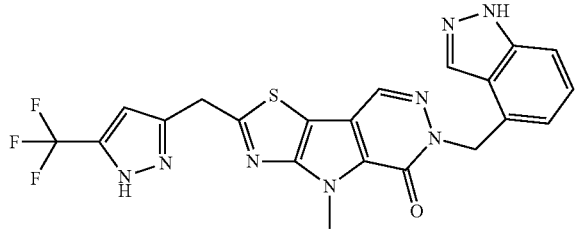 [SMILES: Cn1c2nc(Cc3cc(C(F)(F)F)[nH]n3)sc2c2cnn(Cc3cccc4[nH]ncc34)c(=O)c21] |
| 161 | 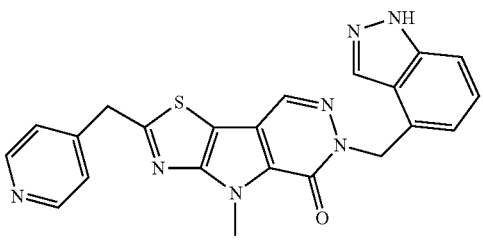 [SMILES: Cn1c2nc(Cc3ccncc3)sc2c2cnn(Cc3cccc4[nH]ncc34)c(=O)c21] |
| 162 | 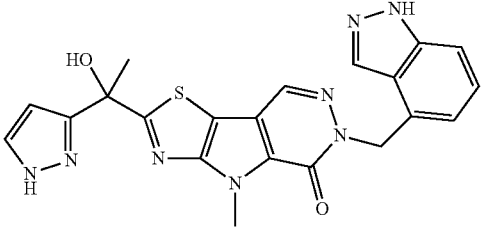 [SMILES: Cn1c2nc(C(C)(O)c3cc[nH]n3)sc2c2cnn(Cc3cccc4[nH]ncc34)c(=O)c21] |
| 163 | 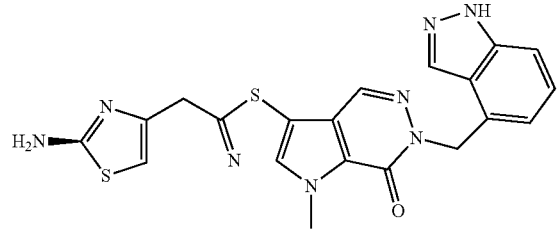 |
| 164 | 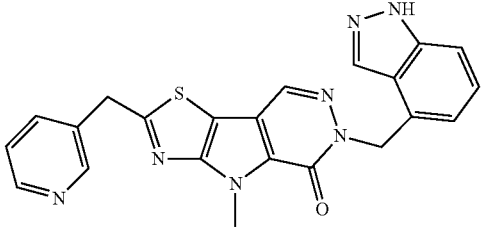 [SMILES: Cn1c2nc(Cc3cccnc3)sc2c2cnn(Cc3cccc4[nH]ncc34)c(=O)c21] |
| 165 | 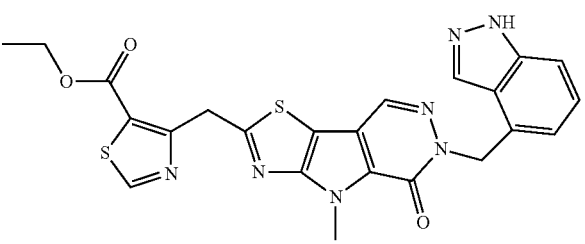 [SMILES: CCOC(=O)c1scnc1Cc1nc2c(s1)c1cnn(Cc3cccc4[nH]ncc34)c(=O)c1n2C] |

TABLE 1-continued

Activation of wild type and mutant PKR by exemplary compounds

| Cpd Nr | Compound |
|---|---|
| 166 | |
| 167 | |
| 168 | |
| 169 | |
| 170 | |
| 171 | |

TABLE 1-continued
Activation of wild type and mutant PKR by exemplary compounds
| Cpd Nr | Compound |
|---|---|
| 172 | 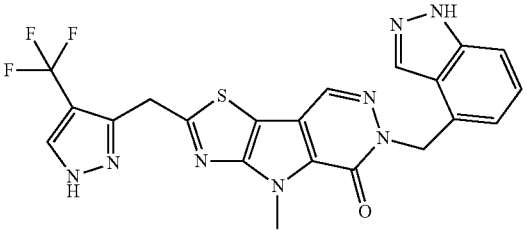 [SMILES: Cn1c2nc(Cc3n[nH]cc3C(F)(F)F)sc2c2cnn(Cc3cccc4[nH]ncc34)c(=O)c21] |
| 173 | 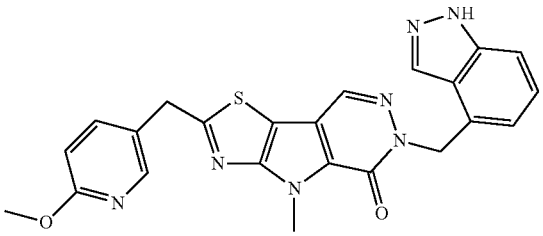 [SMILES: COc1ccc(Cc2nc3c(s2)c2cnn(Cc4cccc5[nH]ncc45)c(=O)c2n3C)cn1] |
| 174 | 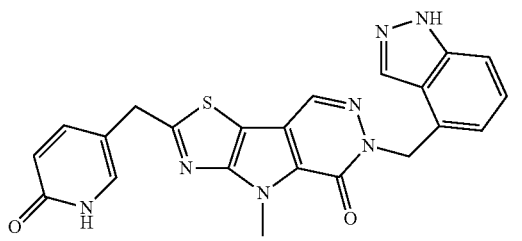 [SMILES: Cn1c2nc(Cc3ccc(=O)[nH]c3)sc2c2cnn(Cc3cccc4[nH]ncc34)c(=O)c21] |
| 175 | 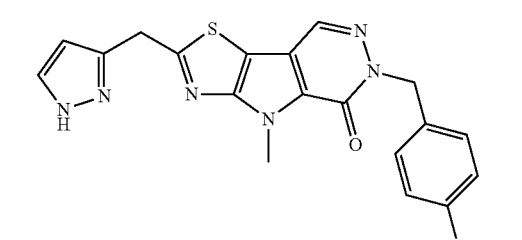 |
| 176 | 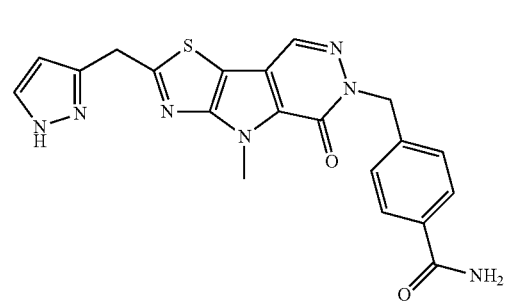 [SMILES: Cn1c2nc(Cc3cc[nH]n3)sc2c2cnn(Cc3ccc(C(N)=O)cc3)c(=O)c21] |
| 177 | 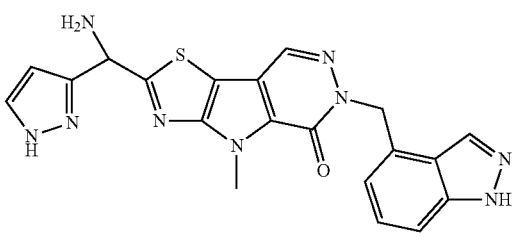 [SMILES: Cn1c2nc(C(N)c3cc[nH]n3)sc2c2cnn(Cc3cccc4[nH]ncc34)c(=O)c21] |

TABLE 1-continued

Activation of wild type and mutant PKR by exemplary compounds

| Cpd Nr | Compound |
|---|---|
| 178 | |
| 180 | |
| 181 | |
| 182 | |
| 183 | |
| 184 | |

TABLE 1-continued

Activation of wild type and mutant PKR by exemplary compounds

| Cpd Nr | Compound |
|---|---|
| 185 | (structure: isoxazole-CH2-thiazole fused pyrrolo-pyridazinone with N-methyl and CH2-indazole substituent) |

TABLE 2

AC$_{50}$ of Exemplary compounds for Wild Type and Mutant PKR

| Cpd Nr | PKR WT AC50 | PKR K410E AC50 | PK R510Q AC50 | Cell based ATP assay AC50 |
|---|---|---|---|---|
| 1 | A | A | A | AA |
| 2 | A | A | N/A | AA |
| 3 | A | A | A | AA |
| 4 | C | No Fit | C | No Fit |
| 5 | A | A | A | AA |
| 6 | C | C | C | BB |
| 7 | A | A | A | AA |
| 8 | C | B | B | BB |
| 9 | A | A | A | AA |
| 10 | C | C | C | No Fit |
| 11 | C | C | C | No Fit |
| 12 | A | A | A | |
| 13 | A | A | A | AA |
| 14 | A | A | A | AA |
| 15 | C | C | A | BB |
| 16 | A | A | A | |
| 17 | A | A | A | AA |
| 18 | B | B | A | AA |
| 19 | B | B | A | BB |
| 20 | C | C | C | BB |
| 21 | C | C | No Fit | No Fit |
| 22 | A | A | A | BB |
| 23 | A | A | A | BB |
| 24 | A | A | A | BB |
| 25 | A | A | A | BB |
| 26 | A | C | A | AA |
| 27 | A | B | B | AA |
| 28 | C | C | C | BB |
| 29 | A | A | A | BB |
| 30 | A | B | A | BB |
| 31 | A | B | A | AA |
| 32 | A | A | A | AA |
| 33 | C | C | B | BB |
| 34 | A | A | A | AA |
| 35 | B | B | B | BB |
| 36 | C | B | B | BB |
| 37 | B | C | A | BB |
| 38 | A | A | A | BB |
| 39 | A | A | A | BB |
| 40 | B | B | A | BB |
| 41 | A | A | A | AA |
| 42 | C | C | C | BB |
| 43 | C | C | B | No Fit |
| 44 | C | C | C | BB |
| 45 | A | A | A | AA |
| 46 | C | C | C | BB |
| 47 | C | C | C | No Fit |
| 48 | No Fit | C | C | No Fit |
| 49 | C | C | C | BB |
| 50 | C | C | C | No Fit |
| 51 | A | A | A | AA |
| 52 | A | A | A | AA |
| 53 | A | A | A | BB |
| 54 | C | C | No Fit | No Fit |
| 55 | B | C | B | BB |
| 56 | B | A | A | BB |
| 57 | A | A | A | AA |
| 58 | A | A | A | BB |
| 59 | A | A | A | AA |
| 60 | A | A | A | AA |
| 61 | C | C | C | No Fit |
| 62 | A | A | A | AA |
| 63 | A | A | A | BB |
| 64 | A | A | A | AA |
| 65 | C | B | B | BB |
| 66 | C | C | No Fit | No Fit |
| 67 | C | C | No Fit | No Fit |
| 68 | A | A | A | AA |
| 69 | C | C | B | BB |
| 70 | A | A | A | AA |
| 71 | B | B | B | AA |
| 72 | C | C | C | BB |
| 73 | C | B | B | BB |
| 74 | A | A | A | AA |
| 75 | C | C | No Fit | AA |
| 76 | C | A | A | AA |
| 77 | A | A | A | AA |
| 78 | C | C | C | AA |
| 79 | A | A | A | AA |
| 80 | C | C | A | BB |
| 81 | A | A | A | AA |
| 82 | A | B | B | BB |
| 83 | A | A | A | AA |
| 84 | A | B | B | BB |
| 85 | A | B | A | AA |
| 86 | A | C | C | BB |
| 87 | A | A | B | AA |
| 88 | A | B | B | AA |
| 89 | A | A | A | AA |
| 90 | A | A | A | BB |
| 91 | A | A | A | AA |
| 92 | A | B | B | AA |
| 93 | C | C | C | BB |
| 94 | C | C | No Fit | BB |
| 95 | No Fit | No Fit | No Fit | No Fit |
| 96 | C | C | No Fit | No Fit |
| 97 | C | C | C | BB |
| 98 | No Fit | C | No Fit | BB |
| 99 | A | B | B | AA |
| 100 | A | A | A | AA |
| 101 | C | C | C | BB |
| 102 | A | A | A | AA |
| 103 | A | A | A | AA |
| 104 | A | C | A | BB |
| 105 | A | A | A | AA |
| 106 | A | A | A | AA |
| 107 | No Fit | C | C | No Fit |
| 108 | A | A | A | AA |

TABLE 2-continued

AC$_{50}$ of Exemplary compounds for Wild Type and Mutant PKR

| Cpd Nr | PKR WT AC50 | PKR K410E AC50 | PK R510Q AC50 | Cell based ATP assay AC50 |
|---|---|---|---|---|
| 109 | A | A | A | AA |
| 110 | C | C | C | No Fit |
| 111 | A | A | A | AA |
| 112 | C | C | C | BB |
| 113 | C | C | C | BB |
| 114 | A | A | A | No Fit |
| 116 | C | C | C | No Fit |
| 117 | A | A | B | BB |
| 118 | A | A | A | BB |
| 119 | A | A | A | AA |
| 120 | B | B | B | AA |
| 121 | B | C | B | BB |
| 122 | A | A | A | AA |
| 123 | A | A | A | AA |
| 124 | A | A | A | AA |
| 125 | C | C | B | BB |
| 126 | A | A | A | AA |
| 127 | A | A | A | AA |
| 128 | A | B | B | BB |
| 129 | C | C | C | BB |
| 130 | C | C | B | AA |
| 131 | B | A | A | BB |
| 132 | C | B | B | BB |
| 133 | C | C | C | BB |
| 134 | C | A | B | BB |
| 135 | C | C | No Fit | No Fit |
| 136 | A | A | A | AA |
| 137 | B | A | A | BB |
| 138 | B | A | B | BB |
| 139 | A | A | A | AA |
| 140 | C | C | C | BB |
| 141 | A | A | A | AA |
| 142 | A | A | B | AA |
| 143 | A | A | A | BB |
| 144 | A | A | A | AA |
| 145 | B | B | C | BB |
| 146 | B | A | B | AA |
| 147 | A | A | B | AA |
| 148 | A | A | A | AA |
| 149 | B | B | B | BB |
| 150 | C | C | C | BB |
| 151 | A | A | A | AA |
| 152 | B | A | B | AA |
| 153 | C | C | C | AA |
| 154 | A | A | A | AA |
| 155 | B | A | A | AA |
| 156 | B | A | A | AA |
| 157 | A | A | A | AA |
| 158 | A | A | A | AA |
| 159 | A | A | A | AA |
| 160 | B | B | B | AA |
| 161 | C | C | C | BB |
| 162 | A | A | A | AA |
| 163 | A | A | A | AA |
| 164 | A | A | A | AA |
| 165 | B | C | B | AA |
| 166 | B | C | B | BB |
| 167 | A | A | A | AA |
| 168 | A | A | A | AA |
| 169 | A | A | A | AA |
| 170 | A | A | A | AA |
| 171 | C | B | C | AA |
| 172 | C | C | C | BB |
| 173 | A | A | A | AA |
| 174 | C | B | C | No Fit |
| 175 | A | A | A | AA |
| 176 | C | C | C | BB |
| 177 | A | A | A | AA |
| 178 | C | C | C | BB |
| 180 | C | C | C | BB |
| 181 | A | A | A | AA |
| 182 | A | A | A | AA |
| 183 | A | A | A | AA |
| 184 | A | A | A | AA |
| 185 | C | B | B | BB |

TABLE 3

Further Exemplary Compounds

Structure

186

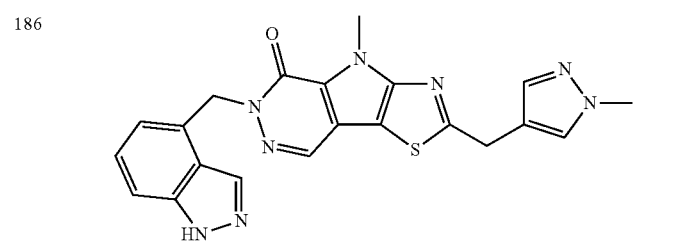

187

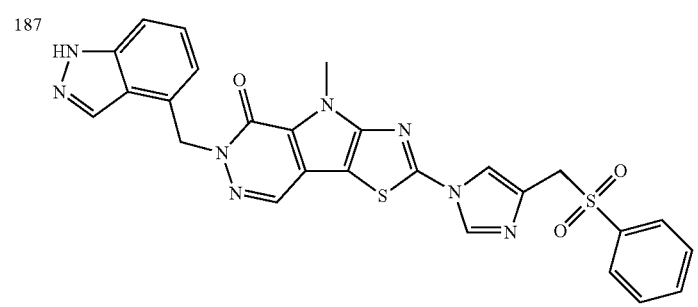

TABLE 3-continued
Further Exemplary Compounds
Structure
190
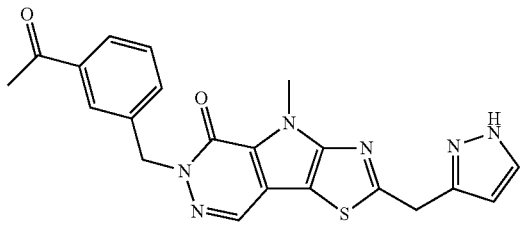 [SMILES: CC(=O)c1cccc(Cn2ncc3c4sc(Cc5cc[nH]n5)nc4n(C)c3c2=O)c1]
192
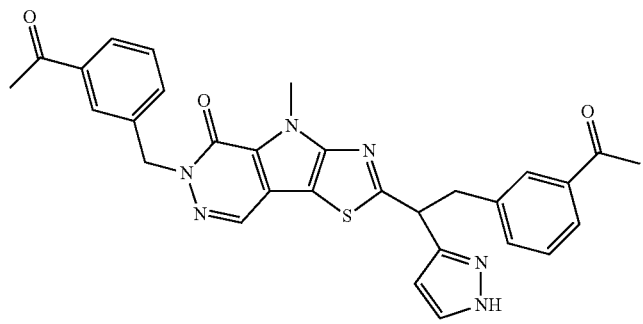 [SMILES: CC(=O)c1cccc(CC(c2cc[nH]n2)c2nc3c(s2)c2cnn(Cc4cccc(C(C)=O)c4)c(=O)c2n3C)c1]
193
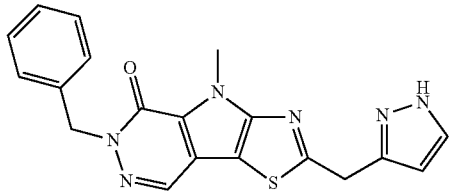 [SMILES: Cn1c2nc(Cc3cc[nH]n3)sc2c2cnn(Cc3ccccc3)c(=O)c21]
195
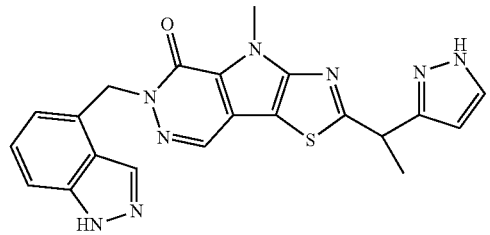 [SMILES: CC(c1cc[nH]n1)c1nc2c(s1)c1cnn(Cc3cccc4[nH]ncc34)c(=O)c1n2C]
196
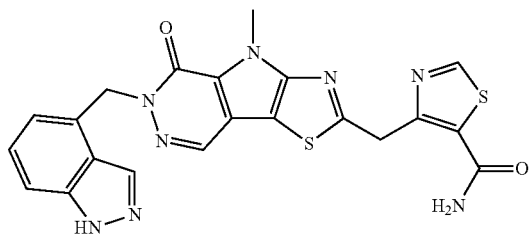 [SMILES: Cn1c2nc(Cc3ncsc3C(N)=O)sc2c2cnn(Cc3cccc4[nH]ncc34)c(=O)c21]
199
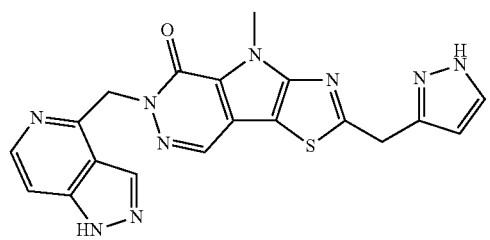 [SMILES: Cn1c2nc(Cc3cc[nH]n3)sc2c2cnn(Cc3nccc4[nH]ncc34)c(=O)c21]

TABLE 3-continued

Further Exemplary Compounds

Structure

200 [chemical structure]

201 [chemical structure]

202 [chemical structure]

205 [chemical structure]

206 [chemical structure]

207 [chemical structure]

US 11,957,680 B2
137                                                                 138
TABLE 3-continued
Further Exemplary Compounds
Structure
208 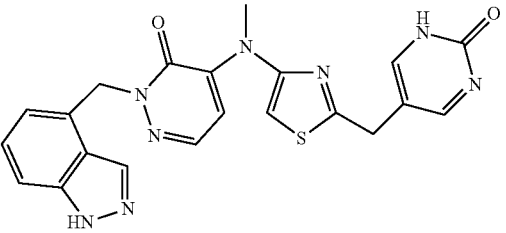 [SMILES: CN(c1csc(Cc2cnc(=O)[nH]c2)n1)c1ccnn(Cc2cccc3[nH]ncc23)c1=O]
209 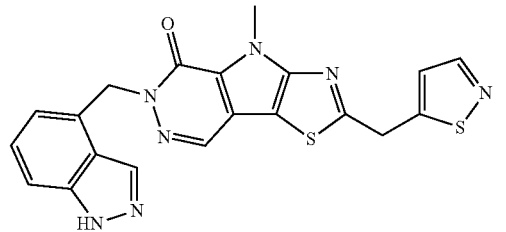 [SMILES: Cn1c2nc(Cc3ccns3)sc2c2cnn(Cc3cccc4[nH]ncc34)c(=O)c21]
210 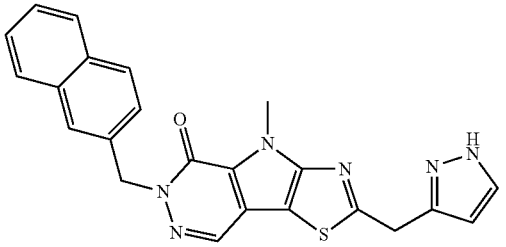 [SMILES: Cn1c2nc(Cc3cc[nH]n3)sc2c2cnn(Cc3ccc4ccccc4c3)c(=O)c21]
211 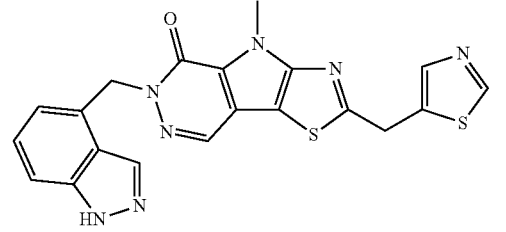
212 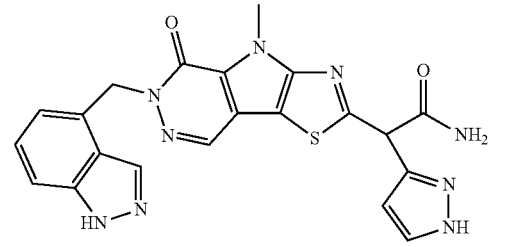 [SMILES: Cn1c2nc(C(C(N)=O)c3cc[nH]n3)sc2c2cnn(Cc3cccc4[nH]ncc34)c(=O)c21]
213 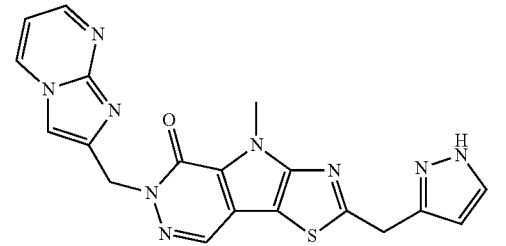 [SMILES: Cn1c2nc(Cc3cc[nH]n3)sc2c2cnn(Cc3cn4cccnc4n3)c(=O)c21]

TABLE 3-continued
Further Exemplary Compounds
Structure
215 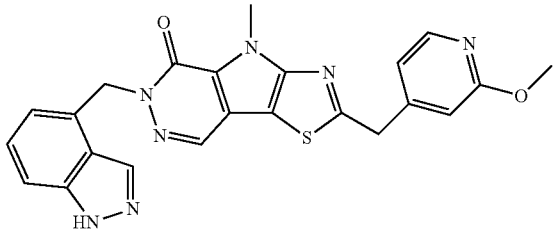 [SMILES: COc1cc(Cc2nc3c(s2)c2cnn(Cc4cccc5[nH]ncc45)c(=O)c2n3C)ccn1]
217 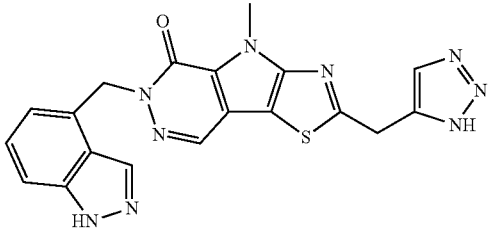 [SMILES: Cn1c2nc(Cc3cnn[nH]3)sc2c2cnn(Cc3cccc4[nH]ncc34)c(=O)c21]
219 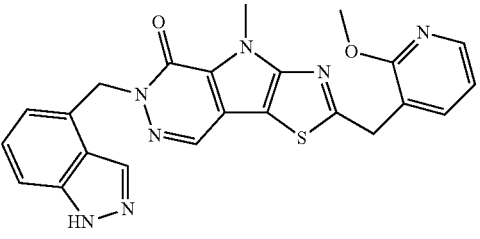 [SMILES: COc1ncccc1Cc1nc2c(s1)c1cnn(Cc3cccc4[nH]ncc34)c(=O)c1n2C]
220 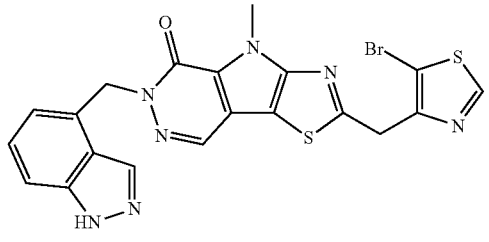 [SMILES: Cn1c2nc(Cc3ncsc3Br)sc2c2cnn(Cc3cccc4[nH]ncc34)c(=O)c21]
221 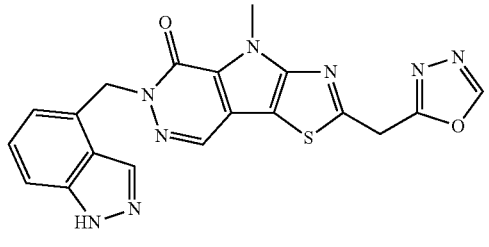 [SMILES: Cn1c2nc(Cc3nnco3)sc2c2cnn(Cc3cccc4[nH]ncc34)c(=O)c21]
222 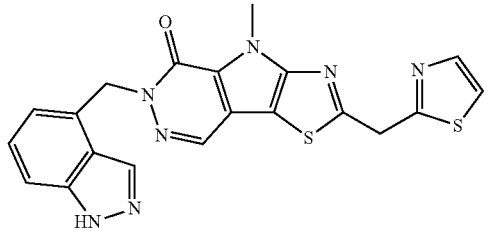 [SMILES: Cn1c2nc(Cc3nccs3)sc2c2cnn(Cc3cccc4[nH]ncc34)c(=O)c21]

141
TABLE 3-continued
Further Exemplary Compounds
Structure
224
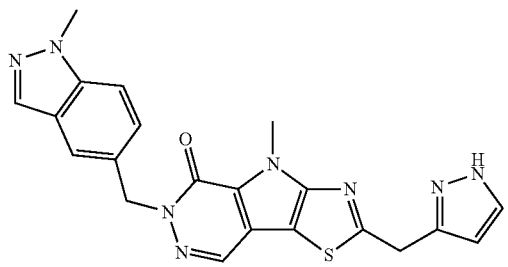 [SMILES: Cn1ncc2cc(Cn3ncc4c5sc(Cc6cc[nH]n6)nc5n(C)c4c3=O)ccc21]
225
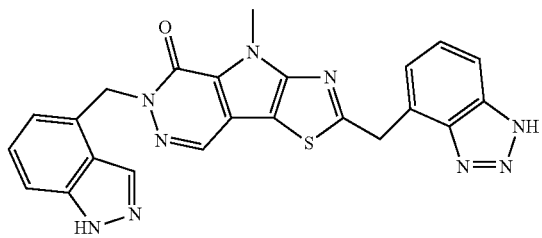 [SMILES: Cn1c2nc(Cc3cccc4[nH]nnc34)sc2c2cnn(Cc3cccc4[nH]ncc34)c(=O)c21]
226
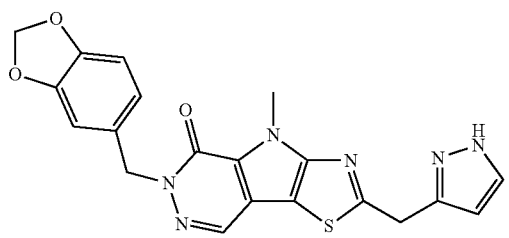
227
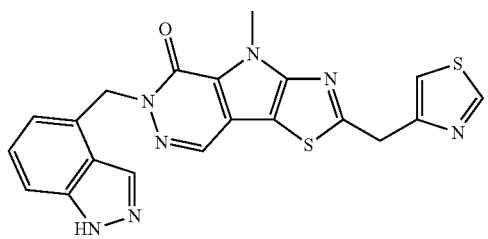 [SMILES: Cn1c2nc(Cc3cscn3)sc2c2cnn(Cc3cccc4[nH]ncc34)c(=O)c21]
228
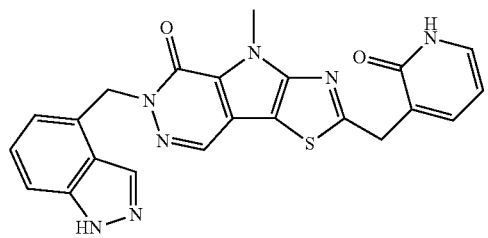 [SMILES: Cn1c2nc(Cc3ccc[nH]c3=O)sc2c2cnn(Cc3cccc4[nH]ncc34)c(=O)c21]
229
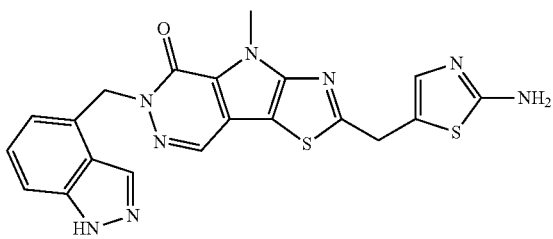 [SMILES: Cn1c2nc(Cc3cnc(N)s3)sc2c2cnn(Cc3cccc4[nH]ncc34)c(=O)c21]

TABLE 3-continued

Further Exemplary Compounds

Structure

230

233

234

381

383

385

TABLE 3-continued
Further Exemplary Compounds
Structure
387
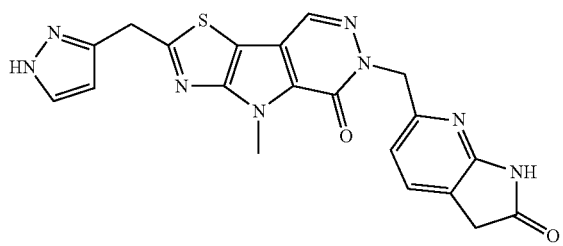 [SMILES: Cn1c2nc(Cc3cc[nH]n3)sc2c2cnn(Cc3ccc4c(n3)NC(=O)C4)c(=O)c21]
389
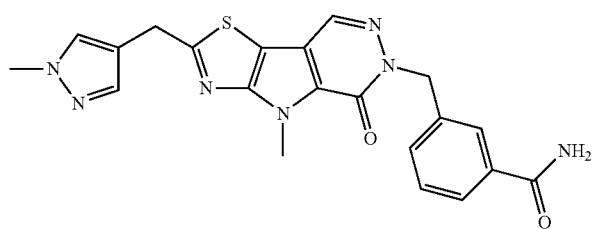 [SMILES: Cn1cc(Cc2nc3c(s2)c2cnn(Cc4cccc(C(N)=O)c4)c(=O)c2n3C)cn1]
391
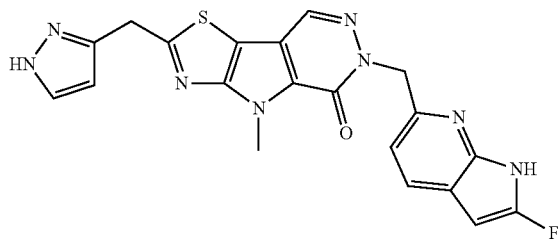 [SMILES: Cn1c2nc(Cc3cc[nH]n3)sc2c2cnn(Cc3ccc4cc(F)[nH]c4n3)c(=O)c21]
393
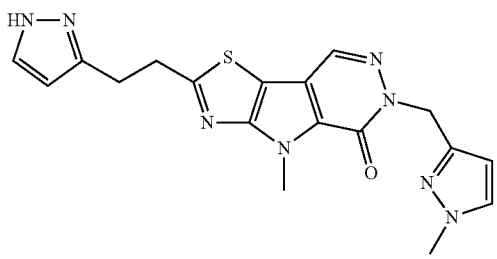 [SMILES: Cn1ccc(Cn2ncc3c4sc(CCc5cc[nH]n5)nc4n(C)c3c2=O)n1]
395
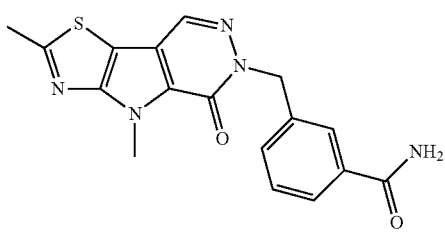 [SMILES: Cc1nc2c(s1)c1cnn(Cc3cccc(C(N)=O)c3)c(=O)c1n2C]
397
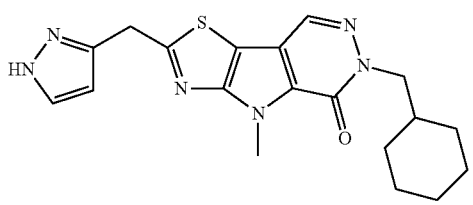 [SMILES: Cn1c2nc(Cc3cc[nH]n3)sc2c2cnn(CC3CCCCC3)c(=O)c21]

TABLE 3-continued

Further Exemplary Compounds

Structure

399

401

403

405

407

409

411

149
TABLE 3-continued
Further Exemplary Compounds
Structure
288
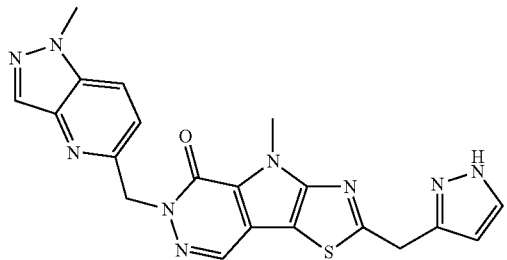 [SMILES: Cn1ncc2nc(Cn3ncc4c5sc(Cc6cc[nH]n6)nc5n(C)c4c3=O)ccc21]
290
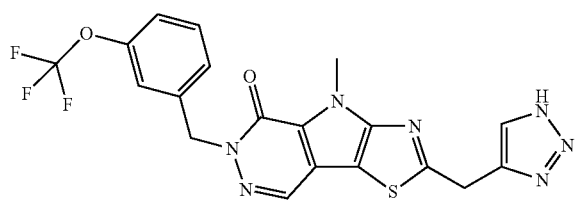 [SMILES: Cn1c2nc(Cc3c[nH]nn3)sc2c2cnn(Cc3cccc(OC(F)(F)F)c3)c(=O)c21]
293
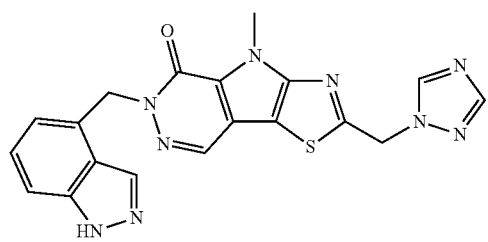 [SMILES: Cn1c2nc(Cn3cncn3)sc2c2cnn(Cc3cccc4[nH]ncc34)c(=O)c21]
329
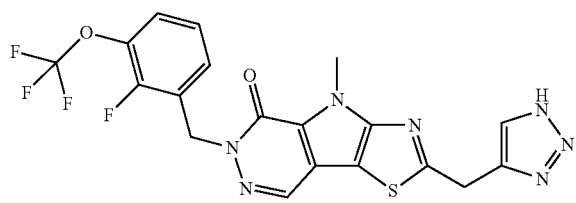 [SMILES: Cn1c2nc(Cc3c[nH]nn3)sc2c2cnn(Cc3cccc(OC(F)(F)F)c3F)c(=O)c21]
292
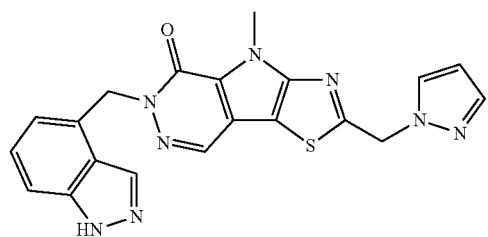 [SMILES: Cn1c2nc(Cn3cccn3)sc2c2cnn(Cc3cccc4[nH]ncc34)c(=O)c21]
294
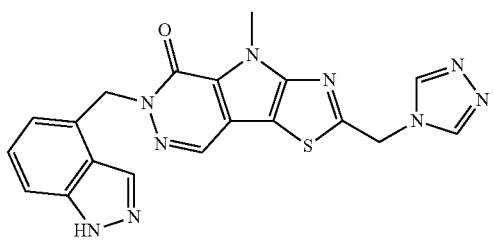 [SMILES: Cn1c2nc(Cn3cnnc3)sc2c2cnn(Cc3cccc4[nH]ncc34)c(=O)c21]

TABLE 3-continued
Further Exemplary Compounds
Structure
295 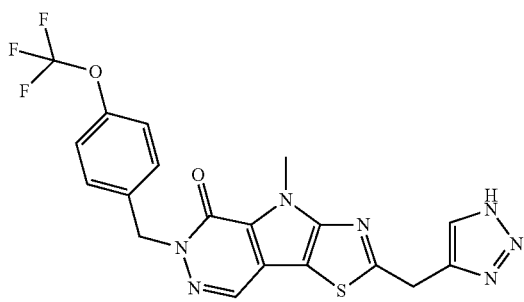 [SMILES: Cn1c2nc(Cc3c[nH]nn3)sc2c2cnn(Cc3ccc(OC(F)(F)F)cc3)c(=O)c21]
256 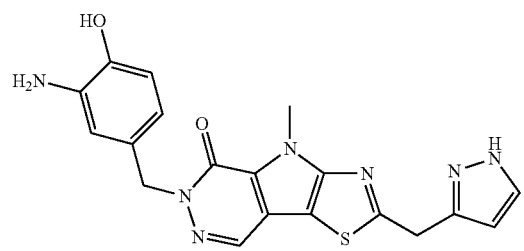 [SMILES: Cn1c2nc(Cc3cc[nH]n3)sc2c2cnn(Cc3ccc(O)c(N)c3)c(=O)c21]
258 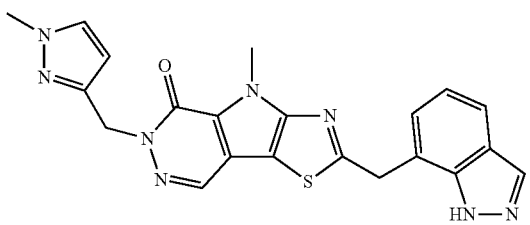 [SMILES: Cn1ccc(Cn2ncc3c4sc(Cc5cccc6cn[nH]c56)nc4n(C)c3c2=O)n1]
263 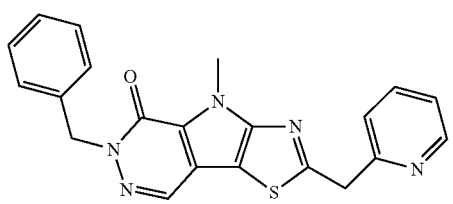 [SMILES: Cn1c2nc(Cc3ccccn3)sc2c2cnn(Cc3ccccc3)c(=O)c21]
304 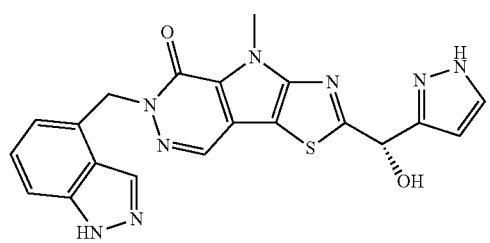 [SMILES: Cn1c2nc([C@@H](O)c3cc[nH]n3)sc2c2cnn(Cc3cccc4[nH]ncc34)c(=O)c21]
305 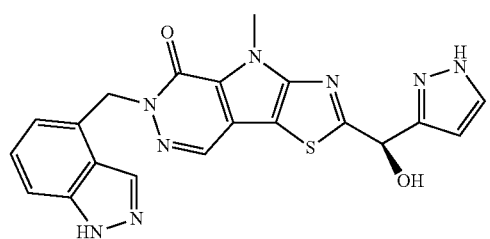 [SMILES: Cn1c2nc([C@H](O)c3cc[nH]n3)sc2c2cnn(Cc3cccc4[nH]ncc34)c(=O)c21]

153
154
TABLE 3-continued
Further Exemplary Compounds
Structure
270
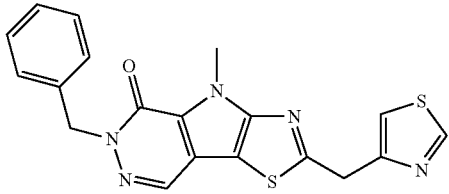 [SMILES: Cn1c2nc(Cc3cscn3)sc2c2cnn(Cc3ccccc3)c(=O)c21]
307
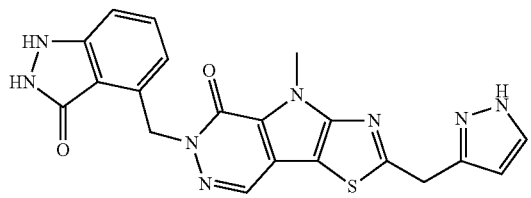 [SMILES: Cn1c2nc(Cc3cc[nH]n3)sc2c2cnn(Cc3cccc4[nH][nH]c(=O)c34)c(=O)c21]
273
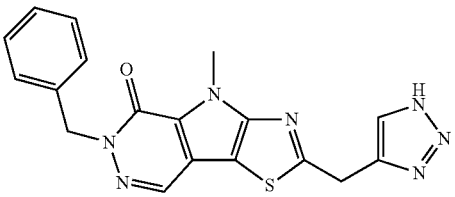 [SMILES: Cn1c2nc(Cc3c[nH]nn3)sc2c2cnn(Cc3ccccc3)c(=O)c21]
235
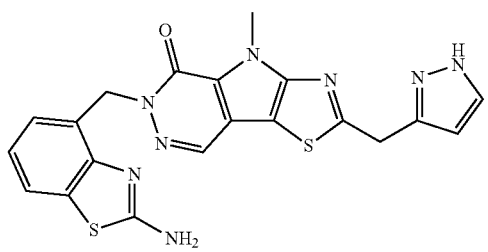 [SMILES: Cn1c2nc(Cc3cc[nH]n3)sc2c2cnn(Cc3cccc4sc(N)nc34)c(=O)c21]
236
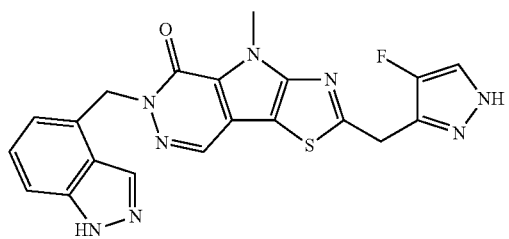 [SMILES: Cn1c2nc(Cc3n[nH]cc3F)sc2c2cnn(Cc3cccc4[nH]ncc34)c(=O)c21]
237
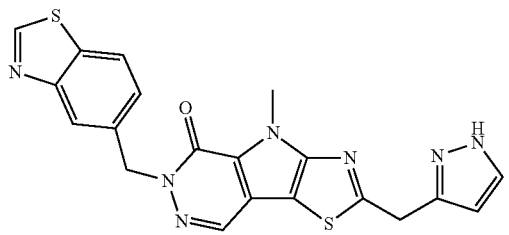 [SMILES: Cn1c2nc(Cc3cc[nH]n3)sc2c2cnn(Cc3ccc4scnc4c3)c(=O)c21]

TABLE 3-continued
Further Exemplary Compounds
Structure
253
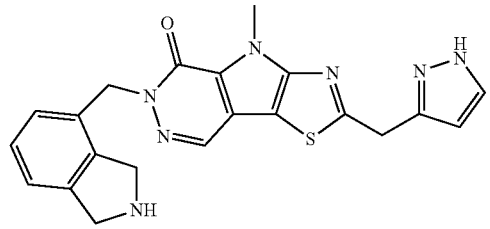 [SMILES: Cn1c2nc(Cc3cc[nH]n3)sc2c2cnn(Cc3cccc4c3CNC4)c(=O)c21]
369
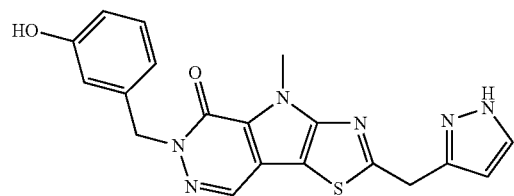 [SMILES: Cn1c2nc(Cc3cc[nH]n3)sc2c2cnn(Cc3cccc(O)c3)c(=O)c21]
372
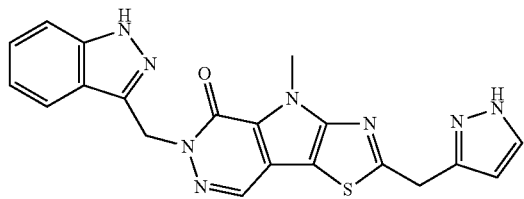 [SMILES: Cn1c2nc(Cc3cc[nH]n3)sc2c2cnn(Cc3n[nH]c4ccccc34)c(=O)c21]
275
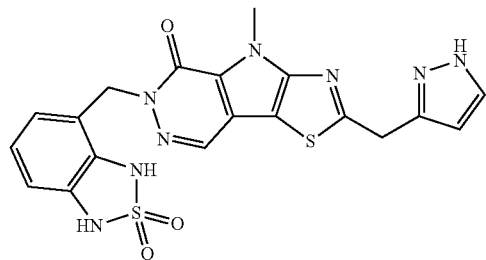 [SMILES: Cn1c2nc(Cc3cc[nH]n3)sc2c2cnn(Cc3cccc4c3NS(=O)(=O)N4)c(=O)c21]
276
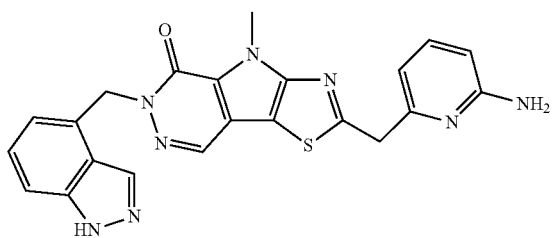 [SMILES: Cn1c2nc(Cc3cccc(N)n3)sc2c2cnn(Cc3cccc4[nH]ncc34)c(=O)c21]
277
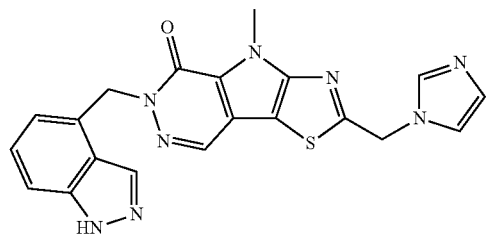 [SMILES: Cn1c2nc(Cn3ccnc3)sc2c2cnn(Cc3cccc4[nH]ncc34)c(=O)c21]

TABLE 3-continued

Further Exemplary Compounds

Structure

278

280

374

379

240

241

TABLE 3-continued

Further Exemplary Compounds

Structure

244

245

246

252

380

382

161
162
TABLE 3-continued
Further Exemplary Compounds
Structure
384 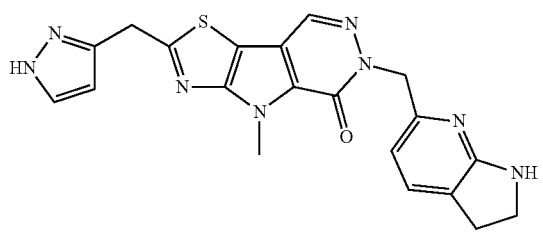 [SMILES: Cn1c2nc(Cc3cc[nH]n3)sc2c2cnn(Cc3ccc4c(n3)NCC4)c(=O)c21]
386 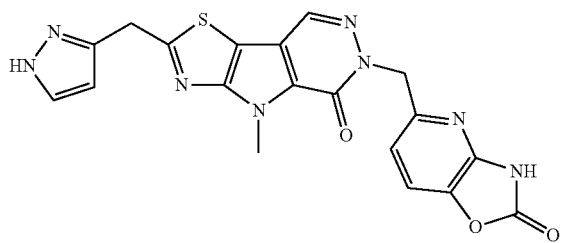 [SMILES: Cn1c2nc(Cc3cc[nH]n3)sc2c2cnn(Cc3ccc4oc(=O)[nH]c4n3)c(=O)c21]
388 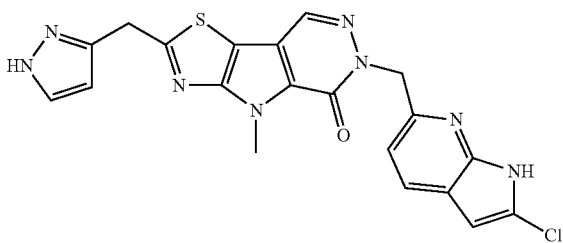 [SMILES: Cn1c2nc(Cc3cc[nH]n3)sc2c2cnn(Cc3ccc4cc(Cl)[nH]c4n3)c(=O)c21]
390 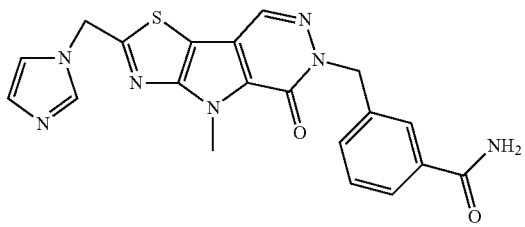 [SMILES: Cn1c2nc(Cn3ccnc3)sc2c2cnn(Cc3cccc(C(N)=O)c3)c(=O)c21]
392 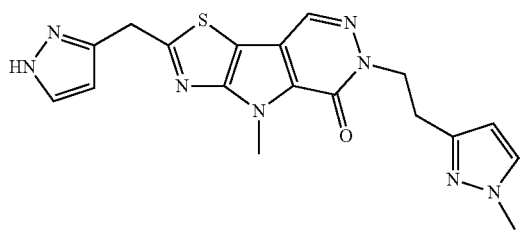 [SMILES: Cn1ccc(CCn2ncc3c4sc(Cc5cc[nH]n5)nc4n(C)c3c2=O)n1]
394 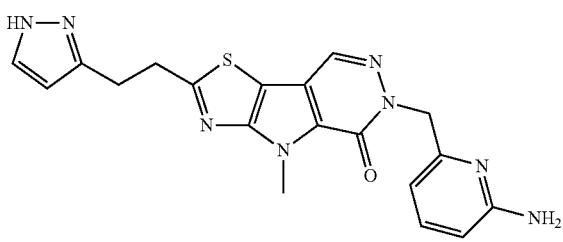 [SMILES: Cn1c2nc(CCc3cc[nH]n3)sc2c2cnn(Cc3cccc(N)n3)c(=O)c21]

TABLE 3-continued

Further Exemplary Compounds

Structure

396

398

400

402

404

406

408

TABLE 3-continued

Further Exemplary Compounds

Structure

410: [Structure shown: methylsulfonyl-thiazolo-pyrrolo-pyridazinone core with N-benzyl and N-thiazol-2-yl substituents]

TABLE 4

AC$_{50}$ of Exemplary Compounds of Wild Type and Mutant PKR

| Cpd Nr | PKR WT | PKR K410E | PK R510Q | Cell based ATP assay |
|---|---|---|---|---|
| 186 | C | C | B | AA |
| 187 | No Fit | C | No Fit | No Fit |
| 190 | A | A | A | AA |
| 192 | C | C | C | BB |
| 193 | A | A | A | AA |
| 195 | A | A | A | AA |
| 196 | A | A | A | AA |
| 199 | A | A | A | AA |
| 200 | A | A | C | AA |
| 201 | A | A | A | AA |
| 202 | A | A | A | AA |
| 205 | A | A | A | AA |
| 206 | C | C | C | BB |
| 207 | B | B | C | AA |
| 208 | C | C | C | BB |
| 209 | C | C | C | AA |
| 210 | A | A | A | AA |
| 211 | A | A | A | AA |
| 212 | A | A | A | AA |
| 213 | B | B | B | AA |
| 215 | A | A | A | AA |
| 216 | A | A | A | AA |
| 217 | A | A | A | AA |
| 219 | A | A | A | AA |
| 220 | A | A | A | AA |
| 221 | A | A | B | BB |
| 222 | A | A | A | AA |
| 224 | A | A | A | AA |
| 225 | A | A | A | AA |
| 226 | A | A | A | AA |
| 227 | A | A | A | AA |
| 228 | A | A | A | AA |
| 229 | B | B | B | BB |
| 230 | A | A | A | AA |
| 233 | A | A | A | AA |
| 234 | A | A | A | BB |
| 235 | A | A | A | AA |
| 236 | A | A | A | AA |
| 237 | A | A | A | AA |
| 240 | B | C | B | AA |
| 241 | A | A | A | AA |
| 244 | A | A | A | AA |
| 245 | B | B | A | AA |
| 246 | A | A | A | AA |
| 252 | A | A | A | AA |
| 253 | A | A | A | AA |
| 256 | A | A | A | AA |
| 258 | A | A | A | AA |
| 263 | A | A | A | AA |
| 270 | A | A | A | AA |
| 273 | C | C | C | BB |
| 275 | C | C | C | BB |
| 276 | A | A | A | AA |
| 277 | C | B | C | BB |
| 278 | A | A | A | AA |
| 280 | A | A | A | AA |
| 288 | A | A | A | AA |
| 290 | A | A | A | AA |
| 292 | A | A | A | AA |
| 293 | A | A | B | AA |
| 294 | C | C | B | BB |
| 295 | A | A | A | AA |
| 304 | A | A | A | AA |
| 305 | A | A | A | AA |
| 307 | A | A | A | AA |
| 329 | B | B | A | AA |
| 369 | A | A | A | AA |
| 372 | A | A | A | AA |
| 374 | A | A | A | AA |
| 379 | A | A | A | AA |
| 380 | A | A | A | AA |
| 381 | A | A | A | AA |
| 382 | A | A | A | AA |
| 383 | A | A | A | AA |
| 384 | A | A | A | AA |
| 385 | A | A | A | AA |
| 386 | A | A | A | AA |
| 387 | B | A | A | BB |
| 388 | A | A | A | AA |
| 389 | C | C | B | BB |
| 390 | C | C | C | No Fit |
| 391 | A | A | A | AA |
| 392 | A | A | A | AA |
| 393 | A | A | A | AA |
| 394 | A | A | A | AA |
| 395 | C | B | C | BB |
| 396 | A | A | A | AA |
| 397 | C | C | C | No Fit |
| 398 | C | C | C | No Fit |
| 399 | C | C | C | No Fit |
| 400 | C | C | C | BB |
| 401 | A | A | A | AA |
| 402 | C | C | C | No Fit |
| 403 | C | C | C | No Fit |
| 404 | A | A | A | AA |
| 405 | C | No Fit | No Fit | No Fit |
| 406 | C | C | C | No Fit |
| 407 | No Fit | C | A | No Fit |
| 408 | C | C | B | BB |
| 409 | C | No Fit | No Fit | No Fit |
| 410 | No Fit | C | No Fit | BB |
| 411 | C | C | C | No Fit |

In certain embodiments, the compound of Formulas (I)-(XV-c) are selected from any one of the compounds set forth in Table 1 or Table 3 and in the Examples.

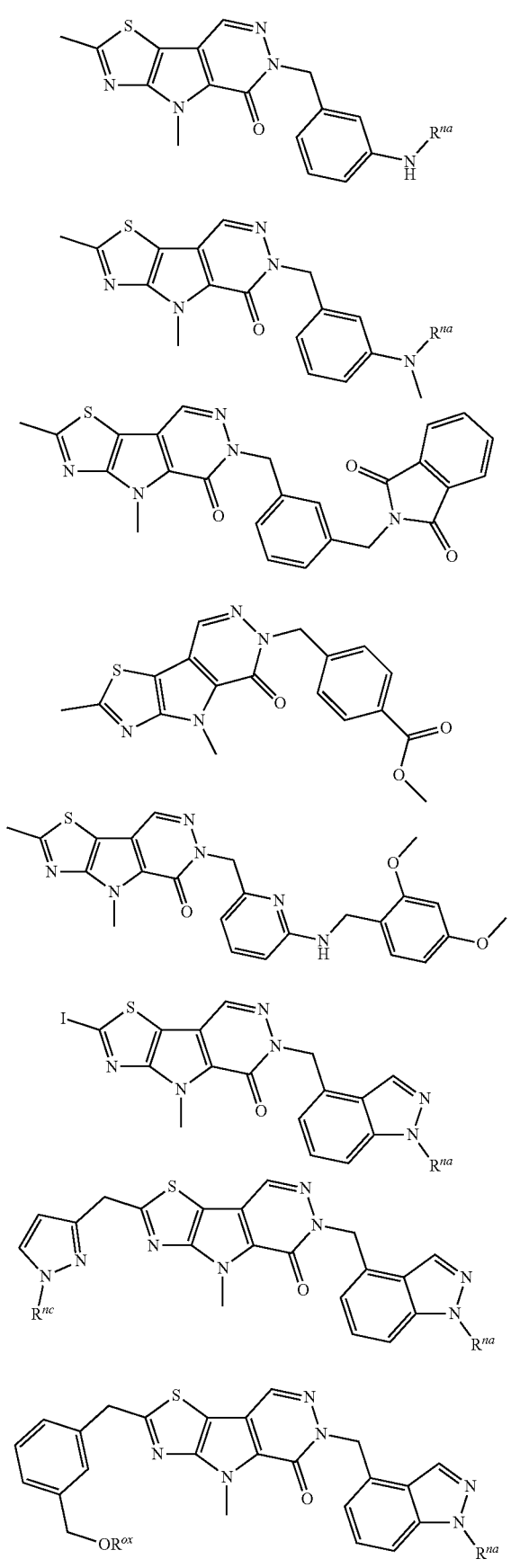
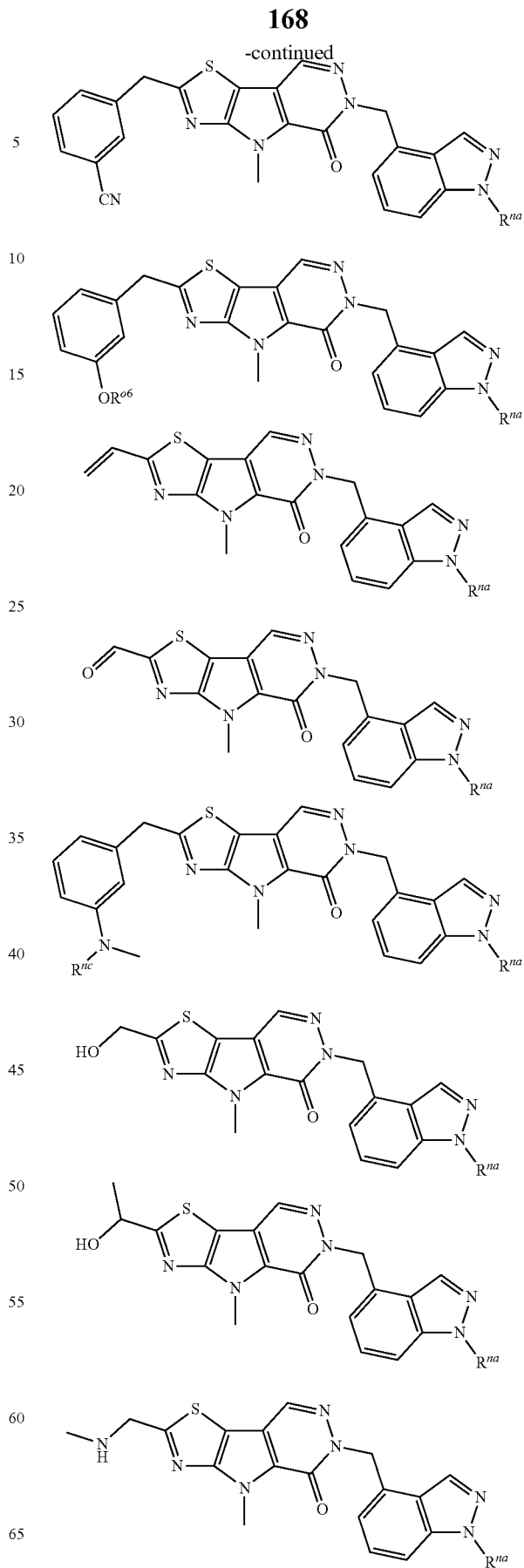

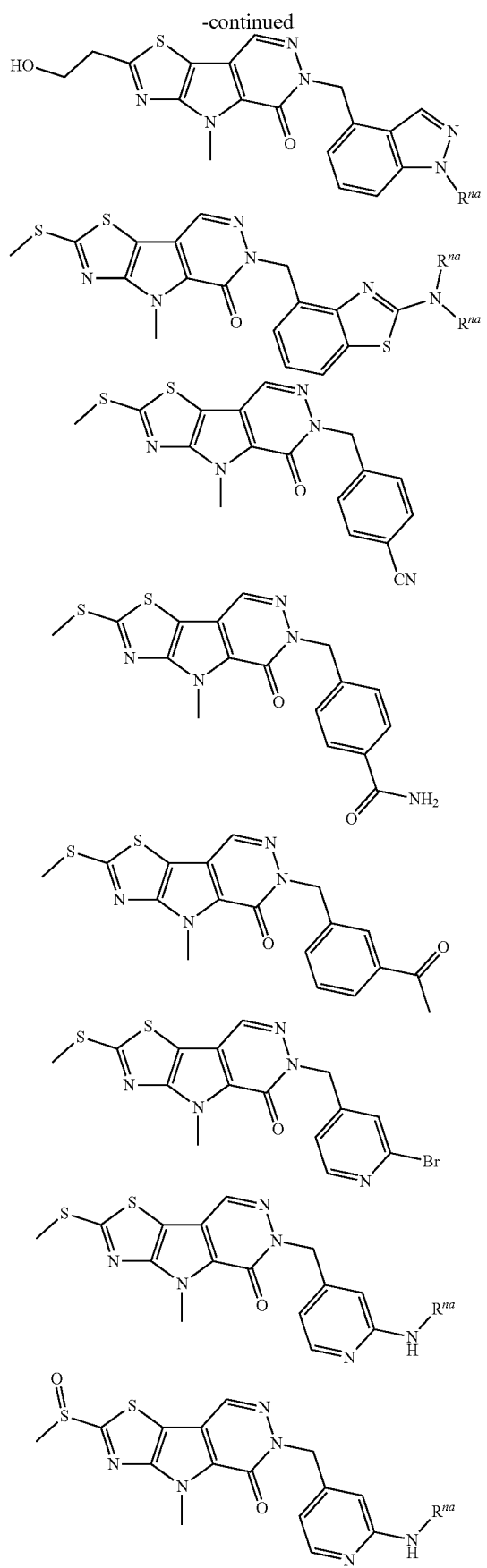
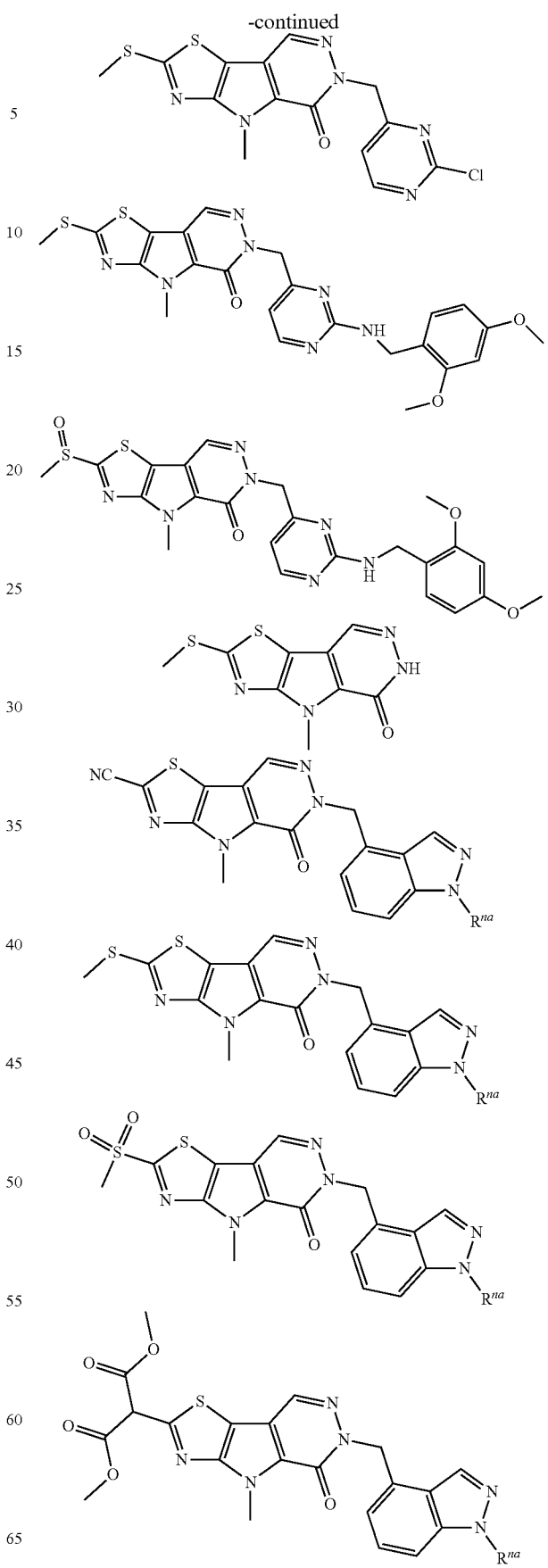

171
-continued
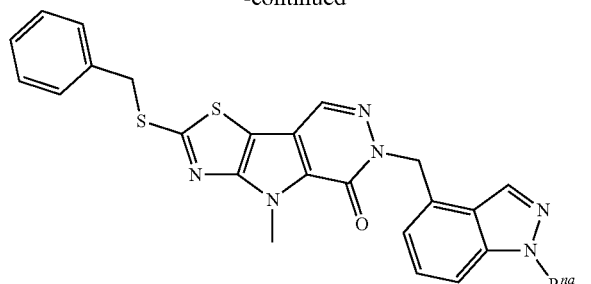
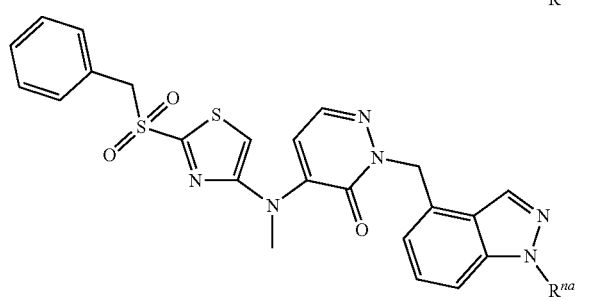
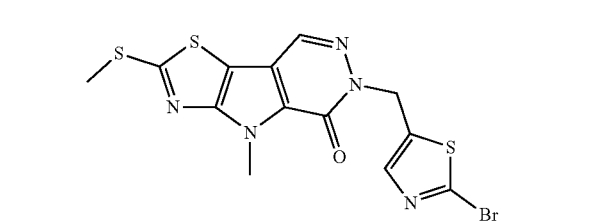
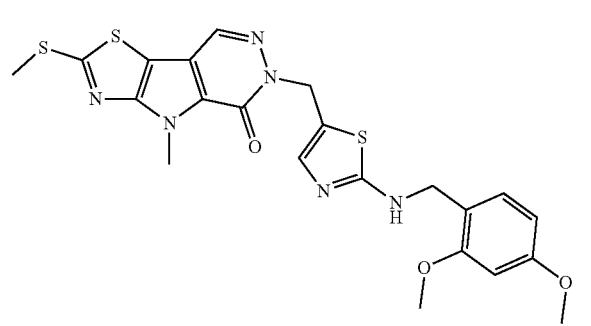
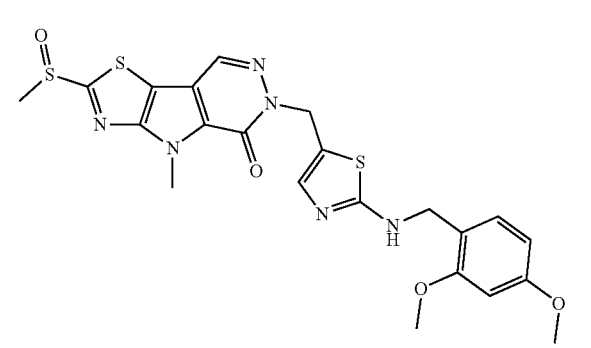
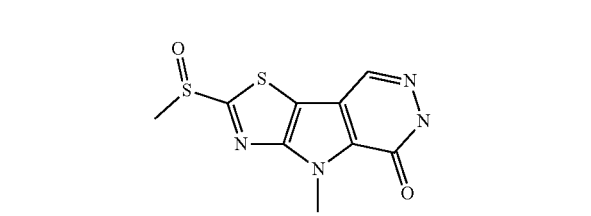
172
-continued
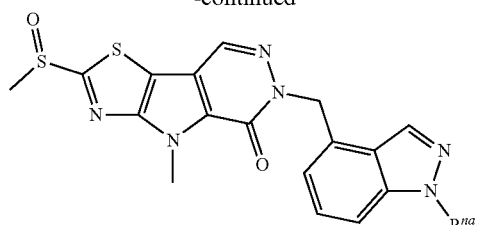
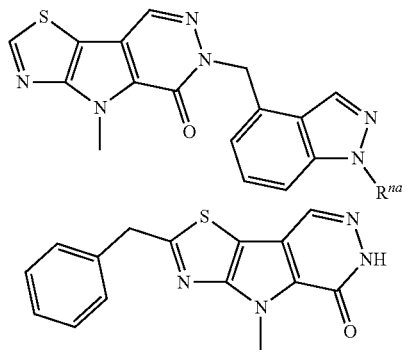
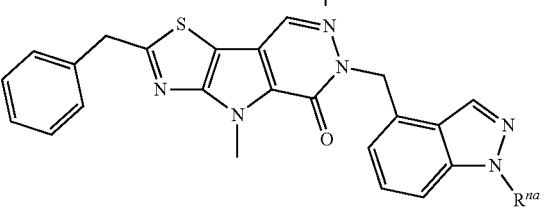
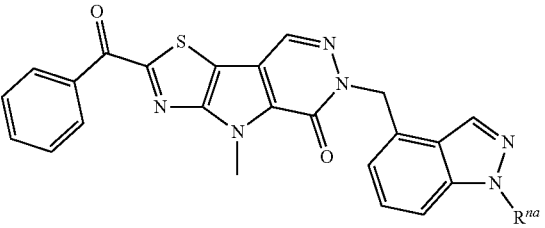
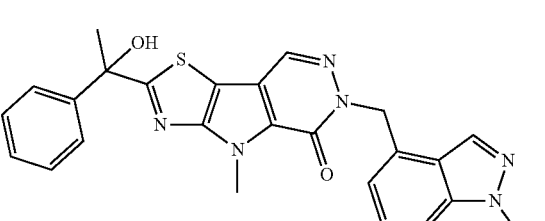
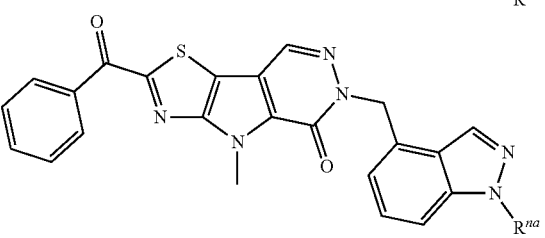
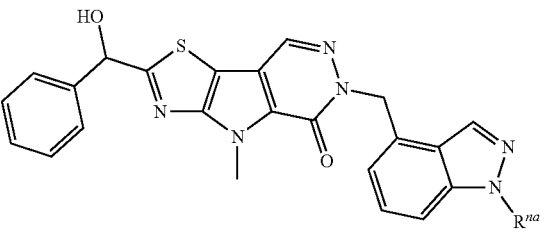

173
-continued
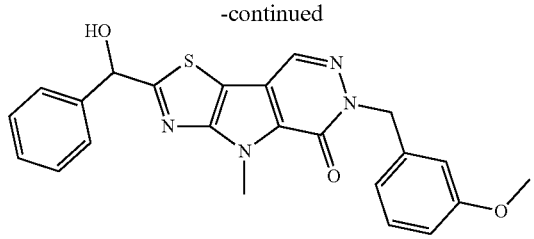
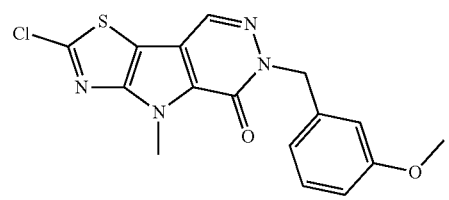 [SMILES: COc1cccc(Cn2ncc3c4sc(Cl)nc4n(C)c3c2=O)c1]
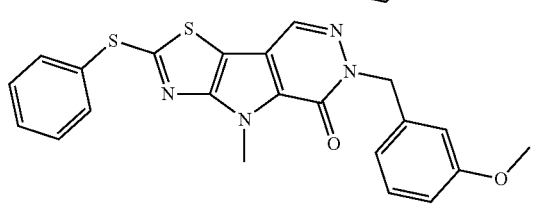
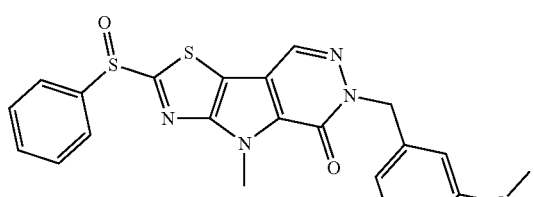
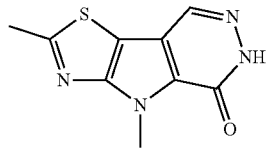
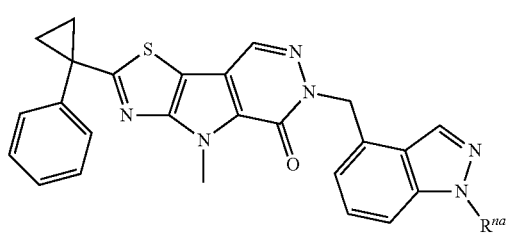
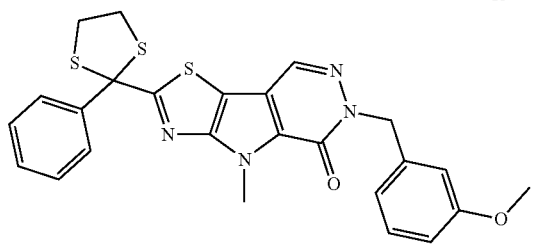
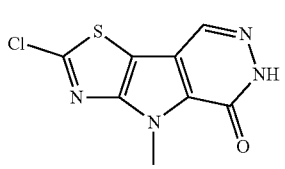
174
-continued
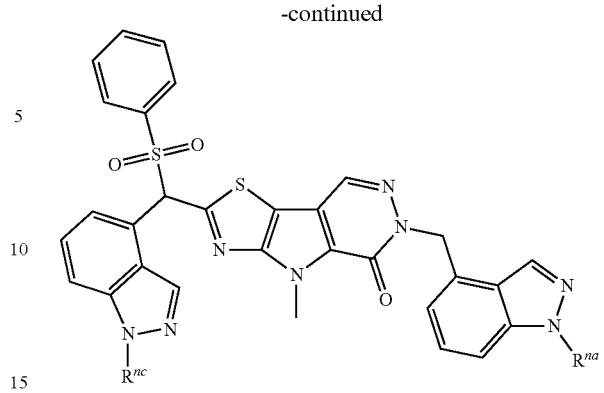
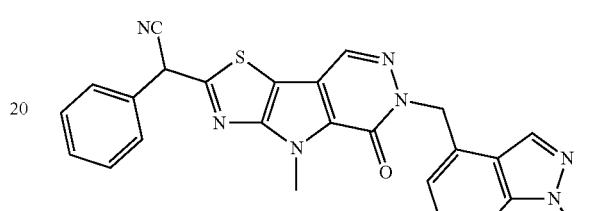
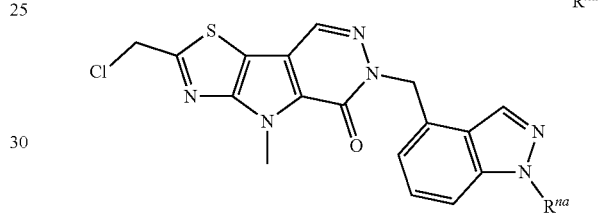
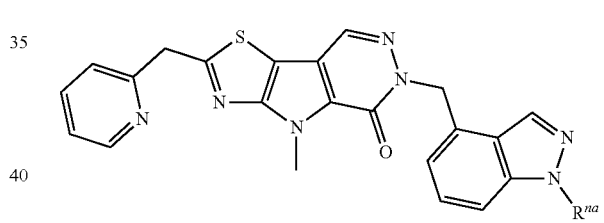
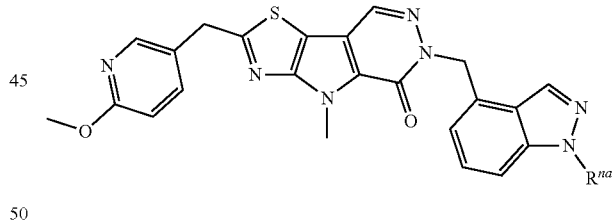
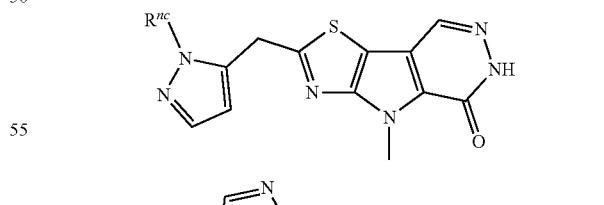
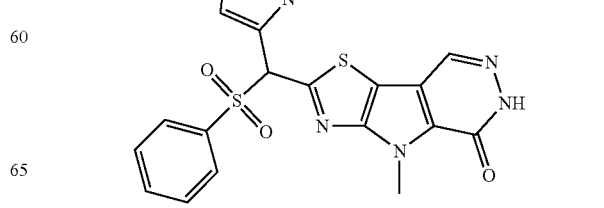

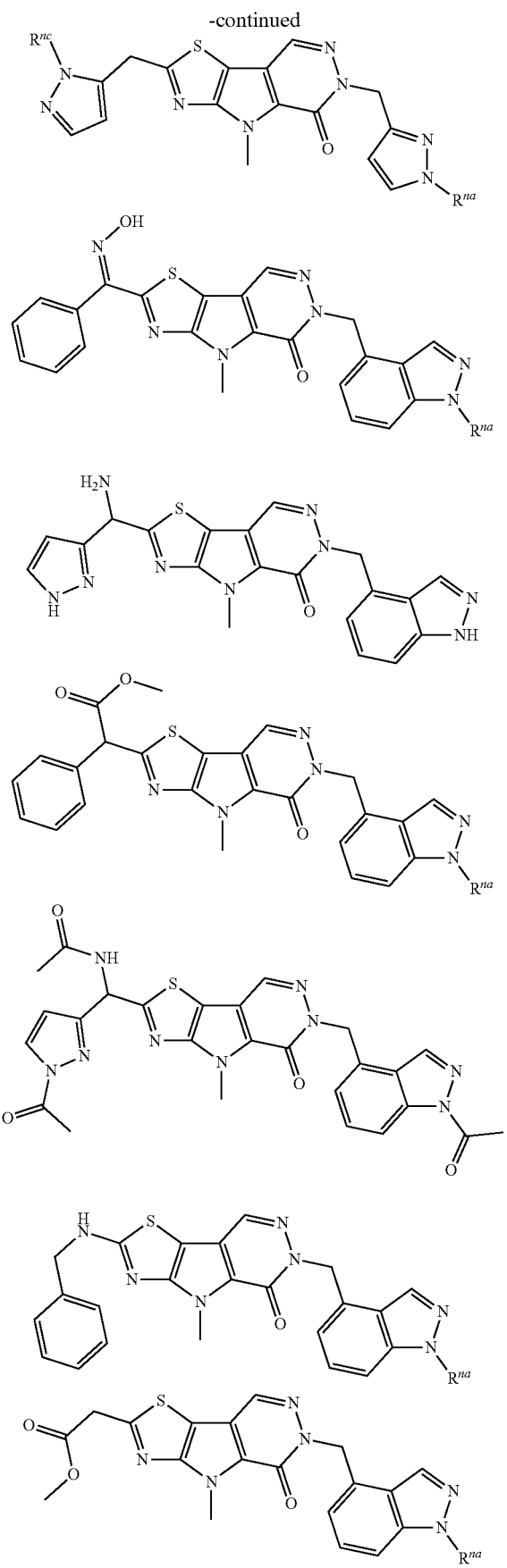
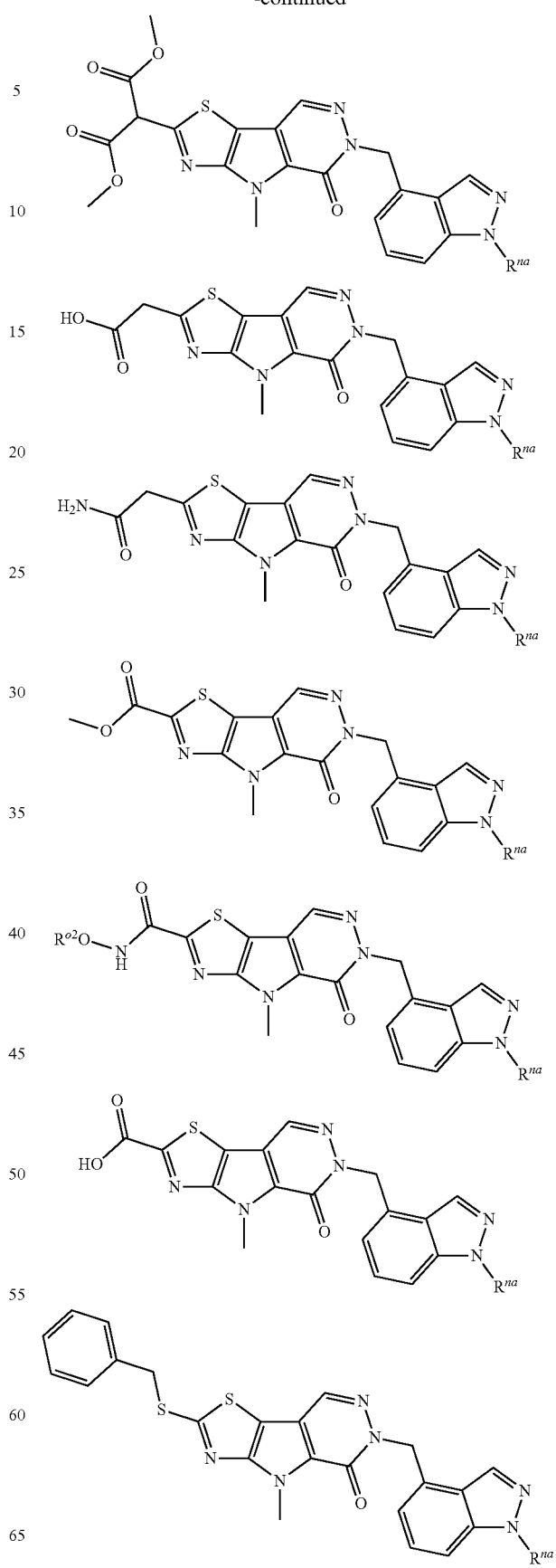

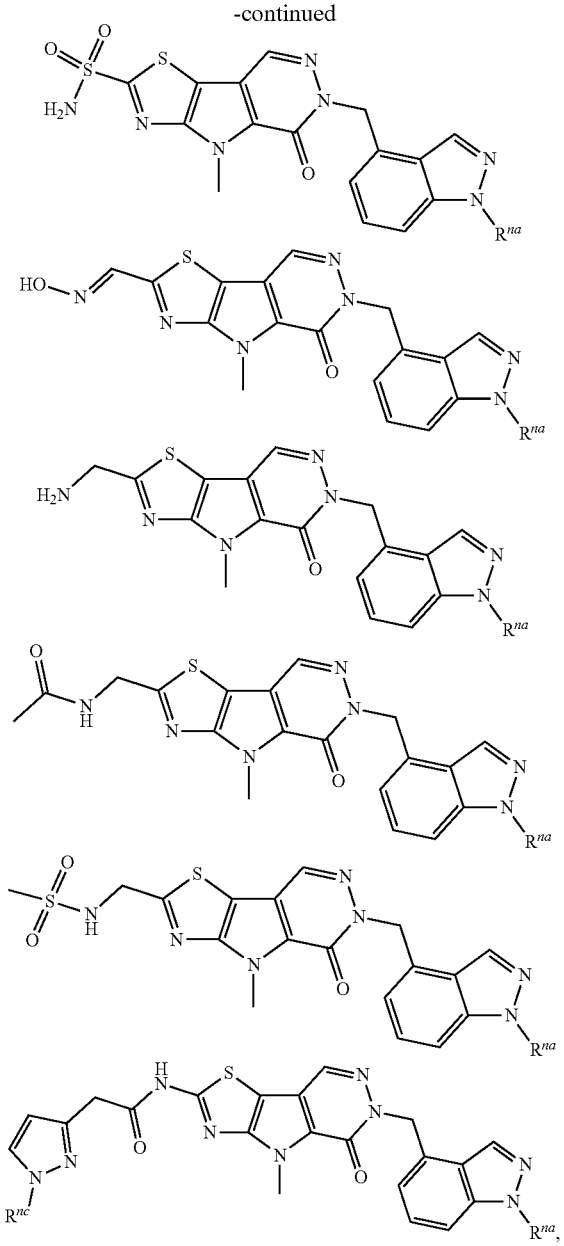

wherein $R^{na}$, $R^{nc}$, $R^{o2}$ and $R^{o6}$ are as defined herein, and $R^{ox}$ is hydrogen or an oxygen protecting group. In certain embodiments, $R^{na}$ is a nitrogen protecting group (e.g. SEM or BO). In certain embodiments, $R^{nc}$ is a nitrogen protecting group (e.g. SEM or BOG). In certain embodiments, $R^{o2}$ is an oxygen protecting group (e.g. THP). In certain embodiments, $R^{o6}$ is an oxygen protecting group (e.g. TBS). In certain embodiments, $R^{ox}$ is an oxygen protecting group (e.g. THP).

The compounds described herein can be made using a variety of synthetic techniques as set forth in the Examples. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Certain activator compounds useful as PKR wild type and/or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

In some embodiments, compounds of Formula (I) can be prepared using methods illustrated in Scheme 1. Thiazolyl aldehyde of formula S1 reacts with ethyl azidoacetate under nucleophilic addition conditions (e.g. a base) in an appropriate solvent (e.g. ethanol) to give intermediates of formula S2. The hydroxyl group of formula S2 can be converted to a leaving group and subject to elimination to give formula S3. Cyclization and subsequent functionalization of the amino group provides bicyclic compound of formula S5, which undergoes nucleophilic displacement with sodium methanethiolate, followed by oxidation to give formula S7. Further cyclization of formula S7 in the presence of hydrazine, followed by nucleophilic displacement with $LG^1$-$CH_2$-$Q^1$ in the presence of a base provides intermediates of formula S9. The sulfur group in formula S9 can be oxidized to sulfinyl or sulfonyl to provide formula S10 or S11, which is a substrate for further nucleophilic displacement to generate a general formula S12. As used herein, $X^1$ is a leaving group as defined herein. In certain embodiments, $X^1$ is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, aryloxy group; $LG^1$ is a leaving group as defined herein; $Q^1$ is optionally substituted cycloalkyl, optionally substituted heterocyclyl, optionally substituted aryl, or optionally substituted heteroaryl; and $Nu^1$ is a nucleophile as defined herein. $Nu^1$ of compound of formula S12 can be further converted to other functionalities with standard chemical transformations. $R^1$ is as defined in the first embodiment.

Scheme 1

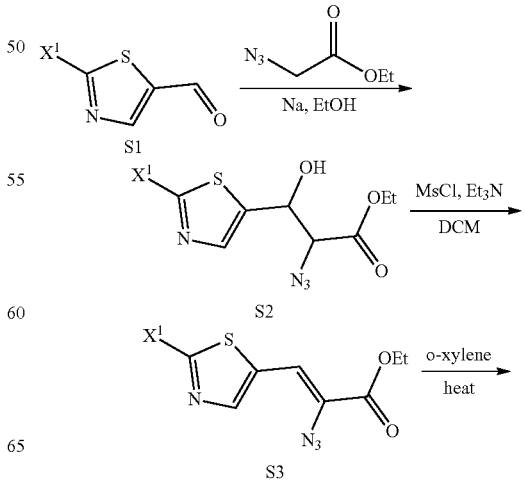

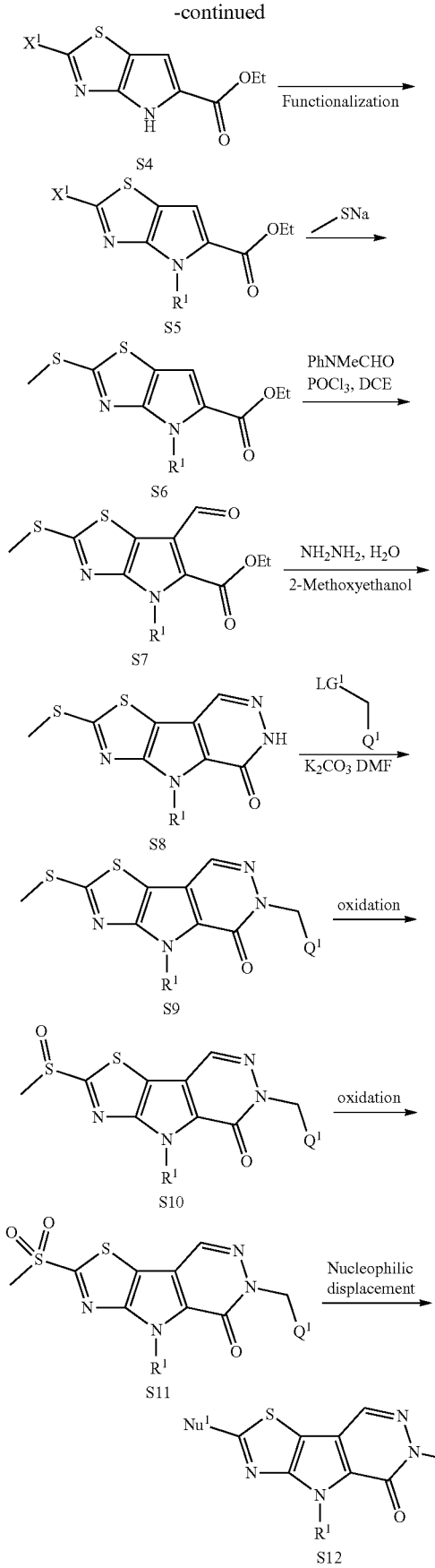
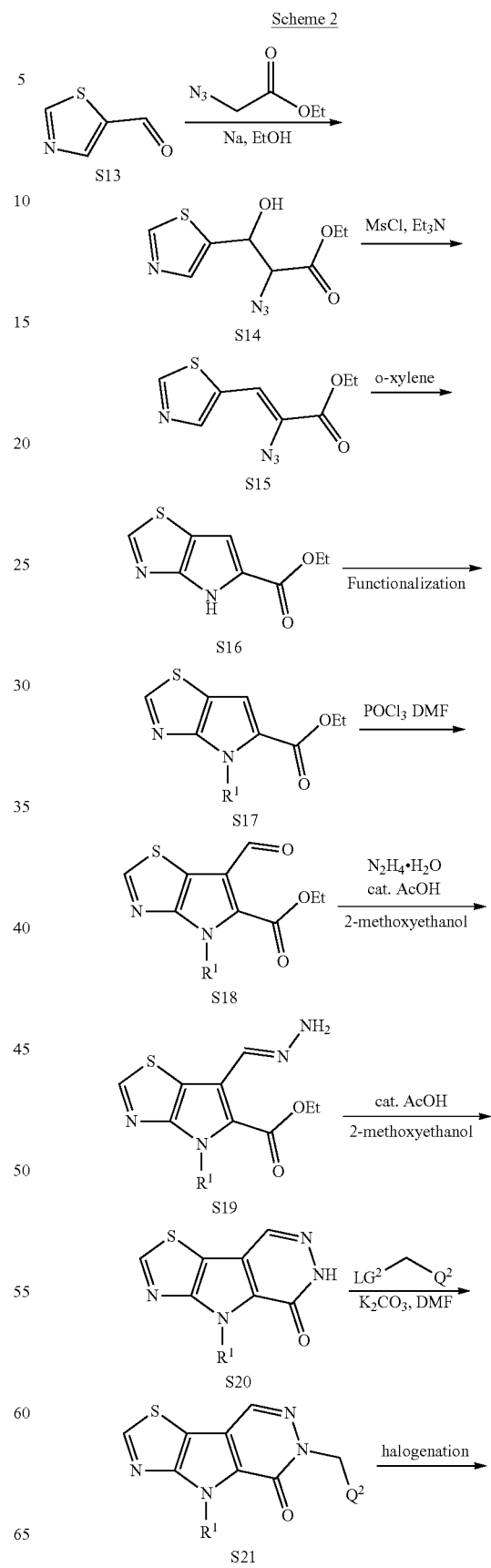
Scheme 2

-continued

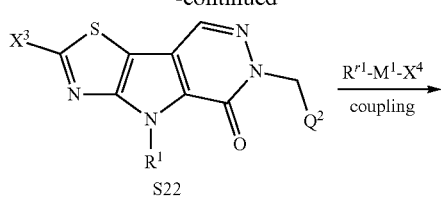
S22

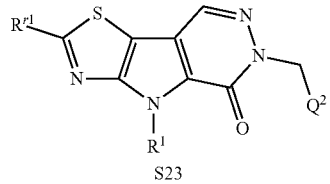
S23

In some embodiments, compounds of Formula (I) can be prepared using methods shown in Scheme 2. Similar to Scheme 1, formula S21 can be prepared from thiazole aldehyde of formula S13. Halogenation of formula S21 gives formula S22, which can undergo an organo coupling reaction with an alkyl metal, alkenyl metal, alkynyl metal, aryl metal, heteroaryl metal, heterocyclyl metal, or cycloalkyl metal to give a compound of formula S23. As used herein, $X^3$ is a halogen; $R^1$ is as defined in the first embodiment of the invention; $LG^2$ is a leaving group as defined herein; $Q^2$ is optionally substituted cycloalkyl, optionally substituted heterocyclyl, optionally substituted aryl, or optionally substituted heteroaryl; $M^1$ is a metal (e.g. Li, Na, K, Mg, Zn, Sn, B, Pd, Si, Cu etc.), $X^4$ is halogen or alkyl sulfonic acid ester or an aryl sulfonic acid ester; $R^r$ is optionally substituted alkyl, optionally substituted alkenyl, optionally substituted alkynyl, optionally substituted cycloalkyl, optionally substituted heterocyclyl, optionally substituted aryl, or optionally substituted heteroaryl, provided that when $Q^2$ is optionally substituted 5-membered or 6-membered monocyclic heteroaryl, and $R^r t$ is not optionally substituted 5-membered or 6-membered monocyclic heteroaryl-methylene-. In certain embodiments, the organo coupling reaction is Negishi reaction; $X^3$ is I; and $M^1$ is Zn.

Compounds of formula S22 and S23 are useful intermediates to introduce more functionalities at $X^3$ and/or $R^{r1}$ position (Scheme 3). In certain embodiments, the compound of formula 23-i can be further oxidized to form formula S24. Nucleophilic addition of S24 with an appropriate nucleophile generates a compound of S25. In another embodiment, compounds of formula S22 can be coupled with vinyl metal to introduce the vinyl group to the thiazole ring. Oxidation of the vinyl group followed by nucleophilic addition provides a compound of formula S28. As used herein, $Nu^2$ is a nucleophile.

Scheme 3

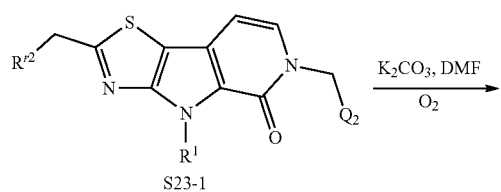
S23-1

-continued

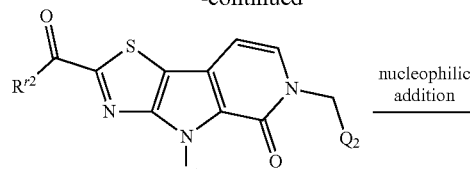
S24

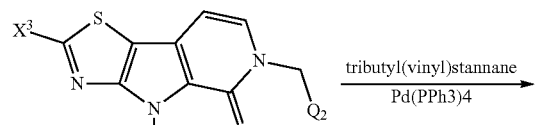
S25

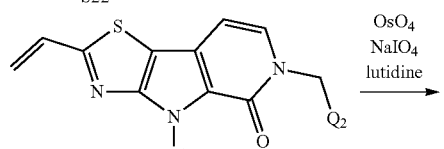
S22

S26

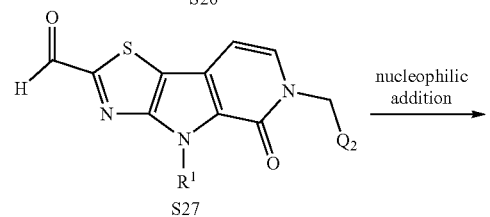
S27

S28

As used herein, $R^{r2}$ is optionally substituted alkyl, optionally substituted alkenyl, optionally substituted alkynyl, optionally substituted cycloalkyl, optionally substituted heterocyclyl, optionally substituted aryl, or optionally substituted heteroaryl.

As used herein, a nucleophile is a chemical species that donates an electron pair to an electrophile to form a chemical bond in relation to a reaction. All molecules or ions with a free pair of electrons or at least one pi bond can act as nucleophiles. Exemplary nucleophiles comprise at least one group possessing nucleophilic functionality, for example, an alpha carbon (e.g. the carbon adjacent to carbonyl, sulfonyl, sulfinyl, aryl group, or heteroaryl), a thiol group, a hydroxyl group, a primary amine group, a secondary amine group, a halide, cyanide, azide, alcoxide, organic metal, or inorganic base.

In some embodiments, compounds of Formula (I) can be prepared using methods shown in Scheme 4. Nucleophilic displacement of formulae S30 with a secondary cyclic amine provides formulae S31. Organo-coupling reactions (e.g. Suzuki coupling, Pd coupling etc.) of compound S32 provide a compound of formulae S33(i)-(iii). Further, the sulfinyl group of formula S34 can be functionalized with ammonium carbamate to give imino-sulfanone of formula S35.
Scheme 4
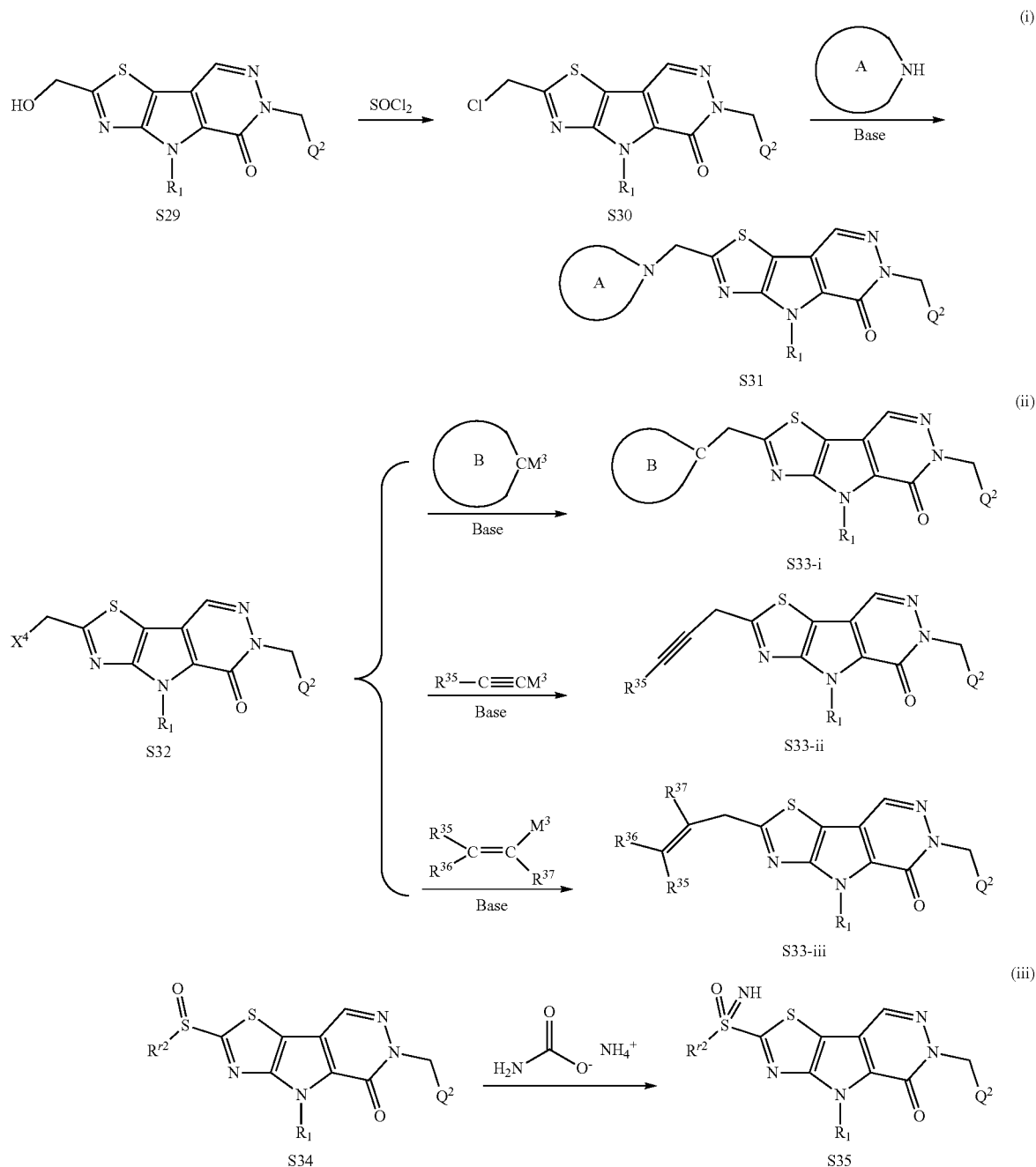
As used herein,
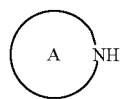

represents Ring A which can be optionally substituted heteroaryl or optionally substituted heterocyclyl, with a nitrogen as a ring atom.

As used herein,

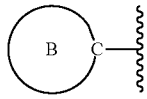

represents Ring B which can be optionally substituted heteroaryl or optionally substituted heterocyclyl, with the point of attachment on the carbon ring atom.

$R^1$ is as defined in the first embodiment. Each instance of $R^{35}$, $R^{36}$, and $R^{37}$ is independently hydrogen, optionally substituted alkyl, optionally substituted alkenyl, optionally substituted alkynyl, optionally substituted aryl, optionally substituted heteroaryl, optionally substituted heterocyclyl, or optionally substituted cycloalkyl.

$X^4$ is halogen or —OTf. $M^4$ is an organic metal with appropriate ligands if needed (organic or inorganic) as valency permits. Exemplified $M^4$ includes, but is not limited to organic Li, Sn, B (e.g. boronic acids and boronic esters), Zn, Mg, Si, Pd, and Cu.

Methods of Treatment

In one embodiment, provided is a method for treating a disease, condition or disorder as described herein (e.g., treating) comprising administering a compound, a pharmaceutically acceptable salt of a compound or pharmaceutical composition comprising a compound described herein (e.g., a compound of Formulas (I)-(XV-c), in the Examples, and in Table 1, Table 3 and FIGS. 1A-1C and 2A-2C).

The compounds and compositions described herein can be administered to cells in culture, e.g. in vitro or ex vivo, or to a subject, e.g., in vivo, to treat, and/or diagnose a variety of disorders, including those described herein below.

In one embodiment of the invention provided is a method for increasing the lifetime of red blood cells (RBCs) in need thereof comprising contacting blood with an effective amount of (1) a compound described herein (e.g., a compound of Formulas (I)-XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier.

In a further embodiment the compound or pharmaceutical composition is added directly to whole blood or packed red blood cells (e.g. extracorporeally). In another embodiment, the compound or pharmaceutical composition is administered to a subject in need thereof.

In one embodiment of the invention provided is a method for regulating 2,3-diphosphoglycerate levels in blood in need thereof contacting blood with an effective amount of (1) a compound, described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier.

In one embodiment of the invention provided is a method for treating sickle cell disease comprising administering to a subject with an effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier.

As used here, sickle cell disease (SCD), Hemoglobin SS disease, and sickle cell anemia are used interchangeably. Sickle cell disease (SCD) describes a group of inherited red blood cell disorders. In certain embodiments, subjects with SCD have abnormal hemoglobin, called hemoglobin S or sickle hemoglobin, in their red blood cells. In certain embodiments, a subject having SCD has at least one abnormal genes causing the body to make hemoglobin S. In certain embodiments, a subject having SCD has two hemoglobin S genes, Hemoglobin SS.

In one embodiment of the invention provided is a method of treating pyruvate kinase deficiency (PKD) in a subject comprising administering to the subject a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier.

As described herein, PKD is a deficiency of PKR. In certain embodiments, the deficiency of PKR is associated with a PKR mutation. In certain embodiments, PKD refers to presence of at least 2 mutant alleles in the PKLR gene. In certain embodiments, at least 1 of the at least 2 mutant alleles in the PKLR gene is a missense mutation. In certain embodiments, a PKD patient has an Hb concentration less than or equal to 10.0 g/dL. In certain embodiments, the patient is not under regular transfusion (e.g. having had no more than 4 transfusion episodes in the 12-month period). In certain embodiments, the patient is under regular transfusion (e.g. having had at least 4 transfusion episodes in the 12-month period). In certain embodiments, the patient is under a regular transfusion having at least 6 transfusion episodes in the 12-month period. In certain embodiments, the patient under regular transfusion has hemoglobin (Hb) ≤12.0 g/dL (if male) or ≤11.0 g/dL (if female). In certain embodiments, the patient has undergone splenectomy.

In an embodiment, the mutant PKR is selected from the group consisting of A31V, A36G, G37Q, R40W, R40Q, L73P, S80P, P82H, R86P, I90N, T93I, G95R, M107T, G111R, A115P, S120F, H121Q, S130P, S130Y, V134D, R135D, A137T, G143S, I153T, A154T, L155P, G159V, R163C, R163L, T164N, G165V, L167M, G169G, E172Q, W201R, I219T, A221Y, D221N, G222A, I224T, G232C, N253D, G263R, G263W, E266K, V269F, L272V, L272P, G275R, G275R, E277K, V280G, D281N, F287V, F287L, V288L, D293N, D293V, A295I, A295V, I310N, I314T, E315K, N316K, V320L, V320M, S330R, D331N, D331G, D331E, G332S, V335M, A336S, R337W, R337P, R337Q, D339N, D339Q, G341A, G341D, I342F, K348N, A352D, I357T, G358R, G358E, R359C, R359H, C360Y, N361D, G364D, K365M, V368F, T371I, L374P, S376I, T384M, R385W, R385K, E387G, D390N, A392T, N393D, N393S, N393K, A394S, A394D, A394V, V395L, D397V, G398A, M403I, G406R, E407K, E407G, T408P, T408A, T408I, K410E, G411S, G411A, Q421K, A423A, A423A, R426W, R426Q, E427A, E427N, A431T, R449C, I457V, G458D, A459V, V460M, A468V, A468G, A470D, T477A, R479C, R479H, S485F, R486W, R486L, R488Q, R490W, I494T, A495T, A495V, R498C, R498H, A503V, R504L, Q505E, V506I, R510Q, G511R, G511E, R518S, R531C, R532W, R532Q, E538D, G540R, D550V, V552M, G557A, R559G, R559P, N566K, M568V, R569Q, R569L, Q58X, E174X, W201X, E241X, R270X, E440X, R486X, Q501X, $L^{508}X$, R510X, E538X, R559X. These mutations are described in Canu et. al., Blood Cells, Molecules and Diseases 2016, 57, pp. 100-109. In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q.

In one embodiment of the invention provided is a method of treating anemia in a subject comprising administering to a subject a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier. In certain embodiments, the anemia is a dyserythropoietic anemia such as congenital dyserythropoietic anemia type I, II, III, or IV. In certain embodiments, the anemia is hemolytic anemia. In certain embodiments, the hemolytic anemia is a congenital and/or hereditary form of hemolytic anemia such as PKD, sickle cell disease, thalassemias (e.g. alpha or beta), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

As used herein, the term "anemia" refers to a deficiency of red blood cells (RBCs) and/or hemoglobin. As used herein, anemia includes all types of clinical anemia, for example (but not limited to): microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle cell disease, warm autoimmune hemolytic anemia, cold agglutinin hemolytic anemia, osteopetrosis, thalassemia, and myelodysplastic syndrome.

In certain embodiments, anemia can be diagnosed on a complete blood count. In certain embodiments, anemia can be diagnosed based on the measurement of one or more markers of hemolysis (e.g. RBC count, hemoglobin, reticulocytes, schistocytes, lactate Dehydrogenase (LDH), haptoglobin, bilirubin, and ferritin) and/or hemosiderinuria mean corpuscular volume (MCV) and/or red cell distribution width (RDW). In the context of the present invention, anemia is present if an individual has a hemoglobin (Hb) less than the desired level, for example, the Hb concentration of less than 14 g/dL, more preferably of less than 13 g/dL, more preferably of less than 12 g/dL, more preferably of less than 11 g/dL, or most preferably of less than 10 g/dL.

In certain embodiments, provided herein is a method of increasing amount of hemoglobin in a subject by administering an effective amount of a compound as described herein, or a pharmaceutically acceptable salt thereof, or a pharmaceutically acceptable composition thereof. In certain embodiments, the provided method increases hemoglobin concentration in the subject. In certain embodiments, the provided method increases Hb concentration to a desired level, for example, above 10 g/dL, more preferably above 11 g/dL, more preferably above 12 g/dL, more preferably above 13 g/dL, or most preferably above 14 g/dL. In certain embodiments, the provided method increases Hb concentration by at least about 0.5 g/dL. In certain embodiments, the provided method increases Hb concentration by at least about 1.0 g/dL. In certain embodiments, the provided method increases Hb concentration by at least about 1.5 g/dL. In certain embodiments, the provided method increases Hb concentration by at least about 2.0 g/dL. In certain embodiments, the provided method increases Hb concentration by at least about 2.5 g/dL. In certain embodiments, the provided method increases Hb concentration by at least about 3.0 g/dL. In certain embodiments, the provided method increases Hb concentration by at least about 3.5 g/dL. In certain embodiments, the provided method increases Hb concentration by at least about 4.0 g/dL. In certain embodiments, the provided method increases Hb concentration by at least about 4.5 g/dL. In certain embodiments, the provided method increases Hb concentration by at least about 5.0 g/dL. In certain embodiments, the provided method increases Hb concentration by at least about 5.5 g/dL. In certain embodiments, the provided method increases Hb concentration by at least about 6.0 g/dL.

In one embodiment of the invention provided is a method for treating hemolytic anemia comprising administering to a subject a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier.

In a further embodiment, the hemolytic anemia is hereditary and/or congenital hemolytic anemia, acquired hemolytic anemia, or anemia as part of a multisystem disease. In certain embodiments, the hemolytic anemia is congenital anemia. In certain embodiments, the hemolytic anemia is hereditary (e.g. non-spherocytic hemolytic anemia or hereditary spherocytosis).

In one embodiment of the invention provided is a method of treating thalassemia; hereditary spherocytosis; hereditary elliptocytosis; abetalipoproteinemia or Bassen-Kornzweig syndrome; paroxysmal nocturnal hemoglobinuria; acquired hemolytic anemia (e.g., congenital anemias (e.g., enzymopathies)); sickle cell disease; or anemia of chronic diseases comprising administering to a subject a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier. In one embodiment, the acquired hemolytic anemia comprises congenital anemias. In certain embodiments, the provided method is to treat thalassemia. In certain embodiments, the provided method is to treat beta thalassemia.

As used herein, thalassemia is an inherited blood disorder in which the body makes an abnormal form of hemoglobin. In certain embodiments, the disorder results in large numbers of red blood cells being destroyed, which leads to anemia. In certain embodiments, the thalassemia is alpha thalassemia. In certain embodiments, the thalassemia is beta thalassemia.

In one embodiment of the invention provided is a method for activating mutant PKR in red blood cells comprising administering to a subject in need thereof a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of pyruvate kinase deficiency (PKD), thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoietic anemia), hemolytic anemia, and anemia of chronic diseases. In some embodiments, the hemolytic anemia is hereditary and/or congenital hemolytic anemia, acquired hemolytic anemia, or anemia as part of a multi-system disease.

In one embodiment of the invention provided is a method for activating wild-type PKR in red blood cells comprising administering to a subject in need thereof a therapeutically effective amount of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of pyruvate kinase deficiency (PKD), thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoietic anemia), hemolytic anemia, and anemia of chronic diseases. In some embodiments, the hemolytic anemia is hereditary and/or congenital hemolytic anemia, acquired hemolytic anemia, or anemia as part of a multi-system disease.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for increasing the lifetime of red blood cells (RBCs) in need thereof.

In a further embodiment the compound or pharmaceutical composition is formulated to be added directly to whole blood or packed red blood cells extracorporeally. In another embodiment, the compound or pharmaceutical composition is formulated to be administered to a subject in need thereof.

In one embodiment of the invention provided is a use of (1) a compound described herein (e.g., a compound of Formulas (I), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for regulating 2,3-diphosphoglycerate levels in blood in need thereof.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating anemia. In certain embodiments, the anemia is a dyserythropoietic anemia such as congenital dyserythropoietic anemia type I, II, 11, or IV. In certain embodiments, the anemia is hemolytic anemia. In certain embodiments, the hemolytic anemia is a congenital and/or hereditary form of hemolytic anemia such as PKD, sickle cell disease, thalassemias (e.g. alpha or beta), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating hemolytic anemia.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating sickle cell disease.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating pyruvate kinase deficiency (PKD) in a subject.

As described herein, PKD is a deficiency of PKR. In certain embodiments, the deficiency of PKR is associated with a PKR mutation.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating thalassemia; hereditary spherocytosis; hereditary elliptocytosis; abetalipoproteinemia or Bassen-Kornzweig syndrome; paroxysmal nocturnal hemoglobinuria; acquired hemolytic anemia; or anemia of chronic diseases.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for activating mutant PKR in red blood cells.

In one embodiment of the invention provided is a use of (1) a compound described herein (e.g., a compound of Formulas (I)-(XV-c), in the Examples, and in Table 1, Table 3, and FIGS. 1A-1C and 2A-2C) or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for activating wild-type PKR in red blood cells.

In one embodiment of the invention, provided is a method of activating pyruvate kinase R (PKR), comprising contacting the PKR with an effective amount of (1) a compound described herein (e.g., a compound of Formulas (I)-(XV-c), in the Examples, and in Table 1 and FIG. 1), or a pharmaceutically acceptable salt thereof; or (2) a pharmaceutically acceptable composition comprising a compound described herein or a pharmaceutically acceptable salt thereof, and a pharmaceutically acceptable carrier. In one embodiment, the PKR is a wild-type PKR. In another embodiment, the PKR is a mutant PKR. In some embodiments, the PKR is expressed in red blood cells. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoietic anemia), hemolytic anemia, and anemia of chronic diseases. In some embodiments, the hemolytic anemia is hereditary and/or congenital hemolytic anemia, acquired hemolytic anemia, or anemia as part of a multi-system disease.

Since the compounds and compositions described herein act on the same biological pathway and have the similar mode of action as the compounds described in WO2012/151451, the compounds and compositions presented herein can activate the PKR mutants as described in WO2012/151451.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-p-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

EXPERIMENTAL

Abbreviations List

| abbrv. | Full Name | abbrv. | Full Name |
|---|---|---|---|
| anhy. | anhydrous | aq. | aqueous |
| min | minute(s) | satd. | saturated |
| mL | milliliter | hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| LCMS | Liquid chromatography-mass spectrometry | CMBP | Cyanomethylenetributylphosphorane |
| DAST | Diethylaminosulfurtrifluoride | $CHCl_3$ | chloroform |
| DCM | dichloromethane | DMF | dimethylformamide |
| Et2O | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| | | Py or Pyr | pyridine |
| TEA | Triethylamine | DEPEA | N,N-diisopropylethylamine |
| DMAP | 4-(dimethylamino)pyridine | dppf | 1,1'-bis(diphenylphosphino)ferrocene |
| BINAP | 2,2'bis(diphenylphosphanyl)-1,1'-binaphthyl | LDH | Lactate Dehydrogenase |
| | | BSA | Bovine serum Albumin |
| PEP | Phospho(enol)pyruvic acid | SEM | 2-(Trimethylsilyl)ethoxymethyl |
| DTT | DL-Dithiothreitol | DCE | 1,2-dichloroethane |
| NADH | β-Nicotinamide adenine dinucleotide, reduced | | |
| p-TsOH | p-Toluenesulfonic acid | | |
| MTBE | Methyl tert-butyl ether | | |

General Experimental

In the following examples, the chemical reagents were purchased from commercial sources (such as Alfa, Acros, Sigma Aldrich, TCI and Shanghai Chemical Reagent Company), and used without further purification. Flash chromatography was performed on an Ez Purifier III via column with silica gel particles of 200-300 esh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland). Chemical shifts were reported in parts per million (ppm, δ) etero (ESI) from a Waters LCT TOF Mass Spectrometer (Waters, USA). HPLC chromatographs were recorded on Agilent 1200 Liquid Chromatography (Agilent, USA, column: Ultimate 4.6 m×50 mm, 5 M, mobile phase A: 0.1% formic acid in water; mobile phase B: acetonitrile). Microwave reactions were run on an Initiator 2.5 Microwave Synthesizer (Biotage, Sweden).

HPLC conditions used in the experiments described herein are as follows:

Method 1:
 Instrument: Shimadzu LC-2010AHT
 Column: YMC-Triart C18, 50×4.6 mm, 5 μm
 Mobilephase: Solvent A: $H_2O/CH_3OH/TFA=90/10/0.1$,
  Solvent B: $H_2O/CH_3OH/TFA=90/10/0.1$
 Flow rate: 2.5 mL/min; Column temperature: 35° C.;
  Wavelength: 220 nm/254 nm Method 2:
 Instrument: Shimadzu LC-2010AHT
 Column: YMC-Triart C18, 50×4.6 mm, 5 μm
 Mobilephase: Solvent A: $H_2O/CH_3OH/TFA=90/10/0.1$,
  Solvent B: $H_2O/CH_3OH/TFA=90/10/0.1$
 Flow rate: 2.5 mL/min; Column temperature: 35° C.;
  Wavelength: 220 nm/254 nm Prep-HPLC conditions used in the experiments described herein are as follows:
 Instrument: Waters 2545B/2767
 Column: YMC-Triart C18, 50×4.6 mm, 5 μm
 Mobilephase: Solvent A: $H_2O$ (01.% FA),
  Solvent B: $CH_3OH$ or $CH_3CN$
 Flow rate: 20 mL/min; Column temperature: 35° C.;
  Wavelength: 220 nm/254 nm Example 1. Preparation of Compounds E1-vii with Scheme E1

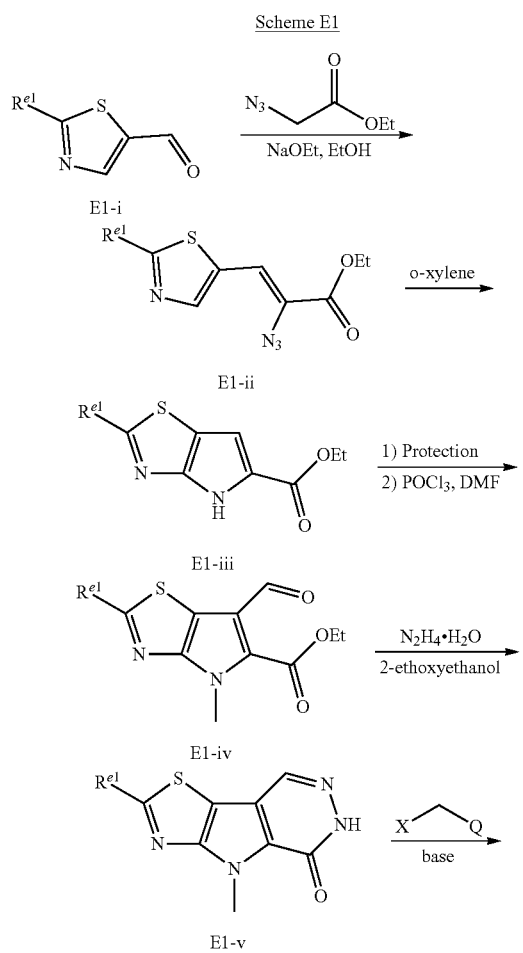

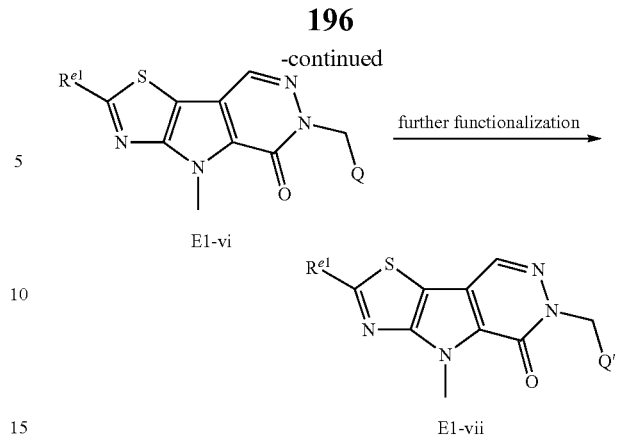

wherein $R^{e1}$ is optionally substituted alkyl (e.g. $C_{1-3}$ alkyl); Q is as defined in the first embodiment of the invention; Q' is a further functionalized Q, and X is a leaving group (e.g. halogen such as Br or I; OMs; or OTs). Thiazole 5-carbaldehyde E1-i undergoes condensation with 2-azidoacetate to give a compound of Formula E1-ii. Compound E1-ii undergoes cyclization in heated o-xylene to give a bicyclic system of E1-iii, followed by methylation of the amino group and subsequent oxidation to give a compound E1-iv. Compound E1-iv reacts with hydrazine followed by cyclization to give a compound of E1-v. Compound E1-v can react with a nucleophile such as X—$CH_2$-Q to give E1-vi, which can be further functionalized to E1-vii having Q'.

Example 1A. Synthesis of 6-(3-methoxybenzyl)-2,4-dimethyl-4,6-dihydro-5H-thiazolo[5',4':4,5] pyrrolo[2,3-d]pyridazin-5-one

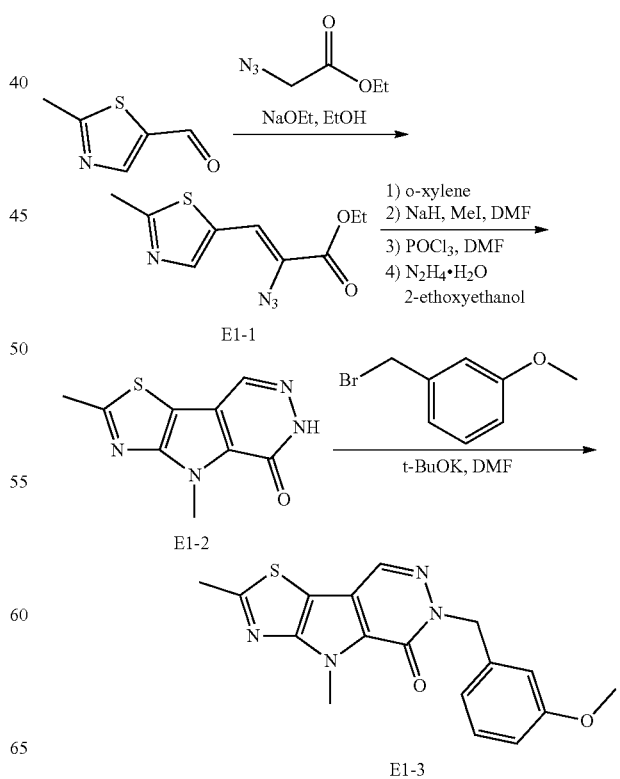

Step A. Ethyl (Z)-2-azido-3-(2-methylthiazol-5-yl)acrylate. To a solution of NaOEt (803 mg, 11.79 mmol) in EtOH (10 mL) between about −10° C. and about −5° C. was added drop wise a solution of 2-methylthiazole-5-carbaldehyde (500 mg, 3.93 mmol) and ethyl 2-azidoacetate (1.53 g, 11.79 mmol) in anhydrous EtOH (3 mL). The reaction mixture was stirred for about 1 hr. while the temperature maintained below 0° C., then warmed to r.t. and stirred for another 2 hr. The resulting mixture was poured into saturated aqueous $NH_4Cl$ (50 mL) at 0° C. and extracted with EtOAc. The combined organic layers were washed with brine, dried over anhydrous $Na_2SO_4$ and concentrated under reduced pressure to give the desired product (500 mg) which was directly used in the next step without any purification. LCMS: m/z 239 $(M+H)^+$.

Step B. Ethyl 2-methyl-4H-pyrrolo[2,3-d]thiazole-5-carboxylate. A mixture of ethyl (Z)-2-azido-3-(2-methylthiazol-5-yl)acrylate (500 mg, 2.1 mmol) in o-xylene (5 mL) was stirred at 140° C. for 2 hr. then cooled down to r.t. and then directly purified by column chromatography on silica gel (eluent: pentane/EtOAc=6/1 to give the desired product (220 mg, 49.8% yield). LCMS: m/z 211 $(M+H)^+$.

Step C. Ethyl 2,4-dimethyl-4H-pyrrolo[2,3-d]thiazole-5-carboxylate. To a solution of ethyl 2-methyl-4H-pyrrolo[2,3-d]thiazole-5-carboxylate (160 mg, 0.76 mmol) in DMF (3 mL) at 0° C. was added NaH (36.5 mg, 1.52 mmol). The reaction mixture was stirred at r.t. for 0.5 hr., followed by addition of $CH_3I$ (47 µL, 0.76 mmol). The resulting mixture was stirred at r.t for 0.5 hr. then poured into saturated aqueous $NH_4Cl$ at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=6/1) to give the desired product (124 mg, 72.6% yield). LCMS: m/z 225 $(M+H)^+$.

Step D. Ethyl 6-formyl-2,4-dimethyl-4H-pyrrolo[2,3-d] thiazole-5-carboxylate. To a mixture of ethyl 2,4-dimethyl-4H-pyrrolo[2,3-d]thiazole-5-carboxylate (100 mg, 0.446 mmol) in DMF (1 mL)) at 0° C. was added $POCl_3$ (122.5 µL, 1.338 mmol). The reaction mixture was stirred at 100° C. for 2 hr. then poured into saturated aqueous $NaHCO_3$ at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=5/1) to give the desired product (57 mg, 50.7% yield). LCMS: m/z 253 $(M+H)^+$.

Step E. 2,4-Dimethyl-4,6-dihydro-5H-thiazolo[5',4':4,5] pyrrolo[2,3-d] pyridazin-5-one. To a mixture of ethyl 6-formyl-2,4-dimethyl-4H-pyrrolo[2,3-d] thiazole-5-carboxylate (57 mg, 0.226 mmol) in 2-ethoxyethanol (2 mL) was added $N_2H_4 \cdot H_2O$ (53.7 µL, 1.130 mmol). The reaction mixture was stirred at 100° C. for 1 hr. then poured into $H_2O$ and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=5/1) to give the desired product (49 mg, 98.4% yield). LCMS: m/z 221 $(M+H)^+$.

Step F. 6-(3-Methoxybenzyl)-2,4-dimethyl-4,6-dihydro-5H-thiazolo[5',4':4,5]pyrrolo[2,3-d]pyridazin-5-one. To a mixture of 2,4-dimethyl-4,6-dihydro-5H-thiazolo[5',4':4,5] pyrrolo[2,3-d]pyridazin-5-one (49 mg, 0.223 mmol) in DMF (1 mL) at 0° C. was added t-BuOK (50.8 mg, 0.454 mmol). The reaction mixture was stirred at r.t. for 0.5 hr., followed by addition of 1-(chloromethyl)-3-methoxybenzene (34.9 mg, 0.223 mmol). The resulting mixture was stirred at r.t. for 1 hr. then poured into saturated aqueous $NH_4Cl$ solution at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=3/1) to give the desired product. LCMS: m/z 341 $(M+H)^+$. $^1H$ NMR (400 MHz, DMSO-$d_6$) δ 8.56 (s, 1H), 7.23 (t, 1H), 6.92-6.72 (m, 3H), 5.32 (s, 2H), 4.26 (s, 3H), 3.72 (s, 3H), 2.85 (s, 3H).

The procedure set forth above was used to produce the following compounds using the appropriate starting materials. Standard protection and deprotection can be used when necessary.

| Cpd No. | Structure | Characterization |
|---|---|---|
| E1-4 | 6-(4-Methoxybenzyl)-2,4-dimethyl-4,6-dihydro-5H-thiazolo[5',4':4,5]pyrrolo[2,3-d]pyridazin-5-one | LC-MS: 341 $(M + H)^+$. $^1H$ NMR (400 MHz, DMSO-$d_6$) δ 8.54 (s, 1H), 7.29 (d, 2H), 6.88 (d, 2H), 5.27 (s, 2H), 4.26 (s, 3H), 3.72 (s, 3H), 2.85 (s, 3H). |

| Cpd No. | Structure | Characterization |
|---|---|---|
| E1-5 | 6-(4-Fluorobenzyl)-2,4-dimethyl-4H-thiazolo[5',4':4,5]pyrrolo[2,3-d]pyridazin-5(6H)-one | LCMS: m/z 329 (M + H)$^+$. $^1$H NMR (400 MHz, DMSO-d$_6$) δ 8.56 (s, 1H), 7.38 (dd, 2H), 7.15 (t, 2H), 5.33 (s, 2H), 4.25 (s, 3H), 2.85 (s, 3H). |
| E1-6 | 6-(3-Fluorobenzyl)-2,4-dimethyl-4H-thiazolo[5',4':4,5]pyrrolo[2,3-d]pyridazin-5(6H)-one | LCMS: m/z 329 (M + H)$^+$. $^1$H NMR (400 MHz, DMSO-d$_6$) δ 8.58 (s, 1H), 7.38 (m, 1H), 7.12 (m, 3H), 5.37 (s, 2H), 4.26 (s, 3H), 2.85 (s, 3H). |
| E1-7 | 6-(2-Fluorobenzyl)-2,4-dimethyl-4H-thiazolo[5',4':4,5]pyrrolo[2,3-d]pyridazin-5(6H)-one | LCMS: m/z 329 (M + H)$^+$. $^1$H NMR (400 MHz, DMSO-d$_6$) δ 8.58 (s, 1H), 7.43-7.30 (m, 1H), 7.25-7.06 (m, 3H), 5.41 (s, 2H), 4.26 (s, 3H), 2.86 (s, 3H) |
| E1-8 | Ethyl-3-((2,4-dimethyl-5-oxo-4H-thiazolo[5',4':4,5]pyrrolo[2,3-d]pyridazin-6(5H)-yl)methyl)benzoate | LCMS: m/z 383 (M + H)$^+$. $^1$H NMR (400 MHz, DMSO-d$_6$) δ 8.59 (s, 1H), 8.00-7.83 (m, 2H), 7.54 (dd, 1H), 7.48 (m, 1H), 5.42 (s, 2H), 4.48-4.16 (m, 5H), 2.85 (s, 3H), 1.30 (t, 3H). |
| E1-9 | 3-((2,4-Dimethyl-5-oxo-4H-thiazolo[5',4':4,5]pyrrolo[2,3-d]pyridazin-6(5H)-yl)methyl)benzoic acid | LCMS: m/z 355 (M + H)$^+$. $^1$H NMR (400 MHz, DMSO-d$_6$) δ 8.60 (s, 1H), 8.0-7.87 (m, 2H), 755-7.40 (m, 2H), 5.40 (s, 2H), 4.26 (s, 3H), 2.85 (s, 3H). |

-continued

| Cpd No. | Structure | Characterization |
|---|---|---|
| E1-10 | 2,4-Dimethyl-6-(3-nitrobenzyl)-4H-thiazolo[5′,4′:4,5]pyrrolo[2,3-d]pyridazin-5(6H)-one | LCMS: m/z 356 (M + H)+. $^1$H NMR (400 MHz, CDCl$_3$) δ 8.20 (s, 1H), 8.16 (s, 1H), 8.08 (d, 1H), 7.70 (d, 1H), 7.44 (t, 1H), 5.46 (S, 2H), 4.32 (s, 3H), 2.80 (s, 3H). |
| E1-11 | 2,4-Dimethyl-6-(4-nitrobenzyl)-4,6-dihydro-5H-thiazolo[5′,4′:4,5]pyrrolo[2,3-d]pyridazin-5-one | LCMS: m/z 356 (M + H)+. $^1$H NMR (400 MHz, DMSO-d$_6$) δ 8.62 (s, 1H), 8.20 (d, 2H), 7.55 (d, 2H), 5.50 (s, 2H), 4.26 (s, 3H), 2.86 (s, 3H). |
| E1-12 | 6-(2-Methoxybenzyl)-2,4-dimethyl-4,6-dihydro-5H-thiazolo[5′,4′:4,5]pyrrolo[2,3-d]pyridazin-5-one | LC-MS: m/z 341 (M + H)+. $^1$H NMR (400 MHz, DMSO-d$_6$) δ 8.58 (s, 1H), 7.25 (s, 1H), 7.04 (d, 1H), 6.83 (d, 1H), 6.74 (d, 1.H), 5.34 (s, 2H), 4.27 (s, 3H), 3.85 (s, 3H), 2.87 (s, 3H). |
| E1-13 | 6-(3-Acetylbenzyl)-2,4-dimethyl-4H-thiazolo[5′,4′:4,5]pyrrolo[2,3-d]pyridazin-5(6H)-one | LC-MS: m/z 353 (M + H)+. $^1$H NMR (400 MHz, DMSO-d$_6$) δ 8.59 (s, 1H), 7.89 (d, 2H), 7.56 (d, 1H), 7.50 (d, 1H), 5.43 (s, 2H), 4.26 (s, 3H), 2.85 (s, 3H), 2.56 (s, 3H). |
| E1-14 | 2,4-Dimethyl-6-((1-methyl-1H-indazol-4-yl)methyl)-4H-thiazolo[5′,4′:4,5]Pyrrolo[2,3-d]pyridazin-5(6H)-one | LCMS: m/z 365 (M + H)+. $^1$H NMR (400 MHz, DMSO-d$_6$) δ 8.56 (s, 1H), 8.12 (s, 1H), 7.56 (d, 1H), 7.38-7.24 (m, 1H), 6.98 (d, 1H), 5.66 (s, 2H), 4.24 (s, 3H), 4.02 (s, 3H), 2.86 (s, 3H). |

| Cpd No. | Structure | Characterization |
|---|---|---|
| E1-15 | 6-((1H-indazol-5-yl)methyl)-2,4-dimethyl-4,6-dihydro-5H-thiazolo[5′,4′:4,5]pyrrolo[2,3-d]pyridazin-5-one | LC-MS: m/z 351 (M + H)+. $^1$H NMR (400 MHz, DMSO-d$_6$) δ 13.02 (s, 1H), 8.58 (s, 1H), 8.04 (s, 1H), 7.70 (s, 1H), 7.50 (d, 1H), 7.40 (d, 1H), 5.44 (s, 2H), 4.28 (s, 3H), 2.86 (s, 3H). |
| E1-16 | 6-((1H-indazol-4-yl)methyl)-2,4-dimethyl-4,6-dihydro-5H-thiazolo[5′,4′:4,5]pyrrolo[2,3-d]pyridazin-5-one | LCMS: m/z 351 (M + H)+. $^1$H NMR (400 MHz, DMSO-d$_6$) δ 13.11 (s, 1H), 8.58 (s, 1H), 8.15 (s, 1.H), 7.45 (d, 1H), 7.33-7.22 (m, 1H), 6.96 (d, 1H), 5.66 (s, 2H), 4.26 (s, 3H), 2.85 (s, 3H). |
| E1-17 | 6-((1H-indazol-7-yl)methyl)-2,4-dimethyl-4H-thiazolo[5′,4′:4,5]pyrrolo[2,3-d]pyridazin-5(6H)-one | LCMS: m/z 351 (M + H)+. $^1$H NMR (400 MHz, DMSO-d$_6$) δ 13.14 (s, 1H), 8.60 (s, 1H), 8.13 (s, 1H), 7.75-7.60 (m, 1H), 7.11-6.92 (m, 2H), 5.68 (s, 2H), 4.27 (s, 3H), 2.85 (s, 3H). |
| E1-18 | 6-((1H-Indazol-6-yl)methyl)-2,4-dimethyl-4H-thiazolo[5′,4′:4,5]pyrrolo[2,3-d]pyridazin-5(6H)-one | LCMS: m/z 351 (M + H)+. $^1$H NMR (400 MHz, DMSO-d$_6$) δ 12.96 (s, 1H), 8.59 (s, 1H), 8.03 (s, 1H), 7.71 (d, 1H), 7.42 (s, 1H), 7.13 (d, 1H), 5.48 (s, 2H), 4.27 (s, 3H), 2.86 (s, 3H). |
| E1-19 | 6-((1H-Benzo[d][1,2,3]triazol-6-yl)methyl)-2,4-dimethyl-4H-thiazolo[5′,4′:4,5]pyrrolo[2,3-d]pyridazin-5(6H)-one | LCMS: m/z 352 (M + H)+. $^1$H NMR (400 MHz, DMSO-d$_6$) 16.0-15.55 (m, 1H), δ 8.59 (s, 1H), 8.08-7.31 (m, 3H), 5.53 (s, 2H), 4.27 (s, 3H), 2.85 (s, 3H). |

| Cpd No. | Structure | Characterization |
|---|---|---|
| E1-20 | 6-((1H-Benzo[d]imidazol-5-yl)methyl)-2,4-dimethyl-4H-thiazolo[5',4':4,5]pyrrolo[2,3-d]pyridazin-5(6H)-one | LCMS: m/z 351 (M + H)$^+$. $^1$H NMR (400 MHz, DMSO-d$_6$) δ 12.37 (s, 1H), 8.56 (s, 1H), 8.19 (s, 1H), 7.54 (m, 2H), 7.23 (s, 1H), 5.45 (s, 2H), 4.26 (s, 3H), 2.87 (s, 3H). |
| E1-21 | 6-((1H-indol-6-yl)methyl)-2,4-dimethyl-4,6-dihydro-5H-thiazolo[5',4':4,5]pyrrolo[2,3-d]pyridazin-5-one | LCMS: m/z 350 (M + H)$^+$. $^1$H NMR (400 MHz, DMSO-d$_6$) δ 11.01 (s, 1H), 8.56 (s, 1H), 7.46 (d, 1H), 7.36 (s, 1H), 7.30 (t, 1H), 7.03 (d, 1H), 6.37 (s, 1H), 5.42 (s, 2H), 4.27 (s, 3H), 2.84 (s, 3H). |
| E1-22 | 2,4-Dimethyl-6-((2-oxo-2,3-dihydro-1H-benzo[d]imidazol-5-yl)methyl)-4,6-dihydro-5H-thiazolo[5',4':4,5]pyrrolo[2,3-d]pyridazin-5-one | LC-MS: m/z 367 (M + H)$^+$. $^1$H NMR (DMSO-d$_6$) δ: 10.57 (s, 1H), 10.52 (s, 1H), 8.55 (s, 1H), 6.94-6.95 (m, 2H), 6.85-6.87 (m, 1H), 5.31 (s, 2H), 4.27 (s, 3H), 2.85 (s, 3H). |
| E1-23 | 2,4-Dimethyl-6-((6-methylpyridin-2-yl)methyl)-4,6-dihydro-5H-thiazolo[5',4':4,5]pyrrolo[2,3-d]pyridazin-5-one | LC-MS: 326 (M + H)$^+$. $^1$H NMR (400 MHz, DMSO-d$_6$) δ 8.58 (s, 1H), 7.60 (t, 1H), 7.13 (d, 1H), 6.83 (d, 1H), 5.40 (s, 2H), 4.26 (s, 3H), 2.86 (s, 3H), 2.44 (s, 3H). |
| E1-24 | 6-((6-Methoxypyridin-2-yl)methyl)-2,4-dimethyl-4,6-dihydro-5H-thiazolo[5'4':4,5]pyrrolo[2,3-d]pyridazin-5-one | LC-MS: 342 (M + H)$^+$. $^1$H NMR (400 MHz, DMSO-d$_6$) δ 8.59 (s, 1H), 7.65-7.58 (m, 1H), 6.69 (d, 1H), 6.61 (d, 1H), 5.37 (s, 2H), 4.26 (s, 3H), 3.77 (s, 3H), 2.86 (s, 3H). |

-continued

| Cpd No. | Structure | Characterization |
|---|---|---|
| E1-25 | 6-((6-Fluoropyridin-2-yl)methyl)-2,4-dimethyl-4,6-dihydro-5H-thiazolo[5',4':4,5]pyrrolo[2,3-d]pyridazin-5-one | LC-MS: 330 (M + H)+. <br> 1H NMR (400 MHz, DMSO-d6) δ 8.58 (s, 1H), 7.96-7.88 (m, 1H), 7.13 (dd, 1H), 7.07 (dd, 1H), 5.42 (s, 2H), 4.25 (s, 3H), 2.86 (s, 3H). |
| E1-26 | 2,8-Dimethyl-6-(1H-pyrazol-3-ylmethyl)-6,8-dihydro-3-thia-1,5,6,8-tetraaza-cyclopenta[a]inden-7-one | LC-MS: m/z 301 (M + H)+. <br> 1H NMR (400 MHz, DMSO-d6) δ 12.70 (s, 1H), 8.58 (s, 1H), 7.67 (s, 1H) 6.18 (s, 1H), 5.38 (s, 2H), 4.32 (s, 3H), 2.91 (s, 3H). |
| E1-27 | 6-((1H-pyrazol-4-yl)methyl)-2,4-dimethyl-4H-thiazolo[5',4':4,5]pyrrolo[2,3-d]pyridazin-5(6H)-one | LCMS: m/z 301 (M + H)+. <br> 1H NMR (400 MHz, DMSO-d6) δ 8.59 (s, 1H), 7.70 (s, 2H), 5.28 (s, 2H), 4.32 (s, 3H), 2.91 (s, 3H). |
| E1-28 | 6-((1H-Imidazol-4-yl)methyl)-2,4-dimethyl-4,6-dihydro-5H-thiazolo[5',4':4,5]pyrrolo[2,3-d]pyridazin-5-one | LCMS: m/z 301 (M + H)+. <br> 1H NMR (400 MHz, DMSO-d6): 12.08 (brs, 1H), δ 8.51 (s, 1H), 7.52 (s, 1H), 6.92 (s, 1H), 5.25 (s, 2H), 4.26 (s, 3H), 2.85 (s, 3H). |
| E1-29 | 6-(2-(2-hydroxyethoxy)ethyl)-2,4-dimethyl-4H-thiazolo [5',4':4,5]pyrrolo[2,3-d]pyridazin-5(6H)-one | LCMS: 309 (M + H)+. <br> 1H NMR (400 MHz, DMSO-d6) δ 8.54 (s, 1H), 4.32 (t, 2H), 4.26 (s, 3H), 3.79 (t, 2H), 3.45 (s, 4H), 2.86 (s, 3H). |

| Cpd No. | Structure | Characterization |
|---|---|---|
| E1-30 | 6-(3-Hydroxypropyl)-2,4-dimethyl-4,6-dihydro-5H-thiazolo[5',4':4,5]pyrrolo[2,3-d]pyridazin-5-one | LCMS: m/z 279 (M + H)$^+$. $^1$H NMR (400 MHz, DMSO-d$_6$) δ 8.52 (s, 1H), 4.52 (t, 1H), 4.26 (s, 3H), 4.21 (t, 2H), 3.46 (dd, 2H), 2.85 (s, 3H), 1.92-1.82 (m, 2H). |
| E1-31 | Ethyl-2-(2,4-dimethyl-5-oxo-4H-thiazolo[5',4':4,5]pyrrolo[2,3-d]pyridazin-6(5H)-yl)acetate | LCMS: 307 (M + H)$^+$. $^1$H NMR (400 MHz, DMSO-d$_6$) δ 8.63 (s, 1H), 5.00 (s, 2H), 4.40-4.12 (m, 5H), 2.92 (s, 3H), 1.35-1.21 (m, 3H). |

Example 1B. Synthesis of 1-(3-((2,4-dimethyl-5-oxo-4H-thiazolo[5',4':4,5]pyrrolo [2,3-d] pyridazin-6(5H)-yl) methyl)phenyl)urea

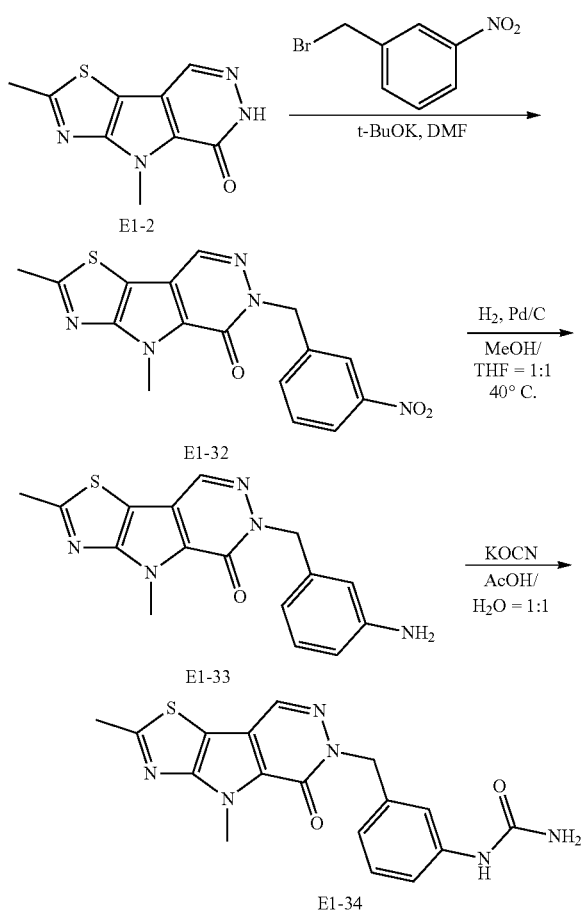

Step A. 2,4-Dimethyl-6-(3-nitrobenzyl)-4H-thiazolo[5',4':4,5]pyrrolo[2,3-d]pyridazin-5(6H)-one. To a mixture of 2,4-dimethyl-4H-thiazolo[5',4':4,5]pyrrolo[2,3-d]pyridazin-5(6H)-one (100 mg, 0.45 mmol) in DMF (5 mL) were added 1-(bromomethyl)-3-nitrobenzene (194 mg, 0.9 mmol) and t-BuOK (76 mg, 0.68 mmol). The reaction was stirred at r.t. for 1 hr. then poured into water and extracted with EtOAc. The combined organic layers were washed with brine, dried over anhydrous Na$_2$SO$_4$ and concentrated under reduced pressure. The residue was purified by prep-TLC to give the desired product (100 mg, 62.5% yield). LCMS: m/z 356 (M+H)$^+$.

Step B. 6-(3-Aminobenzyl)-2,4-di/methyl-4H-thiazolo[5,4':4,5]pyrrolo [2,3-d]pyridazin-5(6H)-one. To a mixture of 2,4-dimethyl-6-(3-nitrobenzyl)-4H-thiazolo[5',4':4,5]pyrrolo[2,3-d]pyridazin-5(6H)-one (100 mg, 0.28 mmol) in MeOH/THF (10 mL/10 mL) under N$_2$ was added Pd/C (10%, 50 mg). The reaction mixture was stirred at 40° C. under H$_2$ for 12 hr. then filtered through Celite. The filtrate was concentrated under reduced pressure and the residue was purified by prep-TLC to afford the desired compound (80 mg, 88% yield). LCMS: m/z 326 (M+H)$^+$. $^1$H NMR (400 MHz, DMSO-d$_6$) δ 8.54 (s, 1H), 6.94 (t, 1H), 6.57-6.32 (m, 3H), 5.19 (s, 2H), 5.04 (s, 2H), 4.26 (s, 3H), 2.85 (s, 3H).

Step C. 1-(3-((2,4-Dimethyl-5-oxo-4H-thiazolo[5',4':4,5]pyrrolo[2,3-d]pyridazin-6(5H)-yl)methyl)phenyl)urea. To a mixture of 6-(3-aminobenzyl)-2,4-dimethyl-4H-thiazolo[5',4':4,5]pyrrolo[2,3-d]pyridazin-5(6H)-one (65 mg, 0.2 mmol) in HOAc (2 mL) was added KOCN (160 mg, in HOAc:H$_2$O=2 mL:4 mL). The reaction mixture was stirred at r.t. for 2 hr. then poured into saturated aqueous NaHCO$_3$ and extracted with EtOAc. The organic layers were concentrated under reduced pressure. The residue was purified by prep-HPLC to afford the desired compound (4 mg, 5% yield). LCMS: m/z 369 (M+H)$^+$. $^1$H NMR (400 MHz, DMSO-d$_6$) δ 8.60-8.50 (m, 2H), 7.39 (d, 1H), 7.23 (s, 1H), 7.16 (t, 1H), 6.85 (d, 1H), 5.78 (s, 2H), 5.28 (s, 2H), 4.27 (s, 3H), 2.86 (s, 3H).

Example 1C. Synthesis of 2,4-dimethyl-6-(3-(methylamino)benzyl)-4,6-dihydro-5H-thiazolo [5',4':4,5] pyrrolo[2,3-d]pyridazin-5-one

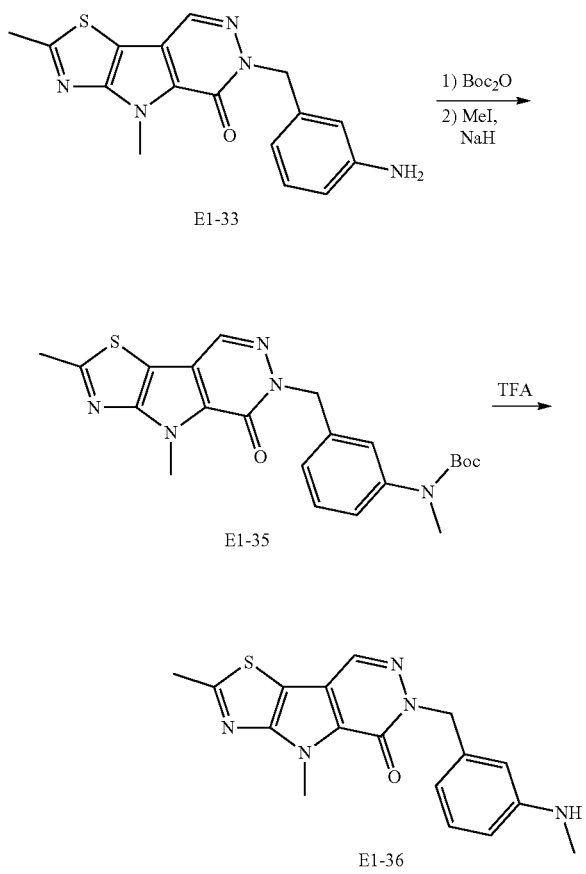

Step A. Tert-butyl (3-((2,4-dimethyl-5-oxo-4,5-dihydro-6H-thiazolo[5',4':4,5]pyrrolo[2,3-d]pyridazin-6-yl)methyl)phenyl)carbamate To a mixture of 6-(3-aminobenzyl)-2,4-dimethyl-4,6-dihydro-5H-thiazolo[5',4':4,5]pyrrolo[2,3-d]pyridazin-5-one (90 mg, 0.28 mmol) in 1,4-dioxane (10 mL) was added Boc$_2$O (73 mg, 0.33 mmol). The reaction mixture was stirred at reflux overnight then concentrated under reduced pressure. The residue was purified by column chromatography on silica gel (eluent: PE/EtOAc=3/1) to give the desired product (90 mg, 76.3% yield). LCMS: m/z 426 (M+H)$^+$.

Step B. Tert-butyl (3-((2,4-dimethyl-5-oxo-4,5-dihydro-6H-thiazolo[5',4':4,5]pyrrolo[2,3-d]pyridazin-6-yl)methyl)phenyl)(methyl)carbamate. To a mixture of tert-butyl (3-((2,4-dimethyl-5-oxo-4,5-dihydro-6H-thiazolo[5',4':4,5]pyrrolo[2,3-d]pyridazin-6-yl)methyl)phenyl)carbamate (90 mg, 0.21 mmol) in anhydrous DMF (5 mL) at 0° C. was added NaH (13 mg, 0.32 mmol, 60% wt). The mixture was stirred at 0° C. for 1 hr., followed by drop wise addition of MeI. The resulting mixture was stirred at 0-5° C. for 3 hr. then poured into cold saturated aqueous NH$_4$Cl and extracted with EtOAc. The combined organic layers were washed with brine, dried over anhydrous Na$_2$SO$_4$ and concentrated under reduced pressure. The residue was purified by prep-TLC to give the desired product (70 mg, 75.2% yield). LCMS: m/z 440 (M+H)$^+$.

Step C. 2,4-Dimethyl-6-(3-(methylamino)benzyl)-4,6-dihydro-5H-thiazolo [5',4':4,5]pyrrolo[2,3-d]pyridazin-5-one. To a mixture of tert-butyl (3-((2,4-dimethyl-5-oxo-4,5-dihydro-6H-thiazolo[5',4':4,5]pyrrolo[2,3-d]pyridazin-6-yl)methyl)phenyl) (methyl)carbamate (90 mg, 0.21 mmol) in DCM (3 mL) was added TFA (1 mL). The mixture was stirred at r.t. for 2 hr. then concentrated under reduced pressure. The residue was purified by prep-HPLC to give the desired product (25 mg, 46.4% yield). LCMS: m/z 340 (M+H)$^+$. $^1$H NMR (400 MHz, DMSO-d$_6$) δ 8.54 (s, 1H), 7.12 (t, 1H), 6.66-6.61 (m, 3H), 5.26 (s, 2H), 4.26 (s, 3H), 2.85 (s, 3H), 2.68 (d, 3H).

The procedure set forth above was used to produce the following compound using the appropriate starting materials. Standard protection and deprotection can be used when necessary.

| Cpd No. | Structure | Characterization |
|---|---|---|
| E1-37 | 6-(4-aminobenzyl)-2,4-dimethyl-4,6-dihydro-5H-thiazolo[5',4':4,5]pyrrolo[2,3-d]pyridazin-5-one | LCMS: m/z 326 (M + H)$^+$. $^1$H NMR (400 MHz, DMSO-d$_6$) δ 8.52 (s, 1H), 7.04 (d, 2H), 6.49 (d, 2H), 5.15 (s, 2H), 5.01 (s, 2H), 4.25 (s, 3H), 2.85 (s, 3H). |

| Cpd No. | Structure | Characterization |
|---|---|---|
| E1-38 | 2,4-Dimethyl-6-(4-(methylamino)benzyl)-4,6-dihydro-5H-thiazolo[5',4':4,5]pyrrolo[2,3-d]pyridazin-5-one | LCMS: m/z 340 (M + H)⁺.<br>$^1$H NMR (400 MHz, DMSO-d$_6$) δ 8.51 (s, 1H), 7.11 (d, 2H), 6.46 (d, 2H), 5.58 (d, 1H), 5.17 (s, 2H), 4.25 (s, 3H), 2.84 (s, 3H), 2.62 (d, 3H). |

Example 1D. Synthesis of 6-(3-hydroxybenzyl)-2,4-dimethyl-4H-thiazolo [5',4':4,5]pyrrolo[2,3-d]pyridazin-5(6H)-one

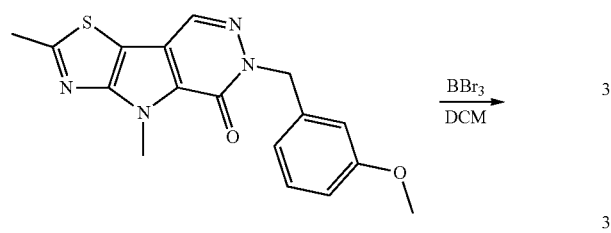

E1-39

To a mixture of 6-(3-methoxybenzyl)-2,4-dimethyl-4H-thiazolo[5',4':4,5]pyrrolo[2,3-d]pyridazin-5(6H)-one (53 mg, 0.16 mmol) in DCM (4 mL) at 0° C. was added BBr$_3$ (195 mg, 0.778 mmol). The mixture was stirred r.t. for 2 hr. then quenched with MeOH. The resulting mixture was concentrated under reduced pressure. The residue was purified by prep-HPLC to give the desired product (15.6 mg, 30.70% yield). LCMS: m/z 327 (M+H)⁺. $^1$H NMR (400 MHz, DMSO-d$_6$) δ 9.34 (s, 1H), 8.58 (s, 1H), 7.12 (t, 1H), 6.78-6.56 (m, 3H), 5.26 (s, 2H), 4.278 (s, 3H), 2.86 (s, 3H).

The procedure set forth above was used to produce the following compounds using the appropriate starting materials. Standard protection and deprotection can be used when necessary.

| Cpd No. | Structure | Characterization |
|---|---|---|
| E1-40 | 6-(2-Hydroxybenzyl)-2,4-dimethyl-4,6-dihydro-5H-thiazolo[5',4':4,5]pyrrolo[2,3-d]pyridazin-5-one | LC-MS: m/z 327 (M + H)⁺.<br>$^1$H NMR (400 MHz, DMSO-d$_6$) δ 9.67 (s, 1H), 8.59 (s, 1H), 7.07 (d, 1H), 6.85-6.60 (m, 3H), 5.32 (s, 2H), 4.27 (s, 3H), 2.87 (s, 3H). |

| Cpd No. | Structure | Characterization |
|---|---|---|
| E1-41 | 6-(4-Hydroxybenzyl)-2,4-dimethyl-4,6-dihydro-5H-thiazolo[5',4':4,5]pyrrolo[2,3-d]pyridazin-5-one | LC-MS: 327 (M + H)⁺.<br>$^1$H NMR (400 MHz, DMSO-$d_6$) δ 9.36 (s, 1H), 8.53 (s, 1H), 7.17 (d, 2H), 6.70 (d, 2H), 5.22 (s, 2H), 4.26 (s, 3H), 2.85 (s, 3H). |

Example 1E. Synthesis of 6-[3-(1-Amino-ethyl)-benzyl]-2,8-dimethyl-6,8-dihydro-3-thia-1,5,6,8-tetraaza-cyclopenta[a]inden-7-one

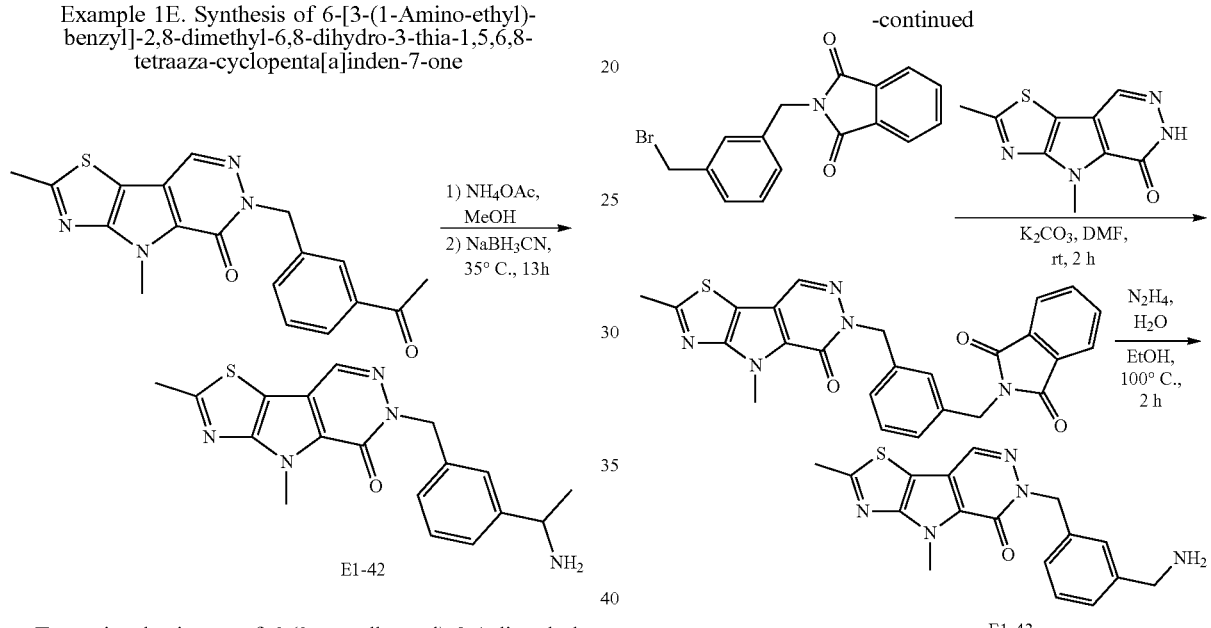

To a stirred mixture of 6-(3-acetylbenzyl)-2,4-dimethyl-4H-thiazolo[5',4':4,5]pyrrolo [2,3-d]pyridazin-5(6H)-one (50 mg, 0.142 mmol) in MeOH (4 mL) were added NH$_4$OAc (109 mg, 1.42 mmol) and NaBH$_3$CN (18 mg, 0.284 mmol). The reaction mixture was stirred at 35° C. for 13 hr. then concentrated under reduced pressure. The residue was purified by prep-HPLC to afford the desired product (20 mg, 40.0% yield). LC-MS: m/z 354 (M+H)⁺. $^1$H NMR (400 MHz, DMSO-$d_6$) δ 8.48 (s, 1H), 7.25 (dd, 3H), 7.12 (d, 1H), 5.26 (s, 2H), 4.17 (s, 3H), 4.15-4.06 (m, 1H), 2.76 (s, 3H), 1.27 (d, 3H).

Example 1F. Synthesis of 6-(3-(aminomethyl)benzyl)-2,4-dimethyl-4,6-dihydro-5H-thiazolo[5',4':4,5]pyrrolo[2,3-d]pyridazin-5-one

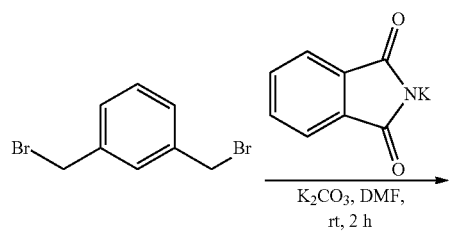

Step A. 2-(3-(Bromomethyl)benzyl)isoindoline-1,3-dione. To a stirred mixture of 1,3-bis(bromomethyl)benzene (1.3 g, 4.96 mmol) in DMF (20 mL) were added potassium 1,3-dioxoisoindolin-2-ide (0.918 g, 4.96 mmol) and K$_2$CO$_3$ (1.03 g, 7.44 mol). The reaction mixture was stirred at r.t. for 2 hr. then poured into saturated aqueous NH$_4$Cl (30 mL) and extracted with DCM. The combined organic layers were washed with brine, dried over anhydrous Na$_2$SO$_4$ and concentrated under reduced pressure. The residue was purified by column chromatography on silica gel (eluent: PE/EtOAc=30/1) to give the desired product (1.1 g, 67.4% yield). LC-MS: m/z 330 (M+H)⁺.

Step B. 2-(3-((2,4-Dimethyl-5-oxo-4H-thiazolo[5',4':4,5]pyrrolo[2,3-d]pyridazin-6(5H)-yl)methyl)benzyl)isoindoline-1,3-dione. To a stirred mixture of 2-(3-(bromomethyl)benzyl)isoindoline-1,3-dione (100 mg, 0.303 mmol) in DMF (4 mL) were added 2,4-dimethyl-4H-thiazolo[5',4':4,5]pyrrolo[2,3-d] pyridazin-5(6H)-one (66.7 mg, 0.303 mmol) and K$_2$CO$_3$ (83.6 mg, 0.606 mol). The reaction mixture was stirred at r.t. for 2 hr. then poured into saturated aqueous NH$_4$Cl (15 mL) and extracted with DCM. The combined organic layers were washed with brine, dried over anhydrous Na$_2$SO$_4$ and concentrated under reduced pressure. The residue was purified by column chromatography on silica gel (eluent: PE/EtOAc=5/1) to give the desired product (80 mg, 56.3% yield). LC-MS: m/z 470 (M+H)+.

Step C. 6-(3-(Aminomethyl)benzyl)-2,4-dimethyl-4H-thiazolo[5',4':4,5]pyrrolo [2,3-d]pyridazin-5(6H)-one. To a stirred mixture of 2-(3-((2,4-dimethyl-5-oxo-4H-thiazolo[5',4':4,5]pyrrolo[2,3-d]pyridazin-6(5H)-yl)methyl)benzyl)isoindoline-1,3-dione (80 mg, 0.17 mmol) in EtOH (5 mL) was added $N_2H_4 \cdot H_2O$ (44 mg, 98% wt, 0.85 mmol). The reaction mixture was stirred at 100° C. for 2 hr. then poured into saturated aqueous $NH_4Cl$ (15 mL) and extracted with DCM twice. The organic layers were washed with brine twice, dried over anhydrous $Na_2SO_4$, and concentrated under reduced pressure. The residue was purified by prep-HPLC to afford the desired product (30 mg, 52.1% yield). LC-MS: m/z 324 (M+H–$NH_3$)+. $^1$H NMR (400 MHz, DMSO-$d_6$) δ 8.57 (s, 1H), 7.32 (m, 3H), 7.23 (d, 1H), 5.35 (s, 2H), 4.27 (s, 3H), 3.84 (s, 2H), 2.86 (s, 3H).

Example 1G. Synthesis of 6-(4-(hydroxymethyl)benzyl)-2,4-dimethyl-4,6-dihydro-5H-thiazolo[5',4':4,5]pyrrolo[2,3-d]pyridazin-5-one

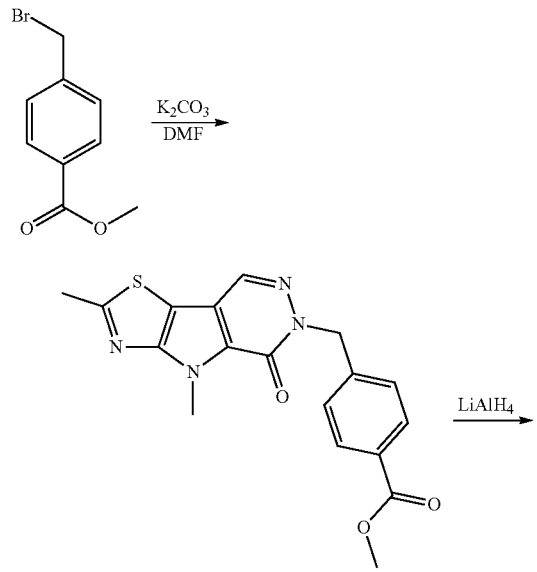

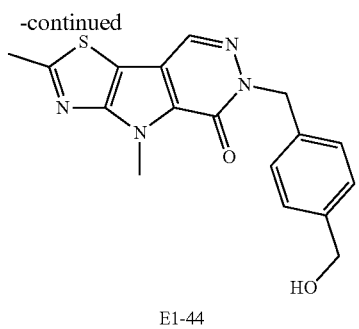

E1-44

Step A. Methyl 4-((2,4-dimethyl-5-oxo-4H-thiazolo[5',4':4,5]pyrrolo[2,3-d]pyridazin-6(5H)-yl)methyl)benzoate. To a mixture of 2,4-dimethyl-4H-thiazolo[5',4':4,5] pyrrolo[2,3-d]pyridazin-5(6H)-one (100 mg, 0.4 mmol) in DMF (20 mL) was added $K_2CO_3$ (181 mg, 1.3 mmol). The mixture was stirred at 60° C. for 30 min, followed by addition of methyl 4-(bromomethyl)benzoate (100 mg, 0.4 mmol) at 0° C. The resulting mixture was stirred at 60° C. for 18 hr. then poured into ice-water and extracted with EtOAc The combined organic layers were washed with brine, dried over anhydrous $Na_2SO_4$ and concentrated under reduced pressure. The residue was purified by column chromatography on silica gel (eluent: PE/EtOAc=50/1 to 10/1) to give the desired product (120 mg, 74.61%). LCMS: m/z 369 (M+H)+.

Step B. 6-(4-(hydroxymethyl)benzyl)-2,4-dimethyl-4H-thiazolo[5',4':4,5]pyrrolo [2,3-d]pyridazin-5(6H)-one. To a mixture of 4-((2,4-dimethyl-5-oxo-4H-thiazolo[5',4':4,5]pyrrolo[2,3-d]pyridazin-6(5H)-yl)methyl)benzoate (100 mg, 0.3 mmol) in THF (20 mL) at 0° C. was added LAH (30 mg, 0.8 mmol). The reaction was stirred at 0° C. under $N_2$ for 30 min then quenched with $NaSO_4 \cdot 10H_2O$ and filtered. The filtrate was concentrated under reduced pressure. The residue was purified by prep-TLC to give the desired product (3 mg, 3.25%). LCMS: m/z 341 (M+H)+. $^1$H NMR (400 MHz, CDCl$_3$) δ 8.12 (s, 1H), 7.36 (d, 2H), 7.25 (d, 2H), 5.37 (s, 2H), 4.59 (s, 2H), 4.31 (s, 3H), 2.80 (s, 3H).

The procedure set forth above was used to produce the following compounds using the appropriate starting materials. Standard protection and deprotection can be used when necessary.

| Cpd No. | Structure | Characterization |
|---|---|---|
| E1-45 | ![structure] 6-(3-(Hydroxymethyl)benzyl)-2,4-dimethyl-4,6-dihydro-5H-thiazolo[5',4':4,5]pyrrolo[2,3-d]pyridazin-5-one | LCMS: m/z 341 (M + H)+. $^1$H NMR (400 MHz, CDCl$_3$) δ 8.22 (s, 1H), 7.44 (s, 1H), 7.40-7.29 (m, 3H), 5.47 (s, 2H), 4.69 (s, 2H), 4.39 (s, 3H), 2.90 (s, 3H). |

| Cpd No. | Structure | Characterization |
|---|---|---|
| E1-46 | 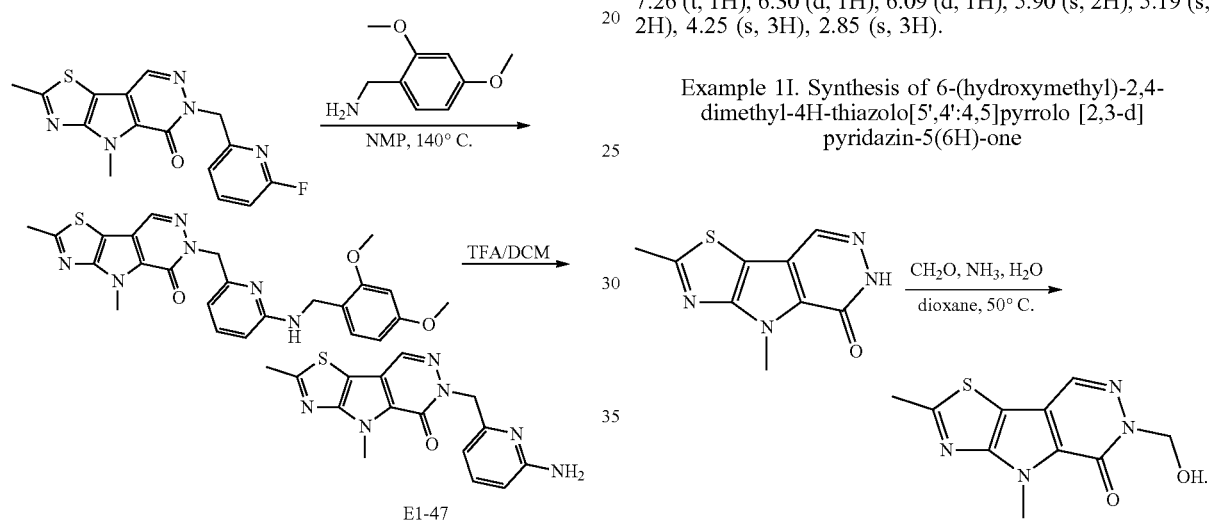  6-(2-hydroxyethyl)-2,4-dimethyl-4H-thiazolo[5',4'4,5]pyrrolo[2,3-d]pyridazin-5(6H)-one | LCMS: 265 (M + H)+. 1H NMR (400 MHz, DMSO-d6) δ 8.52 (s, 1H), 4.80 (t, 1H), 4.45-4.15 (m, 5H), 3.74 (q, 2H), 2.85 (s, 3H). |

Example 1H. Synthesis of 6-((6-aminopyridin-2-yl)methyl)-2,4-dimethyl-4,6-dihydro-5H-thiazolo[5',4':4,5]pyrrolo[2,3-d]pyridazin-5-one

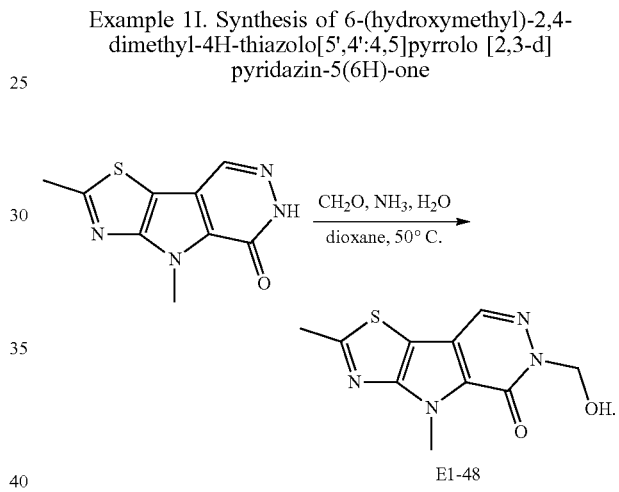

Step A: 6-((6-((2,4-dimethoxybenzyl)amino)pyridin-2-yl)methyl)-2,4-dimethyl-4H-thiazolo[5',4':4,5]pyrrolo[2,3-d]pyridazin-5(6H)-one. A mixture of 6-((6-fluoropyridin-2-yl)methyl)-2,4-dimethyl-4H-thiazolo[5',4':4,5]-pyrrolo[2,3-d]pyridazin-5(6H)-one (40 mg, 0.12 mmol) and (2,4-dimethoxyphenyl)methanamine (102 mg, 0.6 mmol) in NMP (1 mL) was stirred at 140° C. until completion. The resulting mixture was concentrated under reduced pressure. The residue was purified by prep-TLC to obtain the desired product (20 mg, 34.5% yield). LC-MS: 477 (M+H)+.

Step B: 6-((6-aminopyridin-2-yl)methyl)-2,4-dimethyl-4H-thiazolo[5',4':4,5]pyrrolo [2,3-d]pyridazin-5(6H)-one. A mixture of 6-((6-((2,4-dimethoxybenzyl)amino) pyridin-2-yl)methyl)-2,4-dimethyl-4H-thiazolo[5',4':4,5]pyrrolo[2,3-d]pyridazin-5(6H)-one (20 mg, 0.042 mmol) and TFA (45 mg, 0.42 mmol) in DCM (1 mL) was stirred at r.t. until completion. The resulting mixture was concentrated under reduced pressure. The residue was purified by prep-HPLC to obtain the desired product (20 mg, 34.5% yield). LC-MS: 327 (M+H)+. 1H NMR (400 MHz, DMSO-d6) δ 8.55 (s, 1H), 7.26 (t, 1H), 6.30 (d, 1H), 6.09 (d, 1H), 5.90 (s, 2H), 5.19 (s, 2H), 4.25 (s, 3H), 2.85 (s, 3H).

Example 1I. Synthesis of 6-(hydroxymethyl)-2,4-dimethyl-4H-thiazolo[5',4':4,5]pyrrolo [2,3-d]pyridazin-5(6H)-one A mixture of 2,4-dimethyl-4H-thiazolo[5',4':4,5]pyrrolo[2,3-d]pyridazin-5(6H)-one (30 mg, 0.14 mmol), formaldehyde (1.5 mL, 40% wt) and NH3 (0.75 mL, 33% wt) in dioxane (2 mL) was stirred at 50° C. for 1 hr. then poured into water and extracted with DCM. The organic layer was concentrated under reduced pressure. The residue was purified by prep-TLC to give the desired product (4.40 mg, 17% yield). LCMS: 251 (M+H). 1H NMR (400 MHz, DMSO-d6) δ 8.55 (s, 1H), 6.63 (t, 1H), 5.44 (d, 2H), 4.27 (s, 3H), 2.85 (s, 3H).

Examples 2. Preparation of Compounds of Formula E2-vii with Scheme E2

Scheme E2

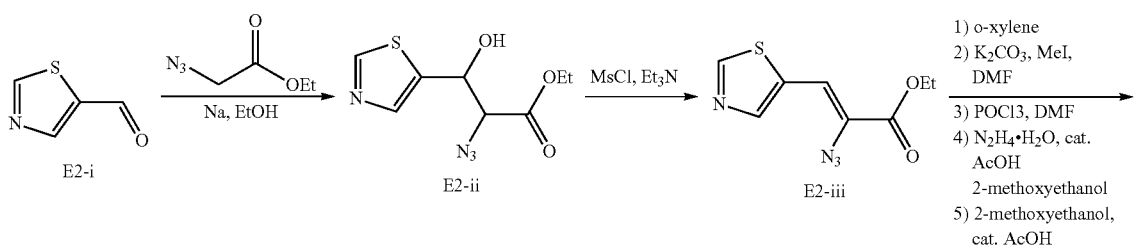

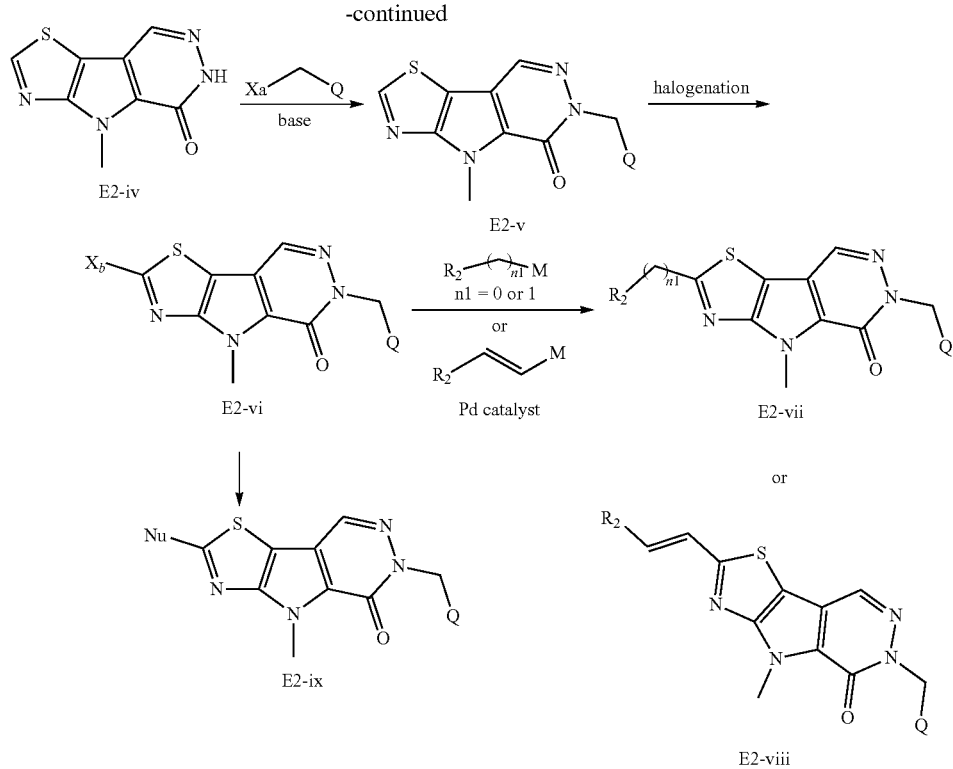

wherein Xa is a leaving group (e.g. halogen such as Br or I; OMs; or OTs); $X_b$ is halogen (e.g. Cl, Br or I); n1 is 0 or 1; M is hydrogen (for example for Heck reaction) or an organic metal complex (e.g. organoboron complex such as boronic acid or pinaco boron complex; organotin complex such as —Sn(Bu$^r$)$_3$; organozinc complex such as —Zn (halogen)); Q and $R^2$ are as defined in the first embodiment of the invention. In certain embodiments, Q and $R_2$ are each independently optionally substituted aryl, optionally substituted heteroaryl, optionally substituted carbocycle or optionally substituted heterocyclyl, optionally substituted alkyl, provided that Q and $R_2$ are not both optionally substituted 5-membered or 6-membered monocyclic heteroaryl when n1=1. Similar to the synthesis of compounds of Formula E1-v in Example 1, compound E2-iv can be synthesized from thiazole aldehyde E2-i with a few modifications (e.g. reaction of compound E2-ii with MsCl followed by elimination to give compound E2-iii; the tricyclic system can be formed with cat. AcOH in 2-methoxyethanol). Substitution and halogenation (e.g. CBr$_4$ or Cl$_3$CCCl$_3$ in the presence of LiHMDS; or 1,2,3,4,5-pentafluoro-6-iodobenzene in the presence of t-BuOK and toluene) of compound E2-iv provides compound E2-vi. Coupling reactions of compound E2-vi with organometal in the presence of a catalyst gives compound E2-vii or E2-viii. Direct nucleophilic reaction of E2-vi with a neucleophile (Nu) can generate compound E2-ix.

Example 2A. Synthesis of 2-(4-fluorobenzyl)-6-(3-methoxybenzyl)-4-methyl-4H-thiazolo [5',4':4,5] pyrrolo[2,3-d] pyridazin-5(6H)-one

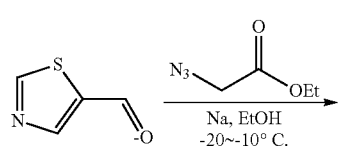

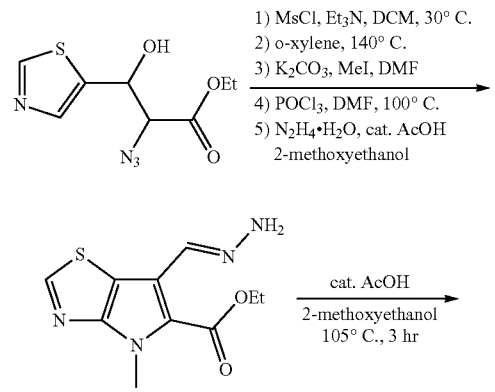

1) MsCl, Et$_3$N, DCM, 30° C.
2) o-xylene, 140° C.
3) K$_2$CO$_3$, MeI, DMF
4) POCl$_3$, DMF, 100° C.
5) N$_2$H$_4$·H$_2$O, cat. AcOH
2-methoxyethanol

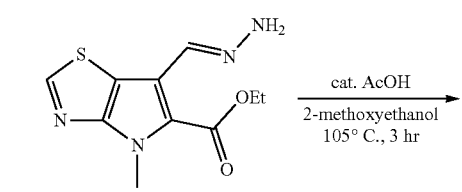

cat. AcOH
2-methoxyethanol
105° C., 3 hr

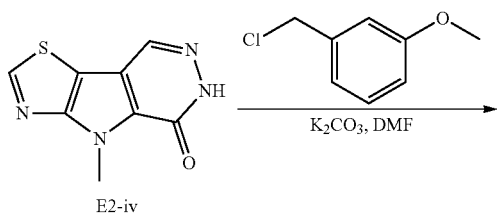

K$_2$CO$_3$, DMF

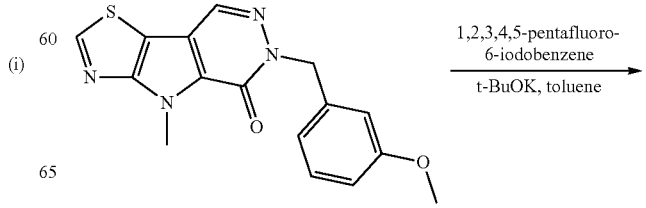

1,2,3,4,5-pentafluoro-6-iodobenzene
t-BuOK, toluene

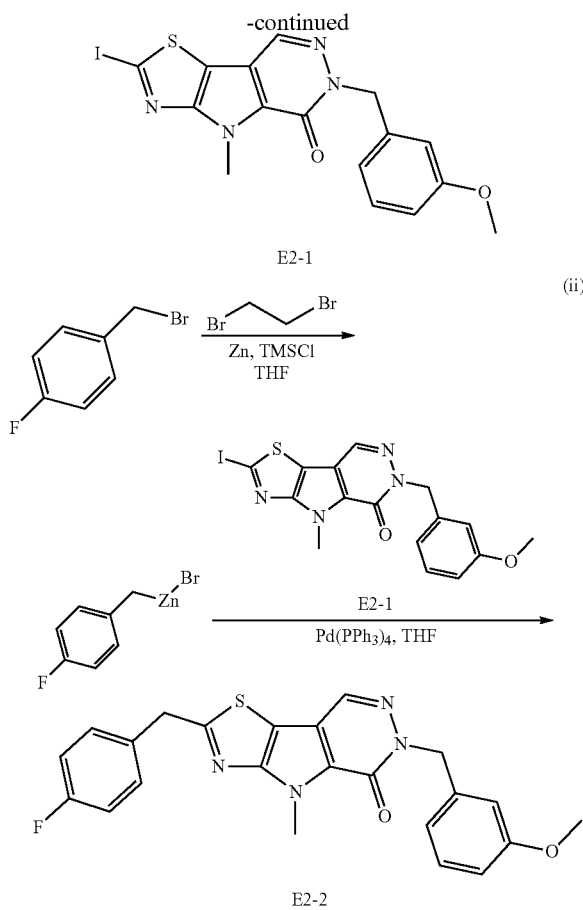

Step A. Ethyl 2-azido-3-hydroxy-3-(thiazol-5-yl)propanoate. Sodium (12.2 g, 0.531 mol) was slowly added at r.t. to a stirred solution of dry EtOH (300 mL). The reaction mixture was then cooled to −20° C., followed by drop wise addition of a solution of ethyl 2-azidoacetate (68.5 g, 0.531 mol) and thiazole-5-carbaldehyde (20.0 g, 0.177 mol) in anhydrous EtOH (100 mL) while keeping the temperature between −20° C. to −15° C. After the addition, the reaction mixture was stirred at −20° C. for additional 1 hr. and then poured into saturated aqueous NH$_4$Cl (1 L). The resulting mixture was saturated with NaCl and extracted with EtOAc. The combined organic phase was washed with brine, dried over anhydrous Na$_2$SO$_4$ and concentrated under reduced pressure. The residue was purified by column chromatography on silica gel using (eluent: PE/EtOAc=6/1 to 5/1 to 1/1) to afford desired product (34 g) as pale. LCMS: m/z=243 (M+H)$^+$.

Step B. Ethyl (Z)-2-azido-3-(thiazol-5-yl)acrylate. To a stirred mixture of ethyl 2-azido-3-hydroxy-3-(thiazol-5-yl)propanoate (103 g, 0.426 mol) in dry DCM (1.5 L) at −35° C. was added MsCl (146 g, 1.28 mol), followed by drop wise addition of TEA (301 g, 2.98 mol) while keeping the temperature between −35° C. to −30° C. After the addition, the reaction mixture was stirred at −30° C. for another 15 min then poured into saturated aqueous NH$_4$Cl (1.5 L). The resulting mixture was saturated with NaCl and extracted with DCM twice. The combined organic layers were washed in sequence with aqueous HCl (1 M) and brine, dried over anhydrous Na$_2$SO$_4$ and concentrated under reduced pressure. The residue was purified by column chromatography on silica gel using (eluent: PE/EtOAc=5/1) to afford the desired product (82.0 g, 86.3% yield). LCMS: m/z=225 (M+H)$^+$.

Steps C-E to synthesize ethyl 4H-pyrrolo[2,3-d]thiazole-5-carboxylate, ethyl 4-methyl-4H-pyrrolo[2,3-d]thiazole-5-carboxylate, and ethyl 6-formyl-4-methyl-4H-pyrrolo[2,3-d]thiazole-5-carboxylate were similar to the procedures in Example 1A.

Step F. Ethyl (E)-6-(hydrazonomethyl)-4-methyl-4H-pyrrolo[2,3-d]thiazole-5-carboxylate. To a stirred mixture of N$_2$H$_4$·H$_2$O (2.0 g, 98%, 40 mmol) in 2-methoxyethanol (50 mL) at r.t. was added ethyl 6-formyl-4-methyl-4H-pyrrolo[2,3-d] thiazole-5-carboxylate (4.8 g, 20 mmol), followed by addition of 20 drops of AcOH. The reaction mixture was stirred at r.t. for about 30 min till the mixture turned clear. The resulting mixture was poured into water (100 mL) with stirring and extracted with DCM. The combined organic layers were dried over anhydrous Na$_2$SO$_4$ and concentrated under reduced pressure to afford the desired product which was used in the next step without further purification. LCMS: m/z=253 (M+H)$^+$.

Step G. 4-Methyl-4,6-dihydro-5H-thiazolo[5',4':4,5]pyrrolo[2,3-d]pyridazin-5-one. To a stirred suspension of ethyl (E)-6-(hydrazonomethyl)-4-methyl-4H-pyrrolo[2,3-d]thiazole-5-carboxylate (4.8 g, 0.19 mol) in 2-methoxyethanol (50 mL) at r.t. was added AcOH (20 drops). The reaction suspension was stirred at 105° C. for 3 hr. and then filtered. The filter cake was washed with water and dried under high vacuum to get the first batch of the desired product. The filtrate was diluted with water and extracted with DCM twice. The organic layers were washed with brine, dried over anhydrous Na$_2$SO$_4$ and concentrated under reduced pressure to afford the second batch of the desired product. The combined two batches of the desired product (2.5 g) was directly used in the next step without further purification. LCMS: m/z=207 (M+H)$^+$. 1H NMR (400 MHz, DMSO) δ 12.68 (s, 1H), 9.35 (s, 1H), 8.55 (s, 1H), 4.30 (s, 3H)Step H. 6-(3-Methoxybenzyl)-4-methyl-4,6-dihydro-5H-thiazolo[5',4':4,5]pyrrolo [2,3-d]pyridazin-5-one. To a stirred mixture of 4-methyl-4,6-dihydro-5H-thiazolo[5',4':4,5]pyrrolo[2,3-d]pyridazin-5-one (2 g, 10.0 mmol) and K$_2$CO$_3$ (2.7 g, 20 mmol) in DMF (15 mL) was added 1-(chloromethyl)-3-methoxybenzene (2.3 g, 15 mmol). The reaction mixture was stirred at 50° C. for 3 hr. then poured into water and extracted with EtOAc twice. The combined organic layers were washed with brine, dried over anhydrous Na$_2$SO$_4$ and concentrated under reduced pressure. The residue was purified by column chromatography on silica gel (eluent: PE/EtOAc=5/1) to give the desired product (2 g, 67% yield). LCMS: m/z=327 (M+H)$^+$. $^1$H NMR (400 MHz, DMSO-d$_6$) δ 9.36 (s, 1H), 8.64 (s, 1H), 7.24 (t, 1H), 6.88-6.80 (m, 3H), 5.33 (s, 2H), 4.31 (s, 3H) 3.72 (s, 3H).

Step I. 2-Iodo-6-(3-methoxybenzyl)-4-methyl-4,6-dihydro-5H-thiazolo[5',4':4,5]pyrrolo[2,3-d]pyridazin-5-one. To a stirred mixture of 6-(3-methoxybenzyl)-4-methyl-4,6-dihydro-5H-thiazolo[5',4':4,5]pyrrolo [2,3-d]pyridazin-5-one (1 g, 3 mmol) and t-BuOK (688 mg, 6 mmol) in toluene (30 mL) at r.t. was added 1,2,3,4,5-pentafluoro-6-iodobenzene (3.6 g, 12 mmol). The reaction mixture was stirred at 135° C. for 4 hr. (oil bath was pre-heated) and then concentrated under reduced pressure. The residue was purified by column chromatography on silica gel (eluent: PE/EtOAc=6/1) to afford the desired product (1 g, 72% yield). LCMS: m/z=453 (M+H)$^+$. $^1$H NMR (400 MHz, DMSO-d$_6$) δ 8.61 (s, 1H), 7.23 (t, 1H), 6.88-6.80 (m, 3H), 5.31 (s, 2H), 4.26 (s, 3H) 3.71 (s, 3H).

Step J. (4-Fluorobenzyl)zinc(II) bromide. To a 25 mL three-necked round bottom flask was added Zn powder (1300 mg, 20 mmol). The mixture was degassed under high vacuum and back purged with $N_2$ three times. Dry THF (15 mL), TMSCl (108 mg, 1 mmol), and 1,2-dibromoethane (186 mg, 1 mmol) were added via syringe at room temperature. The suspension was heated to 65° C. for 30 min then cooled to 0° C., followed by drop wise addition of 1-(bromomethyl)-4-fluorobenzene (1.89 g, 10 mmol). The resulting mixture was stirred at r.t. for 1.5 hr. The supernatant solution was directly used for the next step.

Step K. 2-(4-Fluorobenzyl)-6-(3-methoxybenzyl)-4-methyl-4H-thiazolo[5',4':4,5]pyrrolo[2,3-d]pyridazin-5(6H)-one. To a 25 mL three-necked round bottom flask were added 2-iodo-6-(3-methoxybenzyl)-4-methyl-4H-thiazolo[5',4':4,5]pyrrolo [2,3-d] pyridazin-5(6H)-one (100 mg, 0.22 mmol) and Pd(PPh$_3$)$_4$ (25.4 mg, 10 mol %). The flask was degassed under high vacuum and back purged with $N_2$ three times. The supernatant solution of (4-fluorobenzyl)zinc(II) bromide (6 mL) was added in via syringe to the flask. The resulting mixture was stirred under $N_2$ at 65° C. for 0.5 hr. then concentrated under reduced pressure. The residue was purified by prep-TLC to give the desired product (6 mg). LCMS: m/z=435 (M+H)$^+$. $^1$H NMR (400 MHz, DMSO-d$_6$) δ 8.53 (s, 1H), 7.75-7.50 (m, 1H), 7.47 (s, 2H), 7.23 (s, 3H), 6.84 (s, 2H), 5.31 (s, 2H), 4.52 (s, 2H), 4.26 (s, 3H), 3.71 (s, 3H).

The procedure set forth above was used to produce the following compounds using the appropriate starting materials. Standard amino group protection and deprotection can be used when appropriate. Examples of amino protecting group include but not limited to SEM. Deprotection of SEM can be carried in TFA and DCM.

| Cpd No. | Structure | Characterization |
|---|---|---|
| E2-3 | 6-(3-Methoxybenzyl)-4-methyl-2-(4-methylbenzyl)-4,6-dihydro-5H-thiazolo[5',4':4,5]pyrrolo[2,3-d]pyridazin-5-one | LCMS: m/z 431 (M + H)$^+$. $^1$H NMR (400 MHz, DMSO-d$_6$) δ 8.52 (s, 1H), 7.29 (d, 2H), 7.23 (d, 1H), 7.18 (d, 2H), 6.84 (s, 2H), 6.82 (s, 1H), 5.31 (s, 2H), 4.46 (s, 2H), 4.26 (s, 3H), 3.71 (s, 3H), 2.29 (s, 3H). |
| E2-4 | 6-(3-Methoxybenzyl)-4-methyl-2-(4-(trifluoromethyl)benzyl)-5,6-dihydro-4H-thiazolo[5',4':4,5]pyrrolo[2,3-d]pyridazine | LC-MS: m/z485 [M + 1]$^+$. $^1$H NMR (400 MHz, DMSO-d$_6$) δ 8.55 (s, 1H), 7.75 (d, 2H), 7.65 (d, 2H), 7.22 (t, 1H), 6.84 (s, 2H), 6.82 (s, 1H), 5.31 (s, 2H), 4.65 (s, 2H), 4.26 (s, 3H), 3.71 (s, 3H). |
| E2-5 | 4-((6-(3-Methoxybenzyl)-4-methyl-5-oxo-5,6-dihydro-4H-thiazolo[5',4':4,5]pyrrolo[2,3-d]pyridazin-2-yl)methyl)benzonitrile | LC-MS: m/z 442 [M + 1]$^+$. $^1$H NMR (400 MHz, DMSO-d$_6$) δ 8.56 (s, 1H), 7.85 (s, 2H), 7.63 (s, 2H), 7.23 (s, 1H), 6.84 (s, 3H), 5.31 (s, 2H), 4.65 (s, 2H), 4.25 (s, 3H), 3.71 (s, 3H). |
| E2-6 | 2-(4-Chlorobenzyl)-6-(3-methoxybenzyl)-4-methyl-4H-thiazolo[5',4':4,5]pyrrolo[2,3-d]pyridazin-5(6H)-one | LCMS: m/z 451 (M + H)$^+$. $^1$H NMR (400 MHz, DMSO-d$_6$) δ 8.54 (s, 1H), 7.44 (s, 4H), 7.22 (t, 1H), 6.84-6.82 (m, 3H), 5.31 (s, 2H), 4.53 (s, 2H), 4.26 (s, 3H), 3.71 (s, 3H). |

| Cpd No. | Structure | Characterization |
|---|---|---|
| E2-7 | 2-(Cyclohexylmethyl)-6-(3-methoxybenzyl)-4-methyl-4H-thiazolo[5',4':4,5]pyrrolo[2,3-d]pyridazin-5(6H)-one | LCMS: m/z 423 (M + H)$^+$.<br>$^1$H NMR (400 MHz, DMSO-d$_6$) δ 8.55 (s, 1H), 7.23 (t, 1H), 6.84-6.82 (m, 3H), 5.32 (s, 2H), 4.26 (s, 3H), 3.71 (s, 3H), 3.02 (d, 2H), 1.76-1.59 (m, 5H), 1.25-1.00 (m, 6H). |
| E2-8 | 6-((1H-indazol-4-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: m/z = 417 (M + H)$^+$.<br>$^1$H NMR (400 MHz, DMSO-d$_6$) δ 13.12 (s, 1H), 8 12.72 (s, 1H), 8.55 (s, 1H), 8.15 (s, 1H), 7.67 (s, 1H), 7.45 (d, 1H), 7.28 (dd, 1H), 6.96 (d, 1H), 6.26 (d, 1H), 5.65 (s, 2H), 4.50 (s, 2H), 4.28 (s, 3H). |
| E2-9 | 2-((1H-pyrazol-3-yl)methyl)-6-((2,3-dihydrobenzo[b][1,4]dioxin-6-yl)methyl)-4-methyl-4,6-dihydro-5H-thiazolo[5',4':4,5]pyrrolo[2,3-d]pyridazin-5-one | LCMS: 435 (M + H)$^+$.<br>$^1$H NMR (400 MHz, DMSO-d$_6$) δ 12.77 (s, 1H), 8.51 (s, 1H), 7.71 (s, 1H), 6.78-6.65 (m, 3H), 6.26 (s, 1H), 5.21 (s, 2H), 4.47 (s, 2H), 4.26 (s, 3H), 4.19 (s, 4H). |
| E2-10 | 2-((1H-pyrazol-3-yl)methyl)-6-(4-methoxybenzyl)-4-methyl-4,6-dihydro-5H-thiazolo[5',4':4,5]pyrrolo[2,3-d]pyridazin-5-one | LCMS: m/z 407 (M + H)$^+$.<br>$^1$H NMR (400 MHz, DMSO-d$_6$) δ 12.94 (s, 1H), 8.56 (s, 1H), 7.72 (s, 1H), 7.31 (d, 2H), 6.91 (d, 2H), 6.29 (s, 1H), 5.30 (s, 2H), 4.50 (s, 2H), 4.30 (s, 3H), 3.75 (s, 3H). |

| Cpd No. | Structure | Characterization |
|---|---|---|
| E2-11 | 2-((1H-pyrazol-3-yl)methyl)-4-methyl-6-(quinolin-2-ylmethyl)-4,6-dihydro-5H-thiazolo[5',4':4,5]pyrrolo[2,3-d]pyridazin-5-one | LCMS: 428 (M + H)+. ¹H NMR (400 MHz, DMSO-d₆): δ 12.78 (s, 1H), 5 8.58 (s, 1H), 8.31 (d, 1H), 7.94 (t, 2H), 7.71-7.50 (m, 3H), 7.28 (d, 1H), 6.27 (d, 1H), 5.64 (s, 2H), 4.51 (s, 2H), 4.27 (s, 3H). |
| E2-12 | 6-((1H-indazol-4-yl)methyl)-2-((6-chloropyridin-3-yl)methyl)-4-methyl-4,6-dihydro-5H-thiazolo[5',4':4,5]pyrrolo[2,3-d]pyridazin-5-one | LCMS: m/z 462 (M + H)+. ¹H NMR (400 MHz, DMSO-d₆) δ 13.12 (s, 1H), 8.57 (s, 1H), 8.50 (d, 1H), 8.13 (s, 1H), 7.91 (dd, 1H), 7.54 (d, 1H), 7.45 (d, 1H), 7.26 (d, 1H), 6.95 (d, 1H), 5.65 (s, 2H), 4.59 (s, 2H), 4.26 (s, 3H). |
| E2-13 | 2-((1H-pyrazol-3-yl)methyl)-6-(3-methoxybenzyl)-4-methyl-4,6-dihydro-5H-thiazolo[5',4':4,5]pyrrolo[2,3-d]pyridazin-5-one | LCMS: m/z 407 (M + H)+. ¹H NMR (400 MHz, DMSO-d₆) δ 12.79 (s, 1H), 8.54 (s, 1H), 8.43 (s, 1H), 7.73 (s, 1H), 7.23 (dd, 1H), 6.84-6.74 (m, 2H), 6.26 (d, 1H), 5.31 (s, 2H), 4.49 (s, 2H), 4.27 (s, 3H), 3.71 (s, 3H). |
| E2-14 | 6-((1H-indazol-4-yl)methyl)-2-(3-(hydroxymethyl)benzyl)-4-methyl-4,6-dihydro-5H-thiazolo[5',4':4,5]pyrrolo[2,3-d]pyridazin-5-one. | LCMS: m/z 457 (M + H)+. ¹H NMR (400 MHz, DMSO-d₆) δ 13.12 (s, 1H), 8.54 (s, 1H), 8.14 (s, 1H), 7.45 (d, 1H), 7.38-7.21 (m, 5H), 6.96 (d, 1H), 5.65 (s, 2H), 5.21 (t, 1H), 4.49 (d, 4H), 4.28 (s, 3H). |
| E2-15 | 3-((6-((1H-indazol-4-yl)methyl)-4-methyl-5-oxo-5,6-dihydro-4H-thiazolo[5',4':4,5]pyrrolo[2,3-d]pyridazin-2-yl)methyl)benzamide | LCMS: m/z 470 (M + H)+. ¹H NMR (400 MHz, DMSO-d₆) δ 13.11 (s, 1H), 8.55 (s, 1H), 8.13 (s, 1H), 7.97 (s, 1H), 7.91 (s, 1H), 7.80 (d, 1H), 7.57 (d, 1H), 7.47-7.43 (m, 2H), 7.37 (s, 1H), 7.28 (t, 1H), 6.95 (d, 1H), 5.65 (s, 2H), 4.57 (s, 2H), 4.27 (s, 3H). |

| Cpd No. | Structure | Characterization |
|---|---|---|
| E2-16 | 3-((6-((1H-Indazol-4-yl)methyl)-4-methyl-5-oxo-5,6-dihydro-4H-thiazolo[5',4':4,5]pyrrolo[2,3-d]pyridazin-2-yl)methyl)benzonitrile | LCMS: m/z 452 (M + H)$^+$.<br>$^1$H NMR (400 MHz, DMSO-d$_6$) δ 13.11 (s, 1H), 8.56 (s, 1H), 8.13 (s, 1H), 7.91 (s, 1H), 7.78 (m, 2H), 7.60 (t, 1H), 7.45 (d, 1H), 7.28 (t, 1H), 6.95 (d, 1H), 5.65 (s, 2H), 4.61 (s, 2H), 4.27 (s, 3H). |
| E2-17 | 4-((6-((1H-Indazol-4-yl)methyl)-4-methyl-5-oxo-5,6-dihydro-4H-thiazolo[5',4':4,5]pyrrolo[2,3-d]pyridazin-2-yl)methyl)benzonitrile | LCMS: m/z 452 (M + H)$^+$.<br>$^1$H NMR (400 MHz, DMSO-d$_6$) δ 13.21 (s, 1H), 8.66 (s, 1H), 8.23 (s, 1H), 7.94 (d, 2H), 7.73 (d, 2H), 7.54 (m, 1H), 7.38 (m, 1H), 7.04 (m, 1H), 5.75 (s, 2H), 4.74 (s, 2H), 3.05 (s, 3H). |
| E2-18 | 4-((6-((1H-indazol-4-yl)methyl)-4-methyl-5-oxo-5,6-dihydro-4H-thiazolo[5',4':4,5]pyrrolo[2,3-d]pyridazin-2-yl)methyl)benzamide | LC-MS: m/z 470 (M + H)$^+$.<br>$^1$H NMR (400 MHz, DMSO-d$_6$) δ 13.12 (s, 1H), 8.55 (s, 1H), 8.13 (s, 1H), 7.96 (s, 1H), 7.86 (d, 2H), 7.60-7.43 (m, 3H), 7.35 (s, 1H), 7.27 (d, 1H), 6.95 (d, 1H), 5.65 (s, 2H), 4.57 (s, 2H), 4.27 (s, 3H). |
| E2-19 | 6-((1H-indazol-4-yl)methyl)-2-(3-hydroxybenzyl)-4-methyl-4,6-dihydro-5H-thiazolo[5',4':4,5]pyrrolo[2,3-d]pyridazin-5-one | LCMS: 443 (M + H)$^+$.<br>$^1$H NMR (400 MHz, DMSO-d$_6$) δ 13.12 (s, 1H), 9.46 (s, 1H), 8.54 (s, 1H), 8.13 (s, 1H), 7.44 (d, 1H), 7.30-7.24 (m, 1H), 7.15 (t, 1H), 6.95 (d, 1H), 6.83-6.77(m, 2H), 6.68 (dd, 1H), 5.65 (s, 2H), 4.41 (s, 2H), 4.28 (s, 3H). |
| E2-20 | 6-((1H-indazol-4-yl)methyl)-2-(4-hydroxybenzyl)-4-methyl-4H-thiazolo[5',4':4,5]pyrrolo[2,3-d]pyridazin-5(6H)-one | LCMS: m/z 443 (M + H)$^+$.<br>$^1$H NMR (400 MHz, DMSO-d$_6$) δ 13.12 (s, 1H), 9.43 (s, 1H), 8.53 (s, 1H), 8.14 (s, 1H), 7.45 (d, 1H), 7.30-7.25 (t, 1H), 7.20 (d, 2H), 6.95 (d, 1H), 6.76 (d, 2H), 5.65 (s, 2H), 4.37 (s, 2H), 4.27 (s, 3H). |

-continued

| Cpd No. | Structure | Characterization |
|---|---|---|
| E2-21 | 6-(1H-Indazol-4-ylmethyl)-8-methyl-2-(3-methylamino-benzyl)-6,8-dihydro-3-thia-1,5,6,8-tetraaza-cyclopenta[a]inden-7-one | LC-MS: m/z 456 (M + H)+. <br> 1H NMR (400 MHz, DMSO-d6) δ 13.10 (s, 1H), 8.54 (s, 1H), 8.13 (s, 1H), 7.45 (d, 1H), 7.27 (t, 1H), 7.12 (t, 1H), 6.94 (d, 1H), 6.67 (s, 2H), 6.58 (d, 1H), 5.65 (s, 2H), 4.38 (s, 2H), 4.27 (s, 3H), 2.68 (s, 3H). |
| E2-22 | 6-((1H-Indazol-4-yl)methyl)-4-methyl-2-(4-(methylamino)benzyl)-4,6-dihydro-5H-thiazolo[5',4':4,5]pyrrolo[2,3-d]pyridazin-5-one | LC-MS: m/z 456 (M + 1)+. <br> 1H NMR (400 MHz, DMSO-d6) δ 13.11 (s, 1H), 8.51 (s, 1H), 8.13 (s, 1H), 7.44 (d, 1H), 7.31-7.21 (m, 1H), 7.11 (d, 2H), 6.95 (d, 1H), 6.52 (d, 2H), 5.64 (s, 3H), 4.30 (s, 2H), 4.27 (s, 3H), 2.66 (d, 3H). |
| E2-23 | 2-chloro-6-(3-methoxybenzyl)-4-methyl-4H-thiazolo[5',4':4,5]pryrrolo[2,3-d]pyridazin-5(6H)-one | LCMS: m/z 361 (M + H)+. <br> 1H NMR (400 MHz, DMSO-d6) δ 8.65 (s, 1H), 7.24 (t, 1H), 6.86-6.83 (m, 3H), 5.32 (s, 2H), 4.25 (s, 3H), 3.72 (s, 3H). |
| E2-24 | 6-((1H-indazol-4-yl)methyl)-2-benzyl-4-methyl-4H-thiazolo[5',4':4,5]pyrrolo[2,3-d]pyridazin-5(6H)-one | LCMS: m/z 427 (M + H)+. <br> 1H NMR (400 MHz, DMSO-d6) δ 13.11 (s, 1H), 8.55 (s, 1H), 8.13 (s, 1H), 7.51-7.35 (m, 5H), 7.25-7.33 (m, 2H), 6.95 (d, 1H), 5.65 (s, 2H), 4.51 (s, 2H), 4.28 (s, 3H). |

Example 2B. Synthesis of 2-benzyl-6-(3-methoxy-benzyl)-4-methyl-4H-thiazolo [5',4':4,5]pyrrolo[2,3-d]pyridazin-5(6H)-one

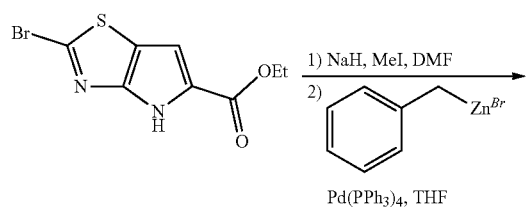

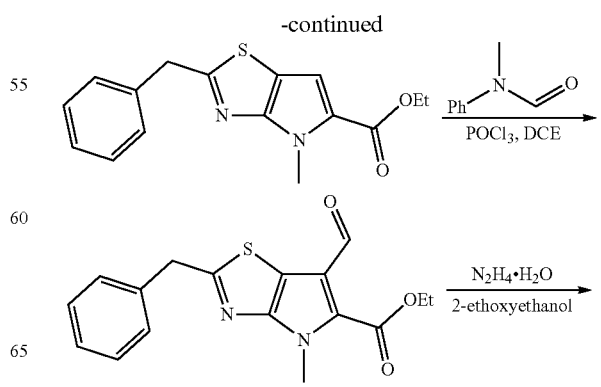

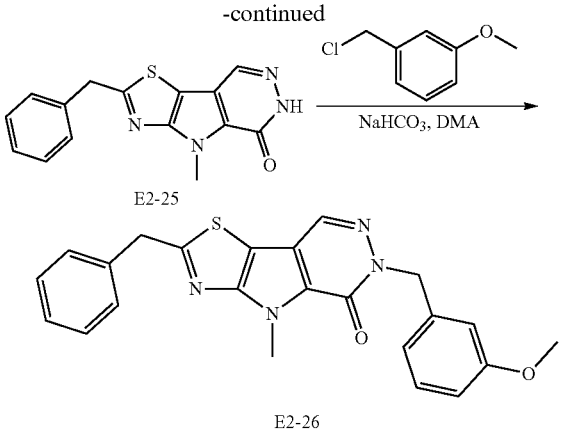

Step A. Ethyl 2-bromo-4-methyl-4H-pyrrolo[2,3-d]thiazole-5-carboxylate To a solution of ethyl 2-bromo-4H-pyrrolo[2,3-d]thiazole-5-carboxylate (1.1 g, 4 mmol) in anhydrous DMF (10 mL) was added NaH (320 mg, 60% in oil, 8 mmol). The reaction mixture was stirred at r.t. for 15 min, followed by addition of MeI (852 mg, 6 mmol). The resulting mixture was stirred at r.t. for another 2 hr. then quenched with saturated aqueous NH$_4$Cl and extracted with EtOAc. The combined organic layers were washed with water and brine, dried over anhydrous Na$_2$SO$_4$ and concentrated under reduced pressure. The residue was purified by column chromatography on silica gel (eluent: PE/EtOAc=5/1) to give the desired product (950 mg, 82.2% yield). LCMS: m/z 289 (M+H)$^+$.

Step B. Ethyl 2-benzyl-4-methyl-4H-pyrrolo[2,3-d]thiazole-5-carboxylate To a mixture of ethyl 2-bromo-4-methyl-4H-pyrrolo[2,3-d]thiazole-5-carboxylate (720 mg, 2.5 mmol) and Pd(PPh$_3$)$_4$ (145 mg, 0.125 mmol) in dry THF under N$_2$ was added benzylzinc bromide (20 mL, 0.5 M). The reaction mixture stirred at 65° C. for 1 hr. then quenched with saturated aqueous NH$_4$Cl and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=4/1) to give the desired product (600 mg, 80.0% yield). LCMS: m/z 301 (M+H)$^+$.

Step C. Ethyl 2-benzyl-6-formyl-4-methyl-4H-pyrrolo[2,3-d]thiazole-5-carboxylate To a solution of ethyl 2-benzyl-4-methyl-4H-pyrrolo[2,3-d]thiazole-5-carboxylate (600 mg, 2 mmol) in 1,2-dichloroethane (6 mL) were added a mixture of phosphorus oxychloride (612 mg, 4 mmol) and N-methyl-N-phenylformamide (540 mg, 4 mmol). The reaction mixture was refluxed overnight then cooled down and poured into ice-water, and then extracted with DCM. The combined organic layers were washed with brine, dried over anhydrous Na$_2$SO$_4$ and concentrated under reduced pressure. The residue was purified by column chromatography on silica gel (eluent: PE/EtOAc=3/1) to give the desired product (140 mg) as yellow oil. LCMS: m/z 329 (M+H)$^+$.

Step D. 2-Benzyl-4-methyl-4H-thiazolo[5',4':4,5]pyrrolo[2,3-d]pyridazin-5(6H)-one To a solution of ethyl 2-benzyl-6-formyl-4-methyl-4H-pyrrolo[2,3-d]thiazole-5-carboxylate (140 mg, crude) in 2-ethoxyethanol (3 mL) was added hydrazine hydrate (0.5 mL, 98% wt). The reaction mixture was stirred at 110° C. for 1 hr. then cooled to r.t. The precipitate was collected by filtration and washed with MeOH to give the desired product (60 mg, 10.1% yield over 2 steps). LCMS: m/z 297 (M+H)$^+$.

Step E. 2-Benzyl-6-(3-methoxybenzyl)-4-methyl-4H-thiazolo[5',4':4,5]pyrrolo[2,3-d]pyridazin-5(6H)-one To a mixture of 2-benzyl-4-methyl-4H-thiazolo[5',4':4,5] pyrrolo[2,3-d]pyridazin-5(6H)-one (50 mg, 0.169 mmol) and NaHCO$_3$ (28 mg, 0.338 mmol) in DMA (1 mL) under N$_2$ was added 1-(chloromethyl)-3-methoxybenzene (40 mg, 0.254 mmol). The reaction mixture was stirred at 120° C. for 3 hr. then quenched with saturated aqueous NH$_4$Cl and extracted with EtOAc. The combined organic layers were concentrated under reduced pressure and the residue was purified by prep-HPLC to give the desired product (8 mg, 11.4% yield). LCMS: m/z 417 (M+H)$^+$. $^1$H NMR (400 MHz, DMSO-d$_6$) δ 8.53 (s, 1H), 7.36-7.43 (m, 4H), 7.30-7.32 (m, 1H), 7.20-7.25 (m, 1H), 6.82-6.85 (m, 3H), 5.31 (s, 2H), 4.51 (s, 2H), 4.27 (s, 3H), 3.71 (s, 3H).

Example 2C. Synthesis of 6-((1H-indazol-4-yl)methyl)-4-methyl-2-(1-phenylethyl)-4H-thiazolo[5',4':4,5]pyrrolo[2,3-d]pyridazin-5(6H)-one

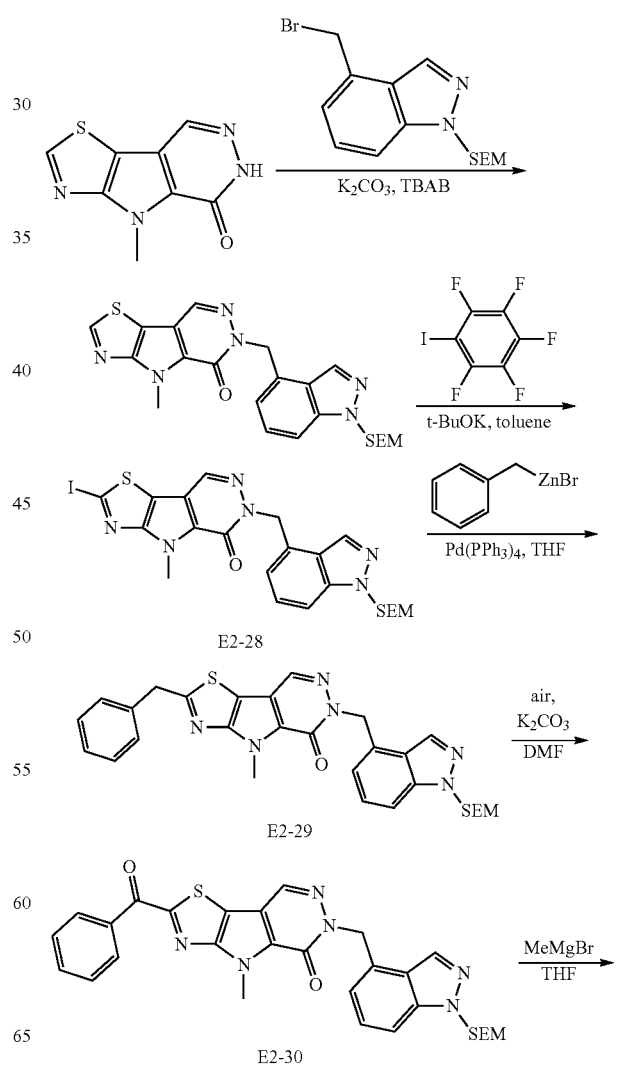

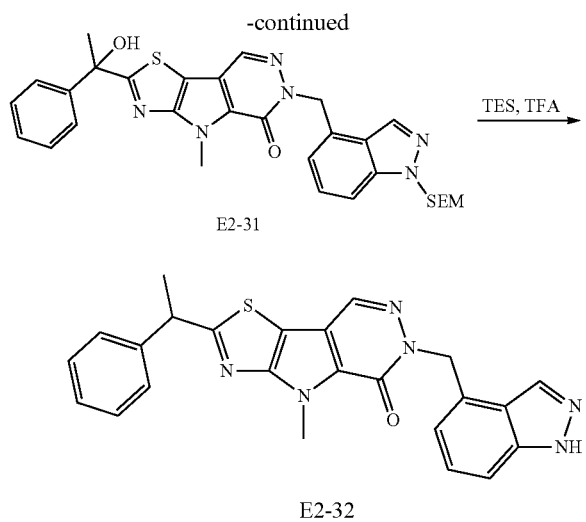

Step A. 4-Methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one was synthesized using the procedure similar to Example 2A. LCMS: m/z 467 (M+H)+.

Step B. 2-Iodo-4-methyl-6-((1-((2-(trimethylsilyl)ethoxy)methyl)-1H-indazol-4-yl) methyl)-4,6-dihydro-5H-thiazolo[5',4':4,5]pyrrolo[2,3-d]pyridazin-5-one was synthesized using the procedure similar to Example 2A. LCMS: 593 (M+H)+.

Step C. 2-Benzyl-4-methyl-6-((1-((2-(trimethylsilyl)ethoxy)methyl)-1H-indazol-4-yl) methyl)-4H-thiazolo[5',4':4,5]pyrrolo[2,3-d]pyridazin-5(6H)-one. Zinc powder (1.3 g, 20 mmol) was suspended in anhydrous THF (5 mL) under N2, followed by addition of 1,2-dibromoethane (0.01 mL). The mixture was heated at 65° C. for 5 min, followed by addition of chlorotrimethylsilane (0.01 mL). The resulting mixture was heated at 65° C. for another 15 min then cooled to 0° C., followed by drop wise addition of a solution of (bromomethyl)benzene (1.7 g, 10 mmol) in anhydrous THF (5 mL). The resulting mixture was stirred for 1 hr. at 65° C. then cooled down to afford benzylzinc (II) bromide (around 1 M in THF) which was used directly in the next step. To a mixture of 2-iodo-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (300 mg, 0.5 mmol) in dry THF (2 mL) under N2 was added in sequence Pd(PPh3)4 (58 mg, 0.05 mmol) and the above benzylzinc(II) bromide (5 ml, 1 M). The resulting mixture was heated at 65° C. for 1 hr. then poured into water and extracted with EtOAc. The combined organic layers were washed with brine, dried over anhydrous Na2SO4 and concentrated under reduced pressure. The residue was purified by column chromatography on silica gel (eluent: PE/EtOAc=5/2) to give the desired product (230 mg, 82.7% yield). LCMS: 557 (M+H)+.

Step D. 2-Benzoyl-4-methyl-6-((1-((2-(trimethylsilyl)ethoxy)methyl)-1H-indazol-4-yl)methyl)-4H-thiazolo[5,4': 4,5]pyrrolo[2,3-d]pyridazin-5(6H)-one. To a mixture of 2-benzyl-4-methyl-6-((1-((2-(trimethylsilyl)ethoxy)methyl)-1H-indazol-4-yl) methyl)-4H-thiazolo[5',4':4,5]pyrrolo[2,3-d]pyridazin-5(6H)-one (100 mg, 0.18 mmol) in DMF (5 mL) was added K2CO3 (74 mg, 0.53 mmol). The mixture was stirred at 50° C. under air for 4 hr. then poured into water. The precipitate was collected by filtration, washed with PE, and dried under high vacuum to afford the desired product (100 mg, 98% yield). LCMS: 571 (M+H)+.

Step E. 2-(1-Hydroxy-1-phenylethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one.

To a mixture of methyl magnesium bromide (0.6 mL, 1.5 M) in dry THF (2 mL) under ice bath was added a solution of 2-benzoyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.175 mmol) in dry THF. The mixture was stirred for 1 hr. and poured into saturated aqueous NH4Cl and extracted with EtOAc. The combined organic layers were washed with brine, dried over anhydrous Na2SO4 and concentrated under reduced pressure. The residue was purified by prep-TLC to give the desired product (30 mg, 29.4% yield) as oil. LCMS: 587 (M+H)+.

Step F. 6-((JH-indazol-4-yl)methyl)-4-methyl-2-(1-phenylethyl)-4H-thiazolo [5',4':4,5]pyrrolo[2,3-d]pyridazin-5(6H)-one. A solution of 2-(1-hydroxy-1-phenylethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (30 mg, 0.05 mmol) in a mixed solution of TFA/TES (2 mL/0.5 mL) was stirred at r.t. for 2 hr. then concentrated under reduced pressure. The residue was purified by prep-HPLC to afford the desired product (5 mg, 22.7% yield). LCMS: m/z 441 (M+H)+. 1H NMR (400 MHz, DMSO-d6) δ 13.11 (s, 1H), 8.53 (s, 1H), 8.12 (s, 1H), 7.46-7.41 (m, 3H), 7.37 (t, 2H), 7.28 (m, 2H), 6.95 (d, 1H), 5.65 (s, 2H), 4.71 (q, 1H), 4.28 (s, 3H), 1.78 (d, 3H).

A byproduct, 4-methyl-6-((1-methyl-1H-indazol-4-yl)methyl)-2-(1-phenylethyl)-4,6-dihydro-5H-thiazolo[5',4':4,5]pyrrolo[2,3-d]pyridazin-5-one was also obtained by prep-HPLC:

E2-33

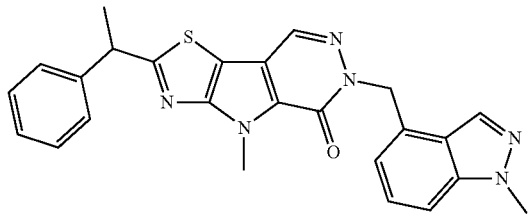

LCMS: n/z 455 (M+H)+. 1H NMR (400 MHz, DMSO-d6) δ 8.52 (s, 1H), 8.09 (s, 1H), 7.41 (d, 1H), 7.42-7.30 (m, 6H), 6.97 (d, 1H), 5.64 (s, 2H), 4.70 (q, 1H), 4.27 (s, 3H), 4.09 (s, 3H), 1.77 (d, 3H).

| Cpd No. | Structure | Characterization |
|---|---|---|
| E2-34 | 6-((1H-indazol-4-yl)methyl)-2-(1-(1H-pyrazol-3-yl)ethyl)-4-methyl-4,6-dihydro-5H-thiazol[5',4':4,5]pyrrolo[2,3-d]pyridazin-5-one | LCMS: m/z 431 (M + H)⁺. $^1$H NMR (400 MHz, DMSO-d$_6$) δ 13.12 (s, 1H), 12.71 (s, 1H), 8.54 (s, 1H), 8.14 (s, 1H), 7.68 (s, 1H), 7.45 (d, 1H), 7.28 (dd, 1H), 6.95 (d, 1H), 6.28 (d, 1H), 5.65 (s, 2H), 4.72 (s, 1H), 4.30 (s, 3H), 1.76 (d, 3H), |

Example 2D. Synthesis of 6-((1H-indazol-4-yl)methyl)-2-(1-hydroxy-1-phenylethyl)-4-methyl-4,6-dihydro-5H-thiazolo[5',4':4,5]pyrrolo[2,3-d]pyridazin-5-one

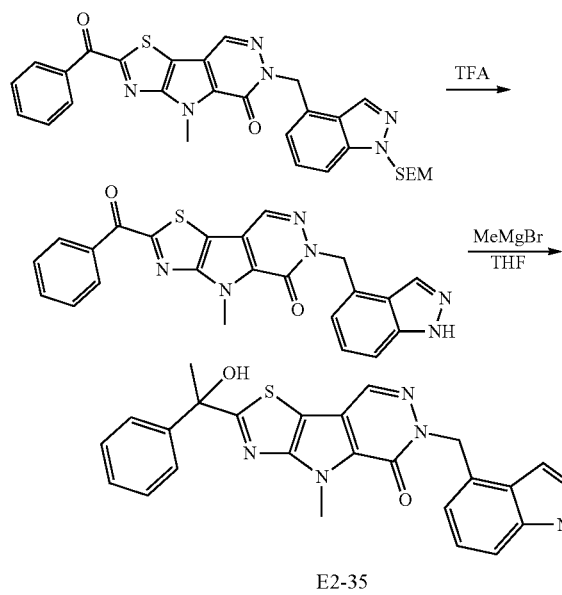

E2-35

Step A. 6-((1H-indazol-4-yl)methyl)-2-benzoyl-4-methyl-4H-thiazolo[5',4':4,5]pyrrolo[2,3-d]pyridazin-5(6H)-one. To a mixture of 2-benzoyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (75 mg, 0.13 mmol) in DCM (2 mL) was added TFA (2 mL). The mixture was stirred at r.t. for 2 hr. then concentrated under reduced pressure. The residue was purified by prep-TLC to afford the desired product (30 mg, 52.6% yield). LCMS: 441 (M+H)⁺.

Step B. 6-((1H-indazol-4 yl)methyl)-2-(1-hydroxy-1-phenylethyl)-4-methyl-4H-thiazolo[5',4':4,S]pyrrolo[2,3-d]pyridazin-5(6H)-one. To a mixture of methyl magnesium bromide (0.22 mL, 1.5 M) in dry THF (1 mL) under ice bath was added a solution of 6-((1H-indazol-4-yl)methyl)-2-benzoyl-4-methyl-4H-thiazolo[5',4':4,5]pyrrolo[2,3-d]pyridazin-5(6H)-one (30 mg, 0.068 mmol) in dry THF. The mixture was stirred for 30 min then poured into saturated aqueous NH$_4$Cl and extracted with EtOAc. The combined organic layers were concentrated under reduced pressure. The residue was purified by prep-HPLC to afford the desired product (8 mg, 25.8% yield). LCMS: 457 (M+H)⁺. $^1$H NMR (400 MHz, DMSO-d$_6$) δ 13.11 (s, 1H), 8.56 (s, 1H), 8.13 (s, 1H), 7.62 (d, 2H), 7.45 (d, 1H), 7.34 (t, 2H), 7.29-7.23 (m, 2H), 6.99-6.93 (m, 2H), 5.65 (s, 2H), 4.26 (s, 3H), 2.01 (s, 3H).

The procedure set forth above was used to produce the following compounds using the appropriate starting materials.

| Cpd No. | Structure | Characterization |
|---|---|---|
| E2-36 | 6-((1H-indazol-4-yl)methyl)-2-(1-hydroxy-1-(1H-pyrazol-3-yl)ethyl)-4-methyl-4,6-dihydro-5H-thiazolo[5',4':4,5]pyrrolo[2,3-d]pyridazin-5-one | LCMS: m/z 447 (M + H)⁺. $^1$H NMR (400 MHz, DMSO-d$_6$) δ 13.11 (s, 1H), 8.58 (s, 1H), 8.13 (d, 1H), 7.56 (d, 1H), 7.45 (d, 1H), 7.28 (dd, 1H), 6.97-6.86 (m, 2H), 6.22 (d, 1H), 5.66 (s, 2H), 4.23 (s, 3H), 2.00 (s, 3H). |

| Cpd No. | Structure | Characterization |
|---|---|---|
| E2-37 | 6-((1H-indazol-4-yl)methyl)-2-(hydroxy(pyridin-2-yl)methyl)-4-methyl-4,6-dihydro-5H-thiazolo[5',4':4,5]pyrrolo[2,3-d]pyridazin-5-one | LCMS: m/z 444 (M + H)+. $^1$H NMR (400 MHz, DMSO-d$_6$) δ 13.12 (s, 1H), 8.60 (s, 1H), 8.53 (d, 1H), 8.14 (s, 1H), 7.85 (d, 1H), 7.59 (d, 1H), 7.45 (d, 1H), 7.35 (s, 1H), 7.29 (d, 1H), 7.16 (d, 1H), 6.96 (d, 1H), 6.09 (d, 1H), 5.66 (s, 2H), 4.22 (s, 3H). |
| E2-38 | 2-(3-hydroxybenzoyl)-6-(3-methoxybenzyl)-4-methyl-4,6-dihydro-5H-thiazolo[5',4':4,5]pyrrolo[2,3-d]pyridazin-5-one | LCMS: m/z 447 (M + H)+. $^1$H NMR (400 MHz, DMSO-d$_6$) δ 9.97 (s, 1H), 8.76 (s, 1H), 7.96 (d, 1H), 7.88 (s, 1H), 7.44 (dd, 1H), 7.23 (dd, 1H), 7.17 (d, 1H), 6.90-6.83 (m, 3H), 5.35 (s, 2H), 4.37 (s, 3H), 3.72 (s, 3H). |

Example 2E. Synthesis of 2-(hydroxy(phenyl)methyl)-6-(3-methoxybenzyl)-4-methyl-4H-thiazolo[5',4':4,5]pyrrolo[2,3-d]pyridazin-5(6H)-one

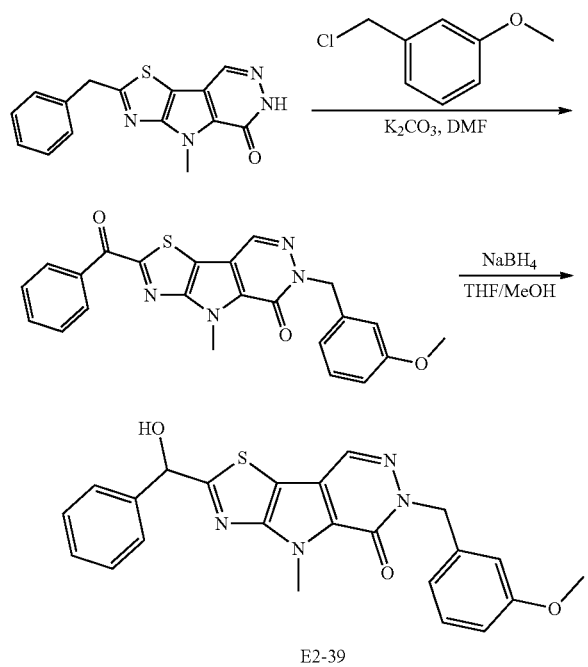

E2-39

Step A. 2-Benzoyl-6-(3-methoxybenzyl)-4-methyl-4H-thiazolo[5',4':4,5]pyrrolo [2,3-d]pyridazin-5(6H)-one. To a solution of 2-benzyl-4-methyl-4H-thiazolo [5',4':4,5]pyrrolo [2,3-d]pyridazin-5(6H)-one (40 mg, 0.135 mmol) and K$_2$CO$_3$ (37 mg, 0.27 mmol) in DMF (1 mL) was added 1-(chloromethyl)-3-methoxybenzene (31 mg, 0.2 mmol). The reaction mixture was stirred at r.t. in the air overnight then poured into water. The precipitate was collected by filtration and washed with EtOAc to give desired product (30 mg, 51.7% yield). LCMS: m/z 431 (M+H)+. $^1$H NMR (400 MHz, DMSO-d$_6$) δ 8.76 (s, 1H), 8.46-8.49 (m, 2H), 7.78 (t, 1H), 7.66 (t, 2H), 7.25 (t, 1H), 6.84-6.89 (m, 3H), 5.36 (s, 2H), 4.37 (s, 3H), 3.73 (s, 3H).

Step B. 2-(Hydroxy(phenyl)methyl)-6-(3-methoxybenzyl)-4-methyl-4H-thiazolo [5',4':4,5]pyrrolo[2,3-d]pyridazin-5(6H)-one. To a mixture of 2-benzoyl-6-(3-methoxybenzyl)-4-methyl-4H-thiazolo[5',4':4,5]pyrrolo[2,3-d]pyridazin-5(6H)-one (20 mg, 0.047 mmol) in THF (1 mL) and MeOH (1 mL) was added NaBH$_4$ (3.5 mg, 0.093 mmol). The mixture was stirred at rt. for 15 min, quenched with water and extracted with EtOAc. The organic layer was separated and concentrated under reduced pressure. The residue was purified by prep-TLC to give desired product (13 mg, 64.0% yield). LCMS: m/z 433 (M+H)+. $^1$H NMR (400 MHz, DMSO-d$_6$) δ 8.58 (s, 1H), 7.49-7.53 (m, 2H), 7.36-7.40 (m, 2H), 7.28-7.33 (m, 1H), 7.20-7.25 (m, 1H), 7.07 (d, 1H), 6.82-6.85 (m, 3H), 6.08 (d, 1H), 5.31 (d, 2H), 4.21 (s, 3H), 3.71 (s, 3H).

The procedure set forth above was used to produce the following compounds using the appropriate starting materials.

| Cpd No. | Structure | Characterization |
|---|---|---|
| E2-40 | 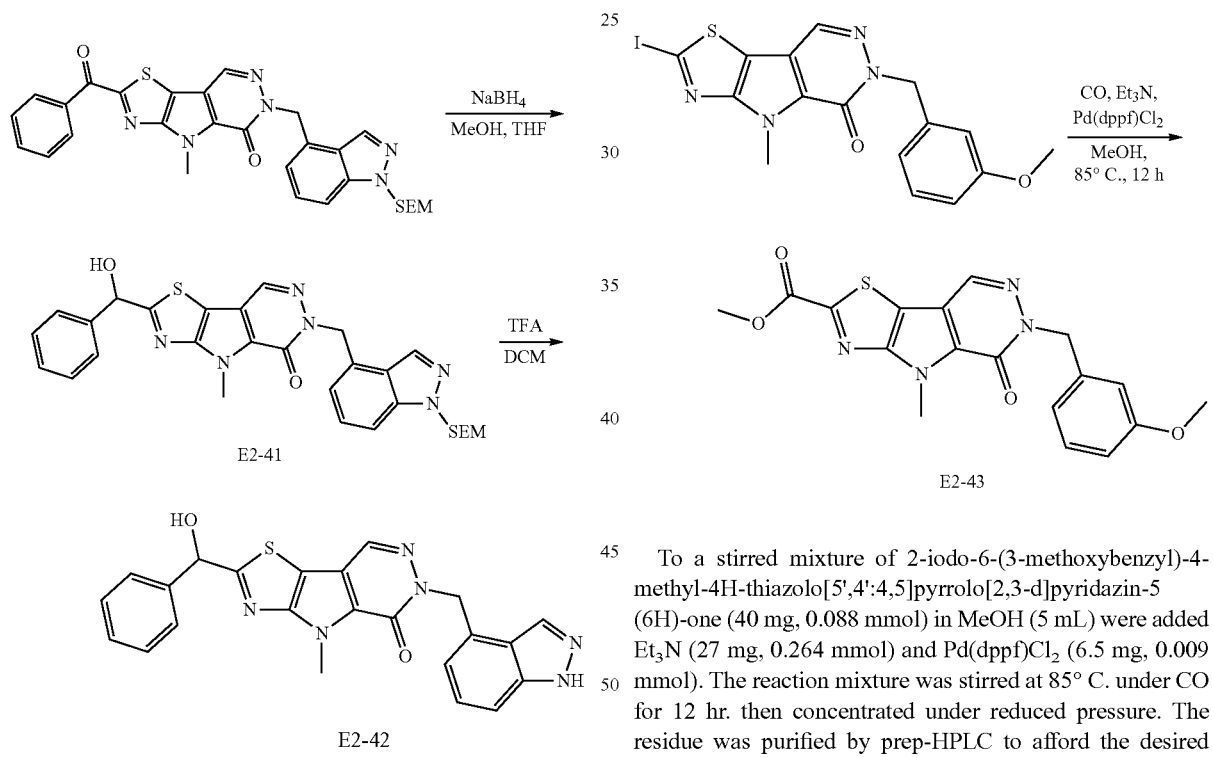<br>6-((1H-indazol-4-yl)methyl)-2-(hydroxy (1H-pyrazol-3-yl)methyl)-4-methyl-4,6-dihydro-5H-thiazolo[5',4':4,5]pyrrolo[2,3-d]pyridazin-5-one | LCMS: m/z 433 (M + H)$^+$.<br>$^1$H NMR (400 MHz, DMSO-d$_6$) δ 13.12 (s, 1H), 12.75 (s, 1H), 8.60 (s, 1H), 8.14 (s, 1H), 7.65 (s, 1H), 7.45 (d, 1H), 7.28 (dd, 1H), 6.96 (d, 1H), 6.85 (s, 1H), 6.21 (s, 1H), 6.09 (s, 1H), 5.66 (s, 2H), 4.23 (s, 3H). |

Example 2F. Synthesis of 6-((1H-indazol-4-yl)methyl)-2-(hydroxy(phenyl) methyl)-4-methyl-4,6-dihydro-5H-thiazolo[5',4':4,5]pyrrolo[2,3-d]pyridazin-5-one Step A. 2-(Hydroxy(phenyl)methyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one was synthesized using the procedure similar to Example 2E. LCMS: m/z 573 (M+H)$^+$.

Step B. 6-((1H-indazol-4-yl)methyl)-2-(hydroxy(phenyl) methyl)-4-methyl-4H-thiazolo[5',4':4,5]pyrrolo[2,3-d]pyridazin-5(6H)-one was synthesized using the procedure similar to Example 2D. LCMS: m/z 443 (M+H)$^+$. $^1$H NMR (400 MHz, DMSO-d$_6$) δ 13.12 (s, 1H), 8.59 (s, 1H), 8.13 (s, 1H), 7.56-7.42 (m, 3H), 7.37 (s, 2H), 7.28 (m, 2H), 7.07 (s, 1H), 6.95 (s, 1H), 6.08 (s, 1H), 5.65 (s, 2H), 4.21 (s, 3H).

Example 2G. Synthesis of methyl 6-(3-methoxybenzyl)-4-methyl-5-oxo-5,6-dihydro-4H-thiazolo[5',4':4,5]pyrrolo[2,3-d]pyridazine-2-carboxylate To a stirred mixture of 2-iodo-6-(3-methoxybenzyl)-4-methyl-4H-thiazolo[5',4':4,5]pyrrolo[2,3-d]pyridazin-5(6H)-one (40 mg, 0.088 mmol) in MeOH (5 mL) were added Et$_3$N (27 mg, 0.264 mmol) and Pd(dppf)Cl$_2$ (6.5 mg, 0.009 mmol). The reaction mixture was stirred at 85° C. under CO for 12 hr. then concentrated under reduced pressure. The residue was purified by prep-HPLC to afford the desired product (2 mg, 5.88% yield). LC-MS: m/z 385 (M+H)$^+$. $^1$H NMR (400 MHz, DMSO-d$_6$) δ 8.72 (s, 1H), 7.24 (t, 1H), 6.95-6.81 (m, 3H), 5.34 (s, 2H), 4.29 (s, 3H), 3.99 (s, 3H), 3.72 (s, 3H).

A similar reaction was carried out with 2-chloro-6-(3-methoxybenzyl)-4-methyl-4H-thiazolo[5',4':4,5]pyrrolo[2,3-d]pyridazin-5(6H)-one, which generated 2-methoxy-6-(3-methoxybenzyl)-4-methyl-4,6-dihydro-5H-thiazolo[5',4':4,5]pyrrolo[2,3-d]pyridazin-5-one as the major byproduct. LC-MS: m/z 357 (M+H)$^+$. $^1$H NMR (400 MHz, DMSO-d$_6$) δ 8.50 (s, 1H), 7.26-7.21 (m, 1H), 6.88-6.80 (m, 3H), 5.30 (s, 2H), 4.19 (brs, 6H), 3.72 (s, 3H).

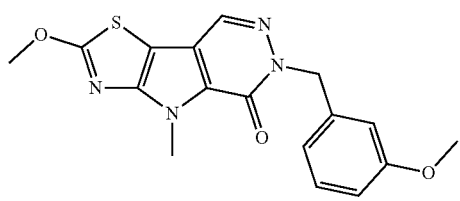

Example 2H. Synthesis of 2-(fluoro(phenyl)methyl)-6-(3-methoxybenzyl)-4-methyl-4H-thiazolo[5',4':4,5]pyrrolo[2,3-d]pyridazin-5(6H)-one

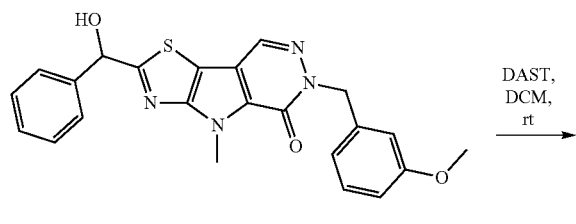

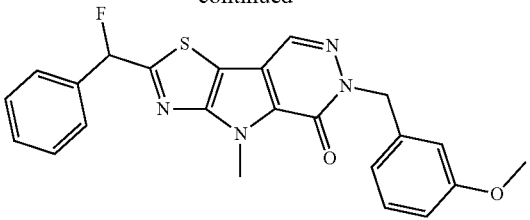

To a solution of 2-(hydroxy(phenyl) methyl)-6-(3-methoxybenzyl)-4-methyl-4H-thiazolo[5',4':4,5]pyrrolo[2,3-d]pyridazin-5(6H)-one (20 mg, 0.046 mmol) in DCM (2 mL) under −78° C. was added DAST (0.3 mL). The mixture was stirred at r.t. for 30 min then concentrated under reduced pressure. The residue was purified by prep-TLC to give the desired product (2.5 mg, 12.5% yield). LCMS: 435. (M+H)$^+$. $^1$H NMR (400 MHz, DMSO-$d_6$) δ 8.64 (s, 1H), 7.55-7.48 (m, 5H), 7.26-7.07 (m, 2H), 6.92-6.74 (m, 3H), 5.32 (s, 2H), 4.25 (s, 3H), 3.71 (s, 3H).

Example 21. Synthesis of 6-((1H-indazol-4-yl)methyl)-2-(amino(phenyl)methyl)-4-methyl-4,6-dihydro-5H-thiazolo[5',4':4,5]pyrrolo[2,3-d]pyridazin-5-one

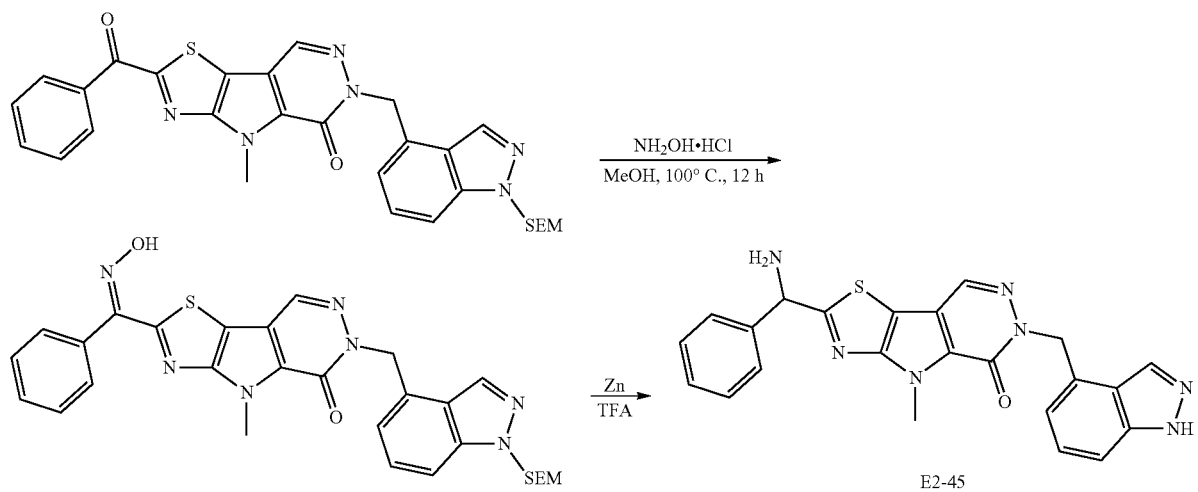

Step A. (Z)-2-((Hydroxyimino)(phenyl)methyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one. A mixture of 2-benzoyl-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (100 mg, 0.175 mmol) and NH$_2$OH·HCl (123 mg, 1.75 mmol). in anhydrous MeOH (5 mL) was stirred at 100° C. in a sealed tube for 12 hr. Then poured into saturated aqueous NH$_4$Cl (20 mL) and extracted with DCM. The combined organic layers were washed with brine, dried over anhydrous Na$_2$SO$_4$, and concentrated under reduced pressure. The residue was purified by column chromatography on silica gel (eluent: PE/EA=2/1) to afford the desired product (40 mg, 39.1% yield). LC-MS: m/z 586 (M+H)$^+$.

Step B. 6-((1H-Indazol-4-yl)methyl)-2-(amino(phenyl) methyl)-4-methyl-4H-thiazolo [5',4':4,5]pyrrolo[2,3-d]pyridazin-5(6H)-one To a stirred mixture of (Z)-2-((hydroxyimino)(phenyl)methyl)-4-methyl-6-((1-((2-

(trimethylsilyl)ethoxy)methyl)-1H-indazol-4-yl)methyl)-4H-thiazolo[5',4':4,5]pyrrolo[2,3-d]pyridazin-5(6H)-one (40 mg, 0.068 mmol) in TFA (3 mL) was added Zn (44 mg, 0.68 mmol). The reaction mixture was stirred at r.t. for 16 hr. then poured into saturated aqueous NaHCO₃ (20 mL) and extracted with DCM. The combined organic layers were washed with brine, dried over anhydrous Na₂SO₄, and concentrated under reduced pressure. The residue was purified by prep-HPLC to afford the desired product (4.6 mg, 14.8% yield). LC-MS: m/z 442 (M+H)⁺. ¹H NMR (400 MHz, DMSO-d₆) δ 13.11 (s, 1H), 8.58 (s, 1H), 8.13 (s, 1H), 7.52-7.40 (m, 3H), 7.39-7.32 (m, 2H), 7.30-7.22 (m, 2H), 6.95 (d, 1H), 5.65 (s, 2H), 5.49 (s, 1H), 4.20 (s, 3H).

The procedure set forth above was used to produce the following compounds using the appropriate starting materials.

| Cpd No. | Structure | Characterization |
|---|---|---|
| E2-46 | 6-((1H-indazol-4-yl)methyl)-2-(amino(1H-pyrazol-3-yl)methyl)-4-methyl-4,6-dihydro-5H-thiazolo[5',4':4,5]pyrrolo[2,3-d]pyridazin-5-one | LC-MS: m/z: 432 (M + H)⁺. ¹H NMR (400 MHz, DMSO-d₆): δ 8.62 (s, 1H), 8.15 (s, 1H), 7.88 (s, 1H), 7.56 (d, 1H), 7.29 (t, H), 6.99 (d, 1H), 6.51 (s, 1H), 6.28 (s, 1H), 5.66 (s, 2H), 4.33 (s, 3H). |

Example 2J. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)(1H-pyrazol-3-yl)methyl)acetamide

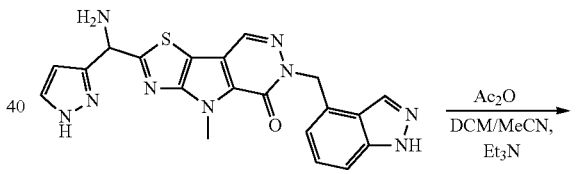

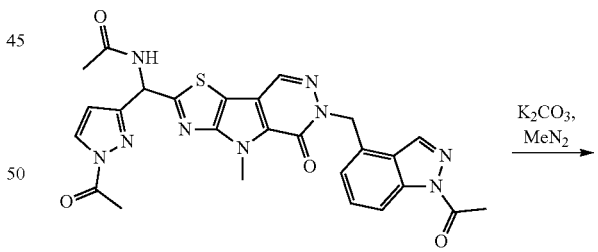

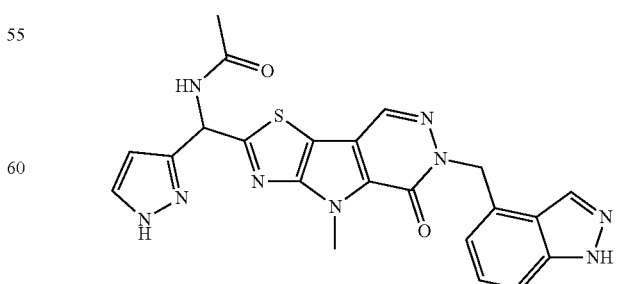

E2-47

Step A. N-((6-((1-acetyl-1H-indazol-4-yl)methyl)-4-methyl-5-oxo-5,6-dihydro-4H-thiazolo[5',4':4,5]pyrrolo[2,3-d]pyridazin-2-yl)(1-acetyl-1H-pyrazol-3-yl)methyl) acetamide. To a stirred mixture of 6-((1H-indazol-4-yl)methyl)-2-(amino(1H-pyrazol-3-yl)methyl)-4-methyl-4H-thiazolo[5',4':4,5]pyrrolo[2,3-d]pyridazin-5(6H)-one (20 mg, 0.046 mmol) in DCM/MeCN (1 mL/1 mL) was added Et₃N (14 mg, 0.139 mmol) and acetic anhydride (24 mg, 0.23 mmol). The resulting mixture was stirred at 23° C. for 1 hr. then quenched with water and extracted with DCM. The combined organic layers were dried over anhydrous Na₂SO₄ and concentrated under reduced pressure to afford the crude product (30 mg) which was directly used in the next step without any further purification. LCMS: m/z 558 (M+H)⁺.

Step B. N-((6-((1H-indazol-4-yl)methyl)-4-methyl-5-oxo-5,6-dihydro-4H-thiazolo[5,4':4,5]pyrrolo[2,3-d]pyridazin-2-yl)(H-pyrazol-3-yl)methyl)acetamide. To a stirred mixture of N-((6-((1-acetyl-1H-indazol-4-yl)methyl)-4-methyl-5-oxo-5,6-dihydro-4H-thiazolo[5',4':4,5]pyrrolo[2,3-d]pyridazin-2-yl)(1-acetyl-1H-pyrazol-3-yl)methyl)acetamide (30 mg, 0.053 mmol) in MeOH (3 mL) under N₂ was added K₂CO₃ (22 mL, 0.16 mmol). The mixture was stirred at 23° C. for 30 min then quenched with saturated aqueous NH₄Cl and extracted with DCM. The combined organic layers were dried over anhydrous Na₂SO₄ and concentrated under reduced pressure. The residue was purified by prep-HPLC to afford the desired product (2.0 mg, 9% yield). LC-MS: m/z: 474 (M+H)⁺. ¹H NMR (400 MHz, DMSO-d₆): δ 8.57 (s, 1H), 8.13 (s, 1H), 7.46 (s, 1H), 7.48-7.60 (d, 1H), 7.31-7.27 (t, 1H), 7.00-6.98 (d, 1H), 6.51 (s, 1H), 6.28 (s, 1H), 5.66 (s, 2H), 4.33 (s, 3H), 1.97 (s, 3H).

Example 2K. Synthesis of 2-(difluoro(phenyl)methyl)-6-(3-methoxybenzyl)-4-methyl-4,6-dihydro-5H-thiazolo[5',4':4,5]pyrrolo[2,3-d]pyridazin-5-one

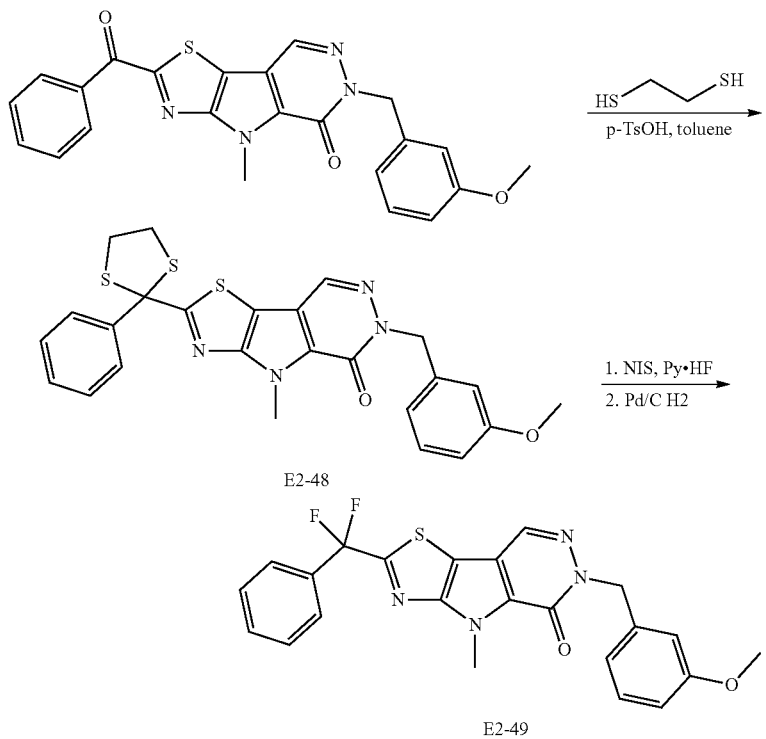

Step A. 6-(3-Methoxybenzyl)-4-methyl-2-(2-phenyl-1,3-dithiolan-2-yl)-4,6-dihydro-5H-thiazolo[5',4':4,5]pyrrolo[2,3-d]pyridazin-5-one. To a mixture of 2-benzoyl-6-(3-methoxybenzyl)-4-methyl-4,6-dihydro-5H-thiazolo[5',4':4,5]pyrrolo[2,3-d]pyridazin-5-one (86 mg, 0.2 mmol) in toluene (3 mL) was added p-TsOH (36 mg, 0.2 mmol) and ethane-1,2-dithiol (39 mg, 0.4 mmol). The mixture was stirred at 110° C. for 4 hr. then poured into water and extracted with EtOAc. The combined organic layers were washed with brine, dried over anhydrous Na₂SO₄ and concentrated under reduced pressure. The residue was purified by column chromatography on silica gel (eluent: PE/EtOAc=3/1) to give the desired product (80 mg, 80% yield). LCMS: m/z 507 (M+H)⁺.

Step B. 2-(Difluoro(phenyl)methyl)-6-(3-methoxybenzyl)-4-methyl-4,6-dihydro-5H-thiazolo[5',4':4,5]pyrrolo[2,3-d]pyridazin-5-one. To a mixture of 6-(3-Methoxybenzyl)-

4-methyl-2-(2-phenyl-1,3-dithiolan-2-yl)-4,6-dihydro-5H-thiazolo [5',4':4,5]pyrrolo[2,3-d]pyridazin-5-one (65 mg, 0.13 mmol) and NIS (little) in DCM (5 mL) was added Py·HF (1 mL). The reaction mixture was stirred at r.t. under N₂ for 2 hr. then poured into water and extracted with DCM. The combined organic layers were washed with brine, dried over anhydrous Na₂SO₄ and concentrated under reduced pressure. The residue was purified by column chromatography on silica gel (eluent: PE/EtOAc=3/1) to give a solid (50 mg, 76% yield). LCMS: m/z 595 (M+H)⁺.

To a mixture of the above solid (25 mg, 0.04 mmol) in THF/MeOH (3 mL/2 mL) was added Pd/C (5 mg). The mixture was stirred at r.t. under H₂ for 40 min then filtered. The filtrate was concentrated under reduced pressure and the residue was purified by prep-TLC to afford the desired product (7 mg, 36.8% yield). LCMS: 453 (M+H)⁺. ¹H NMR (400 MHz, DMSO-d₆) δ 8.70 (s, 1H), 7.74-7.70 (m, 2H), 7.64-7.56 (m, 3H), 7.26-7.20 (m, 1H), 6.88-6.84 (m, 3H), 5.33 (s, 2H), 4.25 (s, 3H), 3.71 (s, 3H).

Example 2L. Synthesis of 6-((1H-indazol-4-yl)methyl)-4-methyl-2-(1-phenylcyclopropyl)-4,6-dihydro-5H-thiazolo[5',4':4,5]pyrrolo[2,3-d]pyridazin-5-one

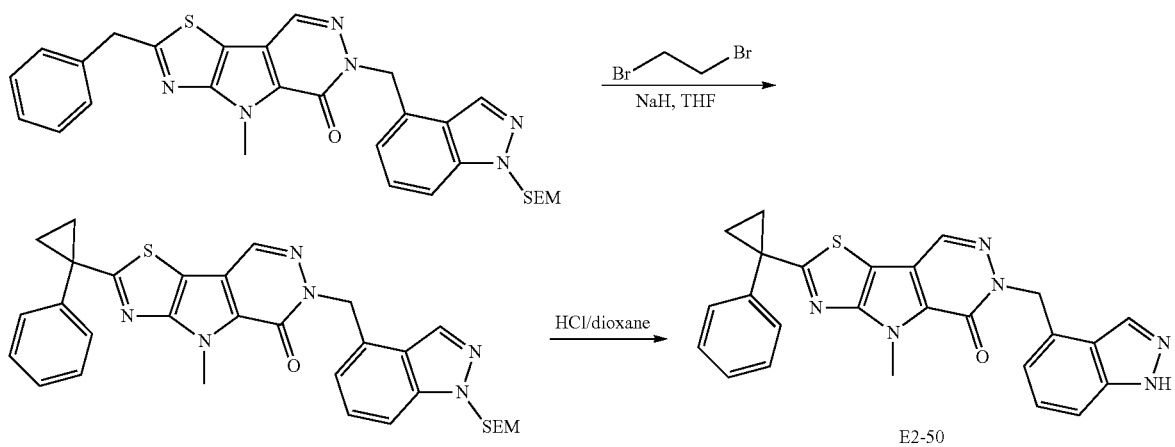

Step A. 4-Methyl-2-(1-phenylcyclopropyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one.

To a mixture of 2-benzyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (60 mg, 0.1 mmol) in dry DMF (2 mL) were added 1,2-dibromoethane (10 μL, 0.1 mmol) and TBAB (3 mg, 0.01 mmol). The mixture was stirred at r.t. for 30 min, followed by addition of NaH (8 mg, 0.2 mmol). The mixture was stirred at r.t. for 3 hr. then poured into saturated aqueous NH₄Cl and extracted with EtOAc. The combined organic layers were concentrated under reduced pressure. The residue was purified by prep-TLC to afford the desired product (26 mg, 44.7% yield). LCMS: 583 (M+H)⁺.

Step B. 6-((1H-indazol-4-yl)methyl)-4-methyl-2-(1-phenylcyclopropyl)-4H-thiazolo [5',4':4,5]pyrrolo[2,3-d]pyridazin-5(6H)-one. A mixture of 4-methyl-2-(1-phenylcyclopropyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (26 mg, 0.044 mmol) in a solution of HCl in dioxane (4M, 2 mL) was stirred at r.t. for 3 hr. then concentrated under reduced pressure. The residue was purified by prep-HPLC to afford the desired product (3 mg, 15% yield). LCMS: 453 (M+H)⁺. ¹H NMR (400 MHz, DMSO-d₆) δ 13.11 (s, 1H), 8.47 (s, 1H), 8.12 (s, 1H), 7.59-7.52 (m, 2H), 7.50-7.38 (m, 4H), 7.32-7.23 (m, 1H), 6.95 (d, 1H), 5.63 (s, 2H), 4.24 (s, 3H), 1.84-1.81 (m, 2H), 1.59-1.57 (m, 2H).

Example 2M Synthesis of 3-((2,4-dimethyl-5-oxo-4H-thiazolo[5',4':4,5]pyrrolo[2,3-d]pyridazin-6(5H)-yl)methyl)benzamide

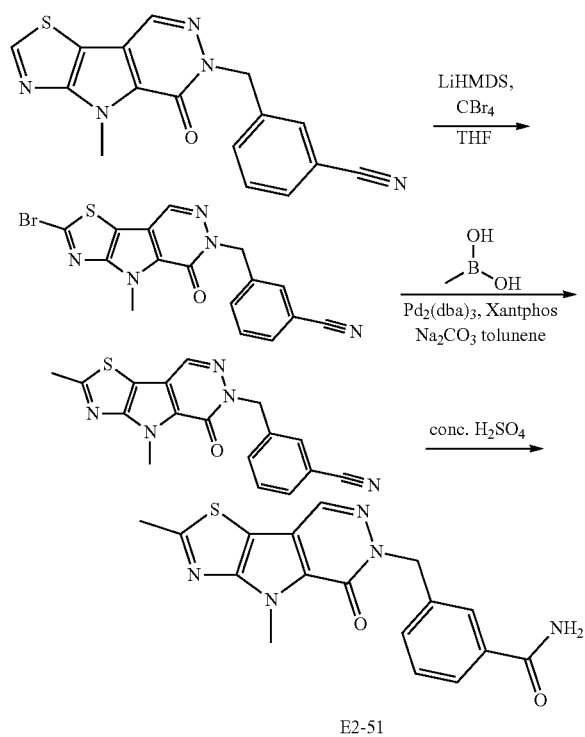

E2-51

Step A. Synthesis of 3-((2-bromo-4-methyl-5-oxo-4H-thiazolo[5',4':4,5]pyrrolo[2,3-d]pyridazin-6(5H)-yl)methyl) benzonitrile At −40° C. under $N_2$ atmosphere, to a mixture of 3-((4-methyl-5-oxo-4H-thiazolo[5',4':4,5]pyrrolo[2,3-d]pyridazin-6(5H)-yl)methyl) benzonitrile (200 mg, 0.62 mmol) and $CBr_4$ (1.03 g, 3.11 mmol) in THF (15 mL) was added LiHMDS (1.24 mL, 1 M in THF) by dropwise. The reaction mixture was stirred at −40° C. for 2 hrs, quenched by satd. $NH_4Cl$ and extracted with EtOAc. The combined organic layers were washed with brine, dried over anhy. $Na_2SO_4$ and concentrated under reduced pressure. The residue was purified by column chromatography (silica gel, 0~25% EtOAc in PE) to afford 3-((2-bromo-4-methyl-5-oxo-4H-thiazolo[5',4':4,5]pyrrolo[2,3-d]pyridazin-6(5H)-yl)methyl)benzonitrile (200 mg, 80.6% yield). LC-MS (ESI): m/z 400 (M+H)+.

Step B. Synthesis of 3-((2,4-dimethyl-5-oxo-4H-thiazolo[5',4':4,5]pyrrolo[2,3-d]pyridazin-6(5H)-yl)methyl)benzonitrile To a mixture of 3-((2-bromo-4-methyl-5-oxo-4H-thiazolo[5',4':4,5]pyrrolo[2,3-d]pyridazin-6(5H)-yl)methyl) benzonitrile (100 mg, 0.25 mmol) and methylboronic acid (45 mg, 0.75 mmol) in toluene (2 mL) was added $Na_2CO_3$ (53 mg, 0.5 mmol), followed by $Pd_2(dba)_3$ (23 mg, 0.025 mmol) and xantphos (14 mg, 0.025 mmol). The reaction mixture was stirred at 100° C. for 15 hr. The reaction mixture was filtered and the filtrate was evaporated. The residue was purified by column chromatography (silica gel, 0~50% EtOAc in petroleum ether) to afford 3-((2,4-dimethyl-5-oxo-4H-thiazolo[5',4':4,5]pyrrolo[2,3-d]pyridazin-6(5H)-yl)methyl)benzonitrile (60 mg, 71.4% yield). LC-MS (ESI): m/z 336 (M+H)+.

Step C. Synthesis of 3-((2,4-dimethyl-5-oxo-4H-thiazolo[5',4':4,5]pyrrolo[2,3-d]pyridazin-6(5H)-yl)methyl)benzamide A solution of 3-((2,4-dimethyl-5-oxo-4H-thiazolo[5',4':4,5]pyrrolo[2,3-d]pyridazin-6(5H)-yl)methyl) benzonitrile (60 mg, 0.18 mmol) in $H_2SO_4$ (1 mL) was stirred at 30° C. overnight. The reaction was quenched by satd. $NaHCO_3$ and extracted with EtOAc. The combined organic layers were washed with brine, dried over anhy. $Na_2SO_4$ and evaporated. The residue was purified by pre-TLC (10% MeOH in DCM) to afford 3-((2,4-dimethyl-5-oxo-4H-thiazolo[5',4':4,5]pyrrol[2,3-d]pyridazin-6(5H)-yl)methyl)benzamide (10 mg, 15.7% yield). LC-MS (ESI): m/z 354 (M+H)+. 1H NMR (400 MHz, DMSO-d6) δ 8.59 (s, 1H), 7.98 (s, 1H), 7.81 (s, 1H), 7.77 (d, 1H), 7.46 (d, 1H), 7.41 (t, 1H), 7.35 (s, 1H), 5.40 (s, 2H), 4.26 (s, 3H), 2.86 (s, 3H).

Example 2N. Synthesis of 2-(2-(1H-pyrazol-3-yl)ethyl)-4-methyl-6-((1-methyl-1H-pyrazol-3-yl)methyl)-4,6-dihydro-5H-thiazolo[5',4':4,5]pyrrolo[2,3-d]pyridazin-5-one

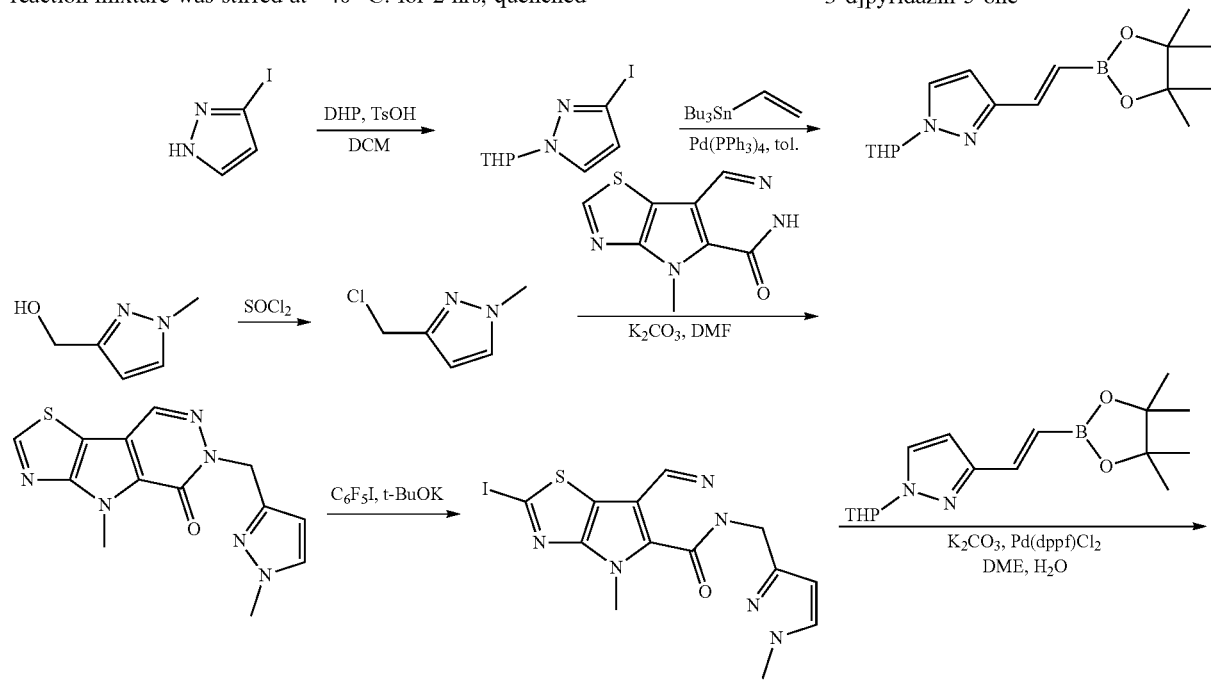

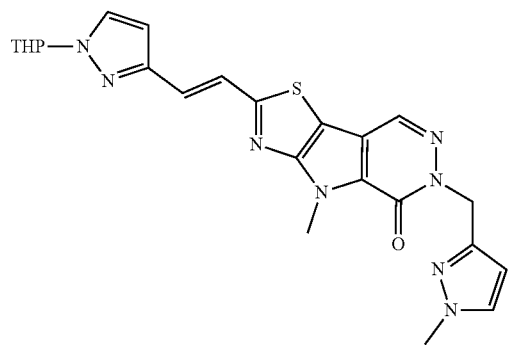 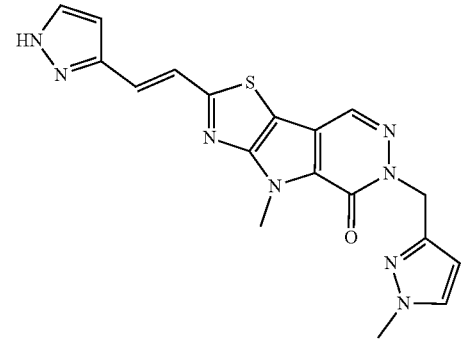

E2-52

Step A. Synthesis of 3-iodo-1-(tetrahydro-2H-pyran-2-yl)-1H-pyrazole To a mixture of 3-iodo-1H-pyrazole (1 g, 5.16 mmol) and p-TsOH (88 mg, 0.52 mmol) in DCM (15 mL) was added DHP (0.56 mL, 6.19 mmol) and stirred at r.t. for 2 hr. The reaction mixture was washed with satd. NaHCO$_3$ and brine, dried over anhy. Na$_2$SO$_4$ and concentrated. The residue was purified by flash chromatography (silica gel, 0~10% EtOAc in PE) to give 3-iodo-1-(oxan-2-yl)-1H-pyrazole (1.4 g). LC-MS (m/z 279 (M+H)$^+$.

Step B. Synthesis of (E)-1-(tetrahydro-2H-pyran-2-yl)-3-(2-(4,4,5,5-tetramethyl-1,3,2-dioxaborolan-2-yl)vinyl)-1H-pyrazole Under nitrogen, to a mixture of 3-iodo-1-(tetrahydro-2H-pyran-2-yl)-1H-pyrazole (150 mg, 0.54 mmol) in toluene (3 mL) was added 2-ethenyl-4,4,5,5-tetramethyl-1,3,2-dioxaborolane (0.18 mL, 1.08 mmol), Et$_3$N (0.37 mL, 2.7 mmol) and Pd(PBu$_3$)$_2$ (14 mg, 0.03 mmol). The reaction was stirred at 100° C. for 3 hr. The mixture was concentrated and purified by prep-TLC (35% EtOAc in PE) to give 1-(oxan-2-yl)-3-[(E)-2-(tetramethyl-1,3,2-dioxaborolan-2-yl)ethenyl]-1H-pyrazole (60 mg, 37% yield). LC-MS (ESI): m/z 305 (M+H)$^+$.

Step C. Synthesis of 4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-4H-thiazolo[5',4':4,5]pyrrolo[2,3-d]pyridazin-5(6H)-one (500 mg, 2.42 mmol) in DMF (15 mL) was added K$_2$CO$_3$ (335 mg, 2.42 mmol). After stirred at 50° C. for 30 min, a solution of 3-(bromomethyl)-1-methyl-1H-pyrazole (636 mg, 3.64 mmol) in DMF (2 mL) was added.

The reaction was stirred at 50° C. overnight. The suspension was poured into satd. NH$_4$Cl, extracted with EtOAc. The organic layer was dried over anhy. Na$_2$SO$_4$, filtered and concentrated. The residue was purified by flash chromatography (silica gel, 0~100 EtOAc in PE) to give 4-methyl-6-((1-methyl-1H-pyrazol-3-yl)methyl)-4H-thiazolo[5',4':4,5]pyrrolo[2,3-d]pyridazin-5(6H)-one (280 mg). LC-MS (ESI): m/z 301 (M+H)$^+$.

Step D. Synthesis of 2-iodo-4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-6-((1-methyl-1H-pyrazol-3-yl)methyl)-4H-thiazolo[5',4':4,5]pyrrolo[2,3-d]pyridazin-5(6H)-one (280 mg, 0.93 mmol) in toluene (10 mL) was added pentafluoroiodobenzene (0.50 mL, 3.73 mmol) and t-BuOK (209 mg, 1.86 mmol). The reaction was stirred at 135° C. for 2 hr under nitrogen. The mixture was cooled to r.t. and concentrated. The residue was purified by flash chromatography (silica gel, 0~100% EtOAc in PE) to give 2-iodo-4-methyl-6-((1-methyl-1H-pyrazol-3-yl)methyl)-4H-thiazolo[5',4':4,5]pyrrolo [2,3-d]pyridazin-5(6H)-one (300 mg). LC-MS (ESI): m/z 427 (M+H)$^+$.

Step E. Synthesis of (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo[5',4':4,5]pyrrolo[2,3-d]pyridazin-5(6H)-one Under nitrogen, to a mixture of 2-iodo-4-methyl-6-((1-methyl-1H-pyrazol-3-yl)methyl)-4H-thiazolo[5',4':4,5]pyrrolo[2,3-d]pyridazin-5(6H)-one (300 mg, 0.71 mmol) and (E)-1-(tetrahydro-2H-pyran-2-yl)-3-(2-(4,4,5,5-tetramethyl-1,3,2-dioxaborolan-2-yl)vinyl)-1H-pyrazole (300 mg, 0.99 mmol) in DME (5 mL) and water (1 mL) were added Na$_2$CO$_3$ (149 mg, 1.41 mmol) and Pd(PPh$_3$)$_2$Cl$_2$ (49 mg, 0.071 mmol). The mixture was stirred at 80° C. for 3 hr. Then the mixture was cooled down, diluted with EtOAc, washed with water and brine. The organic layer was dried over anhy. Na$_2$SO$_4$, filtered and concentrated. The residue was purified by flash chromatography (silica gel, 0~100% EtOAc in PE) to give (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo[5',4':4,5]pyrrolo[2,3-d]pyridazin-5(6H)-one (170 mg). LC-MS (ESI): m/z 477 (M+H)$^+$.

Step F. Synthesis of 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5]pyrrolo [2,3-d]pyridazin-5(6H)-one To a mixture of (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo [5',4':4,5]pyrrolo[2,3-d]pyridazin-5(6H)-one (80 mg, 0.17 mmol) in THF (3 mL) and MeOH (3 mL) was added Pd/C (10 mg). The reaction was stirred under H$_2$ at r.t. for 6 hr. The mixture was filtered and the filtrate was concentrated. The residue was purified by prep-TLC (EtOAc) to give 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5] pyrrolo [2,3-d]pyridazin-5(6H)-one (20 mg). LC-MS (ESI): m/z 479 (M+H)$^+$.

Step G. Synthesis of 2-(2-(1H-pyrazol-3-yl)ethyl)-4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5]pyrrolo[2,3-d]pyridazin-5(6H)-one (20 mg, 0.042 mmol) in ethanol (2 mL) was added HCl (0.5 mL, 4 M in dioxane). The reaction mixture was stirred at 50° C. for 30 min. The reaction mixture was cooled down and poured into satd. NaHCO$_3$, extracted with EtOAc. The organic layer was dried over anhy. Na$_2$SO$_4$, filtered and concentrated. The residue was purified by prep-TLC (10% MeOH in DCM) to give 2-(2-(1H-pyrazol-3-yl)ethyl)-4-methyl-6-((1-methyl-1H-pyrazol-3-yl)methyl)-4H-thiazolo[5',4':4,5]pyrrolo[2,3-d]pyridazin-5(6H)-one (10 mg, 61% yield). LC-MS (ESI): m/z 395 (M+H)$^+$. $^1$H NMR (400 MHz, DMSO-d6) δ 12.56 (s, 1H), 8.51 (s, 1H), 7.56 (d, 1H), 7.52 (s, 1H), 6.12 (d, 1H), 6.08 (d, 1H), 5.27 (s, 2H), 4.27 (s, 3H), 3.77 (s, 3H), 3.48 (t, 2H), 313 (t, 2H).

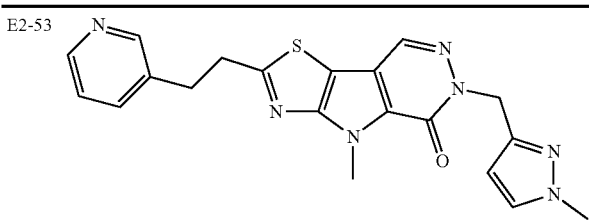
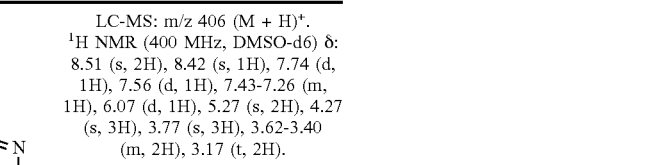

4-methyl-6-((1-methyl-1H-pyrazol-3-yl)methyl)-2-(2-(pyridin-3-yl)ethyl)-4,6-dihydro-5H-thiazolo[5',4':4,5]pyrrolo[2,3-d]pyridazine-5-one LC-MS: m/z 406 (M + H)+.
1H NMR (400 MHz, DMSO-d6) δ: 8.51 (s, 2H), 8.42 (s, 1H), 7.74 (d, 1H), 7.56 (d, 1H), 7.43-7.26 (m, 1H), 6.07 (d, 1H), 5.27 (s, 2H), 4.27 (s, 3H), 3.77 (s, 3H), 3.62-3.40 (m, 2H), 3.17 (t, 2H).

Example 2O. Synthesis of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one

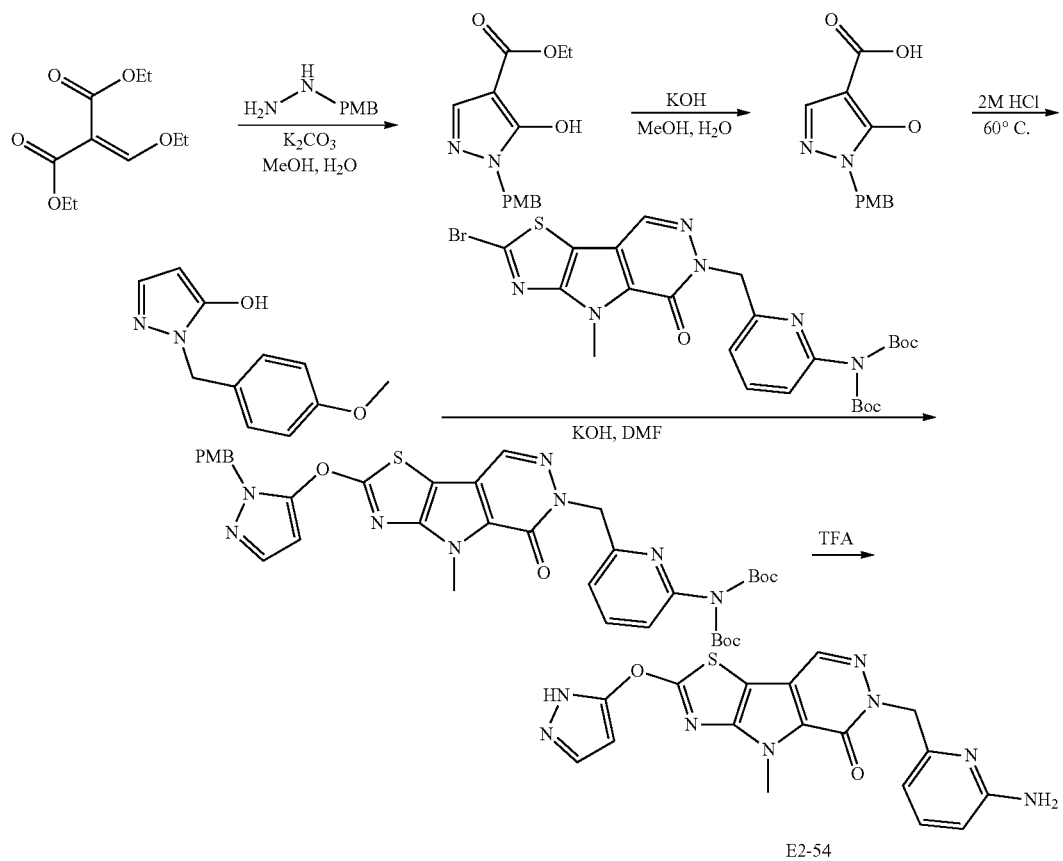

Step A. Synthesis of ethyl 5-hydroxy-1-(4-methoxybenzyl)-1H-pyrazole-4-carboxylate To a mixture of (4-methoxybenzyl)hydrazine dihydrochloride (2.25 g, 10 mmol) and K2CO3 (4.14 g, 30 mmol) in methanol (50 mL) and water (10 mL) was added diethyl 2-(ethoxymethylene)malonate (2.16 g, 10 mmol). The mixture was stirred at 80° C. for 5 hr. Then the mixture was quenched with aq. NH4Cl and extracted with EtOAc. The organic layers were washed with brine, dried over Na2SO4 and concentrated. The residue was purified by column chromatography (silica gel, 0~50% EtOAc in PE) to afford 1.1 g of ethyl 5-hydroxy-1-(4-methoxybenzyl)-1H-pyrazole-4-carboxylate.

Step B. Synthesis of 5-hydroxy-1-(4-methoxybenzyl)-1H-pyrazole-4-carboxylic acid To a solution of ethyl 5-hydroxy-1-(4-methoxybenzyl)-1H-pyrazole-4-carboxylate (800 mg, 2.9 mmol) in methanol (10 mL) was added a solution of KOH (800 mg, 15 mmol) in water (10 mL). The mixture was stirred at room temperature for 16 hr. Then the mixture was concentrated and the residue was used directly in next step. LC-MS (ESI): m/z 249 (M+H)+.

Step C. Synthesis of 1-(4-methoxybenzyl)-1H-pyrazol-5-ol A mixture of 5-hydroxy-1-(4-methoxybenzyl)-1H-pyrazole-4-carboxylic acid was dissolve in 2 M HCl (50 mL) was stirred at 60° C. for 16 hr. The solvent was removed and the residue was purified by pre-TLC to give 120 mg of 1-(4-methoxybenzyl)-1H-pyrazol-5-ol. LC-MS (ESI): m/z 205 (M+H)+.

Step D. Synthesis of tert-butyl N-(tert-butoxy)carbonyl (6-((2-((1-(4-methoxybenzyl)-1H-pyrazol-5-yl)oxy)-4-methyl-5-oxo-4H-thiazolo[5',4':4,5]pyrrolo[2,3-d]pyridazin-6(5H)-yl)methyl)pyridin-2-yl)carbamate To a solution of 1-[(4-methoxyphenyl)methyl]-1H-pyrazol-5-ol (60 mg, 0.29 mmol) in DMF (8 mL) was added KOH (18 mg, 0.32 mmol) at 5° C. The reaction mixture was stirred at 5° C. for 30 min, a solution of tert-butyl N-(tert-butoxy)carbonyl (6-((2-bromo-4-methyl-5-oxo-4H-thiazolo[5',4':4,5]pyrrolo[2,3-d]pyridazin-6(5H)-yl)methyl)pyridin-2-yl)carbamate (174 mg, 0.29 mmol) in DMF (2 mL) was added. The reaction was stirred at r.t. for 16 hr and then poured into 1 M aqueous citric acid, extracted with EtOAc. The combined organic layers were washed with brine, dried over anhy. Na2SO4 and evaporated. The residue was purified by pre-TLC (EA:PE=1:1) to afford 80 mg of tert-butyl N-(tert-butoxy)carbonyl (6-((2-((1-(4-methoxybenzyl)-1H-pyrazol-5-yl)oxy)-4-methyl-5-oxo-4H-thiazolo [5',4':4,5]pyrrolo[2,3-d]pyridazin-6(5H)-yl)methyl)pyridin-2-yl)carbamate. LC-MS: m/z 715 (M+H)+.

Step E. Synthesis of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one A solution of tert-butyl N-(tert-butoxy)carbonyl(6-((2-((1-(4-methoxybenzyl)-1H-pyrazol-5-yl)oxy)-4-methyl-5-oxo-4H-thiazolo[5',4':4,5]pyrrolo[2,3-d]pyridazin-6(5H)-yl)methyl)pyridin-2-yl)carbamate (60 mg, 0.08 mmol) in TFA (2 ML) was stirred at r.t. overnight. The reaction was concentrated and purified by prep-HPLC to give 15 mg of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one. LC-MS (ESI): m/z 395 (M+H)+. 1H NMR (400 MHz, Methanol-d4) δ 8.41 (s, 1H), 7.76-7.63 (m, 2H), 6.79 (d, 1H), 6.64 (d, 1H), 6.31 (d, 1H), 5.42 (s, 2H), 4.26 (s, 3H).

Example 3. Preparation of Compounds of Formula E3-ii and Derivatives with Scheme E3

Scheme E3

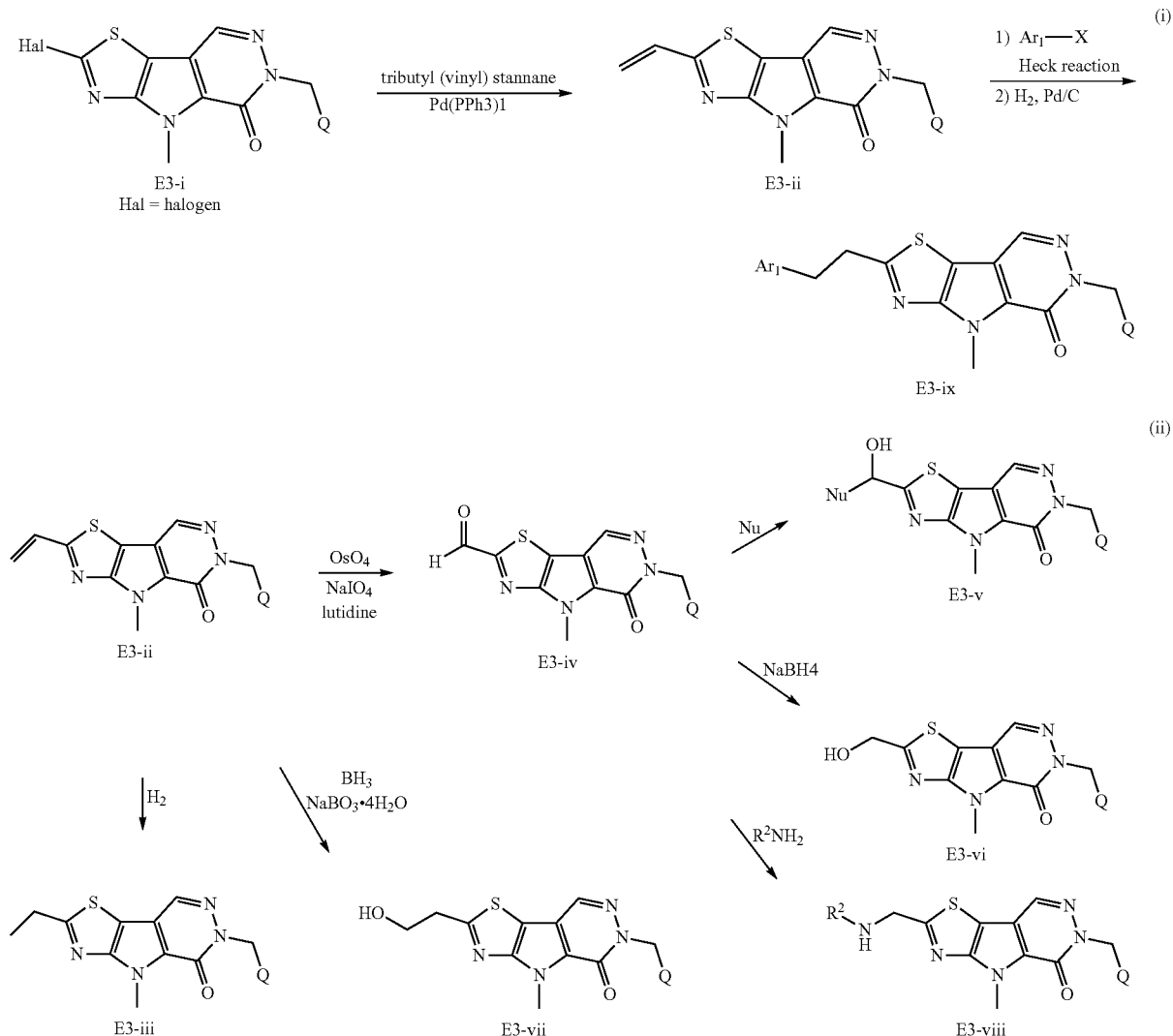

Compound E3-ii can be synthesized by a Stille reaction between compound E3-i and tributyl(vinyl)stannane. Heck reaction of E3-ii in the presence of a catalyst (e.g. Palladium catalyst such as Pd(Pt-Bu3)2, DMF) followed by reduction of the alkenyl group can generate compound E3-ix. Alternatively, standard hydrogenation of compound E3-ii generates compound E3-iii. Hydroboration of compound E3-ii followed by oxidation with sodium perborate gives product E3-vii. Direct oxidation of compound E3-ii with osmium (VIII) oxide and sodium periodate provides aldehyde E3-iv. Nucleophilic addition of aldehyde E3-iv gives product E3-v. Standard reduction of compound E3-iv with sodium borohydride affords compound E3-vi. Reductive amination of compound E3-iv gives compound E3-viii. Wherein Q and $R^2$ are as defined in the first embodiment of the invention. In certain embodiments, Q and $R^2$ are each independently optionally substituted aryl, optionally substituted heteroaryl, optionally substituted carbocycle or optionally substituted heterocyclyl.

Example 3A. Synthesis of 2-ethyl-6-(3-methoxybenzyl)-4-methyl-4H-thiazolo [5',4':4,5]pyrrolo[2,3-d]pyridazin-5(6H)-one

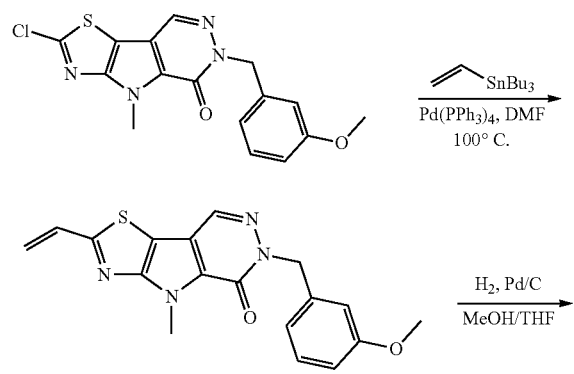

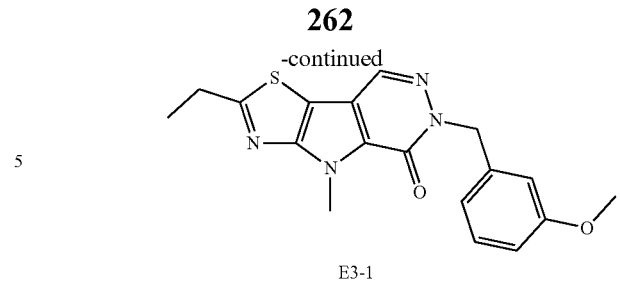

E3-1

Step A. 6-(3-Methoxybenzyl)-4-methyl-2-vinyl-4H-thiazolo[5',4':4,5]pyrrolo [2,3-d]pyridazin-5(6H)-one. To a mixture of 2-chloro-6-(3-methoxybenzyl)-4-methyl-4H-thiazolo[5',4':4,5]pyrrolo[2,3-d]pyridazin-5(6H)-one (600 mg, 1.67 mmol) and tributyl(vinyl)stannane (1 mL, 3.4 mmol) in DMF (6 mL) was added Pd(PPh$_3$)$_4$. The mixture was stirred at 100° C. overnight under N$_2$ then poured into water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/2) to give desired product (410 mg, 68% yield). LCMS: m/z 353 (M+H)$^+$. $^1$H NMR (400 MHz, DMSO-d6) δ 8.61 (s, 1H), 7.23 (t, 1H), 7.10 (dd, 1H), 6.89-6.80 (m, 3H), 6.28 (d, 1H), 5.75 (d, 1H), 5.32 (s, 2H), 4.27 (s, 3H), 3.72 (s, 3H).

Step B. 2-Ethyl-6-(3-methoxybenzyl)-4-methyl-4H-thiazolo[5',4':4,5]pyrrolo[2,3-d]pyridazin-5(6H)-one. To a mixture of 6-(3-methoxybenzyl)-4-methyl-2-vinyl-4H-thiazolo[5',4':4,5]pyrrolo[2,3-d]pyridazin-5(6H)-one (30 mg, 0.88 mmol) in MeOH (1 mL) and THF (1 mL) under N$_2$ was added Pd/C (10 mg). The mixture was stirred under H$_2$ at r.t. for 1 hr. then filtered through Celite. The filtrate was concentrated under reduced pressure and the residue was purified by prep-TLC to afford the desired product (5 mg, 16.7% yield). LCMS: m/z 355 (M+H)$^+$. $^1$H NMR (400 MHz, DMSO-d$_6$) δ 8.56 (s, 1H), 7.23 (t, 1H), 6.89-6.78 (m, 3H), 5.32 (s, 2H), 4.26 (s, 3H), 3.72 (s, 3H), 3.17 (q, 2H), 1.38 (t, 3H).

The procedure set forth above was used to produce the following compounds using the appropriate starting materials.

| Cpd No. | Structure | Characterization |
|---|---|---|
| E3-2 | 6-((1H-indazol-4-yl)methyl)-4-methyl-2-vinyl-4,6-dihydro-5H-thiazolo[5',4':4,5]pyrrolo[2,3-d]pyridazin-5-one | LC-MS: m/z 363 (M + H)$^+$. $^1$H NMR (400 MHz, DMSO-d$_6$) δ 13.13 (s, 1H), 8.63 (s, 1H), 8.16 (s, 1H), 7.46 (d, 1H), 7.31-7.27 (m, 1H), 7.14-7.07 (m, 1H), 6.98 (d, H), 6.28 (d1H), 5.76 (d, 1H), 5.67 (s, 2H), 4.29 (s, 3H). |

Example 3B. Synthesis of 2-(hydroxymethyl)-6-(3-methoxybenzyl)-4-methyl-4H-thiazolo[5',4':4,5]pyrrolo[2,3-d]pyridazin-5(6H)-one

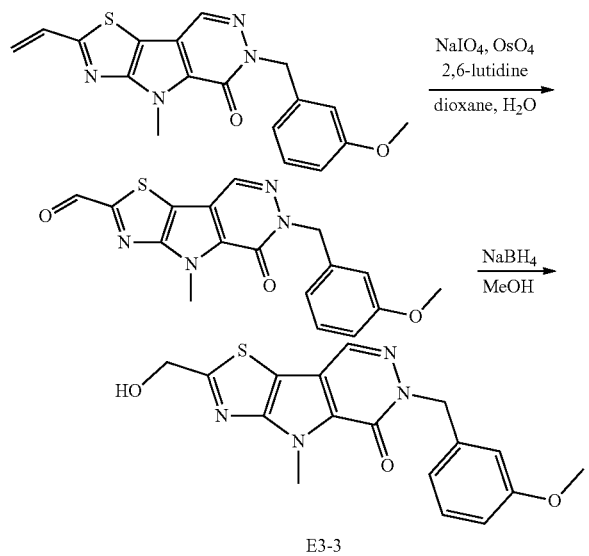

E3-3

Step A. 6-(3-Methoxybenzyl)-4-methyl-5-oxo-5,6-dihydro-4H-thiazolo[5',4':4,5]pyrrolo[2,3-d]pyridazine-2-carbaldehyde. To a mixture of 6-(3-methoxybenzyl)-4-methyl-2-vinyl-4H-thiazolo[5',4':4,5]pyrrolo[2,3-d]pyridazin-5(6H)-one (410 mg, 1.16 mmol) in dioxane (6 mL) and water (2 mL) were added NaIO$_4$ (1 g, 4.6 mmol), 2,6-dimethylpyridine (0.27 mL, 2.32 mmol) and OsO$_4$ (cat.). The mixture was stirred at r.t. for 4 hr. then quenched with saturated aqueous Na$_2$S$_2$O$_3$ and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=1/1) to give the desired product (130 mg, 31.7% yield). LCMS: m/z 387 (M+MeOH+H)$^+$. $^1$H NMR (400 MHz, DMSO-d$_6$) δ 10.08 (s, 1H), 8.75 (s, 1H), 7.24 (t, 1H), 6.88-6.83 (m, 3H), 5.34 (s, 2H), 4.34 (s, 3H), 3.72 (s, 3H).

Step B. 2-(Hydroxymethyl)-6-(3-methoxybenzyl)-4-methyl-4H-thiazolo[5',4':4,5]pyrrolo[2,3-d]pyridazin-5(6H)-one. To a mixture of 6-(3-methoxybenzyl)-4-methyl-5-oxo-5,6-dihydro-4H-thiazolo[5',4':4,5]pyrrolo[2,3-d]pyridazine-2-carbaldehyde (30 mg, 0.08 mmol) in methanol (2 mL) was added NaBH$_4$ (6 mg, 0.16 mmol). The mixture was stirred at r.t. for 10 min then poured into water and extracted with EtOAc. The organic layer was concentrated under reduced pressure and the residue was purified by prep-HPLC to afford the desired product (10 mg, 35.7% yield). LCMS: m/z 357 (M+H)$^+$. $^1$H NMR (400 MHz, DMSO-d$_6$) δ 8.59 (s, 1H), 7.23 (t, 1H), 6.86-6.82 (m, 3H), 6.34 (t, 1H), 5.32 (s, 2H), 4.89 (d, 2H), 4.26 (s, 3H), 3.72 (s, 3H).

The procedure set forth above was used to produce the following compounds using the appropriate starting materials. Standard protection and deprotection can be used when necessary.

| Cpd No. | Structure | Characterization |
|---|---|---|
| E3-4 | 6-((1H-indazol-4-yl)methyl)-2-(hydroxymethyl)-4-methyl-4,6-dihydro-5H-thiazolo[5',4':4,5]pyrrolo[2,3-d]pyridazin-5-one | LC-MS: m/z 367 (M + H)$^+$. $^1$H NMR (400 MHz, DMSO-d$_6$) δ 13.12 (s, 1H), 8.62 (s, 1H), 8.16 (s, 1H), 7.45 (d, 1H), 7.31-7.27 (m, 1H), 6.98-6.97 (m, 1H), 6.34 (t, 1H), 5.67 (s, 2H), 4.89 (d, 2H), 4.27 (s, 3H). |
| E3-5 | 6-((1H-indazol-4-yl)methyl)-2-(1-hydroxyethyl)-4-methyl-4,6-dihydro-5H-thiazolo[5',4':4,5]pyrrolo[2,3-d]pyridazin-5-one | LC-MS: m/z 381 (M + H)$^+$. $^1$H NMR (400 MHz, DMSO-d$_6$) δ 13.13 (s, 1H), 8.60 (s, 1H), 8.15 (s, 1H), 7.45 (d, 1H), 7.30-7.26 (m, 1H), 6.97-6.95 (m, 1H), 6.42 (d, 1H), 5.66 (s, 2H), 5.10-5.07 (m, 1H), 4.26 (s, 3H), 1.53 (d, 3H). |

Example 3C: Synthesis of 2-(2-hydroxypropan-2-yl)-6-(3-methoxybenzyl)-4-methyl-4H-thiazolo[5',4':4,5]pyrrolo[2,3-d]pyridazin-5(6H)-one

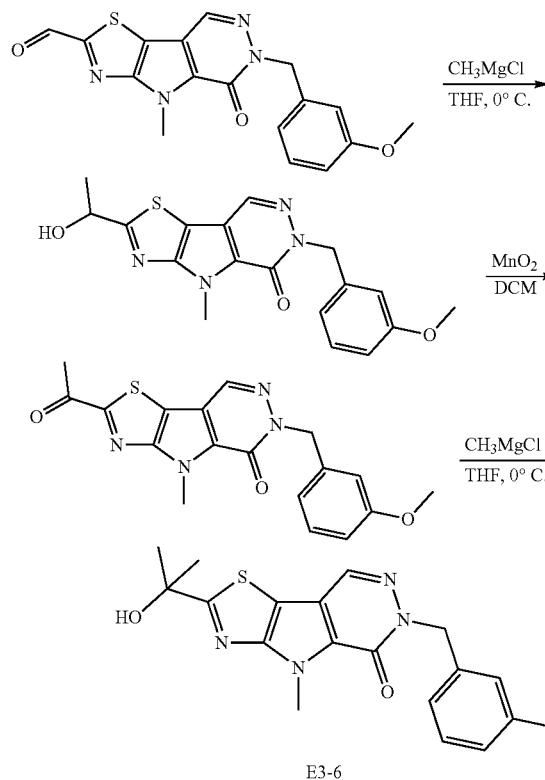

E3-6

Step A. 2-(1-Hydroxyethyl)-6-(3-methoxybenzyl)-4-methyl-4H-thiazolo [5',4':4,5]pyrrolo[2,3-d]pyridazin-5(6H)-one. To a mixture of 6-(3-methoxybenzyl)-4-methyl-5-oxo-5,6-dihydro-4H-thiazolo[5',4':4,5]pyrrolo[2,3-d]pyridazine-2-carbaldehyde (100 mg, 0.28 mmol) in THF (3 mL) at 0° C. was added drop wise methylmagnesium chloride (0.19 mL, 0.56 mmol). The mixture was stirred at r.t. for 10 min then poured into saturated aqueous NH$_4$Cl and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/2) to give the desired product (40 mg). LCMS: m/z 371 (M+H)$^+$. $^1$H NMR (400 MHz, DMSO-d$_6$) δ 8.58 (s, 1H), 7.24 (t, 1H), 6.97-6.77 (m, 3H), 6.41 (d, 1H), 5.40-5.23 (m, 2H), 5.18-5.02 (m, 1H), 4.26 (s, 3H), 3.72 (s, 3H), 1.55 (d, 3H).

Step B. 2-Acetyl-6-(3-methoxybenzyl)-4-methyl-4H-thiazolo[5',4':4,5]pyrrolo [2,3-d] pyridazin-5(6H)-one. To a mixture of 2-(1-hydroxyethyl)-6-(3-methoxybenzyl)-4-methyl-4H-thiazolo[5',4':4,5]pyrrolo[2,3-d]pyridazin-5(6H)-one (30 mg, 0.08 mmol) in DCM (3 mL) was added manganese (IV) oxide (35 mg, 0.4 mmol). The mixture was stirred at r.t. for 1 hr. then filtered through Celite. The filtrate was concentrated under reduced pressure to give the desired product (25 mg). LCMS: m/z 369 (M+H)$^+$. $^1$H NMR (400 MHz, DMSO-d$_6$) δ 8.83 (s, 1H), 7.35 (t, 1H), 6.99-6.94 (m, 3H), 5.45 (s, 2H), 4.45 (s, 3H), 3.83 (s, 3H), 2.85 (s, 3H).

Step C. 2-(2-Hydroxypropan-2-yl)-6-(3-methoxybenzyl)-4-methyl-4H-thiazolo [5',4':4,5]pyrrolo[2,3-d]pyridazin-5(6H)-one. To a mixture of 2-acetyl-6-(3-methoxybenzyl)-4-methyl-4H-thiazolo[5',4':4,5]pyrrolo[2,3-d]pyridazin-5(6H)-one (20 mg, 0.05 mmol) in THF (1 mL) at 0° C. was added drop wise methylmagnesium chloride (0.08 mL, 0.15 mmol). The mixture was stirred at r.t. for 10 then poured into saturated aqueous NH$_4$Cl and extracted with EtOAc. The combined organic layers were washed with brine, dried over anhydrous Na$_2$SO$_4$ and concentrated under reduced pressure. The residue was purified by prep-TLC to give the desired product (10 mg). LCMS: m/z 385 (M+H)$^+$. $^1$H NMR (400 MHz, DMSO-d$_6$) δ 8.58 (s, 1H), 7.24 (t, 1H), 6.89-6.81 (m, 3H), 6.28 (s, 1H), 5.33 (s, 2H), 4.26 (s, 3H), 3.72 (s, 3H), 1.60 (s, 6H).

Example 3D. Synthesis of 6-((1H-indazol-4-yl)methyl)-2-(2-hydroxyethyl)-4-methyl-4,6-dihydro-5H-thiazolo[5',4':4,5]pyrrolo[2,3-d]pyridazin-5-one

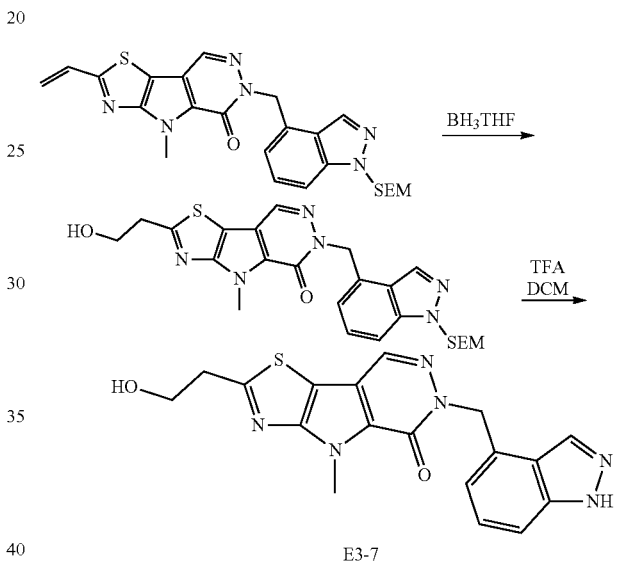

E3-7

Step A. 2-(2-Hydroxyethyl)-4-methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one. To a mixture of 4-methyl-6-((1-((2-(trimethylsilyl)ethoxy)methyl)-1H-indazol-4-yl)methyl)-2-vinyl-4,6-dihydro-5H-thiazolo[5',4':4,5]pyrrolo[2,3-d]pyridazin-5-one (100 mg, 0.20 mmol) in THF (2 mL) at 0° C. under N$_2$ was added BH$_3$-THF (0.2 mL, 1 mol/L, 0.20 mmol). The mixture was stirred at r.t. for 2 h, then cooled to 0° C., followed by addition of water (1 mL) and NaBO$_3$·4H$_2$O (154 mg, 1.00 mmol). The mixture was slowly warmed to r.t. and stirred at that temperature for 3 h. The resulting mixture was poured into saturated aqueous NH$_4$Cl and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/1) to give the desired product (30 mg). LC-MS: m/z 511 (M+H)$^+$.

Step B. 6-((JH-indazol-4-yl)methyl)-2-(2-hydroxyethyl)-4-methyl-4,6-dihydro-5H-thiazolo[5',4':4,5]pyrrolo[2,3-d]pyridazin-5-one. To a solution of 2 (30 mg, 0.18 mmol) in DCM (3 mL) at 0° C. was added drop wise TFA (1 mL). The resulting mixture was stirred at r.t. for 16 hr. then concentrated under reduced pressure. The residue was purified by prep-HPLC to give the desired product (2.0 mg). LC-MS:

m/z 381 (M+H)⁺. ¹H NMR (400 MHz, DMSO-d₆) δ 13.11 (s, 1H), 8.58 (s, 1H), 8.14 (s, 1H), 7.45 (d, 1H), 7.30-7.26 (m, 1H), 6.96 (d, 1H), 5.66 (s, 2H), 5.02-5.00 (m, 1H), 4.27 (s, 3H), 3.85-3.81 (m, 2H), 3.32-3.25 (m, 2H).

Example 3E. Synthesis of 6-((1H-indazol-4-yl)methyl)-4-methyl-2-((methylamino) methyl)-4,6-dihydro-5H-thiazolo[5',4':4,5]pyrrolo[2,3-d]pyridazin-5-one

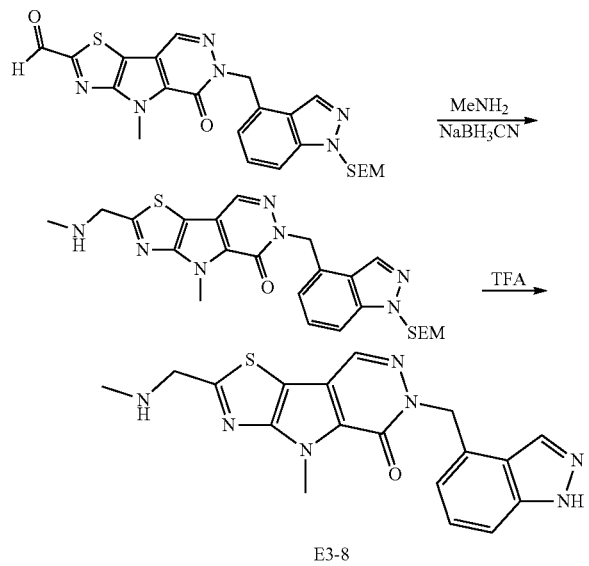

E3-8

Step A. 4-Methyl-2-((methylamino)methyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one. To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde (50 mg, 0.1 mmol) in THF (10 mL) at 0° C. was added drop wise MeNH₂ (30% in MeOH, 21 mg, 0.2 mmol). The reaction mixture was stirred r.t. for 2 hr., followed by addition of sodium cyanoborohydride (19 mg, 0.3 mmol). The resulting mixture was stirred at r.t. overnight then quenched with saturated aqueous NH₄Cl and extracted with EtOAc. The combined organic layers were dried over anhydrous Na₂SO₄, and concentrated under reduced pressure. The residue was purified by prep-TLC to give desired product (35 mg). LCMS: m/z 511 (M+H)⁺.

Step B. 6-((1H-indazol-4-yl)methyl)-4-methyl-2-((methylamino)methyl)-4H-thiazolo [5',4':4,5]pyrrolo[2,3-d]pyridazin-5(6H)-one. To a mixture of 4-methyl-((methylamino)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (35 mg, 0.07 mmol) in DCM (10 mL) at 0° C. was added drop wise TFA (3 mL). The reaction mixture was stirred at r.t. for 2 hr. then concentrated under reduced pressure. The residue was purified by prep-HPLC to give the desired product (5 mg). LCMS: m/z 380 (M+H)⁺. ¹H NMR (400 MHz, DMSO-d₆) δ 13.13 (s, 1H), 8.59 (s, 1H), 8.16 (d, 1H), 7.45 (d, 1H), 7.31-7.25 (m, 1H), 6.96 (d, 1H), 5.66 (s, 2H), 4.26 (s, 3H), 4.09 (s, 2H), 2.40 (s, 3H).

Example 3F. Synthesis of 6-((1H-indazol-4-yl)methyl)-2-(aminomethyl)-4-methyl-4,6-dihydro-5H-thiazolo[5',4':4,5]pyrrolo[2,3-d]pyridazin-5-one

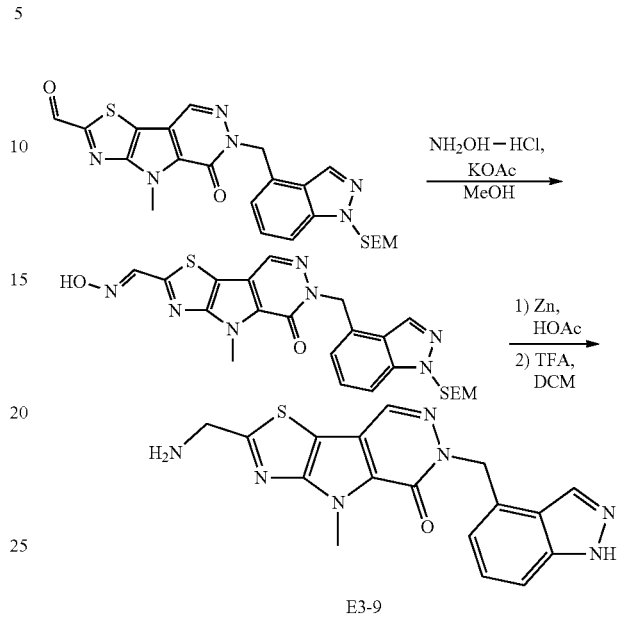

E3-9

Step A. (E)-4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde oxime. To a mixture of 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carbaldehyde (120 mg, 0.24 mmol) in MeOH (10 mL) at 0° C. was added hydroxylamine hydrochloride (50 mg, 0.73 mmol), followed by addition of KOAc (71 mg, 0.73 mmol). The reaction mixture was stirred st r.t. for 8 hr. then quenched with saturated aqueous NH₄Cl and extracted with EtOAc. The combined organic layers were washed with brine, dried over anhydrous Na₂SO₄ and concentrated under reduced pressure. The residue was purified by prep-TLC to give the desired product (90 mg). LCMS: m/z 510 (M+H)⁺.

Step B. 2-(Aminomethyl)-4-methyl-6-((1-((2-(trimethylsilyl)ethoxy)methyl)-1H-indazol-4-yl)methyl)-4H-thiazolo [5',4':4,5]pyrrolo[2,3-d]pyridazin-5(6H)-one. To a mixture of (E)-4-methyl-5-oxo-6-((1-((2-(trimethylsilyl)ethoxy) methyl)-1H-indazol-4-yl)methyl)-5,6-dihydro-4H-thiazolo [5',4':4,5]pyrrolo[2,3-d]pyridazine-2-carbaldehyde oxime (90 mg, 0.18 mmol) in acetic acid (10 mL) was added Zn power (58 mg, 0.88 mmol). The reaction mixture was stirred at r.t. overnight then filtered through Celite. The filtrate was concentrated under reduced pressure and the residue was purified by prep-HPLC to give the desired product (70 mg). LCMS: m/z 496 (M+H)⁺.

Step C. 6-((1H-indazol-4-yl)methyl)-2-(aminomethyl)-4-methyl-4H-thiazolo [5',4':4,5] pyrrolo[2,3-d]pyridazin-5(6H)-one was synthesized using the procedure in Example 3D. LCMS: m/z 366 (M+H)⁺. ¹H NMR (400 MHz, DMSO-d$_6$) δ 13.13 (s, 1H), 8.59 (s, 1H), 8.15 (s, 1H), 7.45 (d, 1H), 7.33-7.20 (m, 1H), 6.97 (d, 1H), 5.66 (s, 2H), 4.24 (d, 3H), 4.17 (s, 2H).

Example 3G. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)methyl)acetamide δ 13.12 (s, 1H), 8.67 (s, 1H), 8.29 (s, 1H), 8.16 (s, 1H), 7.46 (d, 1H), 7.31-7.21 (m, 1H), 6.97 (d, 1H), 5.67 (s, 2H), 4.31 (s, 3H), 1.93 (s, 3H).

Example 3H. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)methyl)methanesulfonamide

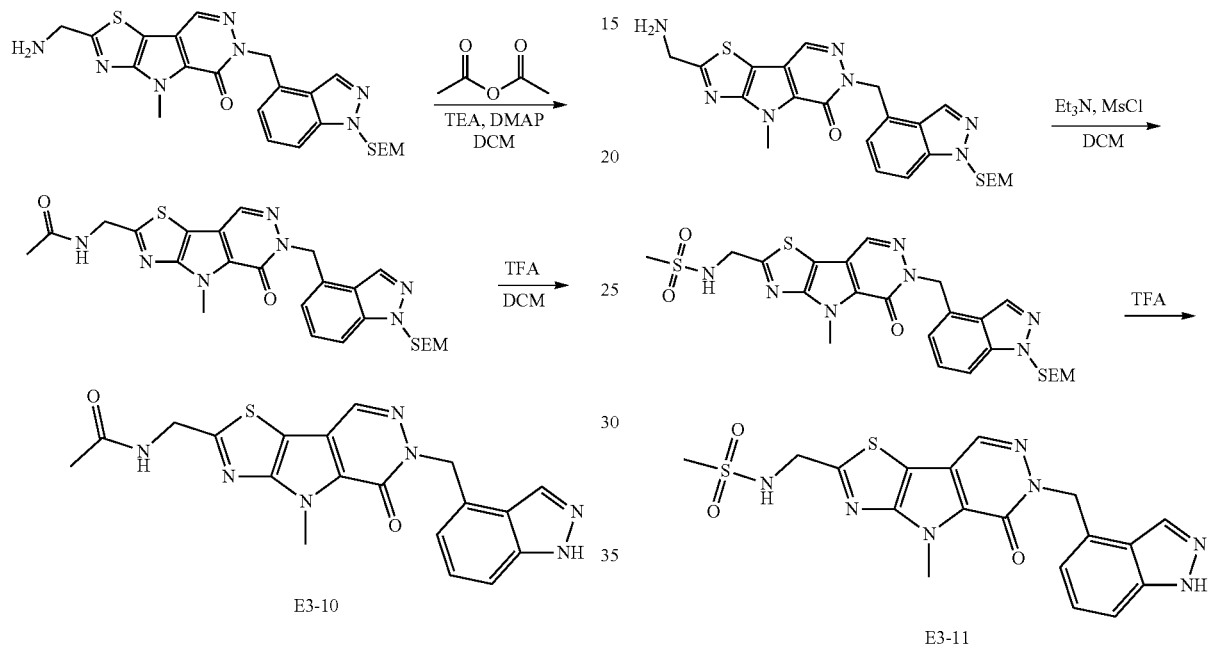

E3-10

E3-11

Step A. N-((4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)methyl)acetamide. To a mixture of 2-(aminomethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (35 mg, 0.07 mmol) in DCM (10 mL) at 0° C. was added acetic anhydride (22 mg, 0.21 mmol), followed by addition of triethylamine (22 mg, 0.21 mmol) and DMAP (0.8 mg, 0.007 mmol). The reaction mixture was stirred at r.t. for 2 hr. then quenched with water and extracted with DCM. The combined organic layers were washed with brine, dried over anhydrous Na$_2$SO$_4$, and concentrated under reduced pressure. The residue was purified by prep-TLC to give the desired product (25 mg) as yellow oil. LCMS: m/z 538 (M+H)$^+$.

Step B. N-((4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)methyl)acetamide was synthesized using the procedure in Example 3D. LCMS: m/z 408 (M+H)$^+$. $^1$H NMR (400 MHz, DMSO-d$_6$)

Step A. N-((4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)methyl)methanesulfonamide. To a mixture of 2-(aminomethyl)-4-methyl-6-((1-((2-(trimethylsilyl)ethoxy)methyl)-1H-indazol-4-yl)methyl)-4H-thiazolo[5',4':4,5]pyrrolo [2,3-d]pyridazin-5(6H)-one (50 mg, 0.1 mmol) in DCM (5 mL) at 0° C. was added Et$_3$N (30.62 mg, 0.3 mmol), followed by addition of MsCl (9.24 mg, 0.081 mmol). The mixture was stirred at 20° C. for 2 hr. then concentrated under reduced pressure. The residue was purified by prep-TLC to give the desired product (20 mg).

Step B. N-((6-((1H-indazol-4-yl)methyl)-4-methyl-5-oxo-5,6-dihydro-4H-thiazolo [5',4':4,5]pyrrolo[2,3-d]pyridazin-2-yl)methyl)methanesulfonamid was synthesized using the procedure in Example 3D. LCMS: m/z 444 (M+H)$^+$. $^1$H NMR (400 MHz, DMSO-d$_6$) δ 13.11 (s, 1H), 8.62 (s, 1H), 8.22 (s, 1H), 8.17 (d, 1H), 7.45 (d, 1H), 7.34-7.20 (m, 1H), 6.97 (d, 1H), 5.66 (s, 2H), 4.64 (d, 2H), 4.27 (s, 3H), 3.04 (s, 3H).

Example 3I. Synthesis of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5(6H)-one

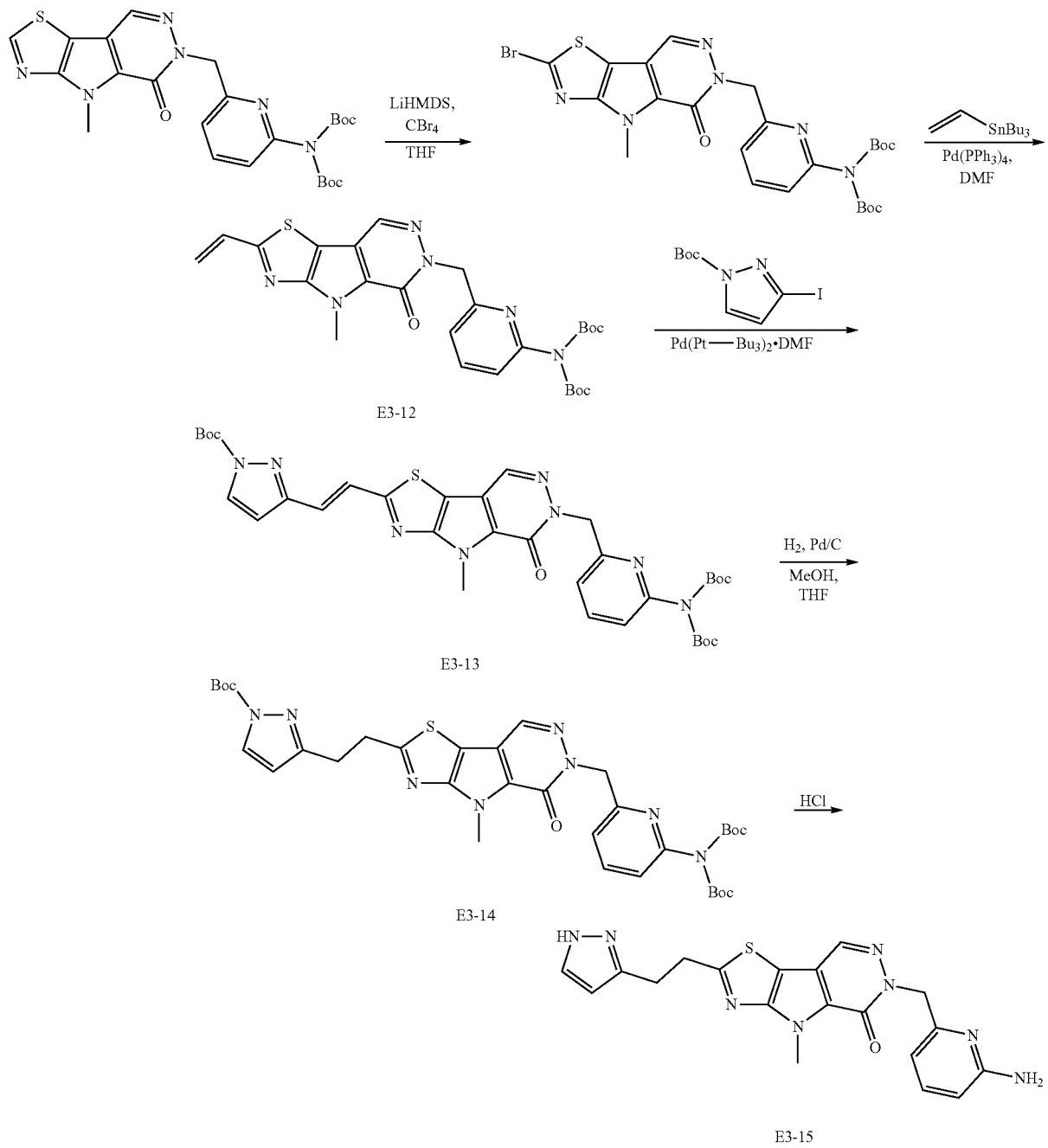

Step A. Synthesis of tert-butyl N-[(tert-butoxy)carbonyl]-N-[6-({4-bromo-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate At −40° C. under N₂ atmosphere, to a mixture of tert-butyl N-[(tert-butoxy)carbonyl]-N-[6-({7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate (1.4 g, 2.73 mmol) and CBr₄ (4.52 g, 13.65 mmol) in THF (20 mL) was added LiHMDS (5.46 mL, 5.46 mmol) by dropwise. The reaction mixture was stirred at −40° C. for 30 min, then quenched by water (4 mL) and extracted with EtOAc. The combined organic layers were washed with brine, dried over anhy. Na₂SO₄ and concentrated under reduced pressure. The residue was purified by flash chromatography (silica gel, PE/EA=10:1-3:1) to afford 500 mg of tert-butyl N-[(tert-butoxy)carbonyl]-N-[6-({4-bromo-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate. LC-MS: m/z 591 (M+H)⁺.

Step B. Synthesis of tert-butyl N-[(tert-butoxy)carbonyl]-N-[6-({4-vinyl-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate To a solution of tert-butyl N-[(tert-butoxy)carbonyl]-N-[6-({4-bromo-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate (500 mg, 0.85 mmol) in DMF (10 mL) was added tributyl (ethenyl)stannane (536 mg, 1.69 mmol) and DIPEA (327 mg, 2.53 mmol), followed by Pd(PPh$_3$)$_4$ (105 mg, 0.08 mmol). The reaction mixture was stirred under N$_2$ atmosphere at 80° C. for 3 hr, then quenched by H$_2$O and extracted with EtOAc. The combined organic layers were washed with brine, dried over anhy. Na$_2$SO$_4$ and concentrated under reduced pressure. The residue was purified by flash chromatography (silica gel, PE/EA=10:1-5:1) to afford 300 mg of tert-butyl N-[(tert-butoxy)carbonyl]-N-[6-({4-vinyl-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate. LC-MS: m/z 539 (M+H)$^+$.

Step C. Synthesis of tert-butyl (E)-3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate To a solution of tert-butyl N-[(tert-butoxy)carbonyl]-N-[6-({4-vinyl-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate (300 mg, 0.56 mmol) in DMF (4 mL) was added tert-butyl 3-iodo-1H-pyrazole-1-carboxylate (180 mg, 0.61 mmol). The reaction mixture was stirred at 100° C. overnight. After cooled down to r.t., the reaction mixture was quenched by H$_2$O and extracted with EtOAc. The combined organic layers were washed with brine, dried over anhy. Na$_2$SO$_4$ and concentrated under reduced pressure. The residue was purified by pre-TLC (PE/EA=1:1) to afford 200 mg of tert-butyl (E)-3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate. LC-MS: m/z 705 (M+H)$^+$.

Step D. Synthesis of tert-butyl 3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate To a solution of tert-butyl (E)-3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate (200 mg, 0.28 mmol) in THF/MeOH (4 mL, 10:1) was added Pd/C (6 mg, 10% wt.). The reaction mixture was stirred under hydrogen at r.t. for 12 hr. The mixture was filtered through a pad of celite, and the filtrate was concentrated. The residue was purified by pre-TLC (PE/EA=1:1) to afford 100 mg of tert-butyl 3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate. LC-MS: m/z 707 (M+H)$^+$.

Step E. Synthesis of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5(6H)-one. At 0° C. under N$_2$ atmosphere, to a mixture of tert-butyl 3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate (100 mg, 0.14 mmol) in EtOH (2 mL) was added HCl (2 mL, 4 M in dioxane). After stirred at 80° C. for 1 hr, the mixture was poured in to satd. NaHCO$_3$, extracted with EtOAc. The combined organic layers were washed with brine, dried over anhy. Na$_2$SO$_4$ and concentrated under reduced pressure. The residue was purified by pre-TLC (DCM/MeOH=10:1) to afford 10 mg of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5(6H)-one. LC-MS: m/z 407 (M+H)$^+$. $^1$H NMR (400 MHz, DMSO-d6) δ 12.52 (s, 1H), 8.55 (s, 1H), 7.60-7.10 (m, 2H), 6.30 (d, 1H), 6.18-6.02 (m, 2H), 5.90 (s, 2H), 5.19 (s, 2H), 4.26 (s, 3H), 3.61-3.41 (m, 2H), 3.19-3.12 (m, 2H).

Example 4. Synthesis of Compounds E4-vii and E4-viii

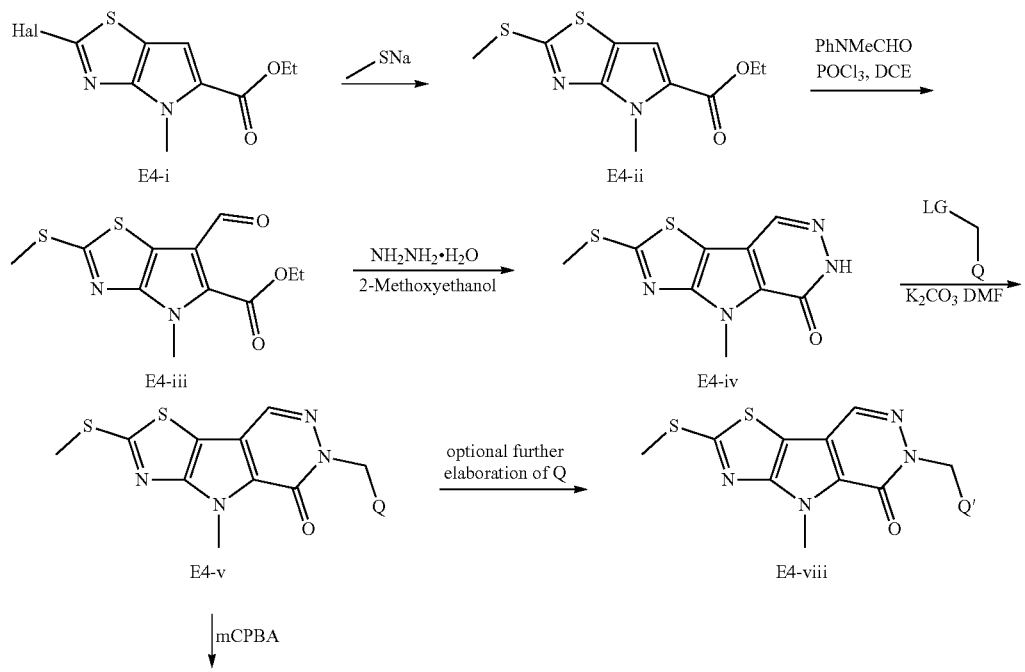

Scheme E4

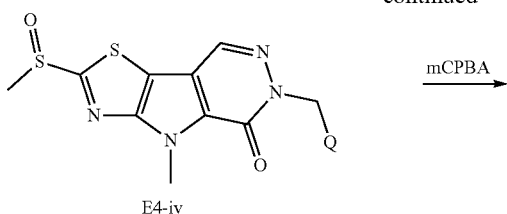
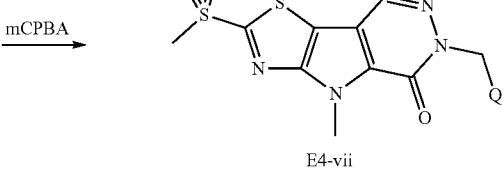

E4-iv → mCPBA → E4-vii wherein Hal is halogen (e.g. Br or I); LG is a leaving group (e.g. halogen such as Br or I; OMs; or OTs); Q is as defined in the first embodiment; and Q' is optionally substituted aryl, optionally substituted heteroaryl, optionally substituted carbocycle or optionally substituted heterocyclyl. Aromatic substitution reaction of compound E4-i with sodium methanethiolate provides compound E4-ii, which can be converted to compound E4-v using the synthesis of compound E1-iii to E1-vi. Oxidation of compound E4-v with mCPBA gives compound E4-vi and E4-vii respectively. Compound E4-viii can be converted from E4-v by further functionalizing Q to Q'.

Example 4A. Synthesis of 6-(3-methoxybenzyl)-4-methyl-2-(methylthio)-4,6-dihydro-5H-thiazolo[5',4':4,5]pyrrolo[2,3-d]pyridazin-5-one

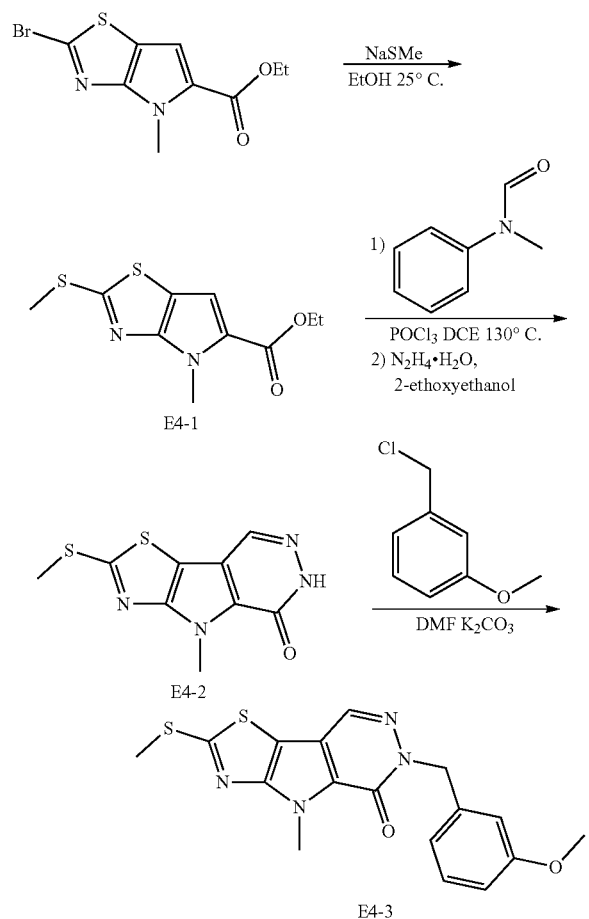

Step A: Ethyl 4-methyl-2-(methylthio)-4H-pyrrolo[2,3-d]thiazole-5-carboxylate. To a mixture of ethyl 2-bromo-4-methyl-4H-pyrrolo[2,3-d]thiazole-5-carboxylate (500.0 mg, 1.73 mmol) in EtOH (10.0 mL) was added NaSMe (240.0 mg, 3.5 mmol). The reaction mixture was stirred at 25° C. for 3 hr then quenched with ice water and extracted with DCM. The combined organic layers were washed with brine, dried over anhydrous $Na_2SO_4$ and concentrated under reduced pressure to afford desired product (460 mg) which was directly used in the next step without any purification. LC-MS: m/z 257 (M+H)$^+$.

Step B: Ethyl 6-formyl-4-methyl-2-(methylthio)-4H-pyrrolo[2,3-d]thiazole-5-carboxylate. To a solution of ethyl 4-methyl-2-(methylthio)-4H-pyrrolo [2,3-d]thiazole-5-carboxylate (460.0 mg, 1.8 mmol) and N-methyl-N-phenylformamide (490 mg, 3.6 mmol) in DCE (10 mL) was added $POCl_3$ (550.0 mg, 3.6 mmol). The resulting mixture was stirred at 130° C. for 3 hr. then quenched with ice water and extracted with DCM. The combined organic layers were washed with brine, dried over anhydrous $Na_2SO_4$ and concentrated under reduced pressure. The residue was purified by column chromatography on silica gel (eluent: PE/EtOAc=8/1) to give the desired product (320.0 mg). LC-MS: m/z 285 (M+H)$^+$.

Step C: 4-Methyl-2-(methylthio)-4,6-dihydro-5H-thiazolo[5',4':4,5]pyrrolo[2,3-d]pyridazin-5-one. To a solution of ethyl 6-formyl-4-methyl-2-(methylthio)-4H-pyrrolo[2,3-d]thiazole-5-carboxylate (300.0 mg, 1.06 mmol) in EtOH (5.0 mL) was added $N_2H_4 \cdot H_2O$ (2 mL, 98% wt). The reaction mixture was stirred at r.t. for 1 hr. then heated to 60° C. for overnight then cooled down. The solid was collected by filtration and dried under high vacuum to afford the desired product (180.0 mg). LC-MS: m/z 253 (M+H)$^+$. $^1$H NMR (400 MHz, DMSO-$d_6$) δ 12.61 (s, 1H), 8.48 (s, 1H), 4.22 (s, 3H), 2.81 (s, 3H).

Step D: 6-(3-Methoxybenzyl)-4-methyl-2-(methylthio)-4,6-dihydro-5H-thiazolo [5',4':4,5]pyrrolo[2,3-d]pyridazin-5-one. To a solution of 4-methyl-2-(methylthio)-4,6-dihydro-5H-thiazolo[5',4':4,5]pyrrolo[2,3-d]pyridazin-5-one (180.0 mg, 0.7 mmol) in DMF (5.0 mL) was added potassium carbonate (200 mg, 1.4 mmol). The mixture was stirred at 60° C. for 1 hr., followed by addition of 1-(chloromethyl)-3-methoxybenzene (170 mg, 1.07 mmol). The resulting mixture was stirred at 60° C. for 3 hr. then quenched with ice water (100.0 mL) and extracted with DCM. (10.0 mL×3). The combined organic layers were washed with brine, dried over anhydrous $Na_2SO_4$ and concentrated under reduced pressure. The residue was purified by column chromatography on silica gel (eluent: DCM/MeOH=10/1) to give the desired product (200.0 mg). LC-MS: m/z 373 (M+H)$^+$. $^1$H NMR (400 MHz, DMSO-$d_6$) δ 8.57 (s, 1H), 7.24 (t, 1H), 6.88-6.82 (7, 3H), 5.32 (s, 2H), 4.24 (s, 3H), 3.72 (s, 3H), 2.82 (s, 3H).

The procedure set forth above was used to produce following compounds using appropriate starting materials. Standard protection and deprotection can be used when necessary.

| Cpd No. | Structure | Characterization |
|---|---|---|
| E4-4 | 6-(Imidazo[1,2-a]pyrimidin-2-ylmethyl)-4-methyl-2-(methylthio)-4,6-dihydro-5H-thiazolo[5',4':4,5]pyrrolo[2,3-d]pyridazin-5-one | LC-MS: m/z 384 (M + H)⁺. ¹H NMR (400 MHz, DMSO-d₆) δ 8.87 (dd, 1H), 8.58 (s, 1H), 8.49 (dd, 1H), 7.70 (s, 1H), 7.02 (dd, 1H), 5.49 (s, 2H), 4.25 (s, 3H), 2.82 (s, 3H). |
| E4-5 | 3-((4-Methyl-2-(methylthio)-5-oxo-4H-thiazolo[5',4':4,5]pyrrolo[2,3-d]pyridazin-6(5H)-yl)methyl)benzenesulfonamide | LCMS: m/z 422(M + H)⁺. ¹H NMR (400 MHz, DMSO-d₆) δ 8.60 (s, 1H), 7.75-7.72 (m, 2H), 7.55-7.53 (m, 2H), 7.36 (s, 2H), 5.42 (s, 2H), 4.23 (s, 3H), 2.81 (s, 3H). |
| E4-6 | 4-((4-Methyl-2-(methylthio)-5-oxo-4,5-dihydro-6H-thiazolo[5',4':4,5]pyrrolo[2,3-d]pyridazin-6-yl)methyl)benzenesulfonamide | LCMS: m/z 422 (M + H)⁺. ¹H NMR (400 MHz, DMSO-d₆) δ 8.59 (s, 1H), 7.77 (d, 2H), 7.46 (d, 2H), 7.31 (s, 2H), 5.41 (s, 2H), 4.23 (s, 3H), 2.82 (s, 3H). |
| E4-7 | 6-((2-aminobenzo[d]thiazol-4-yl)methyl)-4-methyl-2-(methylthio)-4,6-dihydro-5H-thiazolo[5',4':4,5]pyrrolo[2,3-d]pyridazin-5-one | LCMS: m/z 415 (M + H)⁺. ¹H NMR (400 MHz, DMSO-d₆) δ 8.59 (s, 1H), 7.65 (s, 2H), 7.55 (d, 1H), 6.89 (t, 1H), 6.68 (d, 1H), 5.61 (s, 2H), 4.24 (s, 3H), 2.82 (s, 3H). |
| E4-8 | 6-(3-methoxybenzyl)-4-methyl-2-(phenylthio)-4,6-dihydro-5H-thiazolo[5',4':4,5]pyrrolo[2,3-d]pyridazin-5-one | LC-MS: m/z 435(M + H)⁺. ¹H NMR (400 MHz, DMSO-d₆) δ 8.50 (s, 1H), 7.80 (dd, 2H), 7.61 (dd, 3H), 7.21 (d, 1H), 6.83 (d, 3H), 5.29 (s, 2H), 4.23 (s, 3H), 3.71 (s, 3H). |

| Cpd No. | Structure | Characterization |
|---|---|---|
| E4-9 | 6-((2-(2,5-dimethyl-1H-pyrrol-1-yl)thiazol-4-yl)methyl)-4-methyl-2-(methylthio)-4,6-dihydro-5H-thiazolo[5',4':4,5]pyrrolo[2,3-d]pyridazin-5-one | LC-MS: m/z 443(M + H)+. 1H NMR (400 MHz, CDCl3) δ 8.13 (s, 1H), 7.05 (s, 1H), 5.77 (s, 2H), 5.32 (d, 2H), 4.31 (s, 3H), 2.74 (s, 3H), 2.10 (s, 6H). |

Example 4B. Synthesis of 4-methyl-2-(methylthio)-6-((2-oxo-2,3-dihydropyrimidin-4-yl) methyl)-4H-thiazolo[5',4':4,5]pyrrolo[2,3-d]pyridazin-5(6H)-one

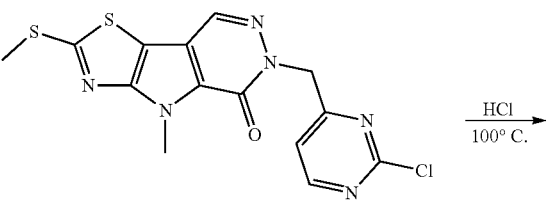

A mixture of 6-((2-chloropyrimidin-4-yl)methyl)-4-methyl-2-(methylthio)-4H-thiazolo[5',4':4,5]pyrrolo[2,3-d]pyridazin-5(6H)-one (50 mg, 0.132 mmol) in HCl (10 mL) was stirred at 100° C. for 1 hr. then concentrated under reduced pressure. The residue was purified by prep-HPLC to give the desired product (5.0 mg, 10.51% yield). LCMS: m/z 361 (M+H)+. 1H NMR (400 MHz, DMSO-d6) δ 11.82 (s, 1H), 8.60 (s, 1H), 7.82 (s, 1H), 6.14 (s, 1H), 5.22 (s, 2H), 4.24 (s, 3H), 2.82 (s, 4H).

The procedure set forth above was used to produce the following compounds using the appropriate starting materials.

| Cpd No. | Structure | Characterization |
|---|---|---|
| E4-11 | 4-Methyl-2-(methylthio)-6-((2-oxo-1,2-dihydropyrimidin-5-yl)methyl)-4,6-dihydro-5H-thiazolo[5',4':4,5]pyrrolo[2,3-d]pyridazin-5-one | LC-MS: 361(M + H)+. 1H NMR (400 MHz, DMSO-d6) δ 11.95 (s, 1H), 8.57 (s, 1H), 8.31 (s, 2H), 5.12 (s, 2H), 4.23 (s, 3H), 2.81 (s, 3H). |

Example 4C. Synthesis of 6-(3-methoxybenzyl)-4-methyl-2-(methylsulfinyl)-4,6-dihydro-5H-thiazolo[5',4':4,5]pyrrolo[2,3-d]pyridazin-5-one

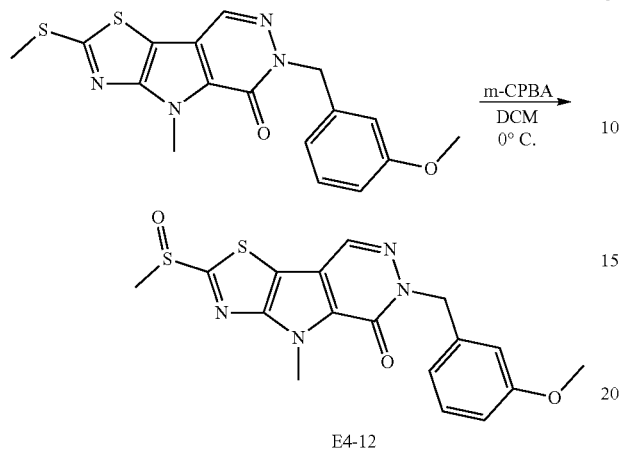

E4-12

To a solution of 6-(3-methoxybenzyl)-4-methyl-2-(methylthio)-4,6-dihydro-5H-thiazolo[5',4':4,5]pyrrolo[2,3-d]pyridazin-5-one (30.0 mg, 0.08 mmol) in DCM (3.0 mL) at 0° C. was added m-CPBA (14.0 mg, 0.08 mmol). The resulting mixture was stirred at 0° C. for 1 hr. then quenched with ice water and extracted with DCM. The combined organic layers were washed with brine, dried over anhydrous $Na_2SO_4$ and concentrated under reduced pressure. The residue was purified by column chromatography on silica gel (eluent: DCM/MeOH=10/1) to give the desired product (15.0 mg). LC-MS: m/z 389 (M+H)$^+$. $^1$H NMR (400 MHz, DMSO-$d_6$) δ 8.74 (s, 1H), 7.25 (t, 1H), 6.86 (dd, 3H), 5.35 (s, 2H), 4.30 (s, 3H), 3.73 (s, 3H), 3.11 (s, 3H).

The procedure set forth above was used to produce following compounds using appropriate starting materials. Standard protection and deprotection can be used when necessary.

| Cpd No. | Structure | Characterization |
|---|---|---|
| E4-13 | 6-(3-methoxybenzyl)-4-methyl-2-(phenylsulfinyl)-4,6-dihydro-5H-thiazolo[5',4':4,5]pyrrolo[2,3-d]pyridazin-5-one | LC-MS: m/z 451(M + H)$^+$. $^1$H NMR (400 MHz, DMSO-$d_6$) δ 8.67 (s, 1H), 7.90 (dd, 2H), 7.70-7.62 (m, 3H), 7.22 (t, 1H), 6.83 (d, 3H), 5.31 (s, 2H), 4.25 (s, 3H), 3.70 (s, 3H). |
| E4-14 | 6-(3-Acetylbenzyl)-4-methyl-2-(methylsulfinyl)-4H-thiazolo[5',4':4,5]pyrrolo[2,3-d]pyridazin-5(6H)-one | LCMS: m/z 401 (M + H)$^+$. $^1$H NMR (400 MHz, DMSO-$d_6$) δ 8.75 (s, 1H), 7.92-7.87 (m, 2H), 7.58-7.56 (m, 1H), 7.49 (t, 1H), 5.45 (s, 2H), 4.29 (s, 3H), 3.11 (s, 3H), 2.56 (s, 3H). |
| E4-15 | 6-(3-(1-hydroxyethyl)benzyl)-4-methyl-2-(methylsulfinyl)-4H-thiazolo[5',4':4,5]pyrrolo[2,3-d]pyridazin-5(6H)-one | LCMS: m/z 425 (M + Na)$^+$. $^1$H NMR (400 MHz, DMSO-$d_6$) δ 8.73 (s, 1H), 7.32 (s, 1H), 7.28-7.21 (m, 2H), 7.15-7.13 (m, 1H), 5.34 (s, 2H), 5.14 (d, 1H), 4.70-4.64 (m, 1H), 4.30 (s, 3H), 3.11 (s, 3H), 1.28 (d, 3H). |

| Cpd No. | Structure | Characterization |
|---|---|---|
| E4-16 | 6-((1H-indazol-4-yl)methyl)-4-methyl-2-(methylsulfinyl)-4,6-dihydro-5H-thiazolo[5',4':4,5]pyrrolo[2,3-d]pyridazin-5-one | LCMS: m/z 399 (M + H)+. $^1$H NMR (400 MHz, DMSO-$d_6$) δ 13.14 (s, 1H), 8.74 (s, 1H), 8.15 (s, 1H), 7.47 (d, 1H), 7.29 (t, 1H), 6.98 (d, 1H), 5.68 (s, 2H), 4.31 (s, 3H), 3.11 (s, 3H). |
| E4-17 | 4-((4-Methyl-2-(methylsulfinyl)-5-oxo-4,5-dihydro-6H-thiazolo[5',4':4,5]Pyrrolo[2,3-d]pyridazin-6-yl)methyl)benzonitrile | LC-MS: 384(M + H)+. $^1$H NMR (400 MHz, DMSO-$d_6$) δ 8.81 (s, 1H), 7.86 (d, 2H), 7.53 (d, 2H), 5.52 (d, 2H), 4.34 (s, 3H), 3.17 (s, 3H). |
| E4-18 | 4-Methyl-2-(methylsulfinyl)-6-(quinolin-2-ylmethyl)-4,6-dihydro-5H-thiazolo[5',4':4,5]pyrrolo[2,3-d]pyridazin-5-one | LCMS: 410 (M + H)+. $^1$H NMR (400 MHz, DMSO-$d_6$) δ 8.78 (s, 1H), 8.32 (d, 1H), 7.94 (dd, 2H), 7.82-7.68 (m, 1H), 7.59 (dd, 1H), 7.33 (d, 1H), 5.75-5.56 (s, 2H), 4.30 (s, 3H), 3.12 (s, 3H). |
| E4-19 | 6-((2,3-Dihydrobenzo[b][1,4]dioxin-6-yl)methyl)-4-methyl-2-(methylsulfinyl)-4,6-dihydro-5H-thiazolo[5',4':4,5]Pyrrolo[2,3-d]pyridazin-5-one | LCMS: 417 (M + H)+. $^1$H NMR (400 MHz, DMSO-$d_6$) δ 8.71 (s, 1H), 8.45 (s, 1H), 6.83 (s, 1H), 6.80 (d, 1H), 5.24 (d, 2H), 4.30 (s, 3H), 4.20 (s, 4H), 3.11 (s, 3H), |

| Cpd No. | Structure | Characterization |
|---|---|---|
| E4-20 | 6-(2,3-Dihydro-1H-indol-4-ylmethyl)-2-methanesulfinyl-8-methyl-6,8-dihydro-3-thia-1,5,6,8-tetraaza-cyclopenta[a]inden-7-one | LC-MS: m/z 400 (M + H)⁺. ¹H NMR (400 MHz, DMSO-d₆) δ 8.71 (s, 1H), 6.83 (dd, 1H), 6.38 (d, 1H), 5.50 (s, 1H), 5.25 (s, 2H), 4.29 (s, 3H), 3.41 (t, 2H), 3.11 (s, 3H), 2.96 (t, 2H). |
| E4-21 | 2-Methanesulfinyl-8-methyl-6-(1,2,3,4-tetrahydro-isoquinolin-5-ylmethyl)-6,8-dihydro-3-thia-1,5,6,8-tetraaza-cyclopenta[a]inden-7-one | LC-MS: m/z 414 (M + H)⁺. ¹H NMR (400 MHz, DMSO-d₆) δ 8.73 (s, 1H), 7.03 (t, 1H), 6.95 (d, 1H), 6.77 (d, 1H), 5.32 (s, 2H), 4.29 (s, 3H), 3.90 (s, 2H), 3.11 (s, 3H), 3.06 (t, 2H), 2.78 (t, 2H). |

Example 4D. Synthesis of 4-((4-methyl-2-(methylsulfinyl)-5-oxo-4,5-dihydro-6H-thiazolo[5',4':4,5]pyrrolo[2,3-d]pyridazin-6-yl)methyl)benzamide

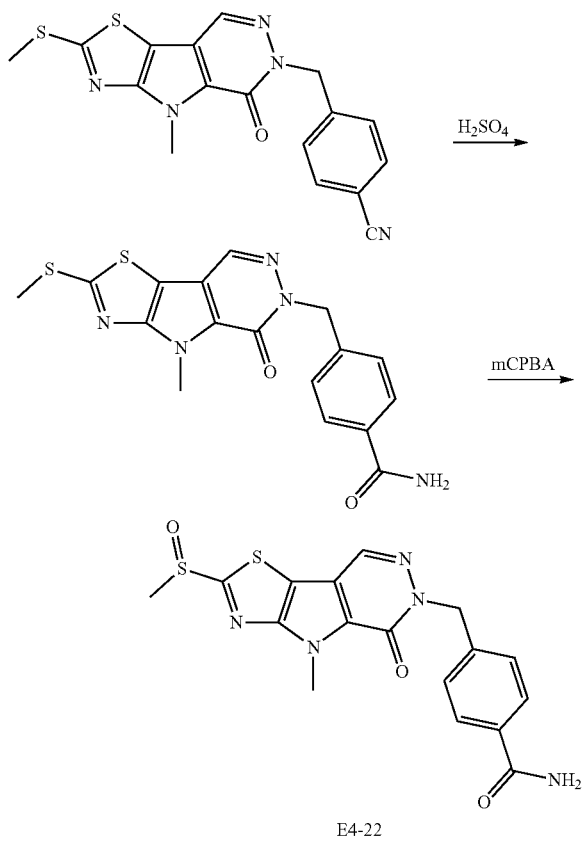

Step A: 4-((4-Methyl-2-(ethylthio)-5-oxo-4,5-dihydro-6H-thiazolo[5,4':4,5]pyrrolo[2,3-d]pyridazin-6-yl)methyl)benzamide. A mixture of 4-((4-methyl-2-(methylthio)-5-oxo-4,5-dihydro-6H-thiazolo[5',4':4,5]pyrrolo [2,3-d] pyridazin-6-yl)methyl)benzonitrile (50.0 mg, 0.13 mmol) in H₂SO₄ (1.0 mL) was stirred at 0° C. for 1 hr. then neutralized with saturated aqueous NaHCO₃ and extracted with DCM. The combined organic layers were washed with brine, dried over anhydrous Na₂SO₄ and concentrated under reduced pressure. The residue was purified by column chromatography on silica gel (eluent: DCM/MeOH=10/1) to give the desired product (20.0 mg). LC-MS: m/z 386 (M+H)⁺.

Step B: 4-((4-Methyl-2-(methylsulfinyl)-5-oxo-4,5-dihydro-6H-thiazolo[5',4':4,5]pyrrolo[2,3-d]pyridazin-6-yl)methyl)benzamide. To a solution of 4-((4-methyl-2-(methylthio)-5-oxo-4,5-dihydro-6H-thiazolo[5',4':4,5]pyrrolo[2,3-d]pyridazin-6-yl)methyl)benzamide (20.0 mg, 0.052 mmol) in DCM (2.0 mL) at 0° C. was added m-CPBA (10.0 mg, 0.052 mmol). The resulting mixture was stirred at 0° C. for 1 hr then quenched with ice water (10.0 mL) and extracted with DCM. The combined organic layers were washed with brine, dried over anhydrous Na₂SO₄ and concentrated under reduced pressure. The residue was purified by column chromatography on silica gel (eluent: DCM/MeOH=10/1) to give the desired product (5.0 mg). LC-MS: m/z 402 (M+H)⁺. ¹H NMR (400 MHz, DMSO-d₆) δ 8.75 (s, 1H), 7.93 (s, 1H), 7.82 (d, 2H), 7.38-7.33 (m, 3H), 5.42 (s, 2H), 4.29 (s, 3H), 3.11 (s, 3H).

Example 4E. Synthesis of 6-(3-(2-hydroxypropan-2-yl)benzyl)-4-methyl-2-(methylsulfinyl)-4H-thiazolo[5',4':4,5]pyrrolo[2,3-d]pyridazin-5(6H)-one

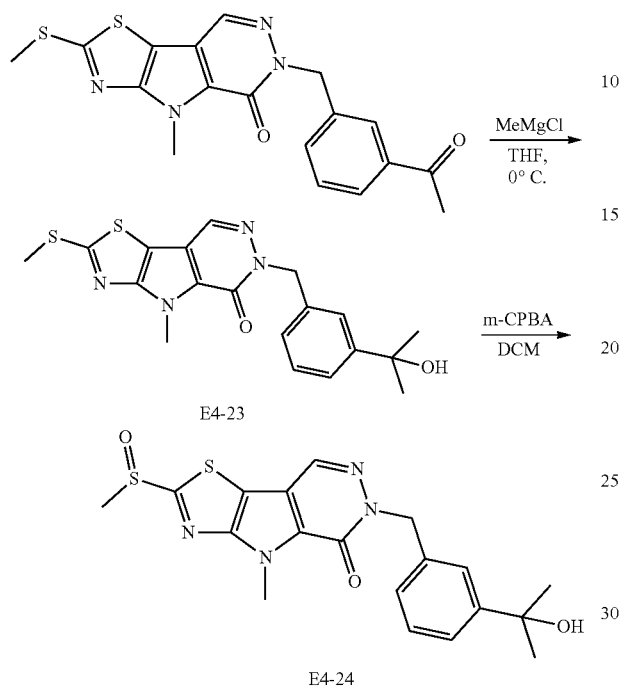

E4-23

E4-24

Step A. 6-(3-(2-Hydroxypropan-2-yl)benzyl)-4-methyl-2-(methylthio)-4H thiazolo[5',4':4,5]pyrrolo[2,3-d]pyridazin-5(6H)-one. To a mixture of 6-(3-acetylbenzyl)-4-methyl-2-(methylthio)-4H-thiazolo[5',4':4,5]pyrrolo[2,3-d]pyridazin-5(6H)-one (120 mg, 0.31 mmol) in dry THF (5 mL) at 0° C. was added dropwise methylmagnesium chloride (0.3 mL, 0.9 mmol). The mixture was stirred at r.t. for 30 min then poured into saturated aq. NH$_4$Cl and extracted with EtOAc. The organic layer was separated and concentrated under reduced pressure. The residue was purified by prep-TLC to afford desired product (70 mg). LCMS: m/z 401 (M+H)$^+$. $^1$H NMR (400 MHz, DMSO-d$_6$) δ 8.56 (s, 1H), 7.49 (s, 1H), 7.33 (d, 1H), 7.23 (t, 1H), 7.09 (d, 1H), 5.33 (s, 2H), 4.98 (s, 1H), 4.24 (s, 3H), 2.81 (s, 3H), 1.39 (s, 6H).

Step B. 6-(3-(2-Hydroxypropan-2-yl)benzyl)-4-methyl-2-(methylsulfinyl)-4H-thiazolo [5',4':4,5]pyrrolo[2,3-d]pyridazin-5(6H)-one. To a mixture of 6-(3-(2-hydroxypropan-2-yl)benzyl)-4-methyl-2-(methylthio)-4H-thiazolo[5',4':4,5]pyrrolo[2,3-d]pyridazin-5(6H)-one (46 mg, 0.115 mmol) in DCM (3 mL) at 0° C. was added m-CPBA (20 mg, 0.1 mmol, 85% w/w). The mixture was stirred at r.t. for 30 min then quenched with saturated aq. Na$_2$S$_2$O$_3$ and extracted with DCM. The organic layer was separated and concentrated under reduced pressure. The residue was purified by prep-HPLC to afford desired product (10 mg). LCMS: m/z 417 (M+H)$^+$. $^1$H NMR (400 MHz, DMSO-d$_6$) δ 8.73 (s, 1H), 7.49 (s, 1H), 7.34 (d, 1H), 7.24 (t, 1H), 7.09 (d, 1H), 5.37 (s, 2H), 4.98 (s, 1H), 4.30 (s, 3H), 3.11 (s, 3H), 1.39 (s, 6H).

Example 4F. Synthesis of 6-((2-aminopyridin-4-yl)methyl)-4-methyl-2-(methylsulfinyl)-4H-thiazolo[5',4':4,5]pyrrolo[2,3-d]pyridazin-5(6H)-one

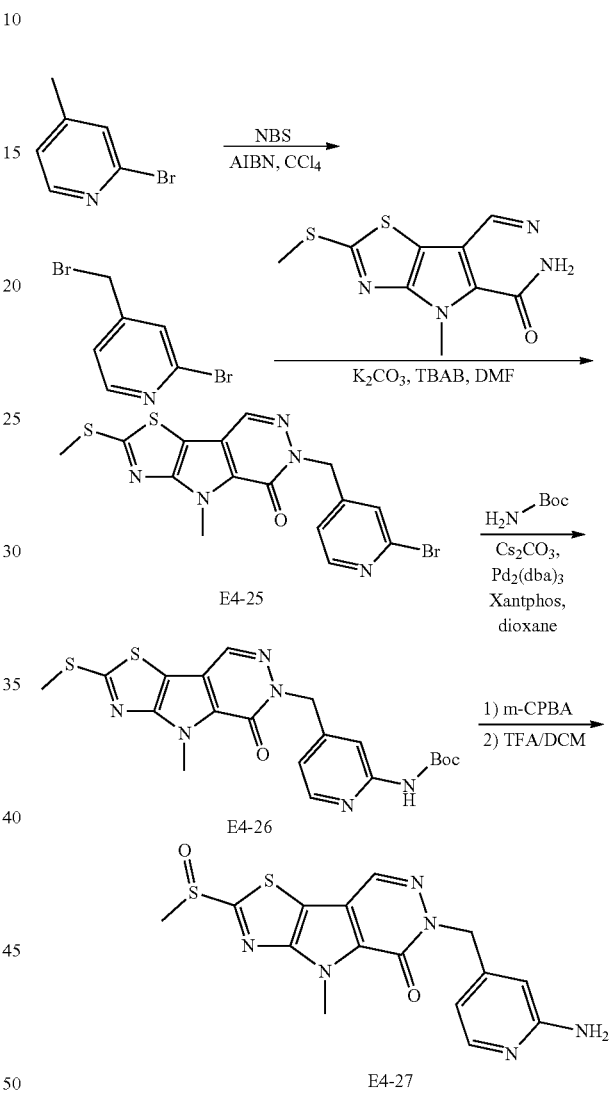

E4-25

E4-26

E4-27

Step A. 2-Bromo-4-(bromomethyl)pyridine. A mixture of 2-bromo-4-methylpyridine (1 g, 5.81 mmol), NBS (1.1 g, 6.39 mmol) and a catalytic amount of AIBN (100 mg) in CCl$_4$ (10 mL) was stirred at 80° C. overnight. The resulting mixture was concentrated under reduced pressure and the residue was purified by column chromatography on silica gel (eluent: PE/EtOAc=200/1) to give the desired product (500 mg).

Step B. 6-((2-Bromopyridin-4-yl)methyl)-4-methyl-2-(methylthio)-4H-thiazolo [5',4':4,5]pyrrolo[2,3-d]pyridazin-5(6H)-one. A mixture of 4-methyl-2-(methylthio)-4H-thiazolo[5',4':4,5]pyrrolo [2,3-d]pyridazin-5(6H)-one (100 mg, 0.40 mmol), and K$_2$CO$_3$ (164 mg, 1.19 mmol) in DMF (8 mL) was stirred at 60° C. for 2 hr., followed by addition of a solution of 2-bromo-4-(bromomethyl)pyridine (199 mg, 0.80 mmol) in DMF (2 mL) and a catalytic amount of TBAB (13 mg). The mixture was stirred at 60° C. overnight then quenched with water (20 mL) and extracted with EtOAc. The combined organic layers were washed with saturated aqueous $NH_4Cl$, dried over anhydrous $Na_2SO_4$ and concentrated under reduced pressure. The residue was purified by column chromatography on silica gel (eluent: PE/EtOAc=10/1) to give the desired product (150 mg). LCMS: m/z 423 (M+H)$^+$.

Step C. Tert-butyl (4-((4-methyl-2-(methylthio)-5-oxo-4H-thiazolo[5',4':4,5]pyrrolo [2,3-d] pyridazin-6(5H)-yl)methyl)pyridin-2-yl)carbamate. A mixture of 6-((2-bromopyridin-4-yl)methyl)-4-methyl-2-(methylthio)-4H-thiazolo[5',4':4,5]pyrrolo[2,3-d]pyridazin-5(6H)-one (100 mg, 0.24 mmol), tert-butyl carbamate (83 mg, 0.71 mmol), $K_3PO_4$ (201 mg, 0.95 mmol), $Pd_2(dba)_3$ (18 mg, 0.02 mmol) and Xantphos (11 mg, 0.02 mmol) in dioxane (10 mL) was stirred at 100° C. under nitrogen overnight. The resulting mixture was quenched with water and extracted with EtOAc. The combined organic layers were washed with brine, dried over anhydrous $Na_2SO_4$ and concentrated under reduced pressure. The residue was purified by column chromatography on silica gel (eluent: PE/EtOAc=3/1) to give the desired product (100 mg). LCMS: m/z 459 (M+H)$^+$.

Step D-E: Tert-butyl (4-((4-methyl-2-(methylsulfinyl)-5-oxo-4H-thiazolo[5',4':4,5]pyrrolo [2,3-d]pyridazin-6(5H)-yl)methyl)pyridin-2-yl)carbamate was synthesized using procedure similar to Example 4C and 6-((2-Aminopyridin-4-yl)methyl)-4-methyl-2-(methylsulfinyl)-4H-thiazolo [5',4':4,5]pyrrolo[2,3-d]pyridazin-5(6H)-one were synthesized using the procedure similar to Example 3G. LCMS: m/z 375 (M+H)$^+$. $^1$H NMR (400 MHz, DMSO-$d_6$) δ 8.67 (s, 1H), 7.73 (d, 1H), 6.30 (d, 1H), 6.12 (s, 1H), 5.89 (s, 2H), 5.24-5.03 (m, 2H), 4.29 (s, 3H), 3.03 (s, 3H).

The procedure set forth above was used to produce following compounds using appropriate starting materials. Standard protection and deprotection can be used when necessary.

| Cpd No. | Structure | Characterization |
|---|---|---|
| E4-28 | 6-((2-aminopyrimidin-4-yl)methyl)-4-methyl-2-(methylsulfinyl)-4H-thiazolo[5',4':4,5]pyrrolo[2,3-d]pyridazin-5(6H)-one | LC-MS: m/z 376 (M + H)$^+$. $^1$H NMR (400 MHz, DMSO-$d_6$) δ 8.76 (s, 1H), 8.12 (d, 1H), 6.60 (s, 2H), 6.22 (d, 1H), 5.20 (t, 2H), 4.28 (s, 3H), 3.12 (s, 3H). |
| E4-29 | 6-((2-Aminopyrimidin-5-yl)methyl)-4-methyl-2-(methylsulfinyl)-4,6-dihydro-5H-thiazolo[5',4':4,5]pyrrolo[2,3-d]pyridazin-5-one | LC-MS: 376(M + H)$^+$. $^1$H NMR (400 MHz, DMSO-$d_6$) δ 8.70 (s, 1H), 8.29 (s, 2H), 6.66 (s, 2H), 5.16 (s, 2H), 4.28 (s, 3H), 3.10 (s, 3H). |

Example 4G. Synthesis of 6-((2-aminothiazol-5-yl)methyl)-4-methyl-2-(methyl sulfinyl)-4H-thiazolo[5',4':4,5]pyrrolo[2,3-d]pyridazin-5(6H)-one

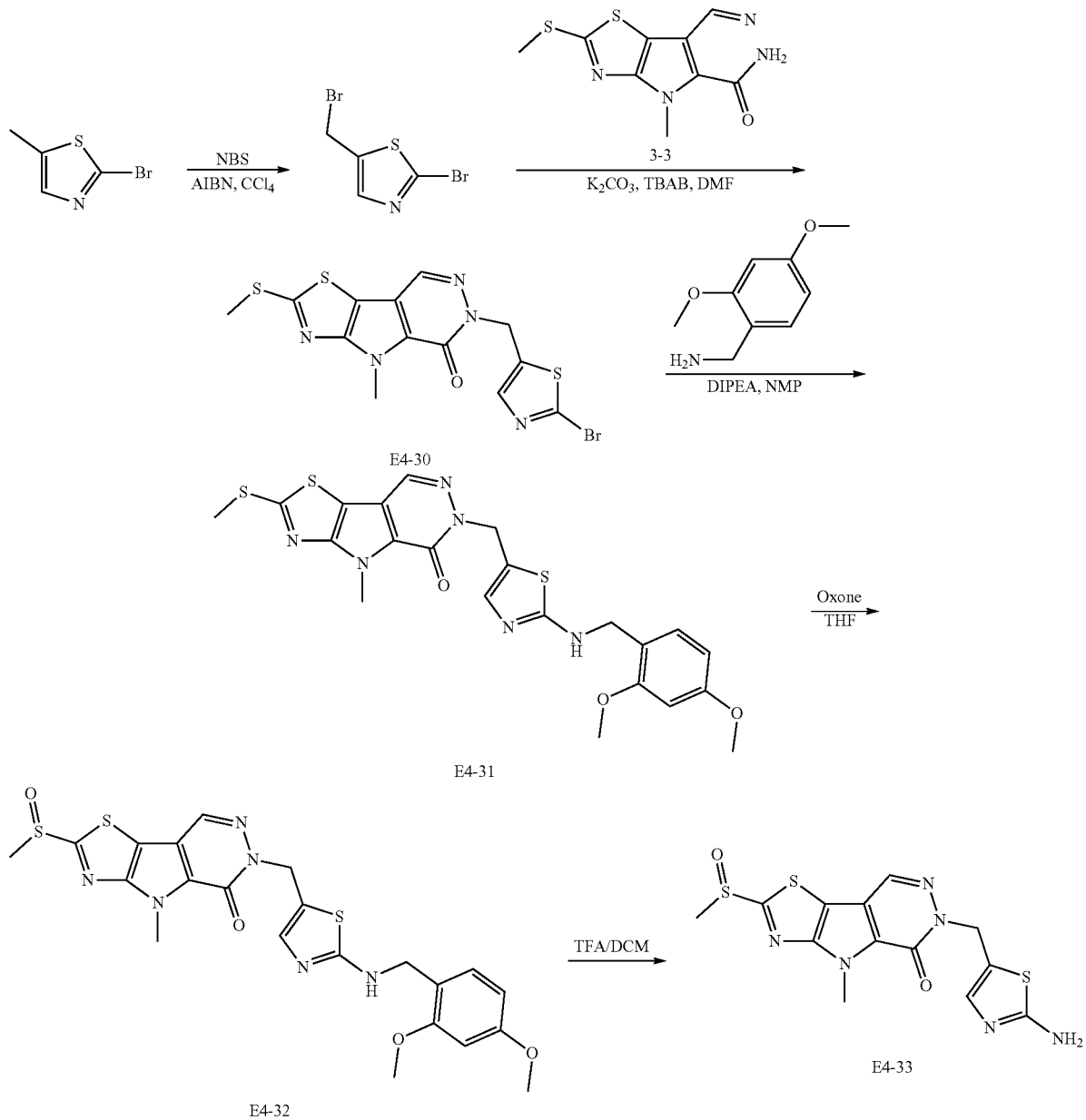

Step A-B. 2-Bromo-5-(bromomethyl)thiazole and 6-((2-Bromothiazol-5-yl)methyl)-4-methyl-2-(methylthio)-4H-thiazolo [5',4':4,5]pyrrolo[2,3-d]pyridazin-5(6H)-one were synthesized similar to Example 4F.

Step C. 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one. A mixture of 6-((2-bromothiazol-5-yl)methyl)-4-methyl-2-(methylthio)-4H-thiazolo[5',4':4,5]pyrrolo [2,3-d]pyridazin-5(6H)-one (130 mg, 0.30 mmol) and DIPEA (0.1 mL) in NMP (0.1 mL) and (2,4-dimethoxyphenyl)methanamine (0.1 mL) was stirred at 150° C. for 4 hr. Then the traction mixture was quenched with water (10 mL), extracted with EtOAc. The combined organic layers were washed with brine, dried over anhydrous Na$_2$SO$_4$ and concentrated under reduced pressure. The residue was purified by column chromatography on silica gel (eluted with PE/EtOAc=5/1) to give the desired product (60 mg, 38.4% yield). LC-MS: m/z 515 (M+H)$^+$.

Step D. 6-((2-((2,4-dimethoxybenzyl)amino)thiazol-5-yl)methyl)-4-methyl-2-(methylsulfinyl)-4H-thiazolo[5',4':4,5]pyrrolo[2,3-d]pyridazin-5(6H)-one. To a mixture of 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one (50 mg, 0.10 mmol) in THF (3 mL) at 0° C. was added oxone (61 mg, 0.10 mmol). The mixture was stirred at 0° C. for 1 hr, then quenched with saturated aqueous Na$_2$S2O$_3$ solution (5 mL) and extracted with DCM. The combined organic layers were washed with brine, dried over anhydrous Na₂SO₄ and concentrated under reduced pressure to give the desired product (30 mg, 50.1% yield) which was used directly in the next step without further purification. LC-MS: m/z 531 (M+H)⁺.

Step E. 6-((2-Aminothiazol-5-yl)methyl)-4-methyl-2-(methylsulfinyl)-4H-thiazolo [5',4':4,5]pyrrolo[2,3-d]pyridazin-5(6H)-one was synthesized similar to Example 3G. LC-MS: m/z 381 (M+H)⁺. ¹H NMR (400 MHz, DMSO-d₆) δ 8.70 (s, 1H), 6.97 (s, 1H), 6.87 (s, 2H), 5.28 (s, 2H), 4.29 (s, 3H), 3.11 (s, 3H).

The procedure set forth above was used to produce following compounds using appropriate starting materials. Standard protection and deprotection can be used when necessary.

| Cpd No. | Structure | Characterization |
|---|---|---|
| E4-34 | 6-((1H-indazol-4-yl)methyl)-4-methyl-2-(methylsulfinyl)-4,6-dihydro-5H-thiazolo[5',4':4,5]pyrrolo[2,3-d]pyridazin-5-one | LCMS: m/z 381 (M + H)⁺. ¹H NMR (400 MHz, DMSO-d₆) δ 8.69 (s, 1H), 6.92 (s, 2H), 6.21 (s, 1H), 5.26-5.05 (m, 2H), 4.30 (s, 3H), 3.11 (s, 3H). |

Example 4H. Synthesis of 6-(3-methoxybenzyl)-4-methyl-2-(methylsulfonyl)-4,6-dihydro-5H-thiazolo [5',4':4,5]pyrrolo[2,3-d]pyridazin-5-one

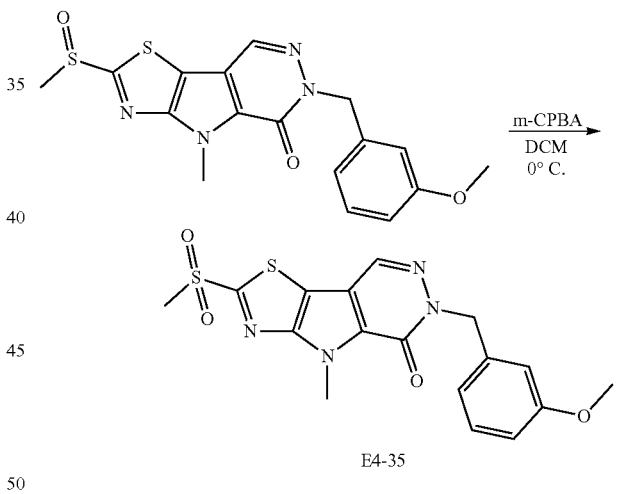

To a solution of 6-(3-methoxybenzyl)-4-methyl-2-(methylsulfinyl)-4,6-dihydro-5H-thiazolo[5',4':4,5]pyrrolo[2,3-d]pyridazin-5-one (30.0 mg, 0.08 mmol) in DCM (3.0 mL) at 0° C. was m-CPBA (35.0 mg, 0.2 mmol). The resulting mixture was stirred at 0° C. for 1 hr. then quenched with ice water and extracted with DCM. The combined organic layers were washed with brine, dried over anhydrous Na₂SO₄ and concentrated under reduced pressure. The residue was purified by column chromatography on silica gel (eluent: DCM/MeOH=10/1) to give the desired product (10.0 mg, 32% yield). LC-MS: m/z 405 (M+H)⁺. ¹H NMR (400 MHz, DMSO-d₆) δ 8.78 (s, 1H), 7.24 (t, 1H), 6.92-6.82 (m, 3H), 5.35 (s, 2H), 4.33 (s, 3H), 3.72 (s, 3H), 3.57 (s, 3H).

| Cpd No. | Structure | Characterization |
|---|---|---|
| E4-36 | 6-(3-methoxybenzyl)-4-methyl-2-(phenylsulfonyl)-4,6-dihydro-5H-thiazolo[5',4':4,5]pyrrolo[2,3-d]pyridazin-5-one | LC-MS: m/z 467(M + H)⁺.<br>¹H NMR (400 MHz, DMSO-$d_6$) δ 8.75 (s, 1H), 8.11 (d, 2H), 7.81 (dd, 1H), 7.73 (dd, 2H), 7.23 (s, 1H), 6.86-6.83 (m, 3H), 5.32 (s, 2H), 4.24 (s, 3H), 3.70 (s, 3H). |
| E4-37 | 6-((1H-indazol-4-yl)methyl)-4-methyl-2-(methylsulfonyl)-4,6-dihydro-5H-thiazolo[5',4':4,5]pyrrolo[2,3-d]pyridazin-5-one | LCMS: m/z 415 (M + H)⁺.<br>¹H NMR (400 MHz, DMSO-$d_6$) δ 13.13 (s, 1H), 8.79 (s, 1H), 8.15 (s, 1H), 7.46 (d, 1H), 7.31-7.25 (m. 1H), 6.99 (d, 1H), 5.69 (s, 2H), 4.34 (s, 3H), 3.56 (s, 3H). |
| E4-38 | 6-((1H-indazol-4-yl)methyl)-2-(benzylsulfonyl)-4-methyl-4,6-dihydro-5H-thiazolo[5',4':4,5]pyrrolo[2,3-d]pyridazin-5-one | LCMS: m/z 491 (M + H)⁺.<br>¹H NMR (400 MHz, DMSO-$d_6$) δ 13.16 (s, 1H), 8.74 (s, 1H), 8.18 (s, 1H), 7.47 (d, 1H), 7.35-7.27 (m, 4H), 7.24 (d, 2H), 7.00 (d, 1H), 5.68 (s, 2H), 5.05 (s, 2H), 4.36 (s, 3H). |

Example 5. Synthesis of Compounds of Formula E5-ii and Derivatives with Scheme E5

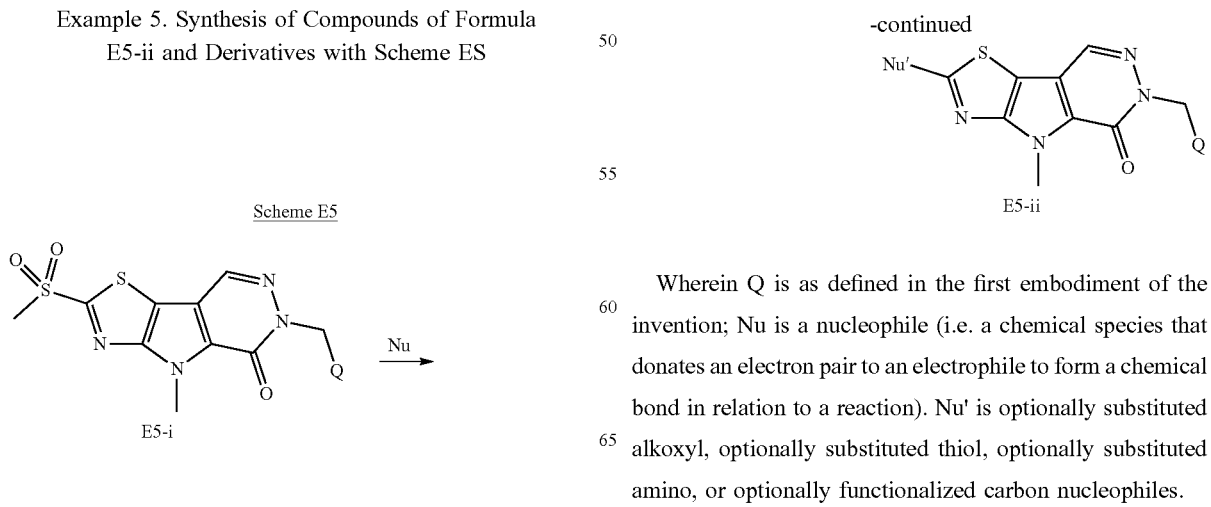

Wherein Q is as defined in the first embodiment of the invention; Nu is a nucleophile (i.e. a chemical species that donates an electron pair to an electrophile to form a chemical bond in relation to a reaction). Nu' is optionally substituted alkoxyl, optionally substituted thiol, optionally substituted amino, or optionally functionalized carbon nucleophiles.

Example 5A. Synthesis of 6-((1H-indazol-4-yl)methyl)-2-(benzylthio)-4-methyl-4,6-dihydro-5H-thiazolo[5',4':4,5]pyrrolo[2,3-d]pyridazin-5-one

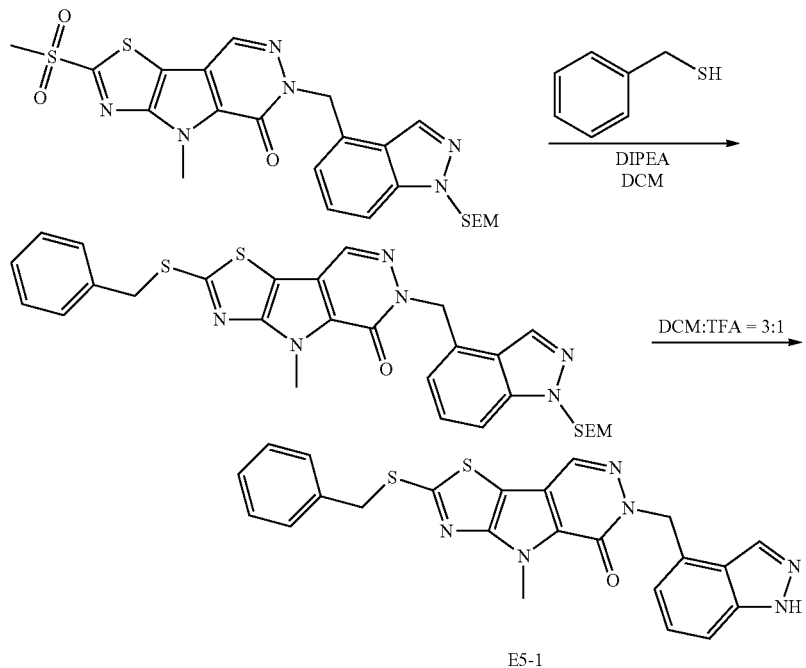

E5-1

Step A. 2-(Benzylthio)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-on. To solution of phenylmethanethiol (91.21 mg, 734.32 μmol) in DCM (5 mL) at 0° C. were added DIPEA (142.3 mg, 1.10 mmol) and 4-methyl-2-(methylsulfonyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (200 mg, 0.37 mmol). The mixture was stirred at 20° C. for 1 hr. then quenched with water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/1 to 3/1) to give the desired product (200 mg). LCMS: m/z 589 (M+H)$^+$ Step B. 6-((1H-indazol-4-yl)methyl)-2-(benzylthio)-4-methyl-4,6-dihydro-5H-thiazolo [5',4':4,5]pyrrolo[2,3-d]pyridazin-5-one. A mixture of 2-(benzylthio)-4-methyl-6-((1-((2-(trimethylsilyl)ethoxy)methyl)-1H-indazol-4-yl)methyl)-4H-thiazolo [5',4':4,5]pyrrolo[2,3-d]pyridazin-5 (6H)-one (30 mg, 50.95 μmol) in DCM/TFA (V:V=3:1) was stirred at 20° C. for 2 hr. then concentrated under reduced pressure. The residue was purified by prep-HPLC to give the desired product (5 mg). LCMS: m/z 459 (M+H)$^+$. $^1$H NMR (400 MHz, DMSO-d$_6$) δ 13.11 (s, 1H), 8.57 (s, 1H), 8.14 (s, 1H), 7.49 (d, 2H), 7.45 (d, 1H), 7.34 (t, 2H), 7.28 (dd, 2H), 6.95 (d, 1H), 5.65 (s, 2H), 4.62 (s, 2H), 4.26 (s, 3H).

Example 5B. Synthesis of 6-((1H-indazol-4-yl)methyl)-4-methyl-5-oxo-5,6-dihydro-4H-thiazolo[5',4':4,5]pyrrolo[2,3-d]pyridazine-2-sulfonamide

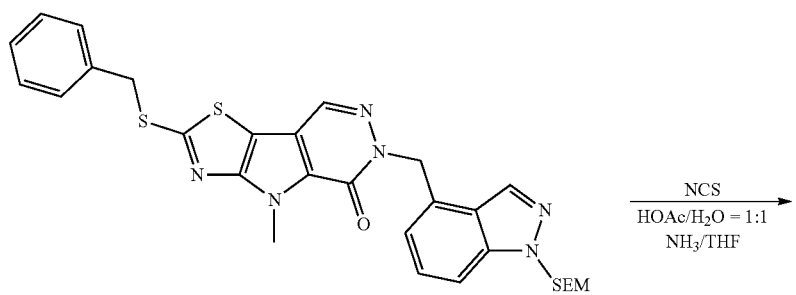

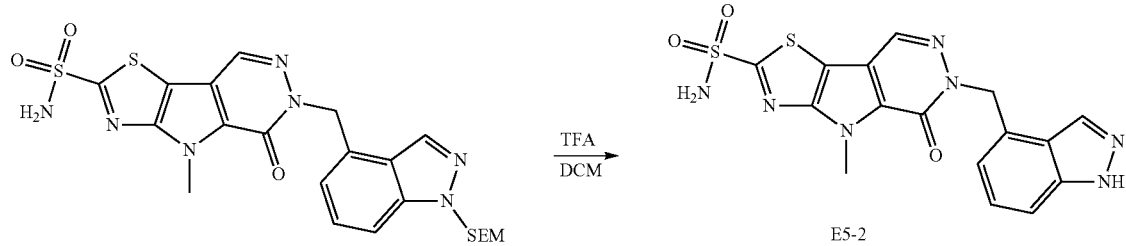

E5-2

Step A. 4-Methyl-5-oxo-6-((1-((2-(trimethylsilyl)ethoxy)methyl)-1H-indazol-4-yl) methyl)-5,6-dihydro-4H-thiazolo[5',4':4,5]pyrrolo[2,3-d]pyridazine-2-sulfonamide. To a solution of 2-(benzylthio)-4-methyl-6-((1-((2-(trimethylsilyl)ethoxy)methyl)-1H-indazol-4-yl)methyl)-4H-thiazolo[5',4':4,5]pyrrolo[I2,3-d]pyridazin-5(6H)-one (100 mg, 0.169 mmol) in HOAc/H$_2$O (V:V=1:1, 10 mL) was added NCS (45 mg, 0.34 mmol). The mixture was stirred at 40° C. for 3 hr. then cooled to 0° C., followed by slow addition of NH$_3$/THF (5 mL) till pH 9 at that temperature. The resulting mixture was stirred at 20° C. for 0.5 hr. then extracted with EtOAc. The combined organic layers were concentrated under reduced pressure. The residue was purified by prep-TLC (eluent: PE/EtOAc=1/1) to afford the desired product (20 mg). LCMS: m/z 546 (M+H)$^+$.

Step B. 6-((1H-indazol-4-yl)methyl)-4-methyl-5-oxo-5,6-dihydro-4H-thiazolo[5',4':4,5]pyrrolo[2,3-d]pyridazine-2-sulfonamide. A mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-sulfonamide (20 mg, 36.65 mol) in DCM/TFA (V/V=3/1) was stirred at 20° C. for 2 hr. then concentrated under reduced pressure. The residue was purified by prep-HPLC to give the desired product (1.7 mg). LCMS: m/z 416 (M+H)$^+$. $^1$H NMR (400 MHz, DMSO-d$_6$) δ 13.13 (s, 1H), 8.73 (s, 1H), 8.31 (brs, 2H), 8.17 (s, 1H), 7.47 (d, 1H), 7.36-7.20 (m, 1H), 6.99 (d, 1H), 5.68 (s, 2H), 4.30 (s, 3H).

| Cpd No. | Structure | Characterization |
|---|---|---|
| E5-3 | 6-((1H-indazol-4-yl)methyl)-2-(benzylamino)-4-methyl-4,6-dihydro-5H-thiazolo[5',4':4,5]pyrrolo[2,3-d]pyridazin-5-one | LCMS: m/z 442 (M + H)$^+$. $^1$H NMR (400 MHz, DMSO-d$_6$) δ 13.10 (s, 1H), 8.96 (s, 1H), 8.33 (s, 1H), 8.12 (s, 1H), 7.46-7.34 (m, 5H), 7.32-7.24 (m, 2H), 6.93 (d, 1H), 5.61 (s, 2H), 4.59 (d, 2H), 4.12 (d, 3H) |
| E5-4 | 6-((1H-indazol-4-yl)methyl)-4-methyl-2-(phenylamino)-4,6-dihydro-5H-thiazolo[5',4':4,5]pyrrolo[2,3-d]pyridazin-5-one | LCMS: m/z 428 (M + H)$^+$. $^1$H NMR (400 MHz, DMSO-d$_6$) δ 13.11 (s, 1H), 10.81 (brs, 1H), 8.44 (s, 1H), 8.14 (s, 1H), 7.75 (d, 2H), 7.45 (d, 1H), 7.38 (dd, 2H), 7.32-7.24 (m, 1H), 7.06 (dd, 1H), 6.95 (d, 1H), 5.63 (s, 2H), 4.22 (s, 3H) |
| E5-5 | N-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl) acetamide | LCMS: m/z 460 (M + H)$^+$. $^1$H NMR (400 MHz, DMSO-d$_6$) δ 13.12 (s, 1H), 8.55 (s, 1H), 8.14 (s, 1H), 7.59 (s, 1H), 7.45 (d, 1H), 7.28 (dd, 1H), 6.95 (d, 1H), 6.22 (s, 1H), 5.65 (s, 2H), 4.22 (s, 3H), 3.84 (s, 2H). |

| Cpd No. | Structure | Characterization |
|---|---|---|
| E5-6 | 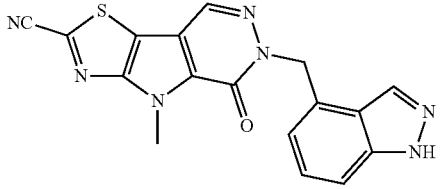 [SMILES: Cn1c2nc(C#N)sc2c2cnn(Cc3cccc4[nH]ncc34)c(=O)c21]<br>6-((1H-indazol-4-yl)methyl)-4-methyl-5-oxo-5,6-dihydro-4H-thiazolo[5',4':4,5]pyrrolo[2,3-d]pyridazine-2-carbonitrile | LC-MS: m/z 362(M + H)$^+$.<br>$^1$H NMR (400 MHz, DMSO-d$_6$) δ 13.14 (s, 1H), 8.80 (s, 1H), 8.18 (s, 1H), 7.46 (d, 1H), 7.34-7.22 (m, 1H), 6.98 (d, 1H), 5.70 (s, 2H), 4.32 (d, 3H). |
| E5-7 | 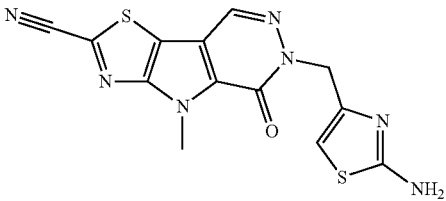 [SMILES: Cn1c2nc(C#N)sc2c2cnn(Cc3csc(N)n3)c(=O)c21]<br>6-((2-Aminothiazol-4-yl)methyl)-4-methyl-5-oxo-5,6-dihydro-4H-thiazolo[5',4':4,5]pyrrolo[2,3-d]pyridazine-2-carbonitrile | LCMS: m/z 344 (M + H)$^+$.<br>$^1$H NMR (400 MHz, DMSO-d$_6$) δ 8.75 (s, 1H), 6.92 (s, 2H), 6.24 (s, 1H), 5.15 (s, 2H), 4.31 (s, 3H). |
| E5-8 | 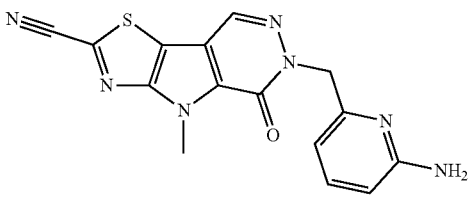 [SMILES: Cn1c2nc(C#N)sc2c2cnn(Cc3cccc(N)n3)c(=O)c21]<br>6-((6-Aminopyridin-2-yl)methyl)-4-methyl-5-oxo-5,6-dihydro-4H-thiazolo[5',4':4,5]pyrrolo[2,3-d]pyridazine-2-carbonitrile | LCMS: m/z 338 (M + H)$^+$.<br>$^1$H NMR (400 MHz, DMSO-d$_6$) δ 8.79 (s, 1H), 7.34-7.18 (m, 1H), 6.31 (d, 1H), 6.14 (d, 1H), 5.91 (s, 2H), 5.22 (s, 2H), 4.31 (s, 3H). |

Example 5C. Synthesis of dimethyl 2-(6-((1H-indazol-4-yl)methyl)-4-methyl-5-oxo-5,6-dihydro-4H-thiazolo [5',4':4,5]pyrrolo [2,3-d]pyridazin-2-yl) malonate

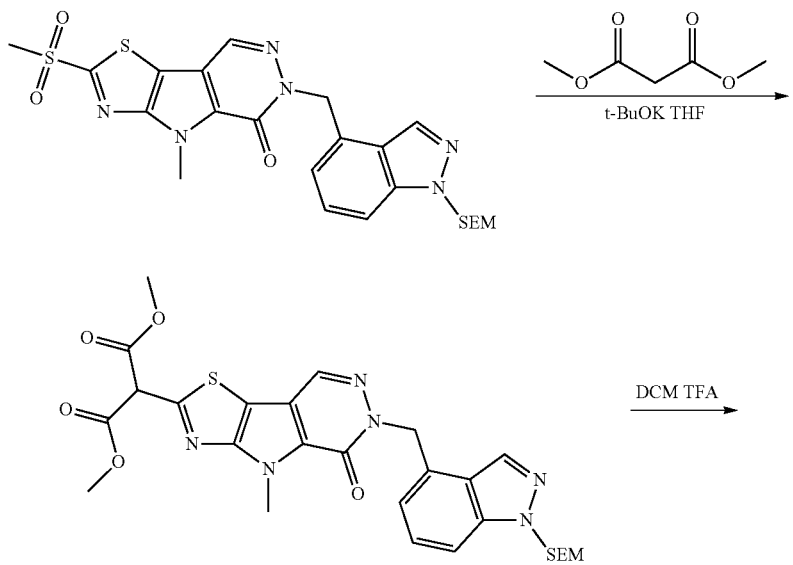

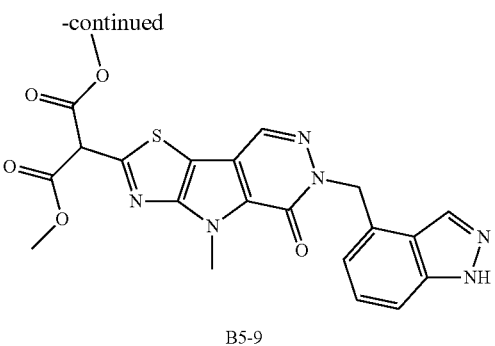

B5-9

Step A. Dimethyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)malonate. To a mixture of t-BuOK (103 mg, 0.92 mmol) and dimethyl malonate (91 mg, 0.69 mmol) in THF (5 mL) under $N_2$ was added 4-methyl-2-(methylsulfonyl)-6-((1-((2-(trimethylsilyl)ethoxy)methyl)-1H-indazol-4-yl)methyl)-4,6-dihydro-5H-thiazolo [5',4':4,5]pyrrolo[2,3-d]pyridazin-5-one (250 mg, 0.46 mmol). The reaction mixture was stirred at 60° C. for 16 hr. then poured into ice water and extracted with EtOAc The combined organic layers were washed with brine, dried over anhydrous $Na_2SO_4$ and concentrated under reduced pressure. The residue was purified by column chromatography on silica gel to give the desired product (160 mg, 36.48% yield). LC-MS: m/z 597 $(M+H)^+$.

Step B. 2-(6-((1H-indazol-4-yl)methyl)-4-methyl-5-oxo-5,6-dihydro-4H-thiazolo [5',4':4,5] pyrrolo [2,3-d] pyridazin-2-yl)malonate was synthesized similar to Example 5A. LC-MS: m/z 467 $(M+H)^+$. $^1$H NMR (400 MHz, DMSO-$d_6$) δ 13.12 (s, 1H), 8.65 (s, 1H), 8.15 (s, 1H), 7.45 (d, 1H), 7.30-7.26 (m, 1H), 6.96 (d, 1H), 5.84 (s, 1H), 5.67 (s, 2H), 4.27 (s, 3H), 3.77 (s, 6H).

Example 5D. Synthesis of methyl 2-(6-((1H-indazol-4-yl)methyl)-4-methyl-5-oxo-5,6-dihydro-4H-thiazolo[5',4':4,5]pyrrolo[2,3-d]pyridazin-2-yl)acetate Step A. Methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetate. To a solution of dimethyl 2-(4-methyl-5-oxo-6-((1-((2-(trimethylsilyl) ethoxy)methyl)-1H-indazol-4-yl)methyl)-5,6-dihydro-4H-thiazolo[5',4':4,5]pyrrolo[2,3-d]pyridazin-2-yl)malonate (130 mg, 0.22 mmol) in DMSO (2 mL) under $N_2$ was added saturated aqueous LiCl (0.1 mL). The resulting mixture was stirred at 130° C. for 10 min then poured into ice water and extracted with EtOAc. The combined organic layers were washed with brine, dried over anhydrous $Na_2SO_4$ and concentrated under reduced pressure. Then the residue was purified by column chromatography on silica gel to afford the desired product (100 mg). LC-MS: m/z 539 $(M+H)^+$.

Step B. Methyl 2-(6-((1H-indazol-4-yl)methyl)-4-methyl-5-oxo-5,6-dihydro-4H-thiazolo [5',4':4,5]pyrrolo[2,3-d]pyridazin-2-yl)acetate was synthesized as in Example 5A. LC-MS: m/z 409 $(M+H)^+$. $^1$H NMR (400 MHz, DMSO-$d_6$) δ 13.12 (s, 1H), 8.62 (s, 1H), 8.15 (s, 1H), 7.45 (d, 1H), 7.30-7.26 (m, 1H), 6.96 (d, 1H), 5.67 (s, 2H), 4.39 (s, 2H), 4.27 (s, 3H), 3.70 (s, 3H).

Example 5E. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)acetamide

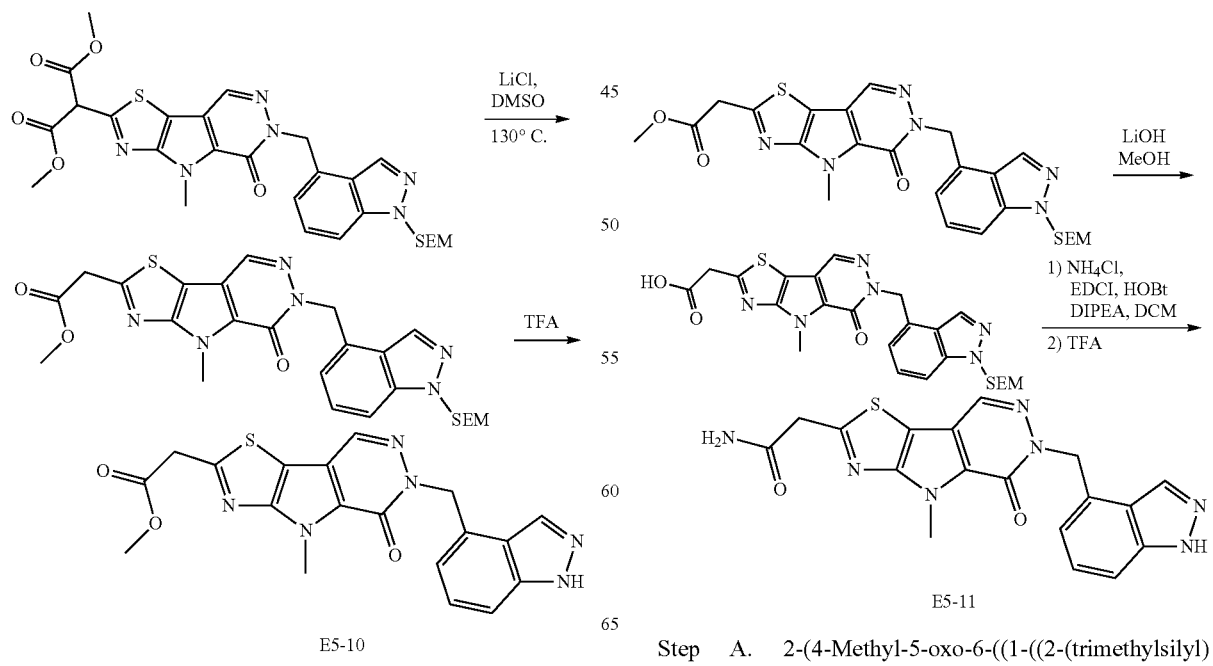

Step A. 2-(4-Methyl-5-oxo-6-((1-((2-(trimethylsilyl)ethoxy)methyl)-1H-indazol-4-yl) methyl)-5,6-dihydro-4H- thiazolo[5',4':4,5]pyrrolo[2,3-d]pyridazin-2-yl)acetic acid. To a mixture of methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetate (100 mg, 0.186 mmol) in MeOH/H₂O (3 mL/1 mL) at 0° C. under N₂ was added LiOH (23 mg, 0.558 mmol). The resulting mixture was stirred at r.t. for 16 hr. then concentrated under reduced pressure. The residue was acidified with aqueous HCl (1 M) and extracted with EtOAc. The combined organic layers were washed with brine, dried over anhydrous Na₂SO₄ and concentrated under reduced pressure. The residue was directly used in next step without further purification. LC-MS: m/z 525 (M+H)⁺.

Step B. 2-(4-Methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetamide. To a mixture of 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetic acid (50 mg, 0.095 mmol), EDCI (37 mg, 0.190 mmol), HOBT (26 mg, 0.190 mmol) and DIPEA (0.05 mL, 0.286 mmol) in DCM (5 mL) at 0° C. was added NH₄Cl (26 mg, 0.477 mmol). The resulting mixture was stirred at r.t. for 16 hr. then poured into ice water and extracted with EtOAc. The combined organic layers were washed with brine, dried over anhydrous Na₂SO₄ and concentrated under reduced pressure. The residue was purified by column chromatography on silica gel to afford the desired product (20 mg). LC-MS: m/z 524 (M+H)⁺.

Step C. 2-(6-((1H-Indazol-4-yl)methyl)-4-methyl-5-oxo-5,6-dihydro-4H-thiazolo [5',4':4,5]pyrrolo[2,3-d]pyridazin-2-yl)acetamide was synthesized using the procedure as in Example 5A. LCMS: m/z 394 (M+H)⁺. ¹H NMR (400 MHz, DMSO-d₆) δ 13.12 (s, 1H), 8.59 (s, 1H), 8.15 (s, 1H), 7.77 (s, 1H), 7.45 (d, 1H), 7.33-7.22 (m, 2H), 6.96 (d, 1H), 5.66 (s, 2H), 4.27 (s, 3H), 4.07 (s, 2H).

Example 5F. Synthesis of 6-((1H-indazol-4-yl)methyl)-4-methyl-5-oxo-5,6-dihydro-4H-thiazolo[5',4':4,5]pyrrolo[2,3-d]pyridazine-2-carboxamide

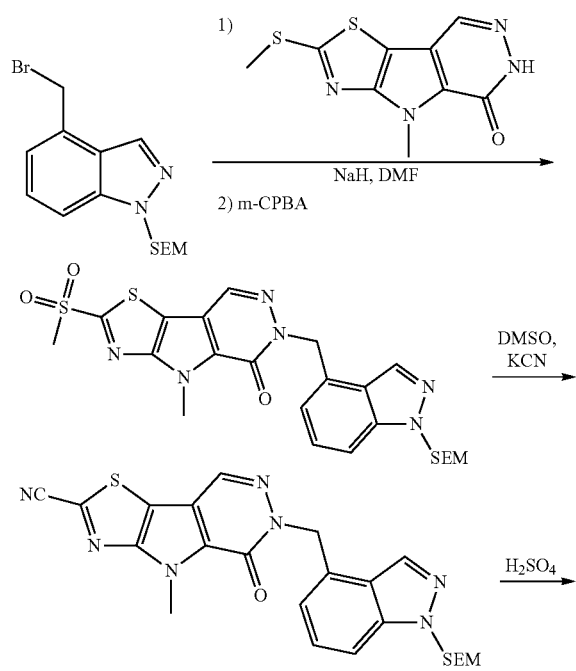

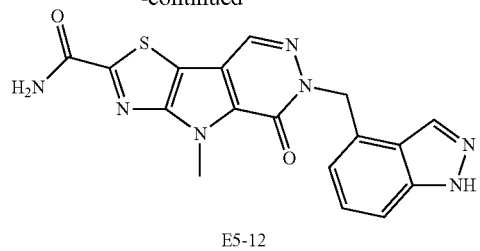

E5-12

Step A. 4-Methyl-2-(methylthio)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one. To a mixture of 4-methyl-2-(methylthio)-4H-thiazolo[5',4':4,5]pyrrolo[2,3-d]pyridazin-5 (6H)-one (1 g, 3.96 mmol) in DMF (25 mL) at 0° C. was added NaH (318 mg, 7.93 mmol). The mixture was stirred at r.t. for 30 min. followed by addition of a solution of 4-(bromomethyl)-1-((2-(trimethylsilyl)ethoxy)methyl)-1H-indazole (2 g, 5.94 mmol) in DMF (10 mL) at 0° C. The mixture was stirred at r.t. for 2 hr. then poured into ice-water and extracted with EtOAc. The combined organic layers were washed with brine, dried over anhydrous Na₂SO₄ and concentrated under reduced pressure. The residue was purified by column chromatography on silica gel (eluent: PE/EtOAc=50/1 to 10/1) to give the desired product (1.85 g). LCMS: m/z 513 (M+H)⁺.

Step B. 4-Methyl-2-(methylsulfonyl)-6-((1-((2-(trimethylsilyl)ethoxy) methyl)-4H-indazol-4-yl)methyl)-4H-thiazolo[5',4':4,5]pyrrolo[2,3-d]pyridazin-5(6H)-one.

To a mixture of 4-methyl-2-(methylthio)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one (700 mg, 1.37 mmol) in DCM (20 mL) at 0° C. was added m-CPBA (831 mg, 4.01 mmol). The mixture was stirred at r.t. overnight then quenched by saturated aqueous Na₂SO₃ and extracted with EtOAc. The combined organic layers were washed with brine, dried over anhydrous Na₂SO₄ and concentrated under reduced pressure. The residue was purified by column chromatography on silica gel to give the desired product (360 mg). LCMS: m/z 545 (M+H)⁺.

Step C. 4-Methyl-5-oxo-6-((1-((2-(trimethylsilyl)ethoxy) methyl)-1H-indazol-4-yl) methyl)-5,6-dihydro-4H-thiazolo[5',4':4,5]pyrrolo[2,3-d]pyridazine-2-carbonitrile. To a mixture of 4-methyl-2-(methylsulfonyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one (300 mg, 0.552 mmol) in DMF (10 mL) at 0° C. was added KCN (72 mg, 1.10 mmol). The mixture was stirred at r.t. for 2 hr. then quenched by water and extracted with EtOAc. The combined organic layers were washed with brine, dried over anhydrous Na₂SO₄ and concentrated under reduced pressure. The residue was purified by column chromatography on silica gel (eluent: PE/EtOAc=5/1) to give the desired product (210 mg). LCMS: m/z 492 (M+H)⁺.

Step D. 6-((1H-indazol-4-yl)methyl)-4-methyl-5-oxo-5,6-dihydro-4H-thiazolo[5',4':4,5]pyrrolo[2,3-d]pyridazine-2-carboxamide. A mixture of 4-methyl-5-oxo-6-((1-((2-(trimethylsilyl)ethoxy)methyl)-1H-indazol-4-yl) methyl)-5,6-dihydro-4H-thiazolo [5',4':4,5]pyrrolo[2,3-d]pyridazine-2-carbonitrile (50 mg, 0.1 mmol) in conc. H₂SO₄ (3 mL) was stirred at r.t. for 12 hr. then quenched with saturated aqueous NaHCO₃(aq) and extracted with DCM. The combined organic layers were washed with brine, dried over anhydrous Na₂SO₄ and concentrated under reduced pressure. The residue was purified by prep-HPLC to give the desired product (6 mg). LCMS: m/z 380 (M+H)+. 1H NMR (400 MHz, DMSO) δ 13.12 (s, 1H), 8.71 (s, 1H), 8.39 (s, 1H), 8.16 (s, 1H), 8.07 (s, 1H), 7.46 (d, 1H), 7.33-7.23 (m, 1H), 6.98 (d, 1H), 5.68 (s, 2H), 4.33 (s, 3H).

The procedure set forth above was used to produce following compounds using appropriate starting materials. Standard protection and deprotection can be used when necessary.

| Cpd No. | Structure | Characterization |
|---|---|---|
| E5-13 | 6-((2-Aminothiazol-4-yl)methyl)-4-methyl-5-oxo-5,6-dihydro-4H-thiazolo[5',4':4,5]pyrrolo [2,3-d]pyridazine-2-carboxamide | LCMS: m/z 362 (M + H)+. 1H NMR (400 MHz, DMSO-d6) δ 8.65 (s, 1H), 8.40 (s, 1H), 8.07 (s, 1H), 6.92 (s, 2H), 6.22 (s, 1H), 5.15 (s, 2H), 4.33 (s, 3H). |
| E5-14 | 6-((6-Aminopyridin-2-yl)methyl)-4-methyl-5-oxo-5,6-dihydro-4H-thiazolo[5',4':4,5]pyrrolo[2,3-d]pyridazine-2-carboxamide | LCMS: m/z 356 (M + H)+. 1H NMR (400 MHz, DMSO-d6) δ 8.69 (s, 1H), 8.40 (s, 1H), 8.08 (s, 1H), 7.34-7.19 (m, 1H), 6.30 (d, 1H), 6.12 (d, 1H), 5.91 (s, 2H), 5.21 (s, 2H), 4.32 (s, 3H). |

Example 5G. Synthesis of 6-((1H-indazol-4-yl)methyl)-N-hydroxy-4-methyl-5-oxo-5,6-dihydro-4H-thiazolo [5',4':4,5]pyrrolo[2,3-d]pyridazine-2-carboxamide

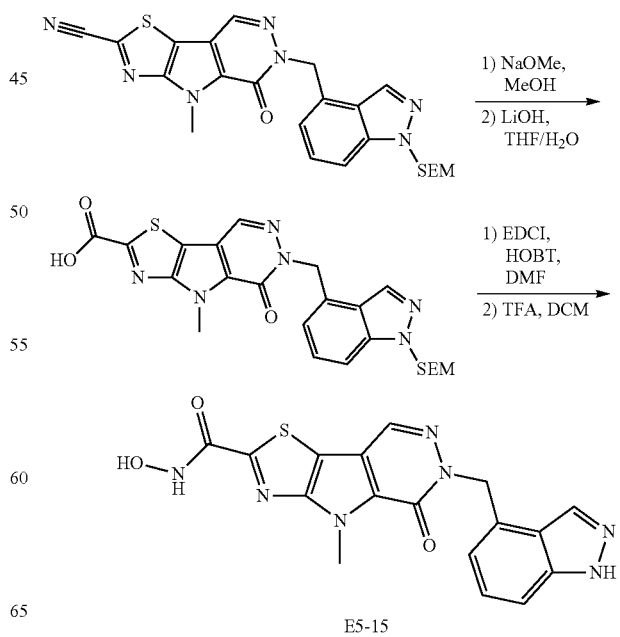

Step A. Methyl 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carboxylate. To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbonitrile (100 mg, 0.20 mmol) in MeOH (10 mL) at 0° C. was added MeONa (110 mg, 0.61 mmol, 30% wt). The reaction mixture was stirred at r.t. for 1.5 hr. then quenched with saturated HCl (1 M) and extracted with DCM (30 mL). The combined organic layers were dried over anhydrous $Na_2SO_4$, and concentrated under reduced pressure to give the desired product (85 mg) as yellow oil which was directly used in next step without further purification. LCMS: m/z 525 $(M+H)^+$.

Step B. 4-Methyl-5-oxo-6-((1-((2-(trimethylsilyl)ethoxy)methyl)-1H-indazol-4-yl) methyl)-5,6-dihydro-4H-thiazolo[5',4':4,5]pyrrolo[2,3-d]pyridazine-2-carboxylic acid. To a mixture of methyl 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carboxylate (90 mg, 0.18 mmol) in THF (10 mL) at 0° C. was added a solution of LiOH (12 mg, 0.48 mmol) in $H_2O$ (10 mL). The reaction mixture was stirred at r.t. overnight, then slowly adjusted to pH 5 with aqueous HCl (1 M) and extracted with DCM. The combined organic layers were washed with brine, dried over anhydrous $Na_2SO_4$, and concentrated under reduced pressure to give the desired product (70 mg, 84% crude yield) as a white oil which was directly used in the next step without any further purification. LCMS: m/z 511 $(M+H)^+$.

Step C. 4-Methyl-5-oxo-N-((tetrahydro-2H-pyran-2-yl)oxy)-6-((1-((2-(trimethyl silyl)ethoxy)methyl)-1H-indazol-4-yl)methyl)-5,6-dihydro-4H-thiazolo[5',4':4,5]pyrrolo[2,3-d]pyridazine-2-carboxamide. To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d] pyridazine-2-carboxylic acid (70 mg, 0.14 mmol) in DCM (10 mL) at 0° C. were added O-(tetrahydro-2H-pyran-2-yl)hydroxylamine (24 mg, 0.21 mmol), EDCI (39 mg, 0.21 mmol) and HOBT (28 mg, 0.21 mmol). The reaction mixture was stirred at r.t. overnight then quenched with water and extracted with DCM. The combined organic layers were washed with brine, dried over anhydrous $Na_2SO_4$, and concentrated under reduced pressure. The residue was purified by prep-TLC to give the desired product (35 mg) as yellow oil. LCMS: m/z 610 $(M+H)^+$.

Step D. 6-((1H-indazol-4-yl)methyl)-N-hydroxy-4-methyl-5-oxo-5,6-dihydro-4H-thiazolo[5',4':4,5]pyrrolo[2,3-d]pyridazine-2-carboxamide was synthesized using the procedure in Example 5A. LCMS: m/z 396 $(M+H)^+$. $^1$H NMR (400 MHz, DMSO-$d_6$) δ 13.12 (s, 1H), 8.67 (s, 1H), 8.29 (s, 1H), 8.16 (s, 1H), 7.46 (d, 1H), 7.31-7.25 (m, 1H), 6.97 (d, 1H), 5.67 (s, 2H), 4.31 (s, 3H).

Example 5H. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetamide

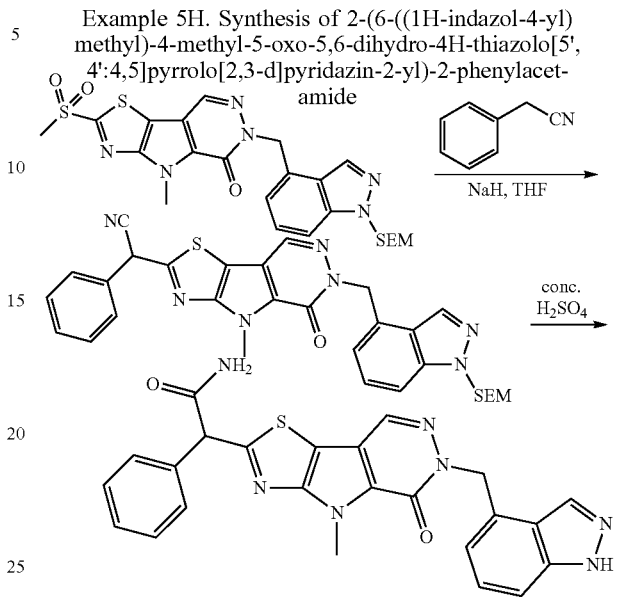

Step A. 2-(4-Methyl-5-oxo-6-((1-((2-(trimethylsilyl)ethoxy)methyl)-1H-indazol-4-yl) methyl)-5,6-dihydro-4H-thiazolo[5',4':4,5]pyrrolo[2,3-d]pyridazin-2-yl)-2-phenylacetonitrile. To a mixture of 2-phenylacetonitrile (43 mg, 0.36 mmol) in THF (3 mL) was added NaH (14 mg, 0.36 mmol). The mixture was stirred at r.t. for 30 min, followed by addition of 4-methyl-2-(methylsulfonyl)-6-((1-((2-(trimethylsilyl) ethoxy)methyl)-1H-indazol-4-yl)methyl)-4,6-dihydro-5H-thiazolo[5',4':4,5]pyrrolo[2,3-d]pyridazin-5-one (100 mg, 0.18 mmol). The reaction mixture was stirred at rt. for another 3 hr. then quenched with water and extracted with EtOAc. The combined organic layers were washed with brine, dried over anhydrous $Na_2SO_4$ and concentrated under reduced pressure. The residue was purified by column chromatography on silica gel (eluent: PE/EtOAc=3/1) to give the product (63 mg, 59% yield). LCMS: 582 $(M+H)^+$.

Step B. 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetamide was synthesized similar to Example 5F. LCMS: m/z 470 $(M+H)^+$. $^1$H NMR (400 MHz, DMSO-$d_6$) δ 13.11 (s, 1H), 8.58 (s, 1H), 8.13 (s, 1H) 8.01 (s, 1H), 7.54-7.24 (m, 8H), 6.94 (d, 1H), 5.65 (s, 2H), 5.51 (s, 1H), 4.24 (s, 3H).

| Cpd No. | Structure | Characterization |
|---|---|---|
| E5-17 | 2-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl) acetamide | LCMS: 460 $(M + H)^+$. $^1$H NMR (400 MHz, DMSO-$d_6$) δ 13.11 (s, 1H), 12.88 (s, 1H), 8.56 (s, 1H), 8.14 (s, 1H), 7.93 (s, 1H), 7.70 (s, 1H), 7.44 (d, 1H), 7.28 (s, 1H), 7.27 (dd, 1H), 6.95 (d, 1H), 6.34 (s, 1H), 5.65 (s, 2H), 5.56 (s, 1H), 4.27 (s, 3H). |

Example 5I. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)-2-hydroxy-2-phenylacetamide

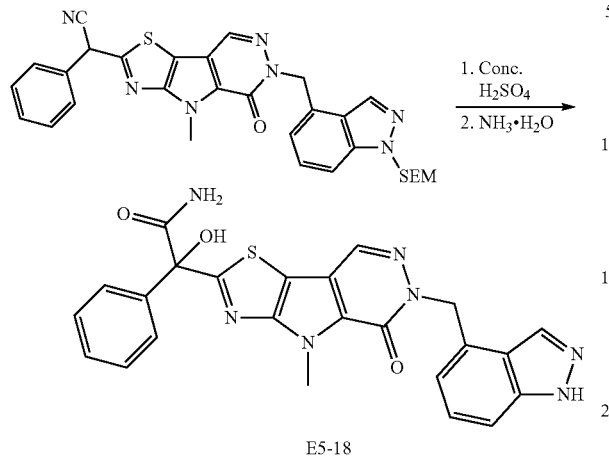

E5-18

A mixture of 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetonitrile (100 mg, 0.18 mmol) in conc. $H_2SO_4$ (1 mL) was stirred at r.t. for 2 hr. then poured into water and extracted with DCM. The combined organic layers were concentrated under reduced pressure. The residue was dissolved in MeOH (3 mL), followed by addition of $NH_3 \cdot H_2O$ (3 mL). The reaction mixture was stirred at r.t. for 2 hr. then under reduced pressure. The residue was purified by prep-HPLC to afford the desired product (2 mg). LCMS: 486 (M+H)$^+$. $^1$H NMR (400 MHz, DMSO-d$_6$) δ 13.12 (s, 1H), 8.61 (s, 1H), 8.14 (s, 1H), 7.71 (d, 2H), 7.64 (d, 2H), 7.52 (s, 1H), 7.45 (d, 1H), 7.40-7.24 (m, 4H), 6.95 (d, 1H), 5.66 (s, 2H) 4.27 (s, 3H).

Example 5J. Synthesis of methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetate

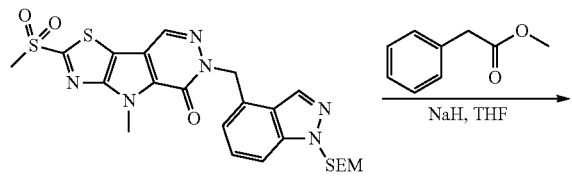

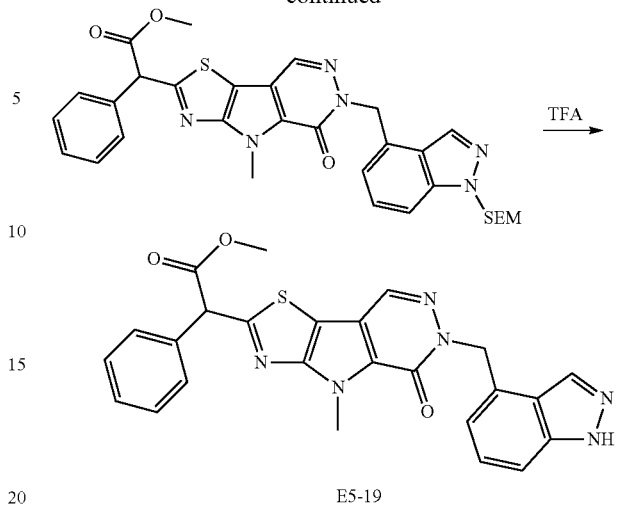

E5-19

Step A. Methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetate. To a mixture of methyl 2-phenylacetate (43 mg, 0.29 mmol) in THF (3 mL) was added NaH (11 mg, 0.29 mmol). The mixture was stirred at rt. for 30 min, followed by addition of 4-methyl-2-(methylsulfonyl)-6-((1-((2-(trimethylsilyl) ethoxy) methyl)-1H-indazol-4-yl)methyl)-4,6-dihydro-5H-thiazolo[5',4':4,5]pyrrolo[2,3-d]pyridazin-5-one (82 mg, 0.15 mmol). The resulting mixture was stirred at r.t. for 3 hr. then quenched with water and extracted with EtOAc. The combined organic layers were concentrated under reduced pressure. The residue was purified by column chromatography on silica gel (eluent: PE/EtOAc=3/1) to afford the desired product (20 mg). LCMS: 615 (M+H)$^+$.

Step B. Methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetate. A mixture of methyl 2-(4-methyl-5-oxo-6-((1-((2-(trimethylsilyl)ethoxy)methyl)-1H-indazol-4-yl) methyl)-5,6-dihydro-4H-thiazolo[5',4':4,5]pyrrolo[2,3-d]pyridazin-2-yl)-2-phenylacetate (40 mg, 0.07 mmol) in DCM/TFA (V:V=1:1, 2 mL) was stirred at r.t. for 2 hr. then poured into water and extracted with DCM. The combined organic layers were concentrated under reduced pressure. The residue was purified by prep-HPLC to afford the desired product (5 mg). LCMS: 485 (M+H)$^+$. $^1$H NMR (400 MHz, DMSO-d$_6$) δ 13.11 (s, 1H), 8.58 (s, 1H), 8.13 (s, 1H) 7.54-7.50 (m, 2H), 7.46-7.36 (m, 4H), 7.30-7.24 (m, 1H), 6.94 (d, 1H), 5.87 (s, 1H), 5.65 (s, 2H), 4.26 (s, 3H), 3.73 (s, 3H).

The procedure set forth above was used to produce the following compounds using the appropriate starting materials.

| Cpd No. | Structure | Characterization |
|---|---|---|
| E5-20 | Methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl)acetate | LCMS: 4759 (M + H)$^+$. $^1$H NMR (400 MHz, DMSO-d$_6$) δ 8.48 (s, 1H), 8.06 (s, 1H), 7.67 (d, 1H), 7.40 (d, 1H), 7.23 (dd, 1H), 6.89 (d, 1H), 6.32 (d, 1H), 5.58 (s, 2H), 4.19 (s, 3H), 3.63 (s, 3H). |

313

Example 6. Synthesis of 6-(3-methoxybenzyl)-4-methyl-2-(trifluoromethyl)-4,6-dihydro-5H-thiazolo[5',4':4,5]pyrrolo[2,3-d]pyridazin-5-one

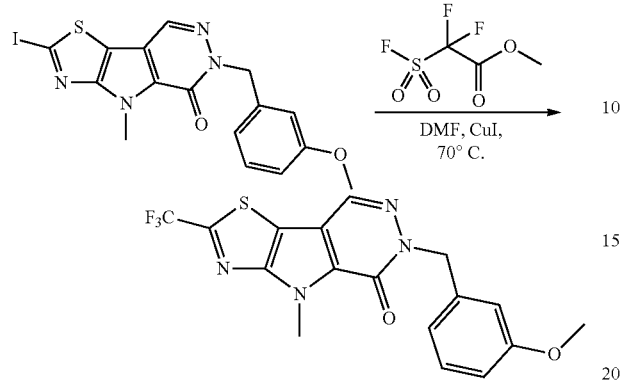

To a stirred mixture of 2-iodo-6-(3-methoxybenzyl)-4-methyl-4,6-dihydro-5H-thiazolo[5',4':4,5]pyrrolo[2,3-d]pyridazin-5-one (90 mg, 0.2 mmol) and CuI (cat.) in DMF (5 mL) was added methyl 2,2-difluoro-2-(fluorosulfonyl)acetate (58 mg, 0.3 mmol). The reaction mixture was stirred at 70° C. for 4 hr. then poured into water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/1) to give the desired product (10 mg). LCMS: m/z=395 (M+H)$^+$. $^1$H NMR (400 MHz, DMSO-d$_6$) δ 8.78 (s, 1H), 7.24 (t, 1H), 6.90-6.82 (m, 3H), 5.34 (s, 2H), 4.32 (s, 3H) 3.72 (s, 3H).

Example 7. Synthesis of Compounds E7-v and E7-viii

Scheme E7

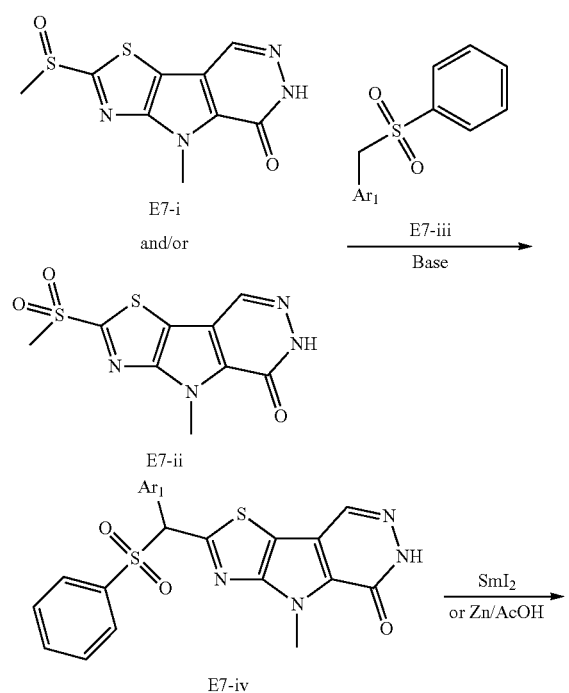

314

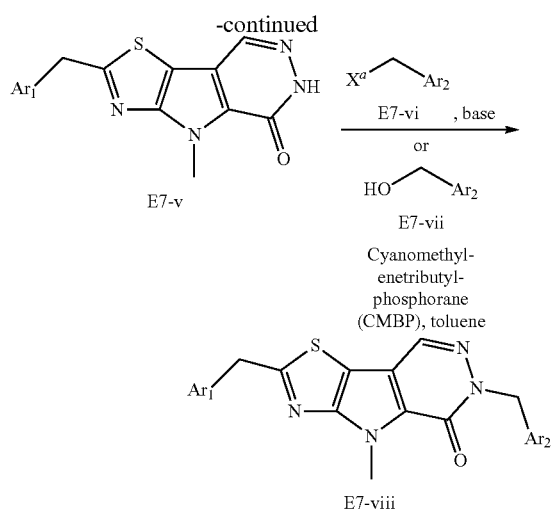

Nucleophilic aromatic substitution between compound E7-iii and compound E7-i and/or compound E7-ii gives intermediate E7-iv. Reduction of the phenylsulfonyl group of compound E7-iv affords intermediate E7-v. Using standard alkylation reaction of E7-vi and base (e.g. K$_2$CO$_3$, K$_3$PO$_4$, t-BuOK, or Cs$_2$CO$_3$) gives compound E7-viii, wherein X$^a$ is a leaving group such as Cl, Br, I, OMs, OTs; Ar$_1$ and Ar$_2$ are each independently optionally substituted aryl, optionally substituted heteroaryl, optionally substituted carbocycle or optionally substituted heterocyclyl; optionally substituted alkyl, alkylaryl, alkylheteroaryl, alkylenyl, and alkynyl groups, provided that Ar1 and Ar2 are not both optionally substituted 5-membered or 6-membered monocyclic heteroaryl. Compound E7-viii can also be synthesized from intermediate E7-v through Mitsunobu reaction using Cyanomethylenetributylphosphorane (CMBP) in toluene.

Example 7A. Synthesis of 4-methyl-2-(methylsulfinyl)-4,6-dihydro-5H-thiazolo[5',4':4,5]pyrrolo[2,3-d]pyridazin-5-one (intermediates E7-i)

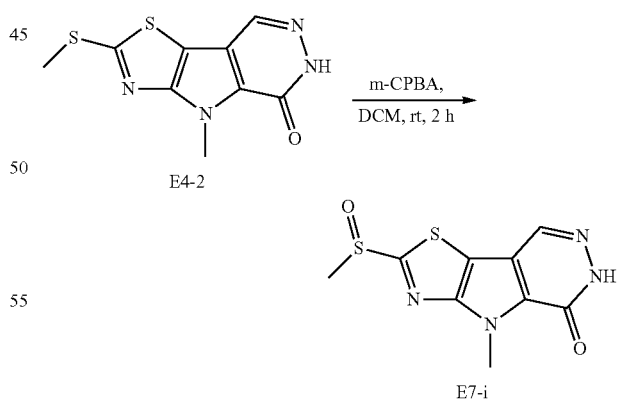

To a stirred suspension of 4-methyl-2-(methylthio)-4,6-dihydro-5H-thiazolo[5',4':4,5]pyrrolo[2,3-d]pyridazin-5-one (1.01 g, 4.0 mmol) in DCM (20 mL) was added 3-chloro-benzoperoxoic acid (0.77 g, 3.8 mmol) at r.t. The mixture stirred at r.t. for 2 hr. Then the mixture was filtered washed with EtOAc and triturated with MeOH to give 4-methyl-2-(methylsulfinyl)-4,6-dihydro-5H-thiazolo[5',4':

4,5]pyrrolo[2,3-d]pyridazin-5-one (600 mg). LCMS: m/z 269 (M+H)+. 1H NMR (400 MHz, DMSO) δ 12.78 (s, 1H), 8.64 (s, 1H), 4.28 (s, 3H), 3.11 (s, 3H).

Example 7B. Synthesis of 4-methyl-2-(methylsulfonyl)-4,6-dihydro-5H-thiazolo [5',4':4,5]pyrrolo[2,3-d]pyridazin-5-one (E7-ii)

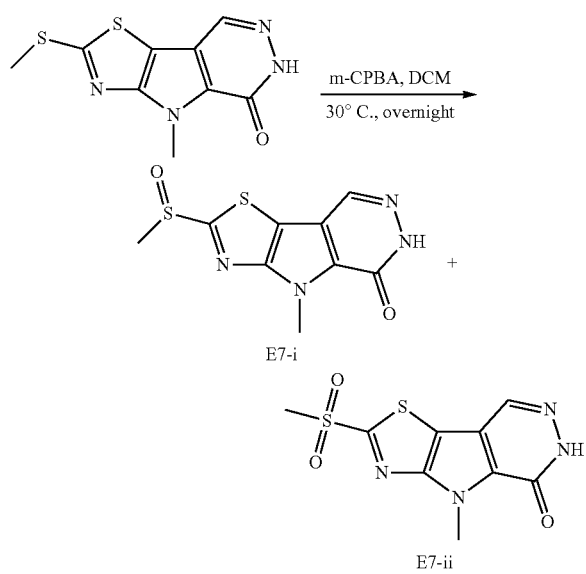

Three necked flask charged with 4-methyl-4,6-dihydro-5H-thiazolo[5',4':4,5]pyrrolo[2,3-d]pyridazin-5-one (30 g, 0.119 mol, 1.0 eq) in DCM (600 mL) m-CPBA (61.5 g, 3 eq) was added at 20° C. in three portions. The mixture was stirred at 30° C. overnight, LC-MS indicated 100% consumption of starting material. The mixture was cooled to r.t., another portion of m-CPBA (1.0 eq) was added. The reaction mixture was stirred at 30° C. for 2 hr, LC-MS indicated E7-ii (LCMS: m/z 269 (M+H)+). The mixture was cooled to r.t. and filtered. The filtered cake was suspension in MeOH (500 mL) and stirred at r.t. for 1 hr. Solid was collected by filtration, washed with ethylacetate, dried in vacuum to afford 28 g of mixture of 5% of E7-i and 95% of E7-ii. The mixture (28 g) was suspended in DMSO (600 mL), heated to 120° C.~130° C. to form a clear solution. Then cooled to r.t., solid precipitated. The mixture was filtered and dried to provide 23 g of pure E5-1, LCMS: m/z 285 (M+H)+. 1H NMR (400 MHz, DMSO) δ12.87 (s, 1H), 8.69 (s, 1H), 4.32 (s, 3H), 3.56 (s, 3H).

Examples 7C. Synthesis of 3-((phenylsulfonyl) methyl)-1-((2-(trimethylsilyl)ethoxy) methyl)-1H-pyrazole

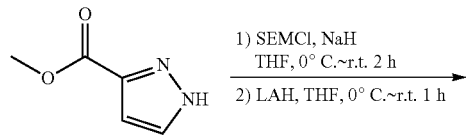

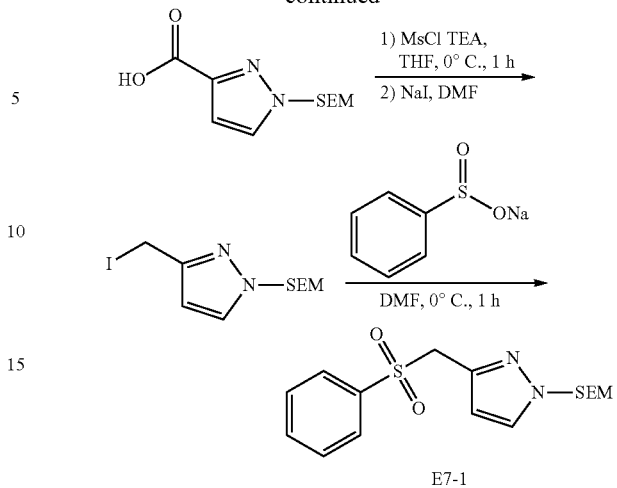

E7-1

Methyl 1-((2-(trimethylsilyl)ethoxy)methyl)-1H-pyrazole-3-carboxylate At 0° C. under N2 atmosphere, to a stirred solution of methyl 1H-pyrazole-3-carboxylate (90 g, 0.72 mol) in THF (1 L) was added NaH (20.7 g, 0.864 mol, 60%). The resulting mixture was slowly warmed up to r.t and stirred for 1 h. The reaction mixture was then cooled back to 0° C. and SEMCl (151.5 mL, 0.842 mol) was added drop wise. The stirring was continued for another 2 hr before quenched with sat. NH4Cl and extracted with ethyl acetate (3×). The combined organic layers were washed with brine and dried over Na2SO4. Solvents were removed under vacuum to provide crude product 210 g which was used in the next step without purification.

(1-((2-(trimethylsilyl)ethoxy)methyl)-1H-pyrazol-3-yl) methanol At 0° C. under N2 atmosphere, to the suspension of LAH (16.9 g, 0.44 mol) in THF (760 mL) was added the crude methyl 1-((2-(trimethylsilyl)ethoxy)methyl)-1H-pyrazole-3-carboxylate (76 g). The resulting mixture was slowly warmed up to r.t. and stirred for 1 hr. The reaction mixture was cooled back to 0° C. and H2O (15.6 mL), 10% NaOH (15.6 mL), H2O (15.6 mL) was added successively. The resulting mixture was filtered through a pad of celite and washed with MTBE (4×). The combined organic fractions were dried over Na2SO4. Solvents were removed under reduced pressure to provide crude product 69.4 g which was used in the next step without purification. LC-MS: m/z 229 (M+H)+.

3-(iodomethyl)-1-((2-(trimethylsilyl)ethoxy)methyl)-1H-pyrazole At 0° C. under N2 atmosphere, to a stirred solution of (1-((2-(trimethylsilyl)ethoxy)methyl)-1H-pyrazol-3-yl) methanol (61.5 g, theoretically 0.262 mol) in THF (310 mL) was added TEA (55.42 mL, 0.393 mol) followed by MsCl (24 mL, 0.314 mol). The reaction was warmed up to r.t and stirred for 1 hr before the introduction of NaI (196.5 g, 1.31 mol, in 310 mL DMF). The resulting mixture was stirred for another 1 hr and quenched with ice-water, extracted with MTBE (3×). The combined organic layers were washed with sat. Na2S2O3 and brine, dried over Na2SO4 and concentrated to provide 77.5 g crude product used in the next step without purification. LC-MS: m/z 339 (M+H)+.

3-((phenylsulfonyl)methyl)-1-((2-(trimethylsilyl)ethoxy) methyl)-1H-pyrazole At 0° C. under N2 atmosphere, to a stirred solution of (1-((2-(trimethylsilyl)ethoxy) methyl)-1H-pyrazol-3-yl)methanol (77.5 g, theoretically 0.229 mol) in DMF (600 mL) was added sodium benzenesulfinate (53.5 g, 0.32 mol) and stirred for 1 hr at 0° C. After warmed up to r.t., the reaction mixture was quenched with ice-water and sat. Na$_2$S$_2$O$_3$, extracted with ethyl acetate (3×). The combined organic layers were washed with sat. NaHCO$_3$ and brined successively, dried over Na$_2$SO$_4$. Solvents were removed under vacuum and the residue was purified by flash chromatography (silica gel, 20%-70% ethyl acetate in petroleum ether) to provide 56.7 g. LCMS: [M+H]$^+$ 353. 1H NMR (400 MHz, DMSO) δ 7.85-7.77 (m, 4H), 7.62 (dd, 2H), 6.19 (d, 1H), 5.35 (d, 2H), 4.70 (d, 2H), 3.44-3.38 (m, 2H), 0.88-0.77 (m, 2H), −0.01 (s, 9H).

Example 7D. Synthesis of 4-methyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one

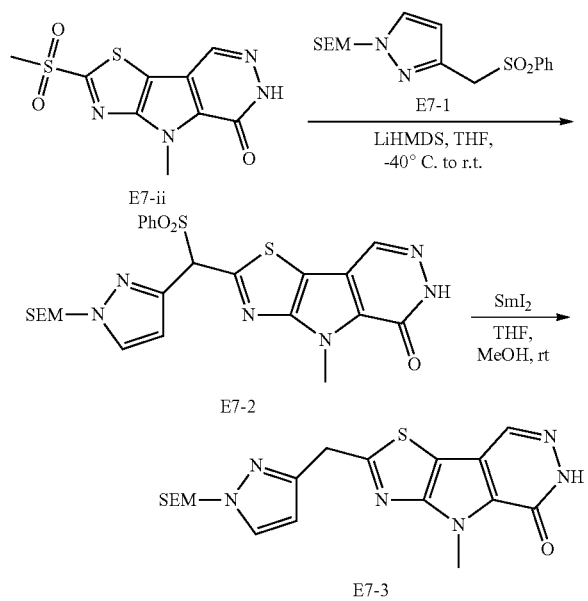

4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one. To a solution of 3-((phenylsulfonyl)methyl)-1-((2-(trimethylsilyl)ethoxy)methyl)-1H-pyrazole (1.8 g, 5.1 mmol) in dry THF (30 mL) at −40° C. was added LiHMDS (7.5 mL, 7.5 mmol) dropwise. The mixture was stirred at room temperature for 30 min, followed by addition of a suspension of 4-methyl-2-(methylsulfinyl)-4H-thiazolo[5',4':4,5]pyrrolo[2,3-d]pyridazin-5(6H)-one (580 mg, 2.7 mmol) in dry THF (30 mL) at room temperature. The mixture was stirred at r.t. for another 1 hr and poured into ice-cooled saturated aqueous NH$_4$Cl (20 mL) and extracted with EtOAc (3×100 mL). The combined organic layers were washed with water (60 mL), dried over anhydrous Na$_2$SO$_4$ and concentrated under reduced pressure. The residue was purified by flash chromatography (silica gel, 0~2.5% methanol in dichloromethane) to give the desired product (800 mg). LC-MS (ESI) found: 557 (M+H)$^+$. 1H NMR (400 MHz, DMSO) δ 12.78 (s, 1H), 8.65 (s, 1H), 8.03 (d, 1H), 7.84-7.78 (m, 3H), 7.67-7.59 (m, 2H), 6.94 (s, 1H), 6.72 (d, 1H), 5.48 (d, 2H), 4.29 (s, 3H), 3.56 (dd, 2H), 0.88 (dd, 2H), 0.00 (s, 9H).

4-methyl-2-((1-((2-(trimethylsilyl)ethoxy)methyl)-1H-pyrazol-5-yl)methyl)-4H-thiazolo[5',4':4,5]pyrrolo[2,3-d]pyridazin-5(6H)-one. To a mixture of 4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one (0.8 g, 1.41 mmol) in THF (5 mL) and MeOH (10 mL) under N$_2$ was added dropwise SmI$_2$ (0.1M/THF, 45 mL) under ice-bath After stirred for 10 min, the reaction was quenched with saturated aqueous NH$_4$Cl (50 mL) and extracted with EAOAc (50 mL×3). The combined organic layers were washed with water (60 mL), dried over anhydrous Na$_2$SO$_4$ and concentrated under reduced pressure. The residue was purified by flash chromatography (silica gel, 0~3% methanol in dichloromethane) to give the desired product (310 mg). LC-MS found: 417 (M+H)$^+$. $^1$H NMR (400 MHz, CDCl$_3$) δ 8.31 (s, 1H), 7.60 (d, 1H), 6.39 (d, 1H), 5.49 (s, 2H), 4.58 (s, 2H), 4.43 (s, 3H), 3.62 (t, 2H), 0.95 (t, 2H), 0.0 (s, 9H).

Example 7E. Synthesis of 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one

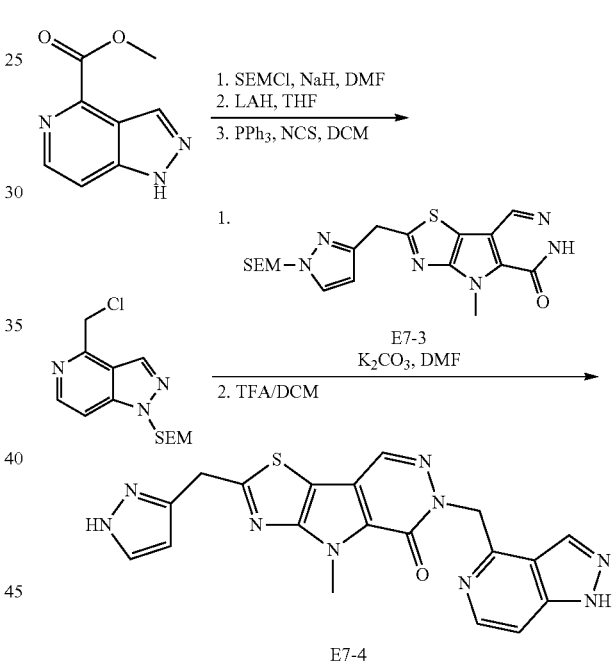

Step A. methyl 1-((2-(trimethylsilyl)ethoxy)methyl)-1H-pyrazolo[4,3-c]pyridine-4-carboxylate. To a solution of methyl 1H-pyrazolo[4,3-c]pyridine-4-carboxylate (900 mg, 5.1 mmol) in dry DMF (10 mL) was added NaH (305 mg, 7.6 mmol, 60%) at 0° C. in portions. The suspension was stirred for 15 min under ice bath before the introduction of (2-(chloromethoxy)ethyl)trimethylsilane (1.07 mL, 6.0 mmol) dropwise and stirred for another 1 hr at rt. Then the mixture was poured into sat. NH$_4$Cl (aq.), extracted with ethyl acetate. The combined organic layers was dried with anhydrous Na$_2$SO$_4$, filtered and concentrated. The residue was purified by flash chromatography (silica gel, 0~30% ethyl acetate in petroleum ether) to afford methyl 1-((2-(trimethylsilyl)ethoxy)methyl)-1H-pyrazolo[4,3-c]pyridine-4-carboxylate (1.32 g). LCMS: m/z 308 (M+H)$^+$.

Step B. (1-((2-(trimethylsilyl)ethoxy)methyl)-1H-pyrazolo[4,3-c]pyridin-4-yl)methanol. To a solution of methyl 1-((2-(trimethylsilyl)ethoxy)methyl)-1H-pyrazolo[4,3-c]

pyridine-4-carboxylate (1 g, 3.2 mmol) in dry THF (10 mL) was added LiHAl₄ (146 mg, 3.8 mmol) by portions under ice bath. The mixture was stirred for 30 min at 0° C. Then the suspension was poured into sat. NH₄Cl (aq.), extracted with ethyl acetate (2×). The combined organic layers were dried with anhydrous Na₂SO₄, filtered and concentrated. The residue was purified by flash chromatography (silica gel, 0~60% ethyl acetate in petroleum ether) to afford (1-((2-(trimethylsilyl)ethoxy)methyl)-1H-pyrazolo[4,3-c]pyridin-4-yl)methanol (500 mg). LCMS: m/z 280 (M+H)⁺.

Step C. 4-(chloromethyl)-1-((2-(trimethylsilyl)ethoxy)methyl)-1H-pyrazolo[4,3-c]pyridine To a solution of (1-((2-(trimethylsilyl)ethoxy)methyl)-1H-pyrazolo[4,3-c]pyridin-4-yl)methanol (120 mg, 0.43 mmol) in dichloromethane (2 mL) was added PPh₃ (225 mg, 0.86 mmol). The mixture was cooled down to 0° C. and NCS (114 mg, 0.86 mmol) was added. The suspension was warmed to rt and stirred for another 1 hr. Then the reaction was poured into sat. NaHCO₃ (aq.). The aqueous was extracted with dichloromethane. The combined organic layers were dried with anhydrous Na₂SO₄, filtered and concentrated. The residue was purified by flash chromatography (silica gel, 0~30% ethyl acetate in petroleum ether) to afford 4-(chloromethyl)-1-((2-(trimethylsilyl)ethoxy)methyl)-1H-pyrazolo[4,3-c]pyridine (70 mg) as an oil. LCMS: m/z 298 (M+H)⁺.

Step D. 4-methyl-2-((1-((2-(trimethylsilyl)ethoxy)methyl)-H-pyrazol-3-yl)methyl)-6-((1-((2-(trimethylsilyl)ethoxy)methyl)-1H-pyrazolo[4,3-c]pyridin-4-yl)methyl)-4H-thiazolo[5',4':4,5]pyrrolo[2,3-d]pyridazin-5(6H)-one. To a mixture of K₂CO₃ (41 mg, 0.3 mmol) in anhydrous DMF (2 mL) was added 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (41 mg, 0.1 mmol) and stirred at 50° C. for 30 min under argon. A solution of 4-(chloromethyl)-1-((2-(trimethylsilyl)ethoxy)methyl)-1H-pyrazolo[4,3-c]pyridine (30 mg, 0.1 mmol) in DMF (1 mL) was added and stirred for another 4 hrs. The suspension was cooled down to r.t and poured into 0.5 N HCl (aq.). The layers were separated and the aqueous layer was extracted with ethyl acetate. The combined organic layers were dried with anhydrous Na₂SO₄, filtered and concentrated. The residue was purified by pre-TLC to afford 4-methyl-2-((1-((2-(trimethylsilyl)ethoxy)methyl)-1H-pyrazol-3-yl)methyl)-6-((1-((2-(trimethylsilyl)ethoxy)methyl)-1H-pyrazolo[4,3-c]pyridin-4-yl)methyl)-4H-thiazolo[5',4':4,5]pyrrolo[2,3-d]pyridazin-5(6H)-one (40 mg, 60%). LCMS: m/z 678 (M+H)⁺.

Step E. 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one. A solution of 4-methyl-2-((1-((2-(trimethylsilyl)ethoxy)methyl)-1H-pyrazol-3-yl)methyl)-6-((1-((2-(trimethylsilyl)ethoxy)methyl)-1H-pyrazolo[4,3-c]pyridin-4-yl)methyl)-4H-thiazolo [5',4':4,5]pyrrolo[2,3-d]pyridazin-5(6H)-one (30 mg, 0.044 mmol) in 35% TFA (1 mL, in dichloromethane) was stirred at r.t overnight. The mixture was concentrated and the residue was purified by pre-HPLC to afford 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one (3 mg). LCMS: m/z 418 (M+H)⁺. ¹H NMR (400 MHz, DMSO-d6) δ 13.51 (s, 1H), 12.78 (s, 1H), 8.55 (s, 1H), 8.18 (d, 1H), 8.00 (s, 1H), 7.68 (s, 1H), 7.43 (d, 1H), 6.27 (d, 1H), 5.78 (s, 2H), 4.51 (s, 2H), 4.25 (s, 3H).

The following compounds were synthesized according to Scheme E7 and the procedure of Example 7C-7E using the appropriate starting material.

| Cpd No. | Structure | Characterization |
|---|---|---|
| E7-5 | 2-((1H-pyrazol-3-yl)methyl)-6-(benzo[d][1,3]dioxol-5-ylmethyl)-4-methyl-4H-thiazolo[5',4':4,5]pyrrolo[2,3-d]pyridazin-5(6H)-one | LCMS: 421 (M + H)+. 1H NMR (400 MHz, DMSO) δ 12.77 (s, 1H), 8.51 (s, 1H), 7.70 (s, 1H), 6.89 (d, 1H), 6.86-6.80 (m, 2H), 6.26 (d, 1H), 5.97 (s, 2H), 5.24 (s, 2H), 4.49 (s, 2H), 4.26 (s, 3H). |
| E7-6 | 2-((1H-pyrazol-3-yl)methyl)-6-(benzo[d]thiazol-5-ylmethyl)-4-methyl-4,6-dihydro-5H-thiazolo[5',4':4,5]pyrrolo[2,3-d]pyridazin-5-one | LCMS: 434 (M + H)+. ¹H NMR (400 MHz, DMSO) δ 12.81 (s, 1H), 9.38 (s, 1H), 8.56 (s, 1H), 8.12 (d, 1H), 7.98 (s, 1H), 7.67 (s, 1H), 7.48 (d, 1H), 6.26 (s, 1H), 5.52 (s, 2H), 4.49 (s, 2H), 4.27 (s, 3H) |

-continued

| Cpd No. | Structure | Characterization |
|---|---|---|
| E7-7 | 2-((1H-pyrazol-3-yl)methyl)-6-((2,2-dioxido-1,3-dihydrobenzo[c][1,2,5]thiadiazol-4-yl)methyl)-4-methyl-4H-thiazolo[5',4':4,5]pyrrolo[2,3-d]pyridazin-5(6H)-one | LCMS: 469 (M + H)+. 1HNMR(400 MHz, DMSO) δ 12.77 (s, 1H), 10.84 (s, 1H), 8.56 (s, 1H), 7.70 (s, 1H), 6.83-6.51 (m, 2H), 6.40 (d, 1H), 6.26 (d, 1H), 5.27 (s, 2H), 4.50 (s, 2H), 4.27 (s, 3H) |
| E7-8 | 6-((1H-benzo[d]imidazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: 417 (M + H)+. 1H NMR (400 MHz, DMSO-d6) δ 12.76 (s, 1H), 12.51 (s, 1H), 8.54 (s, 1H), 8.24 (s, 1H), 7.67 (s, 1H), 7.47 (s, 1H), 7.08 (t, 1H), 6.70 (s, 1H), 6.26 (d, 1H), 5.71 (s, 2H), 4.50 (s, 2H), 4.28 (s, 3H). |
| E7-9 | 2-((1H-pyrazol-3-yl)methyl)-6-(isoindolin-4-ylmethyl)-4-methyl-4H-thiazolo[5',4':4,5]pyrrolo[2,3-d]pyridazin-5(6H)-one | LCMS: m/z 418 (M + H)+. 1H NMR (400 MHz, DMSO-d6) δ 8.54 (s, 1H), 8.27 (s, 1H), 7.66 (s, 1H), 7.24-7.16 (m, 2H), 7.08 (d, 1H), 6.26 (d, 1H), 5.31 (s, 2H), 4.50 (s, 2H), 4.26 (s, 5H), 4.20 (s, 2H) |
| E7-10 | 2-((1H-pyrazol-3-yl)methyl)-6-(3-acetylbenzyl)-4-methyl-4H-thiazolo[5',4':4,5]pyrrolo[2,3-d]pyridazin-5(6H)-one | LCMS: m/z 419 (M + H)+. 1H NMR (400 MHz, DMSO-d6) δ 12.78 (s, 1H), 8.56 (s, 1H), 7.89-7.87 (m, 2H), 7.71 (s, 1H), 7.56 (d, 1H), 7.51-7.47 (m, 1H), 6.26 (d, 1H), 5.43 (s, 2H), 4.49 (s, 2H), 4.27 (s, 3H), 2.56 (s, 3H). |

-continued

| Cpd No. | Structure | Characterization |
|---|---|---|
| E7-11 | 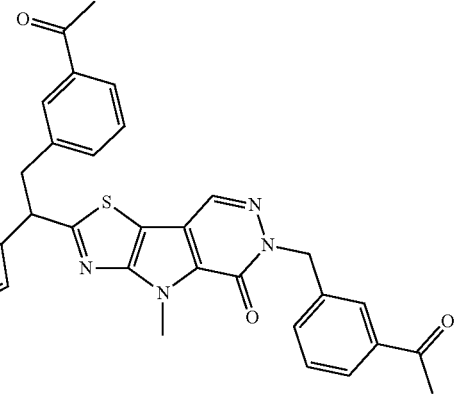<br>6-(3-acetylbenzyl)-2-(2-(3-acetylphenyl)-1-(1H-pyrazol-3-yl)ethyl)-4-methyl-4H-thiazolo[5',4':4,5]pyrrolo[2,3-d]pyridazin-5(6H)-one | LCMS: m/z 551 (M + H)+. 1H NMR (400 MHz, DMSO-d6) δ 12.73 (s, 1H), 8.54 (s, 1H), 7.89-7.87 (m, 2H), 7.83 (s, 1H), 7.73-7.71 (m, 2H), 7.56-7.46 (m, 3H), 7.36-7.33 (m, 1H), 6.32 (d, 1H), 5.42 (s, 2H), 4.99 (s, 1H), 4.27 (s, 3H), 3.67-3.59 (m, 2H), 2.56 (s, 3H), 2.49 (s, 3H). |
| E7-12 | 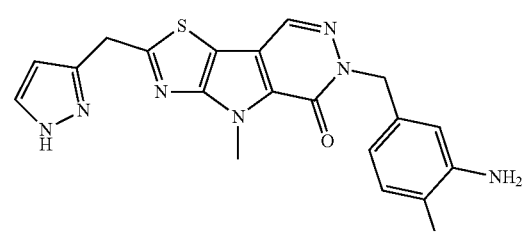<br>2-((1H-pyrazol-3-yl)methyl)-6-(3-amino-4-hydroxybenzyl)-4-methyl-4H-thiazolo[5',4':4,5]pyrrolo[2,3-d]pyridazin-5(6H)-one | LCMS: m/z 408 (M + H)+. 1H NMR (400 MHz, DMSO) δ 12.76 (s, 1H), 8.93 (s, 1H), 8.50 (s, 1H), 7.67 (s, 1H), 6.57 (d, 1H), 6.55 (d, 1H), 6.39 (dd, 1H), 6.26 (s, 1H), 5.11 (s, 2H), 4.49 (br s, 4H), 4.27 (s, 3H). |
| E7-13 | 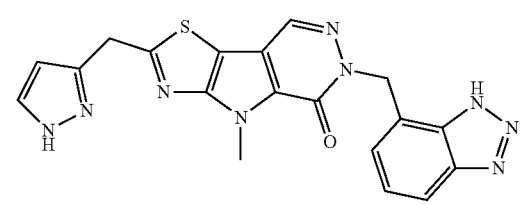 [SMILES: Cn1c2nc(Cc3cc[nH]n3)sc2c2cnn(Cc3cccc4nn[nH]c34)c(=O)c21]<br>6-((1H-benzo[d][1,2,3]triazol-7-yl)methyl)-2-((1H-pyrazol-3-yl)methyl)-4-methyl-4H-thiazolo[5',4':4,5]pyrrolo[2,3-d]pyridazin-5(6H)-one | LC-MS: 418 (M + H)+. 1H NMR (400 MHz, DMSO) δ 12.76 (s, 1H), 8.55 (s, 1H), 7.78 (d, 1H), 7.65 (d, 1H), 7.36 (dd, 1H), 7.05 (d, 1H), 6.25 (d, 1H), 5.78 (s, 2H), 4.48 (s, 2H), 4.24 (s, 3H). |
| E7-14 | 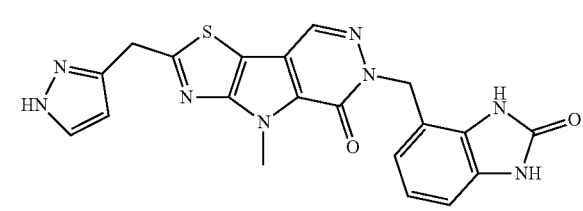 [SMILES: Cn1c2nc(Cc3cc[nH]n3)sc2c2cnn(Cc3cccc4[nH]c(=O)[nH]c34)c(=O)c21]<br>2-((1H-pyrazol-3-yl)methyl)-4-methyl-6-((2-oxo-2,3-dihydro-1H-benzo[d]imidazol-4-yl)methyl)-4H-thiazolo[5',4':4,5]pyrrolo[2,3-d]pyridazin-5(6H)-one | LCMS: m/z 433 (M + H)+. 1H NMR (400 MHz, DMSO) δ 12.78 (s, 1H), 10.69 (d, 2H), 8.55 (s, 1H), 7.68 (s, 1H), 6.84 (d, 2H), 6.73-6.59 (m, 1H), 6.27 (d, 1H), 5.41 (s, 2H), 4.50 (s, 2H), 4.28 (s, 3H). |

| Cpd No. | Structure | Characterization |
|---|---|---|
| E7-15 | 2-((1H-pyrazol-3-yl)methyl)-6-((1H-pyrazolo[3,4-b]pyridin-3-yl)methyl)-4-methyl-4H-thiazolo[5',4':4,5]pyrrolo[2,3-d]pyridazin-5(6H)-one | LC-MS: m/z 418 (M + H)⁺. ¹H NMR (400 MHz, DMSO) δ 13.52 (s, 1H), 12.77 (s, 1H), 8.53 (s, 1H), 8.50-8.46 (m, 1H), 8.15 (d, 1H), 7.70 (s, 1H), 7.14 (dd, 1H), 6.26 (d, 1H), 5.67 (s, 2H), 4.49 (s, 2H), 4.28 (s, 3H). |
| E7-16 | 2-((1H-pyrazol-3-yl)methyl)-6-benzyl-4-methyl-4,6-dihydro-5H-thiazolo[5',4':4,5]pyrrolo[2,3-d]pyridazin-5-one | LCMS: m/z 377(M + 1)⁺. ¹H NMR (400 MHz, DMSO-d₆) δ 12.77 (s, 1H), 8.53 (s, 1H), 7.70 (s, 1H), 7.35-7.22 (m, 5H), 6.26 (d, 1H), 5.34 (s, 2H), 4.48 (s, 2H), 4.27 (s, 3H). |
| E7-17 | 2-((1H-pyrazol-3-yl)methyl)-6-((1H-pyrazolo[4,3-b]pyridin-5-yl)methyl)-4-methyl-4H-thiazolo[5',4':4,5]pyrrolo[2,3-d]pyridazin-5(6H)-one | LCMS: m/z 418 (M + H)⁺. ¹HNMR (400 MHz, DMSO) δ 13.29 (s, 1H), 12.8 (brs, 1H), 8.54 (s, 1H), 8.20 (s, 1H), 7.96 (d, 1H), 7.67 (s, 1H), 7.24 (d, 1H), 6.27 (d, 1H), 5.57 (s, 2H), 4.51 (s, 2H), 4.27 (s, 3H). |
| E7-18 | 2-((1H-pyrazol-3-yl)methyl)-6-(imidazo[1,2-a]pyrimidin-2-ylmethyl)-4-methyl-4,6-dihydro-5H-thiazolo[5',4':4,5]pyrrolo[2,3-d]pyridazin-5-one | LCMS: m/z 418 (M + H)⁺. ¹HNMR (400 MHz, DMSO) δ 12.79 (s, 1H), 8.92 (dd, 1H), 8.61 (s, 1H), 8.55 (dd, 1H), 8.31 (s, 1H), 7.75 (s, 1H), 7.73 (s, 1H), 7.08 (dd, 1H), 6.33 (d, 1H), 5.55 (s, 2H), 4.57 (s, 2H), 4.34 (s, 3H). |
| E7-19 | 6-((1H-indazol-3-yl)methyl)-2-((1H-pyrazol-3-yl)methyl)-4-methyl-4H-thiazolo[5',4':4,5]pyrrolo[2,3-d]pyridazin-5(6H)-one | LCMS: ESI m/z 417 (M + H)⁺. ¹H NMR (400 MHz, DMSO-d₆) δ 12.91 (s, 1H), 12.77 (s, 1H), 8.51 (s, 1H), 7.73-7.70 (m, 2H), 7.48 (d, 1H), 7.30 (dd, 1H), 7.04 (t, 1H), 6.25 (d, 1H), 5.68 (s, 2H), 4.48 (s, 2H), 4.28 (s, 3H). |

| Cpd No. | Structure | Characterization |
|---|---|---|
| E7-20 | 2-((1H-pyrazol-3-yl)methyl)-4-methyl-6-((3-oxo-2,3-dihydro-1H-indazol-4-yl)methyl)-4H-thiazolo[5',4':4,5]pyrrolo[2,3-d]pyridazin-5(6H)-one | LCMS: m/z 433(M + H)$^+$.<br>$^1$H NMR (400 MHz, DMSO) δ 12.78 (s, 1H), 11.37 (s, 1H), 8.57 (s, 1H), 7.70 (s, 1H), 7.13 (d, 2H), 6.38-6.29 (m, 1H), 6.27 (d, 1H), 5.79 (s, 2H), 4.51 (s, 2H), 4.27 (s, 3H). |
| E7-21 | 2-((1H-pyrazol-3-yl)methyl)-6-(3-hydroxybenzyl)-4-methyl-4,6-dihydro-5H-thiazolo[5',4':4,5]pyrrolo[2,3-d]pyridazin-5-one | LCMS: m/z 393 (M + H)$^+$.<br>$^1$H NMR (400 MHz, DMSO-d$_6$) δ 12.82 (s, 1H), 9.39 (s, 1H), 8.58 (s, 1H), 7.76 (s, 1H), 7.15(s, 1H), 6.92-6.55 (m, 3H), 6.31 (s, 1H), 5.30 (s, 2H), 4.53 (s, 2H), 4.28 (s, 3H) |
| E7-22 | 2-((1H-pyrazol-3-yl)methyl)-6-((1H-pyrazolo[4,3-b]pyridin-3-yl)methyl)-4-methyl-4,6-dihydro-5H-thiazolo[5',4':4,5]pyrrolo[2,3-d]pyridazin-5-one | LCMS: m/z 418 (M + H)$^+$.<br>$^1$H NMR (400 MHz, DMSO-d$_6$) δ 13.15 (s, 1H), 12.83 (s, 1H), 8.52(s, 2H), 8.02 (dd, 1H), 7.74 (s, 1H), 7.40 (dd, 1H), 6.32 (d, 1H), 5.81 (s, 2H), 4.55 (s, 2H), 4.33 (s, 3H). |
| E7-23 | 2-((1H-pyrazol-3-yl)methyl)-4-methyl-6-((1-methyl-1H-pyrazolo[4,3-b]pyridin-5-yl)methyl)-4,6-dihydro-5H-thiazolo[5',4':4,5]pyrrolo[2,3-d]pyridazin-5-one | LCMS: m/z 432 (M + H)$^+$.<br>$^1$H NMR (400 MHz, DMSO-d$_6$) δ 12.80 (s, 1H), 8.54 (s, 1H), 8.16 (s, 1H), 8.09 (d, 1H), 7.69 (s, 1H), 7.29 (d, 1H), 6.27 (s, 1H), 5.57 (s, 2H), 4.51 (s, 2H), 4.27 (s, 3H), 4.05 (s, 3H). |

-continued

| Cpd No. | Structure | Characterization |
|---|---|---|
| E7-24 | 2-((1H-pyrazol-3-yl)methyl)-4-methyl-6-(naphthalen-2-ylmethyl)-4,6-dihydro-5H-thiazolo[5',4':4,5]pyrrolo[2,3-d]pyridazin-5-one | LCMS: m/z 427 (M + H)⁺.<br>$^1$H NMR (400 MHz, DMSO-$d_6$) δ 12.78 (s, 1H), 8.56 (s, 1H), 7.89-7.86 (m, 3H), 7.78 (s, 1H), 7.68 (s, 1H), 7.51-7.48 (m, 3H), 6.26 (d, 1H), 5.52 (s, 2H), 4.48 (s, 2H), 4.27 (s, 3H). |
| E7-25 | 2-((1H-pyrazol-3-yl)methyl)-6-((2-aminobenzo[d]thiazol-4-yl)methyl)-4-methyl-4,6-dihydro-5H-thiazolo[5',4':4,5]pyrrolo[2,3-d]pyridazin-5-one | LCMS: m/z 449 (M + H)⁺.<br>$^1$H NMR (400 MHz, DMSO-$d_6$) δ 12.79 (s, IH), 8.55 (s, 1H), 7.70 (s, 1H), 7.63 (s, 2H), 7.54 (d, IH), 6.89 (dd, 1H), 6.66 (d, IH), 6.27 (d, 1H), 5.59 (s, 2H), 4.50 (s, 2H), 4.27 (s, 3H). |
| E7-26 | 6-((1H-indol-4-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: m/z 416 (M + H)⁺.<br>$^1$H NMR (400 MHz, DMSO-$d_6$) δ 12.77 (s, 1H), 11.13 (s, 1H), 8.51 (s, 1H), 7.70 (s, 1H), 7.32-7.28 (m, 2H), 7.00 (dd, 1H), 6.82 (d, 1H), 6.59 (s, 1H), 6.26 (s, IH), 5.58 (s, 2H), 4.48 (s, 2H), 4.28 (s, 3H). |
| E7-27 | 2-((1H-pyrazol-3-yl)methyl)-6-((1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 417 (M + H)⁺.<br>$^1$H NMR (400 MHz, DMSO-d6) δ: 12.79 (s, 1H), 11.59 (s, 1H), 8.53 (s, 1H), 7.89 (d, 1H), 7.69 (s, 1H), 7.40 (s, 1H), 6.92 (d, 1H), 6.40 (s, 1H), 6.27 (s, 1H), 5.51 (s, 2H), 4.50 (s, 2H), 4.27 (s, 3H). |

| Cpd No. | Structure | Characterization |
|---|---|---|
| E7-28 | 2-((1H-pyrazol-3-yl)methyl)-6-((3H-imidazo[4,5-b]pyridin-5-yl)methyl)-4-methyl-4H-thiazolo[5',4':4,5]pyrrolo[2,3-d]pyridazin-5(6H)-one | LC-MS: m/z 418 (M + H)$^+$.<br>$^1$H NMR (400 MHz, DMSO-d6) δ: 13.04 (s, 1H), 12.77 (s, 1H), 8.54 (s, 1H), 8.44-8.28 (m, 1H), 8.07-7.88 (m, 1H), 7.69 (s, 1H), 7.10 (d, 1H), 6.27 (d, 1H), 5.55 (s, 2H), 4.50 (s, 2H), 4.27 (s, 3H). |
| E7-29 | 2-((1H-pyrazol-3-yl)methyl)-6-((3-fluoro-1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 435 (M + H)$^+$.<br>$^1$H NMR (400 MHz, DMSO-d6) δ: 12.85 (s, 1H), 11.47 (s, 1H), 8.59 (s, 1H), 8.00 (d, 1H), 7.76 (s, 1H), 7.43 (t, 1H), 7.06 (d, 1H), 6.34 (d, 1H), 5.58 (s, 2H), 4.56 (s, 2H), 4.33 (s, 3H). |
| E7-30 | 2-((1H-pyrazol-3-yl)methyl)-6-((2,3-dihydro-1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 419 (M + H)$^+$.<br>$^1$H NMR (400 MHz, DMSO-d6) δ: 8.50 (s, 1H), 7.67 (s, 1H), 7.14 (d, 1H), 6.34 (s, 1H), 6.27 (d, 1H), 6.12 (d, 1H), 5.18 (s, 2H), 4.50 (s, 2H), 4.27 (s, 3H), 3.57 (m, 2H), 2.90 (t, 2H). |
| E7-31 | 5-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)oxazolo[4,5-b]pyridin-2(3H)-one | LC-MS: m/z 435 (M + H)$^+$.<br>$^1$H NMR (400 MHz, DMSO-d6) δ: 12.88 (s, 1H), 8.56 (s, 1H), 7.76 (s, 1H), 6.94 (d, 1H), 6.35-6.29 (m, 2H), 5.32 (s, 2H), 4.55 (s, 2H), 4.33 (s, 3H). |

| Cpd No. | Structure | Characterization |
|---|---|---|
| E7-32 | 2-((1H-pyrazol-3-yl)methyl)-4-methyl-6-((2-oxo-2,3-dihydro-1H-pyrrolo[2,3-b]pyridin-6-yl)methyl)-4,6-dihydro-5H-thiazolo[5',4':4,5]pyrrolo[2,3-d]pyridazin-5-one | LC-MS: m/z 433 (M + H)+.<br>1H NMR (400 MHz, DMSO-d6) δ: 12.84 (s, 1H), 11.01 (s, 1H), 8.59 (s, 1H), 7.74 (s, 1H), 7.53 (d, 1H), 6.76 (d, 1H), 6.33 (d, 1H), 5.40 (s, 2H), 4.56 (s, 2H), 4.32 (s, 3H), 3.56 (s, 2H). |
| E7-33 | 2-((1H-pyrazol-3-yl)methyl)-6-((2-chloro-1H-pyrrolo[2,3-b]pyridin-6-yl)methyl)-4-methyl-4,6-dihydro-5H-thiazolo[5',4':4,5]pyrrolo[2,3-d]pyridazin-5-one | LC-MS: m/z 451 (M + H)+.<br>1H NMR (400 MHz, DMSO-d6) δ: 12.87 (s, 1H), 8.59 (s, 1H), 8.46 (s, 1H), 7.88 (d, 1H), 7.73 (s, 1H), 7.02 (d, 1H), 6.51 (s, 1H), 6.33 (d, 1H), 5.55 (s, 2H), 4.57 (s, 2H), 4.33 (s, 3H) |
| E7-34 | 2-((1H-pyrazol-3-yl)methyl)-6-((2-fluoro-1H-pyrrolo[2,3-b]pyridin-6-yl)methyl)-4-methyl-4,6-dihydro-5H-thiazolo[5',4':4,5]pyrrolo[2,3-d]pyridazin-5-one | LC-MS: m/z 435 (M + H)+.<br>1H NMR (400 MHz, DMSO-d6) δ: 12.78 (s, 1H), 8.53 (s, 1H), 7.80 (d, 1H), 7.68 (s, 1H), 6.97 (d, 1H), 6.27 (d, 1H), 5.90 (d, 1H), 5.49 (s, 2H), 4.51 (s, 2H), 4.27 (s, 3H) |
| E7-35 | 2-((1H-pyrazol-3-yl)methyl)-6-(cyclohexylmethyl)-4-methyl-4,6-dihydro-5H-thiazolo[5',4':4,5]pyrrolo[2,3-d]pyridazin-5-one | LC-MS: m/z 383 (M + H)+.<br>1H NMR (400 MHz, DMSO-d6) δ: 12.84 (d, 1H), 8.47 (s, 1H), 7.71 (s, 1H), 6.26 (d, 1H), 4.47 (s, 2H), 4.26 (s, 3H), 4.00 (d, 2H), 1.96-1.83 (m, 1H), 1.76-1.40 (m, 6H), 1.33-0.55 (m, 4H) |

| Cpd No. | Structure | Characterization |
|---|---|---|
| E7-36 | 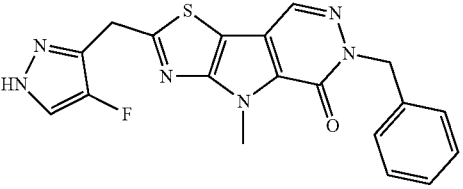 [SMILES: Cn1c2nc(Cc3n[nH]cc3F)sc2c2cnn(Cc3ccccc3)c(=O)c21]<br>6-benzyl-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 395 (M + H)+.<br>1H NMR (400 MHz, DMSO-d6) δ: 12.82 (s, 1H), 8.55 (s, 1H), 7.84 (s, 1H), 7.35-7.20 (m, 5H), 5.35 (s, 2H), 4.51 (s, 2H), 4.26 (s, 3H). |

Example 7F. Synthesis of 2-((1H-pyrazol-3-yl)methyl)-4-methyl-6-(2-(thiazol-4-yl)ethyl)-4H-thiazolo[5',4':4,5]pyrrolo[2,3-d]pyridazin-5(6H)-one

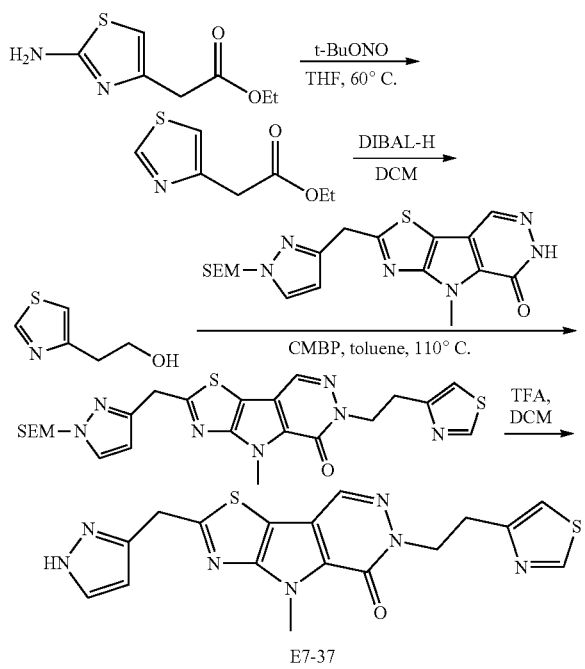

Step A. Synthesis of ethyl 2-(thiazol-4-yl)acetate To a solution of ethyl 2-(2-aminothiazol-4-yl)acetate (2 g, 10.7 mmol) in THF (30 mL) was added t-BuONO (1.6 g, 16.1 mmol). The reaction mixture was stirred at 50° C. for 16 hrs. After cooled to room temperature, the reaction mixture was diluted with EtOAc, washed with water and brine, dried over anhy. Na2SO4, concentrated in vacuum. The residue was purified by flash chromatography (silica gel, 80-100% EtOAc in PE) to afford ethyl 2-(thiazol-4-yl)acetate (400 mg). LC-MS (ESI): m/z 172 (M+1)+.

Step B. Synthesis of 2-(thiazol-4-yl) ethanol To a stirred solution of ethyl 2-(thiazol-4-yl)acetate (400 mg, 2.3 mmol) in DCM (20 mL) was added DIBAL-H (4.7 mL, 7.0 mmol). The reaction mixture was stirred at room temperature under N2 for 3 hrs. The reaction was quenched with satd. NaHCO3, extracted with DCM and the organic layer was washed with brine, dried over anhy. Na2SO4, concentrated in vacuum. The residue was purified by flash chromatography (silica gel, 50-100% EtOAc in PE) to afford 2-(thiazol-4-yl) ethanol (200 mg). LC-MS (ESI): m/z 130 (M+1)+.

Step C. Synthesis of 4-methyl-6-(2-(thiazol-4-yl)ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (60 mg, 0.14 mmol) and 2-(thiazol-4-yl) ethanol (55 mg, 0.4 mmol) in toluene (5 mL) was added CMBP (104 mg, 0.4 mmol). The reaction mixture was stirred at 110° C. under N2 for 3 hrs. After cooled to room temperature, the reaction mixture was diluted with EtOAc, washed with water and brine, dried over anhy. Na2SO4, concentrated in vacuum. The residue was purified by flash chromatography (silica gel, 80-100% EtOAc in PE) to afford 60 mg of 4-methyl-6-(2-(thiazol-4-yl)ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one. LC-MS: m/z 528 (M+1)+.

Step D. Synthesis of 2-((1H-pyrazol-3-yl)methyl)-4-methyl-6-(2-(thiazol-4-yl)ethyl)-4H-thiazolo[5',4':4,5]pyrrolo[2,3-d]pyridazin-5(6H)-one To a solution of 4-methyl-6-(2-(thiazol-4-yl)ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (60 mg, 0.1 mmol) in DCM (1 mL) was added TFA (0.5 mL). The reaction mixture was stirred at room temperature for 3 hrs. The reaction mixture was adjusted pH=7.5 with satd. NaHCO3, extracted with DCM, washed with brine, dried over anhy. Na2SO4, concentrated in vacuum. The residue was purified by prep-TLC (10% MeOH in DCM) to afford 10 mg of 2-((1H-pyrazol-3-yl)methyl)-4-methyl-6-(2-(thiazol-4-yl)ethyl)-4H-thiazolo[5',4':4,5]pyrrolo[2,3-d]pyridazin-5(6H)-one. LC-MS: m/z 398 (M+H)+. 1H NMR (400 MHz, DMSO-d6) δ 9.03 (s, 1H), 8.47 (s, 1H), 7.67 (s, 1H), 7.41 (s, 1H), 6.27 (s, 1H), 4.58-4.40 (m, 4H), 4.26 (s, 3H), 3.23 (t, 2H).

| Cpd No. | Structure | Characterization |
|---|---|---|
| E7-38 | 2-((1H-pyrazol-3-yl)methyl)-4-methyl-6-(2-(pyridin-3-yl)ethyl)-4,6-dihydro-5H-thiazolo[5′,4′:4,5]pyrrolo[2,3-d]pyridazin-5-one | LC-MS: m/z 392 (M + H)⁺.<br>¹H NMR (400 MHz, DMSO-d6) δ: 8.47 (s, 1H), 8.39 (dd, 2H), 7.79-7.47 (m, 2H), 7.28 (dd, 1H), 6.26 (d, 1H), 4.49 (s, 2H), 4.41 (t, 2H), 4.25 (s, 3H), 3.09 (t, 2H) |
| E7-39 | 2-((1H-pyrazol-3-yl)methyl)-4-methyl-6-(2-(1-methyl-1H-pyrazol-3-yl)ethyl)-4,6-dihydro-5H-thiazolo[5′,4′:4,5]pyrrolo[2,3-d]pyridazin-5-one | LC-MS: m/z 395 (M + H)⁺.<br>¹H NMR (400 MHz, DMSO-d6) δ: 12.77 (s, 1H), 8.50 (s, 1H), 7.72 (s, 1H), 7.54 (d, 1H), 6.26 (m, 1H), 6.04 (d, 1H), 4.48 (s, 2H), 4.43-4.31 (m, 2H), 4.27 (s, 3H), 3.76 (s, 3H), 3.01-2.90 (m, 2H). |
| E7-40 | 2-((1H-pyrazol-3-yl)methyl)-6-(2-(6-aminopyridin-2-yl)ethyl)-4-methyl-4H-thiazolo[5′,4′:4,5]pyrrolo[2,3-d]pyridazin-5(6H)-one | LC-MS: m/z 407 (M + H)⁺.<br>¹H NMR (400 MHz, DMSO-d6) δ: 12.80 (s, 1H), 8.49 (s, 1H), 7.71 (s, 1H), 7.26 (t, 1H), 6.35 (d, 1H), 6.31-6.25 (m, 2H), 5.85 (s, 2H), 4.49 (s, 2H), 4.42 (t, 2H), 4.28 (s, 3H), 2.93 (t, 2H). |

Example 8. Synthesis of Compounds E8-v, E8-vi, and E8-viii

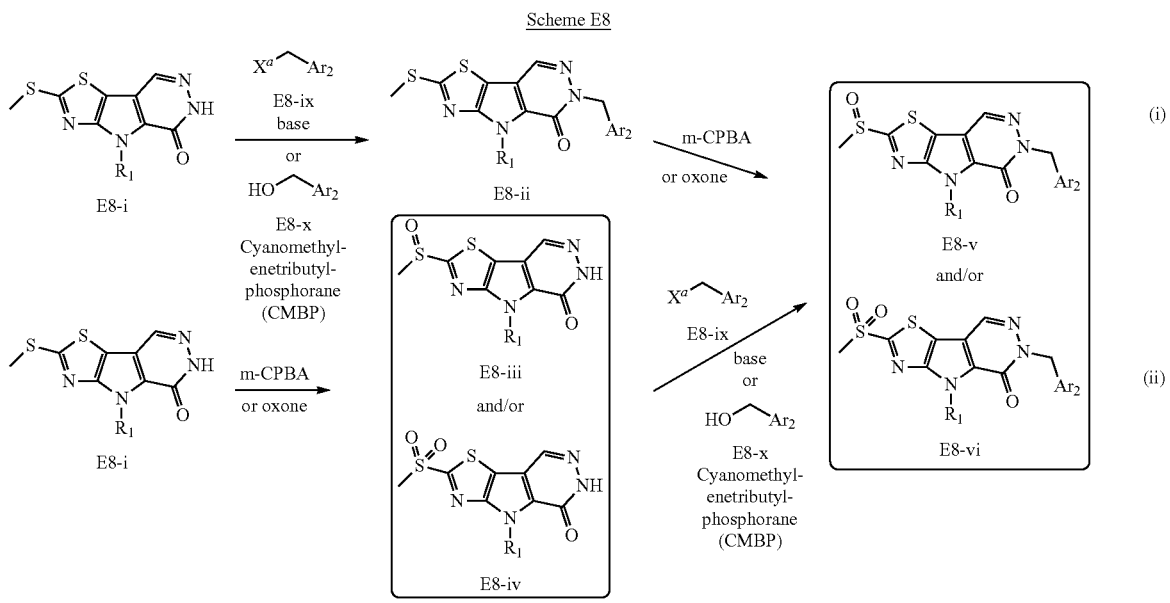

Scheme E8

-continued (iii)

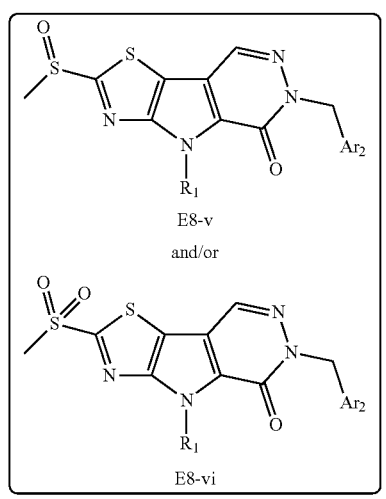

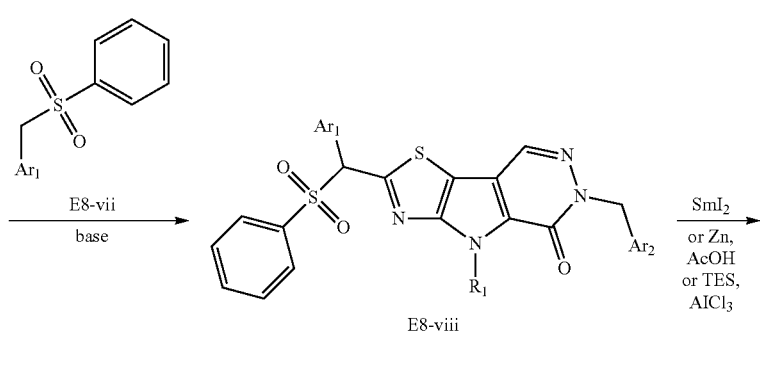

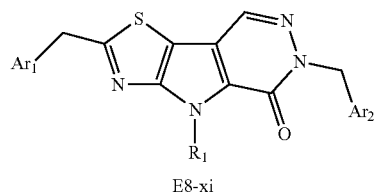

Compound E8-i can be converted to intermediate E8-ii through either akylation or Mitsunobu reaction like in example E7-v to E7-viii. Oxidation of E8-ii with either mCPBA or oxone generate compounds E8-v and E8-vi. Both compounds of E8-v and E8-vi can also be formed from E8-i by oxidation first followed by alkylation or Mitsumobu reaction. Wherein $X^a$ is a leaving group (e.g. Cl, Br, I, OMs, OTs); Compounds E8-v and E8-vi can be converted to intermediate E8-viii through nucleophilic aromatic substitution reaction with compound E8-vii, using LiHMDS or t-BuOK as a base. Compound E8-xi can be synthesized from compound E8-viii using either SmI2 or Zn in AcOH or TES with AlCl3. As used herein, R1 is optionally substituted alkyl, optionally substituted aryl, optionally substituted heteroaryl, optionally substituted carbocycle or optionally substituted heterocyclyl; Ar1 and Ar2 are each independently optionally substituted aryl, optionally substituted heteroaryl, optionally substituted carbocycle or optionally substituted heterocyclyl; optionally substituted alkyl, alkylaryl, alkylheteroaryl, alkyenyl, and alkynyl, provided that Ar1 and Ar2 are not both optionally substituted 5-membered or 6-membered monocyclic heteroaryl. In certain embodiments, R1 is optionally substituted C1-6 alkyl (e.g. methyl or ethyl).

Example 8A. Synthesis of 6-((1H-indazol-4-yl)methyl)-2-((5-chloro-1H-pyrazol-3-yl)methyl)-4-methyl-4H-thiazolo[5',4':4,5]pyrrolo[2,3-d]pyridazin-5(6H)-one

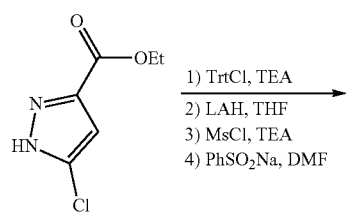

1) TrtCl, TEA
2) LAH, THF
3) MsCl, TEA
4) PhSO2Na, DMF

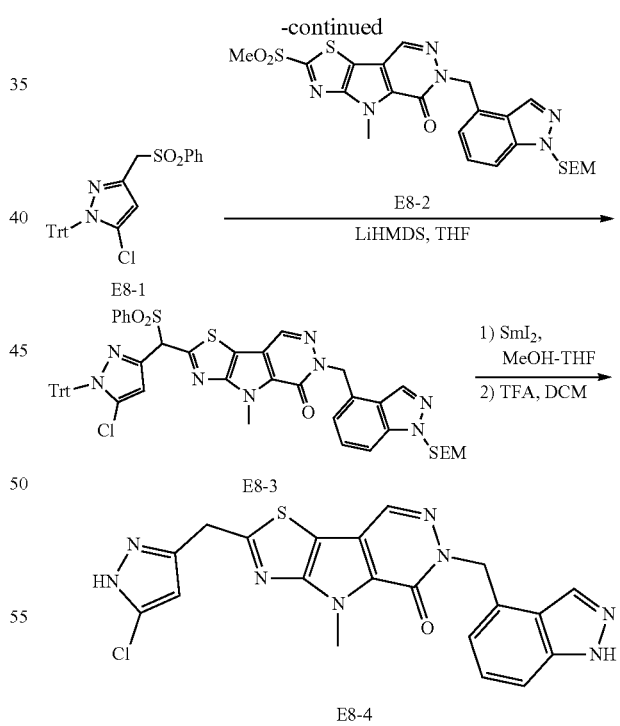

Ethyl 5-chloro-1-trityl-1H-pyrazole-3-carboxylate: To a stirred mixture of ethyl 5-chloro-1H-pyrazole-3-carboxylate (100 mg, 0.575 mmol) and TEA (0.24 mL, 1.44 mmol) in dry DCM (10 mL) was added TrtCl (192 mg, 0.689 mmol) at r.t. The reaction mixture was stirred at r.t. for 2 h and then poured into H2O. The resulting mixture was extracted with DCM. The organic layer was washed with brine (30 mL), dried over anhydrous Na$_2$SO$_4$ and concentrated under reduced pressure. The residue was purified by flash chromatography (silica gel, 0-4% ethyl acetate in petroleum ether) to give the desired product (crude, 240 mg, 100%).

(5-chloro-1-trityl-1H-pyrazol-3-yl)methanol: To a stirred mixture of ethyl 5-chloro-1-trityl-1H-pyrazole-3-carboxylate (1.20 g, 2.88 mmol) in dry THF (10 mL) was added LAH (400 mg, 10.5 mmol) at −30° C. The reaction mixture was stirred at −30° C. for 0.5 h. Na$_2$SO$_4$10H$_2$O (2 g) was added slowly to quench reaction. The resulting mixture was diluted with EtOAc and filtered through a pad of celite. The filtrate was concentrated and residue was purified by flash chromatography (silica gel, 10%-15% ethyl acetate in petroleum ether) to give desired product (540 mg).

(5-chloro-1-trityl-1H-pyrazol-3-yl)methyl methanesulfonate: To a stirred mixture of (5-chloro-1-trityl-1H-pyrazol-3-yl)methanol (100 mg, 0.267 mmol) and DIPEA (0.14 mL, 0.801 mmol) in dry DCM (10 mL) was added MsCl (46 mg, 0.401 mmol) at 10° C. The reaction mixture was stirred at r.t for 1 h. The reaction mixture was quenched with water. The resulting mixture was extracted with DCM (2×). The combined organic layers were washed with brine (30 mL), dried over anhydrous Na2SO4 and concentrated under reduced pressure to give the desired product (crude, 150 mg) as a sticky oil.

5-chloro-3-((phenylsulfonyl)methyl)-1-trityl-1H-pyrazole: To a stirred mixture of (5-chloro-1-trityl-1H-pyrazol-3-yl)methyl methanesulfonate (150 mg crude, 0.267 mmol) in dry DMF (10 mL) was added PhSO$_2$Na (100 mg, 0.610 mmol) at r.t. The reaction mixture was stirred at r.t for 20 h. The reaction mixture was dilutee with water. The resulting mixture was extracted with EtOAc (2X). The organic layers were washed with brine (30 mL), dried over anhydrous Na$_2$SO$_4$ and concentrated under reduced pressure. The residue was purified by prep-TLC (eluent: PE/EtOAc=3/1) to give the desired product (80 mg). LCMS: m/z 521 (M+Na)$^+$.

2-((5-chloro-1-trityl-1H-pyrazol-3-yl)(phenylsulfonyl) methyl)-4-methyl-6-((1-((2-(trimethylsilyl)ethoxy)methyl)-1H-indazol-4-yl)methyl)-4,6-dihydro-5H-thiazolo[5',4':4,5] pyrrolo[2,3-d]pyridazin-5-one: To a mixture of 5-chloro-3-((phenylsulfonyl)methyl)-1-trityl-1H-pyrazole (100 mg, 0.2 mmol) and 4-methyl-2-(methylsulfonyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.2 mmol) in dry THF (10 mL) was added dropwise LiHMDS (1 mL, 10 mmol, 1M in THF) at 10° C. The reaction mixture was stirred at r.t. for 10 min and poured into aqueous NH$_4$Cl. The following mixture was extracted with EtOAc (2X). The combined organic layers were washed with brine (30 mL), dried over anhydrous Na$_2$SO$_4$ and concentrated under reduced pressure. The residue was purified by flash chromatography (silica gel, 0~30% ethyl acetate in petroleum ether) to give the desired product of E8-3 (75 mg) as yellow oil. LCMS: m/z 985 (M+Na)$^+$.

2-((5-chloro-1-trityl-1H-pyrazol-3-yl)methyl)-4-methyl-6-((1-((2-(trimethylsilyl) ethoxy)methyl)-1H-indazol-4-yl) methyl)-4H-thiazolo[5',4':4,5]pyrrolo[2,3-d]pyridazin-5 (6H)-one. To a mixture of compound E8-3 (75 mg, 0.0779 mmol) in THF (5 mL) and MeOH (5 mL) at r.t. under N$_2$ was added SmI$_2$ (5 mL, 0.1M in THF). The reaction mixture was stirred at r.t for 10 min and then quenched with water. The following mixture was extracted with EtOAc (2X). The combined organic layers were washed with brine (30 mL), dried over anhydrous Na$_2$SO$_4$ and concentrated under reduced pressure. The residue was purified by prep-TLC (PE/EtOAc=2/1) to give 2-((5-chloro-1-trityl-1H-pyrazol-3-yl)methyl)-4-methyl-6-((1-((2-(trimethylsilyl)ethoxy)

methyl)-1H-indazol-4-yl)methyl)-4H-thiazolo[5',4':4,5]pyrrolo[2,3-d]pyridazin-5(6H)-one (50 mg). LCMS: m/z 845 (M+23)$^+$.

6-((1H-indazol-4-yl)methyl)-2-((5-chloro-1H-pyrazol-3-yl)methyl)-4-methyl-4H-thiazolo[5',4':4,5]pyrrolo[2,3-d] pyridazin-5(6H)-one. To a mixture of 2-((5-chloro-1-trityl-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50 mg, 0.0608 mmol) in DCM (6 mL) at r.t. under N$_2$ was added TFA (2 mL). The reaction mixture was stirred at r.t. for 1 h. The following mixture was adjusted to pH=8 with aqueous NaHCO$_3$, extracted with 80% DCM/iPrOH (2X). The combined organic layers were washed with brine (30 mL), dried over anhydrous Na$_2$SO$_4$ and concentrated under reduced pressure. The residue was purified by prep-HPLC (C18, 0-50% acetonitrile in H$_2$O with 0.1% formic acid) to give desire product (10 mg). LCMS: m/z 451 (M+H)$^+$. $^1$H NMR (400 MHz, DMSO-d$_6$) δ 13.10-13.2 (brs, 2H), 8.58 (s, 1H), 8.14 (s, 1H), 7.43-7.46 (m, 1H), 7.25-7.30 (m, 1H), 6.94-6.97 (m, 1H), 6.32 (s, 1H), 5.65 (s, 2H), 4.55 (s, 2H), 4.27 (s, 3H).

Example 8B. Synthesis of 2-((1H-1,2,3-triazol-4-yl) methyl)-4-methyl-6-(3-(trifluoromethoxy)benzyl)-4H-thiazolo[5',4':4,5]pyrrolo[2,3-d]pyridazin-5(6H)-one

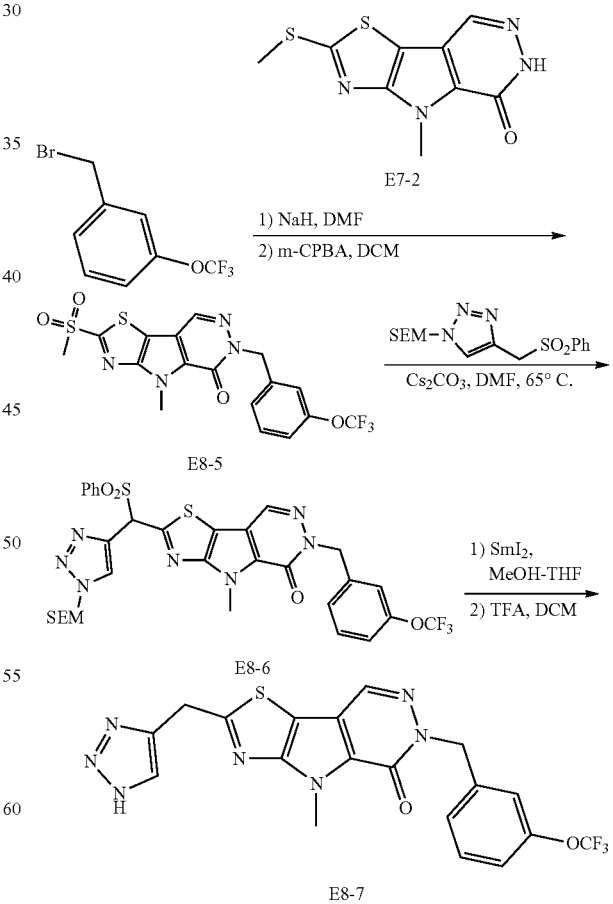

Step A. Synthesis of 4-methyl-2-(methylthio)-6-(3-(trifluoromethoxy)benzyl)-4H-thiazolo[5',4':4,5]pyrrolo[2,3-d]

pyridazin-5(6H)-one. To a solution of NaH (130 mg, 3.2 mmol) in DMF (4 mL) was added 4-methyl-2-(methylthio)-4H-thiazolo[5',4':4,5]pyrrolo[2,3-d]pyridazin-5(6H)-one (270 mg, 1.1 mmol) at 0° C. under $N_2$. After 5 min, the mixture 1-(bromomethyl)-3-(trifluoromethoxy)benzene (420 mg, 1.65 mmol) in DMF (2 mL) was added to the reaction mixture. The mixture was stirred at r.t. for 2 hr. The reaction was quenched with saturated $NH_4Cl$ and extracted with EA. The organic layer was washed with saturated NaCl (3×), dried over anhydrous $Na_2SO_4$ and concentrated under reduced pressure. The residue was purified by flash chromatography (silica gel, 0~30% ethyl acetate in petroleum ether) to give 4-methyl-2-(methylthio)-6-(3-(trifluoromethoxy)benzyl)-4H-thiazolo[5',4':4,5]pyrrolo[2,3-d]pyridazin-5(6H)-one (420 mg). LCMS: 427 (M+H)$^+$.

Step B. Synthesis of 4-methyl-2-(methylsulfonyl)-6-(3-(trifluoromethoxy)benzyl)-4H-thiazolo[5',4':4,5]pyrrolo[2,3-d]pyridazin-5(6H)-one. To a solution of 4-methyl-2-(methylthio)-6-(3-(trifluoromethoxy)benzyl)-4H-thiazolo[5',4':4,5]pyrrolo[2,3-d]pyridazin-5(6H)-one (420 mg, 0.99 mmol) in DCM (10 ml) was added mCPBA (520 mg, 3.0 mmol) at 0° C. under N2. The reaction mixture continued to stir overnight. The solution was quenched with saturated $Na_2S_2O_3$ and extracted with DCM (3×). The combined organic layers were dried over anhydrous $Na_2SO_4$ and concentrated under vacuum. The residue was purified by flash chromatography (silica gel, 0~50% ethyl acetate in petroleum ether) to give 4-methyl-2-(methylsulfonyl)-6-(3-(trifluoromethoxy) benzyl)-4H-thiazolo[5',4':4,5]pyrrolo[2,3-d]pyridazin-5(6H)-one (330 mg). LCMS: m/z 459 (M+H)$^+$.

Step C. Synthesis of 4-methyl-2-((phenylsulfonyl)(1-((2-(trimethylsilyl)ethoxy) methyl)-1H-1,2,3-triazol-4-yl)methyl)-6-(3-(trifluoromethoxy)benzyl)-4,6-dihydro-5H-thiazolo[5',4':4,5]pyrrolo[2,3-d]pyridazin-5-one. To a mixture of 4-methyl-2-(methylsulfonyl)-6-(3-(trifluoromethoxy)benzyl)-4H-thiazolo[5',4':4,5]pyrrolo[2,3-d]pyridazin-5(6H)-one (165 mg, 0.36 mmol) and 4-((phenylsulfonyl)methyl)-1-((2-(trimethylsilyl)ethoxy)methyl)-1H-1,2,3-triazole (50 mg, 0.54 mmol) in dry DMF (10 mL) was added $Cs_2CO_3$ (351 mg, 1.08 mmol) at 65° C. The reaction mixture was stirred at 65° C. for 2 hrs and poured into aqueous $NH_4Cl$. The resulting mixture was extracted with EtOAc (2×). The combined organic layers were washed with brine (30 mL), dried over anhydrous $Na_2SO_4$ and concentrated under reduced pressure. The residue was purified by lash chromatography (silica gel, 0~35% ethyl acetate in petroleum ether) to give the desired product 4-methyl-2-((phenylsulfonyl)(1-((2-(trimethylsilyl)ethoxy) methyl)-1H-1,2,3-triazol-4-yl)methyl)-6-(3-(trifluoromethoxy)benzyl)-4,6-dihydro-5H-thiazolo[5',4':4,5]pyrrolo[2,3-d]pyridazin-5-one (E8-6) (200 mg). LCMS: m/z 732 (M+H)$^+$.

Step D. Synthesis of 2-((1H-1,2,3-triazol-4-yl)methyl)-4-methyl-6-(3-(trifluoromethoxy)benzyl)-4H-thiazolo[5',4':4,5]pyrrolo[2,3-d]pyridazin-5(6H)-one. Similar to Example 8A, Compound E8-6 reacted with $SmI_2$, followed by deprotection with TFA, to give the desired product. LCMS: 462 (M+H)$^+$. $^1$HNMR (400 MHz, DMSO) δ 8.52 (s, 1H), 7.88 (s, 1H), 7.46 (dd, 1H), 7.39-7.2 (m, 3H), 5.40 (s, 2H), 4.63 (s, 2H), 4.26 (s, 3H).

Example 8C. Synthesis of 2,6-bis((1H-indazol-4-yl)methyl)-4-methyl-4H-thiazolo [5',4':4,5] pyrrolo[2,3-d]pyridazin-5(6H)-one

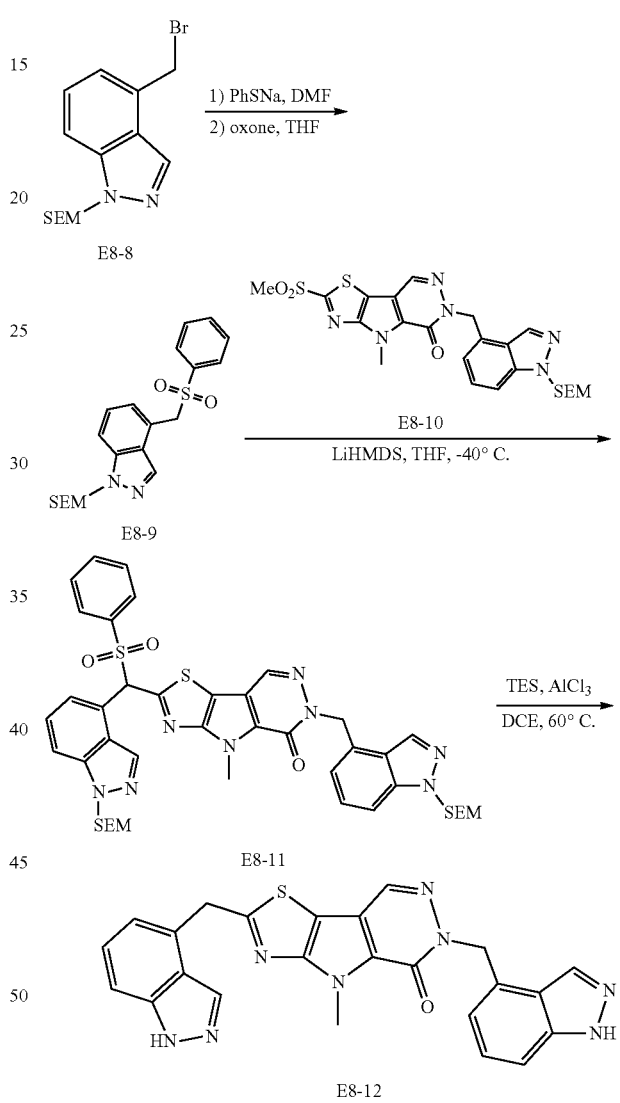

Step A: 4-((phenylthio)methyl)-1-((2-(trimethylsilyl)ethoxy)methyl)-1H-indazole. To a solution of 4-(bromomethyl)-1-((2-(trimethylsilyl)ethoxy)methyl)-1H-indazole (340 mg, 1.0 mmol) in DMF (10 mL) was added sodium benzenethiolate (265 mg, 2 mmol). The mixture was stirred at r.t. for 2 hr. then quenched with ice water (10.0 mL) and extracted with EtOAc (3×50.0 mL). The combined organic layers were washed with brine, dried over anhydrous $Na_2SO_4$ and concentrated under reduced pressure to afford the crude product (370 mg) which was directly used in the next step. LCMS: m/z 371 (M+H)$^+$.

Step B: 4-((Phenylsulfonyl)methyl)-1-((2-(trimethylsilyl)ethoxy)methyl)-1H-indazole. To a solution of 4-((phenylthio)methyl)-1-((2-(trimethylsilyl)ethoxy) methyl)-1H-indazole (370 mg) in THF (20 mL) at 0° C. was added a solution of oxone (2.15 g, 3.5 mmol) in $H_2O$ (20 mL). The mixture was stirred at r.t. for 1 hr. then quenched with ice water (50 mL) and extracted with AcOEt (3×50.0 mL). The combined organic layers were washed with brine, dried over anhydrous $Na_2SO_4$ and concentrated under reduced pressure. The residue was purified by column chromatography on silica gel (eluent: EA/PE=1/5) to afford the desired product (300 mg). LCMS: m/z 403 (M+H)+.

Step C: 4-Methyl-2-((phenylsulfonyl)(1-((2-(trimethylsilyl)ethoxy)methyl)-1H-indazol-4-yl)methyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one. To a solution of 4-((phenylsulfonyl)methyl)-1-((2-(trimethylsilyl)ethoxy)methyl)-1H-indazole (163 mg, 0.40 mmol, 2.2 eq) in dry THF (5 mL) at −40° C. was added drop wise LiHMDS (0.46 mL, 0.46 mmol, 2.5 eq). The mixture was stirred at this temperature for 10 min, followed by drop wise addition of a solution of 4-methyl-2-(methylsulfonyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.18 mmol, 1.0 eq) in dry THF (3 mL) at −40° C. The mixture was stirred at this temperature for another 30 min till completion. The resulting mixture was poured into icy saturated aqueous $NH_4Cl$ (20 mL) and extracted with EtOAc (3×10 mL). The combined organic layers were washed with water (20 mL), dried over anhydrous $Na_2SO_4$ and concentrated under reduced pressure. The residue was purified by prep-TLC to give the desired product (100 mg). LCMS: m/z 867 (M+H)+.

Step D: 2,6-Bis((1H-indazol-4-yl)methyl)-4-methyl-4H-thiazolo[5',4':4,5]pyrrolo [2,3-d]pyridazin-5(6H)-one. To a solution of 4-methyl-2-((phenylsulfonyl)(1-((2-(trimethylsilyl)ethoxy)methyl)-1H-indazol-4-yl)methyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one (50 mg, 0.06 mmol, 1.0 eq) in dry DCE (2 mL) under $N_2$ were added $AlCl_3$ (38 mg, 0.30 mmol, 5.0 eq) and TES (34 mg, 0.30 mmol, 5.0 eq). The mixture was heated to 60° C. for 30 min, then cooled to r.t., poured into water (10 mL) and extracted with DCM/MeOH (V:V=20:1, 3×10 mL). The combined organic layers were dried over anhydrous $Na_2SO_4$ and concentrated under reduced pressure. The residue was purified by prep-HPLC to give the desired product (5 mg). LCMS: m/z 467 (M+H)+. $^1$H NMR (400 MHz, DMSO-$d_6$) δ 13.15 (s, 1H), 13.10 (s, 1H), 8.50 (s, 1H), 8.18 (s, 1H), 8.13 (s, 1H), 7.49 (d, 1H), 7.44 (d, 1H), 7.38-7.30 (m, 1H), 7.29-7.21 (m, 1H), 7.14 (d, 1H), 6.93 (d, 1H), 5.64 (s, 2H), 4.84 (s, 2H), 4.28 (s, 3H).

The following compounds were synthesized according to Scheme E8 and Example 8C using the appropriate starting material. Standard protection and deprotection can be used when necessary.

| Cpd No. | Structure | Characterization |
|---|---|---|
| E8-13 | 6-((1H-indazol-4-yl)methyl)-4-methyl-2-(4-((phenylsulfonyl)methyl)-1H-imidazol-1-yl)-4H-thiazolo[5',4':4,5]pyrrolo[2,3-d]pyridazin-5(6H)-one | LCMS: m/z 557 (M + H)+. 1H-NMR (400 MHz, DMSO-d6) δ 13.13 (s, 1H), 8.70 (s, 1H), 8.48 (d, 1H), 8.16 (s, 1H), 7.91-7.72 (m, 4H), 7.63 (t, 2H), 7.47 (d, 1H), 7.36-7.22 (m, 1H), 6.98 (d, 1H), 5.67 (s, 2H), 4.69 (s, 2H), 4.49 (s, 3H) |
| E8-14 | 2-((1H-imidazol-4-yl)methyl)-6-((1H-indazol-4-yl)methyl)-4-methyl-4H-thiazolo[5',4':4,5]pyrrolo[2,3-d]pyridazin-5(6H)-one | LCMS: m/z 417 (M + H)+. 1H NMR (400 MHz, DMSO-d6) δ 13.11 (s, 1H), 12.01 (s, 1H), 8.53 (s, 1H), 8.14 (s, 1H), 7.64 (s, 1H), 7.45 (d, 1H), 7.27 (dd, 1H), 7.09 (s, 1H), 6.96 (d, 1H), 5.65 (s, 2H), 4.39 (s, 2H), 4.27 (s, 3H) |

| Cpd No. | Structure | Characterization |
|---|---|---|
| E8-15 | 6-((1H-indazol-4-yl)methyl)-2-((2-aminothiazol-5-yl)methyl)-4-methyl-4H-thiazolo[5',4':4,5]pyrrolo[2,3-d]pyridazin-5(6H)-one | LCMS: m/z 449 (M + H)+. 1H NMR (400 MHz, DMSO) δ 8.54 (s, 1H), 8.11 (s, 1H), 7.46 (d, 1H), 7.33-7.24 (m, 1H), 7.08 (s, 1H), 6.96 (d, 1H), 5.64 (s, 2H), 4.53 (s, 2H), 4.24 (s, 3H). |
| E8-16 | 6-((1H-indazol-4-yl)methyl)-4-methyl-2-(oxazol-5-ylmethyl)-4H-thiazolo[5',4':4,5]pyrrolo[2,3-d]pyridazin-5(6H)-one | LCMS: m/z 418 (M + H)+. 1H NMR (400 MHz, DMSO-d6) δ 13.11 (s, 1H), 8.59 (s, 1H), 8.36 (s, 1H), 8.14 (s, 1H), 7.45 (d, 1H), 7.33-7.24 (m, 1H), 7.19 (s, 1H), 6.96 (d, 1H), 5.66 (s, 2H), 4.72 (s, 2H), 4.27 (s, 3H). |
| E8-17 | 3-((6-((1H-indazol-4-yl)methyl)-4-methyl-5-oxo-5,6-dihydro-4H-thiazolo[5',4':4,5]pyrrolo[2,3-d]pyridazin-2-yl)methyl)benzenesulfonamide | LC-MS: m/z 506 (M + H)+. 1H NMR (400 MHz, DMSO) δ 13.12 (s, 1H), 8.56 (s, 1H), 8.13 (s, 1H), 7.85 (s, 1H), 7.76 (d, 1H), 7.65 (d, 1H), 7.58 (dd, 1H), 7.45 (d, 1H), 7.38 (s, 2H), 7.30-7.25 (m, 1H), 6.95 (m, 1H), 5.65 (s, 2H), 4.64 (s, 2H), 4.27 (s, 3H). |
| E8-18 | 6-(1H-Indazol-4-ylmethyl)-2-(1H-indazol-6-ylmethyl)-8-methyl-6,8-dihydro-3-thia-1,5,6,8-tetraaza-cyclopenta[a]inden-7-one | LC-MS: m/z 467 (M + H)+. 1H NMR (400 MHz, DMSO) δ 13.13 (s, 1H), 13.09 (s, 1H), 8.52 (s, 1H), 8.13 (s, 1H), 8.05 (s, 1H), 7.75 (d, 1H), 7.59 (s, 1H), 7.45 (d, 1H), 7.30-7.25 (m, 1H), 7.14 (d, 1H), 6.95 (d, 1H), 5.64 (s, 2H), 4.64 (s, 2H), 4.28 (s, 3H). |

| Cpd No. | Structure | Characterization |
|---|---|---|
| E8-19 | 4-((6-((1H-indazol-4-yl)methyl)-4-methyl-5-oxo-5,6-dihydro-4H-thiazolo[5′,4′:4,5]pyrrolo[2,3-d]pyridazin-2-yl)methyl)thiazole-5-carboxamide | LCMS: m/z 477 (M + H)+. 1H NMR (400 MHz, DMSO-d6) δ 13.11 (s, 1H), 9.14 (s, 1H), 8.54 (s, 1H), 8.13 (s, 1H), 8.01 (s, 1H), 7.70 (s, 1H), 7.45 (d, 1H), 7.27 (dd, 1H), 6.95 (d, 1H), 5.65 (s, 2H), 4.99 (s, 2H), 4.26 (s, 3H) |
| E8-20 | 6-((1H-indazol-4-yl)methyl)-2-((5-fluoro-1H-pyrazol-3-yl)methyl)-4-methyl-4H-thiazolo[5′,4′:4,5]pyrrolo[2,3-d]pyridazin-5(6H)-one | LCMS: m/z 435 (M + H)+. 1H NMR (400 MHz, DMSO-d6) δ 13.12 (s, 1H), 12.53 (s, 1H), 8.59 (s, 1H), 8.14 (s, 1H), 7.45 (d, 1H), 7.28 (d, 1H), 6.96 (d, 1H), 5.96 (d, 1H), 5.66 (s, 2H), 4.53 (s, 2H), 4.27 (s, 3H) |
| E8-21 | 2-((1H-pyrazol-3-yl)methyl)-4-methyl-6-((1-methyl-1H-indazol-4-yl)methyl)-4H-thiazolo[5′,4′:4,5]pyrrolo[2,3-d]pyridazin-5(6H)-one | LCMS: m/z 431 (M + H)+. 1H NMR (400 MHz, DMSO-d6) δ 12.77 (s, 1H), 8.54 (s, 1H), 8.11 (d, 1H), 7.71 (s, 1H), 7.55 (d, 1H), 7.33 (m, 1H), 6.98 (d, 1H), 6.26 (d, 1H), 5.64 (s, 2H), 4.48 (s, 2H), 4.27 (s, 3H), 4.02 (s, 3H). |
| E8-22 | 2-((1H-pyrazol-3-yl)methyl)-4-methyl-6-((1-methyl-1H-indazol-5-yl)methyl)-4H-thiazolo[5′,4′:4,5]pyrrolo[2,3-d]pyridazin-5(6H)-one | LCMS: m/z 431 (M + H)+. 1H NMR (400 MHz, DMSO-d6) δ 12.77 (s, 1H), 8.53 (s, 1H), 8.00 (s, 1H), 7.72-7.64 (m, 2H), 7.58 (d, 1H), 7.43 (dd, 1H), 6.25 (d, 1H), 5.44 (s, 2H), 4.47 (s, 2H), 4.27 (s, 3H), 4.00 (s, 3H) |

-continued

| Cpd No. | Structure | Characterization |
|---|---|---|
| E8-23 | 2-((1H-1,2,3-triazol-4-yl)methyl)-4-methyl-6-(4-(trifluoromethoxy)benzyl)-4,6-dihydro-5H-thiazolo[5',4':4,5]pyrrolo[2,3-d]pyridazin-5-one | LCMS: m/z 462 (M + H)+. 1H NMR (400 MHz, DMSO-d6) δ 15.00 (s, 1H), 8.57 (s, 1H), 7.89 (s, 1H), 7.43 (d, 2H), 7.32 (d, 2H), 5.38 (s, 2H), 4.63 (s, 2H), 4.26 (s, 3H). |
| E8-24 | 2-((1H-pyrazol-3-yl)methyl)-6-(indolin-4-ylmethyl)-4-methyl-4H-thiazolo[5',4':4,5]pyrrolo[2,3-d]pyridazin-5(6H)-one | LC-MS: m/z 418 (M + 1)+. 1H NMR (400 MHz, DMSO) δ 12.77 (s, 1H), 8.51 (s, 1H), 7.70 (s, 1H), 6.80 (dd, 1H), 6.37 (d, 1H), 6.32 (d, 1H), 6.26 (d, 1H), 5.49 (s, 1H), 5.22 (s, 2H), 4.49 (s, 2H), 4.26 (s, 3H), 3.41 (t, 2H), 2.95 (t, 2H). |
| E8-25 | 6-((1H-indazol-4-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 435 (M + 1)+. 1H NMR (400 MHz, DMSO) δ 13.12 (s, 1H), 12.77 (s, 1H), 8.56 (s, 1H), 8.14 (s, 1H), 7.86 (s, 1H), 7.45 (d, 1H), 7.35-7.17 (m, 1H), 6.96 (d, 1H), 5.65 (s, 2H), 4.50 (s, 2H), 4.27 (s, 3H). |
| E8-26 | 4-((6-((1H-indazol-4-yl)methyl)-4-methyl-5-oxo-5,6-dihydro-4H-thiazolo[5',4':4,5]pyrrolo[2,3-d]pyridazin-2-yl)methyl)thiazole-2-carboxamide | LCMS: m/z 477 (M + H)+. 1H NMR (400 MHz, DMSO) δ 13.18 (s, 1H), 8.63 (s, 1H), 8.20 (s, 1H), 8.14 (s, 1H), 8.02 (s, 1H), 7.92 (s, 1H), 7.52 (d, 1H), 7.38-7.26 (m, 1H), 7.03 (d, 1H), 5.72 (s, 2H), 4.79 (s, 2H), 4.34 (s, 3H) |
| E8-27 | 2-((1,3,4-oxadiazol-2-yl)methyl)-6-((1H-indazol-4-yl)methyl)-4-methyl-4H-thiazolo[5',4':4,5]pyrrolo[2,3-d]pyridazin-5(6H)-one | LCMS: m/z 419 (M + H)+. 1H NMR (400 MHz, DMSO) δ 13.13 (s, 1H), 9.26 (s, 1H), 8.63 (s, 1H), 8.15 (s, 1H), 7.46 (d, 1H), 7.33-7.20 (m, 1H), 6.97 (d, 1H), 5.67 (s, 2H), 5.02 (s, 2H), 4.27 (s, 3H) |

| Cpd No. | Structure | Characterization |
|---|---|---|
| E8-28 | 2-((1H-indazol-7-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 417 (M + H)+. 1H NMR (400 MHz, DMSO) δ 13.33 (s, 1H), 12.63 (s, 1H), 8.42 (s, 1H), 8.13 (s, 1H), 7.74 (d, 1H), 7.58 (s, 1H), 7.35 (d, 1H), 7.14 (t, 1H), 6.10 (s, 1H), 5.30 (s, 2H), 4.81 (s, 2H), 4.25 (s, 3H). |
| E8-29 | 2-((1H-1,2,4-triazol-3-yl)methyl)-6-((1H-indazol-4-yl)methyl)-4-methyl-4H-thiazolo[5',4':4,5]pyrrolo[2,3-d]pyridazin-5(6H)-one | LC-MS: m/z 418 (M + H)+. 1H NMR (400 MHz, DMSO-d6) δ 13.14 (s, 1H), 8.54 (s, 1H), 8.38-8.37 (m, 1H), 8.13 (s, 1H), 7.46 (d, 1H), 7.31-7.27 (m, 1H), 6.95 (d, 1H), 5.65 (s, 2H), 4.61 (s, 2H), 4.25 (s, 3H). |
| E8-30 | 6-benzyl-4-methyl-2-(pyridin-2-ylmethyl)-4H-thiazolo[5',4':4,5]pyrrolo[2,3-d]pyridazin-5(6H)-one | LCMS: m/z 388 (M + H)+. 1H NMR (400 MHz, DMSO-d6) δ 8.61 (d, 1H), 8.59 (s, 1H), 7.89-7.83 (m, 1H), 7.55 (d, 1H), 7.39-7.30 (m, 6H), 5.39 (s, 2H), 4.71 (s, 2H), 4.30 (s, 3H). |
| E8-31 | 2-((1H-benzo[d][1,2,3]triazol-4-yl)methyl)-6-((1H-indazol-4-yl)methyl)-4-methyl-4H-thiazolo[5',4':4,5]pyrrolo[2,3-d]pyridazin-5(6H)-one | LC-MS: 468 [M + H]+. 1H NMR (400 MHz, DMSO) δ 13.14 (s, 1H), 8.50 (s, 1H), 8.13 (s, 1H), 7.83 (d, 1H), 7.52-7.42 (m, 3H), 7.27 (dd, 1H), 6.94 (d, 1H), 5.64 (s, 2H), 4.95 (s, 2H), 4.26 (s, 3H). |
| E8-32 | 6-((1H-indazol-4-yl)methyl)-2-((2H-1,2,3-triazol-4-yl)methyl)-4-methyl-4H-thiazolo[5',4':4,5]pyrrolo[2,3-d]pyridazin-5(6H)-one | LC-MS: 418 [M + 1]+. 1H NMR (400 MHz, DMSO) δ 13.13 (s, 1H), 8.57 (s, 1H), 8.14 (s, 1H), 7.88 (s, 1H), 7.46 (d, 1H), 7.34-7.23 (m, 1H), 6.96 (d, 1H), 5.66 (s, 2H), 4.63 (s, 2H), 4.28 (s, 3H). |

| Cpd No. | Structure | Characterization |
|---|---|---|
| E8-33 | 6-benzyl-4-methyl-2-(thiazol-4-ylmethyl)-4H-thiazolo[5′,4′:4,5]pyrrolo[2,3-d]pyridazin-5(6H)-one | LC-MS: 394 [M + 1]+. 1H NMR (400 MHz, DMSO) δ 9.12 (d, 1H), 8.55 (s, 1H), 7.71 (d, 1H), 7.35-7.22 (m, 5H), 5.35 (s, 2H), 4.70 (s, 2H), 4.26 (s, 3H). |
| E8-34 | 6-((1H-indazol-4-yl)methyl)-2-((5-bromothiazol-4-yl)methyl)-4-methyl-4H-thiazolo[5′,4′:4,5]pyrrolo[2,3-d]pyridazin-5(6H)-one | LCMS: m/z 512 (M + 2H)+. $^1$H NMR (400 MHz, DMSO-$d_6$) δ 13.11 (s, 1H), 9.19 (s, 1H), 8.56 (s, 1H), 8.14 (s, 1H), 7.45 (d, 1H), 7.28 (t, 1H), 6.95 (d, 1H), 5.65 (s, 2H), 4.65 (s, 2H), 4.27 (s, 3H). |
| E8-35 | 6-((1H-indazol-4-yl)methyl)-2-((2-methoxypyridin-3-yl)methyl)-4-methyl-4,6-dihydro-5H-thiazolo[5′,4′:4,5]pyrrolo[2,3-d]pyridazin-5-one | LCMS: m/z 458 (M + H)+. $^1$H NMR (400 MHz, DMSO-$d_6$) δ 13.11 (s, 1H), 8.53 (s, 1H), 8.17-8.11 (m, 2H), 7.78 (d, 1H), 7.44 (d, 1H), 7.28 (d, 1H), 7.02 (dd, 1H), 6.94 (d, 1H), 5.65 (s, 2H), 4.43 (s, 2H), 4.26 (s, 3H), 3.87 (s, 3H). |
| E8-36 | 6-((1H-indazol-4-yl)methyl)-4-methyl-2-((2-oxo-1,2-dihydropyridin-3-yl)methyl)-4H-thiazolo[5′,4′:4,5]pyrrolo[2,3-d]pyridazin-5(6H)-one | LCMS: m/z 444 (M + H)+. $^1$H NMR (400 MHz, DMSO-$d_6$) δ 13.12 (s, 1H), 11.76 (s, 1H), 8.53 (s, 1H), 8.14 (s, 1H), 7.57 (dd, 1H), 7.40 (d, 1H), 7.37 (dd, 1H), 7.28 (dd, 1H), 6.95 (d, 1H), 6.21 (t, 1H), 5.65 (s, 2H), 4.24 (s, 3H), 4.22 (s, 2H). |
| E8-37 | 6-((1H-indazol-4-yl)methyl)-4-methyl-2-((2-oxo-2,3-dihydro-1H-benzo[d]imidazol-4-yl)methyl)-4H-thiazolo[5′,4′:4,5]pyrrolo[2,3-d]pyridazin-5(6H)-one. | LCMS: m/z 483 (M + H)+. $^1$H NMR (400 MHz, DMSO) δ 13.11 (s, 1H), 10.93 (s, 1H), 10.71 (s, 1H), 8.52 (s, 1H), 8.13 (s, 1H), 7.45 (d, 1H), 7.33-7.18 (m, 1H), 7.02-6.79 (m, 4H), 5.64 (s, 2H), 4.56 (s, 2H), 4.27 (s, 2H). |

-continued

| Cpd No. | Structure | Characterization |
|---|---|---|
| E8-38 | 2-((2H-1,2,3-triazol-4-yl)methyl)-6-(2-fluoro-3-(trifluoromethoxy)benzyl)-4-methyl-4H-thiazolo[5',4':4,5]pyrrolo[2,3-d]pyridazin-5(6H)-one | LC-MS: m/z 480 (M + H)$^+$.<br>$^1$H NMR (400 MHz, DMSO) δ 8.58 (s, 1H), 7.65 (s, 1H), 7.49 (s, 1H), 7.25 (d, 2H), 5.46 (s, 2H), 4.63 (s, 2H), 4.26 (s, 3H). |
| E8-39 | 2-((1H-1,2,3-triazol-4-yl)methyl)-6-benzyl-4-methyl-4,6-dihydro-5H-thiazolo[5',4':4,5]pyrrolo[2,3-d]pyridazin-5-one | LC-MS m/z 378 (M + H)$^+$.<br>$^1$H NMR (400 MHz, DMSO) δ 8.55 (s, 1H), 7.88 (s, 1H), 7.33-7.24 (m, 5H), 5.35 (s, 2H), 4.63 (s, 2H), 4.26 (s, 3H) |
| E8-40 | 2-((1H-indazol-7-yl)methyl)-4-methyl-6-((1-methyl-1H-pyrazol-3-yl)methyl)-4H-thiazolo[5',4':4,5]pyrrolo[2,3-d]pyridazin-5(6H)-one | LC-MS m/z 431.0 (M + H)$^+$.<br>$^1$H NMR (400 MHz, DMSO) δ 13.33 (s, 1H), 8.44 (s, 1H), 8.13 (s, 1H), 7.74 (d, 1H), 7.55 (d, 1H), 7.36 (d, 1H), 7.17-7.10 (m, 1H), 6.06 (d, 1H), 5.25 (s, 2H), 4.84 (s, 2H), 4.27 (s, 3H), 3.75 (s, 3H) |
| E8-41 | 6-((1H-indazol-4-yl)methyl)-2-((1H-indazol-6-yl)methyl)-4-methyl-4,6-dihydro-5H-thiazolo[5',4':4,5]pyrrolo[2,3-d]pyridazin-5-one | LCMS: m/z 467 (M + H)$^+$.<br>$^1$H NMR (400 MHz, DMSO-d$_6$) δ 13.13 (s, 1H), 13.09 (s, 1H), 8.52 (s, 1H), 8.13 (s, 1H), 8.05 (s, 1H), 7.75 (d, 1H), 7.59 (s, 1H), 7.45 (d, 1H), 7.30-7.22 (m, 1H), 7.14 (d, 1H), 6.95 (d, 1H), 5.64 (s, 2H), 4.64 (s, 2H), 4.28 (s, 3H). |
| E8-42 | 6-((1H-indazol-4-yl)methyl)-2-((1H-indazol-5-yl)methyl)-4-methyl-4,6-dihydro-5H-thiazolo[5',4':4,5]pyrrolo[2,3-d]pyridazin-5-one | LCMS: m/z 467 (M + H)$^+$.<br>$^1$H NMR (400 MHz, DMSO-d$_6$) δ 13.10 (s, 1H), 13.07 (s, 1H), 8.51 (s, 1H), 8.13 (s, 1H), 8.06 (s, 1H), 7.80 (s, 1H), 7.54 (d, 1H), 7.44 (d, 1H), 7.40-7.34 (m, 1H), 7.30-7.22 (m, 1H), 6.94 (d, 1H), 5.64 (s, 2H), 4.60 (s, 2H), 4.28 (s, 3H). |

| Cpd No. | Structure | Characterization |
|---|---|---|
| E8-43 | 6-((1H-indazol-4-yl)methyl)-2-((1H-indazol-7-yl)methyl)-4-methyl-4,6-dihydro-5H-thiazolo[5',4':4,5]pyrrolo[2,3-d]pyridazin-5-one | LCMS: m/z 467 (M + H)$^+$. $^1$H NMR (400 MHz, DMSO-$d_6$) δ 13.33 (s, 1H), 13.11 (s, 1H), 8.50 (s, 1H), 8.13 (s, 2H), 7.74 (d, 1H), 7.44 (d, 1H), 7.36 (d, 1H), 7.26 (d, 1H), 7.13 (t, 1H), 6.95 (d, 1H), 5.64 (s, 2H), 4.84 (s, 2H), 4.28 (s, 3H). |
| E8-44 | 6-((1H-indazol-4-yl)methyl)-2-((4-chloro-1H-pyrazol-3-yl)methyl)-4-methyl-4,6-dihydro-5H-thiazolo[5',4':4,5]pyrrolo[2,3-d]pyridazin-5-one | LCMS: m/z 451 (M + H)$^+$. $^1$H NMR (400 MHz, DMSO) δ 13.20 (s, 1H), 13.14 (s, 1H), 8.52 (s, 1H), 8.12 (s, 1H), 7.96 (s, 1H), 7.46 (d, 1H), 7.28 (dd, 1H), 6.95 (d, 1H), 5.64 (s, 2H), 4.47 (s, 2H), 4.25 (s, 3H). |
| E8-45 | 6-((1H-indazol-4-yl)methyl)-4-methyl-2-((6-methylpyridin-2-yl)methyl)-4,6-dihydro-5H-thiazolo[5',4':4,5]pyrrolo[2,3-d]pyridazin-5-one | LCMS: m/z 442 (M + H)$^+$. $^1$H NMR (400 MHz, DMSO) δ 13.11 (s, 1H), 8.56 (s, 1H), 8.13 (s, 1H), 7.68 (dd, 1H), 7.45 (d, 1H), 7.37-7.25 (m, 2H), 7.18 (d, 1H), 6.95 (d, 1H), 5.65 (s, 2H), 4.61 (s, 2H), 4.27 (s, 3H), 2.47 (s, 3H). |
| E8-46 | 6-((1H-indazol-4-yl)methyl)-4-methyl-2-((1-methyl-1H-pyrazol-3-yl)methyl)-4,6-dihydro-5H-thiazolo[5',4':4,5]pyrolo[2,3-d]pyridazin-5-one | LCMS: m/z 431 (M + H)$^+$. $^1$H NMR (400 MHz, DMSO-$d_6$) δ 13.11 (s, 1H), 8.54 (s, 1H), 8.14 (s, 1H), 7.65 (d, 1H), 7.45 (d, 1H), 7.35-7.16 (m, 1H), 6.96 (d, 1H), 6.22 (d, 1H), 5.65 (s, 2H), 4.43 (s, 2H), 4.27 (s, 3H), 3.81 (s, 3H). |
| E8-47 | 6-((1H-indazol-4-yl)methyl)-4-methyl-2-((5-(trifluoromethyl)-1H-pyrazol-3-yl)methyl)-4,6-dihydro-5H-thiazolo[5',4':4,5]pyrrolo[2,3-d]pyridazin-5-one | LCMS: m/z 485 (M + H)$^+$. $^1$H NMR (400 MHz, DMSO-$d_6$) δ 13.77 (s, 1H), 13.11 (s, 1H), 8.59 (s, 1H), 8.14 (s, 1H), 7.45 (d, 1H), 7.35-7.13 (m, 1H), 6.96 (d, 1H), 6.71 (s, 1H), 5.65 (s, 2H), 4.65 (s, 2H), 4.28 (s, 3H). |

| Cpd No. | Structure | Characterization |
|---|---|---|
| E8-48 | 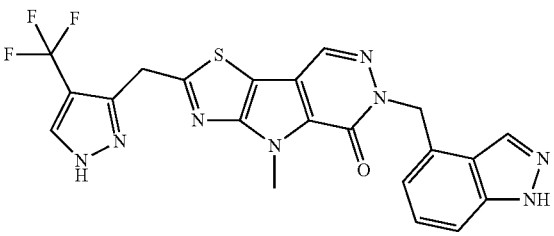<br>6-((1H-indazol-4-yl)methyl)-4-methyl-2-((4-(trifluoromethyl)-1H-pyrazol-3-yl)methyl)-4,6-dihydro-5H-thiazolo[5',4':4,5]pyrrolo[2,3-d]pyridazin-5-one | LCMS: m/z 485 (M + H)$^+$.<br>$^1$H NMR (400 MHz, DMSO-d$_6$) δ 13.58 (s, 1H), 13.11 (s, 1H), 8.55 (s, 1H), 8.42 (s, 1H), 8.14 (s, 1H), 7.45 (d, 1H), 7.27 (t, 1H), 6.95 (d, 1H), 5.65 (s, 2H), 4.58 (s, 2H), 4.26 (s, 3H). |
| E8-49 | 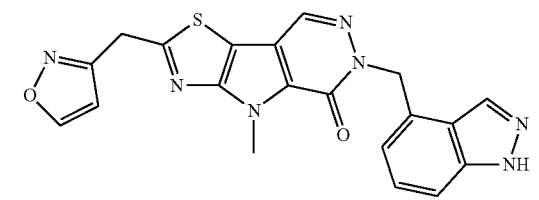<br>6-((1H-indazol-4-yl)methyl)-2-(isoxazol-3-ylmethyl)-4-methyl-4,6-dihydro-5H-thiazolo[5',4':4,5]pyrrolo[2,3-d]pyridazin-5-one | LCMS: m/z 418 (M + H)$^+$.<br>$^1$H NMR (400 MHz, DMSO-d$_6$) δ 8.98 (d, 1H), 8.66 (s, 1H), 8.20 (d, 1H), 7.52 (d, 1H), 7.34 (dd, 1H), 7.02 (d, 1H), 6.71 (d, 1H), 5.72 (s, 2H), 4.74 (s, 2H), 4.33 (s, 3H). |
| E8-50 | 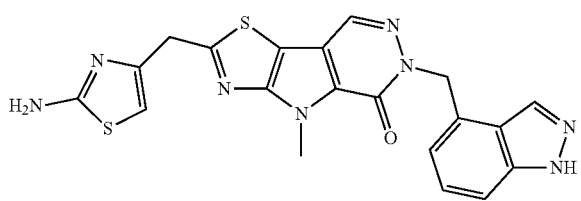<br>6-((1H-indazol-4-yl)methyl)-2-((2-aminothiazol-4-yl)methyl)-4-methyl-4,6-dihydro-5H-thiazolo[5',4':4,5]pyrrolo[2,3-d]pyridazin-5-one | LCMS: m/z 449 (M + H)$^+$.<br>$^1$H NMR (400 MHz, MeOD) δ 8.40 (s, 1H), 8.22 (s, 1H), 7.46 (d, 1H), 7.33 (dd, 1H), 7.11 (d, 1H), 6.46 (s, 1H), 5.74 (s, 2H), 4.58 (s, 3H), 4.33 (s, 2H). |
| E8-51 | 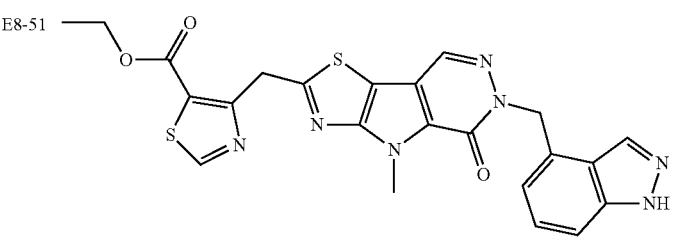<br>Ethyl4-((6-((1H-indazol-4-yl)methyl)-4-methyl-5-oxo-5,6-dihydro-4H-thiazolo[5',4':4,5]pyrrolo[2,3-d]pyridazin-2-yl)methyl)thiazole-5-carboxylate | LCMS: m/z 506 (M + H)$^+$.<br>$^1$H NMR (400 MHz, DMSO-d$_6$) δ 13.11 (s, 1H), 9.31 (s, 1H), 8.55 (s, 1H), 8.13 (s, 1H), 7.45 (d, 1H), 7.35-7.16 (m, 1H), 6.95 (d, 1H), 5.65 (s, 2H), 5.03 (s, 2H), 4.33 (q, 2H), 4.25 (s, 3H), 1.30 (t, 3H). |

-continued

| Cpd No. | Structure | Characterization |
|---|---|---|
| E8-52 | 4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzonitrile | LCMS: m/z 402 (M + H)+. $^1$H NMR (400 MHz, DMSO-d) δ 12.77 (s, 1H), 8.56 (s, 1H), 7.80 (d, 2H), 7.72 (s, 1H), 7.45 (d, 2H), 6.26 (s, 1H), 5.44 (s, 2H), 4.53 (s, 2H), 4.26 (s, 3H). |
| E8-53 | 3-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzonitrile | LCMS: m/z 402 (M + H)+. $^1$H NMR (400 MHz, DMSO-d$_6$) δ 12.79 (s, 1H), 8.56 (s, 1H), 7.78-7.57 (m, 4H), 7.54 (dd, 1H), 6.26 (d, 1H), 5.41 (s, 2H), 4.49 (s, 2H), 4.26 (s, 3H). |
| E8-54 | 4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzamide | LCMS: m/z 420 (M + H)+. $^1$H NMR (400 MHz, DMSO-d$_6$) δ 12.78 (s, 1H), 8.55 (s, 1H), 8.07 (s, 1H), 7.93 (s, 1H), 7.81 (d, 2H), 7.34 (d, 3H), 6.27 (d, 1H), 5.40 (s, 2H), 4.49 (s, 2H), 4.27 (s, 3H). |
| E8-55 | 3-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzamide | LCMS: m/z 420 (M + H)+. $^1$H NMR (400 MHz, DMSO-d$_6$) δ 12.78 (s, 1H), 8.55 (s, 1H), 7.97 (s, 1H), 7.85-7.60 (m, 3H), 7.51-7.27 (m, 3H), 6.26 (d, 1H), 5.39 (s, 2H), 4.49 (s, 2H), 4.27 (s, 3H). |

| Cpd No. | Structure | Characterization |
|---|---|---|
| E8-56 | 6-((1H-indazol-4-yl)methyl)-2-((5-(hydroxymethyl)thiazol-4-yl)methyl)-4-methyl-4,6-dihydro-5H-thiazolo[5',4':4,5]pyrrolo[2,3-d]pyridazin-5-one | LCMS: m/z 464 (M + H)⁺. ¹H NMR (400 MHz, DMSO-d₆) δ 13.11 (s, 1H), 8.99 (s, 1H), 8.54 (s, 1H), 8.14 (s, 1H), 7.45 (d, 1H), 7.31 (dd, 1H), 6.95 (d, 1H), 5.69 (s, 1H), 5.65 (s, 2H), 4.78 (s, 2H), 4.63 (s, 2H), 4.27 (s, 3H). |
| E8-57 | 6-((1H-indazol-4-yl)methyl)-2-((2-(hydroxymethyl)thiazol-4-yl)methyl)-4-methyl-4,6-dihydro-5H-thiazolo[5',4':4,5]pyrrolo[2,3-d]pyridazin-5-one | LCMS: m/z 464 (M + H)⁺. ¹H NMR (400 MHz, DMSO-d₆) 13.12 (s, 1H), 8.56 (s, 1H), 8.14 (s, 1H), 7.56 (s, 1H), 7.45 (d, 1H), 7.31 (dd, 1H), 6.96 (d, 1H), 6.07 (t, 1H), 5.65 (s, 2H), 4.70 (d, 2H), 4.60 (s, 2H), 4.27 (s, 3H). |
| E8-58 | 3-((4-methyl-2-((1-methyl-1H-pyrazol-4-yl)methyl)-5-oxo-4,5-dihydro-6H-thiazolo[5',4':4,5]pyrrolo[2,3-d]pyridazin-6-yl)methyl)benzamide | LCMS: m/z 434 (M + H)⁺. ¹H NMR (400 MHz, DMSO-d₆) 8.55 (s, 1H), 7.97 (s, 1H), 7.81-7.74 (m, 2H), 7.73 (s, 1H), 7.45 (d, 2H), 7.39 (dd, 1H), 7.34 (s, 1H), 5.39 (s, 2H), 4.33 (s, 2H), 4.27 (s, 3H), 3.82 (s, 3H). |

Example 8D Synthesis of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one

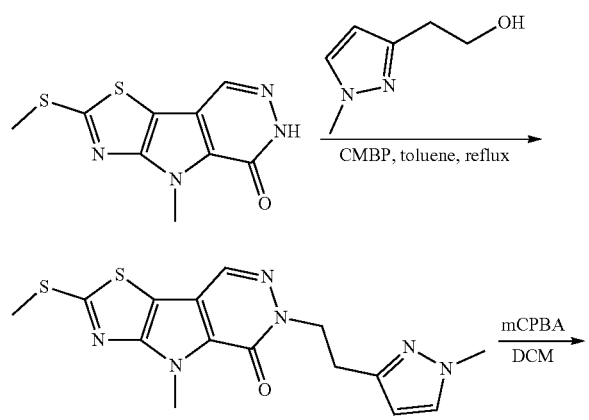

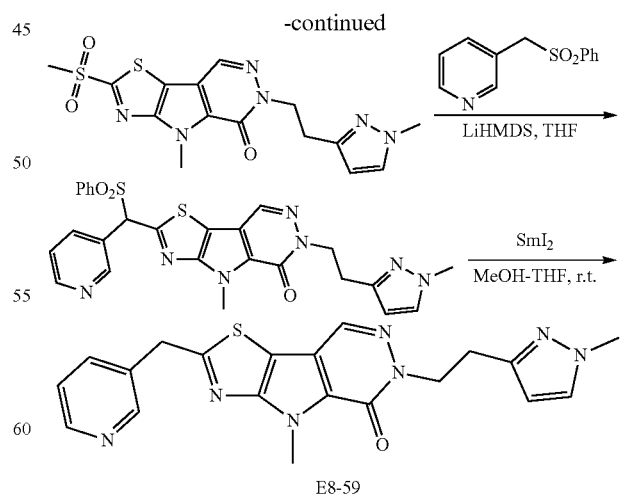

Step A. Synthesis of 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one To a mixture of 4-methyl-2-

(methylthio)-4H-thiazolo[5',4':4,5]pyrrolo[2,3-d]pyridazin-5(6H)-one (360 mg, 1.4 mmol) and 2-(1-methyl-1H-pyrazol-3-yl)ethanol (300 mg, 2.4 mmol) in toluene (10 mL) was added CMBP (600 mg, 2.1 mmol). The reaction mixture was stirred at 110° C. under N₂ for 3 hrs. After cooled to room temperature, the reaction mixture was diluted with EtOAc, washed with water and brine, dried over anhy. Na₂SO₄, concentrated in vacuum. The residue was purified by flash chromatography (silica gel, 80-100% EtOAc in petroleum ether) to afford 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one (500 mg). LC-MS (ESI): m/z 361 (M+1)⁺.

Step B. Synthesis of 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one To a mixture of 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one (600 mg, 1.7 mmol) in DCM (20 mL) was added m-CPBA (1.01 g, 5.0 mmol). The reaction mixture was stirred at room temperature for 3 hrs. The reaction mixture was diluted with EtOAc, washed with satd. NaHCO₃ and brine, dried over anhy. Na₂SO₄, concentrated under vacuum. The residue was purified by flash chromatography (silica gel, 80-100% EtOAc in PE) to afford 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one (600 mg). LC-MS (ESI): m/z 393 (M+1)⁺.

Step C. Synthesis of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one To a mixture of 3-((phenylsulfonyl)methyl)pyridine (300 mg, 1.3 mmol) in THF (20 mL) was added LiHMDS (2 mL, 2.0 mmol) at room temperature. After stirred at room temperature under N₂ for 15 min, 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one (300 mg, 0.8 mmol) was added to the reaction mixture and the resulting solution was stirred at room temperature for 3 hrs. The reaction mixture was quenched with satd. NH₄Cl, extracted with EtOAc. The organic phase was washed with brine, dried over anhy. Na₂SO₄, concentrated in vacuum. The residue was purified by flash chromatography (silica gel, 80-100% EtOAc in petroleum ether) to afford 110 mg of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one. LC-MS: m/z 546 (M+1)⁺.

Step D. Synthesis of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one To a solution of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one (110 mg, 0.2 mmol) in THF (5 mL) and MeOH (5 mL) was added SmI₂ (5 mL, 0.1 M in THF) at r.t. Then the reaction mixture was stirred under N₂ at r.t. for 10 min. The reaction solution was quenched with water, diluted with EtOAc, washed with water and brine, dried over anhy. Na₂SO₄, concentrated in vacuum. The residue was purified by flash chromatography (silica gel, 80-100% EtOAc in petroleum ether) to afford 6 mg of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one. LC-MS (ESI): m/z 406 (M+1)⁺. ¹H NMR (400 MHz, DMSO-d6) δ 8.66 (s, 1H), 8.52 (d, 2H), 7.84 (d, 1H), 7.54 (d, 1H), 7.41 (dd, 1H), 6.04 (d, 1H), 4.58 (s, 2H), 4.48-4.30 (m, 2H), 4.26 (s, 3H), 3.75 (s, 3H), 3.12-2.75 (m, 2H).

Example 8E Synthesis of 4-methyl-6-(prop-2-yn-1-yl)-2-(pyridin-2-ylmethyl)-4H-thiazolo[5',4':4,5]pyrrolo[2,3-d]pyridazin-5(6H)-one

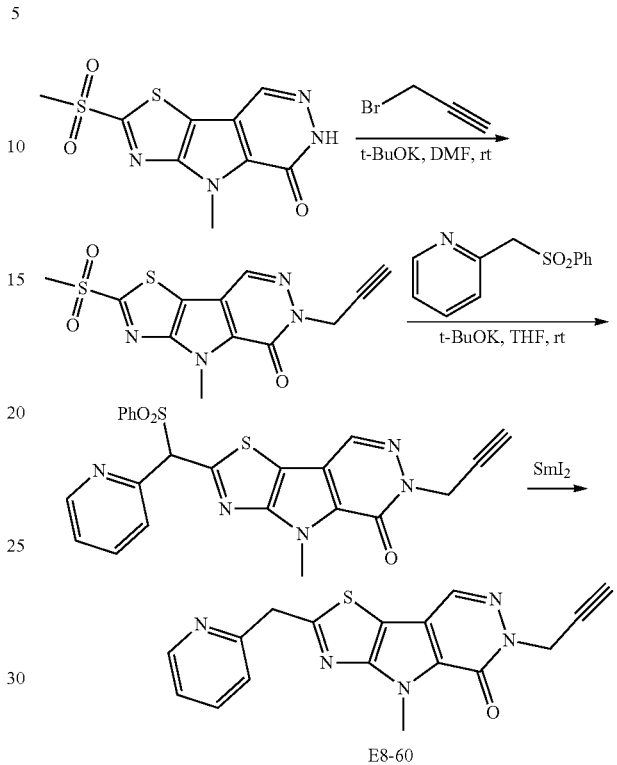

E8-60

Step A. Synthesis of 4-methyl-2-(methylsulfonyl)-6-(prop-2-yn-1-yl)-4H-thiazolo[5',4':4,5]pyrrolo[2,3-d]pyridazin-5(6H)-one. To a mixture of 4-methyl-2-(methylsulfonyl)-4H-thiazolo[5',4':4,5]pyrrolo[2,3-d]pyridazin-5(6H)-one (200 mg, 0.70 mmol) in DMF (5 mL) was added t-BuOK (157 mg, 1.4 mmol), followed by 3-bromoprop-1-yne (0.12 mL, 1.4 mmol). The reaction was stirred at room temperature for 15 min. Then the suspension was poured into satd. NH₄Cl, extracted with EtOAc. The organic layer was washed with brine, dried over anhy. Na₂SO₄ and concentrated under reduced pressure. The residue was purified by flash chromatography (silica gel, 0~50% EtOAc in PE) to afford 60 mg of 4-methyl-2-(methylsulfonyl)-6-(prop-2-yn-1-yl)-4H-thiazolo[5',4':4,5]pyrrolo[2,3-d]pyridazin-5(6H)-one. LC-MS (ESI): m/z 323 (M+H)⁺.

Step B. Synthesis of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one. To a mixture of 4-methyl-2-(methylsulfonyl)-6-(prop-2-yn-1-yl)-4H-thiazolo[5',4':4,5]pyrrolo[2,3-d]pyridazin-5(6H)-one (60 mg, 0.18 mmol) and 2-((phenylsulfonyl)methyl)pyridine (87 mg, 0.37 mmol) in THF (5 mL) was added t-BuOK (63 mg, 0.57 mmol). After stirred at room temperature for 1 hr under nitrogen, the reaction was poured into satd. NH₄Cl, extracted with EtOAc. The organic layer was washed with brine, dried over anhy. Na₂SO₄ and concentrated under reduced pressure. The residue was purified by prep-TLC (eluant: 70% EtOAc in petroleum ether) to afford 50 mg of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one. LC-MS (ESI): m/z 476 (M+H)⁺.

Step C. Synthesis of 4-methyl-6-(prop-2-yn-1-yl)-2-(pyridin-2-ylmethyl)-4H-thiazolo[5',4':4,5]pyrrolo[2,3-d]pyridazin-5(6H)-one To a solution of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one (50 mg, 0.11 mmol) in THF/MeOH (4 mL, 1:1) was added SmI₂ (4.2 mL, 0.1 M in THF) at −70° C. under nitrogen atmosphere. After stirred for 5 min, the reaction was quenched with water. The mixture was diluted with EtOAc and washed with satd. NH₄Cl. The organic layer was washed with brine, dried over anhy. Na₂SO₄ and concentrated under reduced pressure. The residue was purified by prep-HPLC to afford 5 mg of 4-methyl-6-(prop-2-yn-1-yl)-2-(pyridin-2-ylmethyl)-4H-thiazolo[5',4':4,5]pyrrolo[2,3-d]pyridazin-5(6H)-one. LC-MS: m/z 336 (M+H)⁺. ¹H NMR (400 MHz, DMSO-d6) δ 8.60-8.52 (m, 2H), 7.81 (td, 1H), 7.51 (d, 1H), 7.33 (dd, 1H), 4.93 (d, 2H), 4.67 (s, 2H), 4.26 (s, 3H), 3.27 (t, 1H).

Example 8F Synthesis of 2-((1H-pyrazol-3-yl)methyl)-6-benzyl-4-ethyl-4,6-dihydro-5H-thiazolo[5',4':4,5]pyrrolo[2,3-d]pyridazin-5-one

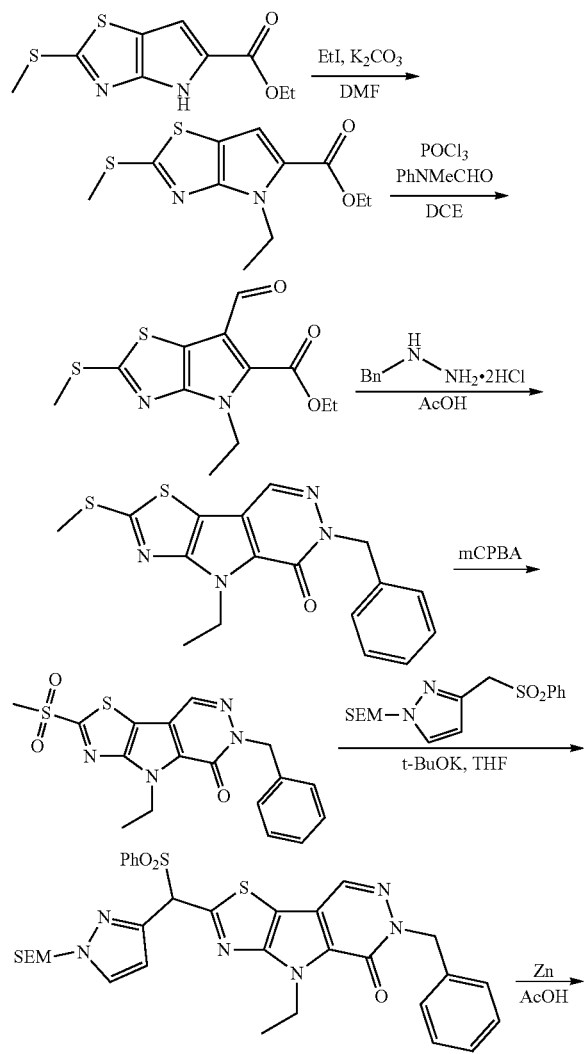

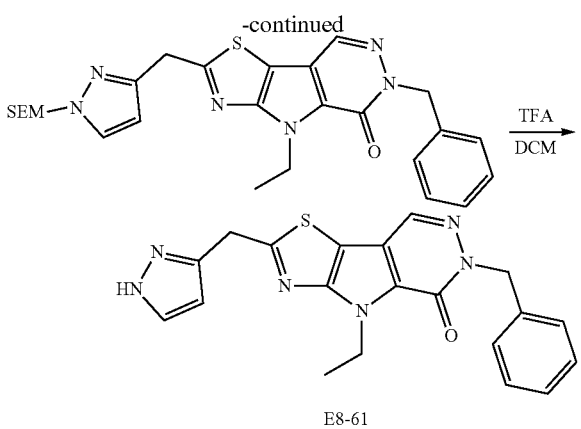

E8-61

Step A. Synthesis of Ethyl 4-ethyl-2-(methylthio)-4H-pyrrolo[2,3-d]thiazole-5-carboxylate To a mixture of ethyl 2-(methylthio)-4H-pyrrolo[2,3-d]thiazole-5-carboxylate (500 mg, 2.06 mmol) in DMF (5 mL) was added K₂CO₃ (856 mg, 6.19 mmol). After stirred at 70° C. for 1.5 hrs, EtI (483 mg, 3.10 mmol) was added. The mixture was stirred at 70° C. for another 1 hrs. The reaction mixture was diluted with H₂O and extracted with EtOAc. The combined organic phase was evaporated under reduced pressure. The residue was purified by flash chromatography (silica gel, 0~30% EtOAc in petroleum ether) to give ethyl 4-ethyl-2-(methylthio)-4H-pyrrolo[2,3-d]thiazole-5-carboxylate (400 mg). LC-MS (ESI): m/z 271 (M+1)⁺.

Step B. Synthesis of ethyl 4-ethyl-6-formyl-2-(methylthio)-4H-pyrrolo[2,3-d]thiazole-5-carboxylate A mixture of POCl₃ (3.6 ml) and PhNMeCHO (5 mL) was stirred at r.t. for 1 hr, then added to a solution of ethyl 4-ethyl-2-(methylthio)-4H-pyrrolo[2,3-d]thiazole-5-carboxylate (400 mg, 1.48 mmol) in DCE (10 mL). After stirred at 100° C. for 2 hrs, the reaction mixture was diluted with H₂O and extracted with EtOAc twice. The combined organic phases were dried over anhy. Na₂SO₄ and evaporated under reduced pressure. The residue was purified by flash chromatography (silica gel, 0~30% EtOAc in PE) to give ethyl 4-ethyl-6-formyl-2-(methylthio)-4H-pyrrolo[2,3-d]thiazole-5-carboxylate (400 mg). LC-MS (ESI): m/z 299 (M+1)⁺.

Step C. Synthesis of 6-benzyl-4-ethyl-2-(methylthio)-4,6-dihydro-5H-thiazolo[5',4':4,5]pyrrolo[2,3-d]pyridazin-5-one To a mixture of 4-ethyl-6-formyl-2-(methylthio)-4H-pyrrolo[2,3-d]thiazole-5-carboxylate (400 mg, 1.34 mmol) in AcOH (4 mL) was added benzylhydrazine dihydrochloride (260 mg, 1.34 mmol) under N₂. The mixture was stirred at 100° C. for 3 hrs. The reaction mixture was evaporated under reduced pressure. The residue was purified by flash chromatography (silica gel, 0~50% EtOAc in petroleum ether) to give 250 mg of 6-benzyl-4-ethyl-2-(methylthio)-4,6-dihydro-5H-thiazolo[5',4':4,5]pyrrolo[2,3-d]pyridazin-5-one. LC-MS: m/z 357 (M+1)⁺.

Step D. Synthesis of 6-benzyl-4-ethyl-2-(methylsulfonyl)-4,6-dihydro-5H-thiazolo[5',4':4,5]pyrrolo[2,3-d]pyridazin-5-one To a mixture of 6-benzyl-4-ethyl-2-(methylthio)-4,6-dihydro-5H-thiazolo[5',4':4,5]pyrrolo[2,3-d]pyridazin-5-one (250 mg, 0.70 mmol) in DCM (5 mL) was added mCPBA (657.5 mg, 3.8 mmol) at 0° C. After stirred for 1.5 hrs, the reaction mixture was evaporated under reduced pressure. The residue was purified by prep-TLC (10% MeOH in DCM) to give 6-benzyl-4-ethyl-2-(methylsulfonyl)-4,6-dihydro-5H-thiazolo[5',4':4,5]pyrrolo[2,3-d]pyridazin-5-one (90 mg). LC-MS: m/z 389 (M+1)⁺.

Step E. Synthesis of 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-ethyl-2-(methylsulfonyl)-4,6-dihydro-5H-thiazolo[5',4':4,5]pyrrolo[2,3-d]pyridazin-5-one (90 mg, 0.23 mmol) and 3-((phenylsulfonyl)methyl)-1-((2-(trimethylsilyl)ethoxy)methyl)-1H-pyrazole (123 mg, 0.35 mmol) in THF (3 mL) was added and KO$^t$Bu (85 mg, 0.76 mmol) under $N_2$ at r.t. After stirred at r.t. for 30 min, the reaction mixture was quenched with satd. $NH_4Cl$ and extracted with EtOAc. The combined organic phase was evaporated under reduced pressure. The residue was purified by flash chromatography (silica gel, 0~50% EtOAc in petroleum ether) to give 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (140 mg, 92.2% yield). LC-MS: m/z 661 (M+1)$^+$.

Step F. Synthesis of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (140 mg, 0.21 mmol) in EtOH (2 mL) and DCE (1 mL) was added acetic acid (0.2 mL, 2.8 mmol) and zinc (360 mg, 5.5 mmol). The mixture was stirred at 80° C. for 3 hrs. The reaction mixture was filtered and the filtrate was evaporated under reduced pressure. The residue was purified by flash chromatography (silica gel, 0-50% EtOAc in petroleum ether) to give 30 mg of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one. LC-MS (ESI): m/z 521 (M+1)$^+$.

Step G. Synthesis of 2-((1H-pyrazol-3-yl)methyl)-6-benzyl-4-ethyl-4,6-dihydro-5H-thiazolo[5',4':4,5]pyrrolo[2,3-d]pyridazin-5-one To a mixture of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (30 mg, 0.06 mmol) in DCM (4 mL) was added TFA (4 mL). After stirred at r.t. for 1.5 hr, the reaction mixture was evaporated under reduced pressure. The residue was purified by prep-TLC (20% MeOH in DCM) to give 2-((1H-pyrazol-3-yl)methyl)-6-benzyl-4-ethyl-4,6-dihydro-5H-thiazolo[5',4':4,5]pyrrolo[2,3-d]pyridazin-5-one (5 mg). LC-MS (ESI): m/z 391 (M+1)$^+$. $^1$H NMR (400 MHz, DMSO-d6) δ 12.79 (s, 1H), 8.53 (s, 1H), 7.72 (s, 1H), 7.42-7.11 (m, 5H), 6.27 (d, 1H), 5.36 (s, 2H), 4.78 (q, 2H), 4.48 (s, 2H), 1.44 (t, 3H).

Example 8G. Synthesis of 6-benzyl-4-phenyl-2-(pyridin-2-ylmethyl)-4H-thiazolo[5',4':4,5]pyrrolo[2,3-d]pyridazin-5(6H)-one

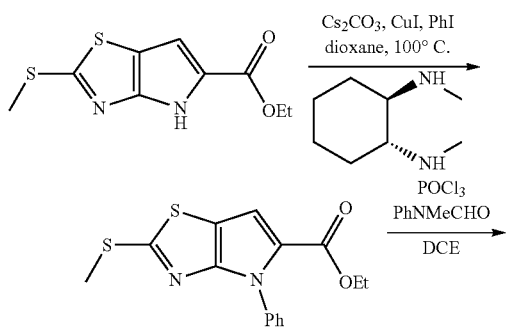

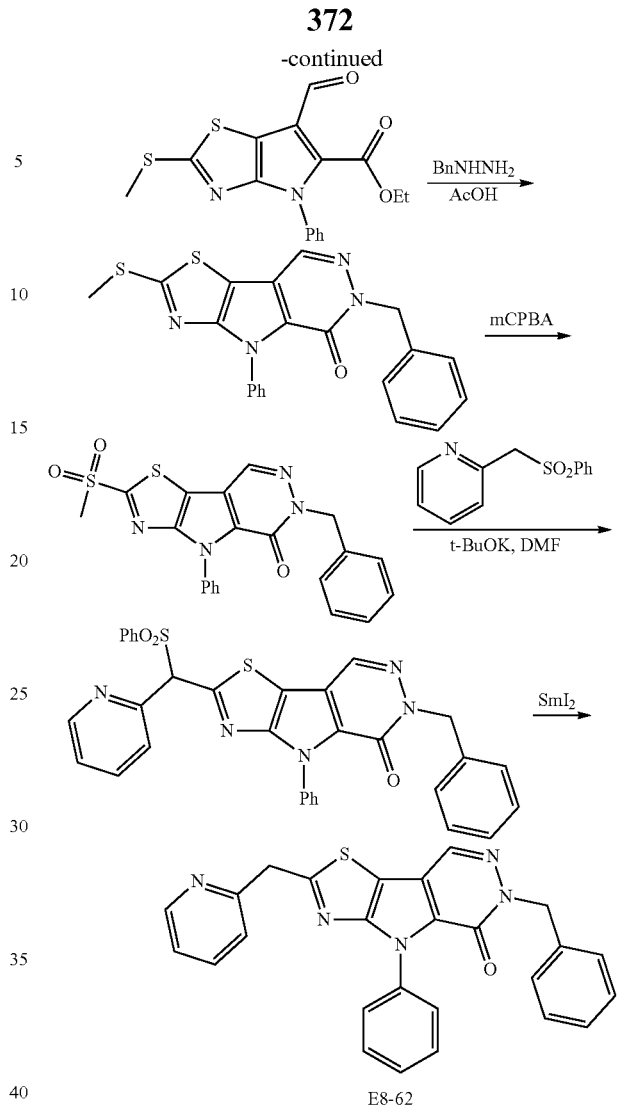

E8-62

Step A. Synthesis of ethyl 2-(methylthio)-4-phenyl-4H-pyrrolo[2,3-d]thiazole-5-carboxylate To a solution of ethyl 2-(methylthio)-4H-pyrrolo[2,3-d]thiazole-5-carboxylate (400 mg, 1.7 mmol) and PhI (265 mg, 2.55 mmol) in dioxane (5 mL) was added $Cs_2CO_3$ (1.1 g, 3.4 mmol), followed by CuI (65 mg, 0.34 mmol) and (1R,2R)—N1,N2-dimethylcyclohexane-1,2-diamine (48 mg, 0.34 mmol). The mixture was stirred under nitrogen atmosphere at 100° C. for 7 hr. The mixture was poured into water and extracted with EtOAc twice. The combined organic layers were washed with brine, dried over anhy. $Na_2SO_4$ and concentrated under reduced pressure. The residue was purified by flash chromatography (silica gel, 0~10% EtOAc in petroleum ether) to give ethyl 2-(methylthio)-4-phenyl-4H-pyrrolo[2,3-d]thiazole-5-carboxylate (400 mg). LC-MS (ESI): m/z 319 (M+1)$^+$.

Step B. Synthesis of ethyl 6-formyl-2-(methylthio)-4-phenyl-4H-pyrrolo[2,3-d]thiazole-5-carboxylate To a solution of PhNMeCHO (1.5 mL) in DCE (5 mL) was added $POCl_3$ (1.2 mL, 12.5 mmol) under 0° C. The mixture was stirred at r.t. for 30 min. Then ethyl 2-(methylthio)-4-phenyl-4H-pyrrolo[2,3-d]thiazole-5-carboxylate (400 mg, 1.25 mmol) was added to the mixture, the mixture was stirred at 50° C. overnight. The mixture was quenched with sat. $NaHCO_3$ and extracted with DCM twice. The combined organic layers were washed with brine, dried over anhy.

Na₂SO₄ and concentrated under reduced pressure. The residue was purified by flash chromatography (silica gel, 0~50% EtOAc in petroleum ether) to give ethyl 6-formyl-2-(methylthio)-4-phenyl-4H-pyrrolo[2,3-d]thiazole-5-carboxylate (280 mg). LC-MS (ESI): m/z 347 (M+1)⁺.

Step C. Synthesis of 6-benzyl-2-(methylthio)-4-phenyl-4H-thiazolo[5',4':4,5]pyrrolo[2,3-d]pyridazin-5(6H)-one To a mixture of ethyl 6-formyl-2-(methylthio)-4-phenyl-4H-pyrrolo[2,3-d]thiazole-5-carboxylate (280 mg, 0.81 mmol) in AcOH (6.0 mL) was added benzylhydrazine dihydrochloride (468 mg, 2.4 mmol). The reaction mixture was stirred at 100° C. for 2 hr. The filtrate was evaporated and purified by flash chromatography (silica gel, 0-70% EtOAc in petroleum ether) to give 100 mg of 6-benzyl-2-(methylthio)-4-phenyl-4H-thiazolo [5',4':4,5]pyrrolo[2,3-d]pyridazin-5 (6H)-one. LC-MS: m/z 405 (M+1)⁺.

Step D. Synthesis of 6-benzyl-2-(methylsulfonyl)-4-phenyl-4H-thiazolo[5',4':4,5]pyrrolo[2,3-d]pyridazin-5(6H)-one To a solution of 6-benzyl-2-(methylthio)-4-phenyl-4H-thiazolo[5',4':4,5]pyrrolo[2,3-d]pyridazin-5(6H)-one (100 mg, 0.25 mmol) in DCM (5 mL) was added mCPBA (151 mg, 0.75 mmol). The mixture was stirred at r.t. for 4 hr. The mixture was quenched with aq. Na₂S₂O₃ and extracted with DCM twice. The combined organic layers were washed with brine, dried over anhy. Na₂SO₄ and concentrated under reduced pressure. The residue was purified by flash chromatography (silica gel, 0~100% EtOAc in petroleum ether) to give 6-benzyl-2-(methylsulfonyl)-4-phenyl-4H-thiazolo [5',4':4,5]pyrrolo[2,3-d]pyridazin-5(6H)-one (60 mg). LC-MS (ESI): m/z 437 (M+1)⁺.

Step E. Synthesis of 6-benzyl-4-phenyl-2-((phenylsulfonyl)(pyridin-2-yl)methyl)-4H-thiazolo[5',4':4,5]pyrrolo[2,3-d]pyridazin-5(6H)-one To a mixture of 6-benzyl-4-phenyl-2-((phenylsulfonyl)(pyridin-2-yl)methyl)-4H-thiazolo[5',4': 4,5]pyrrolo[2,3-d]pyridazin-5(6H)-one (60 mg, 0.14 mmol) and 2-((phenylsulfonyl)methyl)pyridine (50 mg, 0.21 mmol) in dry DMF (5 mL) was added t-BuOK (31 mg, 0.28 mmol) under N₂. The reaction mixture was stirred at 60° C. for 1.5 hr. After cooled down to r.t., the mixture was poured into satd. NH₄Cl. The following mixture was extracted with EtOAc twice. The combined organic layers were washed with brine, dried over anhy. Na₂SO₄ and concentrated under reduced pressure. The residue was purified by prep-TLC (petroleum ether/EtOAc=1/4) to give 40 mg of 6-benzyl-4-phenyl-2-((phenylsulfonyl)(pyridin-2-yl)methyl)-4H-thiazolo[5',4':4,5]pyrrolo[2,3-d]pyridazin-5(6H)-one. LC-MS (ESI): m/z 590 (M+1)⁺.

Step F. Synthesis of 6-benzyl-4-phenyl-2-(pyridin-2-ylmethyl)-4H-thiazolo[5',4':4,5]pyrrolo[2,3-d]pyridazin-5(6H)-one To a mixture of 6-benzyl-4-phenyl-2-((phenylsulfonyl)(pyridin-2-yl)methyl)-4H-thiazolo[5',4':4,5]pyrrolo[2,3-d]pyridazin-5(6H)-one (30 mg, 0.05 mmol) in THF (1.5 mL) and MeOH (1.5 mL) was added SmI₂ (2.5 mL, 0.1 M in THF) at −78° C. under N₂. The reaction mixture was stirred at −78° C. for 10 min and then quenched with water. The mixture was extracted with EtOAc twice. The combined organic layers were washed with brine, dried over anhy. Na₂SO₄ and concentrated under reduced pressure. The residue was purified by HPLC to give 6-benzyl-4-phenyl-2-(pyridin-2-ylmethyl)-4H-thiazolo[5',4':4,5]pyrrolo[2,3-d]pyridazin-5(6H)-one (5 mg). LC-MS (ESI): m/z 450 (M+1)⁺. ¹H NMR (400 MHz, DMSO-d₆) δ 8.67 (s, 1H), 8.56 (d, 1H), 7.82-7.76 (m, 1H), 7.59-7.45 (m, 6H), 7.34-7.23 (m, 6H), 5.32 (s, 2H), 4.63 (s, 2H).

Example 8H Synthesis of 2-((1H-pyrazol-3-yl)methyl)-4,6-dibenzyl-4H-thiazolo[5',4':4,5]pyrrolo[2,3-d]pyridazin-5(6H)-one

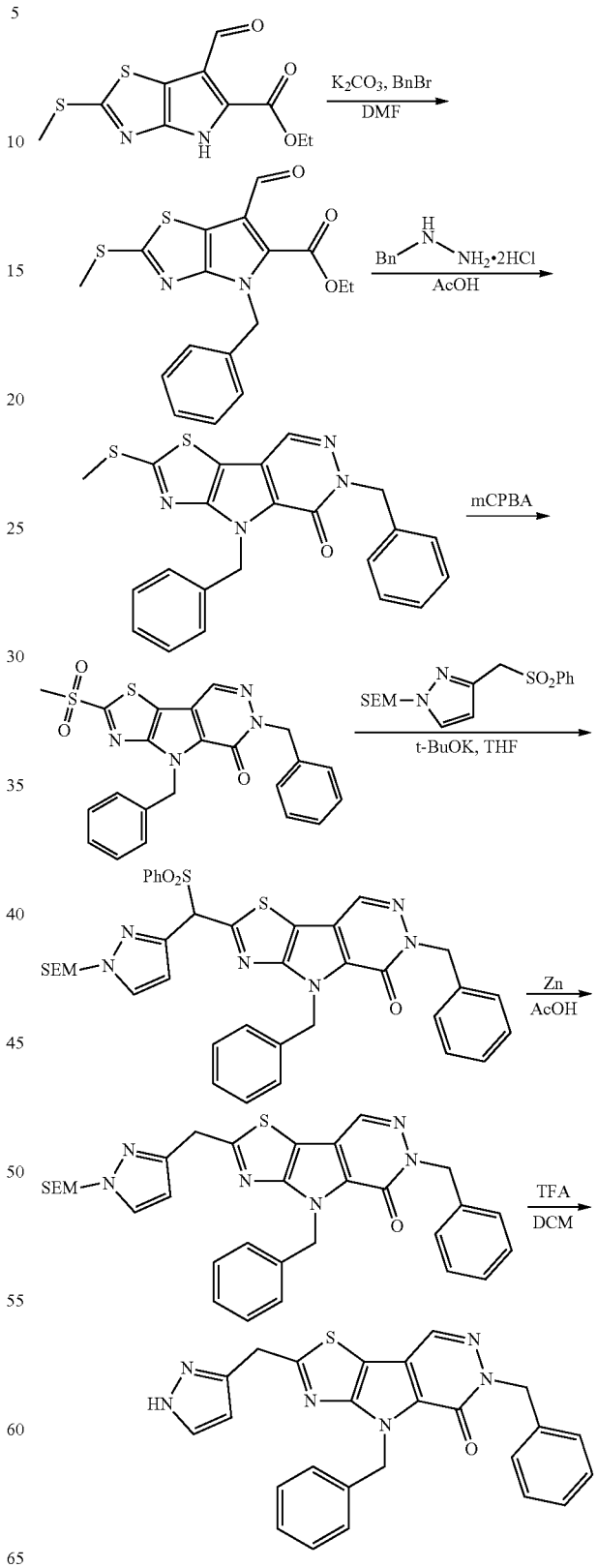

E8-63

Step A. Synthesis of ethyl 4-benzyl-6-formyl-2-(methylthio)-4H-pyrrolo[2,3-d]thiazole-5-carboxylate. To a mixture of ethyl 6-formyl-2-(methylthio)-4H-pyrrolo[2,3-d]thiazole-5-carboxylate (300 mg, 1.1 mmol) in DMF (3 mL) was added $K_2CO_3$ (460 mg, 3.3 mmol). After stirred at 70° C. for 1.5 hrs, BnBr (0.2 mL, 1.6 mmol) was added. The mixture was stirred at 70° C. for 1 hr. The reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~30% EtOAc in petroleum ether) to give ethyl 4-benzyl-6-formyl-2-(methylthio)-4H-pyrrolo[2,3-d]thiazole-5-carboxylate (370 mg). LC-MS (ESI): m/z 361 (M+1)$^+$.

Step B. Synthesis of 4,6-dibenzyl-2-(methylthio)-4H-thiazolo[5',4':4,5]pyrrolo[2,3-d]pyridazin-5(6H)-one To a mixture of ethyl 4-benzyl-6-formyl-2-(methylthio)-4H-pyrrolo[2,3-d]thiazole-5-carboxylate (370 mg, 1.0 mmol) in AcOH (4 mL) was added benzylhydrazine dihydrochloride (390 mg, 2.0 mmol) under $N_2$. The mixture was stirred at 100° C. for 3 hrs. The reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~50% EtOAc in petroleum ether) to give 4,6-dibenzyl-2-(methylthio)-4H-thiazolo[5',4':4,5]pyrrolo[2,3-d]pyridazin-5(6H)-one (320 mg). LC-MS (ESI): m/z 419 (M+1)$^+$.

Step C. Synthesis of 4,6-dibenzyl-2-(methylsulfonyl)-4H-thiazolo[5',4':4,5]pyrrolo[2,3-d]pyridazin-5(6H)-one To a mixture of 4,6-dibenzyl-2-(methylthio)-4H-thiazolo[5',4':4,5]pyrrolo[2,3-d]pyridazin-5(6H)-one (320 mg, 0.76 mmol) in DCM (5 mL) was added mCPBA (657.5 mg, 3.2 mmol). After stirred at 0° C. for 1.5 hrs, the reaction mixture was quenched with satd. $Na_2S_2O_3$, extracted with EtOAc. The organic phase was washed with brine, dried over anhy. $Na_2SO_4$ and evaporated under reduced pressure. The residue was purified by pre-TLC (10% MeOH in DCM) to give 4,6-dibenzyl-2-(methylsulfonyl)-4H-thiazolo[5',4':4,5]pyrrolo[2,3-d]pyridazin-5(6H)-one (170 mg). LC-MS (ESI): m/z 451 (M+1)$^+$.

Step D. Synthesis of 4,6-dibenzyl-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 4,6-dibenzyl-2-(methylsulfonyl)-4H-thiazolo[5',4':4,5]pyrrolo[2,3-d]pyridazin-5(6H)-one (170 mg, 0.38 mmol) and 3-((phenylsulfonyl)methyl)-1-((2-(trimethylsilyl)ethoxy)methyl)-1H-pyrazole (160 mg, 0.46 mmol) in THF (3 mL) was added KO$^t$Bu (85 mg, 0.76 mmol) under $N_2$ at r.t. After stirred at r.t. for 3 hr, the reaction mixture was quenched with satd. $NH_4Cl$ and extracted with EtOAc twice. The combined organic phases were dried over anhy. $Na_2SO_4$ and evaporated under reduced pressure. The residue was purified by flash chromatography (silica gel, 0-50% EtOAc in petroleum ether) to give 4,6-dibenzyl-2-((phenylsulfonyl)(1-((2-(trimethylsilyl)ethoxy)methyl)-1H-pyrazol-3-yl)methyl)-4H-thiazolo[5',4':4,5]pyrrolo [2,3-d]pyridazin-5(6H)-one (200 mg). LC-MS (ESI): m/z 723 (M+1)$^+$.

Step E. Synthesis of 4,6-dibenzyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 6-((4-aminopyrimidin-2-yl)methyl)-4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (200 mg, 0.28 mmol) in EtOH (2 mL) and DCE (1 mL) were added acetic acid (0.2 mL, 2.8 mmol) and zinc (360 mg, 5.5 mmol). After stirred at 100° C. for 3 hrs, the reaction mixture was filtered and the filtrate was evaporated under reduced pressure. The residue was purified by flash chromatography (silica gel, 0~50% EtOAc in petroleum ether) to give 4,6-dibenzyl-2-((1-((2-(trimethylsilyl)ethoxy)methyl)-1H-pyrazol-3-yl)methyl)-4H-thiazolo[5',4':4,5]pyrrolo [2,3-d]pyridazin-5(6H)-one (120 mg). LC-MS: m/z 583 (M+1)$^+$.

Step F. Synthesis of 2-((1H-pyrazol-3-yl)methyl)-4,6-dibenzyl-4H-thiazolo[5',4':4,5]pyrrolo[2,3-d]pyridazin-5(6H)-one. To a mixture of 4,6-dibenzyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (120 mg, 0.21 mmol) in DCM (4 mL) was added TFA (4 mL). The mixture was stirred at r.t. for 1.5 hrs. The reaction mixture was evaporated under reduced pressure. The residue was purified by prep-TLC (20% MeOH in DCM) to give 9 mg of 2-((1H-pyrazol-3-yl)methyl)-4,6-dibenzyl-4H-thiazolo[5',4':4,5]pyrrolo[2,3-d]pyridazin-5(6H)-one. LC-MS: m/z 453 (M+1)$^+$. $^1$H NMR (400 MHz, DMSO-d$_6$) δ 12.78 (s, 1H), 8.57 (s, 1H), 7.71 (s, 1H), 7.42-7.04 (m, 10H), 6.25 (d, 1H), 5.98 (s, 2H), 5.37 (s, 2H), 4.48 (s, 2H).

Example 81. Synthesis of 2-((1H-pyrazol-3-yl)methyl)-6-benzyl-4-cyclopropyl-4,6-dihydro-5H-thiazolo[5',4':4,5]pyrrolo[2,3-d]pyridazin-5-one

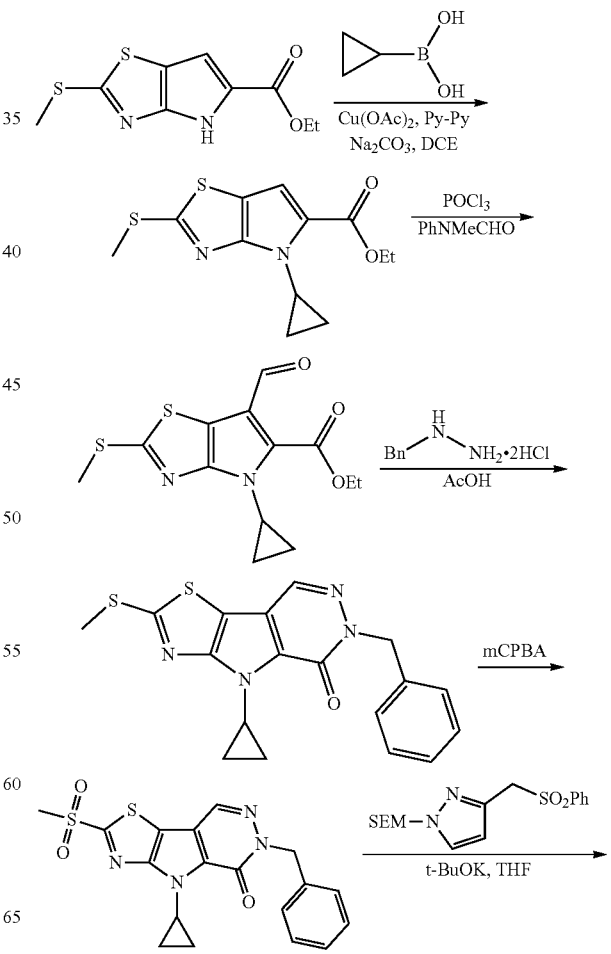

-continued

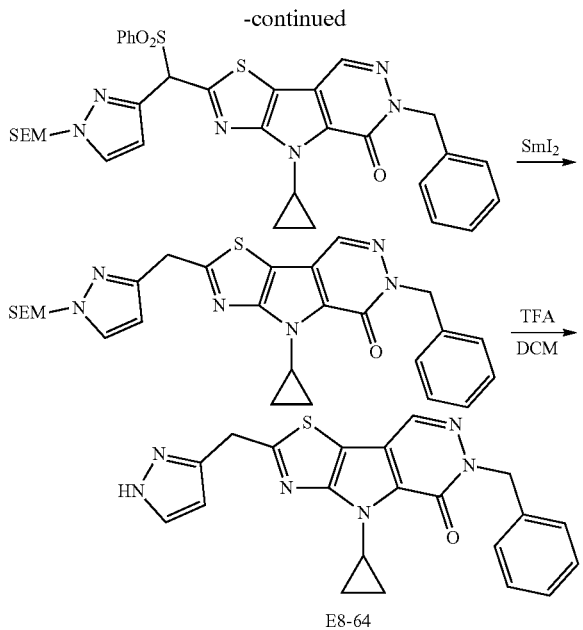

E8-64

Step A. Synthesis of ethyl 4-cyclopropyl-2-(methylthio)-4H-pyrrolo[2,3-d]thiazole-5-carboxylate To a suspension of cyclopropylboronic acid (687 mg, 8 mmol) and ethyl 2-(methylthio)-4H-pyrrolo[2,3-d]thiazole-5-carboxylate (970 mg, 4 mmol) in DCE (10 mL) was added $Na_2CO_3$ (848 mg, 8 mmol), followed by $Cu(OAc)_2$ (727 mg, 4 mmol) and bipyridine (625 mg, 4 mmol). The mixture was stirred at 70° C. for 2 h under air. The resulting mixture was cooled to room temperature, and quenched with satd. $NH_4Cl$, extracted with DCM. The combined organic layers were washed with brine, dried over anhy. $Na_2SO_4$ and concentrated under reduced pressure. The residue was purified by flash chromatography (silica gel, 0~30% EtOAc in petroleum ether) to give ethyl 4-cyclopropyl-2-(methylthio)-4H-pyrrolo [2,3-d]thiazole-5-carboxylate (1.0 g, 88.5% yield). LC-MS (ESI): m/z 283 (M+1)$^+$.

Step B. Synthesis of ethyl 4-cyclopropyl-6-formyl-2-(methylthio)-4H-pyrrolo[2,3-d]thiazole-5-carboxylate A mixture of $POCl_3$ (8.6 mL) and PhNMeCHO (12 mL) was stirred at r.t. for 1 hr, then added to a solution of ethyl 4-cyclopropyl-2-(methylthio)-4H-pyrrolo[2,3-d]thiazole-5-carboxylate (1.0 g, 3.54 mmol) in DCE (10 mL). After stirred at 100° C. for 2 hrs, the reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~30% EtOAc in petroleum ether) to give ethyl 4-cyclopropyl-6-formyl-2-(methylthio)-4H-pyrrolo[2,3-d]thiazole-5-carboxylate (620 mg). LC-MS (ESI): m/z 311 (M+1)$^+$.

Step C. Synthesis of 6-benzyl-4-cyclopropyl-2-(methylthio)-4,6-dihydro-5H-thiazolo[5',4':4,5]pyrrolo[2,3-d] pyridazin-5-one To a mixture of 4-ethyl-6-formyl-2-(methylthio)-4H-pyrrolo[2,3-d]thiazole-5-carboxylate (620 mg, 2 mmol) in AcOH (4 mL) was added benzylhydrazine dihydrochloride (390 mg, 2 mmol) under $N_2$. The mixture was stirred at 100° C. for 3 hrs. The reaction mixture was evaporated under reduced pressure. The residue was purified by flash chromatography (silica gel, 0~50% EtOAc in petroleum ether) to give 6-benzyl-4-ethyl-2-(methylthio)-4,6-dihydro-5H-thiazolo[5',4':4,5]pyrrolo[2,3-d]pyridazin-5-one (320 mg). LC-MS (ESI): m/z 369 (M+1)$^+$.

Step D. Synthesis of 6-benzyl-4-cyclopropyl-2-(methylsulfonyl)-4,6-dihydro-5H-thiazolo[5',4':4,5]pyrrolo[2,3-d] pyridazin-5-one To a mixture of 6-benzyl-4-cyclopropyl-2-(methylthio)-4,6-dihydro-5H-thiazolo[5',4':4,5]pyrrolo[2,3-d]pyridazin-5-one (320 mg, 0.87 mmol) in DCM (5 mL) was added mCPBA (704 mg, 3.5 mmol). After stirred at 0° C. for 1.5 hrs, the reaction mixture was quenched with satd. $Na_2S2O_3$, extracted with EtOAc. The organic phase was washed with brine, dried over anhy. $Na_2SO_4$ and evaporated under reduced pressure. The residue was purified by prep-TLC (10% MeOH in DCM) to give 110 mg of 6-benzyl-4-cyclopropyl-2-(methylsulfonyl)-4,6-dihydro-5H-thiazolo [5',4':4,5]pyrrolo[2,3-d]pyridazin-5-one. LC-MS: m/z 401 (M+1)$^+$.

Step E. Synthesis of 6-benzyl-4-cyclopropyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo [2,3-d]pyridazin-5-one To a mixture of 6-benzyl-4-ethyl-2-(methylsulfonyl)-4,6-dihydro-5H-thiazolo[5',4':4,5]pyrrolo [2,3-d]pyridazin-5-one (110 mg, 0.27 mmol) and 3-((phenylsulfonyl)methyl)-1-((2-(trimethylsilyl)ethoxy) methyl)-1H-pyrazole (123 mg, 0.35 mmol) in THF (3 mL) was added KO$^t$Bu (85 mg, 0.76 mmol) under $N_2$ at r.t. The mixture was stirred at r.t. for 3 hr. The reaction mixture was quenched with satd. $NH_4Cl$ and extracted with EtOAc twice. The combined organic phase was evaporated under reduced pressure. The residue was purified by flash chromatography (silica gel, 0~50% EtOAc in petroleum ether) to give 100 mg of 6-benzyl-4-cyclopropyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one. LC-MS: m/z 673 (M+1)$^+$.

Step F. Synthesis of 6-benzyl-4-cyclopropyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-cyclopropyl-2-((phenylsulfonyl)(1-((2-(trimethylsilyl)ethoxy)methyl)-1H-pyrazol-3-yl)methyl)-4,6-dihydro-5H-thiazolo[5',4':4,5] pyrrolo[2,3-d]pyridazin-5-one (100 mg, 0.15 mmol) in MeOH (3 mL) and THF (3 mL) was added $SmI_2$ (4.5 nl, 0.45 mmol) at −60° C. under $N_2$. The mixture was stirred at −60° C. for 10 min, quenched with $H_2O$ and extracted with EtOAc twice. The combined organic phases were dried over $Na_2SO_4$ and evaporated under reduced pressure. The residue was purified by flash chromatography (silica gel, 0~50% EtOAc in petroleum ether) to give 40 mg of 6-benzyl-4-cyclopropyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one. LC-MS: m/z 533 (M+1)$^+$.

Step G. Synthesis of 2-((1H-pyrazol-3-yl)methyl)-6-benzyl-4-cyclopropyl-4,6-dihydro-5H-thiazolo[5',4':4,5]pyrrolo[2,3-d]pyridazin-5-one To a mixture of 6-benzyl-4-cyclopropyl-2-((1-((2-(trimethylsilyl)ethoxy)methyl)-1H-pyrazol-3-yl)methyl)-4,6-dihydro-5H-thiazolo[5',4':4,5] pyrrolo[2,3-d]pyridazin-5-one (40 mg, 0.07 mmol) in DCM (4 mL) was added TFA (4 mL). The mixture was stirred at r.t. for 1.5 hrs. The reaction mixture was evaporated under reduced pressure. The residue was purified by prep-TLC (20% MeOH in DCM) to give 5 mg of 2-((1H-pyrazol-3-yl)methyl)-6-benzyl-4-cyclopropyl-4,6-dihydro-5H-thiazolo[5',4':4,5]pyrrolo[2,3-d]pyridazin-5-one. LC-MS (ESI): m/z 403 (M+1)$^+$. $^1$H NMR (400 MHz, DMSO-d6) δ 12.77 (s, 1H), 8.50 (s, 1H), 7.68 (s, 1H), 7.35-7.23 (m, 5H), 6.26 (d, 1H), 5.35 (s, 2H), 4.48 (s, 2H), 4.19 (tt, 1H), 1.40 (td, 2H), 1.15 (td, 2H).

Example 8J. Synthesis of 4-methyl-6-((1-methyl-1H-pyrazol-3-yl)methyl)-2-(2-(pyridin-3-yl)ethyl)-4H-thiazolo[5',4':4,5]pyrrolo[2,3-d]pyridazin-5(6H)-one

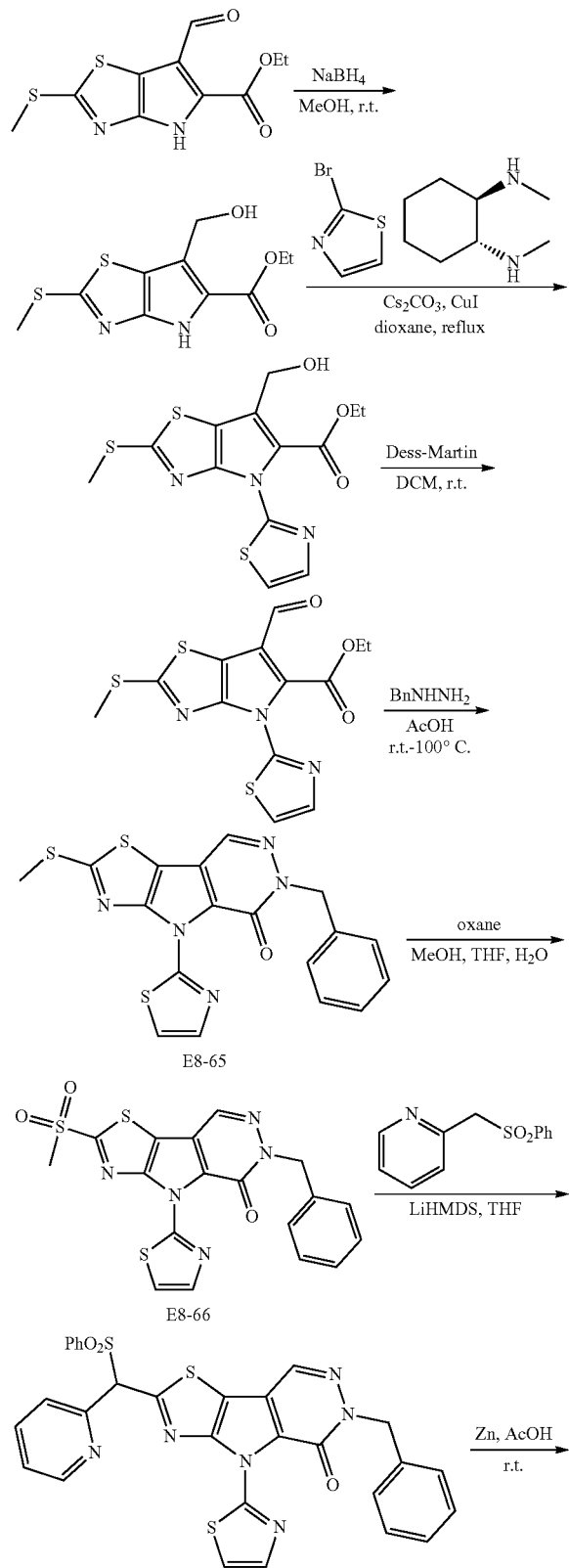

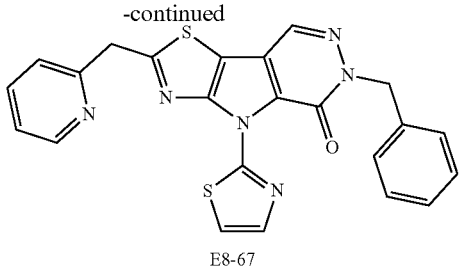

E8-67

Step A. Synthesis of ethyl 6-(hydroxymethyl)-2-(methylthio)-4H-pyrrolo[2,3-d]thiazole-5-carboxylate To a solution of ethyl 6-formyl-2-(methylthio)-4H-pyrrolo[2,3-d]thiazole-5-carboxylate (1.3 g, 4.8 mmol) in MeOH (20 mL) was added NaBH$_4$ (274 mg, 7.2 mmol) at 0° C. After stirred at 0° C. for 20 min, the reaction solution was diluted with EtOAc, washed with water and brine, dried over Na$_2$SO$_4$, concentrated in vacuum. The residue was purified by flash chromatography (silica gel, 0~10% MeOH in DCM) to give ethyl 6-(hydroxymethyl)-2-(methylthio)-4H-pyrrolo[2,3-d]thiazole-5-carboxylate (1 g). LC-MS (ESI): m/z 273 (M+1)$^+$.

Step B. Synthesis of ethyl 6-(hydroxymethyl)-2-(methylthio)-4-(thiazol-2-yl)-4H-pyrrolo[2,3-d]thiazole-5-carboxylate To a solution of ethyl 6-(hydroxymethyl)-2-(methylthio)-4H-pyrrolo[2,3-d]thiazole-5-carboxylate (1 g, 3.7 mmol) and 2-bromothiazole (3 g, 18.4 mmol) in dioxane (30 mL) was added Cs$_2$CO$_3$ (3 g, 9.2 mmol), followed by CuI (700 mg, 3.7 mmol) and N$^1$,N$^2$-dimethylcyclohexane-1,2-diamine (520 mg, 3.7 mmol). The reaction mixture was stirred at 110° C. under N$_2$ atmosphere for 16 hr. The reaction mixture was cooled to room temperature, filtered. The filtrate was diluted with EtOAc, washed with water and brine, dried over anhydrous Na$_2$SO$_4$, concentrated. The residue was purified by flash chromatography (silica gel, 30-50% EtOAc in petroleum ether) to give ethyl 6-(hydroxymethyl)-2-(methylthio)-4-(thiazol-2-yl)-4H-pyrrolo[2,3-d]thiazole-5-carboxylate (1 g). LC-MS (ESI): m/z 356 (M+1)$^+$.

Step C. Synthesis of ethyl 6-formyl-2-(methylthio)-4-(thiazol-2-yl)-4H-pyrrolo[2,3-d]thiazole-5-carboxylate To a solution of ethyl 6-(hydroxymethyl)-2-(methylthio)-4-(thiazol-2-yl)-4H-pyrrolo[2,3-d]thiazole-5-carboxylate (1 g, 2.8 mmol) in DCM (20 mL) was added Dess-martin (1.3 g, 3.4 mmol). After stirred at r.t. for 2 hrs, the reaction solution was diluted with DCM, washed with satd. NaHCO$_3$ and brine, dried over anhy. Na$_2$SO$_4$ and concentrated. The residue was purified by flash chromatography (silica gel, 20-30% EtOAc in petroleum ether) to give ethyl 6-formyl-2-(methylthio)-4-(thiazol-2-yl)-4H-pyrrolo[2,3-d]thiazole-5-carboxylate (800 mg). LC-MS (ESI): m/z 354 (M+1)$^+$.

Step D. Synthesis of 6-benzyl-2-(methylthio)-4-(thiazol-2-yl)-4H-thiazolo[5',4':4,5]pyrrolo[2,3-d]pyridazin-5(6H)-one To a solution of ethyl 6-formyl-2-(methylthio)-4-(thiazol-2-yl)-4H-pyrrolo[2,3-d]thiazole-5-carboxylate (800 mg, 2.3 mmol) in AcOH (10 mL) was added benzylhydrazine dihydrochloride (449 mg, 2.3 mmol). After stirred at r.t. for 1 hr, the reaction mixture was heated to 100° C. for 2 hrs. The reaction mixture was cooled to 0° C., neutralized with 1 M aq. NaOH, extracted with DCM. The organic phase was washed with brine, dried over anhy. Na$_2$SO$_4$ and concentrated in vacuum. The residue was purified by flash chromatography (silica gel, 0~5% MeOH in DCM) to give 6-benzyl-2-(methylthio)-4-(thiazol-2-yl)-4H-thiazolo[5',4': 4,5]pyrrolo[2,3-d]pyridazin-5(6H)-one (300 mg). LC-MS (ESI): m/z 412 (M+1)$^+$. $^1$H NMR (400 MHz, DMSO-d6) δ 8.72 (s, 1H), 7.98 (d, 1H), 7.87 (d, 1H), 7.40-7.15 (m, 5H), 5.31 (s, 2H), 2.76 (s, 3H).

Step E. Synthesis of 6-benzyl-2-(methylsulfonyl)-4-(thiazol-2-yl)-4H-thiazolo[5',4':4,5]pyrrolo[2,3-d]pyridazin-5(6H)-one To a mixture of 6-benzyl-2-(methylthio)-4-(thiazol-2-yl)-4H-thiazolo[5',4':4,5]pyrrolo[2,3-d]pyridazin-5(6H)-one (300 mg, 0.73 mmol) in MeOH (5 mL) and THF (5 mL) was added a solution of oxone (2.2 g, 3.6 mmol) in H$_2$O (5 mL) at 0° C. The reaction mixture was stirred at r.t. for 2 hrs. The reaction mixture was diluted with DCM, washed with satd. NaHCO$_3$ and brine, dried over anhy. Na$_2$SO$_4$ and concentrated in vacuum. The residue was purified by flash chromatography (silica gel, 0~5% MeOH in DCM) to give 6-benzyl-2-(methylsulfonyl)-4-(thiazol-2-yl)-4H-thiazolo[5',4':4,5]pyrrolo[2,3-d]pyridazin-5(6H)-one (260 mg). LC-MS (ESI): m/z 444 (M+1)$^+$. $^1$H NMR (400 MHz, DMSO-d6) δ 8.93 (s, 1H), 8.04 (d, 1H), 7.91 (d, 1H), 7.40-7.18 (m, 5H), 5.35 (s, 2H), 3.53 (s, 3H).

Step F. Synthesis of 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one To a stirring solution of 2-((phenylsulfonyl)methyl)pyridine (120 mg, 0.51 mmol) in THF (3 mL) was added LiHMDS (0.7 mL, 0.7 mmol) at 0° C. under N$_2$ atmosphere. After stirred at 0° C. for 30 min, a solution of 6-benzyl-2-(methylsulfonyl)-4-(thiazol-2-yl)-4H-thiazolo[5',4':4,5]pyrrolo[2,3-d]pyridazin-5(6H)-one (150 mg, 0.34 mmol) in THF (3 mL) was added. The resulting mixture was stirred at r.t. for 1 hr. The reaction was quenched with satd. NH$_4$Cl, extracted with DCM. The organic phase was washed with brine, dried over anhy. Na$_2$SO$_4$ and concentrated in vacuum. The residue was purified by flash chromatography (silica gel, 0~5% MeOH in DCM) to give 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one (100 mg). LC-MS (ESI): m/z 597 (M+1)$^+$.

Step G. Synthesis of 6-benzyl-2-(pyridin-2-ylmethyl)-4-(thiazol-2-yl)-4H-thiazolo[5',4':4,5]pyrrolo[2,3-d]pyridazin-5(6H)-one To a solution of 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one (100 mg, 0.17 mmol) in AcOH (5 mL) was added Zn (110 mg, 1.7 mmol). The reaction mixture was stirred at r.t. for 15 min. The reaction mixture was diluted with DCM, washed with satd. NaHCO$_3$ and brine, dried over anhy. Na$_2$SO$_4$ and concentrated in vacuum. The residue was purified by preTLC (65% EtOAc in petroleum ether) to give 5 mg of 6-benzyl-2-(pyridin-2-ylmethyl)-4-(thiazol-2-yl)-4H-thiazolo[5',4':4,5]pyrrolo[2,3-d]pyridazin-5(6H)-one. LC-MS (ESI): m/z 457 (M+1). $^1$H NMR (400 MHz, DMSO-d6) δ 8.72 (s, 1H), 8.61 (d, 1H), 7.98 (d, 1H), 7.92-7.84 (m, 2H), 7.55 (d, 1H), 7.41 (dd, 1H), 7.35-7.23 (m, 5H), 5.32 (s, 2H), 4.70 (s, 2H).

Example 9. Synthesis of Compounds E9-vi and E9-vii

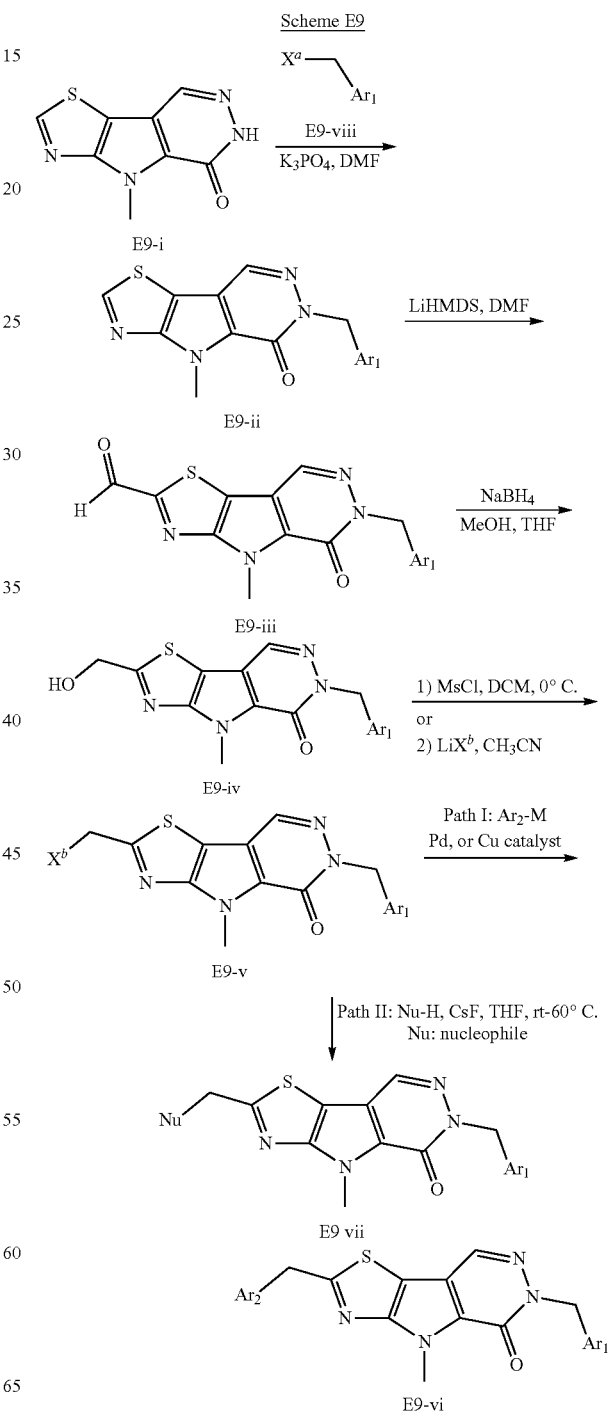

Compound E9-ii can be synthesized from compound E9-i through alkylation reaction as showed in example 7 or 8. Formylation reaction of compound E9-ii with LiHMDS and DMF provides intermediate E9-iii. Reduction of E9-iii with NaBH4 followed with halogenation gives intermediate E9-v. A metal (e.g. Pd or Cu) catalyzed coupling of E9-v with organic tin, boron, zinc or magnesium provides compound E9-vi. Compound E9-v can also reacts with some nucleophiles such as nitrogen in a heterocycle to give product E9-vii. As used herein, M is an organic metal complex (e.g. organoboron complex such as boronic acid or pinaco boron complex, organotin complex such as —Sn(Bu$^r$)$_3$; organozinc complex such as —Zn (halogen)); Ar$_1$ and Ar$_2$ are each independently optionally substituted aryl, optionally substituted heteroaryl, optionally substituted carbocycle or optionally substituted heterocyclyl, provided that Ar1 and Ar2 are not both optionally substituted 5-membered or 6-membered monocyclic heteroaryl; wherein X$^a$ and X$^b$ are each independently a leaving group (e.g. Br, I, OMs, or OTs); Ar1 and Ar2 are as defined in Scheme E8.

Example 9A. Synthesis of 6-((1H-indazol-4-yl) methyl)-4-methyl-2-(thiazol-4-ylmethyl)-4H-thiazolo[5',4':4,5]pyrrolo[2,3-d]pyridazin-5(6H)-one

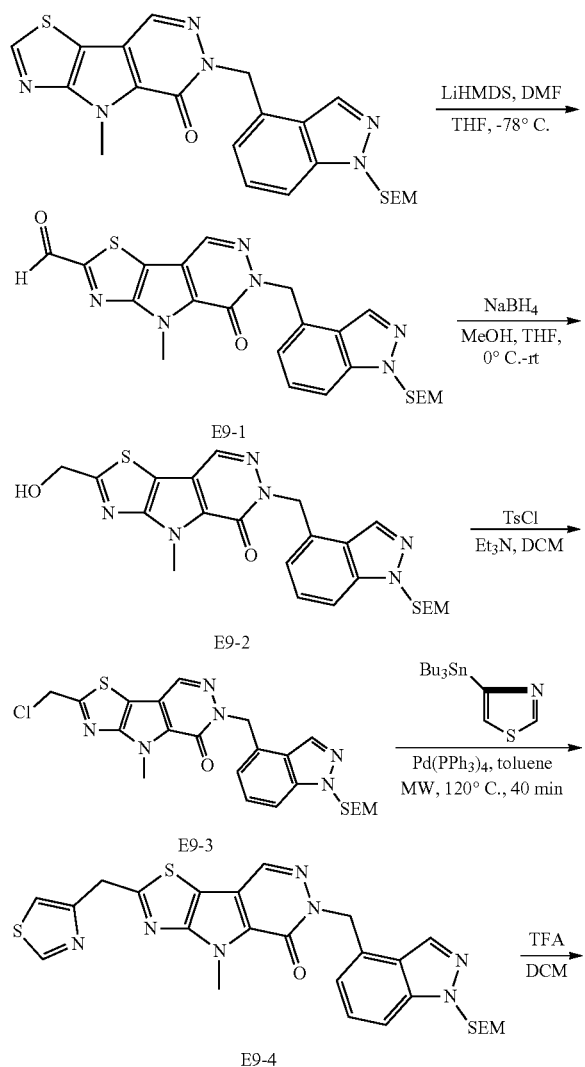

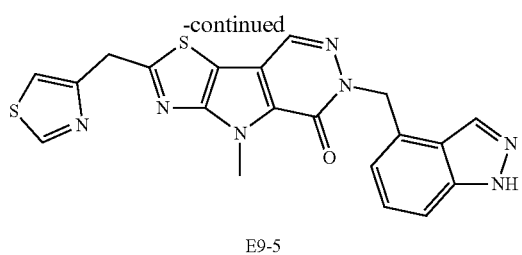

E9-5

Step A. Synthesis of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde. To a mixture of 4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (2.6 g, 5.57 mmol, 1 eq) in dry THF (30 mL) was added LiHMDS (1 M, 11.14 mL, 2.0 eq) at −78° C. The mixture was stirred at −78° C. for 2 hr. Then DMF (2.04 g, 27.86 mmol, 2.14 mL, 5.0 eq) was added dropwise to the above mixture. The mixture was stirred at −78° C. for 2 hr. TLC (PE:EA=2:1, UV=254 nm) showed that one main new spot was formed. The mixture was poured into cold sat. NH$_4$Cl (20 mL). Then the mixture was warmed to room temperature. The mixture was extracted with EtOAc (40 mL×3). The organic layer was washed by water (20 mL×3) and concentrated in vacuo to give the desired product (2.6 g, crude). LCMS: m/z 495.2 [M+H]$^+$ Step B. Synthesis of 2-(hydroxymethyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5 (6H)-one. To a mixture of crude 4-methyl-5-oxo-6-((1-((2-(trimethylsilyl)ethoxy) methyl)-1H-indazol-4-yl)methyl)-5, 6-dihydro-4H-thiazolo[5',4':4,5]pyrrolo[2,3-d]pyridazine-2-carbaldehyde (1.0 g, 2.02 mmol, 1 eq) in THF (10 mL) and MeOH (10 mL) was added NaBH$_4$ (152.97 mg, 4.04 mmol, 2 eq). The mixture was stirred at 30° C. for 14 hr. TLC (DCM:MeOH=10:1, UV=254 nm) showed that the starting material was consumed completely and one main new spot was formed. The reaction was quenched by addition of water (20 mL) and extracted with EtOAc (30 mL×3). The combined organic layers were washed with brine (20 mL). The organic phase was concentrated in vacuo. The residue was purified by flash silica gel chromatography (ISCO®; 40 g SepaFlash® Silica Flash Column, Eluent of 0~5% MeOH/DCM @ 30 mL/min). The eluent was concentrated in vacuo to give the desired product (382 mg). LCMS: m/z 497.1 [M+H]$^+$. $^1$H NMR (400 MHz, DMSO-d$_6$) δ ppm 8.61 (s, 1H), 8.25 (s, 1H), 7.66 (d, 1H), 7.38 (t, 1H), 7.05 (d), 6.36 (t, 1H), 5.74 (s, 2H), 5.68 (s, 2H), 4.89 (d, 2H), 4.26 (s, 3H), 3.50 (t, 2H), 0.78 (t, 2H), −0.12 (s, 9H).

Step C. Synthesis of 2-(chloromethyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5 (6H)-one. To a mixture of 2-(hydroxymethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5 (6H)-one (150.0 mg, 302.02 umol, 1 eq) and Et$_3$N (61.12 mg, 604.04 umol, 84.08 uL, 2.0 eq) in DCM (5 mL) was added 4-methylbenzenesulfonyl chloride (75.0 mg, 393.12 umol, 1.30 eq). The mixture was stirred at 30° C. for 5 hr. TLC (PE:EA=4:1, UV=254 nm) showed the starting material was consumed completely. Water (10 mL) and DCM (20 mL) was added to the mixture. The organic layers were concentrated in vacuo to give a yellow gum (0.1 g). The residue was purified by flash silica gel chromatography (ISCO®; 4 g SepaFlash® Silica Flash Column, Eluent of 0~20% Ethyl acetate/Petroleum ether gradient @ 30 mL/min). The desired fraction was concentrated in vacuo to give the desired product (40.0 mg, 76.88 umol). LCMS: m/z 515.1 [M+H]⁺. ¹H NMR (400 MHz, CHLOROFORM-d) δ ppm 8.27 (d, 1H), 8.26 (s, 1H), 7.52 (d, 1H), 7.39 (dd, 1H), 7.25 (s, 1H), 5.76 (s, 2H), 5.72 (s, 2H), 4.96 (s, 2H), 4.40 (s, 3H), 3.50-3.57 (m, 2H), 0.84-0.90 (m, 2H), −0.09 to −0.06 (m, 9H).

Step D. Synthesis of 4-methyl-2-(thiazol-4-ylmethyl)-6-((1-((2-(trimethylsilyl)ethoxy) methyl)-1H-indazol-4-yl)methyl)-4,6-dihydro-5H-thiazolo[5',4':4,5]pyrrolo[2,3-d]pyridazin-5-one. To a solution of 2-(chloromethyl)-4-methyl-6-((1-((2-(trimothylsilyl)ethoxy)methyl)-1H-indazol-4-yl)methyl)-4H-thiazolo[5',4':4,5]pyrrolo[2,3-d]pyridazin-5(6H)-one (50 mg, 0.97 mmol) and 4-(tributylstannyl)thiazole (114 mg, 2.91 mmol) in toluene (4 mL) was added Pd(PPh₃)₄ (402 mg, 2.91 mmol). Then the mixture was heated in MW reactor at 120° C. for 30 min under N₂. The solution was poured into water and extracted with EtOAc, dried over anhydrous Na₂SO₄. The organic layer was concentrated under reduced pressure. The residue was purified by flash chromatography (silica gel, 0~50% ethyl acetate in petroleum ether) to give 4-methyl-2-(thiazol-4-ylmethyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (compound E9-4) (30 mg). LCMS: 564 (M+H)⁺.

Step E. Synthesis of 6-((1H-indazol-4-yl)methyl)-4-methyl-2-(thiazol-4-ylmethyl)-4,6-dihydro-5H-thiazolo[5',4':4,5]pyrrolo[2,3-d]pyridazin-5-one. To a mixture of compound E9-4 (30 mg, 0.05 mmol) in DCM (3 mL) at r.t. under N₂ was added TFA (3 mL). The reaction mixture was stirred at r.t. for 1 h. The mixture was concentrated under reduced pressure. The residue was purified by prep. HPLC (C18, 0-90% acetonitrile in H₂O with 0.1% formic acid) to give the desired product (3.9 mg). LCMS: 434 (M+H)⁺. ¹H NMR (400 MHz, DMSO) δ 13.12 (s, 1H), 9.12 (d, 1H), 8.56 (s, 1H), 8.14 (s, 1H), 7.71 (d, 1H), 7.45 (d, 1H), 7.35-7.24 (m, 1H), 6.96 (d, 1H), 5.65 (s, 2H), 4.70 (s, 2H), 4.27 (s, 3H).

Example 9B. Synthesis of 2-((1H-imidazol-1-yl)methyl)-6-((1H-indazol-4-yl)methyl)-4-methyl-4,6-dihydro-5H-thiazolo[5',4':4,5]pyrrolo[2,3-d]pyridazin-5-one

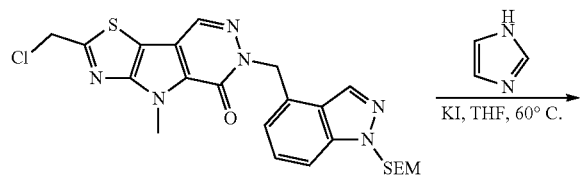

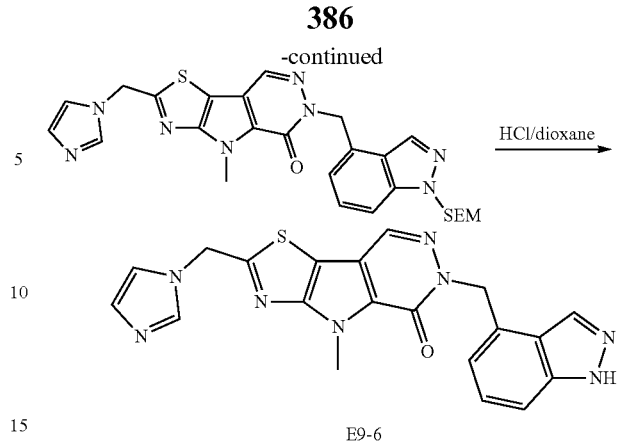

E9-6

Step A. Synthesis of 2-((1H-imidazol-1-yl)methyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one. To a mixture of 2-(chloromethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (25.0 mg, 48.53 umol, 1 eq) and KI (8.06 mg, 48.53 umol, 1 eq) in THF (0.3 mL) was added Imidazole (33.04 mg, 485.34 umol, 10.0 eq). The mixture was warmed up to 60° C. and stirred at 60° C. for 12 hr. LCMS showed that the desired product was generated and the starting material was consumed completely. The reaction mixture was combined with another batch (25 mg). The mixture was concentrated in vacuo to give a yellow crude gum (50.0 mg). The product would be used to next step reaction without any purification. LCMS: m/z 547.2 [M+H]⁺.

Step B. Synthesis of 2-((1H-imidazol-1-yl)methyl)-6-((1H-indazol-4-yl)methyl)-4-methyl-4H-thiazolo[5',4':4,5]pyrrolo[2,3-d]pyridazin-5(6H)-one. To a solution of 2-((1H-imidazol-1-yl)methyl)-4-methyl-6-((1-((2-(trimethylsilyl) ethoxy)methyl)-1H-indazol-4-yl) methyl)-4H-thiazolo[5',4':4,5]pyrrolo[2,3-d]pyridazin-5(6H)-one (50.0 mg, 64.02 umol, 1 eq) in dioxane (1 mL) was added HCl/dioxane (4 M, 2 mL, 124.96 eq) and 2 drops of water. The mixture was stirred at 30° C. for 12 hr. TLC (PE:EA=1:1, UV=254 nm) showed that the starting material was consumed completely. The mixture was concentrated in vacuo to give a yellow gum (0.2 g) which was purified by Preparative HPLC (basic) to give the title product (4.0 mg). LCMS: m/z 417.0 [M+H]⁺. ¹H NMR (400 MHz, METHANOL-d₄) ppm 8.43 (s, 1H), 8.22 (s, NH), 7.89 (s, 1H), 7.43-7.49 (m, 1H), 7.29-7.36 (m, 2H), 7.12 (d, 1H), 7.04 (s, H), 5.74 (s, 2H), 5.73 (s, 2H), 4.34 (s, 3H).

The following compounds were synthesized according to Scheme E9 and the procedure of Examples 9A-9B, using the appropriate starting material.

| Cpd No. | Structure | Characterization |
|---|---|---|
| E9-7 | ![structure] 6-((1H-indazol-4-yl)methyl)-4-methyl-2-(pyridin-4-ylmethyl)-4,6-dihydro-5H-thiazolo[5',4':4,5]pyrrolo[2,3-d]pyridazin-5-one | LCMS: 428 (M + H)⁺. ¹H NMR (400 MHz, DMSO-d₆) δ 13.12 (s, 1H), 8.57 (s, 1H), 8.55 (d, 2H), 8.13 (s, 1H), 7.46 (s, 1H), 7.44-7.41 (m, 2H), 7.29-7.26 (m, 1H), 6.95 (d, 1H), 5.65 (s, 2H), 4.58 (s, 2H), 4.26 (s, 3H). |

-continued

| Cpd No. | Structure | Characterization |
|---|---|---|
| E9-8 | 6-((1H-indazol-4-yl)methyl)-2-(isoxazol-4-ylmethyl)-4-methyl-4,6-dihydro-5H-thiazolo[5',4':4,5]pyrrolo[2,3-d]pyridazin-5-one | LCMS: 418 (M + H)+. $^1$H NMR (400 MHz, DMSO-d$_6$) 13.12 (s, 1H), 9.00 (s, 1H), 8.70 (s, 1H), 8.58 (s, 1H), 8.14 (s, 1H), 7.45 (d, 1H), 7.40-7.21 (m, 1H), 6.96 (d, 1H), 5.66 (s, 2H), 4.44 (s, 2H), 4.27 (s, 3H). |
| E9-9 | 2-(2-Hydroxy-pyrimidin-5-ylmethyl)-6-(1H-indazol-4-ylmethyl)-8-methyl-6,8-dihydro-3-thia-1,5,6,8-tetraaza-cyclopenta[a]inden-7-one | LC-MS: m/z 445 (M + H)+. 1H NMR (400 MHz, DMSO) δ 13.12 (s, 1H), 8.57 (s, 1H), 8.35 (s, 2H), 8.14 (s, 1H), 7.45 (d, 1H), 7.28 (dd, 1H), 6.96 (d, 1H), 5.65 (s, 2H), 4.32 (s, 2H), 4.26 (s, 3H). |
| E9-10 | 6-((1H-indazol-4-yl)methyl)-2-((2-methoxypyrimidin-5-yl)methyl)-4-methyl-4H-thiazolo[5',4':4,5]pyrrolo[2,3-d]pyridazin-5(6H)-one | LC-MS: m/z 459 (M + H)+. 1H NMR (400 MHz, DMSO) δ 13.11 (s, 1H), 8.69 (s, 2H), 8.57 (s, 1H), 8.13 (s, 1H), 7.45 (d, 1H), 7.31-7.24 (m, 1H), 6.96 (d, 1H), 5.65 (s, 2H), 4.52 (s, 2H), 4.26 (s, 3H), 3.92 (s, 3H) |
| E9-11 | 6-((1H-indazol-4-yl)methyl)-2-(isothiazol-5-ylmethyl)-4-methyl-4H-thiazolo[5',4':4,5]pyrrolo[2,3-d]pyridazin-5(6H)-one | LC-MS: m/z 434 (M + H)+. 1H NMR (400 MHz, DMSO) δ 13.13 (s, 1H), 8.60 (s, 1H), 8.52 (d, 1H), 8.15 (s, 1H), 7.48-7.41 (m, 2H), 7.31-7.25 (m, 1H), 6.96 (d, 1H), 5.66 (s, 2H), 5.00 (s, 2H), 4.29 (s, 3H) |

| Cpd No. | Structure | Characterization |
|---|---|---|
| E9-12 | 6-((1H-indazol-4-yl)methyl)-4-methyl-2-(thiazol-2-ylmethyl)-4H-thiazolo[5',4':4,5]pyrrolo[2,3-d]pyridazin-5(6H)-one | LC-MS: m/z 434 (M + H)+. 1H NMR (400 MHz, DMSO) δ 13.11 (s, 1H), 8.59 (s, 1H), 8.14 (s, 1H), 7.81 (d, 1H), 7.72 (d, 1H), 7.45 (d, 1H), 7.34-7.23 (m, 1H), 6.96 (d, 1H), 5.66 (s, 2H), 4.99 (s, 2H), 4.28 (s, 3H). |
| E9-13 | 6-((1H-indazol-4-yl)methyl)-4-methyl-2-(pyridin-3-ylmethyl)-4H-thiazolo[5',4':4,5]pyrrolo[2,3-d]pyridazin-5(6H)-one | LCMS: 428 (M + H)+. 1H NMR (400 MHz, DMSO-d6) δ 13.11 (s, 1H), 8.65 (d, 1H), 8.56 (s, 1H), 8.51 (dd, 1H), 8.13 (s, 1H), 7.84 (d, 1H), 7.47-7.38 (m, 2H), 7.31-7.25 (m, 1H), 6.95 (d, 1H), 5.65 (s, 2H), 4.58 (s, 2H), 4.27 (s, 3H). |
| E9-14 | 6-((1H-indazol-4-yl)methyl)-4-methyl-2-((2-oxo-1,2-dihydropyridin-4-yl)methyl)-4H-thiazolo[5',4':4,5]pyrrolo[2,3-d]pyridazin-5(6H)-one | LCMS: m/z 444 (M + H)+. 1H NMR (400 MHz, DMSO-d6) δ 13.11 (s, 1H), 11.52 (s, 1H), 8.58 (s, 1H), 8.14 (s, 1H), 7.45 (d, 1H), 7.33 (d, 1H), 7.30-7.25 (m, 1H), 6.95 (d, 1H), 6.32 (s, 1H), 6.16 (d, 1H), 5.66 (s, 2H), 4.35 (s, 2H), 4.28 (s, 3H). |
| E9-15 | 6-((1H-indazol-4-yl)methyl)-2-(1H-pyrazol-4-yl)methyl)-4-methyl-4H-thiazolo[5',4':4,5]pyrrolo[2,3-d]pyridazin-5(6H)-one | LCMS: m/z 417 (M + H)+. 1H NMR (400 MHz, DMSO) δ 13.12 (s, 1H), 12.82 (s, 1H), 8.54 (s, 1H), 8.14 (s, 1H), 7.79 (s, 1H), 7.53 (s, 1H), 7.45 (d, 1H), 7.28 (dd, 1H), 6.96 (d, 1H), 5.65 (s, 2H), 4.36 (s, 2H), 4.28 (s, 3H) |
| E9-16 | 6-((1H-indazol-4-yl)methyl)-4-methyl-2-(thiazol-5-ylmethyl)-4H-thiazolo[5',4':4,5]pyrrolo[2,3-d]pyridazin-5(6H)-one | LCMS: m/z 434 (M + H)+. 1H NMR (400 MHz, DMSO) δ 13.12 (s, 1H), 9.06 (s, 1H), 8.58 (s, 1H), 8.14 (s, 1H), 7.93 (s, 1H), 7.44 (d, 1H), 7.32-7.22 (m, 1H), 6.96 (d, 1H), 5.65 (s, 2H), 4.85 (s, 2H), 4.27 (s, 3H). |

| Cpd No. | Structure | Characterization |
|---|---|---|
| E9-17 | 2-((1H-1,2,4-triazol-1-yl)methyl)-6-((1H-indazol-4-yl)methyl)-4-methyl-4H-thiazolo[5',4':4,5]pyrrolo[2,3-d]pyridazin-5(6H)-one | LCMS: m/z 418.0 [M + H]+ $^1$H NMR (400 MHz, CDCl3) δ ppm 8.18 (s, 1H), 7.94 (s, 1H), 7.85 (s, 1H), 7.65 (s, 1H), 7.11 (d, 1H), 6.94 (t, 1H), 6.76 (d, 1H), 5.53 (s, 2H), 5.38 (s, 2H), 4.03 (s, 3H) |
| E9-18 | 6-((1H-indazol-4-yl)methyl)-2-((1H-pyrazol-1-yl)methyl)-4-methyl-4H-thiazolo[5',4':4,5]pyrrolo[2,3-d]pyridazin-5(6H)-one | LC-MS: 417.0 [M + H]+. $^1$H NMR (400 MHz, CDCl3) δ ppm 10.19 (brs, 1H), 8.34 (s, 1H), 8.21 (s, 1H), 7.62-7.67 (m, 2H), 7.40-7.44 (m, 1H), 7.38 (t, 1H), 7.26 (brd, 1H), 6.38-6.41 (m, 1H), 5.78 (s, 2H), 5.76 (s, 2H), 4.42 (s, 3H). |
| E9-19 | 6-((1H-indazol-4-yl)methyl)-2-((4H-1,2,4-triazol-4-yl)methyl)-4-methyl-4H-thiazolo[5',4':4,5]pyrrolo[2,3-d]pyridazin-5(6H)-one | LCMS: m/z 418.0 [M + H]+. $^1$H NMR (400 MHz, CDCl3) δ ppm 12.28 (brs, 1H), 8.27 (s, 2H), 7.97-8.08 (m, 2H), 7.23 (brd, 1H), 7.02-7.09 (m, 1H), 6.90 (brd, 1 H), 5.51 (s, 2H), 5.49 (s, 2H), 4.15 (s, 3H). |
| E9-20 | 6-((1H-indazol-4-yl)methyl)-2-((6-aminopyridin-2-yl)methyl)-4-methyl-4H-thiazolo[5',4':4,5]pyrrolo[2,3-d]pyridazin-5(6H)-one | LCMS: m/z 443 [M + H]+. $^1$H NMR (400 MHz, DMSO-d6) δ 8.60 (s, 1H), 8.11 (s, 1H), 7.86 (t, 2H), 7.42 (d, 1H), 7.24-7.28 (m, 1H), 6.95 (d, 1H), 6.83-6.89 (m, 2H), 5.63 (s, 2H), 4.68 (s, 2H), 4.24 (s, 3H) |
| E9-21 | 6-((1H-indazol-4-yl)methyl)-2-((2-methoxypyridin-4-yl)methyl)-4-methyl-4H-thiazolo[5',4':4,5]pyrrolo[2,3-d]pyridazin-5(6H)-one | LCMS: m/z 458 (M + H)+. 1H NMR (400 MHz, DMSO-d6) δ 13.11 (s, 1H), 8.57 (s, 1H), 8.15-8.12 (m, 2H), 7.45 (d, 1H), 7.30-7.25 (m, 1H), 7.01 (dd, 1H), 6.95 (d, 1H), 6.86 (s, 1H), 5.65 (s, 2H), 4.52 (s, 2H), 4.27 (s, 3H), 3.84 (s, 3H). |

| Cpd No. | Structure | Characterization |
|---|---|---|
| E9-22 | 6-((1H-indazol-4-yl)methyl)-4-methyl-2-(pyridin-2-ylmethyl)-4,6-dihydro-5H-thiazolo[5′,4′:4,5]pyrrolo[2,3-d]pyridazin-5-one | LCMS: 428 (M + H)+.<br>1H NMR (400 MHz, DMSO-d6) δ 13.12 (s, 1H), 8.56 (s, 2H), 8.14 (s, 1H), 7.83-7.79 (m, 1H), 7.51-7.44 (m, 2H), 7.35-7.23 (m, 2H), 6.96 (d, 1H), 5.65 (s, 2H), 4.67 (s, 2H), 4.27 (s, 3H). |
| E9-23 | 6-((1H-indazol-4-yl)methyl)-4-methyl-2-(pyridin-3-ylmethyl)-4,6-dihydro-5H-thiazolo[5′,4′:4,5]pyrrolo[2,3-d]pyridazin-5-one | LCMS: m/z 428 (M + H)+.<br>1H NMR (400 MHz, DMSO-d6) δ 13.11 (s, 1H), 8.65 (d, 1H), 8.56 (s, 1H), 8.51 (dd, 1H), 8.13 (s, 1H), 7.84 (d, 1H), 7.49-7.35 (m, 2H), 7.30-7.19 (m, 1H), 6.95 (d, 1H), 5.65 (s, 2H), 4.58 (s, 2H), 4.27 (s, 3H). |
| E9-24 | 6-((1H-indazol-4-yl)methyl)-4-methyl-2-(pyrimidin-5-ylmethyl)-4,6-dihydro-5H-thiazolo[5′,4′:4,5]pyrrolo[2,3-d]pyridazin-5-one | LCMS: m/z 429 (M + H)+.<br>1H NMR (400 MHz, DMSO-d6) δ 13.13 (s, 1H), 9.14 (s, 1H), 8.90 (s, 2H), 8.58 (s, 1H), 8.14 (s, 1H), 7.45 (d, 1H), 7.28 (t, 1H), 6.96 (d, 1H), 5.65 (s, 2H), 4.62 (s, 2H), 4.25 (s, 3H). |
| E9-25 | 6-((1H-indazol-4-yl)methyl)-2-((6-methoxypyridin-2-yl)methyl)-4-methyl-4,6-dihydro-5H-thiazolo[5′,4′:4,5]pyrrolo[2,3-d]pyridazin-5-one | LCMS: m/z 458 (M + H)+.<br>1H NMR (400 MHz, DMSO-d6) δ 13.11 (s, 1H), 8.57 (s, 1H), 8.14 (s, 1H), 7.71 (dd, 1H), 7.45 (d, 1H), 7.35-7.18 (m, 1H), 7.08 (d, 1H), 6.96 (d, 1H), 6.75 (d, 1H), 5.65 (s, 2H), 4.58 (s, 2H), 4.27 (s, 3H), 3.89 (s, 3H). |
| E9-26 | 6-((1H-indazol-4-yl)methyl)-2-((6-methoxypyridin-3-yl)methyl)-4-methyl-4,6-dihydro-5H-thiazolo[5′,4′:4,5]pyrrolo[2,3-d]pyridazin-5-one | LCMS: m/z 458 (M + H)+.<br>1H NMR (400 MHz, DMSO-d6) δ 13.11 (s, 1H), 8.55 (s, 1H), 8.24 (d, 1H), 8.13 (d, 1H), 7.75 (dd, 1H), 7.45 (d, 1H), 7.27 (dd, 1H), 6.95 (d, 1H), 6.83 (d, 1H), 5.65 (s, 2H), 4.47 (s, 2H), 4.27 (s, 3H), 3.85 (s, 3H). |

-continued

| Cpd No. | Structure | Characterization |
|---|---|---|
| E9-27 | 6-((1H-indazol-4-yl)methyl)-2-((1H-pyrazol-4-yl)methyl)-4-methyl-4,6-dihydro-5H-thiazolo[5′,4′:4,5]pyrrolo[2,3-d]pyridazin-5-one | LCMS: m/z 417 (M + H)$^+$.<br>$^1$H NMR (400 MHz, DMSO-d$_6$) δ 13.12 (s, 1H), 12.82 (s, 1H), 8.54 (s, 1H), 8.14 (s, 1H), 7.79 (s, 1H), 7.53 (s, 1H), 7.45 (d, Hz, 1H), 7.28 (dd, 1H), 6.96 (d, 1H), 5.65 (s, 2H), 4.36 (s, 2H), 4.28 (s, 3H). |
| E9-28 | 6-((1H-indazol-4-yl)methyl)-4-methyl-2-((6-oxo-1,6-dihydropyridin-3-yl)methyl)-4,6-dihydro-5H-thiazolo[5′,4′:4,5]pyrrolo[2,3-d]pyridazin-5-one | LCMS: m/z 444 (M + H)$^+$.<br>$^1$H NMR (400 MHz, DMSO-d$_6$) δ 13.11 (s, 1H), 11.58 (s, 1H), 8.56 (s, 1H), 8.13 (s, 1H), 7.43-7.49 (m, 3H), 7.27 (t, 1H), 6.95 (d, 1H), 6.33 (d, 1H), 5.65 (s, 2H), 4.25-4.27 (m, 5H). |
| E9-29 | 6-((1H-indazol-4-yl)methyl)-4-methyl-2-((6-oxo-1,6-dihydropyridin-2-yl)methyl)-4,6-dihydro-5H-thiazolo[5′,4′:4,5]pyrrolo[2,3-d]pyridazin-5-one | LCMS: m/z 444 (M + H)$^+$.<br>$^1$H NMR (400 MHz, DMSO-d$_6$) δ 13.11 (s, 1H), 11.83 (s, 1H), 8.59 (s, 1H), 8.14 (s, 1H), 7.43 (m, 2H), 7.28 (dd, 1H), 6.96 (d, 1H), 6.28 (d, 2H), 5.65 (s, 2H), 4.39 (s, 2H), 4.27 (s, 3H) |
| E9-30 | 6-((1H-indazol-4-yl)methyl)-4-methyl-2-((1-methyl-1H-pyrazol-4-yl)methyl)-4,6-dihydro-5H-thiazolo[5′,4′:4,5]pyrrolo[2,3-d]pyridazin-5-one | LCMS: m/z 431 (M + H)$^+$.<br>$^1$H NMR (400 MHz, DMSO-d$_6$) δ 8.56 (s, 1H), 8.14 (s, 1H), 7.49 (d, 1H), 7.41 (s, 1H), 7.32 (dd, 1H), 6.98 (d, 1H), 6.29 (d, 1H), 5.67 (s, 2H), 4.66 (s, 2H), 4.27 (s, 3H), 3.24 (s, 3H). |
| E9-31 | 3-((2-((1H-imidazol-1-yl)methyl)-4-methyl-5-oxo-4,5-dihydro-6H-thiazolo[5′,4′:4,5]pyrrolo[2,3-d]pyridazin-6-yl)methyl)benzamide | LC-MS: m/z 420 (M + H)$^+$.<br>$^1$H NMR (400 MHz, DMSO-d6) δ: δ 8.60 (s, 1H), 7.96 (s, 1H), 7.87 (s, 1H), 7.80-7.74 (m, 2H), 7.46-7.37 (m, 2H), 7.35 (s, 2H), 6.99 (s, 1H), 5.78 (s, 2H), 5.39 (s, 2H), 4.27 (s, 3H). |

| Cpd No. | Structure | Characterization |
|---|---|---|
| E9-32 | 6-allyl-4-methyl-2-(pyridin-2-ylmethyl)-4,6-dihydro-5H-thiazolo[5',4':4,5]pyrrolo[2,3-d]pyridazin-5-one | LC-MS: m/z 338 (M + H)⁺.<br>¹H NMR (400 MHz, DMSO-d6) δ: 8.56 (d, 1H), 8.53 (s, 1H), 7.81 (td, 1H), 7.51 (d, 1H), 7.33 (dd, 1H), 5.99 (dq, 1H), 5.12 (ddd, 2H), 4.76 (d, 2H), 4.67 (s, 2H), 4.26 (s, 3H) |
| E9-33 | 4-methyl-2-(pyridin-2-ylmethyl)-6-((tetrahydro-2H-pyran-4-yl)methyl)-4,6-dihydro-5H-thiazolo[5',4':4,5]pyrrolo[2,3-d]pyridazin-5-one | LC-MS: m/z 396 (M + H)⁺.<br>¹H NMR (400 MHz, DMSO-d6) δ: 8.56 (d, 1H), 8.51 (s, 1H), 7.81 (td, 1H), 7.50 (d, 1H), 7.38-7.27 (m, 1H), 4.67 (s, 2H), 4.26 (s, 3H), 4.05 (d, 2H), 3.82 (d, 2H), 3.23 (d, 2H), 2.13 (d, 1H), 1.46 (d, 2H), 1.35-1.26 (m, 2H) |

Example 10. Synthesis of Compound E10-ii

Scheme E10

As shown in Scheme E10, reaction of E10-i with an aldehyde in the presence of a base (e.g. LiHMDS) generates compound E10-ii, which can be separated with chiral HPLC or SFC to give two enantiomers. As used herein, Ar1 and Ar2 are each independently optionally substituted alkyl, optionally substituted haloalkyl, optionally substituted alkenyl, optionally substituted alkynyl, optionally substituted cycloalkyl, optionally substituted heterocyclyl, optionally substituted aryl, provided that Ar1 and Ar2 are not both optionally substituted 5-membered or 6-membered monocyclic heteroaryl.

Example 10A. Synthesis of (S)-6-((1H-indazol-4-yl)methyl)-2-(hydroxy(1H-pyrazol-3-yl)methyl)-4-methyl-4,6-dihydro-5H-thiazolo[5',4':4,5]pyrrolo[2,3-d]pyridazin-5-one and (R)-6-((1H-indazol-4-yl)methyl)-2-(hydroxy(1H-pyrazol-3-yl)methyl)-4-methyl-4,6-dihydro-5H-thiazolo[5',4':4,5]pyrrolo[2,3-d]pyridazin-5-one

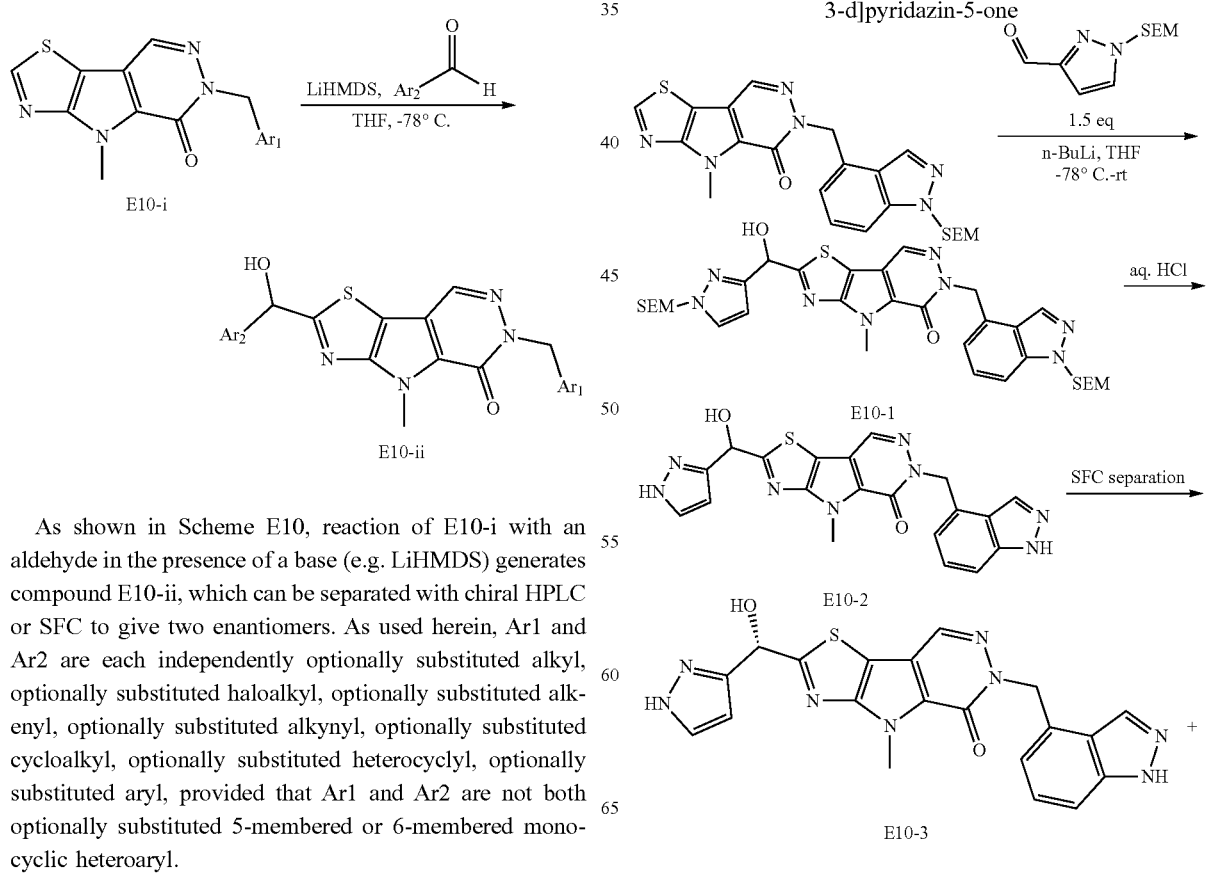

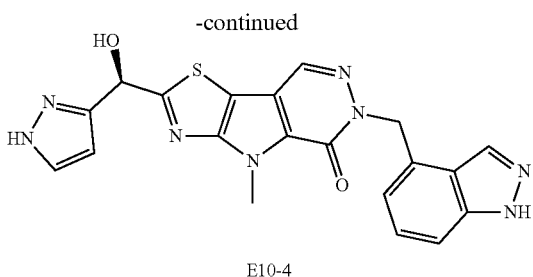

E10-4

Step A. Synthesis of 2-(hydroxy(1-((2-(trimethylsilyl) ethoxy)methyl)-1H-pyrazol-3-yl)methyl)-4-methyl-6-((1-((2-(trimethylsilyl)ethoxy)methyl)-1H-indazol-4-yl) methyl)-4H-thiazolo[5',4':4,5]pyrrolo[2,3-d]pyridazin-5 (6H)-one. Under argon, to a solution of 4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (0.5 g, 1.07 mmol, 1 eq) in THF (15 mL) was slowly added LiHMDS (1.0 M, 2.14 mL, 2.0 eq) at −78° C., and the reaction mixture was stirred at −78° C. for 1 hr. Then a solution of 1-(2-trimethylsilylethoxymethyl) pyrazole-3-carbaldehyde (1.21 g, 5.36 mmol, 5 eq) in THF (2 mL) was added dropwise to the reaction mixture. The resulting mixture was stirred at −78° C. for 1 hr. TLC (petroleum ether:EtOAc=2:1) showed two new spots formed. The reaction mixture was quenched by aq NH$_4$Cl (15 mL) at −70° C., and diluted with water (20 mL). The mixture was extracted with EtOAc (20 mL×3). The combined organic layers were washed with brine (20 mL), and dried over Na$_2$SO$_4$. The solvent was concentrated in vacuo. The residue was purified by Combiflash (from 100% of petroleum ether to 100% of EtOAc) to afford desired product (70 mg, 101.01 umol). LCMS: m/z 693.2 (M+H)+

Step B. Synthesis of 6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one. To a solution of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (0.04 g, 57.72 umol, 1 eq) in DCM (3 mL) was added TFA (65.82 mg, 577.22 umol, 42.74 uL, 10 eq) at 0° C., and the reaction mixture was stirred at room temperature for 36 hr. LCMS showed the starting material was consumed completely, and 57% of desired product was formed. The reaction mixture was concentrated in vacuo, and the residue was purified by Prep-HPLC to give the desired product (11 mg). LCMS: m/z 432.9 [M+H]+. $^1$H NMR (400 MHz, DMSO-d$_6$) δ ppm 13.10 (brs, 2H), 8.58 (s, 1H), 8.12 (s, 1H), 7.60 (s, 1H), 7.43 (d, 1H), 7.26 (dd, 1H), 6.93 (d, 2H), 6.19 (d, 1H), 6.07 (s, 1H), 5.63 (s, 2H), 4.20 (s, 3H).

Step C. Synthesis of (S)-6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one and (R)-6-((1H-indazol-4-yl)methyl)-2-(hydroxy(1H-pyrazol-3-yl) methyl)-4-methyl-4H-thiazolo[5',4':4,5]pyrrolo[2,3-d] pyridazin-5(6H)-one. The compound 6-((1H-indazol-4-yl) methyl)-2-(hydroxy(1H-pyrazol-3-yl)methyl)-4-methyl-4H-thiazolo[5',4':4,5]pyrrolo[2,3-d]pyridazin-5(6H)-one was separated by SFC. SFC condition: Column is DAICEL CHIRALCEL OJ-H (250 mm*30 mm, 5 um); mobile phase: A: 55% of CO2; B: 45% [0.19, 15. NH$_3$H2O in EtOH]/min. The SFC separation afforded two enantiomers. One enantiomer (2.6 mg): LCMS: m/z 433.0 [M+H]+. $^1$H NMR (400 MHz, DMSO-d$_6$) δ ppm 8.63 (s, 1H), 8.16 (s, 1H), 7.64 (brs, 1H), 7.47 (brd, 1H), 7.27-7.32 (m, 1H), 6.97 (brd, 1H), 6.22 (d, 1H), 6.11 (s, 1H), 5.64 (s, 2H), 5.34 (brs, 1H), 4.24 (s, 3H). And 3.5 mg of another enantiomer: LCMS: m/z 433.0 (M+H)+. $^1$H NMR (400 MHz, DMSO-d$_6$) δ ppm 8.63 (s, 1H), 8.17 (s, 1H), 7.64 (brs, 1H), 7.48 (brd, 1H), 7.28-7.32 (m, 1H), 6.98 (brd, 1H), 6.23 (d, 1H), 6.11 (s, 1H), 5.64 (s, 2H), 5.34 (brs, 1H), 4.25 (s, 3H).

Example 11. PKR Mutant Assay

Procedure:

PKR or PKR mutant enzyme solution was diluted into a reaction mix, which contains 1× buffer (100 mM KCl, 50 mM Tris pH 7.5, 5 mM MgCl$_2$) as well as PEP (conc depends on enzyme), 180 μM NADH, 0.5 units LDH, 1 mM DTT, 0.03% BSA; final assay concentrations after 1.11 fold dilution are indicated.

2 μL of test compound was added into wells first, and then 180 μL reaction mix was added.

Reactions mixture with test compound was assembled except for ADP, and plates were stored for 60 minutes at room temperature.

20 uL ADP was added to start reaction at room temperature and reaction progress was measured as changes in absorbance at 340 nm wavelength at room temperature.

Test Compound Preparation:

Test compound stock was made at 100× concentration in 100% DMSO (10 mM)

1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)

1 to 100 dilution into assay (2 μl in 200 μl) yielded starting concentration of 100 μM, decreasing 3 fold for 11 points.

Assay Buffer: 100 mM KCl, 50 mM Tris 7.5, 5 mM MgCl$_2$, 1 mM DTT, 0.03% BSA

Reaction Mixture: PKR mutant enzyme: 40-400 ng/well; ADP: 0.2-1.65 mM; PEP: 0.1-0.5 mM; NADH: 180 μM; LDH: 0.5 units (Sigma #59023); DTT: 1 mM; BSA: 0.03%.

Example 12. PKR WT Single Point Percent Activation Assay

A compound described herein was diluted with DMSO and tested at 1 M concentration. The enzyme was diluted in an enzyme solution, which contains 1× buffer (100 mM KCl, 50 mM Tris pH 7.5, 5 mM MgCl$_2$) as well as PEP (conc depends on enzyme), 180 μM NADH, 0.5 units LDH, 1 mM DTT, 0.03% BSA; final assay concentrations after 1.11 fold dilution are indicated.

2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340. The assay was run at room temperature.

Final concentration: PKR wt (100 ng/well), Tris pH 7.5 (50 mM), KCl (100 mM), MgCl$_2$ (5 mM), ADP (0.48 mM), PEP (0.15 mM), NADH (180 μM), LDH (0.5 units, Sigma 59023), DTT (1 mM) and BSA (0.03%).

Example 13. PKR R510Q Single Point Percent Activation Assay

A compound described herein was diluted with DMSO and tested at 1 M concentration. The enzyme was diluted in into an enzyme solution, which contains 1× buffer (100 mM KCl, 50 mM Tris pH 7.5, 5 mM MgCl2) as well as PEP (conc depends on enzyme), 180 μM NADH, 0.5 units LDH, 1 mM DTT, 0.03% BSA; final assay concentrations after 1.11 fold dilution are indicated.

2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340. The assay was run at room temperature.
Final concentration: PKR R510Q (40 ng/well), Tris pH 7.5 (50 mM), KCl (100 mM), MgCl$_2$ (5 mM), ADP (0.2 mM), PEP (0.11 mM), NADH (180 μM), LDH (0.5 units, Sigma 59023), DTT (1 mM) and BSA (0.03%).

Example 14. PKR R532W Single Point Percent Activation Assay

A compound described herein was diluted with DMSO and tested at 1 μM concentration. The enzyme was diluted in an enzyme solution, which contains 1× buffer (100 mM KCl, 50 mM Tris pH 7.5, 5 mM MgCl2) as well as PEP (conc depends on enzyme), 180 M NADH, 0.5 units LDH, 1 mM DTT, 0.03% BSA; final assay concentrations after 1.11 fold dilution are indicated.

2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340. The assay was run at room temperature.
Final concentration: PKR R532W (100 ng/well), Tris pH 7.5 (50 mM), KCl (100 mM), MgCl2 (5 mM), ADP (0.36 mM), PEP (0.1 mM), NADH (180 μM), LDH (0.5 units, Sigma 59023), DTT (1 mM) and BSA (0.03%).

Example 15. PKR T384M Single Point Percent Activation Assay

A compound described herein was diluted with DMSO and tested at 1 μM concentration. The enzyme was diluted in into an enzyme solution, which contains 1× buffer (100 mM KCl, 50 mM Tris pH 7.5, 5 mM MgCl2) as well as PEP (conc depends on enzyme), 180 μM NADH, 0.5 units LDH, 1 mM DTT, 0.03% BSA; final assay concentrations after 1.11 fold dilution are indicated.

2 μL of compound solution was first added into wells, and then 1-80 μL enzyme solution was added. Assays were assembled except for ADP, and plates were stored for 60 minutes at RT. 20 μL ADP was added to start the assay and assay output was evaluated using OD340. The assay was run at room temperature.
Final concentration: PKR T384M soluble (300 ng/well), Tris pH 7.5 (50 mM), KCl (100 mM), MgCl2 (5 mM), ADP (0.08 mM), PEP (0.23 mM), NADH (180 μM), LDH (0.5 units, Sigma 59023), DTT (1 mM) and BSA (0.03%).

Example 16. Red Blood Cell (RBC) Purification

Fresh blood drawn from healthy volunteers into K$_2$EDTA tubes was collected. Whole blood was pelleted by spinning at 500 g for 10 minutes. Cut transfusion bag port off of Purecell leukocyte reduction neofilter (Fisher NC0267633) one (1) inch above filter. Attach a 10 ml syringe barrel to the remaining cut tubing attached to neofilter. The plasma layer was removed from the pellet of the whole blood and the pellet was resuspended in 2× volume of phosphate buffered saline (PBS). Transfer 9 ml re-suspended blood cell pellet to prepared 10 ml syringe that is attached to the neofilter. Allow whole blood to gravity flow through filter until all fluid runs through upper tubing into filter disc. Add plunger to the syringe, remove syringe from clamp and invert the filter, then plunge air through the syringe filter system. Using a new 5 ml syringe, remove filtered RBCs from the bag by the syringe port and transfer purified RBCs to a 5 ml snap cap tube that has been incubated on ice. Spin 5 ml snap cap tube at 500 g for 10 minutes at 15 C, aspirate supernatant and resuspend in AGAM (1×PBS, 1% glucose, 170 mg/L adenine, 5.25 g/L mannitol) at a density of 4×10$^9$ cells/mL.

Example 17. Cell Based ATP Assay

For cell based ATP assays, the compound as described herein was prepared in 100% DMSO as a 10 mM stock. Serial dilutions (1:4) were performed in 96-well V-bottom storage plate and then added 1:100 to 96-well V-bottom plates containing AGAM. RBCs were diluted in AGAM media to a density of 1×10$^7$ cells/mL before added 90 μL/well to black clear bottom assay plates (final compound concentration at 0.1% DMSO concentration). Assay plates were sealed using aluminum foil seals and incubated overnight at 37° C. in a humidified chamber. ATP levels were read out using Cell-Titer-Glo (Promega).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:
1. A compound having a structural formula selected from:

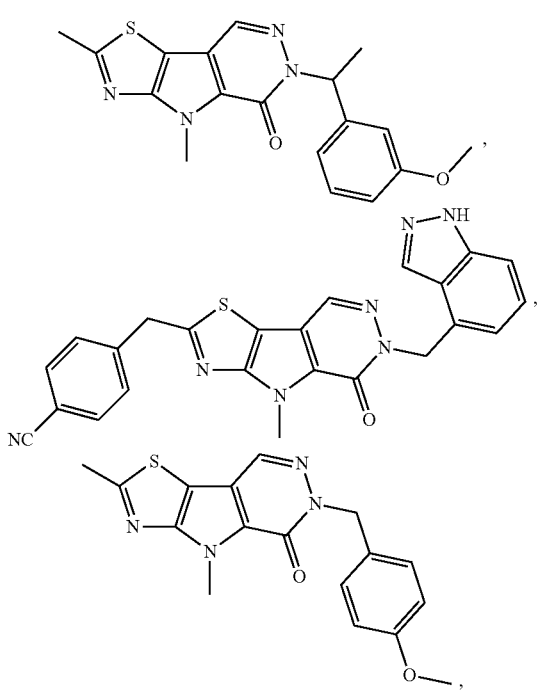

403
-continued
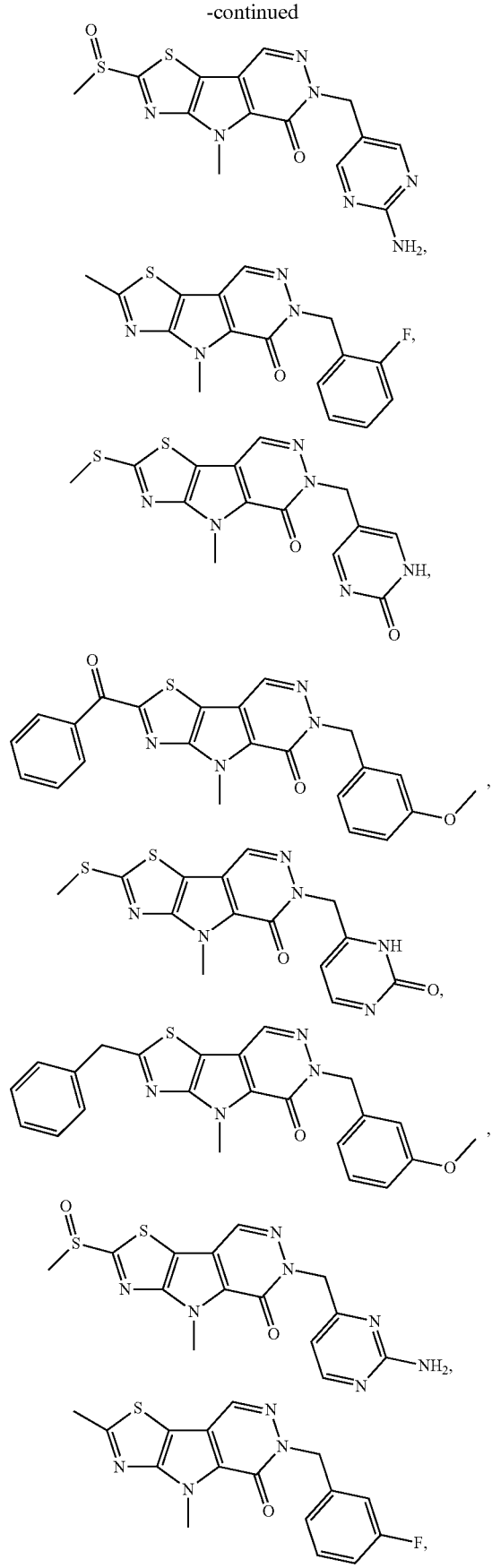
404
-continued
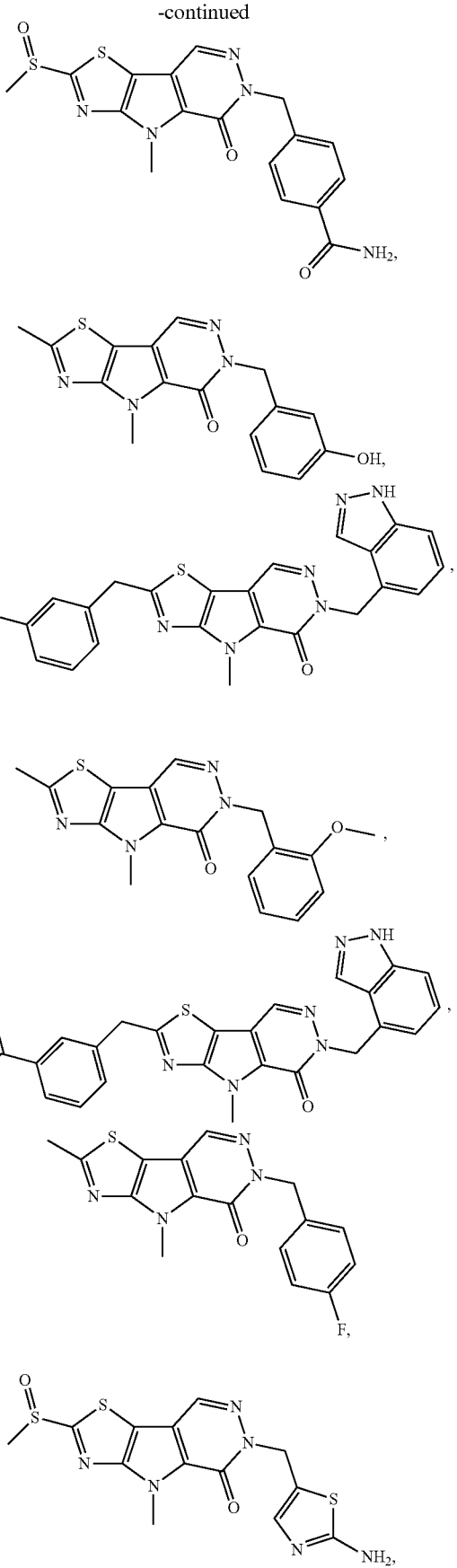

405
-continued
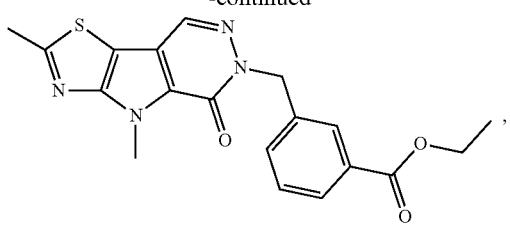
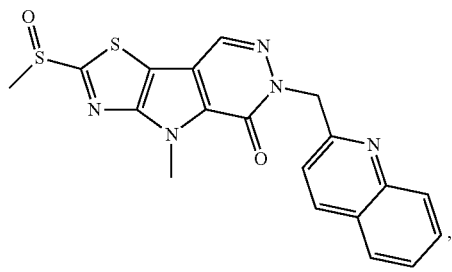
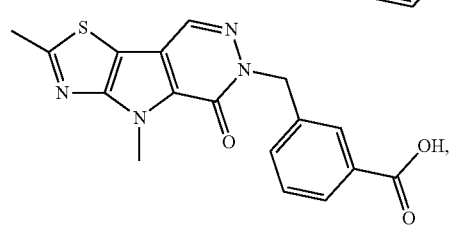
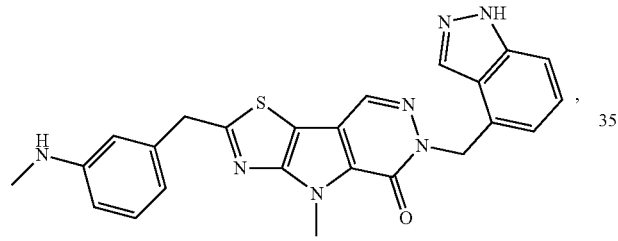
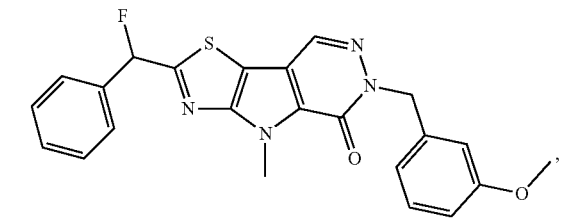
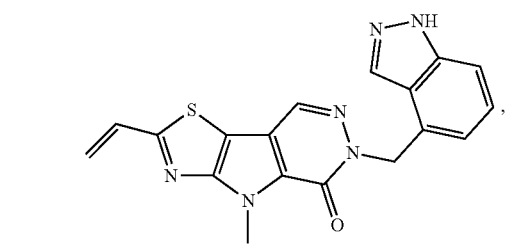
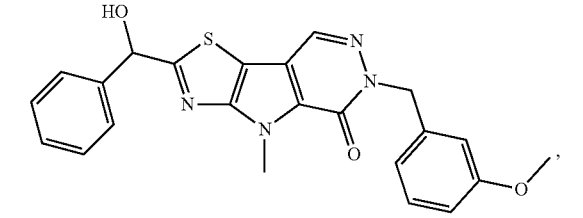
406
-continued
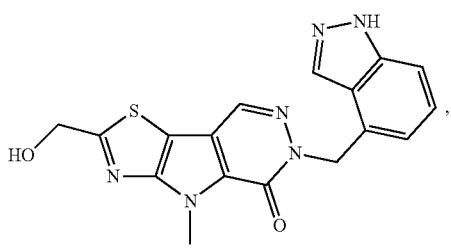
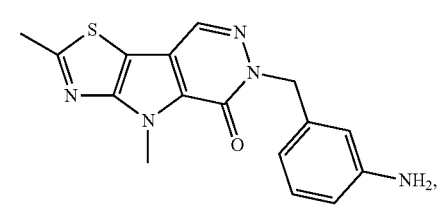
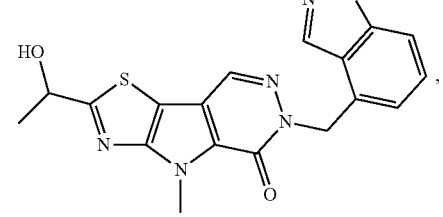
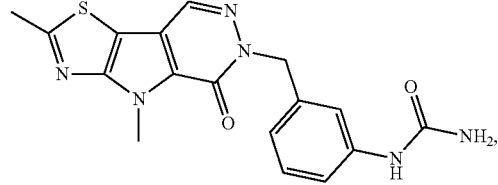
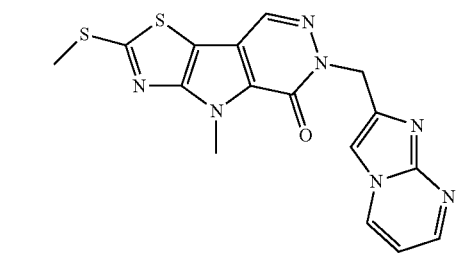
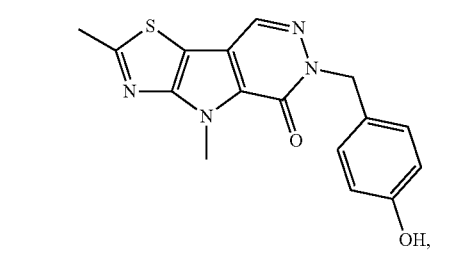
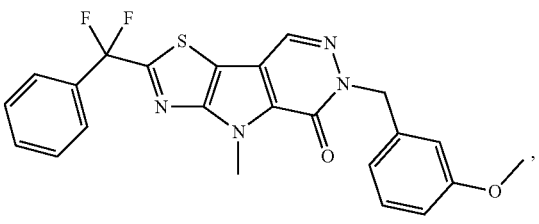

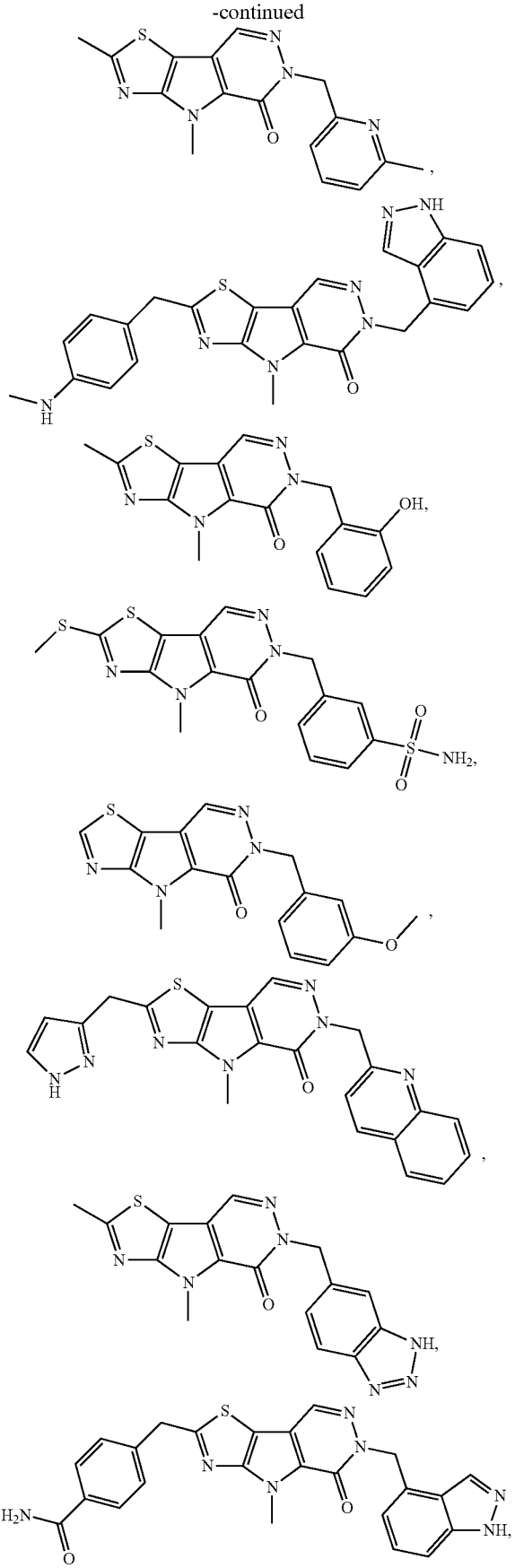
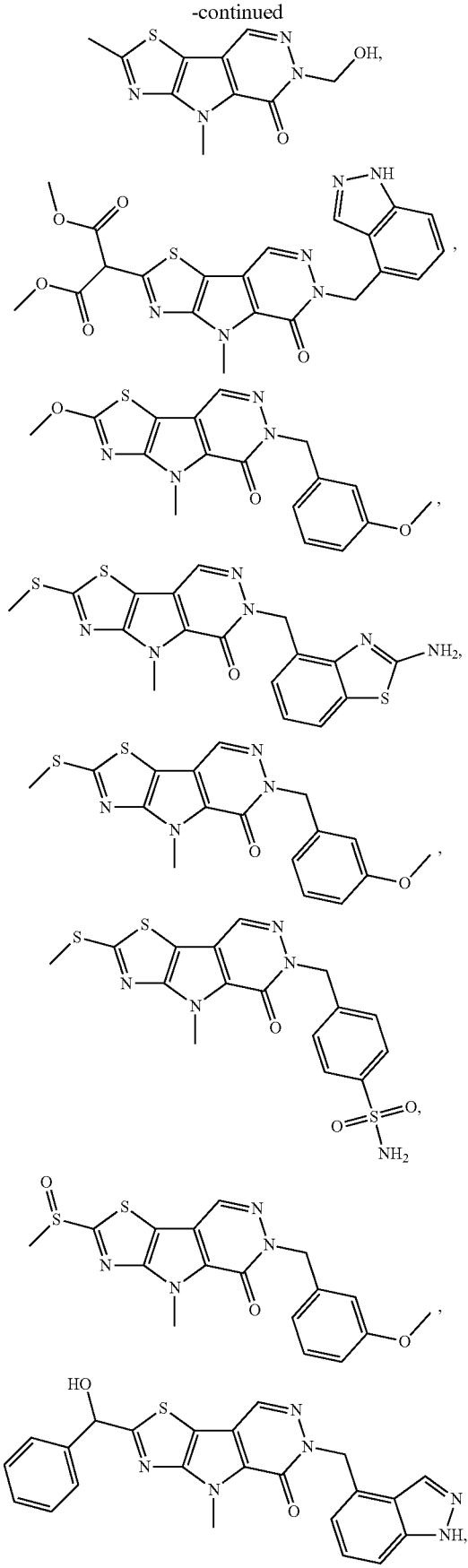

409
-continued
410
-continued
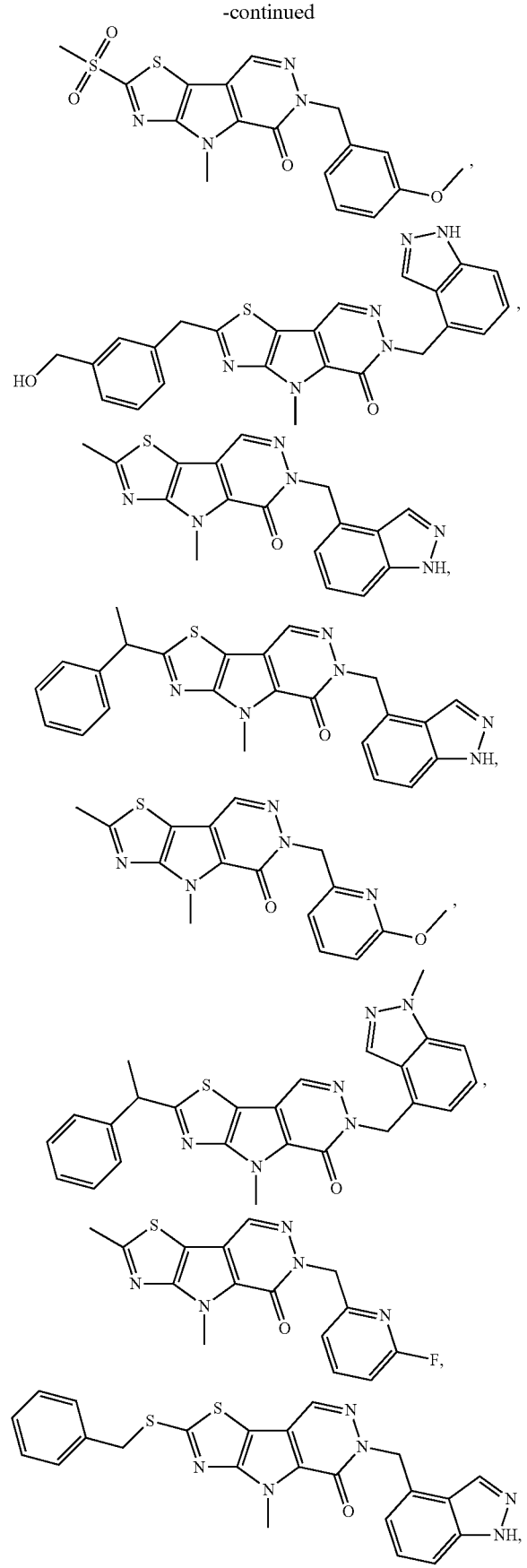
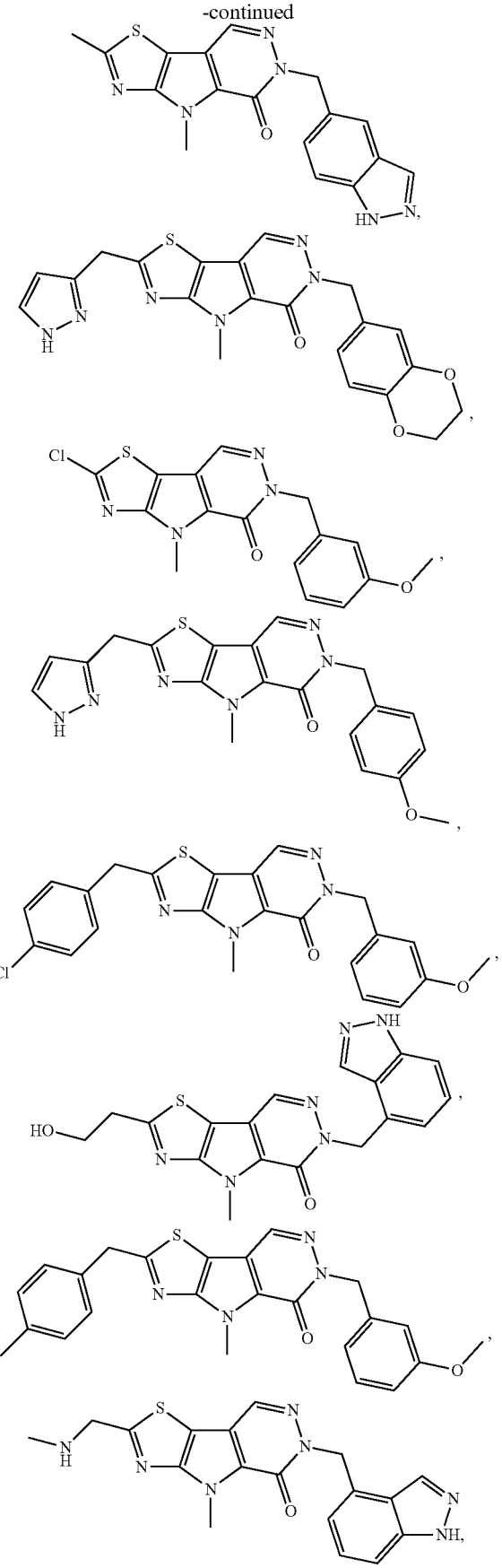

411
-continued
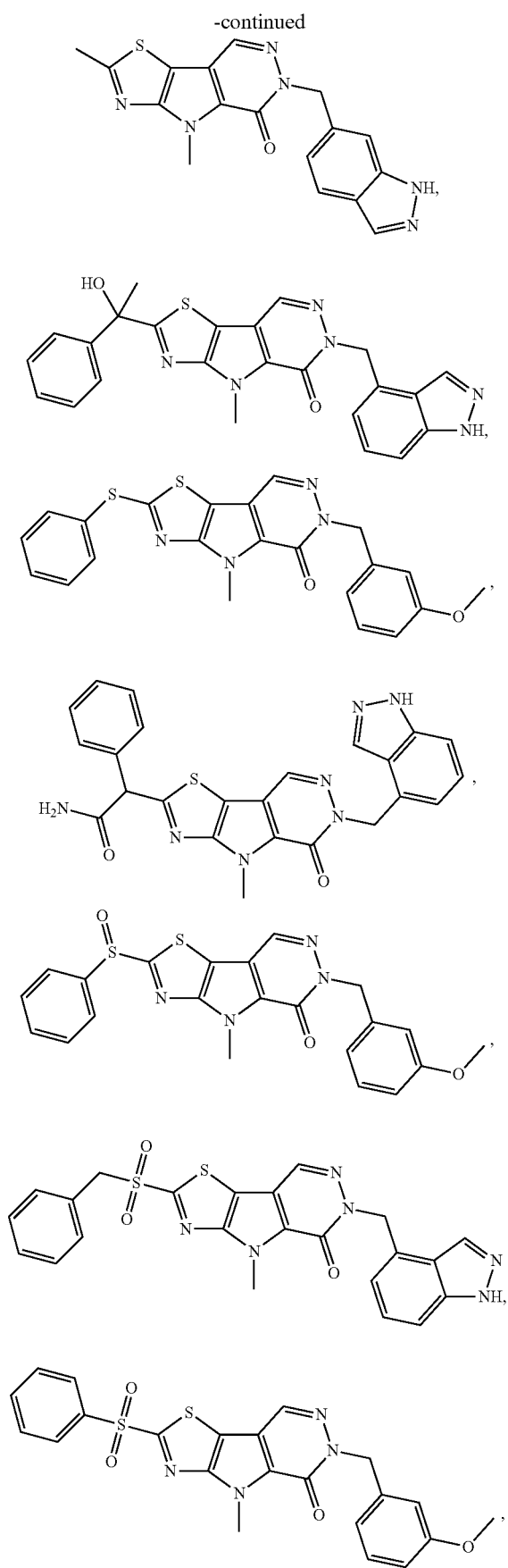
412
-continued
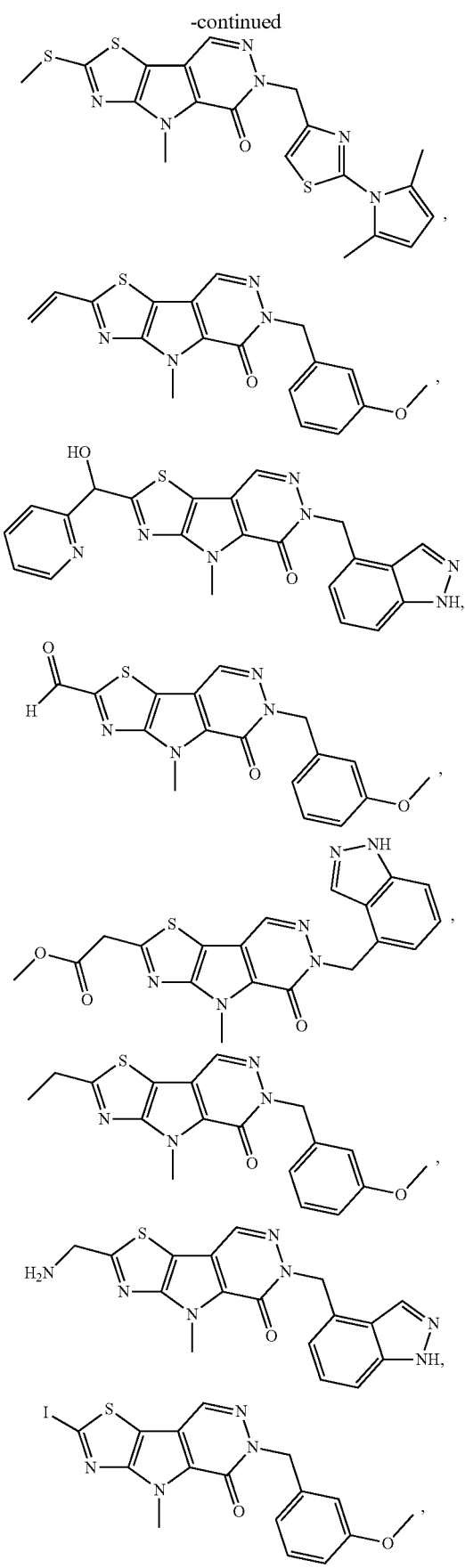

413
-continued
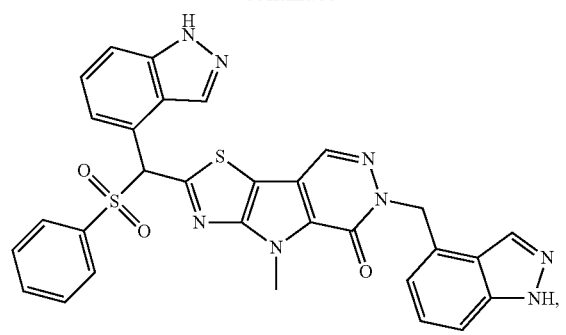
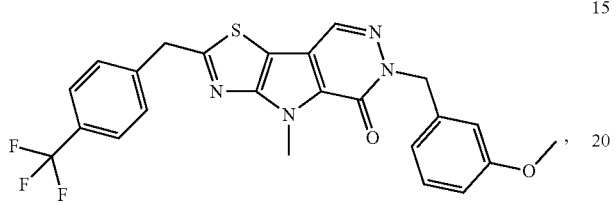
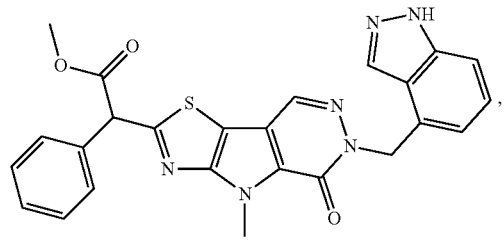
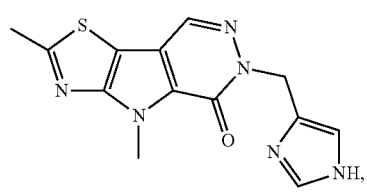
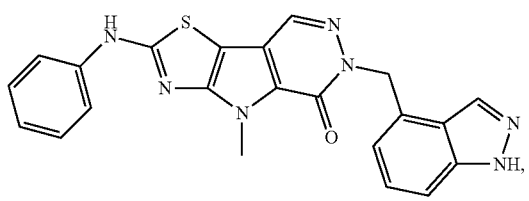
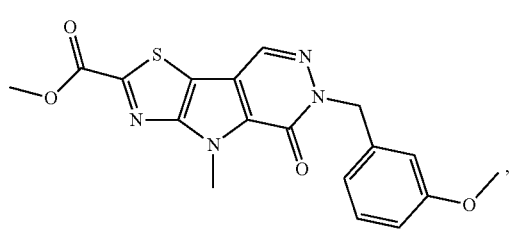
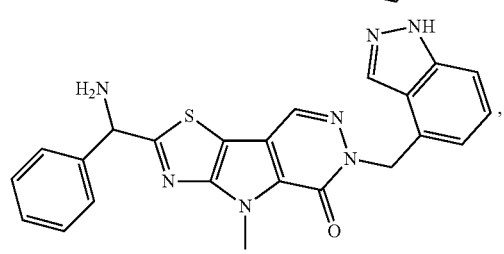
414
-continued
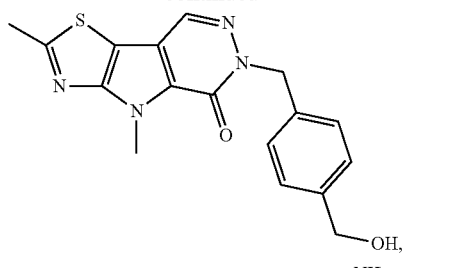
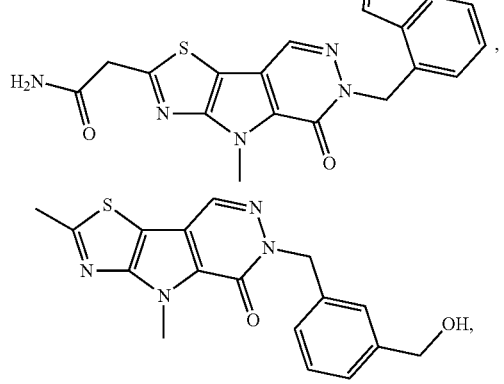
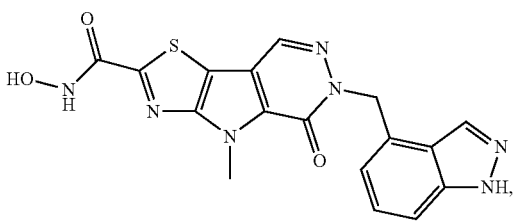
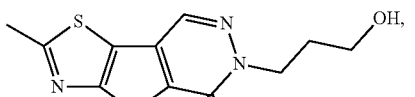
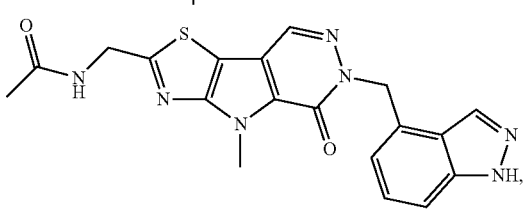
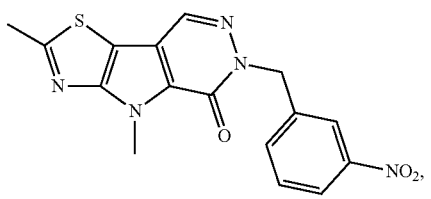
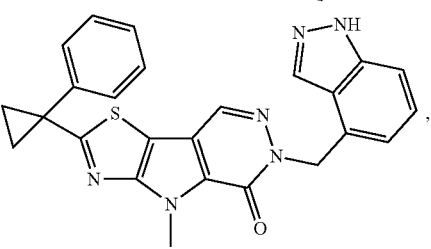

-continued
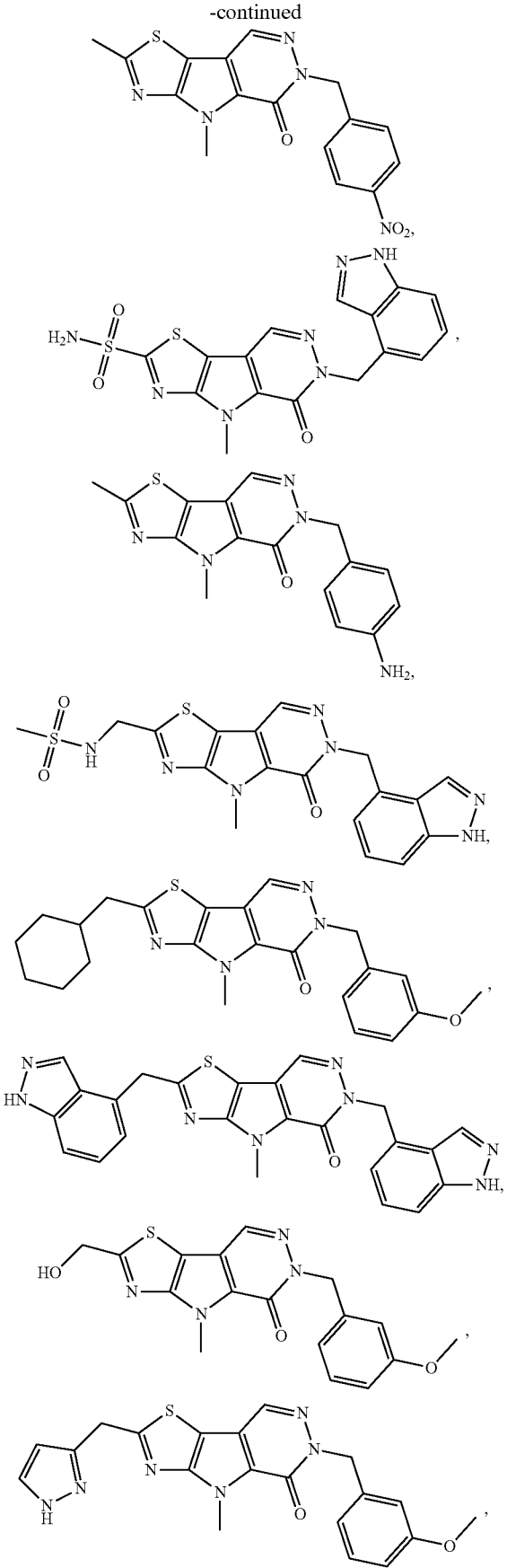
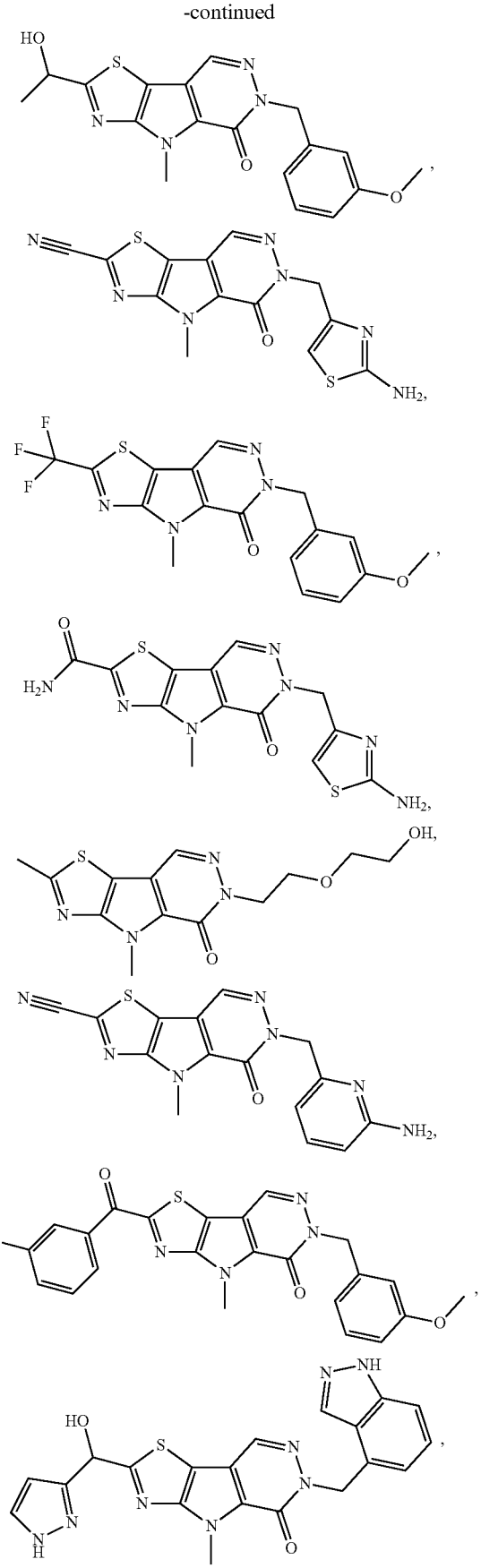

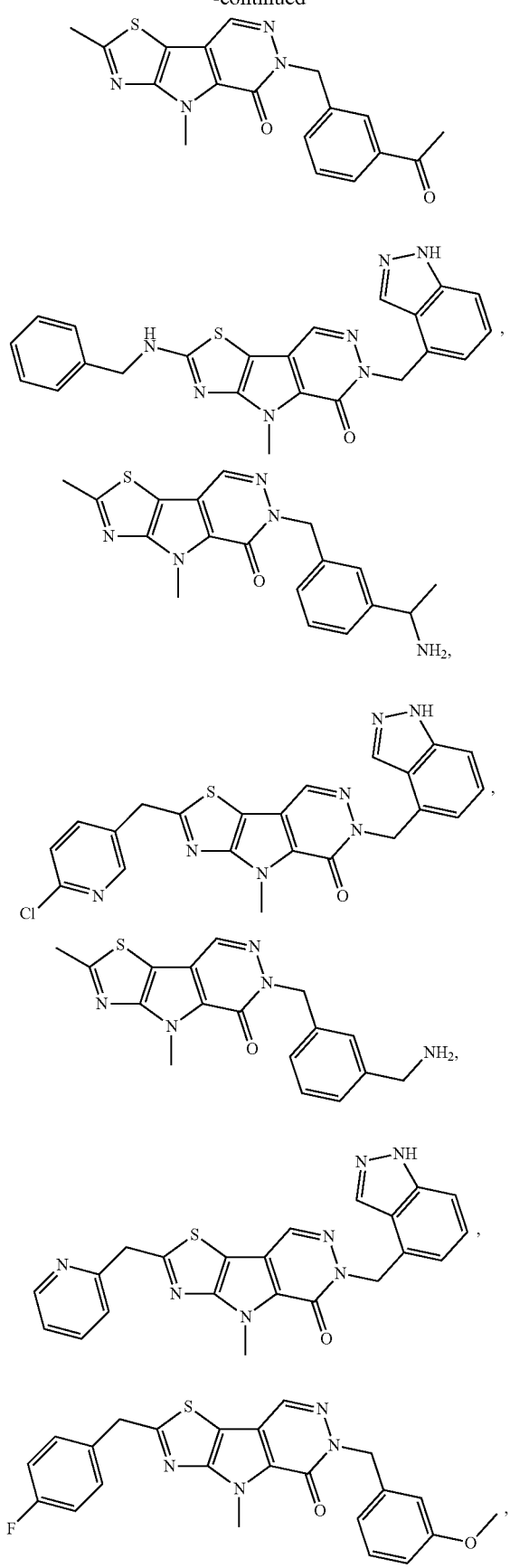
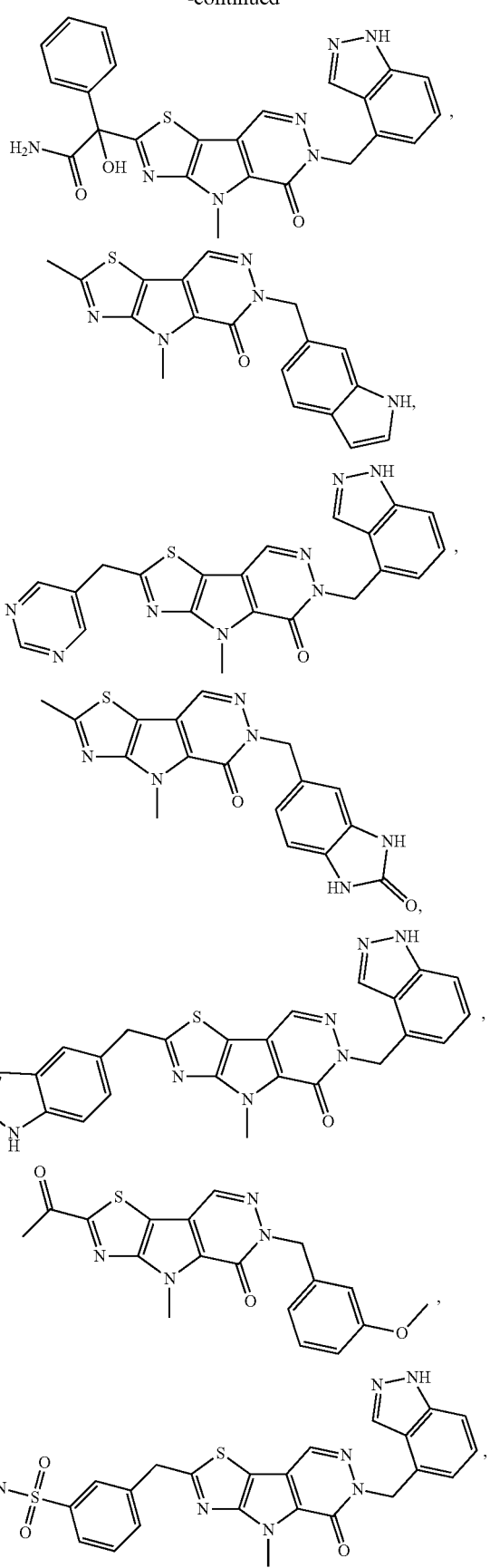

419
-continued
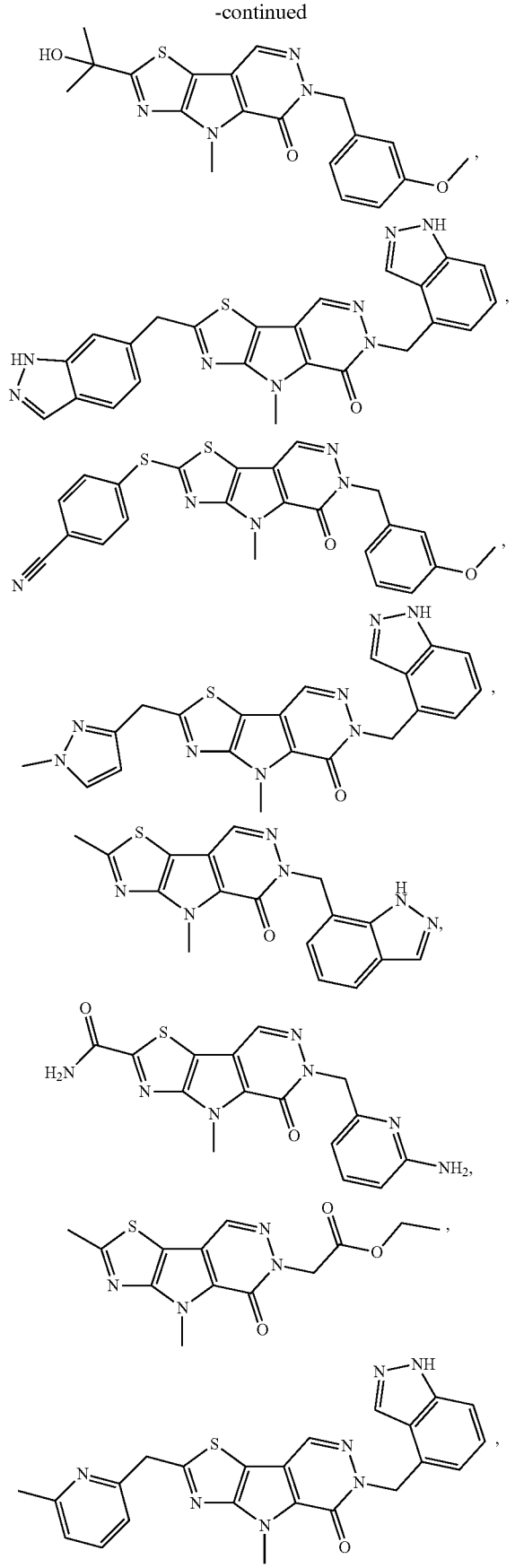
420
-continued
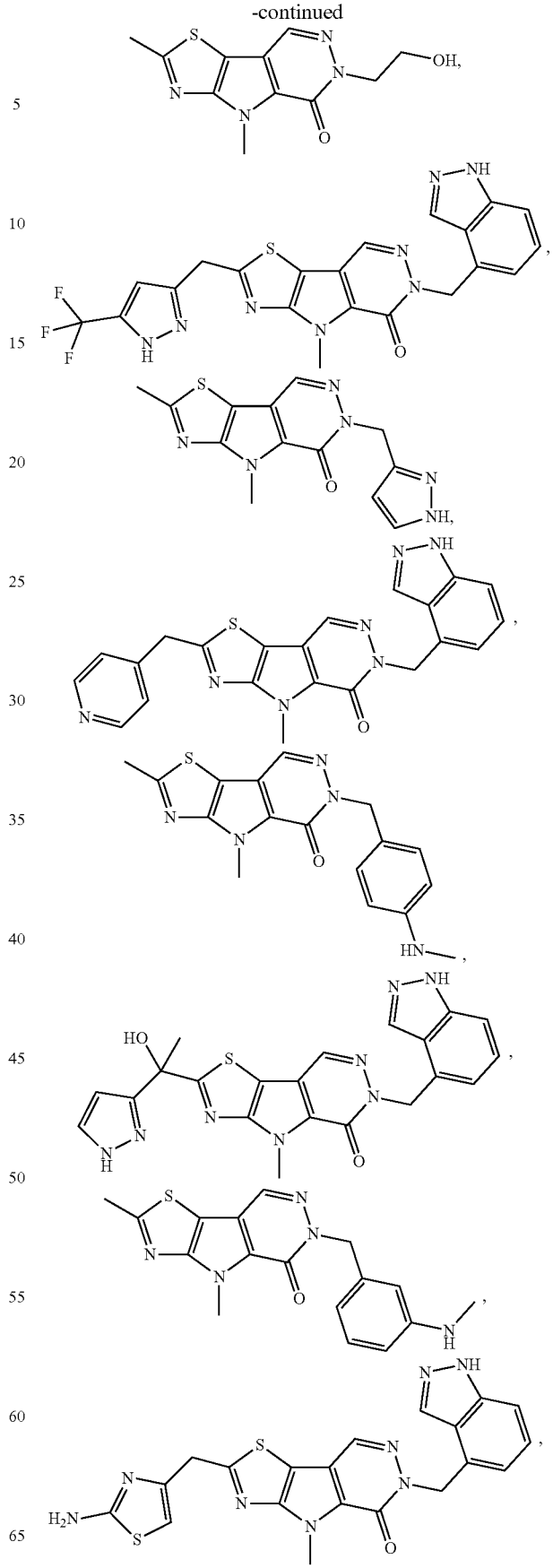

421
-continued
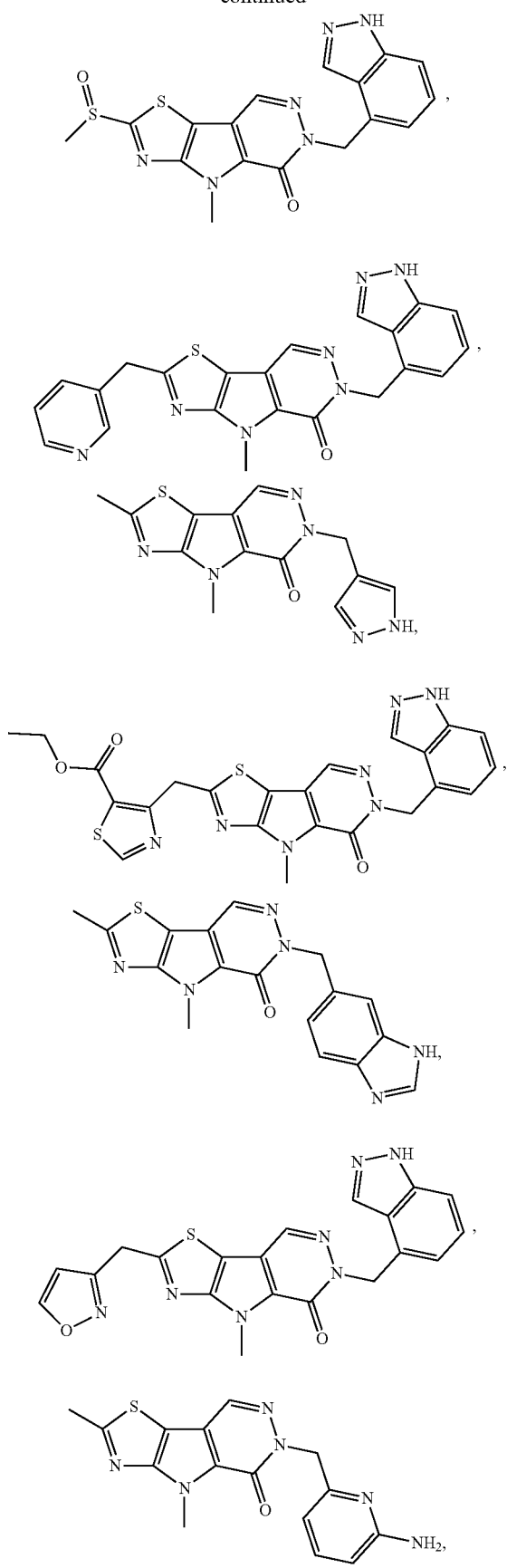
422
-continued
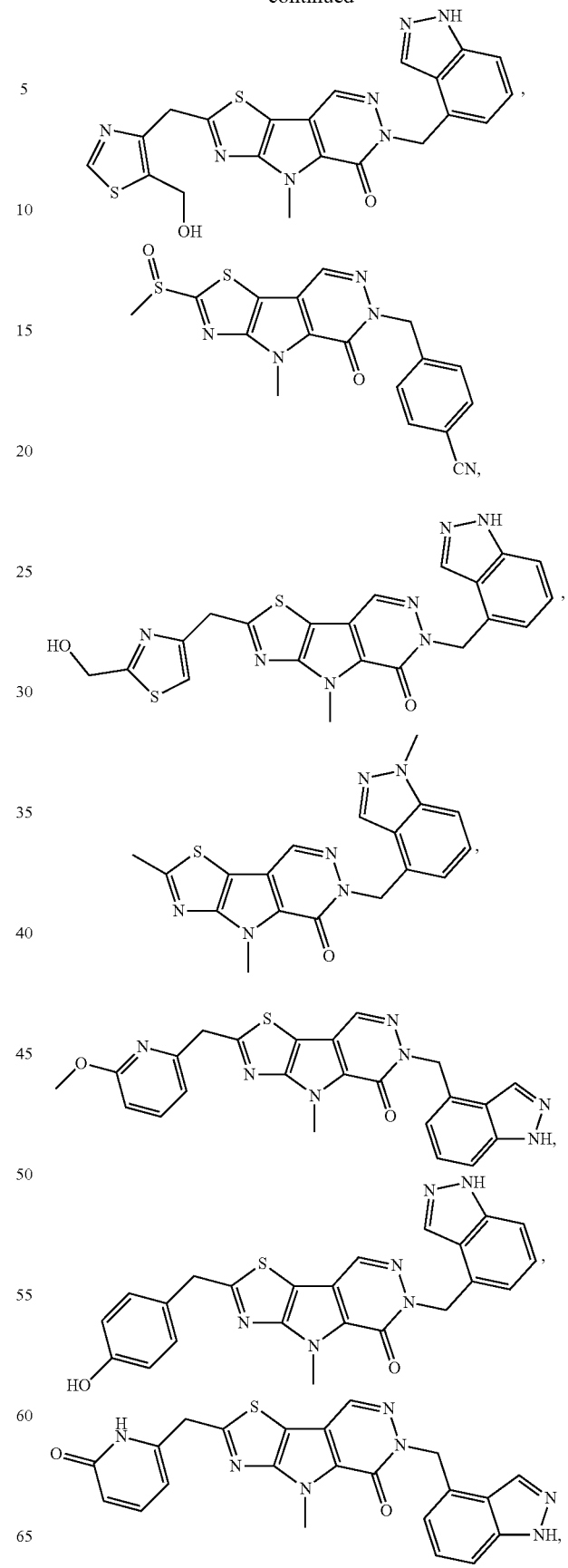

423
-continued
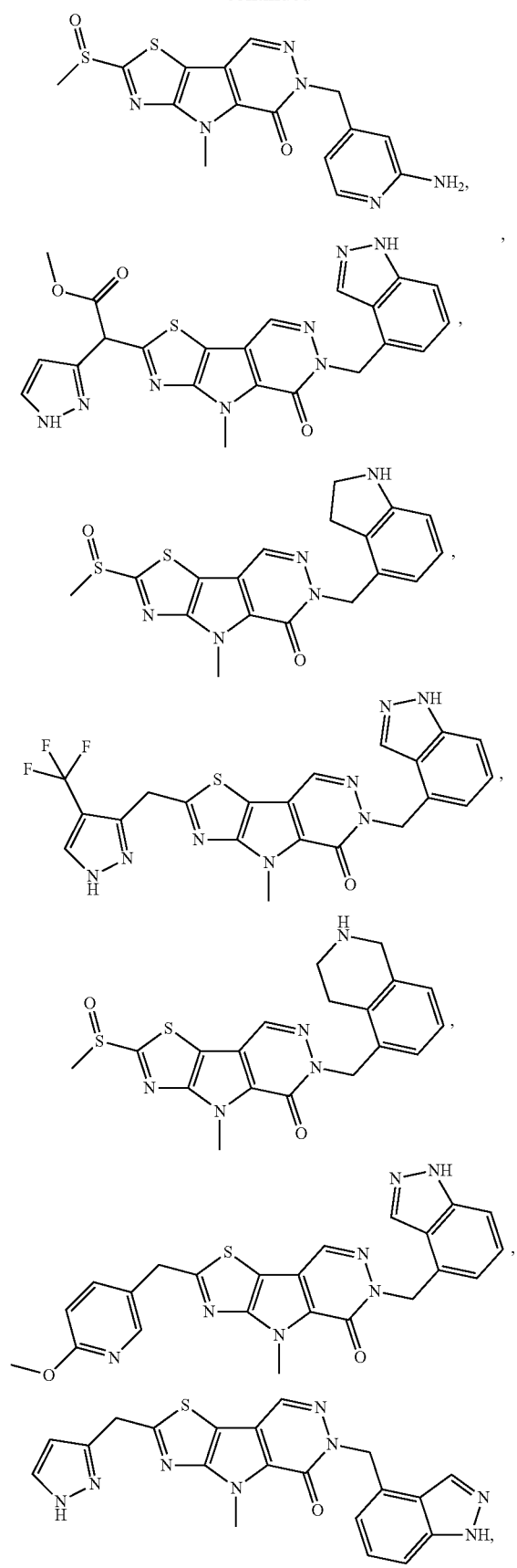
424
-continued
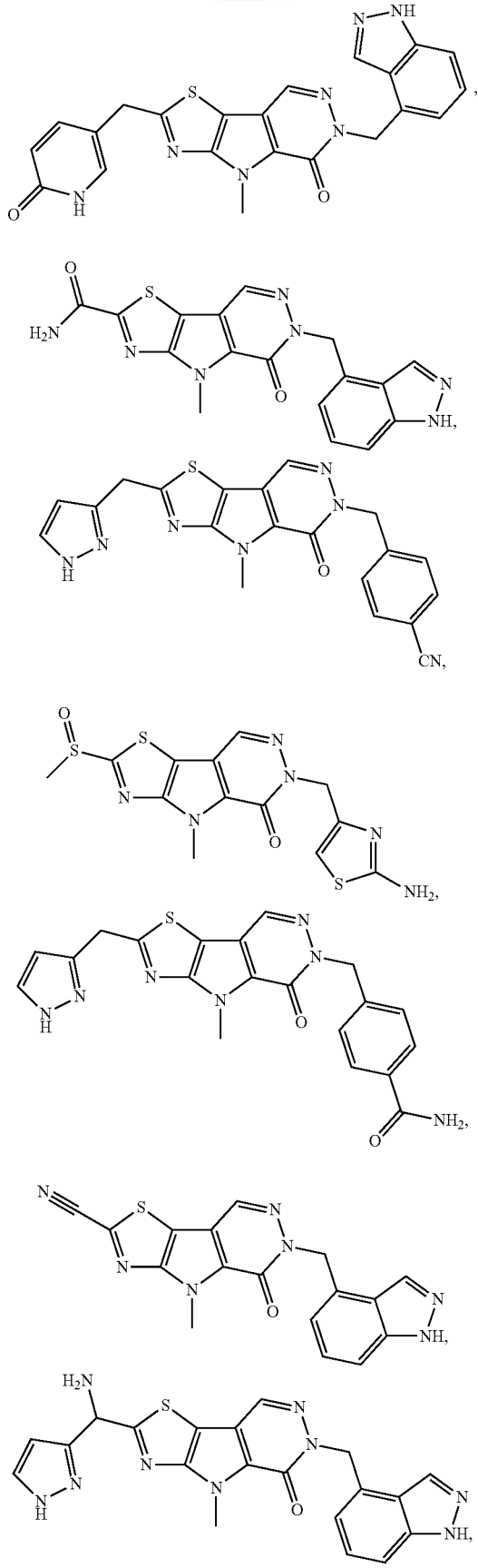

425
-continued
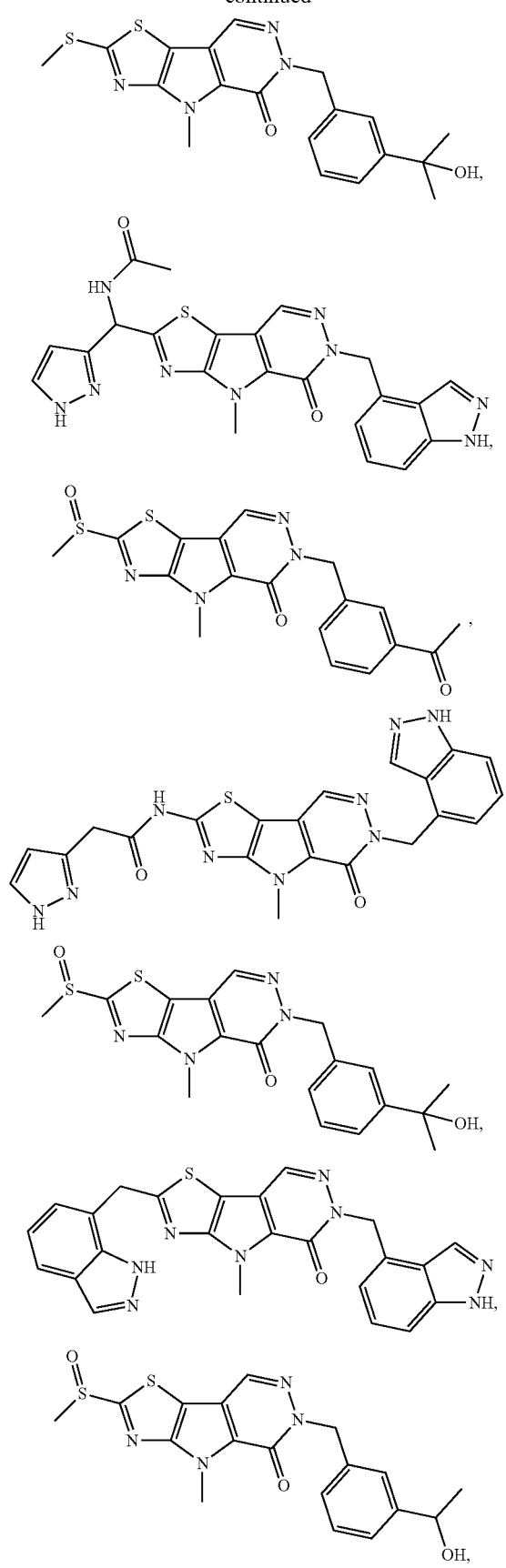
426
-continued
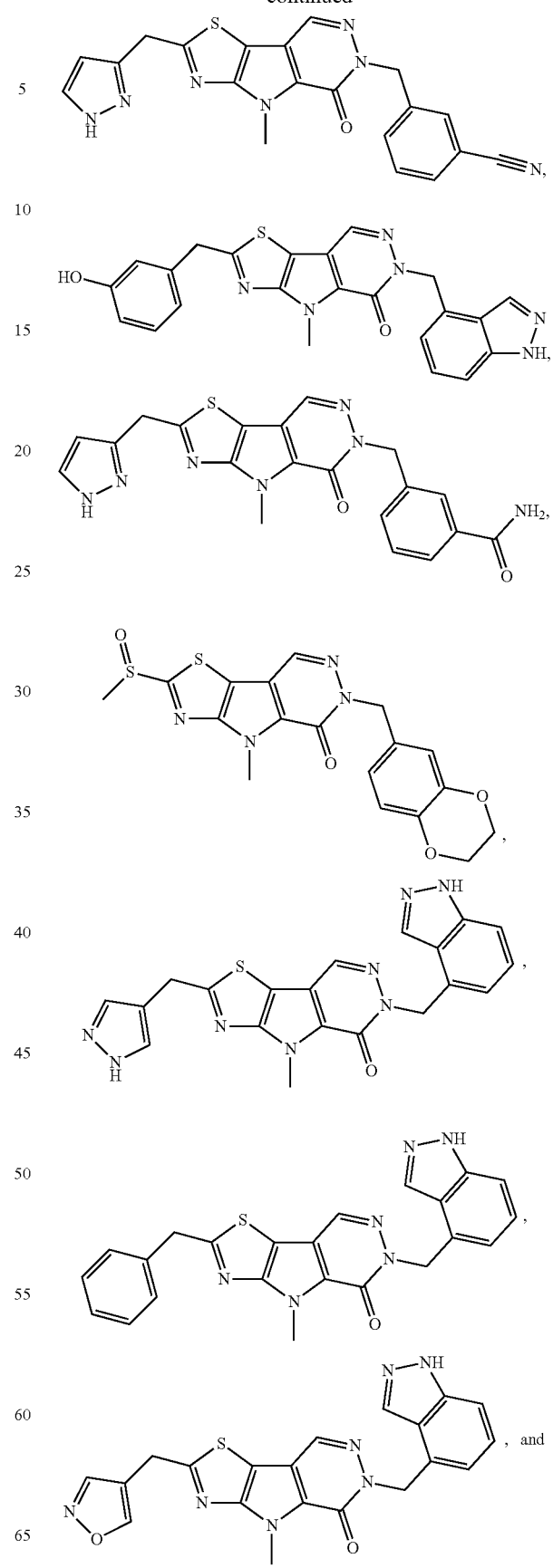

-continued

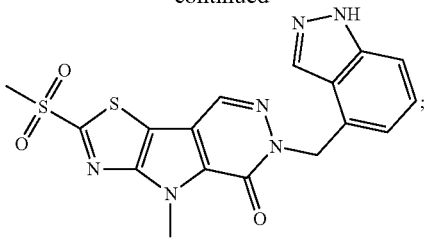

or a pharmaceutically acceptable salt thereof.

2. The compound of claim 1, or a pharmaceutically acceptable salt thereof, wherein the compound is of the structural formula:

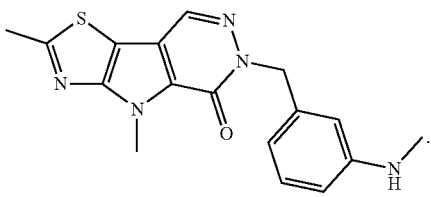

3. A pharmaceutical composition comprising a compound of claim 1, or a pharmaceutically acceptable salt thereof.

4. A pharmaceutical composition comprising the compound of claim 2, or a pharmaceutically acceptable salt thereof.

5. A method for treating a condition selected from sickle cell disease, pyruvate kinase deficiency (PKD), and thalassemia in a subject comprising administering to the subject an effective amount of the compound according to claim 1, or a pharmaceutically acceptable salt thereof.

6. A method for treating a condition selected from sickle cell disease, pyruvate kinase deficiency (PKD), and thalassemia in a subject comprising administering to the subject an effective amount of the compound according to claim 2, or a pharmaceutically acceptable salt thereof.

7. The method of claim 5, wherein the condition is sickle cell disease.

8. The method of claim 5, wherein the condition is pyruvate kinase deficiency (PKD).

9. The method of claim 5, wherein the condition is thalassemia.

10. The method of claim 6, wherein the condition is sickle cell disease.

11. The method of claim 6, wherein the condition is pyruvate kinase deficiency (PKD).

12. The method of claim 6, wherein the condition is thalassemia.

13. A method of treating hereditary spherocytosis, hereditary elliptocytosis, abetalipoproteinemia or Bassen-Kornzweig syndrome, sickle cell disease, paroxysmal nocturnal hemoglobinuria, anemia, hemolytic anemia, acquired hemolytic anemia, or anemia of chronic diseases in a subject in need thereof, a method of increasing amount of hemoglobin in a subject in need thereof, a method of increasing the lifetime of red blood cells (RBCs) in a subject in need thereof, a method for regulating 2,3-diphosphoglycerate levels in blood in a subject in need thereof, or a method for activating pyruvate kinase R (PKR) in red blood cells in a subject in need thereof, comprising administering to a subject an effective amount of a compound according to claim 1 or a pharmaceutically acceptable salt thereof.

14. A method of treating hereditary spherocytosis, hereditary elliptocytosis, abetalipoproteinemia or Bassen-Kornzweig syndrome, sickle cell disease, paroxysmal nocturnal hemoglobinuria, anemia, hemolytic anemia, acquired hemolytic anemia, or anemia of chronic diseases in a subject in need thereof, a method of increasing amount of hemoglobin in a subject in need thereof, a method of increasing the lifetime of red blood cells (RBCs) in a subject in need thereof, a method for regulating 2,3-diphosphoglycerate levels in blood in a subject in need thereof, or a method for activating pyruvate kinase R (PKR) in red blood cells in a subject in need thereof, comprising administering to a subject an effective amount of the compound according to claim 2 or a pharmaceutically acceptable salt thereof.

* * * * *

UNITED STATES PATENT AND TRADEMARK OFFICE
CERTIFICATE OF CORRECTION

PATENT NO. : 11,957,680 B2  Page 1 of 1
APPLICATION NO. : 17/744806
DATED : April 16, 2024
INVENTOR(S) : Giovanni Cianchetta et al.

It is certified that error appears in the above-identified patent and that said Letters Patent is hereby corrected as shown below:

In the Claims

At Column 402, Claim number 1, Line number 40, please replace

" 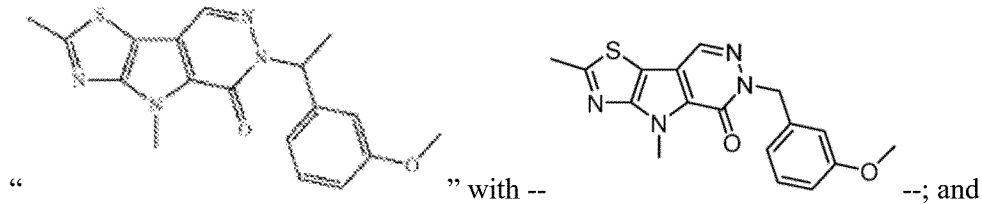 " with -- -- ; and

At Column 419, Claim number 1, Line number 5, please replace

" 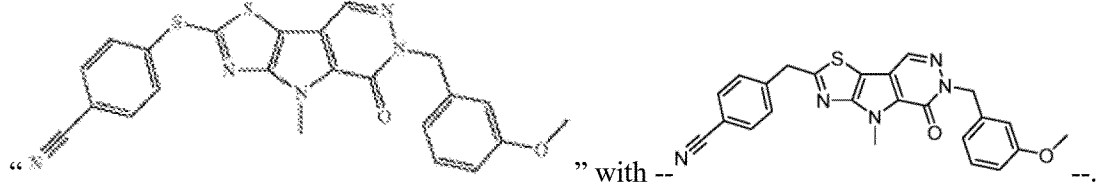 " with -- --.

Signed and Sealed this
Twenty-eighth Day of May, 2024

Katherine Kelly Vidal
*Director of the United States Patent and Trademark Office*